United States Patent
Fan et al.

(10) Patent No.: US 10,696,659 B2
(45) Date of Patent: Jun. 30, 2020

(54) COMPOUNDS HAVING ESTROGEN RECEPTOR ALPHA DEGRADATION ACTIVITY AND USES THEREOF

(71) Applicant: ACCUTAR BIOTECHNOLOGY INC., Brooklyn, NY (US)

(72) Inventors: Jie Fan, New York, NY (US); Ke Liu, Shanghai (CN); Hui Zhang, Brooklyn, NY (US); Wei He, Zionsville, IN (US)

(73) Assignee: Accutar Biotechnology Inc., Brooklyn, NY (US)

( * ) Notice: Subject to any disclaimer, the term of this patent is extended or adjusted under 35 U.S.C. 154(b) by 0 days.

(21) Appl. No.: 16/690,611

(22) Filed: Nov. 21, 2019

(65) Prior Publication Data

US 2020/0157078 A1 May 21, 2020

Related U.S. Application Data

(60) Provisional application No. 62/770,476, filed on Nov. 21, 2018.

(51) Int. Cl.
| | | |
|---|---|---|
| *C07D 401/14* | (2006.01) | |
| *C07D 471/10* | (2006.01) | |
| *C07D 401/04* | (2006.01) | |
| *A61P 35/00* | (2006.01) | |

(52) U.S. Cl.
CPC ............ *C07D 401/14* (2013.01); *A61P 35/00* (2018.01); *C07D 401/04* (2013.01); *C07D 471/10* (2013.01)

(58) Field of Classification Search
CPC .......................... C07D 401/14; C07D 471/10
See application file for complete search history.

(56) References Cited

U.S. PATENT DOCUMENTS

| | | | |
|---|---|---|---|
| 6,875,775 B2* | 4/2005 | Sodervall et al. | |
| 2015/0018341 A1* | 1/2015 | Xiao et al. | |
| 2018/0208590 A1* | 7/2018 | Fan et al. | |

FOREIGN PATENT DOCUMENTS

WO    WO 2013/097773 A1 *   7/2013

OTHER PUBLICATIONS

Lahoz, et al. Organic Electronics 14 (2013), pp. 1225-1230.*
International Search Report for International Application No. PCT/US19/62564, dated Mar. 3, 2020.*
Written Opinion of the International Search Authority for International Application No. PCT/US19/62564, dated Mar. 3, 2020.*

* cited by examiner

*Primary Examiner* — Shawquia Jackson
(74) *Attorney, Agent, or Firm* — Finnegan, Henderson, Farabow Garrett & Dunner, LLP

(57) ABSTRACT

The present disclosure relates to novel compounds having estrogen receptor alpha degradation activity, pharmaceutical compositions containing such compounds, and their use in prevention and treatment of cancer and related diseases and conditions.

30 Claims, 25 Drawing Sheets

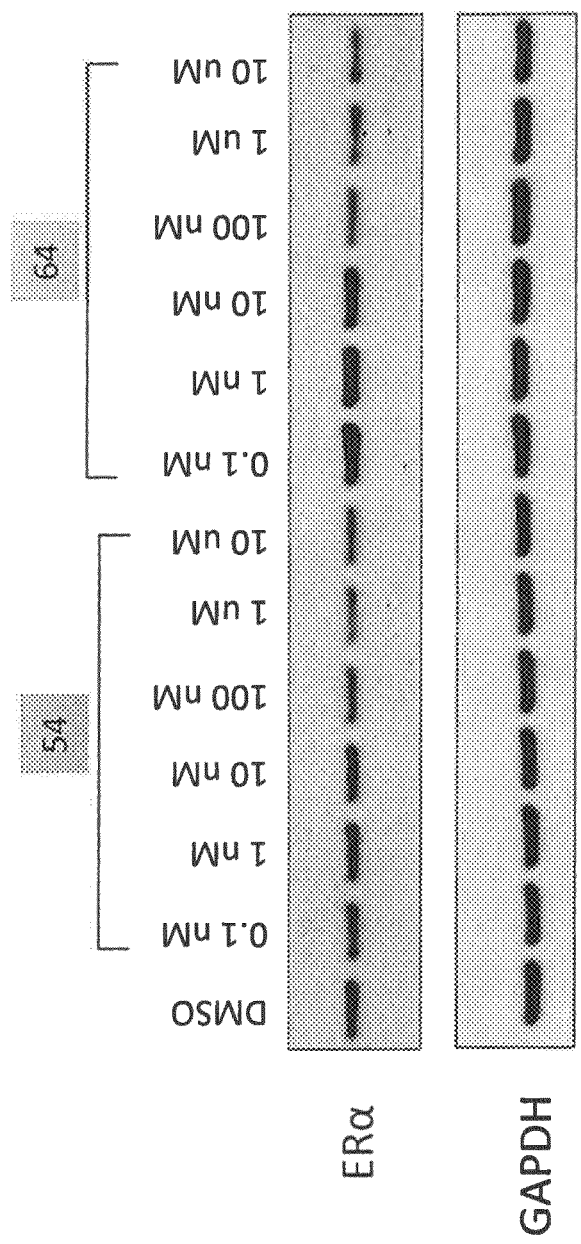

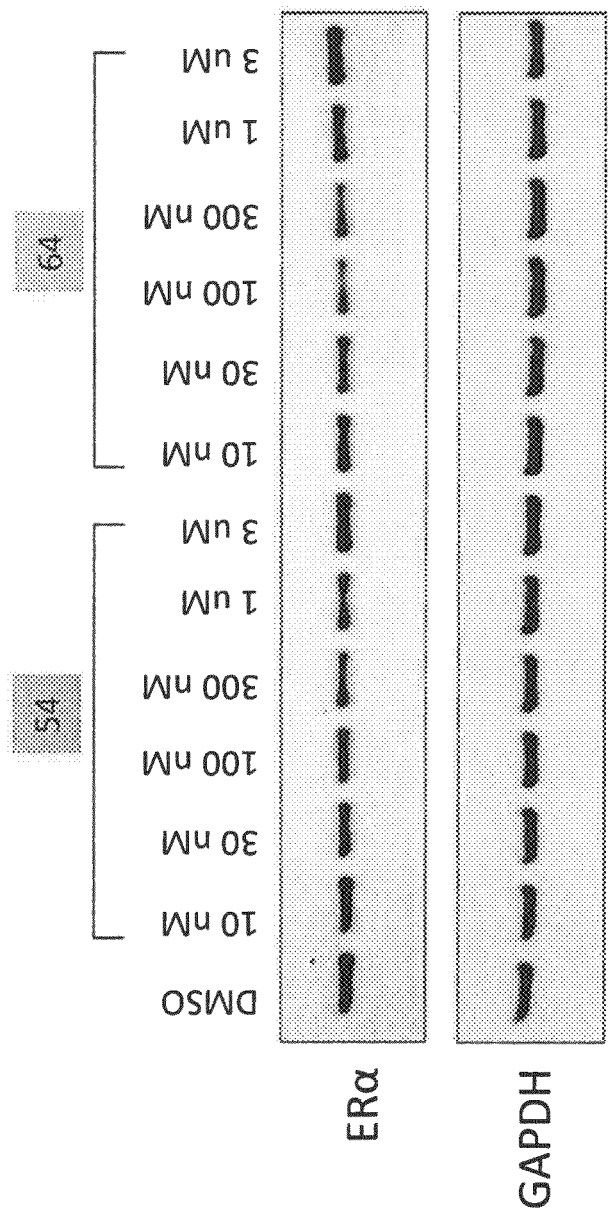

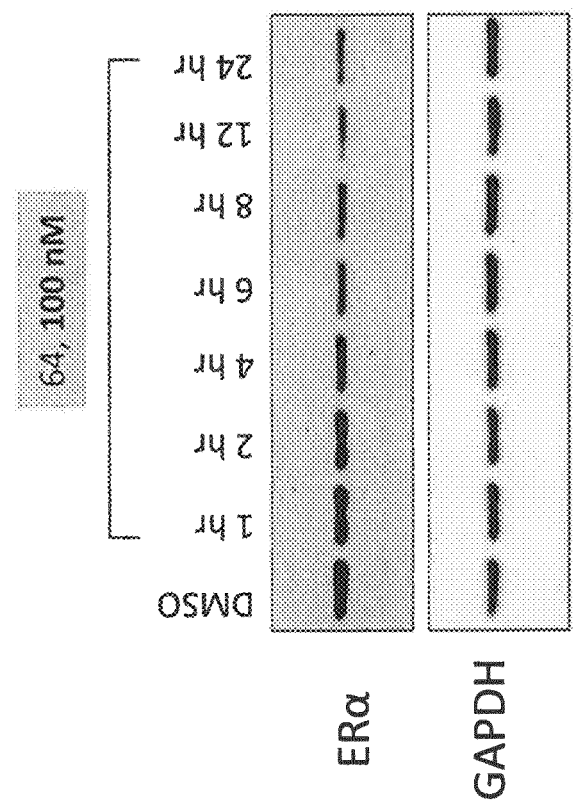

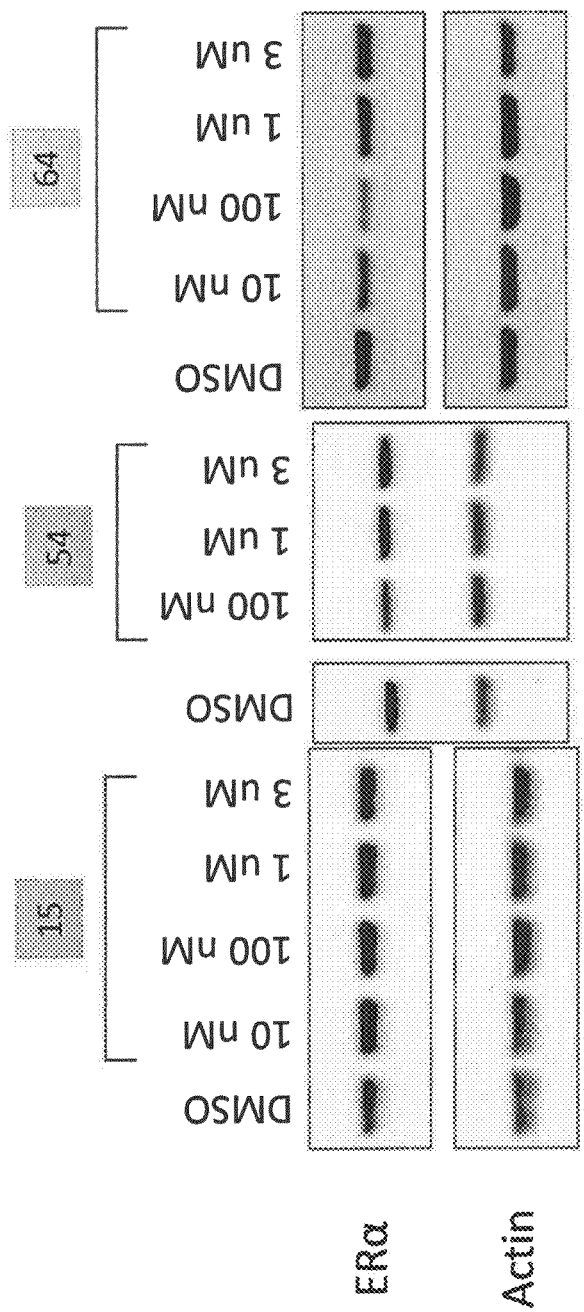

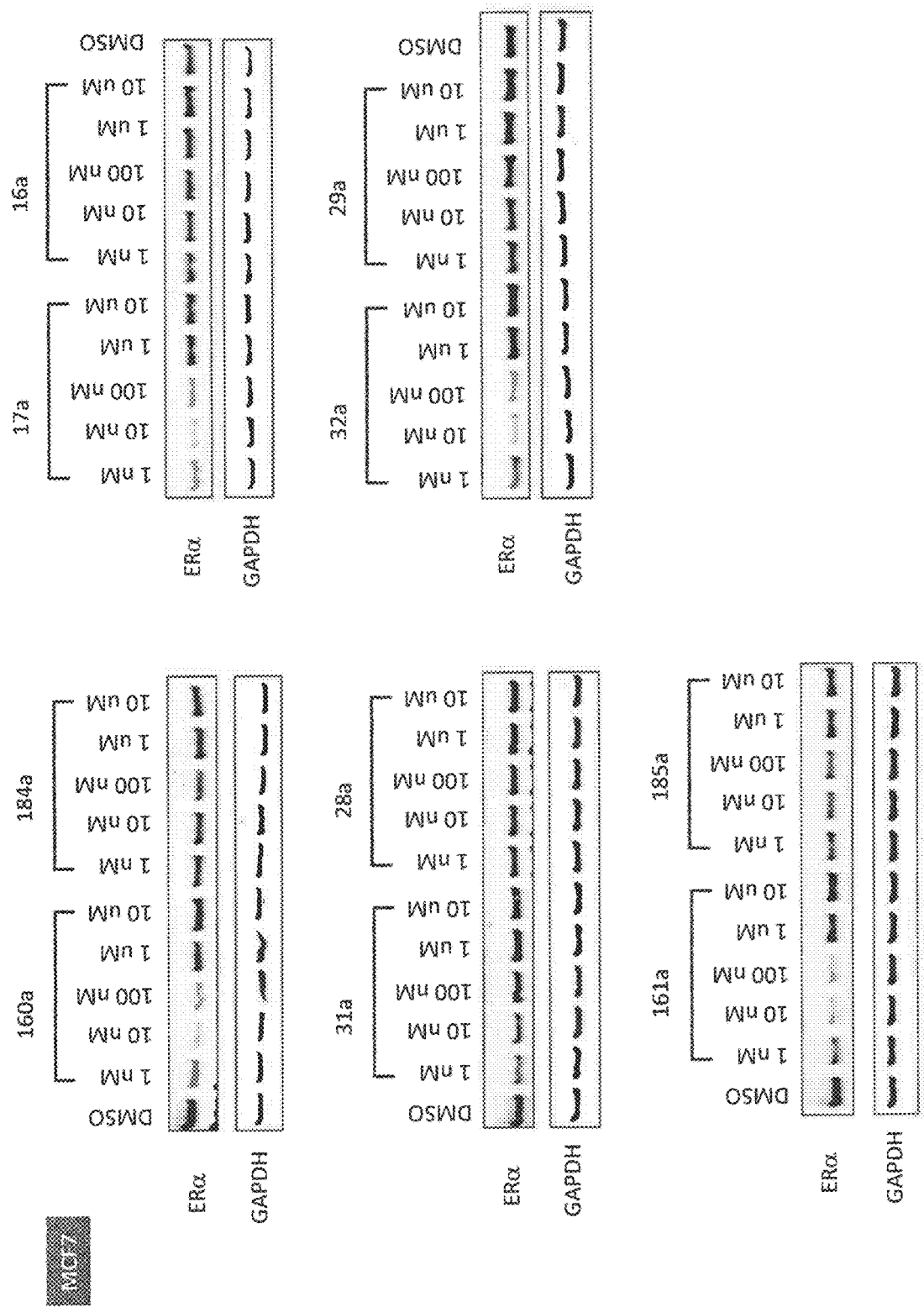

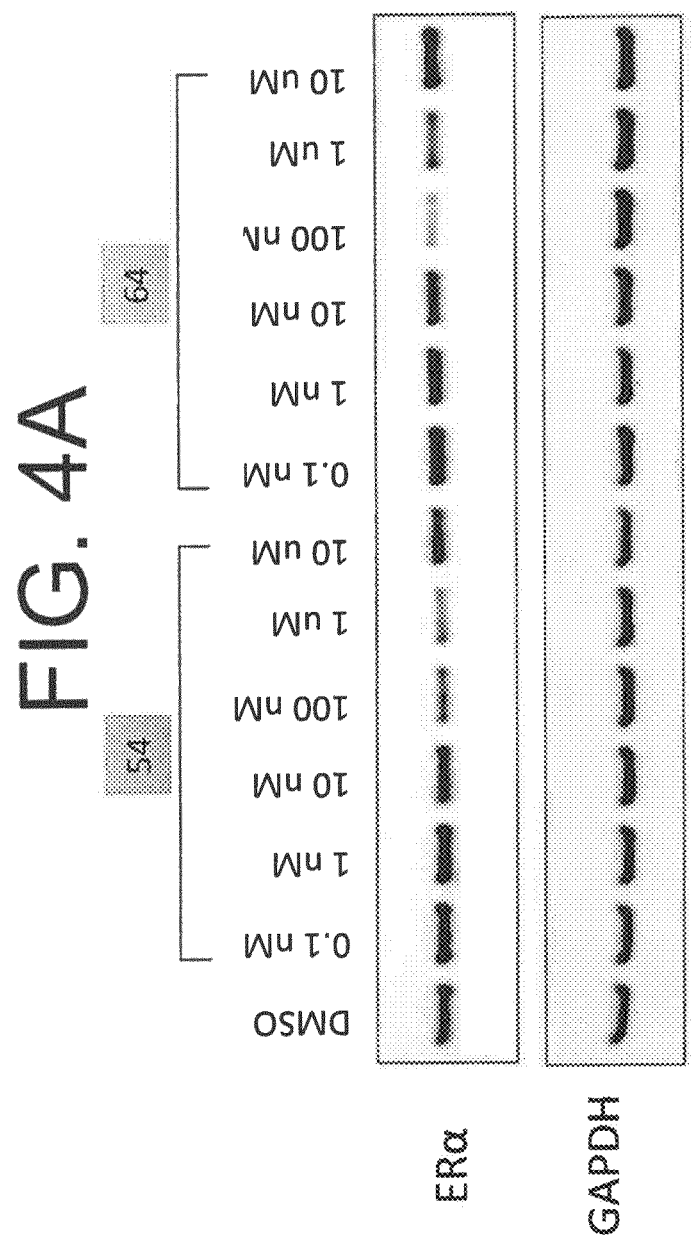

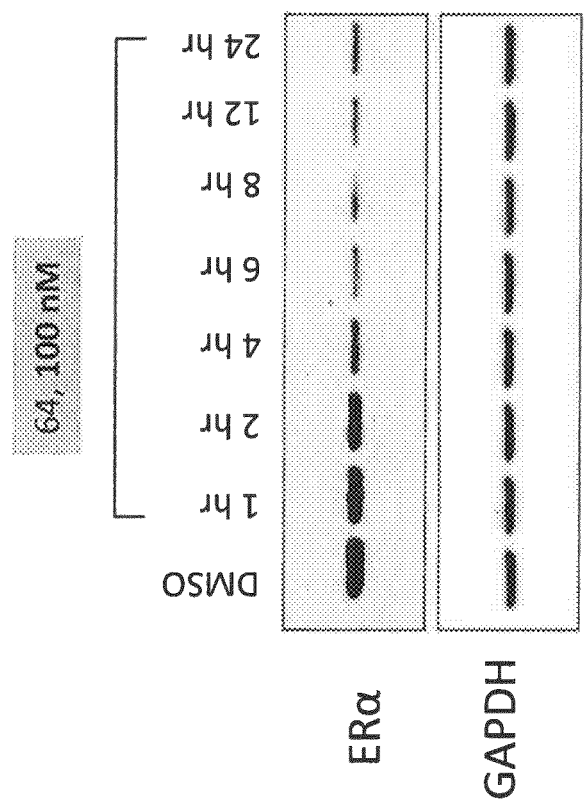

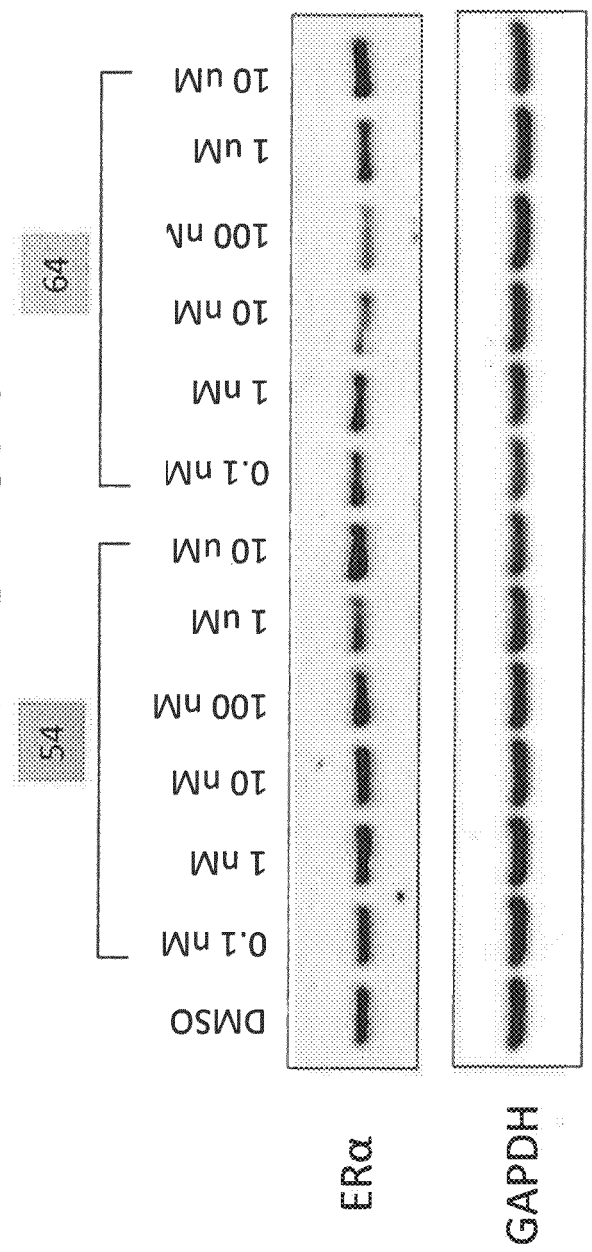

COMPOUNDS HAVING ESTROGEN RECEPTOR ALPHA DEGRADATION ACTIVITY AND USES THEREOF

This application claims priority from U.S. Provisional Patent Application No. 62/770,476, filed Nov. 21, 2018, which is hereby incorporated by reference in its entirety.

FIELD OF THE DISCLOSURE

The present disclosure relates to novel compounds having estrogen receptor alpha degradation activity, pharmaceutical compositions containing such compounds, and their use in prevention and treatment of diseases and conditions, e.g., cancer.

BACKGROUND OF THE DISCLOSURE

Estrogen, a female sex hormone, through binding to its cognate Estrogen receptors, ERα and ERβ, governs a wide range of physiological processes, e.g., the development of the female reproductive system, the maintenance of bone mass, and the protection of cardiovascular tissue and the central nervous system. Upon estrogen's binding to an estrogen receptor ("ER"), the receptor undergoes a conformational change resulting in its homodimerization. The ER homodimer then binds to estrogen-response elements ("EREs") that are present in the promoters of a specific set of target genes and regulates their expression with the help of transcriptional coregulators. Several thousand canonical ER target genes have been identified, many of which regulate cell proliferation and survival.

Because ER signaling is implicated in many pathways, it is well known that deregulation of ER signaling, specifically through ERα, results in uncontrolled cellular proliferation which eventually results into cancer. ER+ breast cancer accounts for approximately 75% of all breast cancers diagnosed, as well as some ovarian and endometrial cancers. The prevalence of ER+ cancer has led to decades of investigation and development of antiestrogens as therapeutic agents.

Antiestrogen (i.e., hormonal) therapy is the first choice for treatment of most ER+ breast cancers. There are three major classes of antiestrogen therapies, including aromatase inhibitors (e.g., letrozole and anastrozole); selective estrogen receptor modulators (e.g., tamoxifen, toremifene, and raloxifene); and selective estrogen receptor degraders (e.g., fulvestrant). These classes of antiestrogen therapy operate by different mechanisms of action, such as inhibiting aromatase enzyme, competitively binding to ERα, and/or causing ERα degradation.

The aforementioned therapies may result in deleterious effects. For example, administration of aromatase inhibitors results in a decrease in bone mineral density, which can result in an increased risk of fractures. Administration of selective estrogen modulators can result in development of endometrial cancer and/or cardiovascular issues, e.g., deep thrombosis and pulmonary embolism. Additionally, the aforementioned therapies may suffer from insufficient clinical efficacy.

Accordingly, there exists a need to treat ER+ cancer without the harmful side effects known for current therapies. One approach to achieve this goal would be to utilize the naturally occurring cellular ubiquitin-mediated degradation. Without being bound to any theory, it is believed that ERα degradation may occur when both ERα and a ubiquitin ligase are bound and brought into close proximity.

Cereblon ("CRBN") E3 ubiquitin ligase is a ubiquitin ligase that CRBN forms an E3 ubiquitin ligase complex with damaged DNA binding protein 1 and Cullin 4. It functions as a substrate receptor by bringing the substrates to close proximity for ubiquitination and subsequent degradation by proteasomes. Recently, it has been discovered that small molecules drugs, e.g., thalidomide and its close analogs, lenalidomide and pomalidomide, can simultaneously interact with CRBN and some other proteins. In doing so, CRBN may be exploited for target protein degradation, such as IKZF1 and IKZF3. This is thought to account for the anti-myeloma effects of thalidomide and related compounds.

SUMMARY OF THE DISCLOSURE

In some embodiments, provided herein are compounds of Formula (I), or a tautomer, stereoisomer or a mixture of stereoisomers, pharmaceutically acceptable salt, or hydrate thereof:

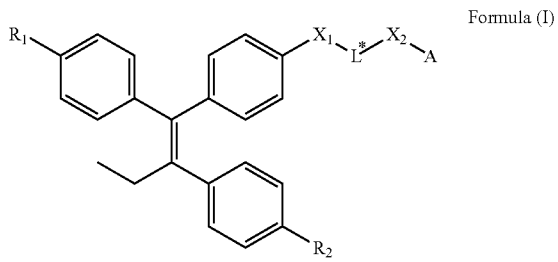

Formula (I)

wherein:

$X^1$ and $X^2$ are each independently selected from $C(R^3)_2$, $NR^4$, O, S, cycloalkyl, aryl, heterocycle, and heteroaryl, each of which is independently substituted with 0, 1, 2, or 3 $R^5$;

A is selected from:

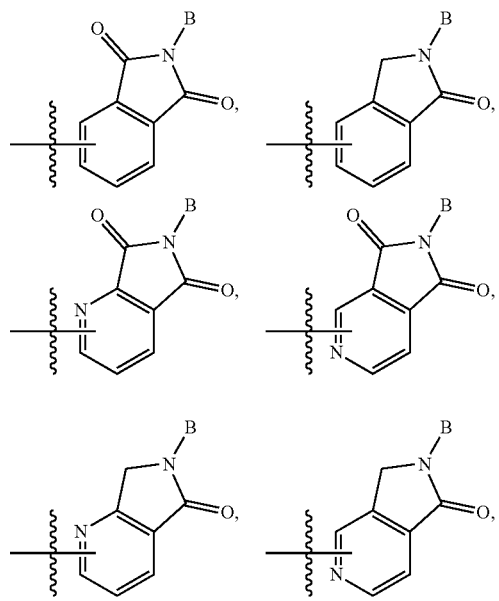

-continued

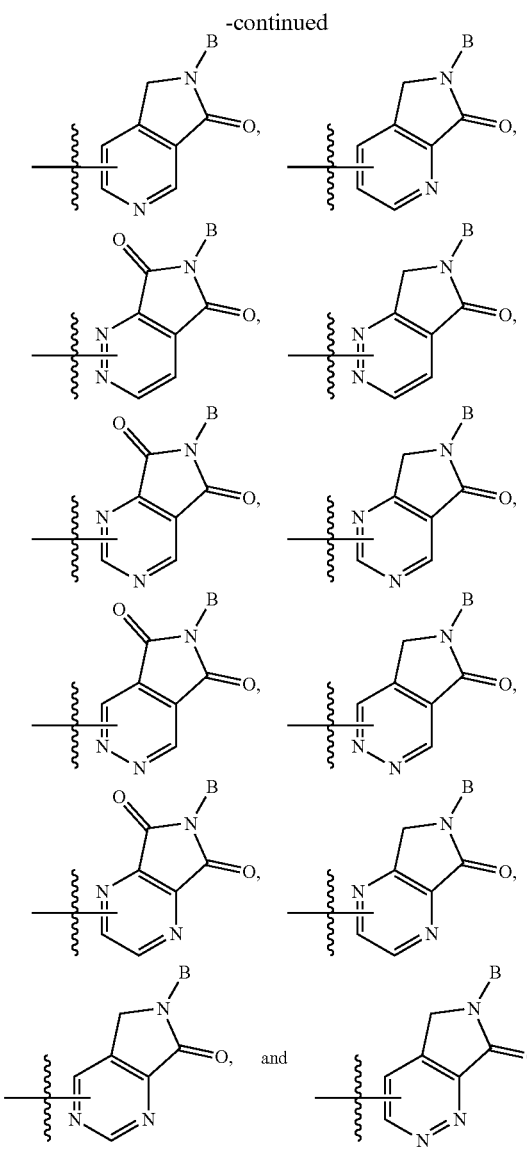

each of which is substituted with 0, 1, 2, or 3 R⁵;

B is selected from 5- to 6-member cycloalkyl, 5- to 6-member aryl, 5- to 6-member heterocycle, and 5- to 6-member heteroaryl, each of which is substituted with 0, 1, 2, or 3 R⁵;

L* is a linker of 1 to 22 carbon atoms in length, wherein one or more carbon atoms are each optionally and independently replaced by a group selected from C(O), O, NR⁴, S, C₂-alkenyl, C₂-alkynyl, cycloalkyl, aryl, heterocycle, and heteroaryl, each of which is substituted with 0, 1, 2, or 3 R⁵;

R¹ and R² are each independently selected from H, C₁-C₆ alkyl, halo, alkoxy, acyloxy, hydroxy, and sulfhydryl, each of which is substituted with 0, 1, 2, or 3 R⁵;

each R³ is independently selected from H, C₁-C₆ alkyl, halo, and hydroxy;

each R⁴ is independently selected from H, C₁-C₆ alkyl, and acyl, each of which is substituted with 0, 1, 2, or 3 R⁵; and each R⁵ is independently selected from C₁-C₆ alkyl, halo, cyano, and hydroxy, wherein

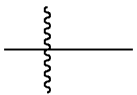

represents the point of attachment of A to X².

In some embodiments, the compound of Formula (I) may encompass both the E and Z isomers. In some embodiments, the compound of Formula (I) may be a mixture of trans- and -cis olefin.

In some embodiments, A may be

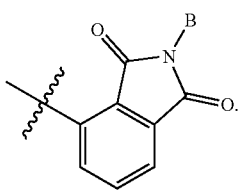

In some embodiments, A may be

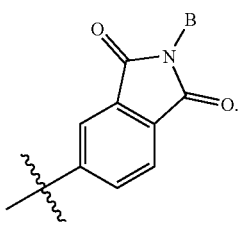

In some embodiments, A may be

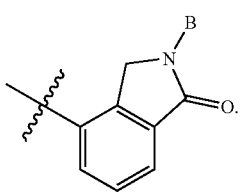

In some embodiments, A may be

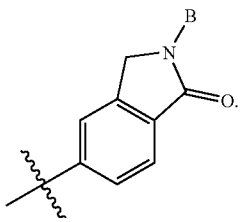

In some embodiments, provided herein are compounds of Formula (II), or a tautomer, stereoisomer, pharmaceutically salt, or hydrate thereof:

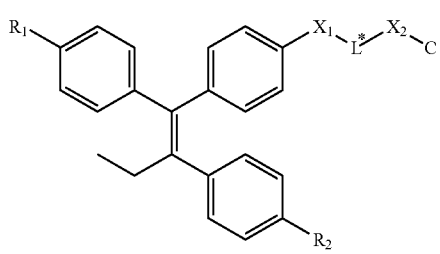

Formula (II)

wherein:

$X^1$ and $X^2$ are each independently selected from $C(R^3)_2$, $NR^4$, O, S, cycloalkyl, aryl, heterocycle, and heteroaryl, each of which is independently substituted with 0, 1, 2, or 3 $R^5$;

B is selected from 5- to 6-member cycloalkyl, 5- to 6-member aryl, 5- to 6-member heterocycle, and 5- to 6-member heteroaryl, each of which is substituted with 0, 1, 2, or 3 $R^5$;

C is selected from:

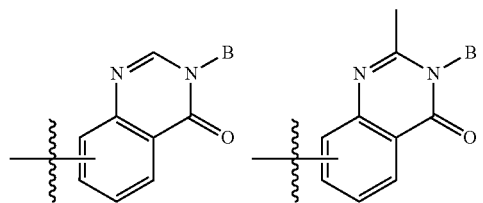

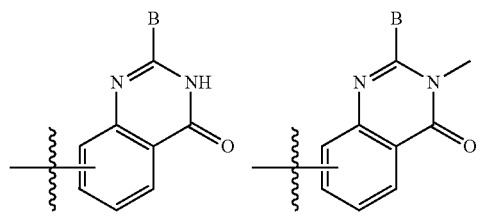

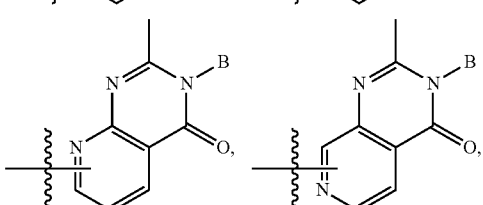

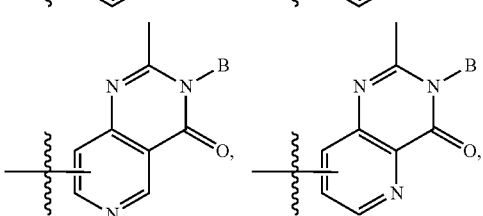

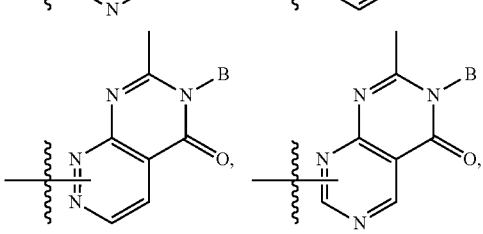

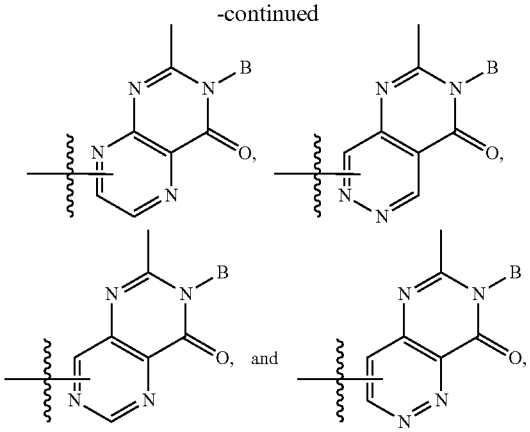

each of which is substituted with 0, 1, 2, or 3 $R^5$;

L* is a linker of 1 to 22 carbon atoms in length, wherein one or more carbon atoms are each optionally and independently replaced by a group selected from C(O), O, $NR^4$, S, $C_2$-alkenyl, $C_2$-alkynyl, cycloalkyl, aryl, heterocycle, and heteroaryl, each of which is substituted with 0, 1, 2, or 3 $R^5$;

$R^1$ and $R^2$ are each independently selected from H, $C_1$-$C_6$ alkyl, halo, alkoxy, acyloxy, hydroxy, and sulfhydryl, each of which is substituted with 0, 1, 2, or 3 $R^5$;

each $R^3$ is independently selected from H, $C_1$-$C_6$ alkyl, halo, and hydroxy;

each $R^4$ is independently selected from H, $C_1$-$C_6$ alkyl, and acyl, each of which is substituted with 0, 1, 2, or 3 $R^5$; and each $R^5$ is independently selected from $C_1$-$C_6$ alkyl, halo, cyano, and hydroxy, wherein

represents the point of attachment of C to $X^2$.

In some embodiments, C may be

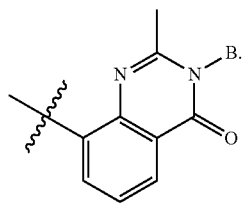

In some embodiments, C may be

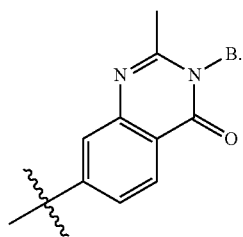

Also provided herein is a method of treating cancer in a subject in need thereof, comprising administering to said subject an effective amount of a compound disclosed herein. In some embodiments, the cancer is selected from breast cancer, lung cancer, ovarian cancer, endometrial cancer, prostate cancer, and esophageal cancer.

BRIEF DESCRIPTION OF DRAWINGS

The foregoing summary, as well as the following detailed description of the disclosure, will be better understood when read in conjunction with the appended drawings. For the purpose of illustrating the present disclosure, the attached drawings illustrate some, but not all, alternative embodiments. It should be understood, however, that the disclosure is not limited to the precise arrangements and instrumentalities shown. These figures, which are incorporated into and constitute part of the specification, assist in explaining the principles of the disclosure.

FIG. 2B illustrates the ERα degradative activity of exemplary compounds 54 and 64 of the present disclosure in a T47D cell line 6 hours after administration.

FIG. 2C illustrates the ERα degradative activity of exemplary compounds 54 and 64 of the present disclosure in a T47D cell line 6 hours after administration.

FIG. 2E illustrates the ERα degradative activity of exemplary compound 64 of the present disclosure at a concentration of 100 nM, as a function of time, in a T47D cell line.

FIG. 3A illustrates the ERα degradative activity of exemplary compounds 15, 54, and 64 of the present disclosure in an MCF7 cell line 4 hours after administration.

FIG. 3C illustrates the ERα degradative activity of exemplary compounds 160a, 184a, 17a, 16a, 31a, 28a, 32a, 29a, 161a, and 185a of the present disclosure in an MCF7 cell line 6 hours after administration.

FIG. 4A illustrates the ERα degradative activity of exemplary compounds 54 and 64 of the present disclosure in a CAMA1 cell line 6 hours after administration.

FIG. 4C illustrates the ERα degradative activity of an exemplary compound 64 of the present disclosure at a concentration of 100 nM, as a function of time, in a CAMA1 cell line.

FIG. 5A illustrates the ERα degradative activity of exemplary compounds 54 and 64 of the present disclosure at various concentrations in a ZR-75-1 cell line 6 hours after administration.

DETAILED DESCRIPTION OF THE DISCLOSURE

Definitions

Figure 1:
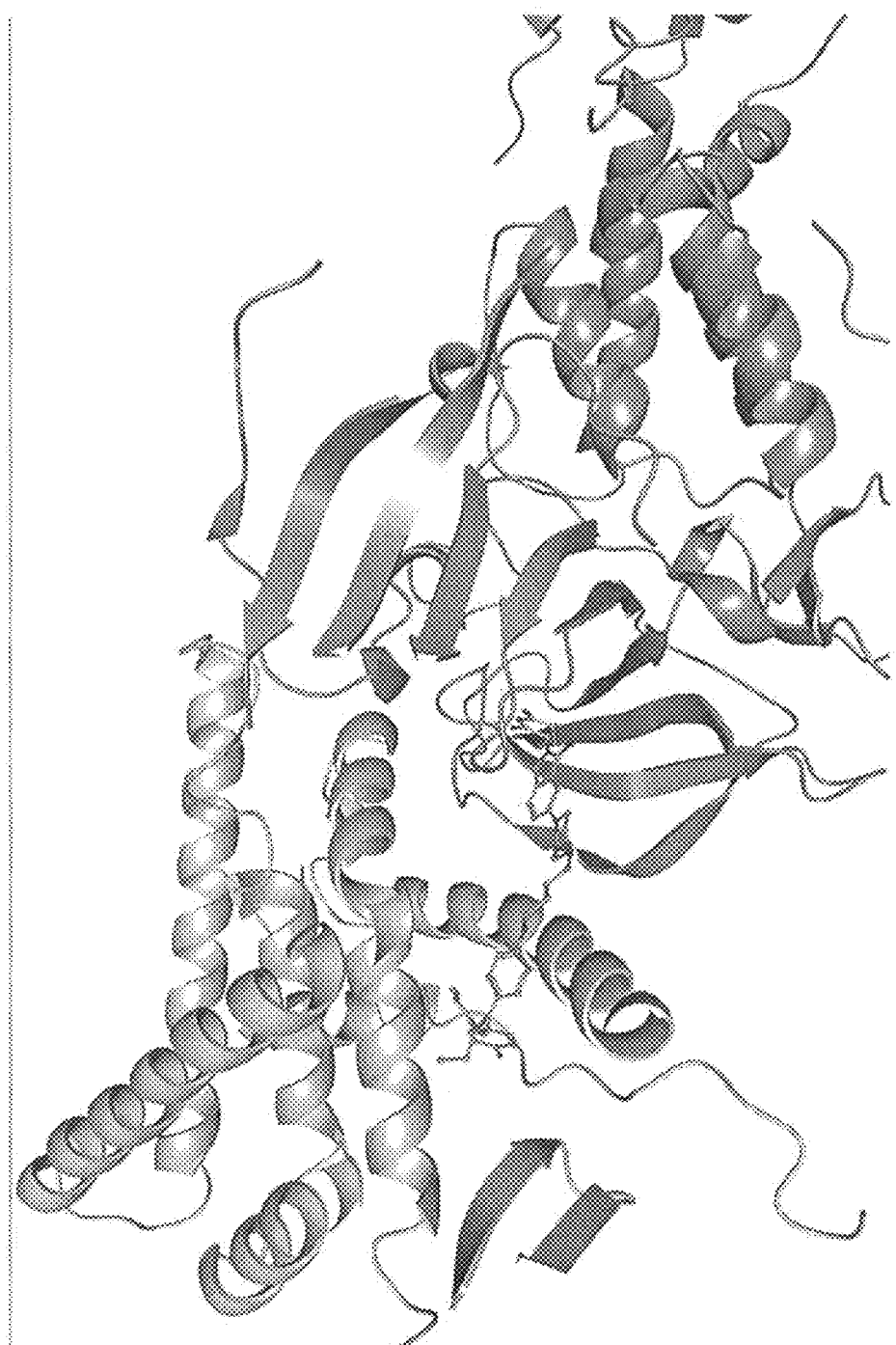
FIG. 1 illustrates an exemplary compound of the present disclosure bound to ERα and an E3 ubiquitin ligase cereblon.
Figure 2A:
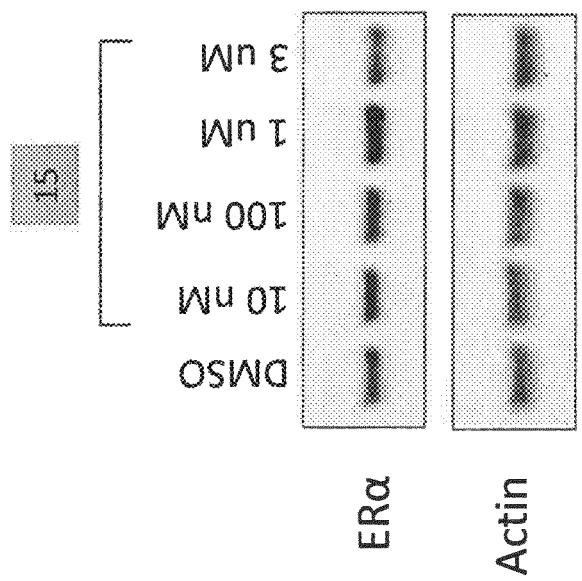
FIG. 2A illustrates the ERα degradative activity of exemplary compound 15 of the present disclosure in a T47D cell line 4 hours after administration.
Figure 2D:
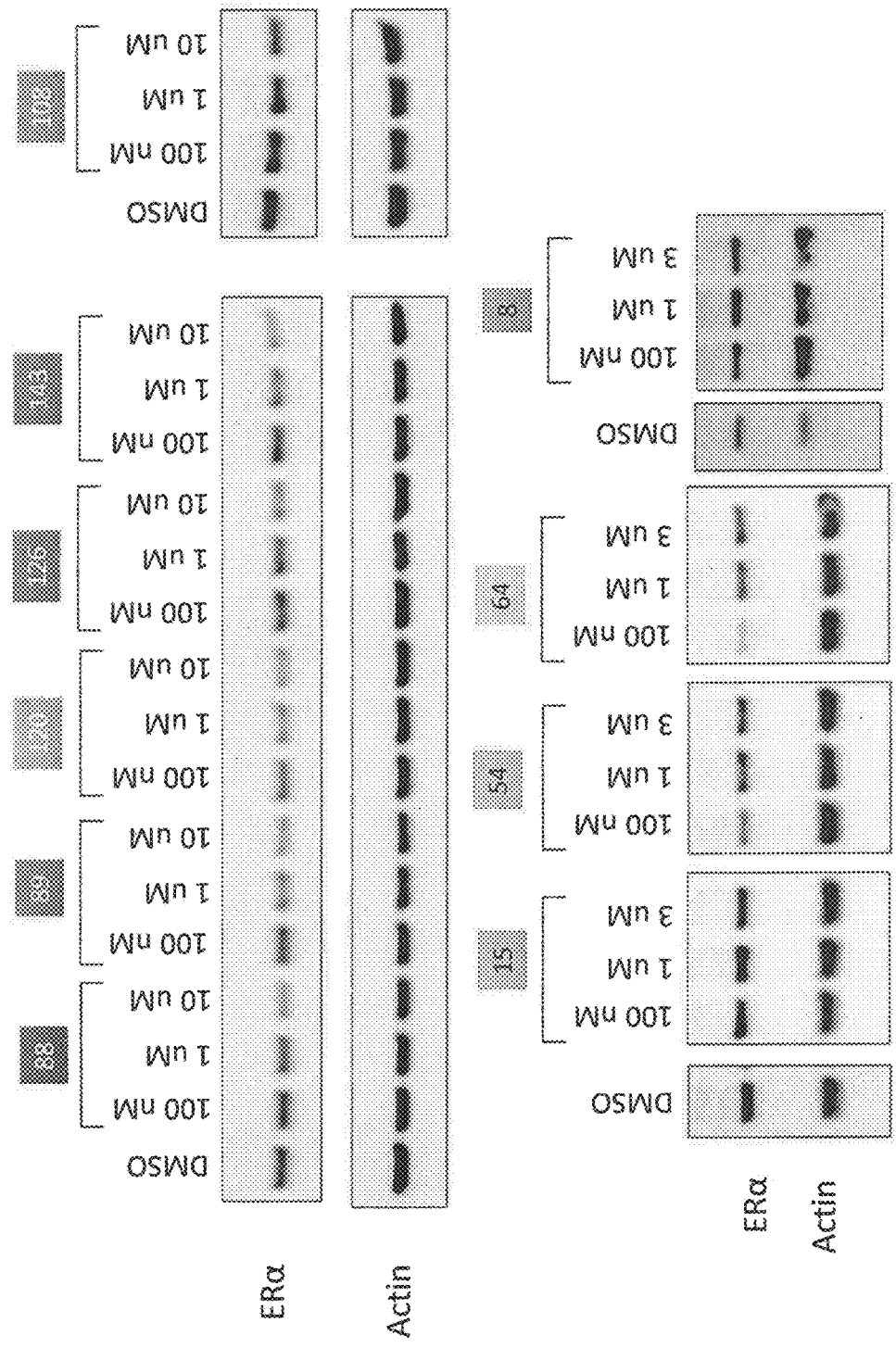
FIG. 2D illustrates the ERα degradative activity of exemplary compounds 8, 15, 54, 64, 88, 89, 108, 126, 143, and 120 of the present disclosure in a T47D cell line 8 hours after administration.

As used herein, "cancer" refers to diseases, disorders, and conditions that involve abnormal cell growth with the potential to invade or spread to other parts of the body. Exemplary cancers, include, but are not limited to, breast cancer, lung cancer, ovarian cancer, endometrial cancer, prostate cancer, and esophageal cancer.

"Subject" refers to an animal, such as a mammal, that has been or will be the object of treatment, observation, or experiment. The methods described herein may be useful for both human therapy and veterinary applications. In one embodiment, the subject is a human.

As used herein, "treatment" or "treating" refers to an amelioration of a disease or disorder, or at least one discernible symptom thereof. In another embodiment, "treatment" or "treating" refers to an amelioration of at least one measurable physical parameter, not necessarily discernible by the patient. In yet another embodiment, "treatment" or "treating" refers to inhibiting the progression of a disease or disorder, either physically, e.g., stabilization of a discernible symptom, physiologically, e.g., stabilization of a physical parameter, or both. In yet another embodiment, "treatment" or "treating" refers to delaying the onset of a disease or disorder. For example, treating a cholesterol disorder may comprise decreasing blood cholesterol levels.

As used herein, "prevention" or "preventing" refers to a reduction of the risk of acquiring a given disease or disorder.

A dash ("-") that is not between two letters or symbols is used to indicate a point of attachment for a substituent. For example, —CN is attached through the carbon atom.

By "optional" or "optionally" it is meant that the subsequently described event or circumstance may or may not occur, and that the description includes instances where the event or circumstance occurs and instances in which is does not. For example, "optionally substituted aryl" encompasses both "aryl" and "substituted aryl" as defined below. It will be understood by those skilled in the art, with respect to any group containing one or more substituents, that such groups are not intended to introduce any substitution or substitution patterns that are sterically impractical, synthetically non-feasible and/or inherently unstable.

When a range of values is listed, it is intended to encompass each value and sub-range within the range. For example, "$C_1$-$C_6$ alkyl" is intended to encompass $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "acyl" as used herein refers to R—C(O)— groups such as, but not limited to, (alkyl)-C(O)—, (alkenyl)-C(O)—, (alkynyl)-C(O)—, (aryl)-C(O)—, (cycloalkyl)-C(O)—, (heteroaryl)-C(O)—, and (heterocyclyl)-C(O)—, wherein the group is attached to the parent molecular structure through the carbonyl functionality. In some embodiments, it is a $C_{1-10}$ acyl radical which refers to the total number of chain or ring atoms of the, for example, alkyl, alkenyl, alkynyl, aryl, cycloalkyl, or heteroaryl, portion plus the carbonyl carbon of acyl. For example, a $C_4$-acyl has three other ring or chain atoms plus carbonyl.

The term "alkenyl" as used herein refers to an unsaturated straight or branched hydrocarbon having at least one carbon-carbon double bond, such as a straight or branched group of 2-8 carbon atoms, referred to herein as ($C_2$-$C_8$)alkenyl. Exemplary alkenyl groups include, but are not limited to, vinyl, allyl, butenyl, pentenyl, hexenyl, butadienyl, pentadienyl, hexadienyl, 2-ethylhexenyl, 2-propyl-2-butenyl, and 4-(2-methyl-3-butene)-pentenyl.

The term "alkyl" as used herein refers to a saturated straight or branched hydrocarbon, such as a straight or branched group of 1-8 carbon atoms, referred to herein as ($C_1$-$C_8$)alkyl. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, and octyl. In some embodiments, "alkyl" is a straight-chain hydrocarbon. In some embodiments, "alkyl" is a branched hydrocarbon.

The term "alkynyl" as used herein refers to an unsaturated straight or branched hydrocarbon having at least one carbon-carbon triple bond, such as a straight or branched group of 2-8 carbon atoms, referred to herein as ($C_2$-$C_8$)alkynyl. Exemplary alkynyl groups include, but are not limited to, ethynyl, propynyl, butynyl, pentynyl, hexynyl, methylpropynyl, 4-methyl-1-butynyl, 4-propyl-2-pentynyl, and 4-butyl-2-hexynyl.

The term "aryl" as used herein refers to a mono-, bi-, or other multi-carbocyclic, aromatic ring system with 5 to 14 ring atoms. The aryl group can optionally be fused to one or more rings selected from aryls, cycloalkyls, heteroaryls, and heterocyclyls. The aryl groups of this present disclosure can be substituted with groups selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone. Exemplary aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. Exemplary aryl groups also include, but are not limited to, a monocyclic aromatic ring system, wherein the ring comprises 6 carbon atoms, referred to herein as "$C_6$-aryl."

The term "cyano" as used herein refers to —CN.

The term "cycloalkyl" as used herein refers to a saturated or unsaturated cyclic, bicyclic, or bridged bicyclic hydrocarbon group of 3-16 carbons, or 3-8 carbons, referred to herein as "($C_3$-$C_8$)cycloalkyl," derived from a cycloalkane. Exemplary cycloalkyl groups include, but are not limited to, cyclohexanes, cyclohexenes, cyclopentanes, and cyclopentenes. Cycloalkyl groups may be substituted with alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Cycloalkyl groups can be fused to other cycloalkyl (saturated or partially unsaturated), aryl, or heterocyclyl groups, to form a bicycle, tetracycle, etc. The term "cycloalkyl" also includes bridged and spiro-fused cyclic structures which may or may not contain heteroatoms.

The terms "halo" or "halogen" as used herein refer to —F, —Cl, —Br, and/or —I.

The term "heteroaryl" as used herein refers to a mono-, bi-, or multi-cyclic, aromatic ring system containing one or more heteroatoms, for example 1-3 heteroatoms, such as nitrogen, oxygen, and sulfur. Heteroaryls can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Heteroaryls can also be fused to non-aromatic rings. Illustrative examples of heteroaryl groups include, but are not limited to, pyridinyl, pyridazinyl, pyrimidyl, pyrazyl, triazinyl, pyrrolyl, pyrazolyl, imidazolyl, (1,2,3)- and (1,2,4)-triazolyl, pyrazinyl, pyrimidilyl, tetrazolyl, furyl, thienyl, isoxazolyl, thiazolyl, furyl, phenyl, isoxazolyl, and oxazolyl. Exemplary heteroaryl groups include, but are not limited to, a monocyclic aromatic ring, wherein the ring comprises 2-5 carbon atoms and 1-3 heteroatoms, referred to herein as "($C_2$-$C_5$)heteroaryl."

The terms "heterocycle," "heterocyclyl," or "heterocyclic" as used herein each refer to a saturated or unsaturated 3- to 18-membered ring containing one, two, three, or four heteroatoms independently selected from nitrogen, oxygen, phosphorus, and sulfur. Heterocycles can be aromatic (heteroaryls) or non-aromatic. Heterocycles can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Heterocycles also include bicyclic, tricyclic, and tetracyclic groups in which any of the above heterocyclic rings is fused to one or two rings independently selected from aryls, cycloalkyls, and heterocycles. Exemplary heterocycles include acridinyl, benzimidazolyl, benzofuryl, benzothiazolyl, benzothienyl, benzoxazolyl, biotinyl, cinnolinyl, dihydrofuryl, dihydroindolyl, dihydropyranyl, dihydrothienyl, dithiazolyl, furyl, homopiperidinyl, imidazolidinyl, imidazolinyl, imidazolyl, indolyl, isoquinolyl, isothiazolidinyl, isothiazolyl, isoxazolidinyl, isoxazolyl, morpholinyl, oxadiazolyl, oxazolidinyl, oxazolyl, piperazinyl, piperidinyl, pyranyl, pyrazolidinyl, pyrazinyl, pyrazolyl, pyrazolinyl, pyridazinyl, pyridyl, pyrimidinyl, pyrimidyl, pyrrolidinyl, pyrrolidin-2-onyl, pyrrolinyl, pyrrolyl, quinolinyl, quinoxaloyl, tetrahydrofuryl, tetrahydroisoquinolyl, tetrahydropyranyl, tetrahydroquinolyl, tetrazolyl, thiadiazolyl, thiazolidinyl, thiazolyl, thienyl, thiomorpholinyl, thiopyranyl, and triazolyl.

The terms "hydroxy" and "hydroxyl" as used herein refer to —OH.

The term "pharmaceutically acceptable carrier" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutically acceptable composition" as used herein refers to a composition comprising at least one compound as disclosed herein formulated together with one or more pharmaceutically acceptable carriers.

The term "pharmaceutically acceptable prodrugs" as used herein represents those prodrugs of the compounds of the present disclosure that are, within the scope of sound medical judgment, suitable for use in contact with the tissues of humans and lower animals without undue toxicity, irritation, allergic response, commensurate with a reasonable benefit/risk ratio, and effective for their intended use, as well as the zwitterionic forms, where possible, of the compounds of the present disclosure. A discussion is provided in Higuchi et al., "Prodrugs as Novel Delivery Systems," *ACS Symposium Series*, Vol. 14, and in Roche, E. B., ed. *Bioreversible Carriers in Drug Design*, American Pharmaceutical Association and Pergamon Press, 1987, both of which are incorporated herein by reference.

The term "pharmaceutically acceptable salt(s)" refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to sulfate, citrate, matate, acetate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Compounds included in the present compositions, that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts.

Chemical names were generated using PerkinElmer ChemDraw® Professional, version 17.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present disclosure encompasses various stereoisomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly. In some embodiments, an enantiomer or stereoisomer may be provided substantially free of the corresponding enantiomer.

In some embodiments, the compound is a racemic mixture of (S)- and (R)-isomers. In other embodiments, provided herein is a mixture of compounds wherein individual compounds of the mixture exist predominately in an (S)- or (R)-isomeric configuration. For example, the compound mixture has an (S)-enantiomeric excess of greater than about 55%, about 60%, about 65%, about 70%, about 75%, about 80%, about 85%, about 90%, about 95%, about 96%, about 97%, about 98%, about 99%, about 99.5%, or more. In other embodiments, the compound mixture has an (S)-enantiomeric excess of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5%, or more. In other embodiments, the compound mixture has an (R)-enantiomeric purity of greater than about 55%, about 60%, about 65%, about 70%, about 75%, about 80%, about 85%, about 90%, about 95%, about 96%, about 97%, about 98%, about 99%, about 99.5% or more. In some other embodiments, the compound mixture has an (R)-enantiomeric excess of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5% or more.

Individual stereoisomers of compounds of the present disclosure can be prepared synthetically from commercially available starting materials that contain asymmetric or stereogenic centers, or by preparation of racemic mixtures followed by resolution methods well known to those of ordinary skill in the art. These methods of resolution are exemplified by: (1) attachment of a mixture of enantiomers to a chiral auxiliary, separation of the resulting mixture of diastereomers by recrystallization or chromatography and liberation of the optically pure product from the auxiliary; (2) salt formation employing an optically active resolving agent; or (3) direct separation of the mixture of optical enantiomers on chiral chromatographic columns. Stereoisomeric mixtures can also be resolved into their component stereoisomers by well-known methods, such as chiral-phase gas chromatography, chiral-phase high performance liquid chromatography, crystallizing the compound as a chiral salt complex, or crystallizing the compound in a chiral solvent. Stereoisomers can also be obtained from stereomerically-pure intermediates, reagents, and catalysts by well-known asymmetric synthetic methods.

Geometric isomers can also exist in the compounds of the present disclosure. The present disclosure encompasses the various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the E and Z isomers.

Substituents around a carbon-carbon double bond alternatively can be referred to as "cis" or "trans," where "cis" represents substituents on the same side of the double bond and "trans" represents substituents on opposite sides of the double bond. The arrangements of substituents around a carbocyclic ring are designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

The compounds disclosed herein may exist as tautomers and both tautomeric forms are intended to be encompassed by the scope of the present disclosure, even though only one tautomeric structure is depicted.

Additionally, unless otherwise stated, structures described herein are also meant to include compounds that differ only in the presence of one or more isotopically enriched atoms. For example, compounds having the present structures except for the replacement of hydrogen by deuterium ($^2$H) or tritium ($^3$H), or the replacement of a carbon by a $^{13}$C- or $^{14}$C-carbon atom are within the scope of this disclosure. Such compounds may be useful as, for example, analytical tools, probes in biological assays, or therapeutic agents.

Compounds

In some embodiments, provided herein are compounds of Formula (I), or a tautomer, stereoisomer or a mixture of stereoisomers, pharmaceutically acceptable salt, or hydrate thereof:

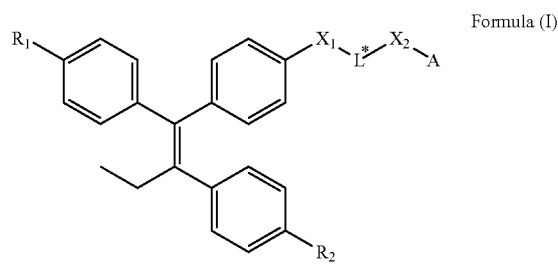

Formula (I)

wherein:

$X^1$ and $X^2$ are each independently selected from $C(R^3)_2$, $NR^4$, O, S, cycloalkyl, aryl, heterocycle, and heteroaryl, each of which is independently substituted with 0, 1, 2, or 3 $R^5$;

A is selected from:

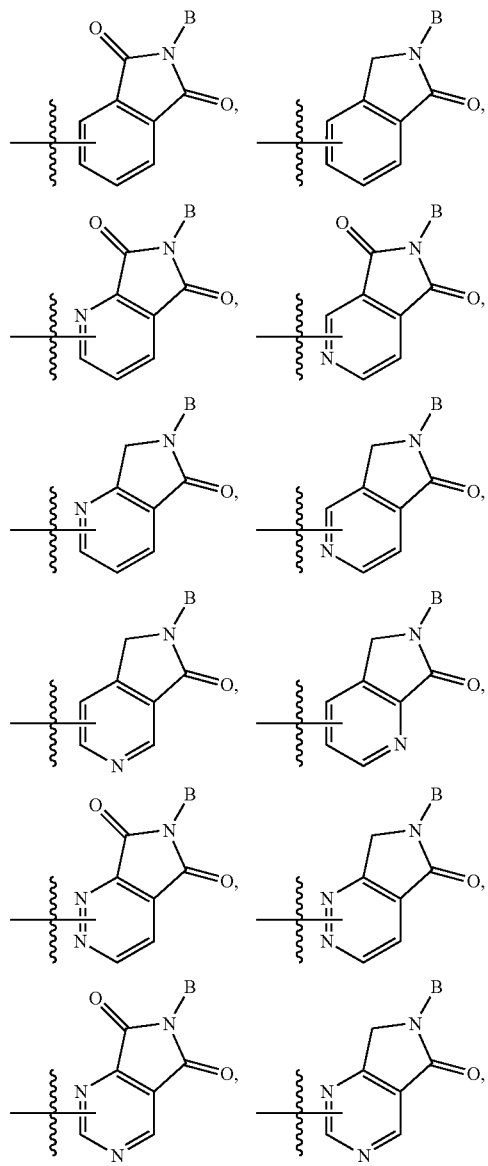

-continued

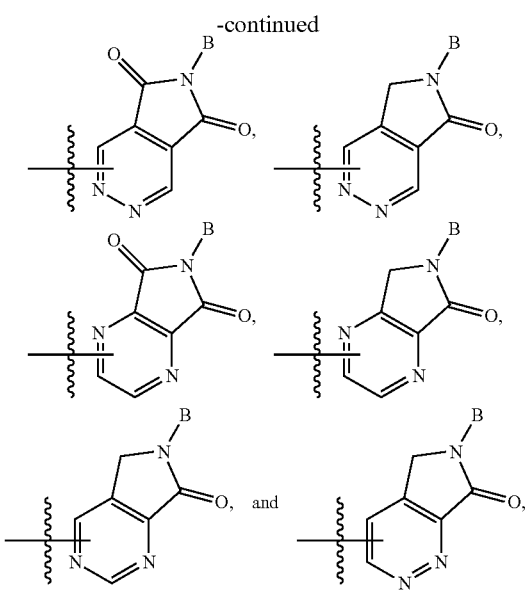

each of which is substituted with 0, 1, 2, or 3 $R^5$;

B is selected from 5- to 6-member cycloalkyl, 5- to 6-member aryl, 5- to 6-member heterocycle, and 5- to 6-member heteroaryl, each of which is substituted with 0, 1, 2, or 3 $R^5$;

L* is a linker of 1 to 22 carbon atoms in length, wherein one or more carbon atoms are each optionally and independently replaced by a group selected from C(O), O, $NR^4$, S, $C_2$-alkenyl, $C_2$-alkynyl, cycloalkyl, aryl, heterocycle, and heteroaryl, each of which is substituted with 0, 1, 2, or 3 $R^5$;

$R^1$ and $R^2$ are each independently selected from H, $C_1$-$C_6$ alkyl, halo, alkoxy, acyloxy, hydroxy, and sulfhydryl, each of which is substituted with 0, 1, 2, or 3 $R^5$;

each $R^3$ is independently selected from H, $C_1$-$C_6$ alkyl, halo, and hydroxy;

each $R^4$ is independently selected from H, $C_1$-$C_6$ alkyl, and acyl, each of which is substituted with 0, 1, 2, or 3 $R^5$; and each $R^5$ is independently selected from $C_1$-$C_6$ alkyl, halo, cyano, and hydroxy, wherein

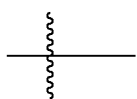 [SMILES: *CC]

represents the point of attachment of A to $X^2$.

In some embodiments, the compound of Formula (I) may encompass both the E and Z isomers. In some embodiments, the compound of Formula (I) may be a mixture of trans- and -cis olefin.

In some embodiments, A may be

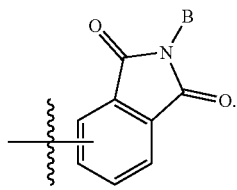

In some embodiments, A may be

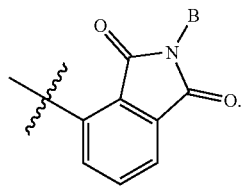

In some embodiments, A may be

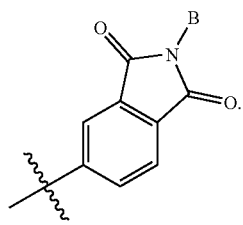

In some embodiments, A may be

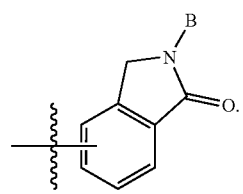

In some embodiments, A may be

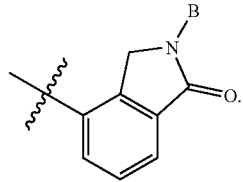

In some embodiments, A may be

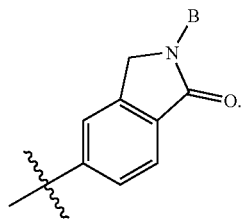

In some embodiments, A may be

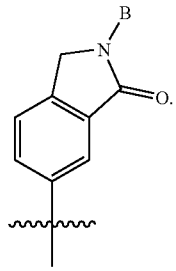

In some embodiments, A may be

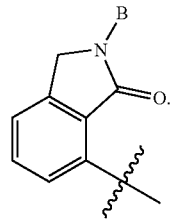

In some embodiments, provided herein are compounds of Formula (II), or a tautomer, stereoisomer, pharmaceutically salt, or hydrate thereof:

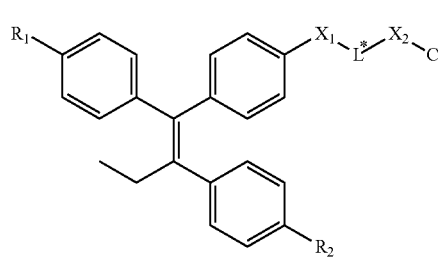

Formula (II)

wherein:

$X^1$ and $X^2$ are each independently selected from $C(R^3)_2$, $NR^4$, O, S, cycloalkyl, aryl, heterocycle, and heteroaryl, each of which is independently substituted with 0, 1, 2, or 3 $R^5$;

B is selected from 5- to 6-member cycloalkyl, 5- to 6-member aryl, 5- to 6-member heterocycle, and 5- to 6-member heteroaryl, each of which is substituted with 0, 1, 2, or 3 $R^5$;

C is selected from:

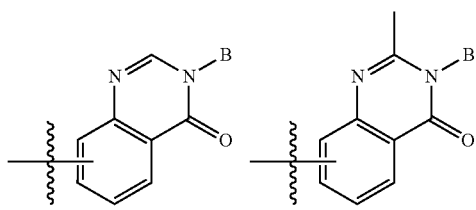

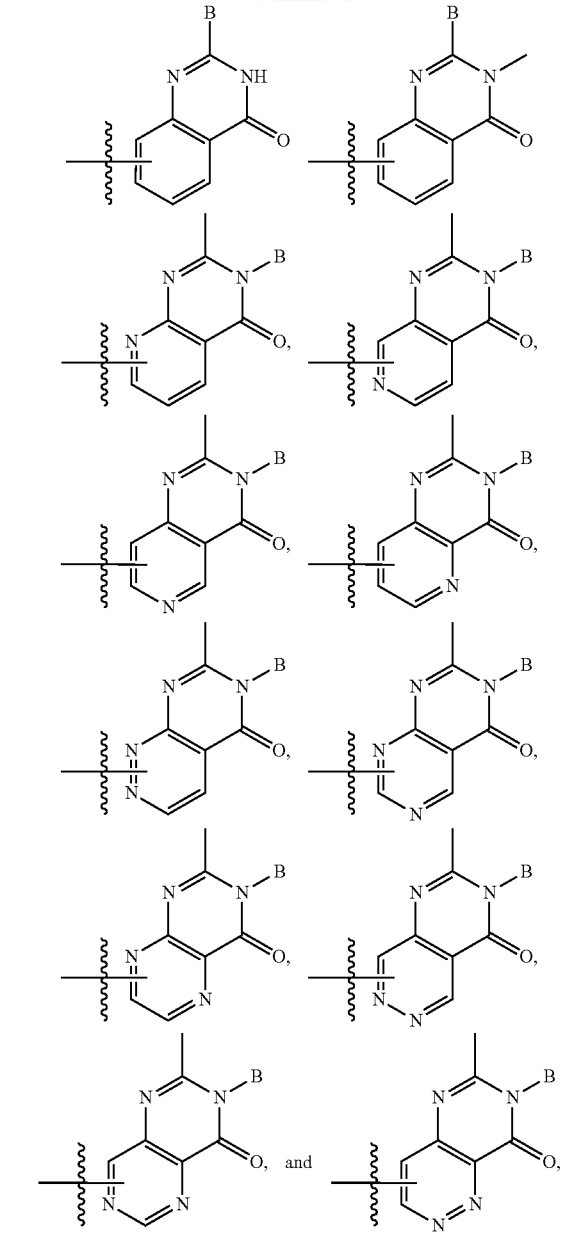

each of which is substituted with 0, 1, 2, or 3 $R^5$;

L* is a linker of 1 to 22 carbon atoms in length, wherein one or more carbon atoms are each optionally and independently replaced by a group selected from C(O), O, $NR^4$, S, $C_2$-alkenyl, $C_2$-alkynyl, cycloalkyl, aryl, heterocycle, and heteroaryl, each of which is substituted with 0, 1, 2, or 3 $R^5$;

$R^1$ and $R^2$ are each independently selected from H, $C_1$-$C_6$ alkyl, halo, alkoxy, acyloxy, hydroxy, and sulfhydryl, each of which is substituted with 0, 1, 2, or 3 $R^5$;

each $R^3$ is independently selected from H, $C_1$-$C_6$ alkyl, halo, and hydroxy;

each $R^4$ is independently selected from H, $C_1$-$C_6$ alkyl, and acyl, each of which is substituted with 0, 1, 2, or 3 $R^5$; and each $R^5$ is independently selected from $C_1$-$C_6$ alkyl, halo, cyano, and hydroxy, wherein

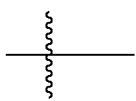

represents the point of attachment of C to $X^2$.

In some embodiments, C may be

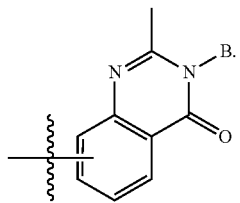

In some embodiments, C may be

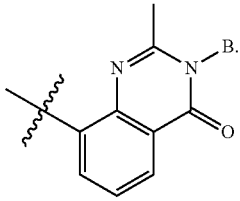

In some embodiments, C may b

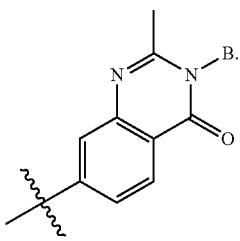

In some embodiments, C may be

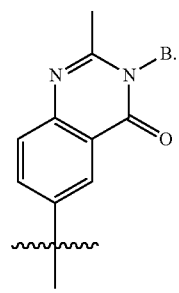

In some embodiments, C may be

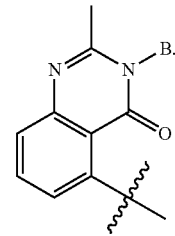

In some embodiments, B may be a 5-member heterocycle substituted with 0, 1, 2, or 3 $R^5$. In some embodiments, B may be a 5-member heterocycle. In some embodiments, B may be a 5-member heterocycle substituted with 1 $R^5$. In some embodiments, $R^5$ may be $C_1$ alkyl.

In some embodiments, B may be a 6-member heterocycle substituted with 0, 1, 2, or 3 $R^5$. In some embodiments, B may be a 6-member heterocycle. In some embodiments, B may be a 6-member heterocycle substituted with 1 $R^5$. In some embodiments, $R^5$ may be $C_1$ alkyl.

In some embodiments, B may be selected from

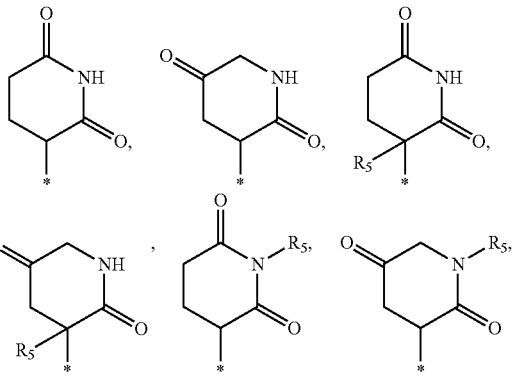

where

represents the point of attachment of B to A.

In some embodiments, B may be

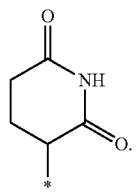 [SMILES: *C1CCC(=O)NC1=O]

In some embodiments, $R^1$ and $R^2$ may each be independently selected from H, $C_1$-$C_3$ alkyl, halo, alkoxy, acyloxy, hydroxy, and sulfhydryl, each of which may be substituted with 0, 1, 2, or 3 $R^5$. In some embodiments, $R^1$ and $R^2$ may each be independently selected from H, $C_1$ alkyl, halo, and hydroxy, each of which may be substituted with 0, 1, 2, or 3 $R^5$. In some embodiments, $R^1$ and $R^2$ may each be independently H or OH.

In some embodiments, $R^1$ may be H. In some embodiments, $R^1$ may be OH. In some embodiments, $R^2$ may be H. In some embodiments, $R^2$ may be OH.

In some embodiments, $R^1$ may be OH and $R^2$ may be H. In some embodiments, $R^1$ may be H and $R^2$ may be H. In some embodiments, $R^1$ may be H and $R^2$ may be OH. In some embodiments, $R^1$ may be OH and $R^2$ may be OH.

In some embodiments, $X^1$ and $X^2$ may each be independently selected from $C(R^3)_2$, $NR^4$, O, S, 5 or 6-member cycloalkyl, 5- or 6-member aryl, 5- or 6-member heterocycle, and 5- or 6-member heteroaryl, each of which is independently substituted with 0, 1, 2, or 3 $R^5$. In some embodiments, wherein $X^1$ and $X^2$ may each be independently selected from $CH_2$, $NR^4$, O, S, 5 or 6-member cycloalkyl, 5- or 6-member aryl, 5- or 6-member heterocycle, and 5- or 6-member heteroaryl, each of which is independently substituted with 0, 1, 2, or 3 $R^5$.

In some embodiments, $X^1$ may be O. In some embodiments, $X^1$ may be $C(R^3)_2$. In some embodiments, $R^3$ may be H or halo. In some embodiments, halo may be fluoro. In some embodiments, $R^3$ may be H. In some embodiments, $X^1$ may be $NR^4$. In some embodiments, $R^4$ may be selected from H, $C_1$-$C_3$ alkyl, and acyl, each of which may be substituted with 0, 1, 2, or 3 $R^5$. In some embodiments, $R^4$ may be H. In some embodiments, $R^4$ may be $C_1$-$C_3$ alkyl substituted with 0, 1, 2, or 3 $R^5$. In some embodiments, $R^4$ may be $C_1$ alkyl substituted with 0, 1, 2, or 3 $R^5$. In some embodiments, $R^4$ may be $C_1$ alkyl. In some embodiments, $R^4$ may be acyl substituted with 0, 1, 2, or 3 $R^5$.

In some embodiments, $X^1$ may be a 5 or 6-member cycloalkyl. In some embodiments, $X^1$ may be a 5- or 6-member aryl. In some embodiments, $X^1$ may be a 5- or 6-member heterocycle. In some embodiments, $X^1$ may be a 5- or 6-member heteroaryl. In some embodiments, $X^1$ may be a 5 or 6-member cycloalkyl substituted with 0, 1, 2, or 3 $R^5$. In some embodiments, $X^1$ may be a 5- or 6-member aryl substituted with 0, 1, 2, or 3 $R^5$. In some embodiments, $X^1$ may be a 5- or 6-member heterocycle substituted with 0, 1, 2, or 3 $R^5$. In some embodiments, $X^1$ may be a 5- or 6-member heteroaryl substituted with 0, 1, 2, or 3 $R^5$.

In some embodiments, $X^1$ may be selected from aziridinyl, azetidinyl, pyrrolidinyl, piperidinyl, piperazinyl, pyrrolyl, pyridinyl, pyrimidinyl, oxiranyl, oxetanyl, tetrahydrofuranyl, furanyl, pyranyl, tetrahydropyranyl, dioxanyl, imidazolyl, pyrazolyl, oxazole, isoxazole, thiazole, isothiazole, triazole, tetrazole, indole, benzimidazole, benzofuran, benzoxazole, benzothiazole, quinoline, isoquinoline, and quinazoline, each of which is independently substituted with 0, 1, 2, or 3 $R^5$. In some embodiments, $X^1$ may be selected from

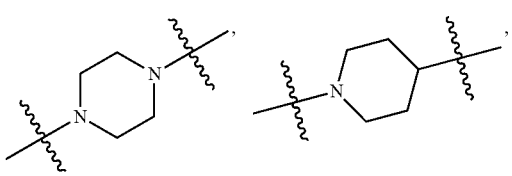

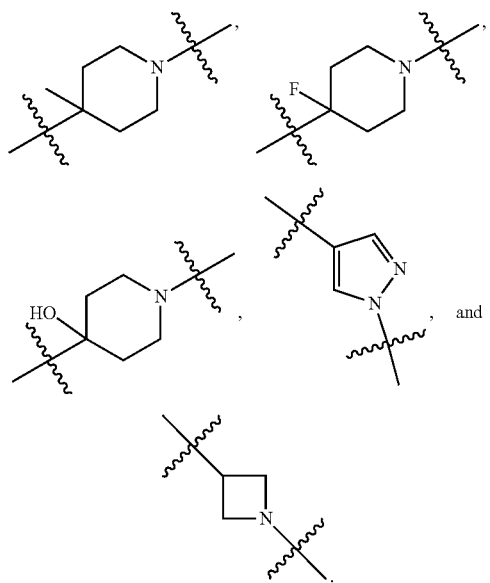

In some embodiments, X2 may be selected from

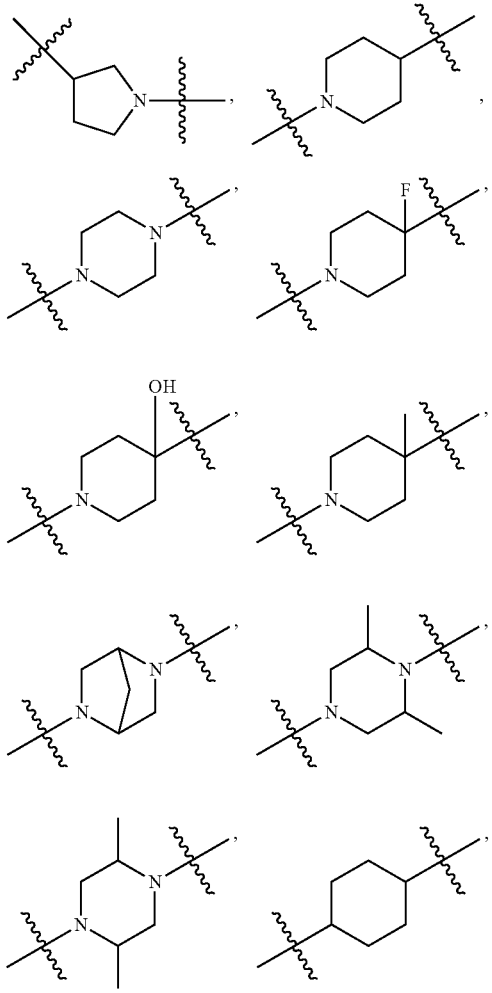

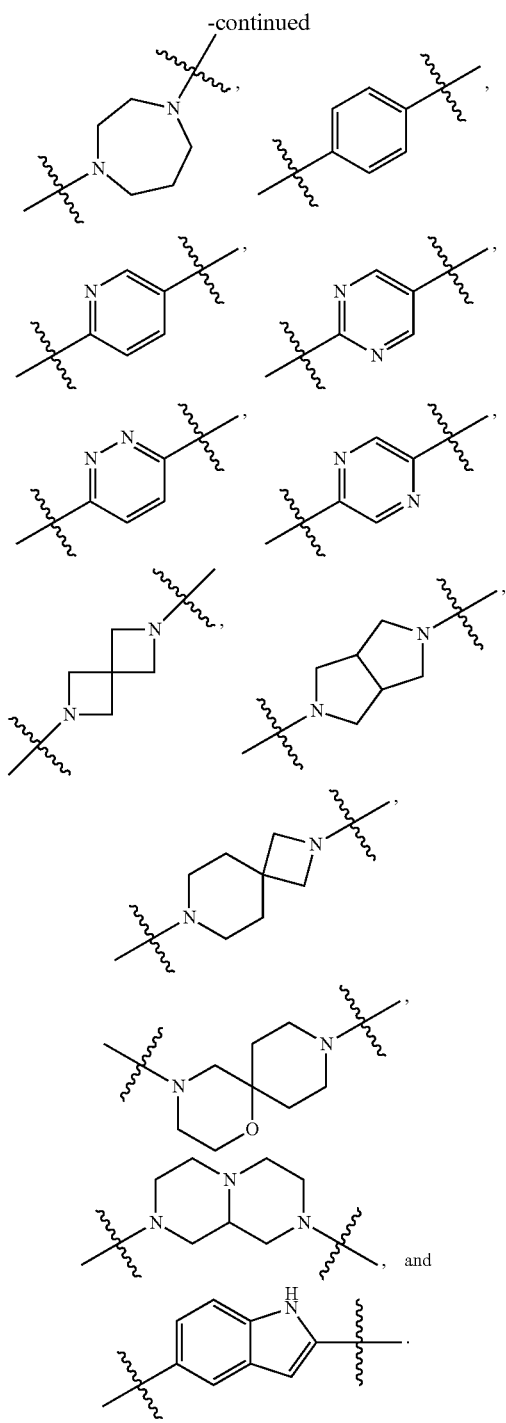

, and

In some embodiments, L* may be linker of 1 to 16 carbon atoms in length, wherein one or more carbon atoms are each optionally and independently replaced by a group selected from C(O), O, $NR^4$, S, $C_2$-alkenyl, $C_2$-alkynyl, cycloalkyl, aryl, heterocycle, and heteroaryl, each of which is independently substituted with 0, 1, 2, or 3 $R^5$. In some embodiments, L* may be a linker of 1 to 14 carbon atoms in length, wherein one or more carbon atoms are each optionally and independently replaced by a group selected from C(O), O, $NR^4$, S, $C_2$-alkenyl, $C_2$-alkynyl, cycloalkyl, aryl, heterocycle, and heteroaryl, each of which is independently substituted with 0, 1, 2, or 3 $R^5$. In some embodiments, L* may be a linker of 1 to 12 carbon atoms in length, wherein one or more carbon atoms are each optionally and independently replaced by a group selected from C(O), O, $NR^4$, S, $C_2$-alkenyl, $C_2$-alkynyl, cycloalkyl, aryl, heterocycle, and heteroaryl, each of which is independently substituted with 0, 1, 2, or 3 $R^5$. In some embodiments, L* may be a linker of 1 to 10 carbon atoms in length, wherein one or more carbon atoms are each optionally and independently replaced by a group selected from C(O), O, $NR^4$, S, $C_2$-alkenyl, $C_2$-alkynyl, cycloalkyl, aryl, heterocycle, and heteroaryl, each of which is independently substituted with 0, 1, 2, or 3 $R^5$.

In some embodiments, L* may be a linker of 1 to 8 carbon atoms in length, wherein one or more carbon atoms are each optionally and independently replaced by a group selected from C(O), O, $NR^4$, S, $C_2$-alkenyl, $C_2$-alkynyl, cycloalkyl, aryl, heterocycle, and heteroaryl, each of which is independently substituted with 0, 1, 2, or 3 $R^5$. In some embodiments, L* may be a linker of 1 to 6 carbon atoms in length, wherein one or more carbon atoms are each optionally and independently replaced by a group selected from C(O), O, $NR^4$, S, $C_2$-alkenyl, $C_2$-alkynyl, cycloalkyl, aryl, heterocycle, and heteroaryl, each of which is independently substituted with 0, 1, 2, or 3 $R^5$.

In some embodiments, L* may be a linker wherein two carbon atoms are each independently replaced by a heterocycle, each of which is independently substituted with 0, 1, 2, or 3 $R^5$. In some embodiments, L* may be a linker wherein one carbon atom is replaced by a heterocycle and one carbon atom is replaced by a cycloalkyl, each of which is independently substituted with 0, 1, 2, or 3 $R^5$. In some embodiments, L* may be a linker wherein more than one carbon atoms are each independently replaced by a group selected from C(O), O, $NR^4$, S, $C_2$-alkenyl, $C_2$-alkynyl, cycloalkyl, aryl, heterocycle, and heteroaryl, each of which is substituted with 0, 1, 2, or 3 $R^5$. In some embodiments, L* may be a linker wherein more than one carbon atoms are each independently replaced by a group selected from C(O), O, and $NR^4$, each of which is substituted with 0, 1, 2, or 3 $R^5$.

In some embodiments, L* may be

.

In some embodiments, L* may be

In some embodiments, L* may be

.

In some embodiments, L* may be
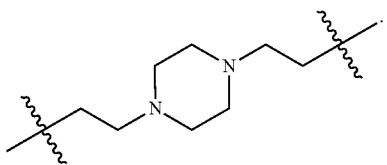 [SMILES: *CCN1CCN(CC*)CC1]
In some embodiments, L* may be
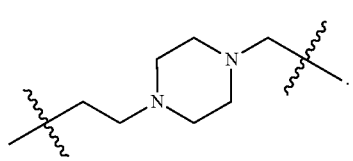 [SMILES: *CCN1CCN(C*)CC1]
In some embodiments, L* may be
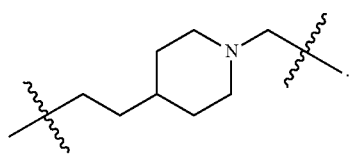 [SMILES: *CCC1CCN(C*)CC1]
In some embodiments, L* may be
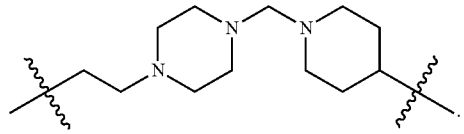 [SMILES: *CCN1CCN(CN2CCC(*)CC2)CC1]
In some embodiments, L* may be
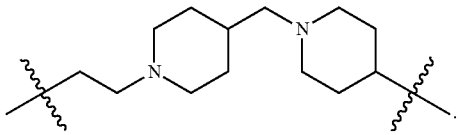 [SMILES: *CCN1CCC(CN2CCC(*)CC2)CC1]
In some embodiments, L* may be
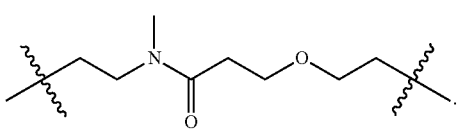 [SMILES: *CCOCCC(=O)N(C)CC*]
In some embodiments, L* may be
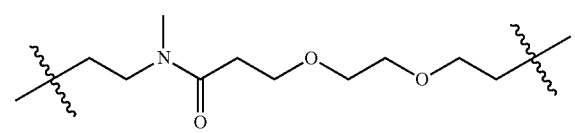
In some embodiments, L* may be
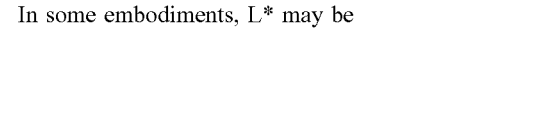
In some embodiments, L* may be
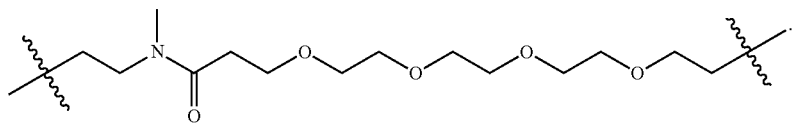 [SMILES: *CCOCCOCCOCCOCCC(=O)N(C)CC*]
In some embodiments, L* may be
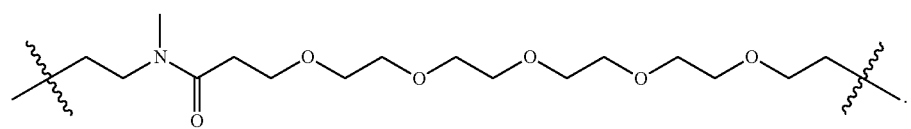 [SMILES: *CCOCCOCCOCCOCCOCCC(=O)N(C)CC*]

In some embodiments, L* may be

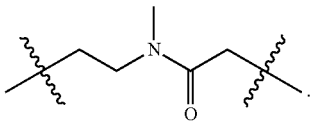 [SMILES: *CCN(C)C(=O)C*]

In some embodiments, L* may be

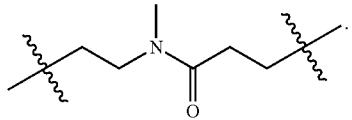 [SMILES: *CCC(=O)N(C)CC*]

In some embodiments, L* may be

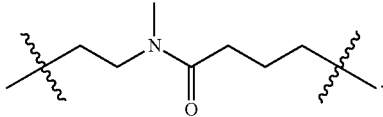 [SMILES: *CCCC(=O)N(C)CC*]

In some embodiments, L* may be

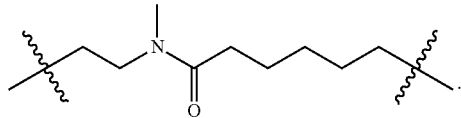 [SMILES: *CCCCCC(=O)N(C)CC*]

In some embodiments, L* may be

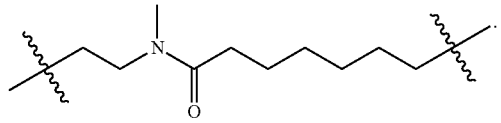 [SMILES: *CCCCCCC(=O)N(C)CC*]

In some embodiments, L* may be

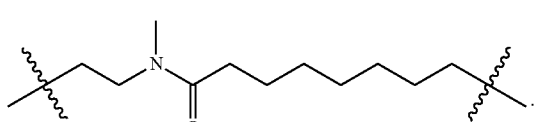

In some embodiments, L* may be

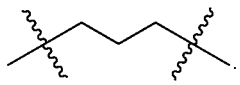

In some embodiments, L* may be

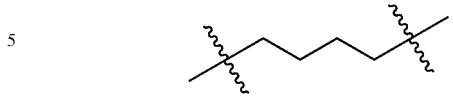

In some embodiments, L* may be

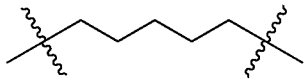

In some embodiments, L* may be

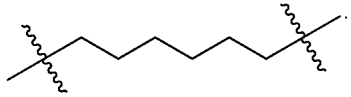 [SMILES: *CCCCCC*]

In some embodiments, provided herein is a compound, or tautomer, stereoisomer, pharmaceutically acceptable salt, or hydrate thereof, chosen from:

(Z)-3-(4-(3-(4-(2-(4-(1-(4-hydroxyphenyl)-2-phenylbut-1-en-1-yl)phenoxy)ethyl)piperazin-1-yl)propoxy)-1-oxoisoindolin-2-yl)piperidine-2,6-dione;

(Z)-3-(4-(2-(4-(2-(4-(1-(4-hydroxyphenyl)-2-phenylbut-1-en-1-yl)phenoxy)ethyl)piperazin-1-yl)ethoxy)-1-oxoisoindolin-2-yl)piperidine-2,6-dione;

(Z)-3-(5-(2-(4-(2-(4-(1-(4-hydroxyphenyl)-2-phenylbut-1-en-1-yl)phenoxy)ethyl)piperazin-1-yl)ethoxy)-1-oxoisoindolin-2-yl)piperidine-2,6-dione;

(Z)-3-(5-(2-(5-(2-(4-(1-(4-hydroxyphenyl)-2-phenylbut-1-en-1-yl)phenoxy)ethyl)-2,5-diazabicyclo[2.2.1]heptan-2-yl)ethoxy)-1-oxoisoindolin-2-yl)piperidine-2,6-dione;

(Z)-3-(5-((2-(4-(2-(4-(1-(4-hydroxyphenyl)-2-phenylbut-1-en-1-yl)phenoxy)ethyl)piperazin-1-yl)ethyl)amino)-1-oxoisoindolin-2-yl)piperidine-2,6-dione;

(Z)-3-(5-((3-(4-(2-(4-(1-(4-hydroxyphenyl)-2-phenylbut-1-en-1-yl)phenoxy)ethyl)piperazin-1-yl)propyl)amino)-1-oxoisoindolin-2-yl)piperidine-2,6-dione;

(Z)-3-(5-((3-(2-(2-(4-(1-(4-hydroxyphenyl)-2-phenylbut-1-en-1-yl)phenoxy)ethoxy)ethoxy)propyl)amino)-1-oxoisoindolin-2-yl)piperidine-2,6-dione;

(Z)-3-(2-((2-(2-(2,6-dioxopiperidin-3-yl)-1,3-dioxoisoindolin-4-yl)amino)ethoxy)-N-(2-(4-(1,2-diphenylbut-1-en-1-yl)phenoxy)ethyl)-N-methylpropanamide;

(Z)-3-(4-(2-(6-(2-(4-(1-(4-hydroxyphenyl)-2-phenylbut-1-en-1-yl)phenoxy)ethyl)-2,6-diazaspiro[3.3]heptan-2-yl)ethoxy)-1-oxoisoindolin-2-yl)piperidine-2,6-dione;

(Z)-3-(5-(5-(4-(2-(4-(1-(4-hydroxyphenyl)-2-phenylbut-1-en-1-yl)phenoxy)ethyl)piperazin-1-yl)-5-oxopentyl)-1-oxoisoindolin-2-yl)piperidine-2,6-dione;

(Z)-2-(2,6-dioxopiperidin-3-yl)-5-(4-(2-(4-(1-(4-hydroxyphenyl)-2-phenylbut-1-en-1-yl)phenoxy)ethyl)piperazin-1-yl)isoindoline-1,3-dione;

(Z)-3-(5-((4-(4-(2-(4-(1-(4-hydroxyphenyl)-2-phenylbut-1-en-1-yl)phenoxy)ethyl)piperazin-1-yl)butyl)amino)-1-oxoisoindolin-2-yl)piperidine-2,6-dione;

(Z)-3-(5-(3-(4-(2-(4-(1-(4-hydroxyphenyl)-2-phenylbut-1-en-1-yl)phenoxy)ethyl)piperazin-1-yl)-3-oxopropyl)-1-oxoisoindolin-2-yl)piperidine-2,6-dione;

(Z)-3-(5-((3-(3-(4-(1-(4-hydroxyphenyl)-2-phenylbut-1-en-1-yl)phenoxy)propoxy)propyl)amino)-1-oxoisoindolin-2-yl)piperidine-2,6-dione;

(Z)-3-(2-(2-((2-(2,6-dioxopiperidin-3-yl)-1,3-dioxoisoindolin-4-yl)amino)ethoxy)ethoxy)-N-(2-(4-(1,2-diphenylbut-1-en-1-yl)phenoxy)ethyl)-N-methylpropanamide;

(E)/(Z)-2-(2,6-dioxopiperidin-3-yl)-5-(4-(4-(4-(1-(4-hydroxyphenyl)-2-phenylbut-1-en-1-yl)phenoxy)butyl)piperazin-1-yl)isoindoline-1,3-dione;

(Z)-2-(2,6-dioxopiperidin-3-yl)-5-(4-(4-(4-(1-(4-hydroxyphenyl)-2-phenylbut-1-en-1-yl)phenoxy)butyl)piperazin-1-yl)isoindoline-1,3-dione;

(E)/(Z)—(S)-3-(5-(4-(4-(4-(4-(4-hydroxyphenyl)-2-phenylbut-1-en-1-yl)phenoxy)butyl)piperazin-1-yl)-1-oxoisoindolin-2-yl)piperidine-2,6-dione;

(Z)-3-(5-(4-(4-(1-(4-hydroxyphenyl)-2-phenylbut-1-en-1-yl)phenoxy)butyl)piperazin-1-yl)-1-oxoisoindolin-2-yl)piperidine-2,6-dione;

(Z)-3-(5-(4-(2-(4-(1-(4-hydroxyphenyl)-2-phenylbut-1-en-1-yl)phenoxy)ethyl)piperazin-1-yl)-1-oxoisoindolin-2-yl)piperidine-2,6-dione;

(Z)-2-(2,6-dioxopiperidin-3-yl)-5-((2-(1-(2-(4-(1-(4-hydroxyphenyl)-2-phenylbut-1-en-1-yl)phenoxy)ethyl)piperidin-4-yl)ethyl)amino)isoindoline-1,3-dione;

(Z)-3-(5-((2-(1-(2-(4-(1-(4-hydroxyphenyl)-2-phenylbut-1-en-1-yl)phenoxy)ethyl)piperidin-4-yl)ethyl)amino)-1-oxoisoindolin-2-yl)piperidine-2,6-dione;

(Z)-2-(2,6-dioxopiperidin-3-yl)-5-((3-(1-(2-(4-(1-(4-hydroxyphenyl)-2-phenylbut-1-en-1-yl)phenoxy)ethyl)piperidin-4-yl)propyl)amino)isoindoline-1,3-dione;

(Z)-3-(5-((3-(1-(2-(4-(1-(4-hydroxyphenyl)-2-phenylbut-1-en-1-yl)phenoxy)ethyl)piperidin-4-yl)propyl)amino)-1-oxoisoindolin-2-yl)piperidine-2,6-dione;

(Z)-2-(2,6-dioxopiperidin-3-yl)-5-(((1-(2-(4-(1-(4-hydroxyphenyl)-2-phenylbut-1-en-1-yl)phenoxy)ethyl)piperidin-4-yl)methyl)amino)isoindoline-1,3-dione;

(Z)-3-(5-((1-(2-(4-(1-(4-hydroxyphenyl)-2-phenylbut-1-en-1-yl)phenoxy)ethyl)piperidin-4-yl)amino)-1-oxoisoindolin-2-yl)piperidine-2,6-dione;

(Z)-2-(2,6-dioxopiperidin-3-yl)-5-((1-(2-(4-(1-(4-hydroxyphenyl)-2-phenylbut-1-en-1-yl)phenoxy)ethyl)piperidin-4-yl)amino)isoindoline-1,3-dione;

(Z)-3-(5-(3-((1-(2-(4-(1-(4-hydroxyphenyl)-2-phenylbut-1-en-1-yl)phenoxy)ethyl)piperidin-4-yl)oxy)propyl)-1-oxoisoindolin-2-yl)piperidine-2,6-dione;

(Z)-2-(2,6-dioxopiperidin-3-yl)-5-(3-((1-(2-(4-(1-(4-hydroxyphenyl)-2-phenylbut-1-en-1-yl)phenoxy)ethyl)piperidin-4-yl)oxy)propyl)isoindoline-1,3-dione;

(E)/(Z)-2-(2,6-dioxopiperidin-3-yl)-5-(4-(5-(4-(1-(4-hydroxyphenyl)-2-phenylbut-1-en-1-yl)phenoxy)pentyl)piperazin-1-yl)isoindoline-1,3-dione;

(Z)-2-(2,6-dioxopiperidin-3-yl)-5-(4-(5-(4-(1-(4-hydroxyphenyl)-2-phenylbut-1-en-1-yl)phenoxy)pentyl)piperazin-1-yl)isoindoline-1,3-dione;

(E)/(Z)-2-(2,6-dioxopiperidin-3-yl)-5-(4-(6-(4-(1-(4-hydroxyphenyl)-2-phenylbut-1-en-1-yl)phenoxy)hexyl)piperazin-1-yl)isoindoline-1,3-dione;

(Z)-2-(2,6-dioxopiperidin-3-yl)-5-(4-(6-(4-(1-(4-hydroxyphenyl)-2-phenylbut-1-en-1-yl)phenoxy)hexyl)piperazin-1-yl)isoindoline-1,3-dione;

(Z)-3-(5-(3-(3-(4-(1-(4-hydroxyphenyl)-2-phenylbut-1-en-1-yl)phenoxy)propoxy)propoxy)-1-oxoisoindolin-2-yl)piperidine-2,6-dione;

(E)/(Z)—(S)-3-(5-(4-(5-(4-(1-(4-hydroxyphenyl)-2-phenylbut-1-en-1-yl)phenoxy)pentyl)piperazin-1-yl)-1-oxoisoindolin-2-yl)piperidine-2,6-dione;

(Z)-3-(5-(4-(5-(4-(1-(4-hydroxyphenyl)-2-phenylbut-1-en-1-yl)phenoxy)pentyl)piperazin-1-yl)-1-oxoisoindolin-2-yl)piperidine-2,6-dione;

(E)/(Z)—(S)-3-(5-(4-(6-(4-(1-(4-hydroxyphenyl)-2-phenylbut-1-en-1-yl)phenoxy)hexyl)piperazin-1-yl)-1-oxoisoindolin-2-yl)piperidine-2,6-dione;

(Z)-3-(5-(4-(6-(4-(1-(4-hydroxyphenyl)-2-phenylbut-1-en-1-yl)phenoxy)hexyl)piperazin-1-yl)-1-oxoisoindolin-2-yl)piperidine-2,6-dione;

(Z)-3-(5-(4-(3-(4-(1-(4-hydroxyphenyl)-2-phenylbut-1-en-1-yl)phenoxy)propoxy)butoxy)-1-oxoisoindolin-2-yl)piperidine-2,6-dione;

(Z)-3-(2-(2-(2-((2-(2,6-dioxopiperidin-3-yl)-1,3-dioxoisoindolin-4-yl)amino)ethoxy)ethoxy)ethoxy)-N-(2-(4-(1,2-diphenylbut-1-en-1-yl)phenoxy)ethyl)-N-methylpropanamide;

(Z)-3-(5-((6-(4-(1-(4-hydroxyphenyl)-2-phenylbut-1-en-1-yl)phenoxy)hexa-2,4-diyn-1-yl)oxy)-1-oxoisoindolin-2-yl)piperidine-2,6-dione;

(Z)-3-(5-(4-(3-(4-(1-(4-hydroxyphenyl)-2-phenylbut-1-en-1-yl)phenoxy)propyl)piperazin-1-yl)-1-oxoisoindolin-2-yl)piperidine-2,6-dione;

(Z)-2-(2,6-dioxopiperidin-3-yl)-5-(4-(3-(4-(1-(4-hydroxyphenyl)-2-phenylbut-1-en-1-yl)phenoxy)propyl)piperazin-1-yl)isoindoline-1,3-dione;

(Z)-3-(5-(2-(4-(2-(4-(1-(4-hydroxyphenyl)-2-phenylbut-1-en-1-yl)phenoxy)ethyl)-1,4-diazepan-1-yl)ethoxy)-1-oxoisoindolin-2-yl)piperidine-2,6-dione;

(E)-2-(2,6-dioxopiperidin-3-yl)-5-((5-(4-(4-(1-(4-hydroxyphenyl)-2-phenylbut-1-en-1-yl)phenyl)piperazin-1-yl)pentyl)oxy)isoindoline-1,3-dione;

(E)-3-(5-((5-(4-(4-(1-(4-hydroxyphenyl)-2-phenylbut-1-en-1-yl)phenyl)piperazin-1-yl)pentyl)oxy)-1-oxoisoindolin-2-yl)piperidine-2,6-dione;

(E)-2-(2,6-dioxopiperidin-3-yl)-5-(4-(4-(4-(1-(4-hydroxyphenyl)-2-phenylbut-1-en-1-yl)phenyl)piperazin-1-yl)butoxy)isoindoline-1,3-dione;

(E)-3-(5-(4-(4-(4-(1-(4-hydroxyphenyl)-2-phenylbut-1-en-1-yl)phenyl)piperazin-1-yl)butoxy)-1-oxoisoindolin-2-yl)piperidine-2,6-dione;

(E)-2-(2,6-dioxopiperidin-3-yl)-5-((5-(4-(4-(1-(4-hydroxyphenyl)-2-phenylbut-1-en-1-yl)phenyl)piperazin-1-yl)pentyl)amino)isoindoline-1,3-dione;

(E)-2-(2,6-dioxopiperidin-3-yl)-5-((4-(4-(4-(1-(4-hydroxyphenyl)-2-phenylbut-1-en-1-yl)phenyl)piperazin-1-yl)butyl)amino)isoindoline-1,3-dione;

(Z)—N-((2-(2,6-dioxopiperidin-3-yl)-1-oxoisoindolin-5-yl)methyl)-2-(4-(2-(4-(1-(4-hydroxyphenyl)-2-phenylbut-1-en-1-yl)phenoxy)ethyl)piperazin-1-yl)acetamide;

(Z)-3-(5-(3-(3-(3-(4-(1-(4-hydroxyphenyl)-2-phenylbut-1-en-1-yl)phenoxy)propoxy)propoxy)propoxy)-1-oxoisoindolin-2-yl)piperidine-2,6-dione;

(Z)-3-(5-(2-(2-(2-(4-(1-(4-hydroxyphenyl)-2-phenylbut-1-en-1-yl)phenoxy)ethoxy)ethoxy)ethoxy)-1-oxoisoindolin-2-yl)piperidine-2,6-dione;

(Z)-3-(5-(3-(2-(2-(4-(1-(4-hydroxyphenyl)-2-phenylbut-1-en-1-yl)phenoxy)ethoxy)ethoxy)propoxy)-1-oxoisoindolin-2-yl)piperidine-2,6-dione;

(Z)-3-(5-(2-(1-(2-(4-(1-(4-hydroxyphenyl)-2-phenylbut-1-en-1-yl)phenoxy)ethyl)piperidin-3-yl)ethoxy)-1-oxoisoindolin-2-yl)piperidine-2,6-dione;

(Z)-3-(5-(4-((4-(1-(4-hydroxyphenyl)-2-phenylbut-1-en-1-yl)phenoxy)butyl)amino)phenyl)-1-oxoisoindolin-2-yl)piperidine-2,6-dione;

(Z)-3-(5-(2-(2-(4-(1-(4-hydroxyphenyl)-2-phenylbut-1-en-1-yl)phenoxy)ethoxy)ethoxy)-1-oxoisoindolin-2-yl)piperidine-2,6-dione;

(Z)-2-(2,6-dioxopiperidin-3-yl)-5-(2-(2-(4-(1-(4-hydroxyphenyl)-2-phenylbut-1-en-1-yl)phenoxy)ethoxy)ethoxy)isoindoline-1,3-dione;

(Z)-3-(5-(4-(5-(4-(1-(4-hydroxyphenyl)-2-phenylbut-1-en-1-yl)phenoxy)pentyl)-2,5-dimethylpiperazin-1-yl)-1-oxoisoindolin-2-yl)piperidine-2,5-dione;

(Z)-1-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methyl-3,6,9,12-tetraoxapentadecan-15-amide;

(Z)-3-(5-(4-(5-(4-(1-(4-hydroxyphenyl)-2-phenylbut-1-en-1-yl)phenoxy)pentyl)piperazin-1-yl)-1-oxoisoindolin-2-yl)piperidine-2,5-dione;

(Z)-2-(2,5-dioxopiperidin-3-yl)-5-(4-(5-(4-(1-(4-hydroxyphenyl)-2-phenylbut-1-en-1-yl)phenoxy)pentyl)piperazin-1-yl)isoindoline-1,3-dione;

(Z)-2-(2,6-dioxopiperidin-3-yl)-5-(4-((4-(4-(1-(4-hydroxyphenyl)-2-phenylbut-1-en-1-yl)phenoxy)cyclohexyl)methyl)piperazin-1-yl)isoindoline-1,3-dione;

(Z)-3-(5-(4-((4-(4-(1-(4-hydroxyphenyl)-2-phenylbut-1-en-1-yl)phenoxy)cyclohexyl)methyl)piperazin-1-yl)-1-oxoisoindolin-2-yl)piperidine-2,6-dione;

(Z)-2-(2,6-dioxopiperidin-3-yl)-5-(4-(2-((4-(4-(1-(4-hydroxyphenyl)-2-phenylbut-1-en-1-yl)phenoxy)cyclohexyl)oxy)ethyl)piperazin-1-yl)isoindoline-1,3-dione;

(Z)-3-(5-(4-(2-((4-(4-(1-(4-hydroxyphenyl)-2-phenylbut-1-en-1-yl)phenoxy)cyclohexyl)oxy)ethyl)piperazin-1-yl)-1-oxoisoindolin-2-yl)piperidine-2,6-dione;

(Z)-3-(5-(2-((2-(2-(4-(1-(4-hydroxyphenyl)-2-phenylbut-1-en-1-yl)phenoxy)ethyl)-2-azaspiro[3.3]heptan-6-yl)oxy)ethoxy)-1-oxoisoindolin-2-yl)piperidine-2,6-dione;

(E)-3-(6-((4-(4-(4-(1-(4-hydroxyphenyl)-2-phenylbut-1-en-1-yl)phenyl)piperazin-1-yl)butyl)amino)-1-oxoisoindolin-2-yl)piperidine-2,6-dione;

(Z)-3-(5-((2-(2-(4-(1-(4-hydroxyphenyl)-2-phenylbut-1-en-1-yl)phenoxy)ethoxy)ethyl)amino)-1-oxoisoindolin-2-yl)piperidine-2,6-dione;

(Z)-1-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methyl-3,6,9,12,15-pentaoxaoctadecan-18-amide;

(Z)-2-(2,6-dioxopiperidin-3-yl)-5-((2-(2-(4-(1-(4-hydroxyphenyl)-2-phenylbut-1-en-1-yl)phenoxy)ethoxy)ethyl)amino)isoindoline-1,3-dione;

(Z)—N-((2-(2,6-dioxopiperidin-3-yl)-1-oxoisoindolin-5-yl)methyl)-2-(4-(1-(4-(1-(4-hydroxyphenyl)-2-phenylbut-1-en-1-yl)phenoxy)propan-2-yl)piperazin-1-yl)acetamide;

(Z)-3-(5-(3-(4-(3-(4-(1-(4-hydroxyphenyl)-2-phenylbut-1-en-1-yl)phenoxy)propyl)-1,4-diazepan-1-yl)propyl)-1-oxoisoindolin-2-yl)piperidine-2,6-dione;

(E)-3-(5-((5-(4-(4-(1-(4-hydroxyphenyl)-2-phenylbut-1-en-1-yl)phenyl)piperazin-1-yl)pentyl)amino)-1-oxoisoindolin-2-yl)piperidine-2,6-dione;

(Z)-3-(5-(3-(2-(4-(1-(4-hydroxyphenyl)-2-phenylbut-1-en-1-yl)phenoxy)ethoxy)propoxy)-1-oxoisoindolin-2-yl)piperidine-2,6-dione;

(Z)-2-(2,6-dioxopiperidin-3-yl)-5-(3-(2-(4-(1-(4-hydroxyphenyl)-2-phenylbut-1-en-1-yl)phenoxy)ethoxy)propoxy)isoindoline-1,3-dione;

(Z)-3-(5-(3-(3-(2-(4-(1-(4-hydroxyphenyl)-2-phenylbut-1-en-1-yl)phenoxy)ethoxy)propoxy)propoxy)-1-oxoisoindolin-2-yl)piperidine-2,6-dione;

(Z)-3-(5-(2-(4-(4-(4-(1-(4-hydroxyphenyl)-2-phenylbut-1-en-1-yl)phenoxy)butyl)-1,4-diazepan-1-yl)ethyl)-1-oxoisoindolin-2-yl)piperidine-2,6-dione;

(Z)-3-(5-(4-amino-3-((5-(4-(1-(4-hydroxyphenyl)-2-phenylbut-1-en-1-yl)phenoxy)pentyl)oxy)phenyl)-1-oxoisoindolin-2-yl)piperidine-2,6-dione;

(Z)-3-(5-(4-amino-3-(4-(4-(1-(4-hydroxyphenyl)-2-phenylbut-1-en-1-yl)phenoxy)butoxy)phenyl)-1-oxoisoindolin-2-yl)piperidine-2,6-dione;

(Z)-3-(5-((3-(2-(4-(1-(4-hydroxyphenyl)-2-phenylbut-1-en-1-yl)phenoxy)ethoxy)propyl)amino)-1-oxoisoindolin-2-yl)piperidine-2,6-dione;

(Z)-2-(2,6-dioxopiperidin-3-yl)-5-((3-(2-(4-(1-(4-hydroxyphenyl)-2-phenylbut-1-en-1-yl)phenoxy)ethoxy)propyl)amino)isoindoline-1,3-dione;

(Z)-3-(5-(3-(3-(4-(4-(1-(4-hydroxyphenyl)-2-phenylbut-1-en-1-yl)phenoxy)butoxy)propoxy)propoxy)-1-oxoisoindolin-2-yl)piperidine-2,6-dione;

(Z)-3-(5-(3-(1-(2-(4-(1-(4-hydroxyphenyl)-2-phenylbut-1-en-1-yl)phenoxy)ethyl)piperidin-3-yl)propyl)-1-oxoisoindolin-2-yl)piperidine-2,6-dione;

(Z)-3-(5-(2-(4-(2-(4-(1-(4-hydroxyphenyl)-2-phenylbut-1-en-1-yl)phenoxy)ethyl)-1,4-diazepan-1-yl)ethyl)-1-oxoisoindolin-2-yl)piperidine-2,6-dione;

(Z)-3-(5-(2-(3-(4-(1-(4-hydroxyphenyl)-2-phenylbut-1-en-1-yl)phenoxy)propyl)-1H-indol-5-yl)-1-oxoisoindolin-2-yl)piperidine-2,6-dione;

(Z)-3-(5-(2-(4-(4-(1-(4-hydroxyphenyl)-2-phenylbut-1-en-1-yl)phenoxy)butyl)-1H-indol-5-yl)-1-oxoisoindolin-2-yl)piperidine-2,6-dione;

(Z)-3-(5-(2-(5-(4-(1-(4-hydroxyphenyl)-2-phenylbut-1-en-1-yl)phenoxy)pentyl)-1H-indol-5-yl)-1-oxoisoindolin-2-yl)piperidine-2,6-dione;

(Z)-3-(5-(2-((1-(3-(4-(1-(4-hydroxyphenyl)-2-phenylbut-1-en-1-yl)phenoxy)propyl)piperidin-3-yl)oxy)ethyl)-1-oxoisoindolin-2-yl)piperidine-2,6-dione;

(Z)-3-(5-(2-((1-(2-(4-(1-(4-hydroxyphenyl)-2-phenylbut-1-en-1-yl)phenoxy)ethyl)piperidin-3-yl)oxy)ethyl)-1-oxoisoindolin-2-yl)piperidine-2,6-dione;

(E)-3-(5-(4-((2-((4-(1-(4-hydroxyphenyl)-2-phenylbut-1-en-1-yl)benzyl)oxy)ethyl)(methyl)amino)cyclohexyl)-1-oxoisoindolin-2-yl)piperidine-2,6-dione;

(Z)-3-(5-(4-(5-(4-(1-(4-hydroxyphenyl)-2-phenylbut-1-en-1-yl)phenoxy)pentyl)-1,4-diazepan-1-yl)-1-oxoisoindolin-2-yl)piperidine-2,6-dione;

(Z)-2-(2,6-dioxopiperidin-3-yl)-5-(4-(5-(4-(1-(4-hydroxyphenyl)-2-phenylbut-1-en-1-yl)phenoxy)pentyl)-1,4-diazepan-1-yl)isoindoline-1,3-dione;

(Z)-2-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylacetamide;

(Z)-3-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylpropanamide;

(Z)-3-(5-(4-(4-(4-(1-(4-hydroxyphenyl)-2-phenylbut-1-en-1-yl)phenoxy)butyl)-1,4-diazepan-1-yl)-1-oxoisoindolin-2-yl)piperidine-2,6-dione;

(Z)-2-(2,6-dioxopiperidin-3-yl)-5-(4-(4-(4-(1-(4-hydroxyphenyl)-2-phenylbut-1-en-1-yl)phenoxy)butyl)-1,4-diazepan-1-yl)isoindoline-1,3-dione;

(Z)-3-(5-(4-(2-(2-((4-(1-(4-hydroxyphenyl)-2-phenylbut-1-en-1-yl)phenoxy)methyl)cyclopropyl)ethyl)piperazin-1-yl)-1-oxoisoindolin-2-yl)piperidine-2,6-dione;

(Z)-2-(2,6-dioxopiperidin-3-yl)-5-(4-(2-(2-((4-(1-(4-hydroxyphenyl)-2-phenylbut-1-en-1-yl)phenoxy)methyl)cyclopropyl)ethyl)piperazin-1-yl)isoindoline-1,3-dione;

(Z)-2-(2,6-dioxopiperidin-3-yl)-5-(4-((4-(4-(1-(4-hydroxyphenyl)-2-phenylbut-1-en-1-yl)phenoxy)piperidin-1-yl)methyl)piperidin-1-yl)isoindoline-1,3-dione;

(Z)-2-(2,6-dioxopiperidin-3-yl)-5-(4-(1-(2-(4-(1-(4-hydroxyphenyl)-2-phenylbut-1-en-1-yl)phenoxy)ethyl)piperidin-4-yl)piperazin-1-yl)isoindoline-1,3-dione;

(Z)-2-(2,6-dioxopiperidin-3-yl)-5-(4-((1-(2-(4-(1-(4-hydroxyphenyl)-2-phenylbut-1-en-1-yl)phenoxy)ethyl)piperidin-4-yl)methyl)piperazin-1-yl)isoindoline-1,3-dione;

(Z)-2-(2,6-dioxopiperidin-3-yl)-5-(4-((1-(2-(4-(1-(4-hydroxyphenyl)-2-phenylbut-1-en-1-yl)phenoxy)ethyl)azetidin-3-yl)methyl)piperazin-1-yl)isoindoline-1,3-dione;

(Z)-3-(5-(4-(4,4-difluoro-5-(4-(1-(4-hydroxyphenyl)-2-phenylbut-1-en-1-yl)phenoxy)pentyl)piperazin-1-yl)-1-oxoisoindolin-2-yl)piperidine-2,6-dione;

(Z)-2-(2,6-dioxopiperidin-3-yl)-5-(4-(2-(1-(2-(4-(1-(4-hydroxyphenyl)-2-phenylbut-1-en-1-yl)phenoxy)ethyl)azetidin-3-yl)ethyl)piperazin-1-yl)isoindoline-1,3-dione;

(Z)-3-(5-(4-(5-(4-(1-(4-hydroxyphenyl)-2-phenylbut-1-en-1-yl)phenoxy)pentyl)piperazin-1-yl)-1-oxoisoindolin-2-yl)-1-methylpiperidine-2,6-dione;

(Z)-3-(5-(6-((1-(2-(4-(1-(4-hydroxyphenyl)-2-phenylbut-1-en-1-yl)phenoxy)ethyl)pyrrolidin-3-yl)oxy)pyridin-3-yl)-1-oxoisoindolin-2-yl)piperidine-2,6-dione;

(Z)-2-(2,6-dioxopiperidin-3-yl)-5-(4-((1-(2-(4-(1-(4-hydroxyphenyl)-2-phenylbut-1-en-1-yl)phenoxy)ethyl)pyrrolidin-3-yl)methyl)piperazin-1-yl)isoindoline-1,3-dione;

(Z)-2-(2,6-dioxopiperidin-3-yl)-5-(4-((4-(2-(4-(1-(4-hydroxyphenyl)-2-phenylbut-1-en-1-yl)phenoxy)ethyl)piperazin-1-yl)methyl)piperidin-1-yl)isoindoline-1,3-dione;

(Z)-2-(2,6-dioxopiperidin-3-yl)-5-(5-(1-(2-(4-(1-(4-hydroxyphenyl)-2-phenylbut-1-en-1-yl)phenoxy)ethyl)piperidin-4-yl)-2,5-diazabicyclo[2.2.1]heptan-2-yl)isoindoline-1,3-dione;

(Z)-2-(2,6-dioxopiperidin-3-yl)-5-(5-((1-(2-(4-(1-(4-hydroxyphenyl)-2-phenylbut-1-en-1-yl)phenoxy)ethyl)piperidin-4-yl)methyl)-2,5-diazabicyclo[2.2.1]heptan-2-yl)isoindoline-1,3-dione;

(Z)-3-(5-(4-(5-(4-(1-(4-hydroxyphenyl)-2-phenylbut-1-en-1-yl)phenoxy)pentyl)-3,5-dimethylpiperazin-1-yl)-1-oxoisoindolin-2-yl)piperidine-2,6-dione;

(Z)-3-(5-(4-((4-(4-(1-(4-hydroxyphenyl)-2-phenylbut-1-en-1-yl)phenoxy)piperidin-1-yl)methyl)piperidin-1-yl)-1-oxoisoindolin-2-yl)piperidine-2,6-dione;

(Z)-4-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylbutanamide;

(Z)-2-(2,6-dioxopiperidin-3-yl)-5-(7-(4-(4-(1-(4-hydroxyphenyl)-2-phenylbut-1-en-1-yl)phenoxy)butyl)-2,7-diazaspiro[3.5]nonan-2-yl)isoindoline-1,3-dione;

(Z)-2-(2,6-dioxopiperidin-3-yl)-6-(4-(5-(4-(1-(4-hydroxyphenyl)-2-phenylbut-1-en-1-yl)phenoxy)pentyl)piperazin-1-yl)-1H-pyrrolo[3,4-c]pyridine-1,3(2H)-dione;

(Z)-3-(5-(7-(4-(4-(1-(4-hydroxyphenyl)-2-phenylbut-1-en-1-yl)phenoxy)butyl)-2,7-diazaspiro[3.5]nonan-2-yl)-1-oxoisoindolin-2-yl)piperidine-2,6-dione;

(Z)-3-(5-(4-((1-(2-(4-(1-(4-hydroxyphenyl)-2-phenylbut-1-en-1-yl)phenoxy)ethyl)pyrrolidin-3-yl)methyl)piperazin-1-yl)-1-oxoisoindolin-2-yl)piperidine-2,6-dione;

(Z)-2-(2,6-dioxopiperidin-3-yl)-5-(6-(4-(4-(1-(4-hydroxyphenyl)-2-phenylbut-1-en-1-yl)phenoxy)butyl)-2,6-diazaspiro[3.3]heptan-2-yl)isoindoline-1,3-dione;

(Z)-3-(5-(2-(4-(6-(4-(1-(4-hydroxyphenyl)-2-phenylbut-1-en-1-yl)phenoxy)pyridin-3-yl)piperazin-1-yl)ethoxy)-1-oxoisoindolin-2-yl)piperidine-2,6-dione;

(Z)-2-(2,6-dioxopiperidin-3-yl)-5-(2-(4-(6-(4-(1-(4-hydroxyphenyl)-2-phenylbut-1-en-1-yl)phenoxy)pyridin-3-yl)piperazin-1-yl)ethoxy)isoindoline-1,3-dione;

(Z)-2-(2,6-dioxopiperidin-3-yl)-5-(3-(4-(6-(4-(1-(4-hydroxyphenyl)-2-phenylbut-1-en-1-yl)phenoxy)pyridin-3-yl)piperazin-1-yl)propoxy)isoindoline-1,3-dione;

(Z)-3-(5-(3-(4-(6-(4-(1-(4-hydroxyphenyl)-2-phenylbut-1-en-1-yl)phenoxy)pyridin-3-yl)piperazin-1-yl)propoxy)-1-oxoisoindolin-2-yl)piperidine-2,6-dione;

(Z)-2-(2,6-dioxopiperidin-3-yl)-5-(4-(3-(4-(1-(4-hydroxyphenyl)-2-phenylbut-1-en-1-yl)phenoxy)propyl)-1-oxa-4,9-diazaspiro[5.5]undecan-9-yl)isoindoline-1,3-dione;

(Z)-3-(5-(4-(5-(4-(1-(4-hydroxyphenyl)-2-phenylbut-1-en-1-yl)phenoxy)pentyl)-2,5-dimethylpiperazin-1-yl)-1-oxoisoindolin-2-yl)piperidine-2,6-dione;

(Z)-6-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylhexanamide;

(Z)-2-(2,6-dioxopiperidin-3-yl)-5-(5-((1-(2-(4-(1-(4-hydroxyphenyl)-2-phenylbut-1-en-1-yl)phenoxy)ethyl)pyrrolidin-3-yl)oxy)pyrazin-2-yl)isoindoline-1,3-dione;

(Z)-2-(2,6-dioxopiperidin-3-yl)-5-(5-(4-(2-(4-(1-(4-hydroxyphenyl)-2-phenylbut-1-en-1-yl)phenoxy)ethyl)piperazin-1-yl)pyrazin-2-yl)isoindoline-1,3-dione;

(Z)-2-(2,6-dioxopiperidin-3-yl)-5-(5-((1-(2-(4-(1-(4-hydroxyphenyl)-2-phenylbut-1-en-1-yl)phenoxy)ethyl)azetidin-3-yl)methoxy)pyrazin-2-yl)isoindoline-1,3-dione;

(Z)-2-(2,6-dioxopiperidin-3-yl)-5-((2-(4-(2-(4-(1-(4-hydroxyphenyl)-2-phenylbut-1-en-1-yl)phenoxy)ethyl)piperazin-1-yl)pyrimidin-5-yl)oxy)isoindoline-1,3-dione;

(Z)-6-(2,6-dioxopiperidin-3-yl)-2-(4-(5-(4-(1-(4-hydroxyphenyl)-2-phenylbut-1-en-1-yl)phenoxy)pentyl)piperazin-1-yl)-5H-pyrrolo[3,4-b]pyrazine-5,7(6H)-dione;

(Z)-7-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylheptanamide;

(Z)-2-(2,6-dioxopiperidin-3-yl)-5-(1'-(2-(4-(1-(4-hydroxyphenyl)-2-phenylbut-1-en-1-yl)phenoxy)ethyl)-[1,4'-bipiperidin]-4-yl)isoindoline-1,3-dione;

(Z)-2-(2,6-dioxopiperidin-3-yl)-5-((6-(4-(2-(4-(1-(4-hydroxyphenyl)-2-phenylbut-1-en-1-yl)phenoxy)ethyl)piperazin-1-yl)pyridin-3-yl)oxy)isoindoline-1,3-dione;

(E)-3-(5-(4-(3-(4-(4-(1-(4-hydroxyphenyl)-2-phenylbut-1-en-1-yl)phenyl)-1H-pyrazol-1-yl)propyl)piperazin-1-yl)-1-oxoisoindolin-2-yl)piperidine-2,6-dione;

(Z)-6-(2,6-dioxopiperidin-3-yl)-2-(4-(5-(4-(1-(4-hydroxyphenyl)-2-phenylbut-1-en-1-yl)phenoxy)pentyl)piperazin-1-yl)-5H-pyrrolo[3,4-d]pyrimidine-5,7(6H)-dione;

(Z)-3-(5-(1'-(2-(4-(1-(4-hydroxyphenyl)-2-phenylbut-1-en-1-yl)phenoxy)ethyl)-[1,4'-bipiperidin]-4-yl)-1-oxoisoindolin-2-yl)piperidine-2,6-dione;

(Z)-2-(2,6-dioxopiperidin-3-yl)-5-(4-(2-(4-(4-(1-(4-hydroxyphenyl)-2-phenylbut-1-en-1-yl)phenoxy)piperidin-1-yl)ethyl)piperazin-1-yl)isoindoline-1,3-dione;

(E)-3-(5-(4-(1-(3-(4-(1-(4-hydroxyphenyl)-2-phenylbut-1-en-1-yl)phenyl)propyl)pyrrolidin-3-yl)piperazin-1-yl)-1-oxoisoindolin-2-yl)piperidine-2,6-dione;

(E)-2-(2,6-dioxopiperidin-3-yl)-5-(4-((1-(3-(4-(1-(4-hydroxyphenyl)-2-phenylbut-1-en-1-yl)phenyl)propyl)azetidin-3-yl)methyl)piperazin-1-yl)isoindoline-1,3-dione;

(E)-3-(5-(4-((1-(3-(4-(1-(4-hydroxyphenyl)-2-phenylbut-1-en-1-yl)phenyl)propyl)azetidin-3-yl)methyl)piperazin-1-yl)-1-oxoisoindolin-2-yl)piperidine-2,6-dione;

(Z)-3-(5-((6-(4-(2-(4-(1-(4-hydroxyphenyl)-2-phenylbut-1-en-1-yl)phenoxy)ethyl)piperazin-1-yl)pyridin-3-yl)oxy)-1-oxoisoindolin-2-yl)piperidine-2,6-dione;

(E)-3-(5-(4-(2-(4-(4-(1-(4-hydroxyphenyl)-2-phenylbut-1-en-1-yl)phenyl)piperazin-1-yl)ethyl)piperazin-1-yl)-1-oxoisoindolin-2-yl)piperidine-2,6-dione;

(E)-3-(5-(4-(2-(4-(4-(1-(4-hydroxyphenyl)-2-phenylbut-1-en-1-yl)phenyl)piperidin-1-yl)ethyl)piperazin-1-yl)-1-oxoisoindolin-2-yl)piperidine-2,6-dione;

(E)-2-(2,6-dioxopiperidin-3-yl)-5-(4-(2-(4-(4-(1-(4-hydroxyphenyl)-2-phenylbut-1-en-1-yl)phenyl)piperidin-1-yl)ethyl)piperazin-1-yl)isoindoline-1,3-dione;

(Z)-3-(5-(4-(2-(2-(4-(1-(4-hydroxyphenyl)-2-phenylbut-1-en-1-yl)phenoxy)ethyl)-2-azaspiro[3.3]heptan-6-yl)piperazin-1-yl)-1-oxoisoindolin-2-yl)piperidine-2,6-dione;

(E)-2-(2,6-dioxopiperidin-3-yl)-5-(4-(3-(4-(4-(1-(4-hydroxyphenyl)-2-phenylbut-1-en-1-yl)phenyl)-1H-pyrazol-1-yl)propyl)piperazin-1-yl)isoindoline-1,3-dione;

(E)-2-(2,6-dioxopiperidin-3-yl)-5-(4-(3-(5-(4-(1-(4-hydroxyphenyl)-2-phenylbut-1-en-1-yl)phenyl)-2H-tetrazol-2-yl)propyl)piperazin-1-yl)isoindoline-1,3-dione;

(Z)-8-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methyloctanamide;

(Z)-3-(5-(4-(3-(4-(1-(4-hydroxyphenyl)-2-phenylbut-1-en-1-yl)phenoxy)propyl)-1-oxa-4,9-diazaspiro[5.5]undecan-9-yl)-1-oxoisoindolin-2-yl)piperidine-2,6-dione;

(E)-3-(5-(4-((1-(3-(4-(1-(4-hydroxyphenyl)-2-phenylbut-1-en-1-yl)phenyl)propyl)piperidin-4-yl)methyl)piperazin-1-yl)-1-oxoisoindolin-2-yl)piperidine-2,6-dione;

(E)-2-(2,6-dioxopiperidin-3-yl)-5-(4-((1-(3-(4-(1-(4-hydroxyphenyl)-2-phenylbut-1-en-1-yl)phenyl)propyl)piperidin-4-yl)methyl)piperazin-1-yl)isoindoline-1,3-dione;

(E)-3-(5-(4-(1-(3-(4-(1-(4-hydroxyphenyl)-2-phenylbut-1-en-1-yl)phenyl)propyl)piperidin-4-yl)piperazin-1-yl)-1-oxoisoindolin-2-yl)piperidine-2,6-dione;

(E)-2-(2,6-dioxopiperidin-3-yl)-5-(4-(1-(3-(4-(1-(4-hydroxyphenyl)-2-phenylbut-1-en-1-yl)phenyl)propyl)piperidin-4-yl)piperazin-1-yl)isoindoline-1,3-dione;

(E)-3-(5-(4-(3-(4-(4-(1-(4-hydroxyphenyl)-2-phenylbut-1-en-1-yl)phenyl)piperidin-1-yl)propyl)piperazin-1-yl)-1-oxoisoindolin-2-yl)piperidine-2,6-dione;

(E)-2-(2,6-dioxopiperidin-3-yl)-5-(4-(3-(4-(4-(1-(4-hydroxyphenyl)-2-phenylbut-1-en-1-yl)phenyl)piperidin-1-yl)propyl)piperazin-1-yl)isoindoline-1,3-dione;

(Z)-2-(2,6-dioxopiperidin-3-yl)-4-((1-((4-(2-(4-(1-(4-hydroxyphenyl)-2-phenylbut-1-en-1-yl)phenoxy)ethyl)piperazin-1-yl)methyl)piperidin-4-yl)amino)isoindoline-1,3-dione;

(Z)-2-(2,6-dioxopiperidin-3-yl)-4-((1-((1-(2-(4-(1-(4-hydroxyphenyl)-2-phenylbut-1-en-1-yl)phenoxy)ethyl)piperidin-4-yl)methyl)piperidin-4-yl)amino)isoindoline-1,3-dione;

(Z)-3-(4-((1-((1-(2-(4-(1-(4-hydroxyphenyl)-2-phenylbut-1-en-1-yl)phenoxy)ethyl)piperidin-4-yl)methyl)piperidin-4-yl)amino)-1-oxoisoindolin-2-yl)piperidine-2,6-dione;

(Z)-3-(4-((1-((4-(2-(4-(1-(4-hydroxyphenyl)-2-phenylbut-1-en-1-yl)phenoxy)ethyl)piperazin-1-yl)methyl)piperidin-4-yl)amino)-1-oxoisoindolin-2-yl)piperidine-2,6-dione;

(Z)-3-(2-(2-((2-(2,6-dioxopiperidin-3-yl)-1,3-dioxoisoindolin-4-yl)amino)ethoxy)ethoxy)-N-(2-(4-(1-(4-hydroxyphenyl)-2-phenylbut-1-en-1-yl)phenoxy)ethyl)-N-methylpropanamide;

(Z)-1-((2-(2,6-dioxopiperidin-3-yl)-1-oxoisoindolin-4-yl)amino)-N-(2-(4-(1-(4-hydroxyphenyl)-2-phenylbut-1-en-1-yl)phenoxy)ethyl)-N-methyl-3,6,9,12,15-pentaoxaoctadecan-18-amide;

(Z)-1-((2-(2,6-dioxopiperidin-3-yl)-1,3-dioxoisoindolin-4-yl)amino)-N-(2-(4-(1-(4-hydroxyphenyl)-2-phenylbut-1-en-1-yl)phenoxy)ethyl)-N-methyl-3,6,9,12,15-pentaoxaoctadecan-18-amide;

(Z)-3-(5-((2-(4-(2-(4-(1-(4-hydroxyphenyl)-2-phenylbut-1-en-1-yl)phenoxy)ethyl)piperazin-1-yl)pyrimidin-5-yl)oxy)-1-oxoisoindolin-2-yl)piperidine-2,6-dione;

(Z)-3-(7-chloro-5-(4-(5-(4-(1-(4-hydroxyphenyl)-2-phenylbut-1-en-1-yl)phenoxy)pentyl)piperazin-1-yl)-1-oxoisoindolin-2-yl)piperidine-2,6-dione;

(E)/(Z)—(S)-3-(5-(4-((1-(4-(1-(4-hydroxyphenyl)-2-phenylbut-1-en-1-yl)phenyl)piperidin-4-yl)methyl)piperazin-1-yl)-1-oxoisoindolin-2-yl)piperidine-2,6-dione;

(E)-3-(5-(4-((1-(4-(1-(4-hydroxyphenyl)-2-phenylbut-1-en-1-yl)phenyl)piperidin-4-yl)methyl)piperazin-1-yl)-1-oxoisoindolin-2-yl)piperidine-2,6-dione;

(E)-(S)-3-(5-(4-((1-(4-(1-(4-hydroxyphenyl)-2-phenylbut-1-en-1-yl)phenyl)piperidin-4-yl)methyl)piperazin-1-yl)-1-oxoisoindolin-2-yl)piperidine-2,6-dione;

(E)/(Z)—(S)-3-(5-(4-(2-(1-(4-(1-(4-hydroxyphenyl)-2-phenylbut-1-en-1-yl)phenyl)piperidin-4-yl)ethyl)piperazin-1-yl)-1-oxoisoindolin-2-yl)piperidine-2,6-dione;

(E)-3-(5-(4-(2-(1-(4-(1-(4-hydroxyphenyl)-2-phenylbut-1-en-1-yl)phenyl)piperidin-4-yl)ethyl)piperazin-1-yl)-1-oxoisoindolin-2-yl)piperidine-2,6-dione;

(Z)-3-(5-fluoro-6-(4-(5-(4-(1-(4-hydroxyphenyl)-2-phenylbut-1-en-1-yl)phenoxy)pentyl)piperazin-1-yl)-1-oxoisoindolin-2-yl)piperidine-2,6-dione;

(Z)-3-(4-fluoro-5-(4-(5-(4-(1-(4-hydroxyphenyl)-2-phenylbut-1-en-1-yl)phenoxy)pentyl)piperazin-1-yl)-1-oxoisoindolin-2-yl)piperidine-2,6-dione;

(E)-3-(5-(2-(4-((1-(4-(1-(4-hydroxyphenyl)-2-phenylbut-1-en-1-yl)phenyl)piperidin-4-yl)methyl)-1,4-diazepan-1-yl)ethyl)-1-oxoisoindolin-2-yl)piperidine-2,6-dione;

(Z)-3-(5-(6-(4-(4-(1-(4-hydroxyphenyl)-2-phenylbut-1-en-1-yl)phenoxy)butyl)-2,6-diazaspiro[3.3]heptan-2-yl)-1-oxoisoindolin-2-yl)piperidine-2,6-dione;

(Z)-3-(5-(8-(4-(4-(1-(4-hydroxyphenyl)-2-phenylbut-1-en-1-yl)phenoxy)butyl)octahydro-2H-pyrazino[1,2-a]pyrazin-2-yl)-1-oxoisoindolin-2-yl)piperidine-2,6-dione;

(Z)-3-(5-(4-(2-hydroxy-5-(4-(1-(4-hydroxyphenyl)-2-phenylbut-1-en-1-yl)phenoxy)pentyl)piperazin-1-yl)-1-oxoisoindolin-2-yl)piperidine-2,6-dione;

(Z)-3-(7-fluoro-5-(4-(5-(4-(1-(4-hydroxyphenyl)-2-phenylbut-1-en-1-yl)phenoxy)pentyl)piperazin-1-yl)-1-oxoisoindolin-2-yl)piperidine-2,6-dione;

(Z)-3-(5-(4-(3-hydroxy-5-(4-(1-(4-hydroxyphenyl)-2-phenylbut-1-en-1-yl)phenoxy)-3-methylpentyl)piperazin-1-yl)-1-oxoisoindolin-2-yl)piperidine-2,6-dione;

(Z)-3-(5-(4-(5-(4-(1-(4-hydroxyphenyl)-2-phenylbut-1-en-1-yl)phenoxy)-2-oxopentyl)piperazin-1-yl)-1-oxoisoindolin-2-yl)piperidine-2,6-dione;

(Z)-3-(4-fluoro-5-(4-(2-hydroxy-5-(4-(1-(4-hydroxyphenyl)-2-phenylbut-1-en-1-yl)phenoxy)pentyl)piperazin-1-yl)-1-oxoisoindolin-2-yl)piperidine-2,6-dione;

(Z)-3-(4,6-difluoro-5-(4-(2-hydroxy-5-(4-(1-(4-hydroxyphenyl)-2-phenylbut-1-en-1-yl)phenoxy)pentyl)piperazin-1-yl)-1-oxoisoindolin-2-yl)piperidine-2,6-dione;

(Z)-2-(2,6-dioxopiperidin-3-yl)-5-(5-(4-(4-(1-(4-hydroxyphenyl)-2-phenylbut-1-en-1-yl)phenoxy)butyl)hexahydropyrrolo[3,4-c]pyrrol-2(1H)-yl)isoindoline-1,3-dione;

(Z)-2-(2,6-dioxopiperidin-3-yl)-5-(5-(3-(4-(1-(4-hydroxyphenyl)-2-phenylbut-1-en-1-yl)phenoxy)propyl)hexahydropyrrolo[3,4-c]pyrrol-2(1H)-yl)isoindoline-1,3-dione;

(Z)-3-(5-(4-(2-(2-(4-(1-(4-hydroxyphenyl)-2-phenylbut-1-en-1-yl)phenoxy)ethoxy)ethyl)piperazin-1-yl)-1-oxoisoindolin-2-yl)piperidine-2,6-dione;

(Z)-3-(5-(4-(2-(3-(4-(1-(4-hydroxyphenyl)-2-phenylbut-1-en-1-yl)phenoxy)cyclobutoxy)ethyl)piperazin-1-yl)-1-oxoisoindolin-2-yl)piperidine-2,6-dione;

(Z)-5-(4-(4,4-difluoro-5-(4-(1-(4-hydroxyphenyl)-2-phenylbut-1-en-1-yl)phenoxy)pentyl)piperazin-1-yl)-2-(2,6-dioxopiperidin-3-yl)isoindoline-1,3-dione;

(Z)-3-(5-(4-(3-hydroxy-5-(4-(1-(4-hydroxyphenyl)-2-phenylbut-1-en-1-yl)phenoxy)pentyl)piperazin-1-yl)-1-oxoisoindolin-2-yl)piperidine-2,6-dione;

(Z)-3-(5-(5-(4-(4-(1-(4-hydroxyphenyl)-2-phenylbut-1-en-1-yl)phenoxy)butyl)hexahydropyrrolo[3,4-c]pyrrol-2(1H)-yl)-1-oxoisoindolin-2-yl)piperidine-2,6-dione;

(Z)-3-(5-(5-(3-(4-(1-(4-hydroxyphenyl)-2-phenylbut-1-en-1-yl)phenoxy)propyl)hexahydropyrrolo[3,4-c]pyrrol-2(1H)-yl)-1-oxoisoindolin-2-yl)piperidine-2,6-dione;

(Z)-3-(5-(4-(5-((4-(1-(4-hydroxyphenyl)-2-phenylbut-1-en-1-yl)phenyl)sulfonyl)pentyl)piperazin-1-yl)-1-oxoisoindolin-2-yl)piperidine-2,6-dione;

(E)-3-(5-(2-(4-((1-(4-(1-(4-hydroxyphenyl)-2-phenylbut-1-en-1-yl)phenyl)azetidin-3-yl)methyl)-1,4-diazepan-1-yl)ethyl)-1-oxoisoindolin-2-yl)piperidine-2,6-dione;

(Z)-3-(5-(4-(2-((2-(4-(1-(4-hydroxyphenyl)-2-phenylbut-1-en-1-yl)phenoxy)ethyl)amino)ethyl)piperazin-1-yl)-1-oxoisoindolin-2-yl)piperidine-2,6-dione;

(E)/(Z)-2-(2,6-dioxopiperidin-3-yl)-5-(4-((1-(4-(1-(4-hydroxyphenyl)-2-phenylbut-1-en-1-yl)phenyl)piperidin-4-yl)methyl)piperazin-1-yl)isoindoline-1,3-dione;

(E)-2-(2,6-dioxopiperidin-3-yl)-5-(4-((1-(4-(1-(4-hydroxyphenyl)-2-phenylbut-1-en-1-yl)phenyl)piperidin-4-yl)methyl)piperazin-1-yl)isoindoline-1,3-dione;

(E)/(Z)-2-(2,6-dioxopiperidin-3-yl)-5-(4-(2-(1-(4-(1-(4-hydroxyphenyl)-2-phenylbut-1-en-1-yl)phenyl)piperidin-4-yl)ethyl)piperazin-1-yl)isoindoline-1,3-dione;

(E)-2-(2,6-dioxopiperidin-3-yl)-5-(4-(2-(1-(4-(1-(4-hydroxyphenyl)-2-phenylbut-1-en-1-yl)phenyl)piperidin-4-yl)ethyl)piperazin-1-yl)isoindoline-1,3-dione;

(Z)-3-(5-(4-(5-((4-(1-(4-hydroxyphenyl)-2-phenylbut-1-en-1-yl)phenyl)thio)pentyl)piperazin-1-yl)-1-oxoisoindolin-2-yl)piperidine-2,6-dione;

(Z)-3-(5-(4-((5-((4-(1-(4-hydroxyphenyl)-2-phenylbut-1-en-1-yl)phenoxy)methyl)tetrahydrofuran-2-yl)methyl)piperazin-1-yl)-1-oxoisoindolin-2-yl)piperidine-2,6-dione;

(Z)-3-(5-(4-(2-(3-(4-(1-(4-hydroxyphenyl)-2-phenylbut-1-en-1-yl)phenoxy)cyclobutyl)ethyl)piperazin-1-yl)-1-oxoisoindolin-2-yl)piperidine-2,6-dione;

(Z)-3-(6-(4-(5-(4-(1-(4-hydroxyphenyl)-2-phenylbut-1-en-1-yl)phenoxy)pentyl)piperazin-1-yl)-1-oxoisoindolin-2-yl)piperidine-2,6-dione;

(Z)-3-(2-(4-(5-(4-(1-(4-hydroxyphenyl)-2-phenylbut-1-en-1-yl)phenoxy)pentyl)piperazin-1-yl)-5-oxo-5,7-dihydro-6H-pyrrolo[3,4-b]pyridin-6-yl)piperidine-2,6-dione;

(Z)-3-(2-(4-(4,4-difluoro-5-(4-(1-(4-hydroxyphenyl)-2-phenylbut-1-en-1-yl)phenoxy)pentyl)piperazin-1-yl)-5-oxo-5,7-dihydro-6H-pyrrolo[3,4-b]pyridin-6-yl)piperidine-2,6-dione;

(Z)-3-(6-(4-(5-(4-(1-(4-hydroxyphenyl)-2-phenylbut-1-en-1-yl)phenoxy)pentyl)piperazin-1-yl)-3-oxo-1,3-dihydro-2H-pyrrolo[3,4-c]pyridin-2-yl)piperidine-2,6-dione;

(Z)-2-(2,6-dioxopiperidin-3-yl)-5-(4-(1-(2-(4-(1-(4-hydroxyphenyl)-2-phenylbut-1-en-1-yl)phenoxy)ethyl)pyrrolidin-3-yl)butyl)isoindoline-1,3-dione;

(Z)-3-(5-(4-((3-((4-(1-(4-hydroxyphenyl)-2-phenylbut-1-en-1-yl)phenoxy)methyl)cyclobutyl)methyl)piperazin-1-yl)-1-oxoisoindolin-2-yl)piperidine-2,6-dione;

(Z)-3-(2-(4-(1-(2-(4-(1-(4-hydroxyphenyl)-2-phenylbut-1-en-1-yl)phenoxy)ethyl)pyrrolidin-3-yl)butyl)-5-oxo-5,7-dihydro-6H-pyrrolo[3,4-b]pyridin-6-yl)piperidine-2,6-dione;

(E)-3-(5-((1-((1-(4-(1-(4-hydroxyphenyl)-2-phenylbut-1-en-1-yl)phenyl)piperidin-4-yl)methyl)piperidin-4-yl)methoxy)-1-oxoisoindolin-2-yl)piperidine-2,6-dione;

(Z)-2-(2,6-dioxopiperidin-3-yl)-4-(4-(1-(2-(4-(1-(4-hydroxyphenyl)-2-phenylbut-1-en-1-yl)phenoxy)ethyl)pyrrolidin-3-yl)butyl)isoindoline-1,3-dione;

(E)-3-(2-(4-((1-(4-(1-(4-hydroxyphenyl)-2-phenylbut-1-en-1-yl)phenyl)piperidin-4-yl)methyl)piperazin-1-yl)-5-oxo-5,7-dihydro-6H-pyrrolo[3,4-b]pyridin-6-yl)piperidine-2,6-dione;

(E)-3-(2-(4-(2-(1-(4-(1-(4-hydroxyphenyl)-2-phenylbut-1-en-1-yl)phenyl)piperidin-4-yl)ethyl)piperazin-1-yl)-5-oxo-5,7-dihydro-6H-pyrrolo[3,4-b]pyridin-6-yl)piperidine-2,6-dione;

(E)-2-(2,6-dioxopiperidin-3-yl)-5-((1-((1-(4-(1-(4-hydroxyphenyl)-2-phenylbut-1-en-1-yl)phenyl)piperidin-4-yl)methyl)piperidin-4-yl)methoxy)isoindoline-1,3-dione;

(Z)-3-(5-(4-((6-((4-(1-(4-hydroxyphenyl)-2-phenylbut-1-en-1-yl)phenoxy)methyl)pyridazin-3-yl)methyl)piperazin-1-yl)-1-oxoisoindolin-2-yl)piperidine-2,6-dione;

(E)-3-(5-(4-((1-(4-(1-(4-hydroxyphenyl)-2-phenylbut-1-en-1-yl)phenyl)piperidin-4-yl)methyl)piperazin-1-yl)-1-oxoisoindolin-2-yl)-3-methylpiperidine-2,6-dione;

(E)-3-(5-(7-((1-(4-(1-(4-hydroxyphenyl)-2-phenylbut-1-en-1-yl)phenyl)piperidin-4-yl)methyl)-2,7-diazaspiro[3.5]nonan-2-yl)-1-oxoisoindolin-2-yl)piperidine-2,6-dione;

(Z)-3-(6-(2-(4-(3-(4-(1-(4-hydroxyphenyl)-2-phenylbut-1-en-1-yl)phenoxy)cyclobutoxy)piperidin-1-yl)ethoxy)-1-oxoisoindolin-2-yl)piperidine-2,6-dione;

(Z)-2-(2,6-dioxopiperidin-3-yl)-5-(4-(6,6,6-trifluoro-5-(4-(1-(4-hydroxyphenyl)-2-phenylbut-1-en-1-yl)phenoxy)hexyl)piperazin-1-yl)isoindoline-1,3-dione;

(Z)-3-(1-oxo-5-(4-(6,6,6-trifluoro-5-(4-(1-(4-hydroxyphenyl)-2-phenylbut-1-en-1-yl)phenoxy)hexyl)piperazin-1-yl)isoindolin-2-yl)piperidine-2,6-dione;

(Z)-3-(5-(4-((5-((4-(1-(4-hydroxyphenyl)-2-phenylbut-1-en-1-yl)phenoxy)methyl)pyridin-2-yl)methyl)piperazin-1-yl)-1-oxoisoindolin-2-yl)piperidine-2,6-dione;

(E)-3-(6-(4-((1-(4-(1-(4-hydroxyphenyl)-2-phenylbut-1-en-1-yl)phenyl)piperidin-4-yl)methyl)piperazin-1-yl)-3-oxo-1,3-dihydro-2H-pyrrolo[3,4-c]pyridin-2-yl)piperidine-2,6-dione;

(E)-3-(5-(4-(7-(4-(1-(4-hydroxyphenyl)-2-phenylbut-1-en-1-yl)phenyl)-7-azaspiro[3.5]nonan-2-yl)piperazin-1-yl)-1-oxoisoindolin-2-yl)piperidine-2,6-dione;

(E)-3-(2-(4-(7-(4-(1-(4-hydroxyphenyl)-2-phenylbut-1-en-1-yl)phenyl)-7-azaspiro[3.5]nonan-2-yl)piperazin-1-yl)-5-oxo-5,7-dihydro-6H-pyrrolo[3,4-b]pyridin-6-yl)piperidine-2,6-dione;

(E)-3-(6-(4-(2-(1-(4-(1-(4-hydroxyphenyl)-2-phenylbut-1-en-1-yl)phenyl)piperidin-4-yl)ethyl)piperazin-1-yl)-3-oxo-1,3-dihydro-2H-pyrrolo[3,4-c]pyridin-2-yl)piperidine-2,6-dione;

(E)-3-(5-(4-((1-(4-(1-(4-hydroxyphenyl)-2-phenylbut-1-en-1-yl)phenyl)-4-methylpiperidin-4-yl)methyl)piperazin-1-yl)-1-oxoisoindolin-2-yl)piperidine-2,6-dione;

(E)-3-(4,6-difluoro-5-(4-((1-(4-(1-(4-hydroxyphenyl)-2-phenylbut-1-en-1-yl)phenyl)piperidin-4-yl)methyl)piperazin-1-yl)-1-oxoisoindolin-2-yl)piperidine-2,6-dione;

(E)-3-(5-((1-((1-(4-(1-(4-hydroxyphenyl)-2-phenylbut-1-en-1-yl)phenyl)piperidin-4-yl)methyl)piperidin-4-yl)oxy)-1-oxoisoindolin-2-yl)piperidine-2,6-dione;

(E)-3-(2-(3-(((1-(4-(1-(4-hydroxyphenyl)-2-phenylbut-1-en-1-yl)phenyl)piperidin-4-yl)methyl)amino)pyrrolidin-1-yl)-5-oxo-5,7-dihydro-6H-pyrrolo[3,4-b]pyridin-6-yl)piperidine-2,6-dione;

(E)-3-(4-fluoro-5-(4-((1-(4-(1-(4-hydroxyphenyl)-2-phenylbut-1-en-1-yl)phenyl)piperidin-4-yl)methyl)piperazin-1-yl)-1-oxoisoindolin-2-yl)piperidine-2,6-dione;

(E)-3-(6-(4-((1-(4-(1-(4-hydroxyphenyl)-2-phenylbut-1-en-1-yl)phenyl)piperidin-4-yl)methyl)piperazin-1-yl)-1-oxoisoindolin-2-yl)piperidine-2,6-dione;

(E)-3-(5-(3-(((1-(4-(1-(4-hydroxyphenyl)-2-phenylbut-1-en-1-yl)phenyl)piperidin-4-yl)methyl)amino)pyrrolidin-1-yl)-1-oxoisoindolin-2-yl)piperidine-2,6-dione;
(E)-3-(5-(4-((1-(4-(1-(4-hydroxyphenyl)-2-phenylbut-1-en-1-yl)phenyl)piperidin-4-yl)methyl)piperazin-1-yl)-1-oxoisoindolin-2-yl)-1-methylpiperidine-2,6-dione;
(E)-3-(5-(4-((4-hydroxy-1-(4-(1-(4-hydroxyphenyl)-2-phenylbut-1-en-1-yl)phenyl)piperidin-4-yl)methyl)piperazin-1-yl)-1-oxoisoindolin-2-yl)piperidine-2,6-dione;
(E)-3-(5-(4-(((1-(4-(1-(4-hydroxyphenyl)-2-phenylbut-1-en-1-yl)phenyl)piperidin-4-yl)methyl)amino)piperidin-1-yl)-1-oxoisoindolin-2-yl)piperidine-2,6-dione;
(E)-3-(5-(4-((1-(4-(1-(4-hydroxyphenyl)-2-phenylbut-1-en-1-yl)phenyl)piperidin-4-yl)amino)piperidin-1-yl)-1-oxoisoindolin-2-yl)piperidine-2,6-dione;
(E)-3-(5-(4-((4-fluoro-1-(4-(1-(4-hydroxyphenyl)-2-phenylbut-1-en-1-yl)phenyl)piperidin-4-yl)methyl)piperazin-1-yl)-1-oxoisoindolin-2-yl)piperidine-2,6-dione;
(Z)-3-(4-((2-(4-(2-(4-(1-(4-hydroxyphenyl)-2-phenylbut-1-en-1-yl)phenoxy)ethyl)piperazin-1-yl)ethyl)amino)-1-oxoisoindolin-2-yl)piperidine-2,6-dione;
(Z)-2-(2,6-dioxopiperidin-3-yl)-4-((2-(4-(2-(4-(1-(4-hydroxyphenyl)-2-phenylbut-1-en-1-yl)phenoxy)ethyl)piperazin-1-yl)ethyl)amino)isoindoline-1,3-dione;
(Z)-3-(5-(2-(4-(2-(4-(1-(4-hydroxyphenyl)-2-phenylbut-1-en-1-yl)phenoxy)ethyl)piperazin-1-yl)-2-oxoethoxy)-1-oxoisoindolin-2-yl)piperidine-2,6-dione;
(Z)-3-(4-((6-((4-(2-(4-(1-(4-hydroxyphenyl)-2-phenylbut-1-en-1-yl)phenoxy)ethyl)piperazin-1-yl)methyl)pyridin-3-yl)methoxy)-1-oxoisoindolin-2-yl)piperidine-2,6-dione;
(Z)-3-(4-(2-(4-(1-(4-(1-(4-hydroxyphenyl)-2-phenylbut-1-en-1-yl)phenoxy)propan-2-yl)piperazin-1-yl)ethoxy)-1-oxoisoindolin-2-yl)piperidine-2,6-dione;
(Z)-3-(4-(2-(2-(4-(1-(4-hydroxyphenyl)-2-phenylbut-1-en-1-yl)phenoxy)ethoxy)ethoxy)-1-oxoisoindolin-2-yl)piperidine-2,6-dione;
(Z)-3-(4-((14-(4-(1-(4-hydroxyphenyl)-2-phenylbut-1-en-1-yl)phenoxy)-3,6,9,12-tetraoxatetradecyl)amino)-1-oxoisoindolin-2-yl)piperidine-2,6-dione;
(Z)-3-(4-(2-(2-(2-(4-(1-(4-hydroxyphenyl)-2-phenylbut-1-en-1-yl)phenoxy)ethoxy)ethoxy)ethoxy)-1-oxoisoindolin-2-yl)piperidine-2,6-dione;
(Z)-2-(2,6-dioxopiperidin-3-yl)-4-((14-(4-(1-(4-hydroxyphenyl)-2-phenylbut-1-en-1-yl)phenoxy)-3,6,9,12-tetraoxatetradecyl)amino)isoindoline-1,3-dione;
(Z)-3-(4-(2-(2-(2-(2-(4-(1-(4-hydroxyphenyl)-2-phenylbut-1-en-1-yl)phenoxy)ethoxy)ethoxy)ethoxy)ethoxy)-1-oxoisoindolin-2-yl)piperidine-2,6-dione;
(Z)-3-(4-((2-(2-(2-(2-(4-(1-(4-hydroxyphenyl)-2-phenylbut-1-en-1-yl)phenoxy)ethoxy)ethoxy)ethoxy)ethyl)amino)-1-oxoisoindolin-2-yl)piperidine-2,6-dione;
(Z)-2-(2,6-dioxopiperidin-3-yl)-4-((2-(2-(2-(2-(4-(1-(4-hydroxyphenyl)-2-phenylbut-1-en-1-yl)phenoxy)ethoxy)ethoxy)ethoxy)ethyl)amino)isoindoline-1,3-dione;
(Z)-3-(4-((2-(2-(2-(4-(1-(4-hydroxyphenyl)-2-phenylbut-1-en-1-yl)phenoxy)ethoxy)ethoxy)ethyl)amino)-1-oxoisoindolin-2-yl)piperidine-2,6-dione;
(Z)-2-(2,6-dioxopiperidin-3-yl)-4-((2-(2-(2-(4-(1-(4-hydroxyphenyl)-2-phenylbut-1-en-1-yl)phenoxy)ethoxy)ethoxy)ethyl)amino)isoindoline-1,3-dione;
(Z)-3-(4-((2-(4-(1-(4-hydroxyphenyl)-2-phenylbut-1-en-1-yl)phenoxy)ethyl)amino)-1-oxoisoindolin-2-yl)piperidine-2,6-dione;
(Z)-3-(4-(2-(4-(1-(4-hydroxyphenyl)-2-phenylbut-1-en-1-yl)phenoxy)ethoxy)-1-oxoisoindolin-2-yl)piperidine-2,6-dione;
(Z)-2-(2,6-dioxopiperidin-3-yl)-4-((2-(2-(4-(1-(4-hydroxyphenyl)-2-phenylbut-1-en-1-yl)phenoxy)ethoxy)ethyl)amino)isoindoline-1,3-dione;
(Z)-2-(2,6-dioxopiperidin-3-yl)-4-((2-(4-(1-(4-hydroxyphenyl)-2-phenylbut-1-en-1-yl)phenoxy)ethyl)amino)isoindoline-1,3-dione;
(Z)-3-(4-((2-(4-(1-(4-hydroxyphenyl)-2-phenylbut-1-en-1-yl)phenoxy)ethyl)amino)-1-oxoisoindolin-2-yl)piperidine-2,6-dione;
(Z)-3-(4-(3-(3-(4-(1-(4-hydroxyphenyl)-2-phenylbut-1-en-1-yl)phenoxy)propoxy)propoxy)-1-oxoisoindolin-2-yl)piperidine-2,6-dione;
(Z)-3-(4-(3-(3-(3-(4-(1-(4-hydroxyphenyl)-2-phenylbut-1-en-1-yl)phenoxy)propoxy)propoxy)propoxy)-1-oxoisoindolin-2-yl)piperidine-2,6-dione;
(Z)-3-(4-(2-(5-(2-(4-(1-(4-hydroxyphenyl)-2-phenylbut-1-en-1-yl)phenoxy)ethyl)-2,5-diazabicyclo[2.2.1]heptan-2-yl)ethoxy)-1-oxoisoindolin-2-yl)piperidine-2,6-dione;
(Z)-3-(5-(2-(6-(2-(4-(1-(4-hydroxyphenyl)-2-phenylbut-1-en-1-yl)phenoxy)ethyl)-2,6-diazaspiro[3.3]heptan-2-yl)ethoxy)-1-oxoisoindolin-2-yl)piperidine-2,6-dione;
(Z)-3-(5-(2-((1-(2-(4-(1-(4-hydroxyphenyl)-2-phenylbut-1-en-1-yl)phenoxy)ethyl)piperidin-4-yl)oxy)ethoxy)-1-oxoisoindolin-2-yl)piperidine-2,6-dione;
(Z)-3-(5-((7-(2-(4-(1-(4-hydroxyphenyl)-2-phenylbut-1-en-1-yl)phenoxy)ethyl)-7-azaspiro[3.5]nonan-2-yl)oxy)-1-oxoisoindolin-2-yl)piperidine-2,6-dione;
(Z)-3-(5-(4-(4-(1-(4-(1-(4-hydroxyphenyl)-2-phenylbut-1-en-1-yl)phenoxy)propan-2-yl)piperazin-1-yl)butyl)-1-oxoisoindolin-2-yl)piperidine-2,6-dione;
(Z)—N-((2-(2,6-dioxopiperidin-3-yl)-1-oxoisoindolin-5-yl)methyl)-1-(2-(4-(1-(4-hydroxyphenyl)-2-phenylbut-1-en-1-yl)phenoxy)ethyl)piperidine-4-carboxamide;
(Z)—N-((2-(2,6-dioxopiperidin-3-yl)-1-oxoisoindolin-5-yl)methyl)-2-(1-(2-(4-(1-(4-hydroxyphenyl)-2-phenylbut-1-en-1-yl)phenoxy)ethyl)piperidin-4-yl)acetamide;
(Z)-2-(2,6-dioxopiperidin-3-yl)-5-((2-(2-(2-(4-(1-(4-hydroxyphenyl)-2-phenylbut-1-en-1-yl)phenoxy)ethoxy)ethoxy)ethyl)amino)isoindoline-1,3-dione;
(Z)-2-(2,6-dioxopiperidin-3-yl)-5-(4-(7-(4-(1-(4-hydroxyphenyl)-2-phenylbut-1-en-1-yl)phenoxy)heptyl)piperazin-1-yl)isoindoline-1,3-dione;
(Z)-3-(5-((3-(4-(2-(4-(1-(4-hydroxyphenyl)-2-phenylbut-1-en-1-yl)phenoxy)ethyl)-1,4-diazepan-1-yl)propyl)amino)-1-oxoisoindolin-2-yl)piperidine-2,6-dione;
(Z)-2-(2,6-dioxopiperidin-3-yl)-5-(3-(3-(4-(1-(4-hydroxyphenyl)-2-phenylbut-1-en-1-yl)phenoxy)propoxy)propoxy)isoindoline-1,3-dione;
(Z)-2-(2,6-dioxopiperidin-3-yl)-5-(2-(2-(2-(4-(1-(4-hydroxyphenyl)-2-phenylbut-1-en-1-yl)phenoxy)ethoxy)ethoxy)ethoxy)isoindoline-1,3-dione;
(Z)-2-(2,6-dioxopiperidin-3-yl)-5-(3-(2-(2-(4-(1-(4-hydroxyphenyl)-2-phenylbut-1-en-1-yl)phenoxy)ethoxy)ethoxy)propoxy)isoindoline-1,3-dione;
(Z)-2-(2,6-dioxopiperidin-3-yl)-5-(3-(3-(3-(4-(1-(4-hydroxyphenyl)-2-phenylbut-1-en-1-yl)phenoxy)propoxy)propoxy)propoxy)isoindoline-1,3-dione;
(Z)-2-(2,6-dioxopiperidin-3-yl)-5-((3-(3-(4-(1-(4-hydroxyphenyl)-2-phenylbut-1-en-1-yl)phenoxy)propoxy)propyl)amino)isoindoline-1,3-dione;
(Z)-2-(2,6-dioxopiperidin-3-yl)-5-((3-(2-(2-(4-(1-(4-hydroxyphenyl)-2-phenylbut-1-en-1-yl)phenoxy)ethoxy)ethoxy)propyl)amino)isoindoline-1,3-dione;

(Z)-2-(2,6-dioxopiperidin-3-yl)-5-((3-(3-(3-(4-(1-(4-hydroxyphenyl)-2-phenylbut-1-en-1-yl)phenoxy)propoxy)propoxy)propyl)amino)isoindoline-1,3-dione;
(Z)-3-(5-((2-(2-(2-(4-(1-(4-hydroxyphenyl)-2-phenylbut-1-en-1-yl)phenoxy)ethoxy)ethoxy)ethyl)amino)-1-oxoisoindolin-2-yl)piperidine-2,6-dione;
(Z)-2-(2,6-dioxopiperidin-3-yl)-5-(3-(3-(2-(4-(1-(4-hydroxyphenyl)-2-phenylbut-1-en-1-yl)phenoxy)ethoxy)propoxy)propoxy)isoindoline-1,3-dione;
(Z)-3-(5-((3-(3-(2-(4-(1-(4-hydroxyphenyl)-2-phenylbut-1-en-1-yl)phenoxy)ethoxy)propoxy)propyl)amino)-1-oxoisoindolin-2-yl)piperidine-2,6-dione;
(Z)-2-(2,6-dioxopiperidin-3-yl)-5-(3-(3-(4-(4-(1-(4-hydroxyphenyl)-2-phenylbut-1-en-1-yl)phenoxy)butoxy)propoxy)propoxy)isoindoline-1,3-dione;
(Z)-2-(2,6-dioxopiperidin-3-yl)-5-((3-(3-(2-(4-(1-(4-hydroxyphenyl)-2-phenylbut-1-en-1-yl)phenoxy)ethoxy)propoxy)propyl)amino)isoindoline-1,3-dione;
(Z)-2-(2,6-dioxopiperidin-3-yl)-5-((3-(3-(4-(4-(1-(4-hydroxyphenyl)-2-phenylbut-1-en-1-yl)phenoxy)butoxy)propoxy)propyl)amino)isoindoline-1,3-dione;
(Z)-3-(5-((3-(3-(4-(4-(1-(4-hydroxyphenyl)-2-phenylbut-1-en-1-yl)phenoxy)butoxy)propoxy)propyl)amino)-1-oxoisoindolin-2-yl)piperidine-2,6-dione;
(Z)-3-(5-((3-(3-(3-(4-(1-(4-hydroxyphenyl)-2-phenylbut-1-en-1-yl)phenoxy)propoxy)propoxy)propyl)amino)-1-oxoisoindolin-2-yl)piperidine-2,6-dione;
(Z)-2-(2,6-dioxopiperidin-3-yl)-5-((3-(4-(2-(4-(1-(4-hydroxyphenyl)-2-phenylbut-1-en-1-yl)phenoxy)ethyl)piperazin-1-yl)propyl)amino)isoindoline-1,3-dione;
(Z)-2-(2,6-dioxopiperidin-3-yl)-5-((3-(4-(2-(4-(1-(4-hydroxyphenyl)-2-phenylbut-1-en-1-yl)phenoxy)ethyl)-1,4-diazepan-1-yl)propyl)amino)isoindoline-1,3-dione;
(E)-2-(2,6-dioxopiperidin-3-yl)-5-((3-(4-(3-(4-(1-(4-hydroxyphenyl)-2-phenylbut-1-en-1-yl)phenyl)propyl)piperazin-1-yl)propyl)amino)isoindoline-1,3-dione;
(E)-2-(2,6-dioxopiperidin-3-yl)-5-((3-(4-(3-(4-(1-(4-hydroxyphenyl)-2-phenylbut-1-en-1-yl)phenyl)propyl)-1,4-diazepan-1-yl)propyl)amino)isoindoline-1,3-dione;
(E)-2-(2,6-dioxopiperidin-3-yl)-5-((3-(4-(4-(1-(4-hydroxyphenyl)-2-phenylbut-1-en-1-yl)phenyl)piperidin-1-yl)propyl)amino)isoindoline-1,3-dione;
(E)-2-(2,6-dioxopiperidin-3-yl)-5-((4-(4-(4-(1-(4-hydroxyphenyl)-2-phenylbut-1-en-1-yl)phenyl)piperidin-1-yl)butyl)amino)isoindoline-1,3-dione;
(E)-3-(5-((3-(4-(3-(4-(1-(4-hydroxyphenyl)-2-phenylbut-1-en-1-yl)phenyl)propyl)piperazin-1-yl)propyl)amino)-1-oxoisoindolin-2-yl)piperidine-2,6-dione;
(E)-3-(5-((3-(4-(3-(4-(1-(4-hydroxyphenyl)-2-phenylbut-1-en-1-yl)phenyl)propyl)-1,4-diazepan-1-yl)propyl)amino)-1-oxoisoindolin-2-yl)piperidine-2,6-dione;
(E)-3-(5-((3-(4-(4-(1-(4-hydroxyphenyl)-2-phenylbut-1-en-1-yl)phenyl)piperidin-1-yl)propyl)amino)-1-oxoisoindolin-2-yl)piperidine-2,6-dione;
(E)-3-(5-((5-(4-(4-(1-(4-hydroxyphenyl)-2-phenylbut-1-en-1-yl)phenyl)piperidin-1-yl)pentyl)amino)-1-oxoisoindolin-2-yl)piperidine-2,6-dione; and
(E)-3-(5-(2-(4-(5-(4-(1-(4-hydroxyphenyl)-2-phenylbut-1-en-1-yl)phenyl)pentyl)-1,4-diazepan-1-yl)ethyl)-1-oxoisoindolin-2-yl)piperidine-2,6-dione.

In some embodiments, provided herein is a compound, or tautomer, stereoisomer, pharmaceutically acceptable salt, or hydrate thereof, chosen from:
(Z)-3-(2-((2-(2-(2,6-dioxopiperidin-3-yl)-1,3-dioxoisoindolin-4-yl)amino)ethoxy)-N-(2-(4-(1,2-diphenylbut-1-en-1-yl)phenoxy)ethyl)-N-methylpropanamide;
(Z)-3-(2-(2-((2-(2,6-dioxopiperidin-3-yl)-1,3-dioxoisoindolin-4-yl)amino)ethoxy)ethoxy)-N-(2-(4-(1,2-diphenylbut-1-en-1-yl)phenoxy)ethyl)-N-methylpropanamide;
(Z)-3-(2-(2-(2-((2-(2,6-dioxopiperidin-3-yl)-1,3-dioxoisoindolin-4-yl)amino)ethoxy)ethoxy)ethoxy)-N-(2-(4-(1,2-diphenylbut-1-en-1-yl)phenoxy)ethyl)-N-methylpropanamide;
(Z)-1-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methyl-3,6,9,12-tetraoxapentadecan-15-amide;
(Z)-1-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methyl-3,6,9,12,15-pentaoxaoctadecan-18-amide;
(Z)-2-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylacetamide;
(Z)-3-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylpropanamide;
(Z)-4-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylbutanamide;
(Z)-6-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylhexanamide;
(Z)-7-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylheptanamide;
(Z)-8-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methyloctanamide;
(Z)-2-(2,6-dioxopiperidin-3-yl)-4-((1-((4-(2-(4-(1-(4-hydroxyphenyl)-2-phenylbut-1-en-1-yl)phenoxy)ethyl)piperazin-1-yl)methyl)piperidin-4-yl)amino)isoindoline-1,3-dione;
(Z)-2-(2,6-dioxopiperidin-3-yl)-4-((1-((1-(2-(4-(1-(4-hydroxyphenyl)-2-phenylbut-1-en-1-yl)phenoxy)ethyl)piperidin-4-yl)methyl)piperidin-4-yl)amino)isoindoline-1,3-dione;
(Z)-3-(4-((1-((1-(2-(4-(1-(4-hydroxyphenyl)-2-phenylbut-1-en-1-yl)phenoxy)ethyl)piperidin-4-yl)methyl)piperidin-4-yl)amino)-1-oxoisoindolin-2-yl)piperidine-2,6-dione;
(Z)-3-(4-((1-((4-(2-(4-(1-(4-hydroxyphenyl)-2-phenylbut-1-en-1-yl)phenoxy)ethyl)piperazin-1-yl)methyl)piperidin-4-yl)amino)-1-oxoisoindolin-2-yl)piperidine-2,6-dione;
(Z)-3-(2-(2-((2-(2,6-dioxopiperidin-3-yl)-1,3-dioxoisoindolin-4-yl)amino)ethoxy)ethoxy)-N-(2-(4-(1,2-diphenylbut-1-en-1-yl)phenoxy)ethyl)-N-methylpropanamide;
(Z)-3-(2-(2-((2-(2,6-dioxopiperidin-3-yl)-1,3-dioxoisoindolin-4-yl)amino)ethoxy)ethoxy)-N-(2-(4-(1-(4-hydroxyphenyl)-2-phenylbut-1-en-1-yl)phenoxy)ethyl)-N-methylpropanamide;
(Z)-1-((2-(2,6-dioxopiperidin-3-yl)-1-oxoisoindolin-4-yl)amino)-N-(2-(4-(1-(4-hydroxyphenyl)-2-phenylbut-1-en-1-yl)phenoxy)ethyl)-N-methyl-3,6,9,12,15-pentaoxaoctadecan-18-amide;
(Z)-1-((2-(2,6-dioxopiperidin-3-yl)-1,3-dioxoisoindolin-4-yl)amino)-N-(2-(4-(1-(4-hydroxyphenyl)-2-phenylbut-1-en-1-yl)phenoxy)ethyl)-N-methyl-3,6,9,12,15-pentaoxaoctadecan-18-amide; and
(Z)-1-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methyl-3,6,9,12,15-pentaoxaoctadecan-18-amide.

In some embodiments, provided herein is a compound, or tautomer, stereoisomer, pharmaceutically acceptable salt, or hydrate thereof, chosen from:

(Z)-3-(2-((2-(2,6-dioxopiperidin-3-yl)-1,3-dioxoisoindolin-4-yl)amino)ethoxy)-N-(2-(4-(1,2-diphenylbut-1-en-1-yl)phenoxy)ethyl)-N-methylpropanamide;

(Z)-3-(2-(2-((2-(2,6-dioxopiperidin-3-yl)-1,3-dioxoisoindolin-4-yl)amino)ethoxy)ethoxy)-N-(2-(4-(1,2-diphenylbut-1-en-1-yl)phenoxy)ethyl)-N-methylpropanamide;

(Z)-3-(2-(2-(2-((2-(2,6-dioxopiperidin-3-yl)-1,3-dioxoisoindolin-4-yl)amino)ethoxy)ethoxy)ethoxy)-N-(2-(4-(1,2-diphenylbut-1-en-1-yl)phenoxy)ethyl)-N-methylpropanamide;

(Z)-1-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methyl-3,6,9,12-tetraoxapentadecan-15-amide;

(Z)-1-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methyl-3,6,9,12,15-pentaoxaoctadecan-18-amide;

(Z)-2-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylacetamide;

(Z)-3-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylpropanamide;

(Z)-4-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylbutanamide;

(Z)-6-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylhexanamide;

(Z)-7-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylheptanamide; and (Z)-8-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methyloctanamide.

In some embodiments, provided herein is a compound, or tautomer, stereoisomer, pharmaceutically acceptable salt, or hydrate thereof, chosen from:

(Z)-3-(2-(2-((2-(2,6-dioxopiperidin-3-yl)-1,3-dioxoisoindolin-4-yl)amino)ethoxy)ethoxy)-N-(2-(4-(1,2-diphenylbut-1-en-1-yl)phenoxy)ethyl)-N-methylpropanamide;

(Z)-1-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methyl-3,6,9,12-tetraoxapentadecan-15-amide;

(Z)-1-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methyl-3,6,9,12,15-pentaoxaoctadecan-18-amide;

(Z)-7-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylheptanamide; and (Z)-8-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methyloctanamide.

In some embodiments, provided herein is a compound, or tautomer, stereoisomer, pharmaceutically acceptable salt, or hydrate thereof, chosen from:

(Z)-2-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylacetamide;

(Z)-3-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylpropanamide;

(Z)-4-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylbutanamide;

(Z)-6-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylhexanamide;

(Z)-7-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylheptanamide; and (Z)-8-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methyloctanamide.

In some embodiments, provided herein is a compound, or tautomer, stereoisomer, pharmaceutically acceptable salt, or hydrate thereof, chosen from:

(Z)-2-(2,6-dioxopiperidin-3-yl)-4-((1-((4-(2-(4-(1-(4-hydroxyphenyl)-2-phenylbut-1-en-1-yl)phenoxy)ethyl)piperazin-1-yl)methyl)piperidin-4-yl)amino)isoindoline-1,3-dione;

(Z)-2-(2,6-dioxopiperidin-3-yl)-4-((1-((1-(2-(4-(1-(4-hydroxyphenyl)-2-phenylbut-1-en-1-yl)phenoxy)ethyl)piperidin-4-yl)methyl)piperidin-4-yl)amino)isoindoline-1,3-dione;

(Z)-3-(4-((1-((1-(2-(4-(1-(4-hydroxyphenyl)-2-phenylbut-1-en-1-yl)phenoxy)ethyl)piperidin-4-yl)methyl)piperidin-4-yl)amino)-1-oxoisoindolin-2-yl)piperidine-2,6-dione; and (Z)-3-(4-((1-((4-(2-(4-(1-(4-hydroxyphenyl)-2-phenylbut-1-en-1-yl)phenoxy)ethyl)piperazin-1-yl)methyl)piperidin-4-yl)amino)-1-oxoisoindolin-2-yl)piperidine-2,6-dione.

In some embodiments, provided herein is a compound, or tautomer, stereoisomer, or pharmaceutically acceptable salt, or hydrate thereof, chosen from:

(Z)-3-(2-((2-(2,6-dioxopiperidin-3-yl)-1,3-dioxoisoindolin-4-yl)amino)ethoxy)-N-(2-(4-(1,2-diphenylbut-1-en-1-yl)phenoxy)ethyl)-N-methylpropanamide;

(Z)-3-(2-(2-((2-(2,6-dioxopiperidin-3-yl)-1,3-dioxoisoindolin-4-yl)amino)ethoxy)ethoxy)-N-(2-(4-(1,2-diphenylbut-1-en-1-yl)phenoxy)ethyl)-N-methylpropanamide;

(Z)-3-(2-(2-((2-(2,6-dioxopiperidin-3-yl)-1,3-dioxoisoindolin-4-yl)amino)ethoxy)ethoxy)-N-(2-(4-(1,2-diphenylbut-1-en-1-yl)phenoxy)ethyl)-N-methylpropanamide;

(Z)-3-(2-(2-((2-(2,6-dioxopiperidin-3-yl)-1,3-dioxoisoindolin-4-yl)amino)ethoxy)ethoxy)-N-(2-(4-(1-(4-hydroxyphenyl)-2-phenylbut-1-en-1-yl)phenoxy)ethyl)-N-methylpropanamide;

(Z)-1-((2-(2,6-dioxopiperidin-3-yl)-1-oxoisoindolin-4-yl)amino)-N-(2-(4-(1-(4-hydroxyphenyl)-2-phenylbut-1-en-1-yl)phenoxy)ethyl)-N-methyl-3,6,9,12,15-pentaoxaoctadecan-18-amide;

(Z)-1-((2-(2,6-dioxopiperidin-3-yl)-1,3-dioxoisoindolin-4-yl)amino)-N-(2-(4-(1-(4-hydroxyphenyl)-2-phenylbut-1-en-1-yl)phenoxy)ethyl)-N-methyl-3,6,9,12,15-pentaoxaoctadecan-18-amide; and (Z)-1-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methyl-3,6,9,12,15-pentaoxaoctadecan-18-amide.

In some embodiments, provided herein is a compound, or tautomer, stereoisomer, or pharmaceutically acceptable salt, or hydrate thereof, chosen from:

(Z)-3-(8-((2-(4-(2-(4-(1-(4-hydroxyphenyl)-2-phenylbut-1-en-1-yl)phenoxy)ethyl)piperazin-1-yl)ethyl)amino)-2-methyl-4-oxoquinazolin-3(4H)-yl)piperidine-2,6-dione; and (Z)-3-(8-(2-(4-(2-(4-(1-(4-hydroxyphenyl)-2-phenylbut-1-en-1-yl)phenoxy)ethyl)piperazin-1-yl)ethoxy)-2-methyl-4-oxoquinazolin-3(4H)-yl)piperidine-2,6-dione.

In some embodiments, provided herein is a pharmaceutically acceptable salt of a compound of Formula (I), or (II). In some embodiments, provided herein is a compound of Formula (I), or (II).

In some embodiments, provided herein is a compound, or pharmaceutically acceptable salt thereof, chosen from the compounds listed in Table 1.

TABLE 1

Exemplary Compound of the Present Disclosure

| # | Structure | IUPAC Name |
|---|-----------|------------|
| 1 | 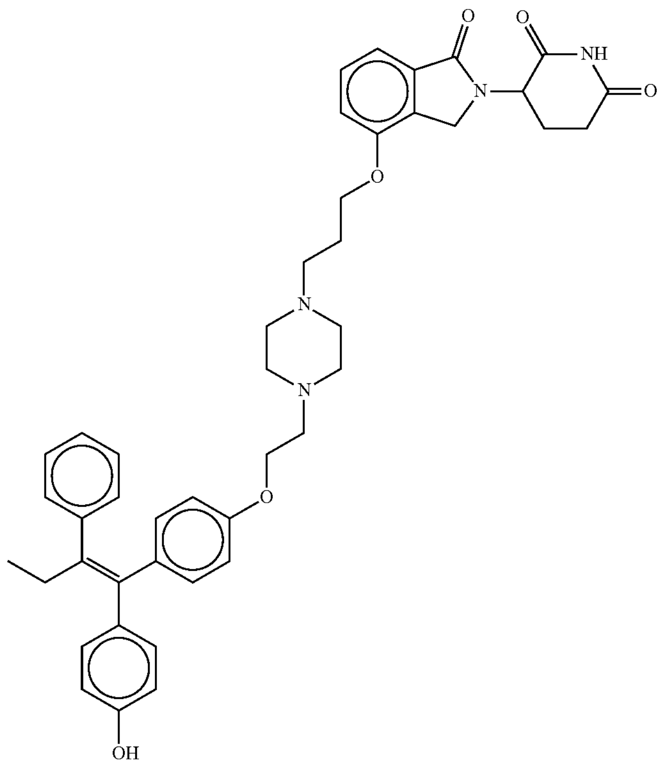 | (Z)-3-(4-(3-(4-(2-(4-(1-(4-hydroxyphenyl)-2-phenylbut-1-en-1-yl)phenoxy)ethyl)piperazin-1-yl)propoxy)-1-oxoisoindolin-2-yl)piperidine-2,6-dione |

TABLE 1-continued
Exemplary Compound of the Present Disclosure
| # | Structure | IUPAC Name |
|---|---|---|
| 2 | 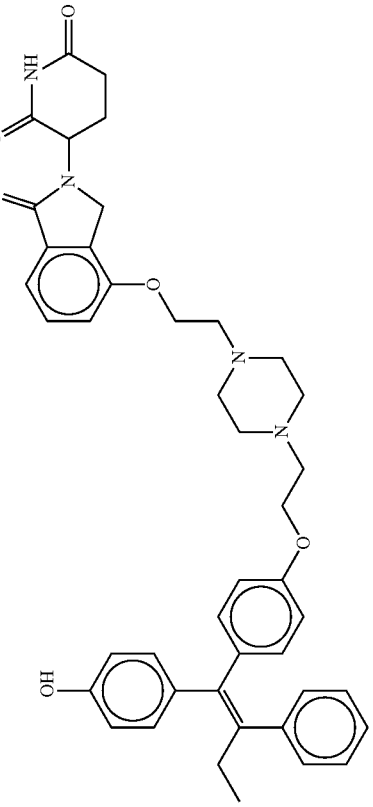 | (Z)-3-(4-(2-(4-(2-(4-(1-(4-hydroxyphenyl)-2-phenylbut-1-en-1-yl)phenoxy)ethyl)piperazin-1-yl)ethoxy)-1-oxoisoindolin-2-yl)piperidine-2,6-dione |
| 3 | 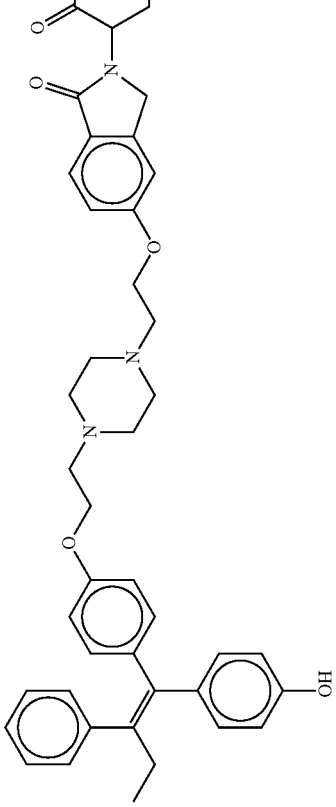 | (Z)-3-(5-(2-(4-(2-(4-(1-(4-hydroxyphenyl)-2-phenylbut-1-en-1-yl)phenoxy)ethyl)piperazin-1-yl)ethoxy)-1-oxoisoindolin-2-yl)piperidine-2,6-dione |

TABLE 1-continued

Exemplary Compound of the Present Disclosure

| # | Structure | IUPAC Name |
|---|---|---|
| 4 | 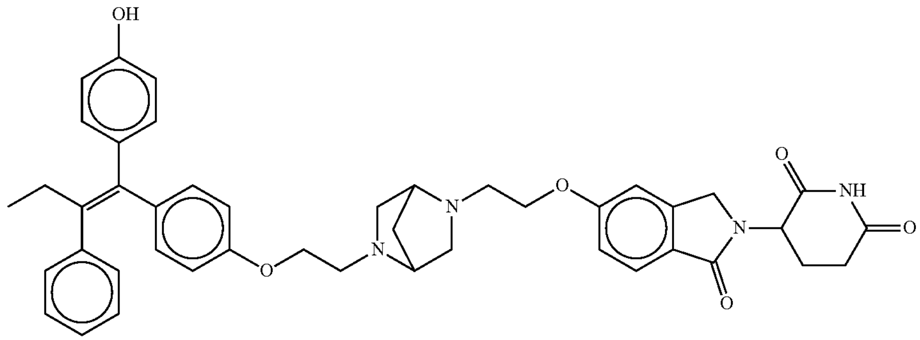 | (Z)-3-(5-(2-(5-(2-(4-(1-(4-hydroxyphenyl)-2-phenylbut-1-en-1-yl)phenoxy)ethyl)-2,5-diazabicyclo[2.2.1]heptan-2-yl)ethoxy)-1-oxoisoindolin-2-yl)piperidine-2,6-dione |
| 5 | 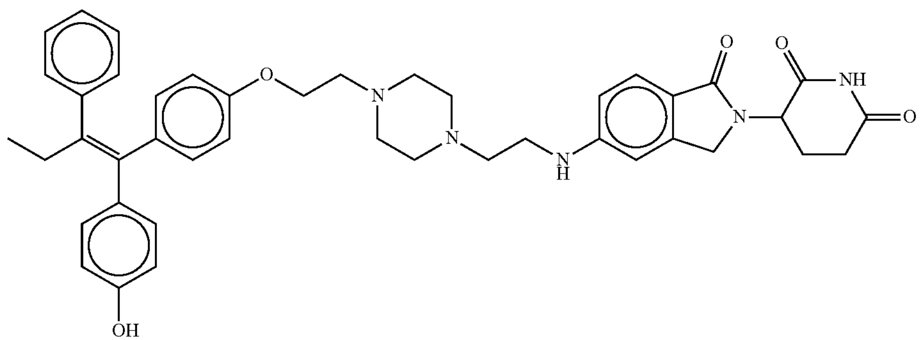 | (Z)-3-(5-((2-(4-(2-(4-(1-(4-hydroxyphenyl)-2-phenylbut-1-en-1-yl)phenoxy)ethyl)piperazin-1-yl)ethyl)amino)-1-oxoisoindolin-2-yl)piperidine-2,6-dione |
| 6 | 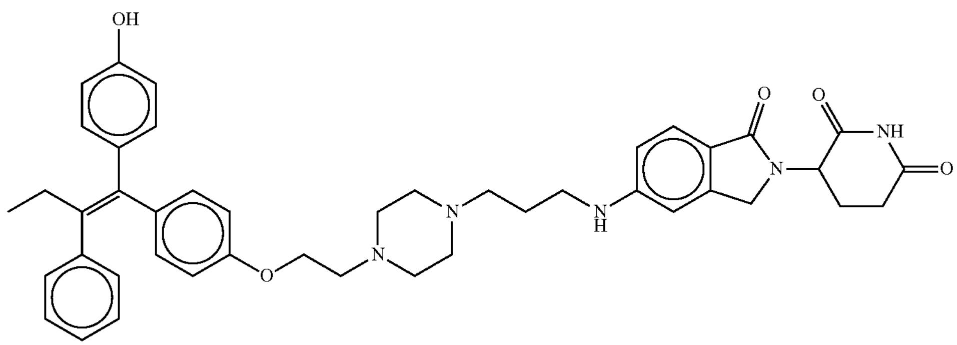 | (Z)-3-(5-((3-(4-(2-(4-(1-(4-hydroxyphenyl)-2-phenylbut-1-en-1-yl)phenoxy)ethyl)piperazin-1-yl)propyl)amino)-1-oxoisoindolin-2-yl)piperidine-2,6-dione |

TABLE 1-continued
Exemplary Compound of the Present Disclosure
| # | Structure | IUPAC Name |
|---|---|---|
| 7 | 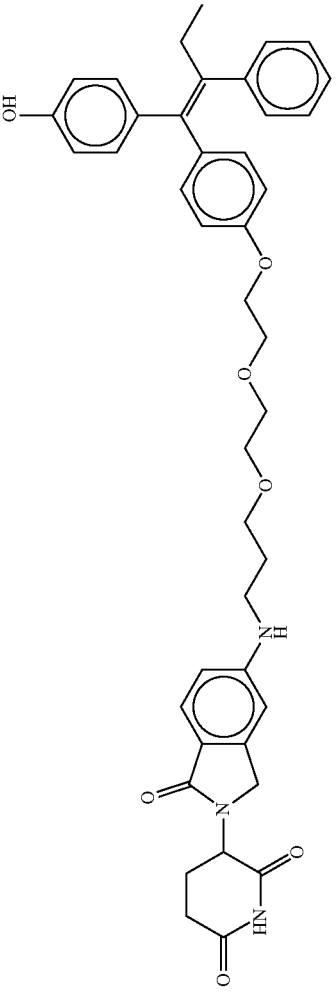 | (Z)-3-(5-((3-(2-(2-(4-(1-(4-hydroxyphenyl)-2-phenylbut-1-en-1-yl)phenoxy)ethoxy)ethoxy)propyl)amino)-1-oxoisoindolin-2-yl)piperidine-2,6-dione |
| 8 | 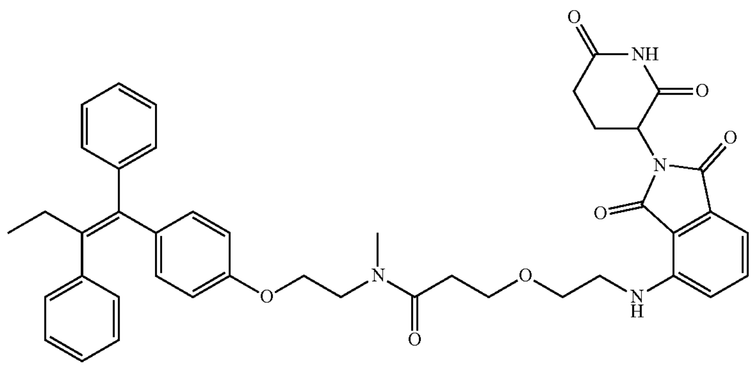 [SMILES: CC/C(=C(\c1ccccc1)c1ccc(OCCN(C)C(=O)CCOCCNc2cccc3c2C(=O)N(C2CCC(=O)NC2=O)C3=O)cc1)c1ccccc1] | (Z)-3-(2-((2-(2,6-dioxopiperidin-3-yl)-1,3-dioxoisoindolin-4-yl)amino)ethoxy)-N-(2-(4-(1,2-diphenylbut-1-en-1-yl)phenoxy)ethyl)-N-methylpropanamide |

TABLE 1-continued

Exemplary Compound of the Present Disclosure

| # | Structure | IUPAC Name |
|---|-----------|------------|
| 9 | 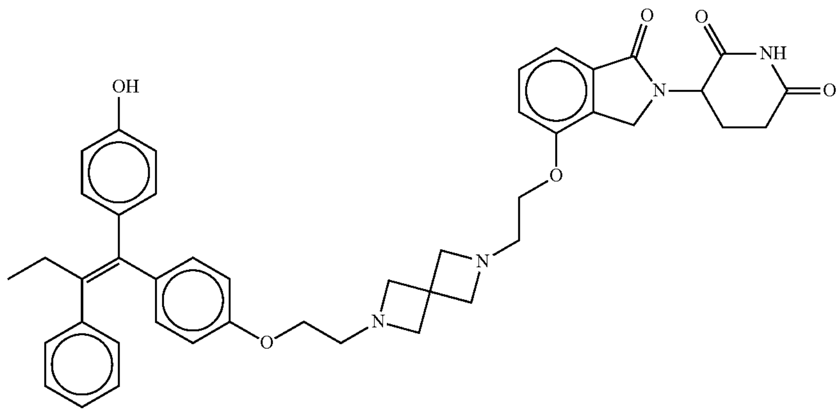 | (Z)-3-(4-(2-(6-(2-(4-(1-(4-hydroxyphenyl)-2-phenylbut-1-en-1-yl)phenoxy)ethyl)-2,6-diazaspiro[3.3]heptan-2-yl)ethoxy)-1-oxoisoindolin-2-yl)piperidine-2,6-dione |
| 10 | 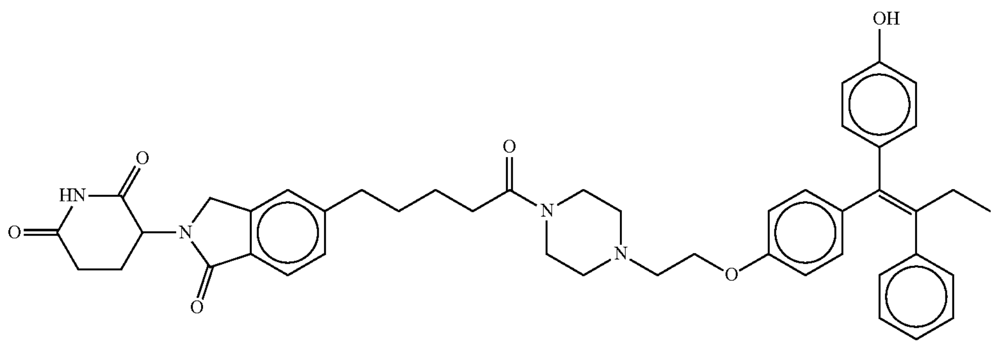 | (Z)-3-(5-(5-(4-(2-(4-(1-(4-hydroxyphenyl)-2-phenylbut-1-en-1-yl)phenoxy)ethyl)piperazin-1-yl)-5-oxopentyl)-1-oxoisoindolin-2-yl)piperidine-2,6-dione |

TABLE 1-continued

Exemplary Compound of the Present Disclosure

| # | Structure | IUPAC Name |
|---|---|---|
| 11 | 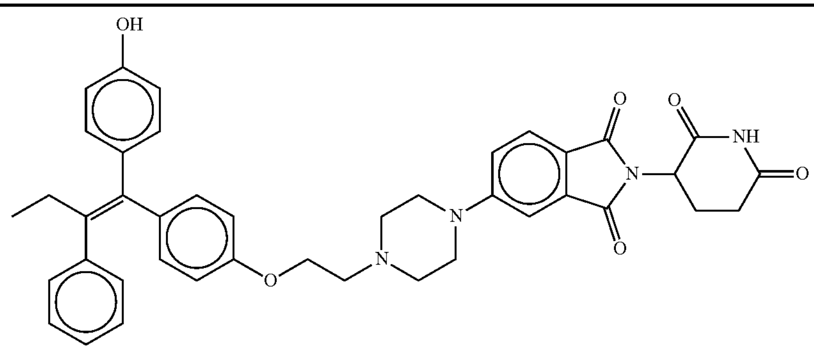 | (Z)-2-(2,6-dioxopiperidin-3-yl)-5-(4-(2-(4-(1-(4-hydroxyphenyl)-2-phenylbut-1-en-1-yl)phenoxy)ethyl)piperazin-1-yl)isoindoline-1,3-dione |
| 12 | 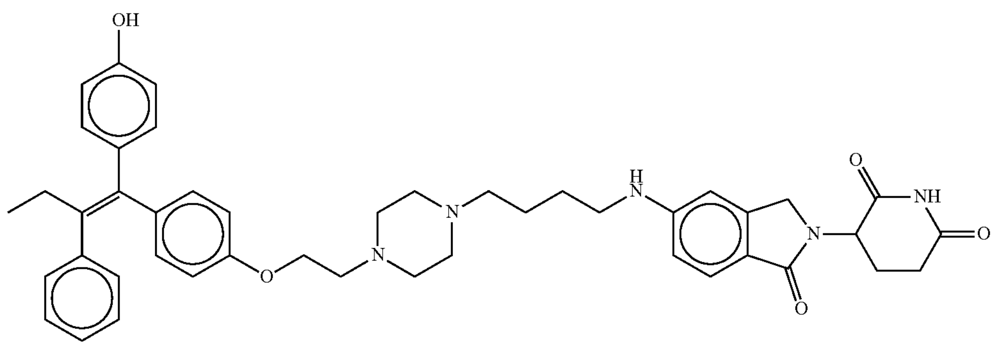 | (Z)-3-(5-((4-(4-(2-(4-(1-(4-hydroxyphenyl)-2-phenylbut-1-en-1-yl)phenoxy)ethyl)piperazin-1-yl)butyl)amino)-1-oxoisoindolin-2-yl)piperidine-2,6-dione |
| 13 | 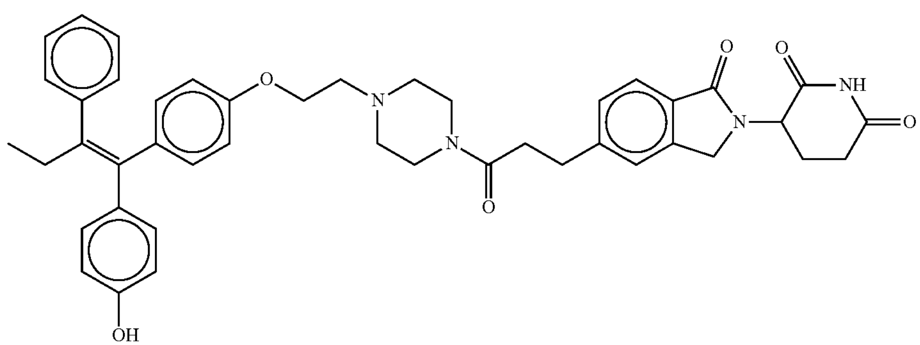 | (Z)-3-(5-(3-(4-(2-(4-(1-(4-hydroxyphenyl)-2-phenylbut-1-en-1-yl)phenoxy)ethyl)piperazin-1-yl)-3-oxopropyl)-1-oxoisoindolin-2-yl)piperidine-2,6-dione |

TABLE 1-continued

Exemplary Compound of the Present Disclosure

| # | Structure | IUPAC Name |
|---|---|---|
| 14 | 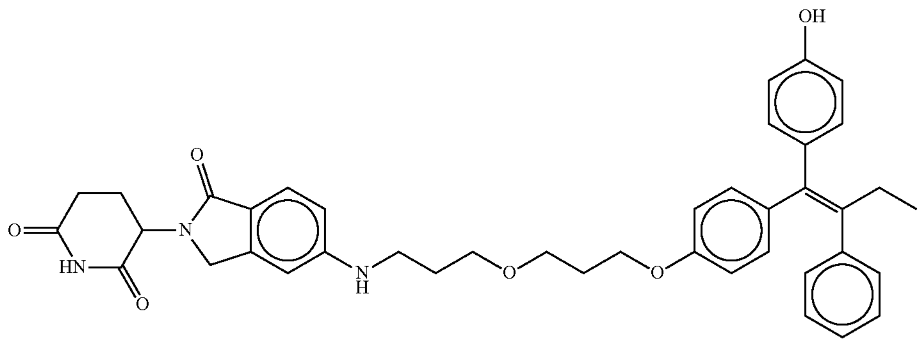 | (Z)-3-(5-((3-(3-(4-(1-(4-hydroxyphenyl)-2-phenylbut-1-en-1-yl)phenoxy)propoxy)propyl)amino)-1-oxoisoindolin-2-yl)piperidine-2,6-dione |
| 15 | 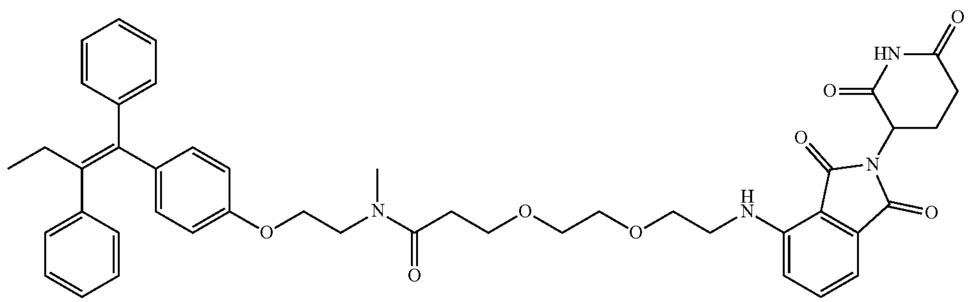 [SMILES: CC/C(=C(\c1ccccc1)c1ccc(OCCN(C)C(=O)CCOCCOCCNc2cccc3c2C(=O)N(C2CCC(=O)NC2=O)C3=O)cc1)c1ccccc1] | (Z)-3-(2-(2-((2-(2,6-dioxopiperidin-3-yl)-1,3-dioxoisoindolin-4-yl)amino)ethoxy)ethoxy)-N-(2-(4-(1,2-diphenylbut-1-en-1-yl)phenoxy)ethyl)-N-methylpropanamide |
| 16a | 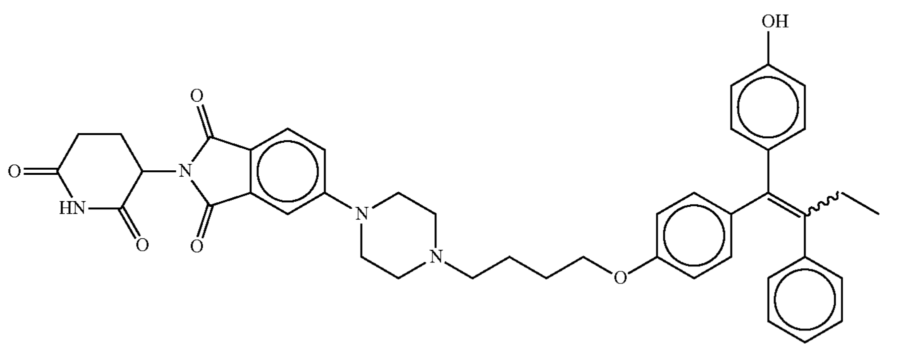 | (E)/(Z)-2-(2,6-dioxopiperidin-3-yl)-5-(4-(4-(1-(4-hydroxyphenyl)-2-phenylbut-1-en-1-yl)phenoxy)butyl)piperazin-1-yl)isoindoline-1,3-dione |

TABLE 1-continued

Exemplary Compound of the Present Disclosure

| # | Structure | IUPAC Name |
|---|-----------|------------|
| 16 | 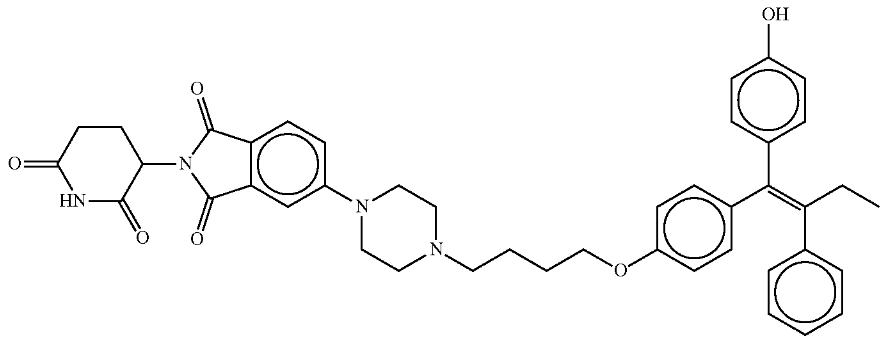 | (Z)-2-(2,6-dioxopiperidin-3-yl)-5-(4-(4-(1-(4-hydroxyphenyl)-2-phenylbut-1-en-1-yl)phenoxy)butyl)piperazin-1-yl)isoindoline-1,3-dione |
| 17a | 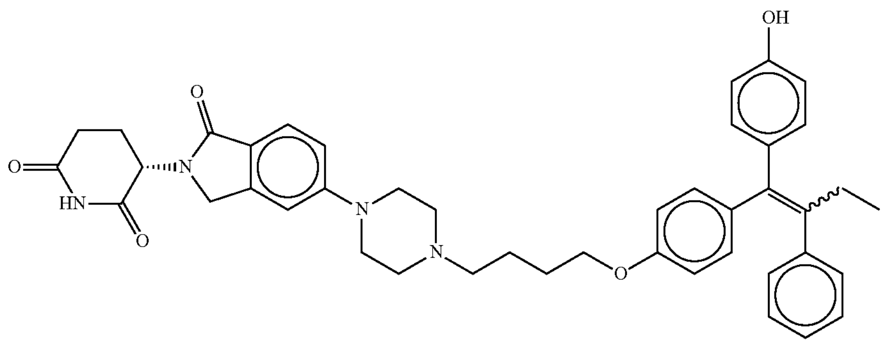 | (E)/(Z)-(S)-3-(5-(4-(4-(1-(4-hydroxyphenyl)-2-phenylbut-1-en-1-yl)phenoxy)butyl)piperazin-1-yl)-1-oxoisoindolin-2-yl)piperidine-2,6-dione |
| 17 | 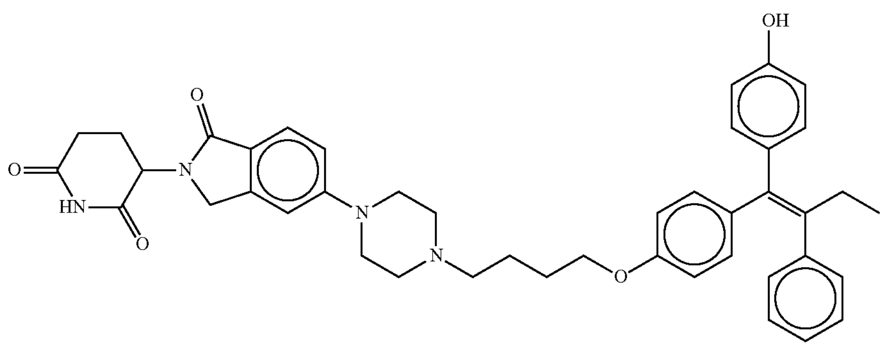 | (Z)-3-(5-(4-(4-(1-(4-hydroxyphenyl)-2-phenylbut-1-en-1-yl)phenoxy)butyl)piperazin-1-yl)-1-oxoisoindolin-2-yl)piperidine-2,6-dione |

TABLE 1-continued

Exemplary Compound of the Present Disclosure

| # | Structure | IUPAC Name |
|---|---|---|
| 18 | 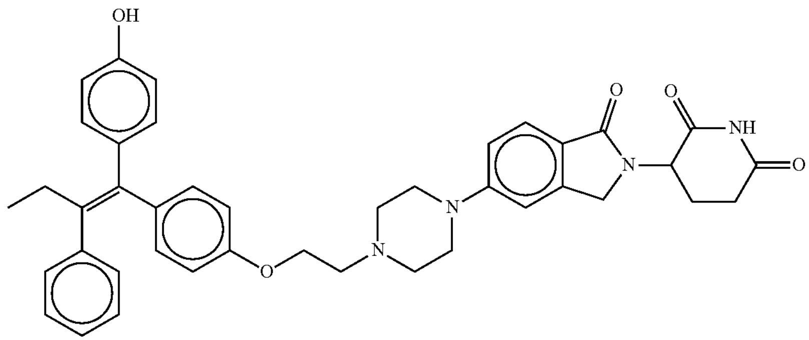 | (Z)-3-(5-(4-(2-(4-(1-(4-hydroxyphenyl)-2-phenylbut-1-en-1-yl)phenoxy)ethyl)piperazin-1-yl)-1-oxoisoindolin-2-yl)piperidine-2,6-dione |
| 19 | 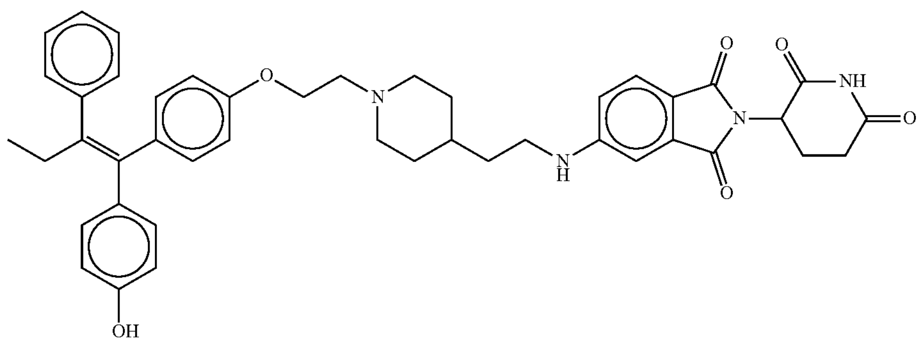 | (Z)-2-(2,6-dioxopiperidin-3-hydroxyphenyl)-2-phenylbut-1-en-1-yl)phenoxy)ethyl)piperidin-4-yl)ethyl)amino)isoindoline-1,3-dione |

TABLE 1-continued

Exemplary Compound of the Present Disclosure

| # | Structure | IUPAC Name |
|---|---|---|
| 20 | 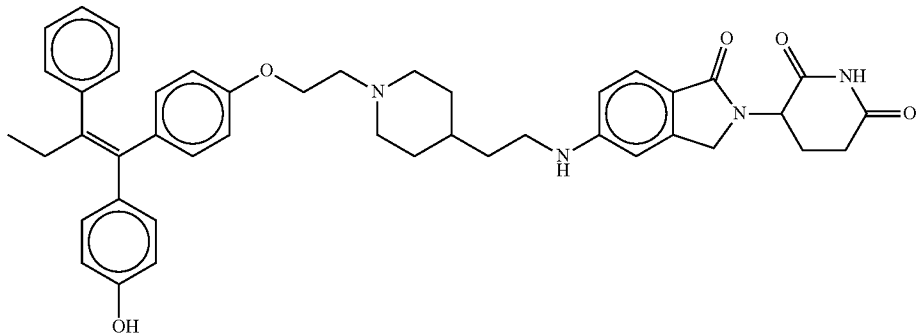 | (Z)-3-(5-((2-(1-(2-(4-(1-(4-hydroxyphenyl)-2-phenylbut-1-en-1-yl)phenoxy)ethyl)piperidin-4-yl)ethyl)amino)-1-oxoisoindolin-2-yl)piperidine-2,6-dione |
| 21 | 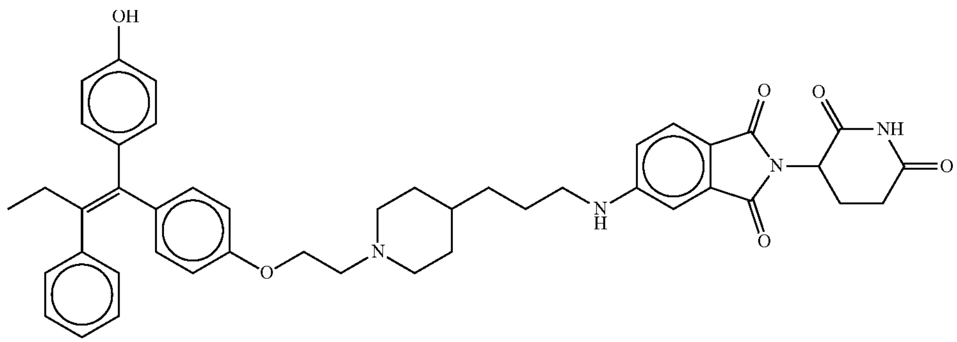 | (Z)-2-(2,6-dioxopiperidin-3-yl)-5-((3-(1-(2-(4-(1-(4-hydroxyphenyl)-2-phenylbut-1-en-1-yl)phenoxy)ethyl)piperidin-4-yl)propyl)amino)isoindoline-1,3-dione |
| 22 | 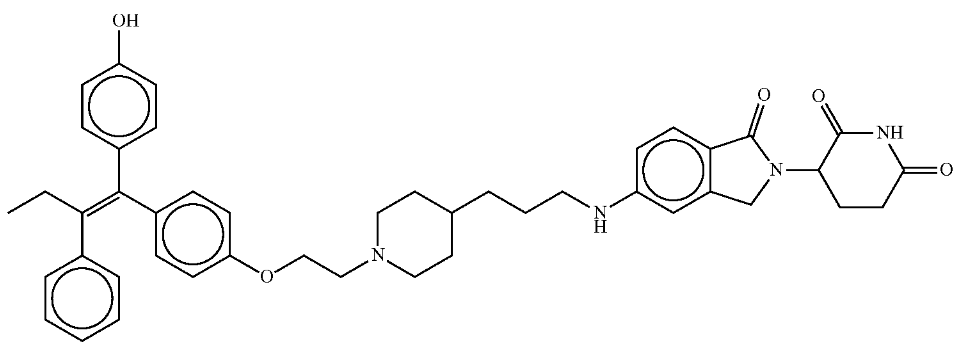 | (Z)-3-(5-((3-(1-(2-(4-(1-(4-hydroxyphenyl)-2-phenylbut-1-en-1-yl)phenoxy)ethyl)piperidin-4-yl)propyl)amino)-1-oxoisoindolin-2-yl)piperidine-2,6-dione |

TABLE 1-continued

Exemplary Compound of the Present Disclosure

| # | Structure | IUPAC Name |
|---|-----------|------------|
| 23 | | (Z)-2-(2,6-dioxopiperidin-3-yl)-5-((1-(2-(4-(1-(4-hydroxyphenyl)-2-phenylbut-1-en-1-yl)phenoxy)ethyl)piperidin-4-yl)methyl)amino)isoindoline-1,3-dione |
| 24 | | (Z)-3-(5-((1-(2-(4-(1-(4-hydroxyphenyl)-2-phenylbut-1-en-1-yl)phenoxy)ethyl)piperidin-4-yl)amino)-1-oxoisoindolin-2-yl)piperidine-2,6-dione |

TABLE 1-continued

Exemplary Compound of the Present Disclosure

| # | Structure | IUPAC Name |
|---|---|---|
| 25 | 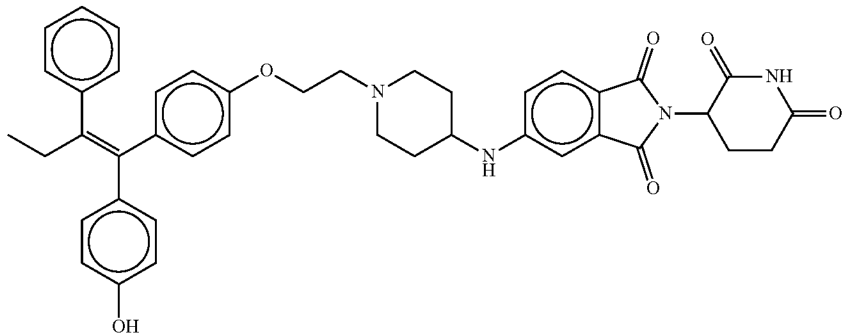 | (Z)-2-(2,6-dioxopiperidin-3-yl)-5-((1-(2-(4-(1-(4-hydroxyphenyl)-2-phenylbut-1-en-1-yl)phenoxy)ethyl)piperidin-4-yl)amino)isoindoline-1,3-dione |
| 26 | 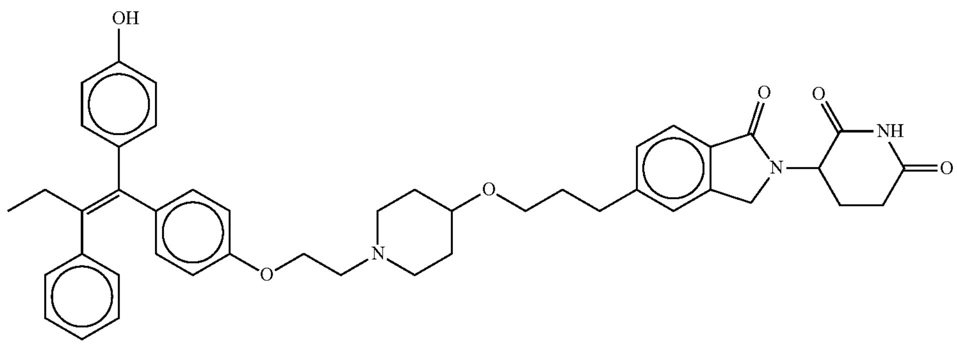 | (Z)-3-(5-(3-((1-(2-(4-(1-(4-hydroxyphenyl)-2-phenylbut-1-en-1-yl)phenoxy)ethyl)piperidin-4-yl)oxy)propyl)-1-oxoisoindolin-2-yl)piperidine-2,6-dione |
| 27 | 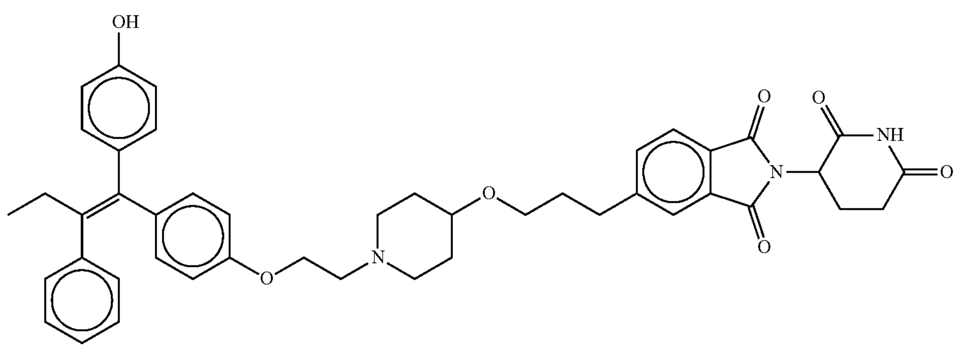 | (Z)-2-(2,6-dioxopiperidin-3-yl)-5-(3-((1-(2-(4-(1-(4-hydroxyphenyl)-2-phenylbut-1-en-1-yl)phenoxy)ethyl)piperidin-4-yl)oxy)propyl)isoindoline-1,3-dione |

TABLE 1-continued
Exemplary Compound of the Present Disclosure
| # | Structure | IUPAC Name |
|---|---|---|
| 28a | 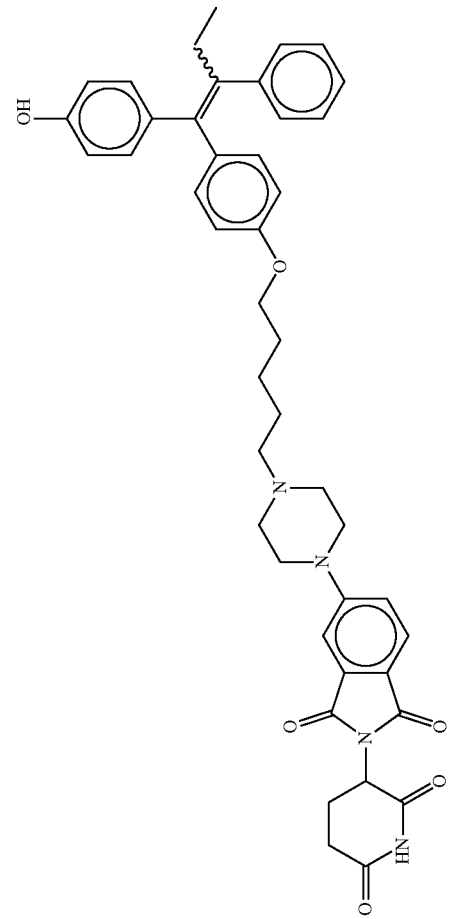 | (E)/(Z)-2-(2,6-dioxopiperidin-3-yl)-5-(4-(5-(4-(1-(4-hydroxyphenyl)-2-phenylbut-1-en-1-yl)phenoxy)pentyl)piperazin-1-yl)isoindoline-1,3-dione |
| 28 | 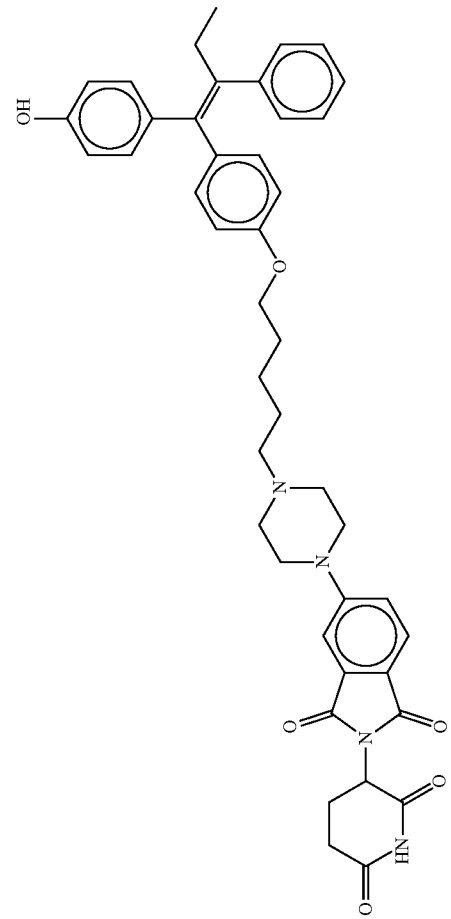 | (Z)-2-(2,6-dioxopiperidin-3-yl)-5-(4-(5-(4-(1-(4-hydroxyphenyl)-2-phenylbut-1-en-1-yl)phenoxy)pentyl)piperazin-1-yl)isoindoline-1,3-dione |

TABLE 1-continued

Exemplary Compound of the Present Disclosure

| # | Structure | IUPAC Name |
|---|---|---|
| 29a | 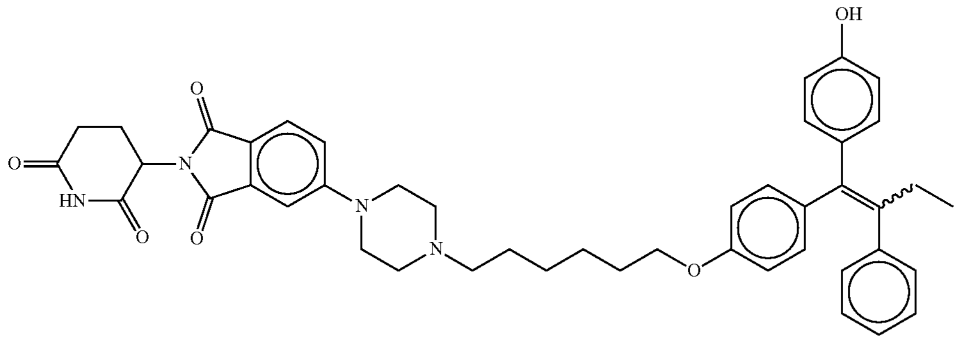 | (E)/(Z)-2-(2,6-dioxopiperidin-3-yl)-5-(4-(6-(4-(1-(4-hydroxyphenyl)-2-phenylbut-1-en-1-yl)phenoxy)hexyl)piperazin-1-yl)isoindoline-1,3-dione |
| 29 | 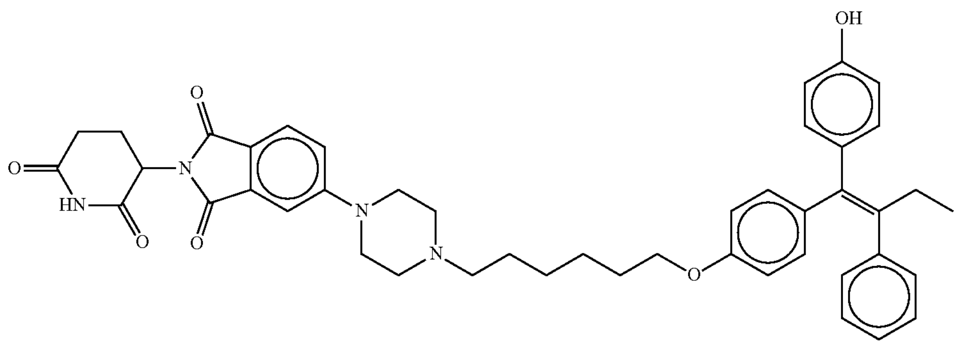 | (Z)-2-(2,6-dioxopiperidin-3-yl)-5-(4-(6-(4-(1-(4-hydroxyphenyl)-2-phenylbut-1-en-1-yl)phenoxy)hexyl)piperazin-1-yl)isoindoline-1,3-dione |
| 30 | 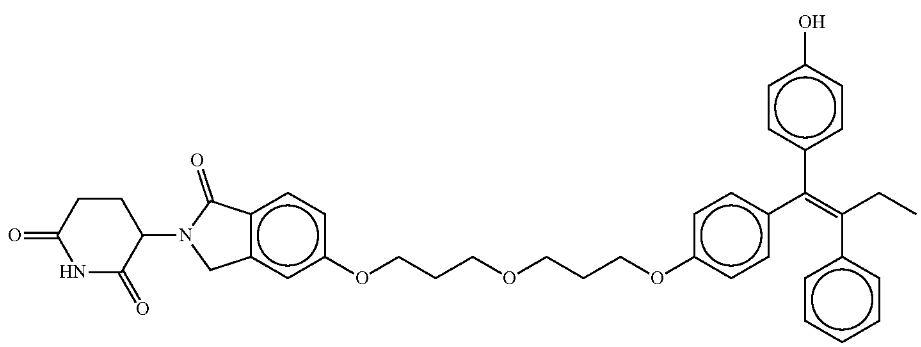 | (Z)-3-(5-(3-(4-(1-(4-hydroxyphenyl)-2-phenylbut-1-en-1-yl)phenoxy)propoxy)-1-oxoisoindolin-2-yl)piperidine-2,6-dione |

TABLE 1-continued
Exemplary Compound of the Present Disclosure
| # | Structure | IUPAC Name |
|---|---|---|
| 31a | 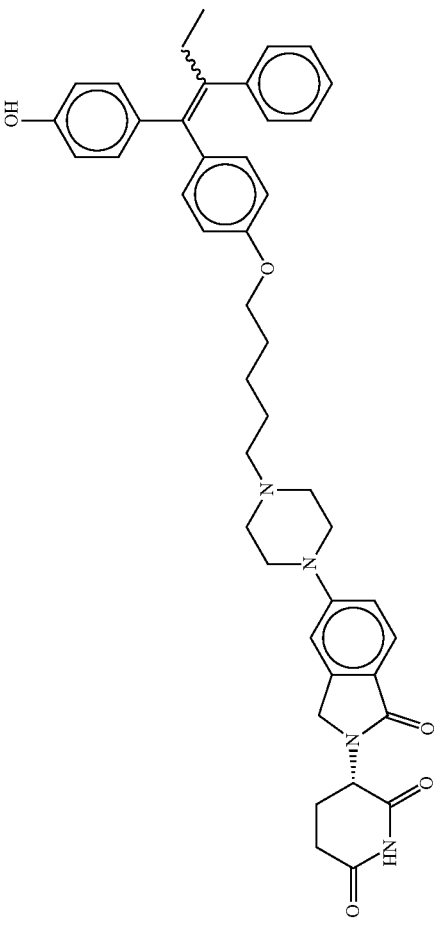 | (E)/(Z)-(S)-3-(5-(4-(5-(4-(1-(4-hydroxyphenyl)-2-phenylbut-1-en-1-yl)phenoxy)pentyl)piperazin-1-yl)-1-oxoisoindolin-2-yl)piperidine-2,6-dione |
| 31 | 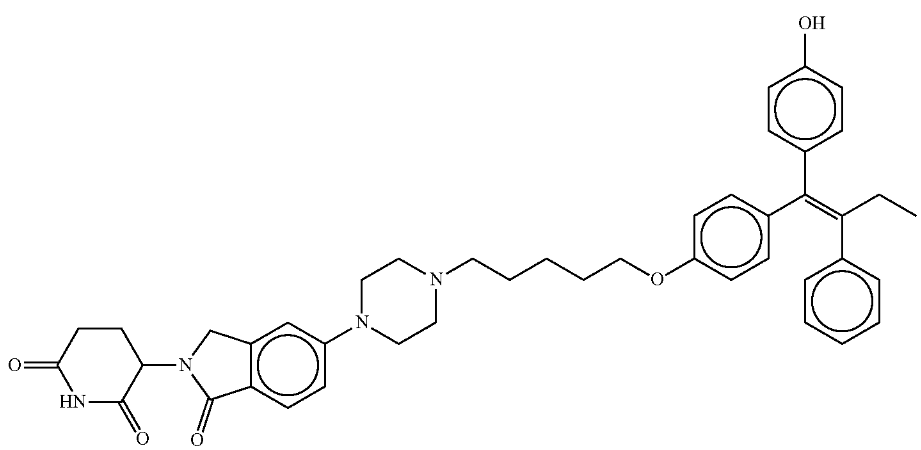 | (Z)-3-(5-(4-(5-(4-(1-(4-hydroxyphenyl)-2-phenylbut-1-en-1-yl)phenoxy)pentyl)piperazin-1-yl)-1-oxoisoindolin-2-yl)piperidine-2,6-dione |

TABLE 1-continued
Exemplary Compound of the Present Disclosure
| # | Structure | IUPAC Name |
|---|---|---|
| 32a | 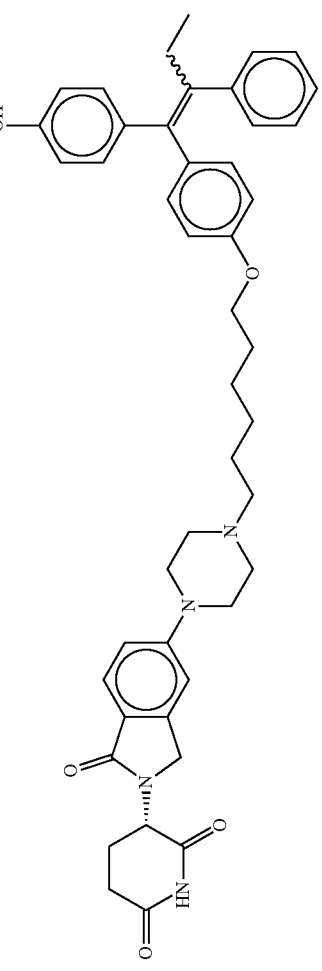 | (E)/(Z)-(S)-3-(5-(4-(6-(4-(1-(4-hydroxyphenyl)-2-phenylbut-1-en-1-yl)phenoxy)hexyl)piperazin-1-yl)-1-oxoisoindolin-2-yl)piperidine-2,6-dione |
| 32 | 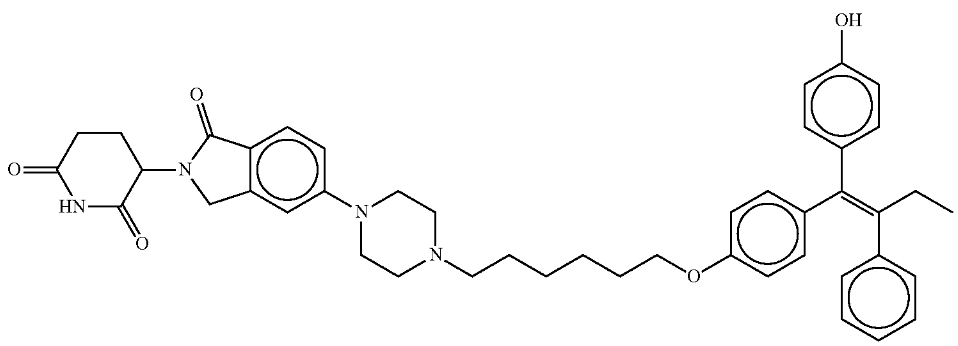 | (Z)-3-(5-(4-(6-(4-(1-(4-hydroxyphenyl)-2-phenylbut-1-en-1-yl)phenoxy)hexyl)piperazin-1-yl)-1-oxoisoindolin-2-yl)piperidine-2,6-dione |

TABLE 1-continued
Exemplary Compound of the Present Disclosure
| # | Structure | IUPAC Name |
|---|---|---|
| 33 | 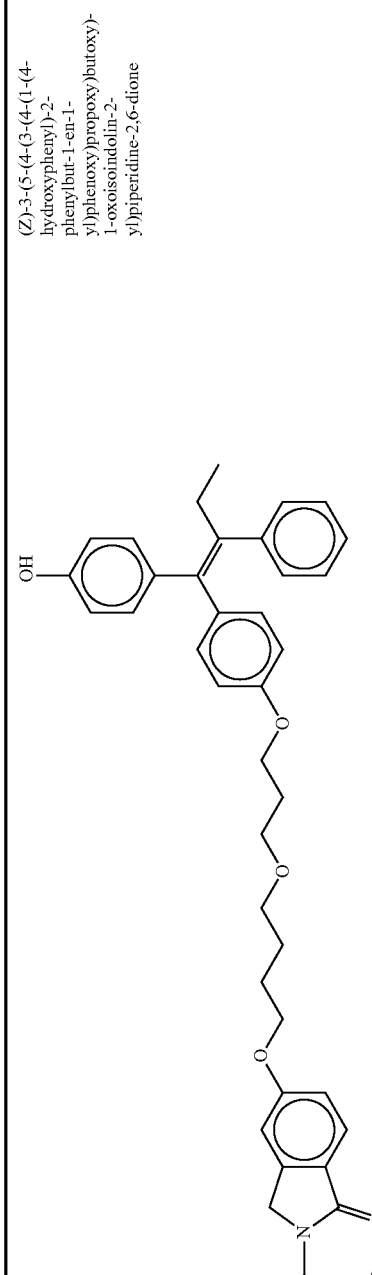 | (Z)-3-(5-(4-(3-(4-(1-(4-hydroxyphenyl)-2-phenylbut-1-en-1-yl)phenoxy)propoxy)butoxy)-1-oxoisoindolin-2-yl)piperidine-2,6-dione |
| 34 | 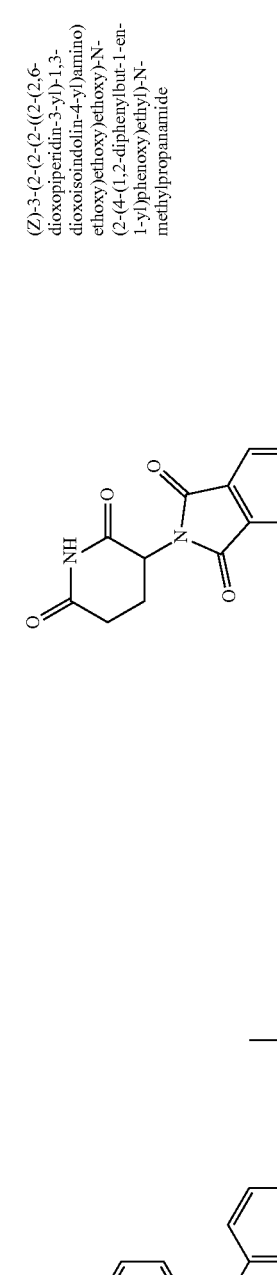 | (Z)-3-(2-(2-(2-((2-(2,6-dioxopiperidin-3-yl)-1,3-dioxoisoindolin-4-yl)amino)ethoxy)ethoxy)ethoxy)-N-(2-(4-(1,2-diphenylbut-1-en-1-yl)phenoxy)ethyl)-N-methylpropanamide |

TABLE 1-continued
Exemplary Compound of the Present Disclosure
| # | Structure | IUPAC Name |
|---|-----------|------------|
| 35 | 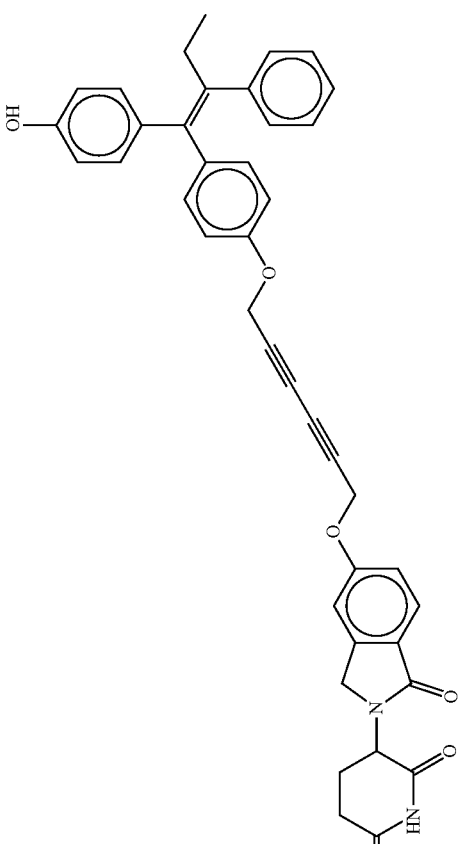 | (Z)-3-(5-((6-(4-(1-(4-hydroxyphenyl)-2-phenylbut-1-en-1-yl)phenoxy)hexa-2,4-diyn-1-yl)oxy)-1-oxoisoindolin-2-yl)piperidine-2,6-dione |
| 36 | 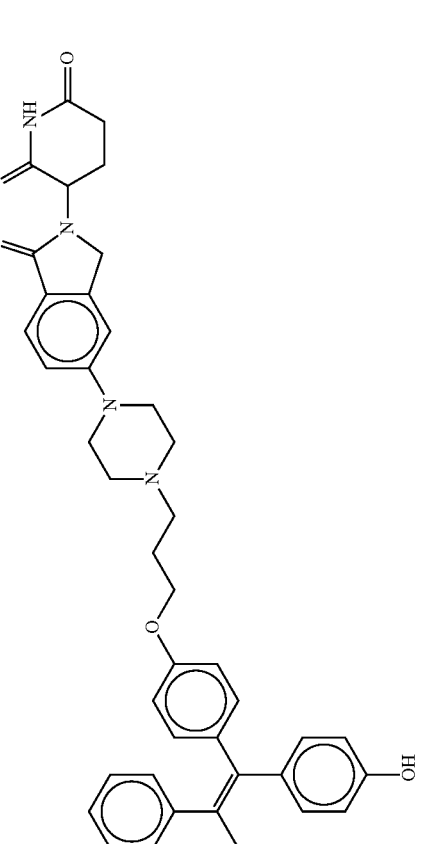 | (Z)-3-(5-(4-(3-(4-(1-(4-hydroxyphenyl)-2-phenylbut-1-en-1-yl)phenoxy)propyl)piperazin-1-yl)-1-oxoisoindolin-2-yl)piperidine-2,6-dione |

TABLE 1-continued
Exemplary Compound of the Present Disclosure
| # | Structure | IUPAC Name |
|---|---|---|
| 37 | 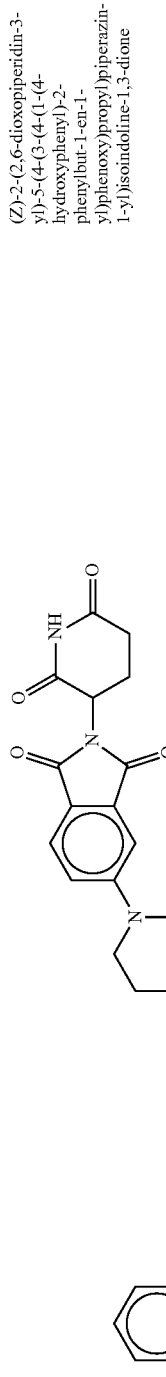 | (Z)-2-(2,6-dioxopiperidin-3-yl)-5-(4-(3-(4-(1-(4-hydroxyphenyl)-2-phenylbut-1-en-1-yl)phenoxy)propyl)piperazin-1-yl)isoindoline-1,3-dione |
| 38 | 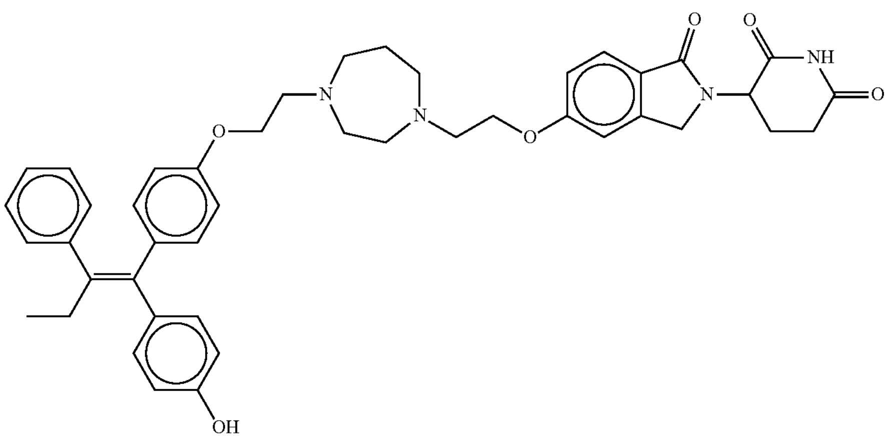 | (Z)-3-(5-(2-(4-(2-(4-(1-(4-hydroxyphenyl)-2-phenylbut-1-en-1-yl)phenoxy)ethyl)-1,4-diazepan-1-yl)ethoxy)-1-oxoisoindolin-2-yl)piperidine-2,6-dione |

TABLE 1-continued
Exemplary Compound of the Present Disclosure
| # | Structure | IUPAC Name |
|---|-----------|------------|
| 39 | 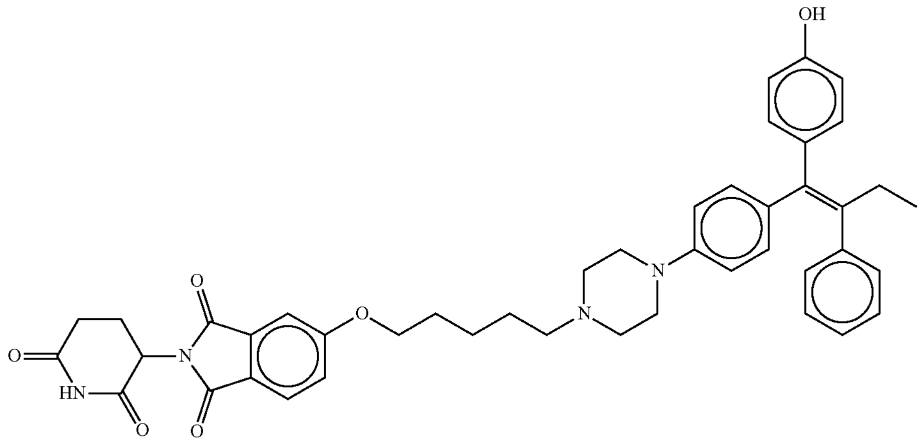 | (E)-2-(2,6-dioxopiperidin-3-yl)-5-((5-(4-(1-(4-hydroxyphenyl)-2-phenylbut-1-en-1-yl)phenyl)piperazin-1-yl)pentyl)oxy)isoindoline-1,3-dione |
| 40 | 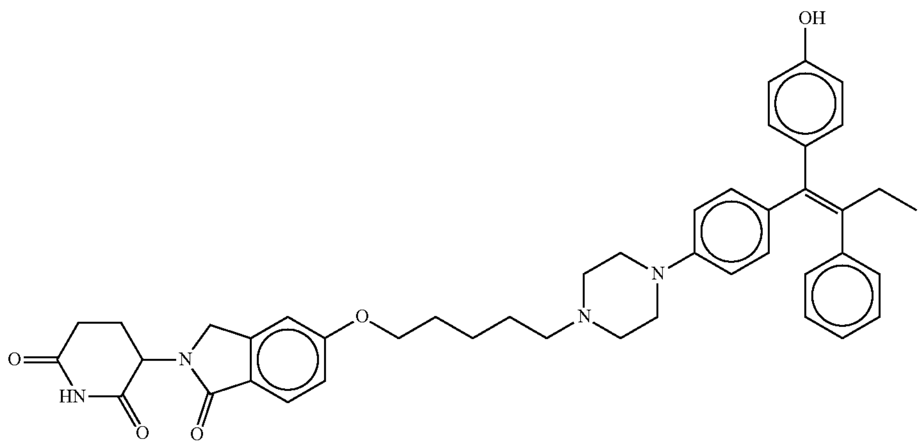 | (E)-3-(5-((5-(4-(1-(4-hydroxyphenyl)-2-phenylbut-1-en-1-yl)phenyl)piperazin-1-yl)pentyl)oxy)-1-oxoisoindolin-2-yl)piperidine-2,6-dione |

TABLE 1-continued
Exemplary Compound of the Present Disclosure
| # | Structure | IUPAC Name |
|---|---|---|
| 41 | 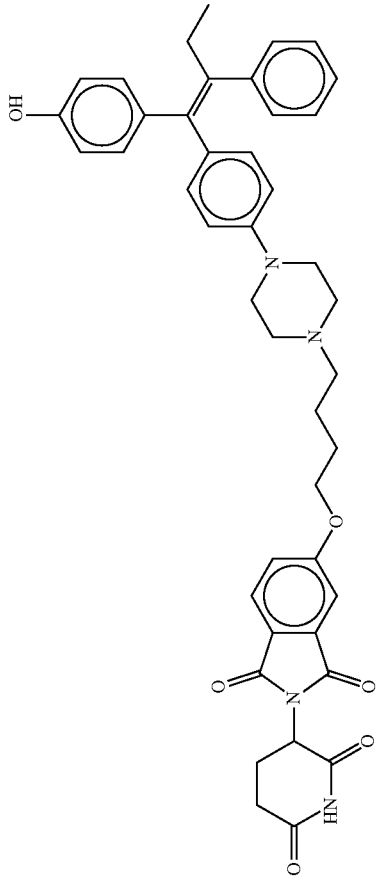 | (E)-2-(2,6-dioxopiperidin-3-yl)-5-(4-(4-(4-(1-(4-hydroxyphenyl)-2-phenylbut-1-en-1-yl)phenyl)piperazin-1-yl)butoxy)isoindoline-1,3-dione |
| 42 | 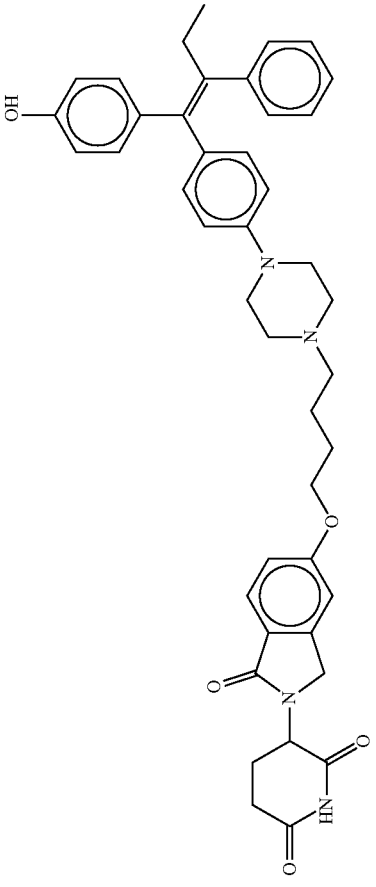 | (E)-3-(5-(4-(4-(4-(1-(4-hydroxyphenyl)-2-phenylbut-1-en-1-yl)phenyl)piperazin-1-yl)butoxy)-1-oxoisoindolin-2-yl)piperidine-2,6-dione |

TABLE 1-continued
Exemplary Compound of the Present Disclosure
| # | Structure | IUPAC Name |
|---|---|---|
| 43 | 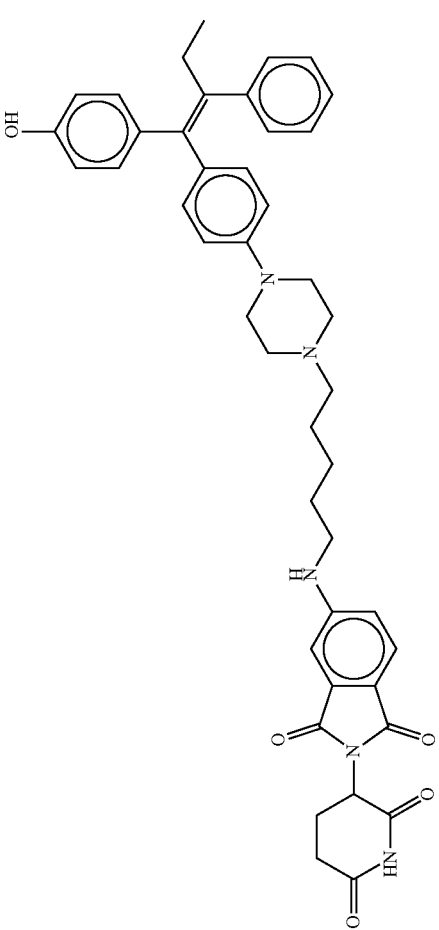 | (E)-2-(2,6-dioxopiperidin-3-yl)-5-((5-(4-(4-(1-(4-hydroxyphenyl)-2-phenylbut-1-en-1-yl)phenyl)piperazin-1-yl)pentyl)amino)isoindoline-1,3-dione |
| 44 | 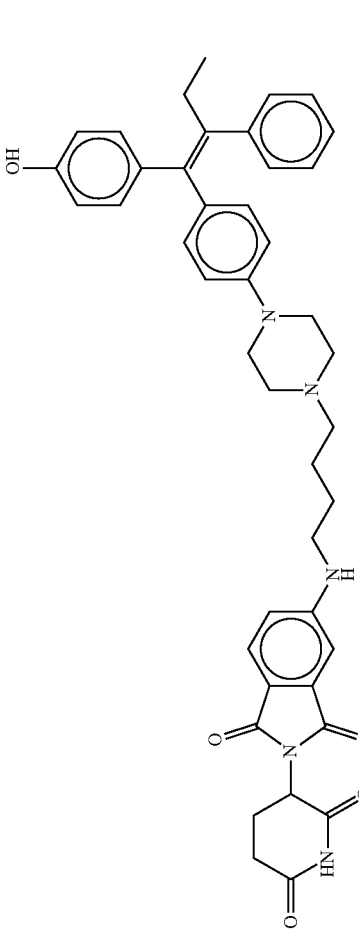 | (E)-2-(2,6-dioxopiperidin-3-yl)-5-((4-(4-(1-(4-hydroxyphenyl)-2-phenylbut-1-en-1-yl)phenyl)piperazin-1-yl)butyl)amino)isoindoline-1,3-dione |

TABLE 1-continued
Exemplary Compound of the Present Disclosure
| # | Structure | IUPAC Name |
|---|---|---|
| 45 | 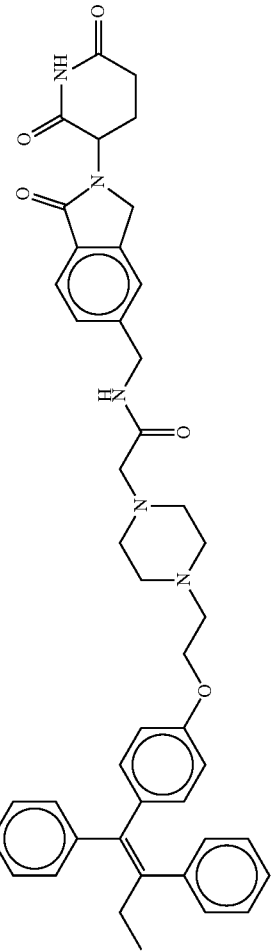 | (Z)-N-((2-(2,6-dioxopiperidin-3-yl)-1-oxoisoindolin-5-yl)methyl)-2-(4-(2-(4-(1-(4-hydroxyphenyl)-2-phenylbut-1-en-1-yl)phenoxy)ethyl)piperazin-1-yl)acetamide |
| 46 | 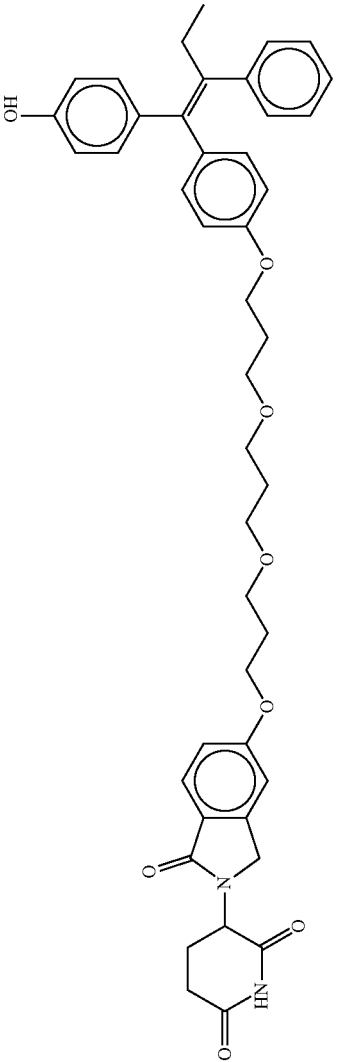 | (Z)-3-(5-(3-(3-(4-(1-(4-hydroxyphenyl)-2-phenylbut-1-en-1-yl)phenoxy)propoxy)propoxy)-1-oxoisoindolin-2-yl)piperidine-2,6-dione |

TABLE 1-continued
Exemplary Compound of the Present Disclosure
| # | Structure | IUPAC Name |
|---|-----------|------------|
| 47 | 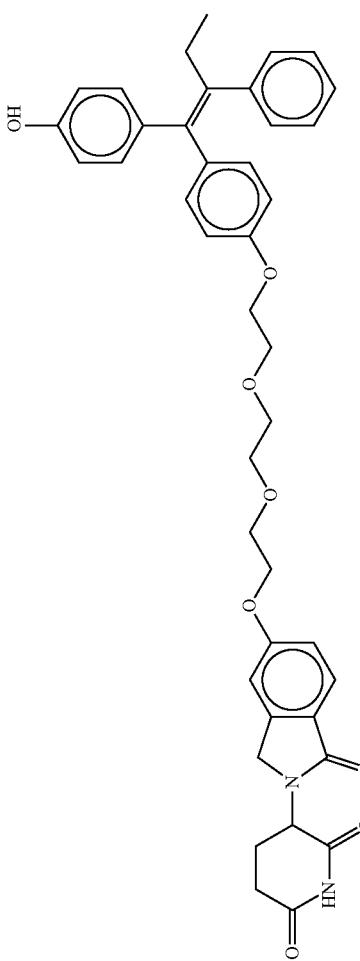 | (Z)-3-(5-(2-(2-(2-(4-(1-(4-hydroxyphenyl)-2-phenylbut-1-en-1-yl)phenoxy)ethoxy)ethoxy)ethoxy)-1-oxoisoindolin-2-yl)piperidine-2,6-dione |
| 48 | 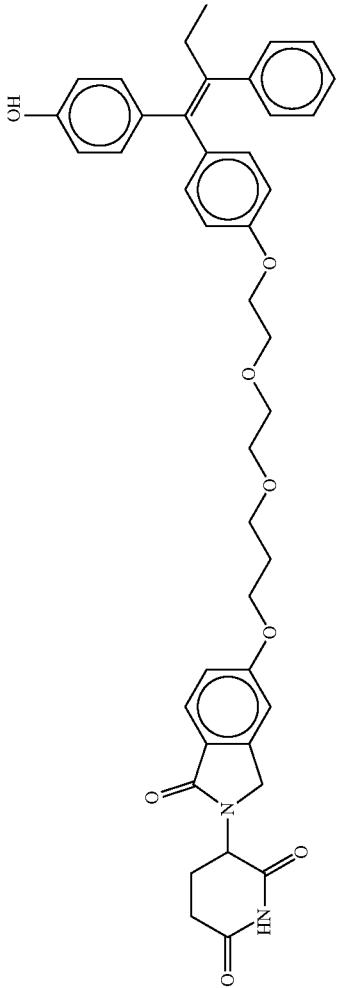 | (Z)-3-(5-(3-(2-(2-(4-(1-(4-hydroxyphenyl)-2-phenylbut-1-en-1-yl)phenoxy)ethoxy)ethoxy)propoxy)-1-oxoisoindolin-2-yl)piperidine-2,6-dione |

TABLE 1-continued
Exemplary Compound of the Present Disclosure
| # | Structure | IUPAC Name |
|---|---|---|
| 49 | 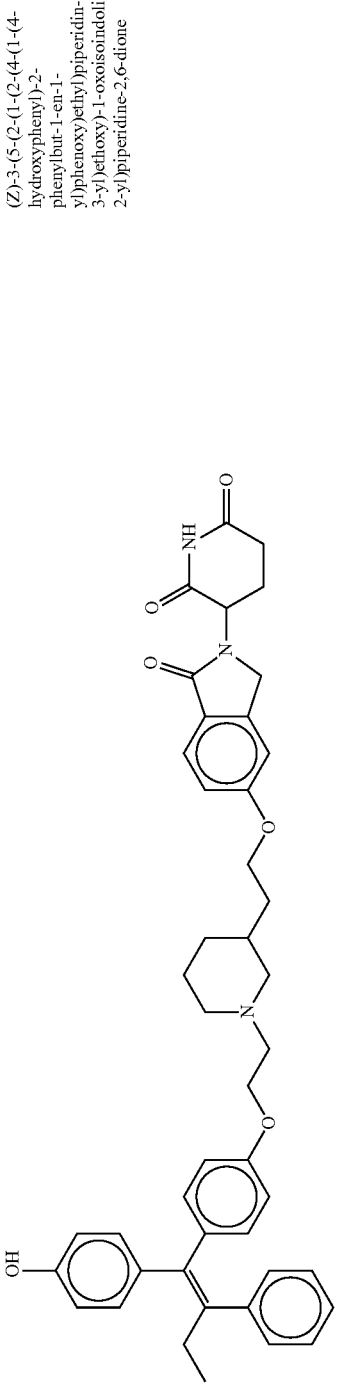 | (Z)-3-(5-(2-(1-(2-(4-(1-(4-hydroxyphenyl)-2-phenylbut-1-en-1-yl)phenoxy)ethyl)piperidin-3-yl)ethoxy)-1-oxoisoindolin-2-yl)piperidine-2,6-dione |
| 50 | 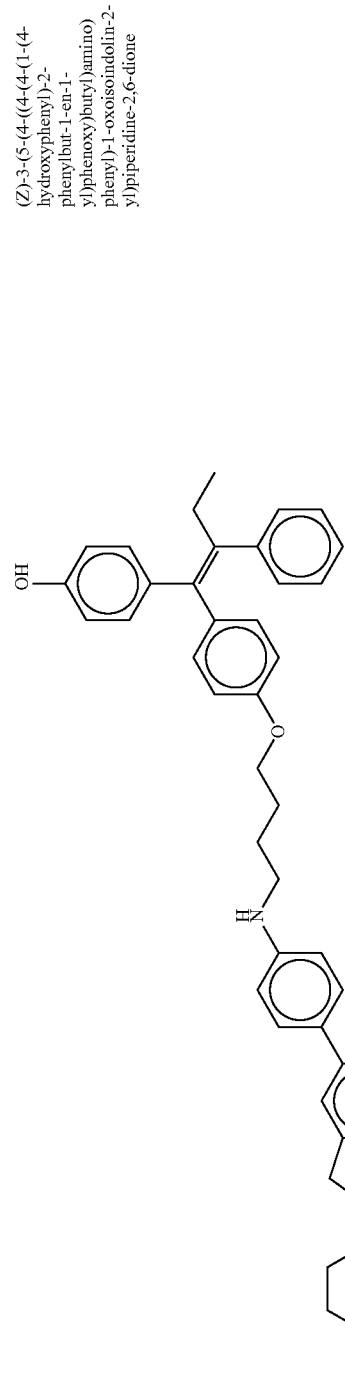 | (Z)-3-(5-(4-((4-(4-(1-(4-hydroxyphenyl)-2-phenylbut-1-en-1-yl)phenoxy)butyl)amino)phenyl)-1-oxoisoindolin-2-yl)piperidine-2,6-dione |

TABLE 1-continued
Exemplary Compound of the Present Disclosure
| # | Structure | IUPAC Name |
|---|---|---|
| 51 | 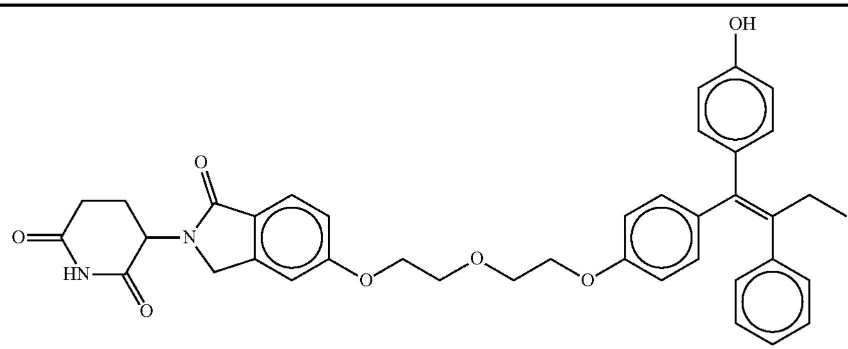 | (Z)-3-(5-(2-(2-(4-(1-(4-hydroxyphenyl)-2-phenylbut-1-en-1-yl)phenoxy)ethoxy)ethoxy)-1-oxoisoindolin-2-yl)piperidine-2,6-dione |
| 52 | 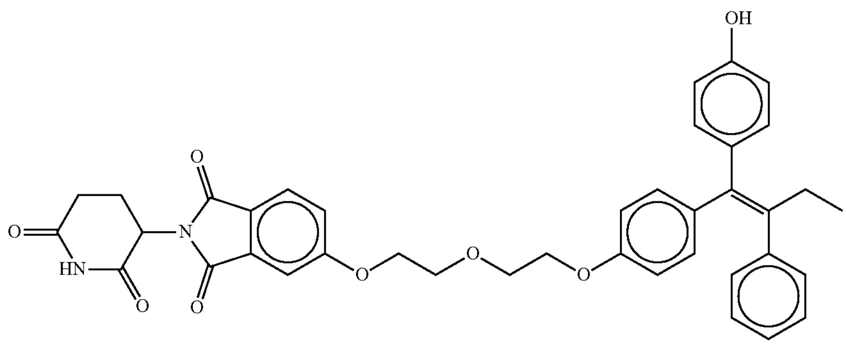 | (Z)-2-(2,6-dioxopiperidin-3-yl)-5-(2-(2-(4-(1-(4-hydroxyphenyl)-2-phenylbut-1-en-1-yl)phenoxy)ethoxy)ethoxy)isoindoline-1,3-dione |

TABLE 1-continued

Exemplary Compound of the Present Disclosure

| # | Structure | IUPAC Name |
|---|---|---|
| 53 | 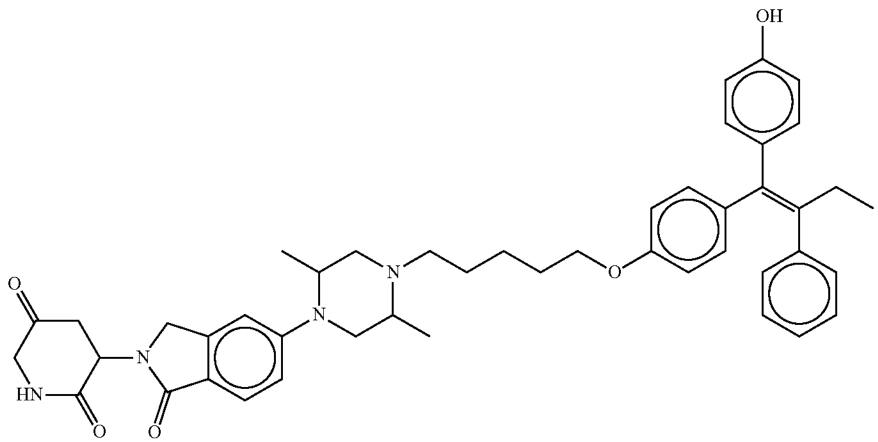 | (Z)-3-(5-(4-(5-(4-(1-(4-hydroxyphenyl)-2-phenylbut-1-en-1-yl)phenoxy)pentyl)-2,5-dimethylpiperazin-1-yl)-1-oxoisoindolin-2-yl)piperidine-2,5-dione |
| 54 | 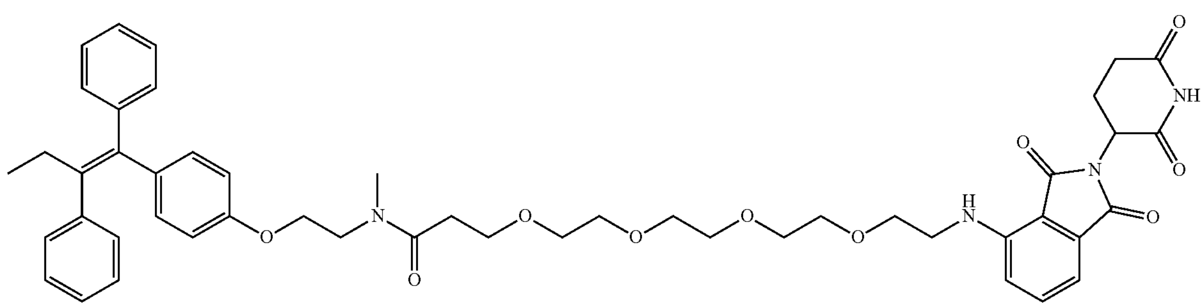 [SMILES: CC/C(=C(\c1ccccc1)c1ccc(OCCN(C)C(=O)CCOCCOCCOCCOCCNc2cccc3c2C(=O)N(C2CCC(=O)NC2=O)C3=O)cc1)c1ccccc1] | (Z)-1-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methyl-3,6,9,12-tetraoxapentadecan-15-amide |

TABLE 1-continued
Exemplary Compound of the Present Disclosure
| # | Structure | IUPAC Name |
|---|---|---|
| 55 | 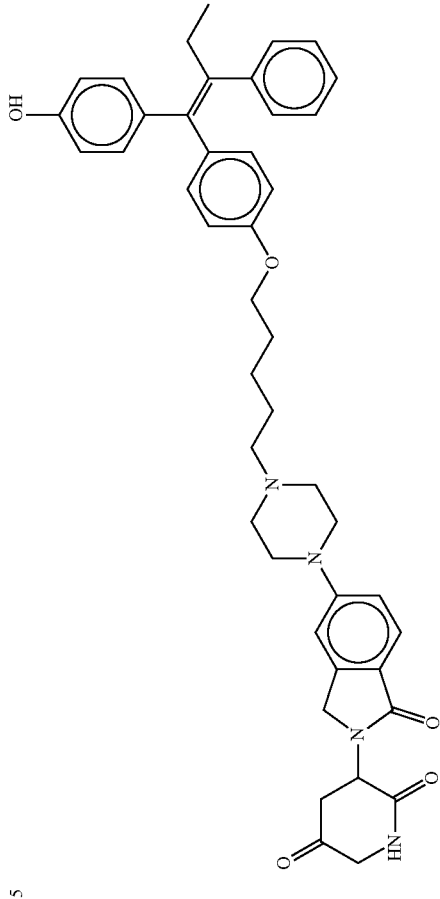 | (Z)-3-(5-(4-(5-(4-(1-(4-hydroxyphenyl)-2-phenylbut-1-en-1-yl)phenoxy)pentyl)piperazin-1-yl)-1-oxoisoindolin-2-yl)piperidine-2,5-dione |
| 56 | 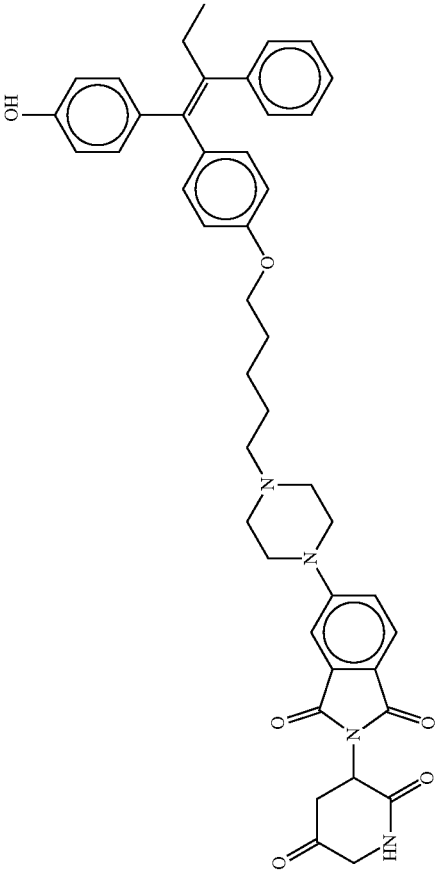 | (Z)-2-(2,5-dioxopiperidin-3-yl)-5-(4-(5-(4-(1-(4-hydroxyphenyl)-2-phenylbut-1-en-1-yl)phenoxy)pentyl)piperazin-1-yl)isoindoline-1,3-dione |

TABLE 1-continued

Exemplary Compound of the Present Disclosure

| # | Structure | IUPAC Name |
|---|---|---|
| 57 | 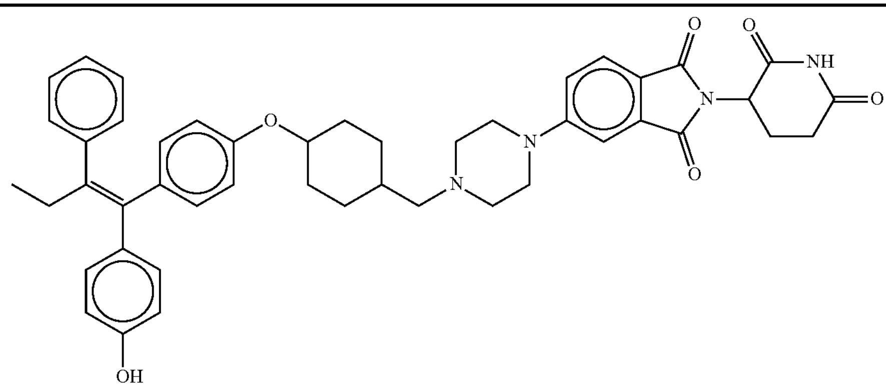 | (Z)-2-(2,6-dioxopiperidin-3-yl)-5-(4-((4-(4-(1-(4-hydroxyphenyl)-2-phenylbut-1-en-1-yl)phenoxy)cyclohexyl)methyl)piperazin-1-yl)isoindoline-1,3-dione |
| 58 | 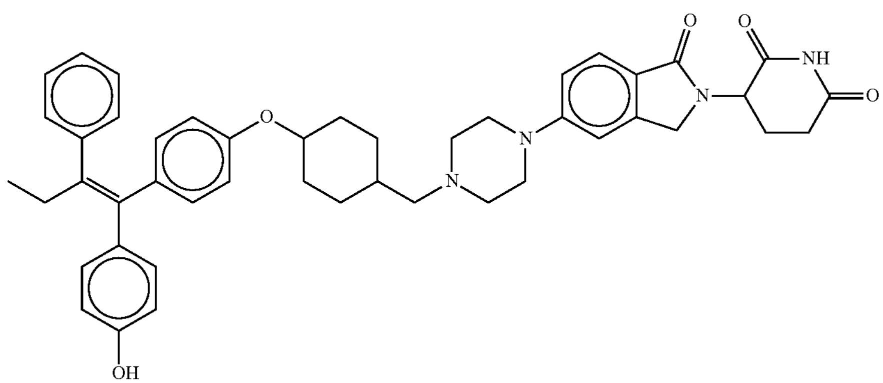 | (Z)-3-(5-(4-((4-(4-(1-(4-hydroxyphenyl)-2-phenylbut-1-en-1-yl)phenoxy)cyclohexyl)methyl)piperazin-1-yl)-1-oxoisoindolin-2-yl)piperidine-2,6-dione |

TABLE 1-continued

Exemplary Compound of the Present Disclosure

| # | Structure | IUPAC Name |
|---|---|---|
| 59 | 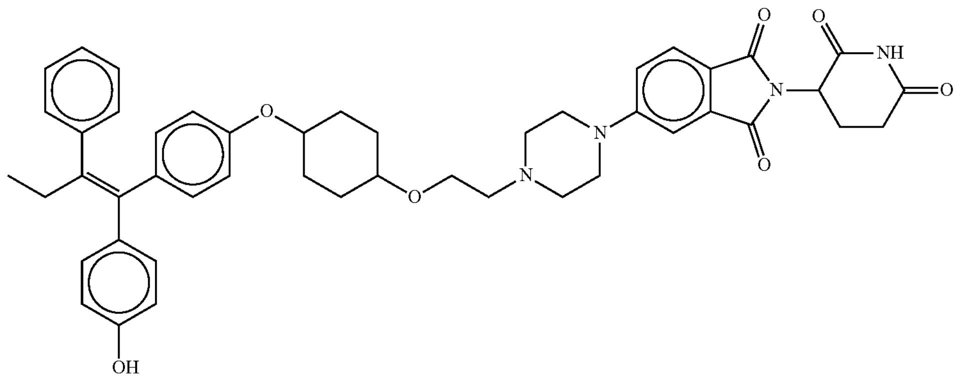 | (Z)-2-(2,6-dioxopiperidin-3-yl)-5-(4-(2-((4-(4-(1-(4-hydroxyphenyl)-2-phenylbut-1-en-1-yl)phenoxy)cyclohexyl)oxy)ethyl)piperazin-1-yl)isoindoline-1,3-dione |
| 60 | 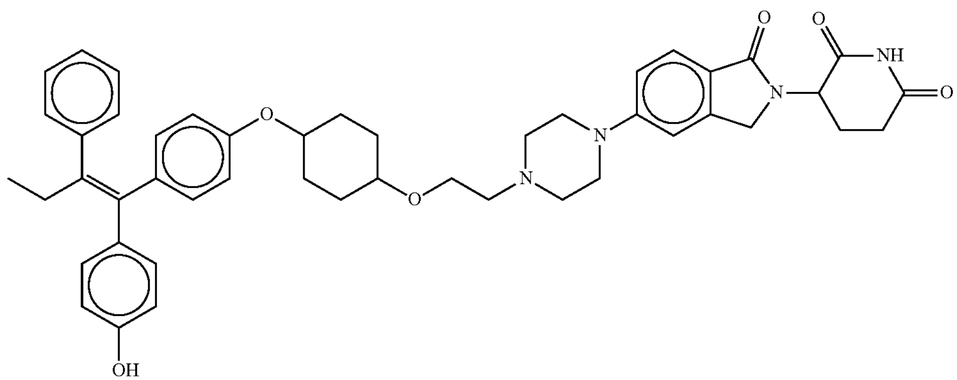 | (Z)-3-(5-(4-(2-((4-(4-(1-(4-hydroxyphenyl)-2-phenylbut-1-en-1-yl)phenoxy)cyclohexyl)oxy)ethyl)piperazin-1-yl)-1-oxoisoindolin-2-yl)piperidine-2,6-dione |

TABLE 1-continued
Exemplary Compound of the Present Disclosure
| # | Structure | IUPAC Name |
|---|---|---|
| 61 | 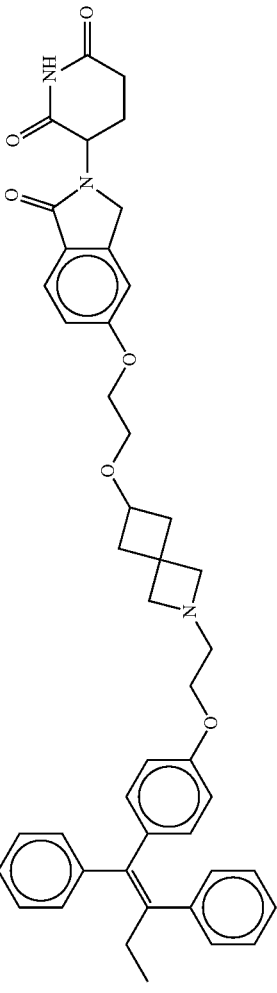 | (Z)-3-(5-(2-(2-((2-(2-(4-(1-(4-hydroxyphenyl)-2-phenylbut-1-en-1-yl)phenoxy)ethyl)-2-azaspiro[3.3]heptan-6-yl)oxy)ethoxy)-1-oxoisoindolin-2-yl)piperidine-2,6-dione |
| 62 | 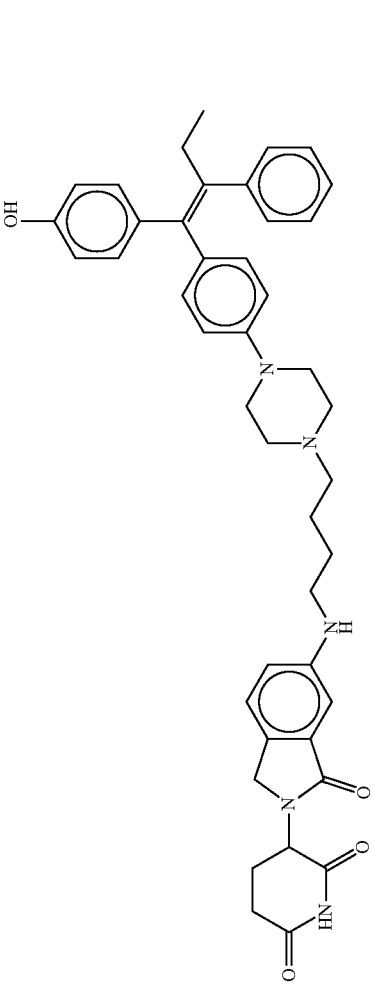 | (E)-3-(6-((4-(4-(1-(4-hydroxyphenyl)-2-phenylbut-1-en-1-yl)phenyl)piperazin-1-yl)butyl)amino)-1-oxoisoindolin-2-yl)piperidine-2,6-dione |

TABLE 1-continued
Exemplary Compound of the Present Disclosure
| # | Structure | IUPAC Name |
|---|---|---|
| 63 | 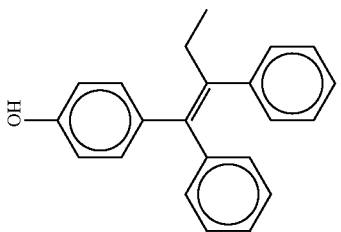 | (Z)-3-(5-((2-(4-(1-(4-hydroxyphenyl)-2-phenylbut-1-en-1-yl)phenoxy)ethoxy)ethyl)amino)-1-oxoisoindolin-2-yl)piperidine-2,6-dione |
| 64 | 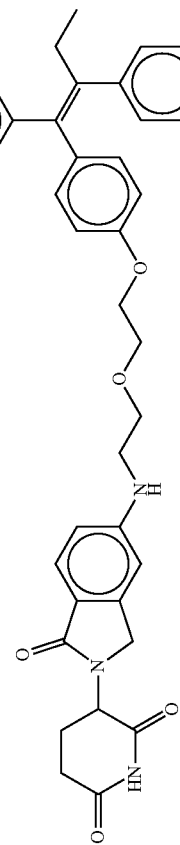 | (Z)-1-(2-(2,6-dioxopiperidin-3-yl)-1,3-dioxoisoindolin-4-yl)amino)-N-(2-(4-(1,2-diphenylbut-1-en-1-yl)phenoxy)ethyl)-N-methyl-3,6,9,12,15-pentaoxaoctadecan-18-amide |

TABLE 1-continued

Exemplary Compound of the Present Disclosure

| # | Structure | IUPAC Name |
|---|---|---|
| 65 | 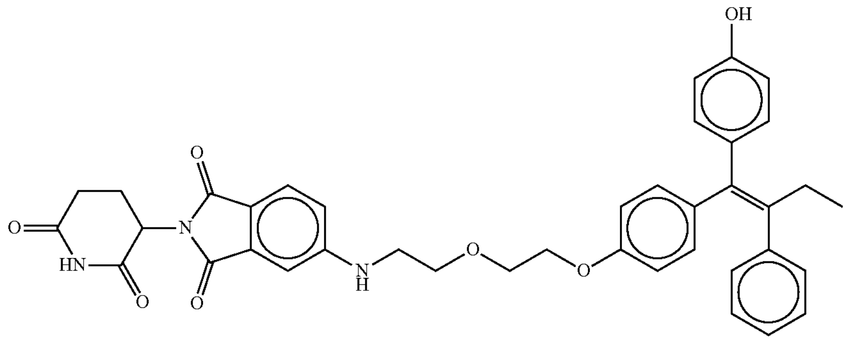 | (Z)-2-(2,6-dioxopiperidin-3-yl)-5-((2-(2-(4-(1-(4-hydroxyphenyl)-2-phenylbut-1-en-1-yl)phenoxy)ethoxy)ethyl)amino)isoindoline-1,3-dione |
| 66 | 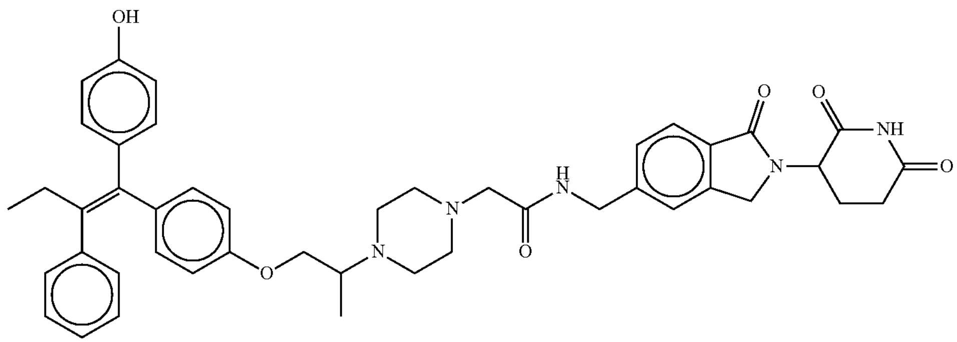 | (Z)-N-((2-(2,6-dioxopiperidin-3-yl)-1-oxoisoindolin-5-yl)methyl)-2-(4-(1-(4-(1-(4-hydroxyphenyl)-2-phenylbut-1-en-1-yl)phenoxy)propan-2-yl)piperazin-1-yl)acetamide |
| 67 | 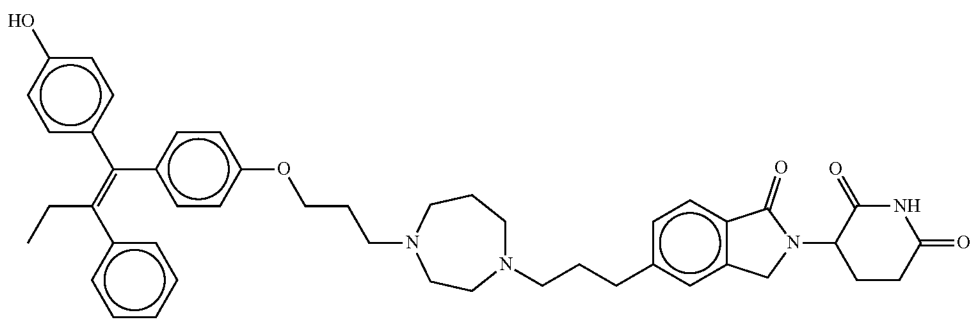 | (Z)-3-(5-(3-(4-(3-(4-(1-(4-hydroxyphenyl)-2-phenylbut-1-en-1-yl)phenoxy)propyl)-1,4-diazepan-1-yl)propyl)-1-oxoisoindolin-2-yl)piperidine-2,6-dione |

TABLE 1-continued
Exemplary Compound of the Present Disclosure
| # | Structure | IUPAC Name |
|---|---|---|
| 68 | 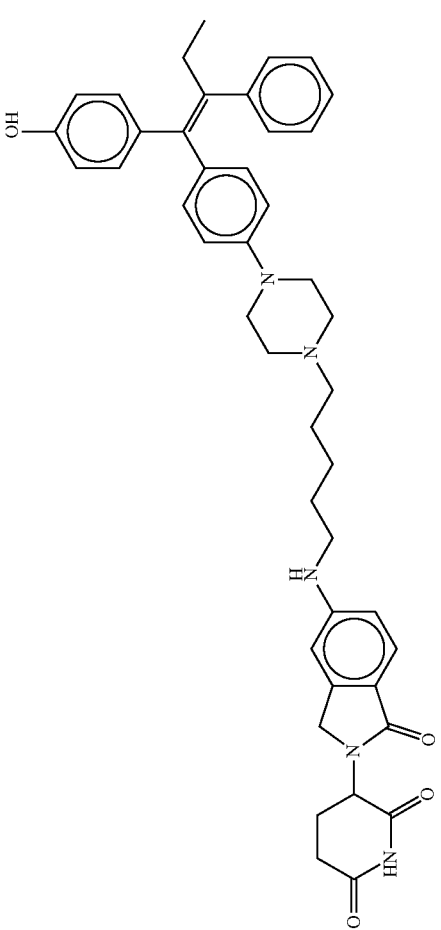 | (E)-3-(5-((5-(4-(4-(1-(4-hydroxyphenyl)-2-phenylbut-1-en-1-yl)phenyl)piperazin-1-yl)pentyl)amino)-1-oxoisoindolin-2-yl)piperidine-2,6-dione |
| 69 | 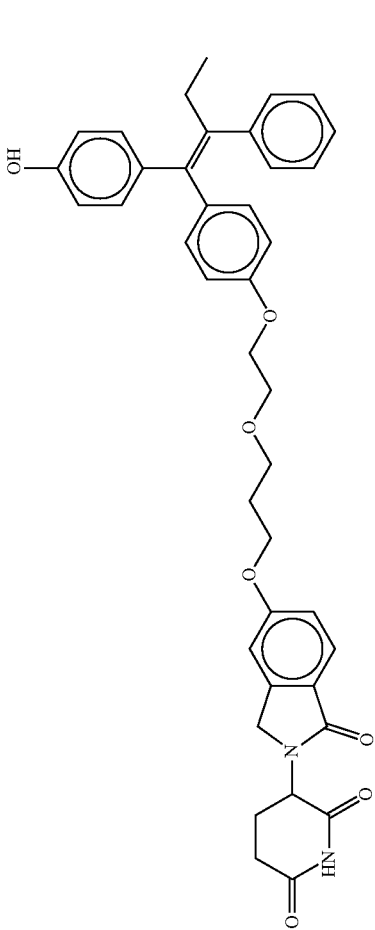 | (Z)-3-(5-(3-(2-(4-(1-(4-hydroxyphenyl)-2-phenylbut-1-en-1-yl)phenoxy)ethoxy)propoxy)-1-oxoisoindolin-2-yl)piperidine-2,6-dione |

TABLE 1-continued
Exemplary Compound of the Present Disclosure
| # | Structure | IUPAC Name |
|---|---|---|
| 70 | 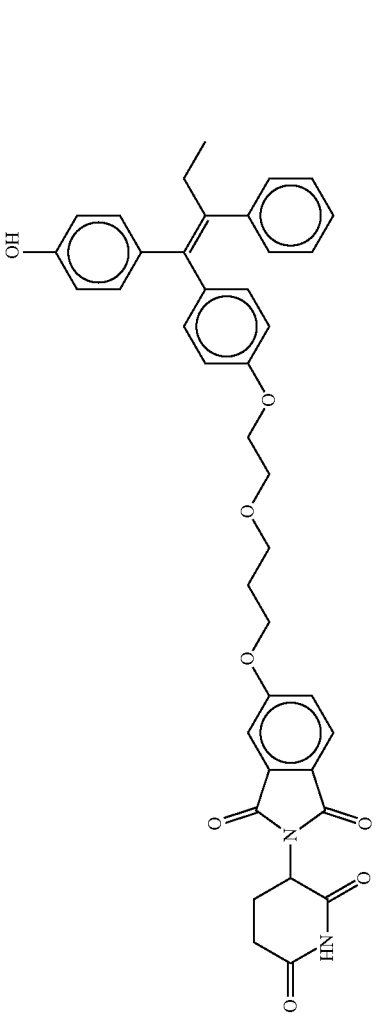 | (Z)-2-(2,6-dioxopiperidin-3-yl)-5-(3-(2-(4-(1-(4-hydroxyphenyl)-2-phenylbut-1-en-1-yl)phenoxy)ethoxy)propoxy)isoindoline-1,3-dione |
| 71 | 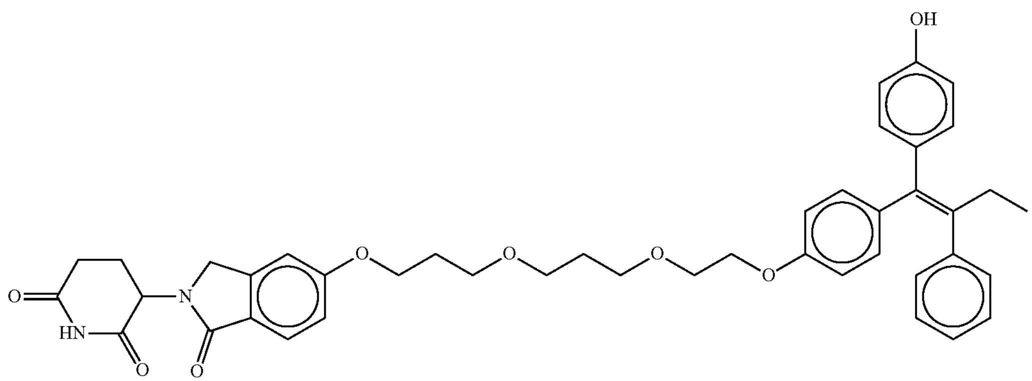 | (Z)-3-(5-(3-(3-(2-(4-(1-(4-hydroxyphenyl)-2-phenylbut-1-en-1-yl)phenoxy)ethoxy)propoxy)-1-oxoisoindolin-2-yl)piperidine-2,6-dione |

TABLE 1-continued
Exemplary Compound of the Present Disclosure
| # | Structure | IUPAC Name |
|---|---|---|
| 72 | 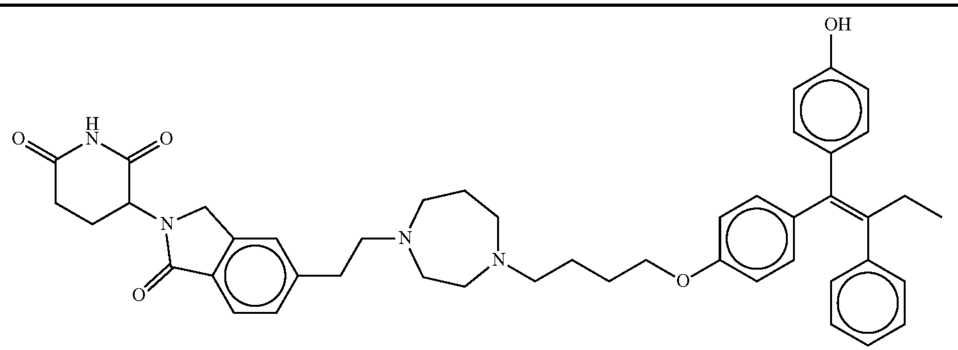 | (Z)-3-(5-(2-(4-(4-(4-(1-(4-hydroxyphenyl)-2-phenylbut-1-en-1-yl)phenoxy)butyl)-1,4-diazepan-1-yl)ethyl)-1-oxoisoindolin-2-yl)piperidine-2,6-dione |
| 73 | 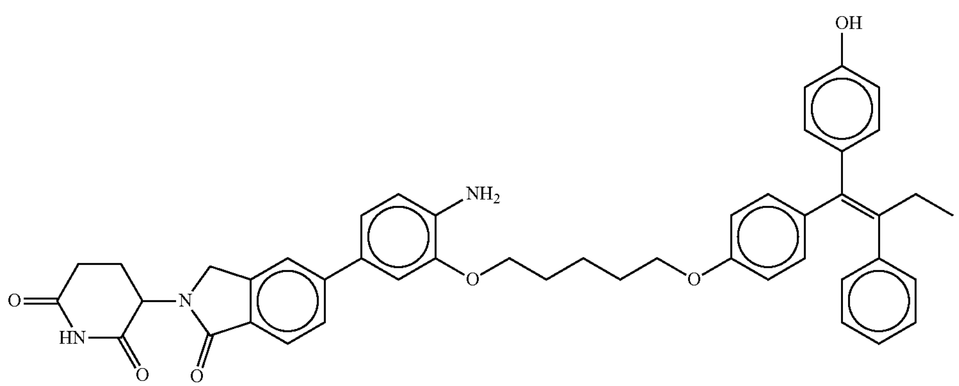 | (Z)-3-(5-(4-amino-3-((5-(4-(1-(4-hydroxyphenyl)-2-phenylbut-1-en-1-yl)phenoxy)pentyl)oxy)phenyl)-1-oxoisoindolin-2-yl)piperidine-2,6-dione |

TABLE 1-continued
Exemplary Compound of the Present Disclosure
| # | Structure | IUPAC Name |
|---|---|---|
| 74 | 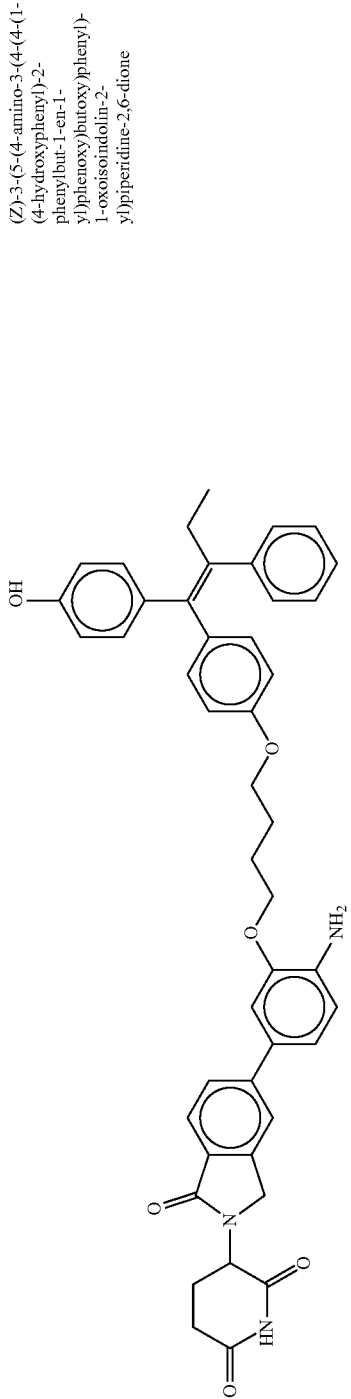 | (Z)-3-(5-(4-amino-3-(4-(4-(1-(4-hydroxyphenyl)-2-phenylbut-1-en-1-yl)phenoxy)butoxy)phenyl)-1-oxoisoindolin-2-yl)piperidine-2,6-dione |
| 75 | 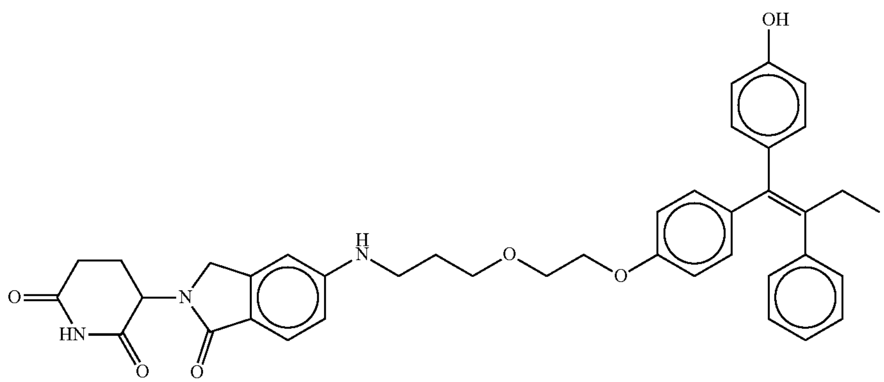 | (Z)-3-(5-((3-(2-(4-(1-(4-hydroxyphenyl)-2-phenylbut-1-en-1-yl)phenoxy)ethoxy)propyl)amino)-1-oxoisoindolin-2-yl)piperidine-2,6-dione |

TABLE 1-continued
Exemplary Compound of the Present Disclosure
| # | Structure | IUPAC Name |
|---|---|---|
| 76 | 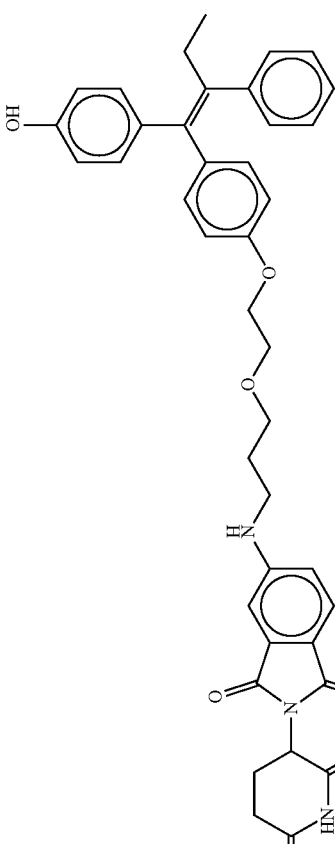 | (Z)-2-(2,6-dioxopiperidin-3-yl)-5-((3-(2-(4-(1-(4-hydroxyphenyl)-2-phenylbut-1-en-1-yl)phenoxy)ethoxy)propyl)amino)isoindoline-1,3-dione |
| 77 | 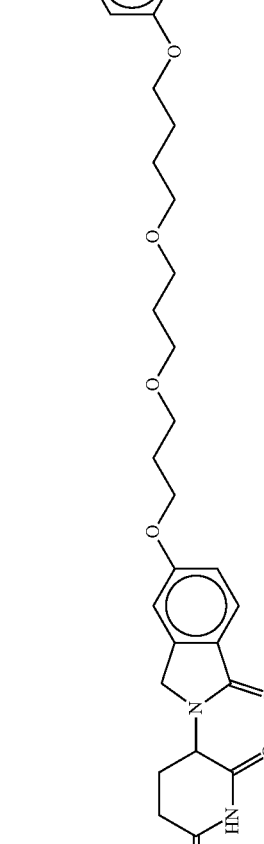 | (Z)-3-(5-(3-(3-(4-(4-(1-(4-hydroxyphenyl)-2-phenylbut-1-en-1-yl)phenoxy)butoxy)propoxy)propoxy)-1-oxoisoindolin-2-yl)piperidine-2,6-dione |

TABLE 1-continued
Exemplary Compound of the Present Disclosure
| # | Structure | IUPAC Name |
|---|---|---|
| 78 | 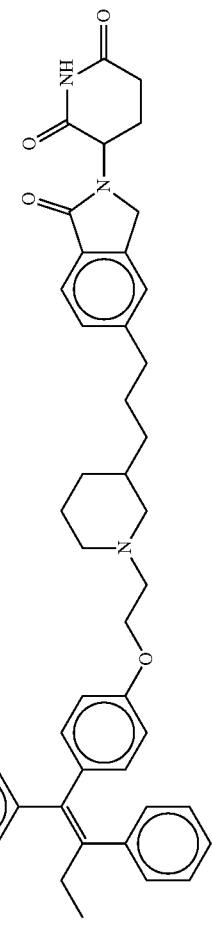 | (Z)-3-(5-(3-(1-(2-(4-(1-(4-hydroxyphenyl)-2-phenylbut-1-en-1-yl)phenoxy)ethyl)piperidin-3-yl)propyl)-1-oxoisoindolin-2-yl)piperidine-2,6-dione |
| 79 | 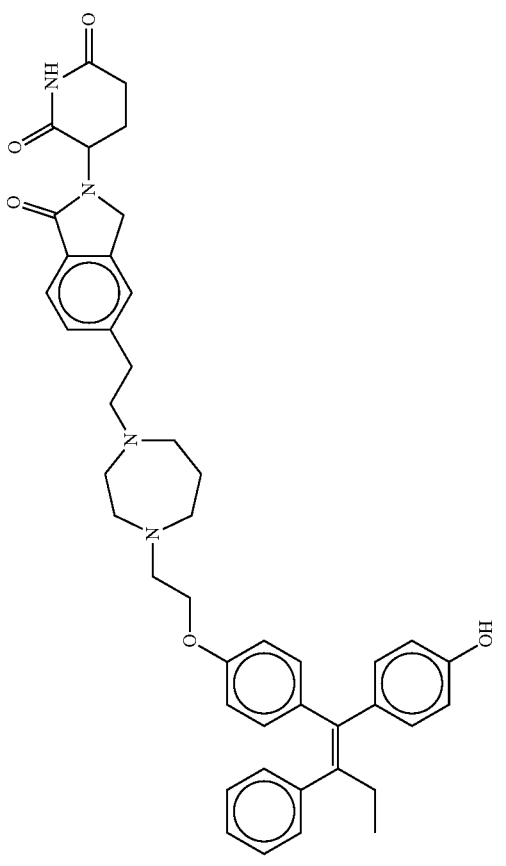 | (Z)-3-(5-(2-(4-(2-(4-(1-(4-hydroxyphenyl)-2-phenylbut-1-en-1-yl)phenoxy)ethyl)-1,4-diazepan-1-yl)ethyl)-1-oxoisoindolin-2-yl)piperidine-2,6-dione |

TABLE 1-continued

Exemplary Compound of the Present Disclosure

| # | Structure | IUPAC Name |
|---|---|---|
| 80 | 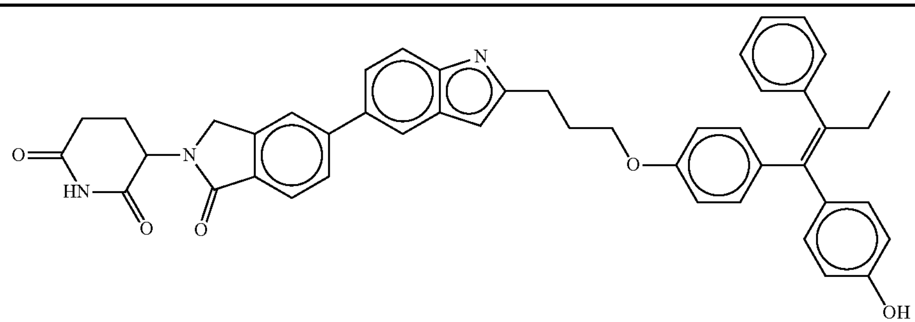 | (Z)-3-(5-(2-(3-(4-(1-(4-hydroxyphenyl)-2-phenylbut-1-en-1-yl)phenoxy)propyl)-1H-indol-5-yl)-1-oxoisoindolin-2-yl)piperidine-2,6-dione |
| 81 | 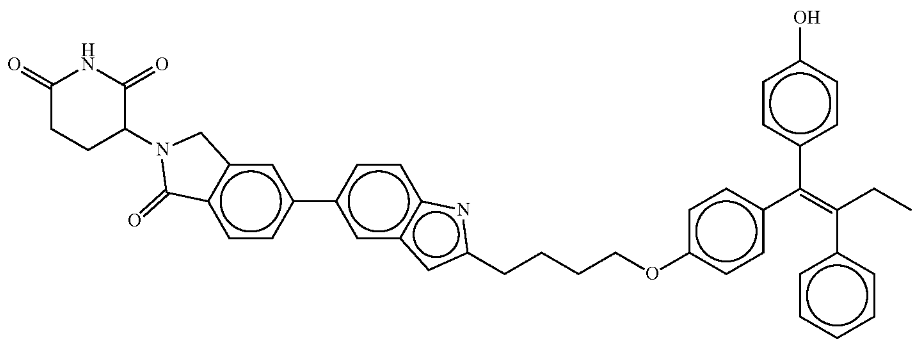 | (Z)-3-(5-(2-(4-(4-(1-(4-hydroxyphenyl)-2-phenylbut-1-en-1-yl)phenoxy)butyl)-1H-indol-5-yl)-1-oxoisoindolin-2-yl)piperidine-2,6-dione |
| 82 | 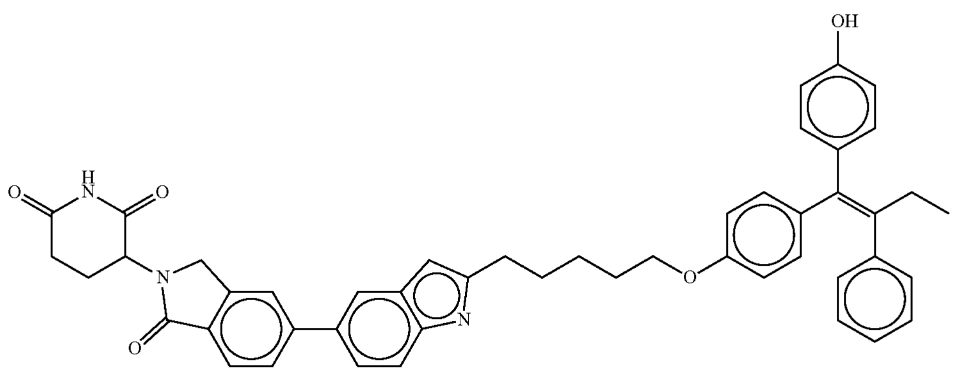 | (Z)-3-(5-(2-(5-(4-(1-(4-hydroxyphenyl)-2-phenylbut-1-en-1-yl)phenoxy)pentyl)-1H-indol-5-yl)-1-oxoisoindolin-2-yl)piperidine-2,6-dione |

TABLE 1-continued
Exemplary Compound of the Present Disclosure
| # | Structure | IUPAC Name |
|---|---|---|
| 83 | 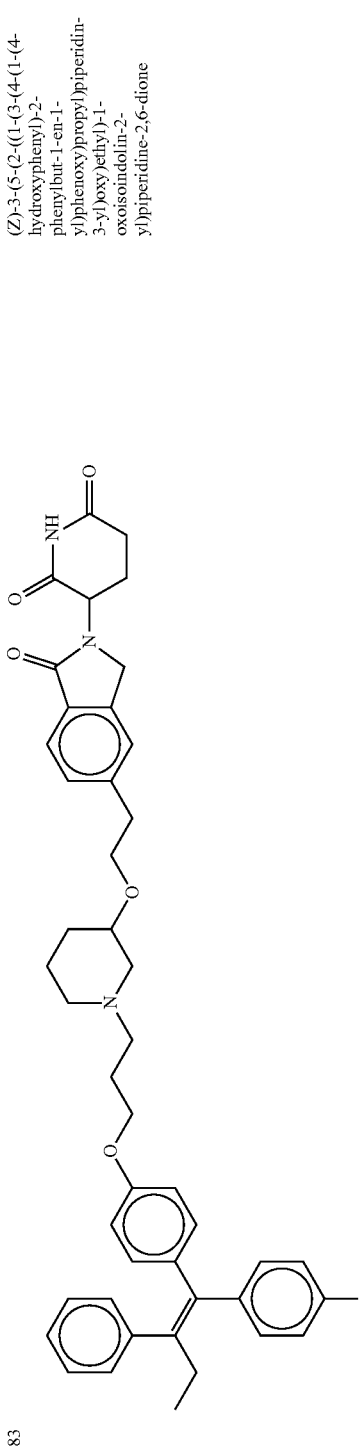 | (Z)-3-(5-(2-((1-(3-(4-(1-(4-hydroxyphenyl)-2-phenylbut-1-en-1-yl)phenoxy)propyl)piperidin-3-yl)oxy)ethyl)-1-oxoisoindolin-2-yl)piperidine-2,6-dione |
| 84 | 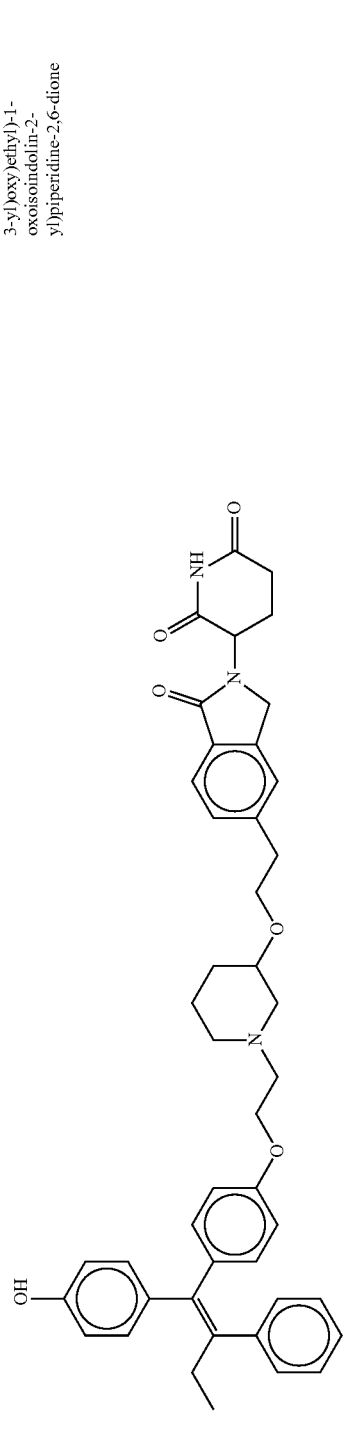 | (Z)-3-(5-(2-((1-(2-(4-(1-(4-hydroxyphenyl)-2-phenylbut-1-en-1-yl)phenoxy)ethyl)piperidin-3-yl)oxy)ethyl)-1-oxoisoindolin-2-yl)piperidine-2,6-dione |

TABLE 1-continued
Exemplary Compound of the Present Disclosure
| # | Structure | IUPAC Name |
|---|---|---|
| 85 | 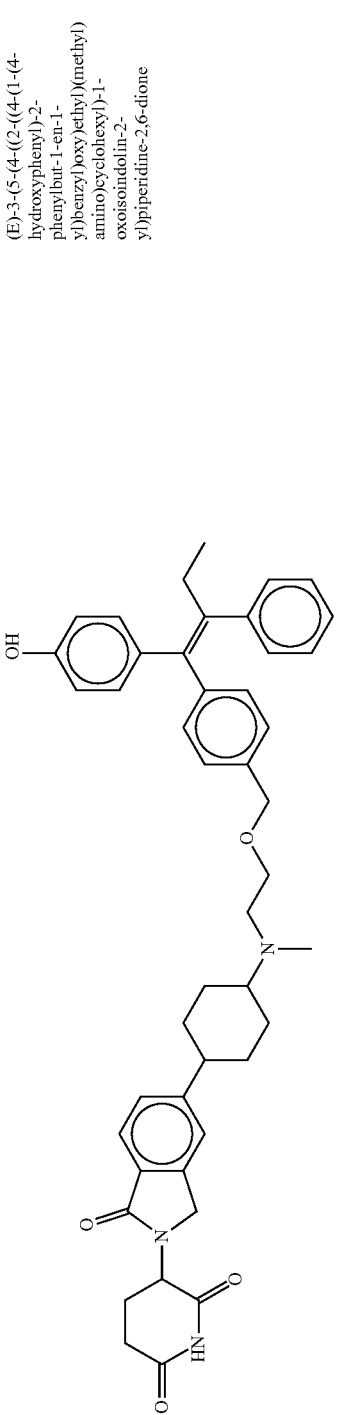 | (E)-3-(5-(4-((2-((4-(1-(4-hydroxyphenyl)-2-phenylbut-1-en-1-yl)benzyl)oxy)ethyl)(methyl)amino)cyclohexyl)-1-oxoisoindolin-2-yl)piperidine-2,6-dione |
| 86 | 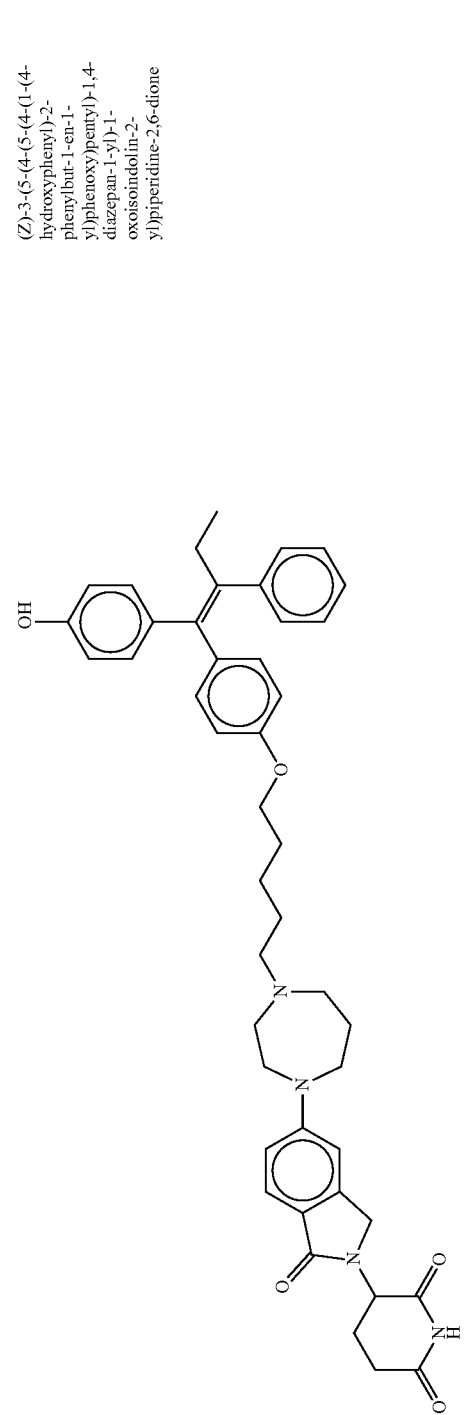 | (Z)-3-(5-(4-(5-(4-(1-(4-hydroxyphenyl)-2-phenylbut-1-en-1-yl)phenoxy)pentyl)-1,4-diazepan-1-yl)-1-oxoisoindolin-2-yl)piperidine-2,6-dione |

TABLE 1-continued
Exemplary Compound of the Present Disclosure
| # | Structure | IUPAC Name |
|---|---|---|
| 87 | 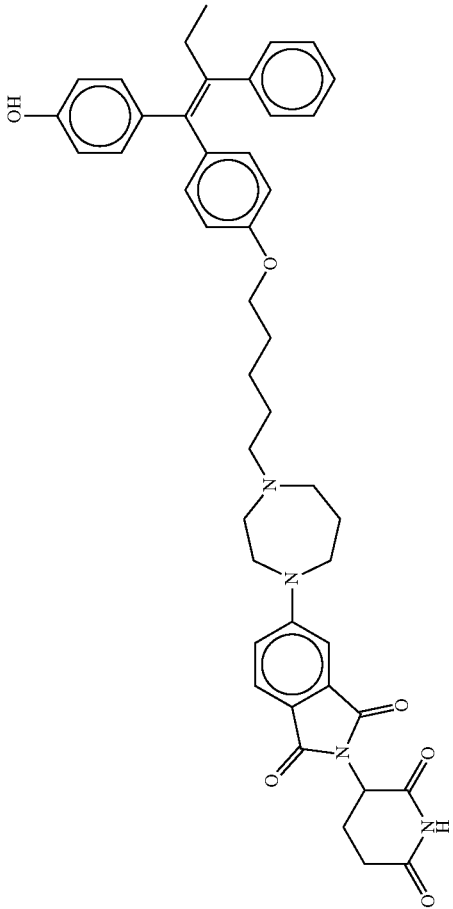 | (Z)-2-(2,6-dioxopiperidin-3-yl)-5-(4-(5-(4-(1-(4-hydroxyphenyl)-2-phenylbut-1-en-1-yl)phenoxy)pentyl)-1,4-diazepan-1-yl)isoindoline-1,3-dione |
| 88 | 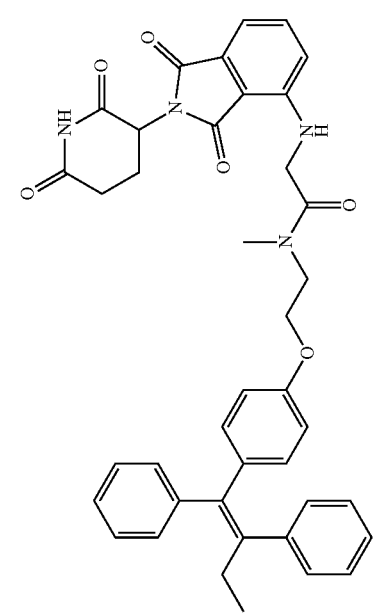 | (Z)-2-(2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylacetamide |

TABLE 1-continued

Exemplary Compound of the Present Disclosure

| # | Structure | IUPAC Name |
|---|-----------|------------|
| 89 | 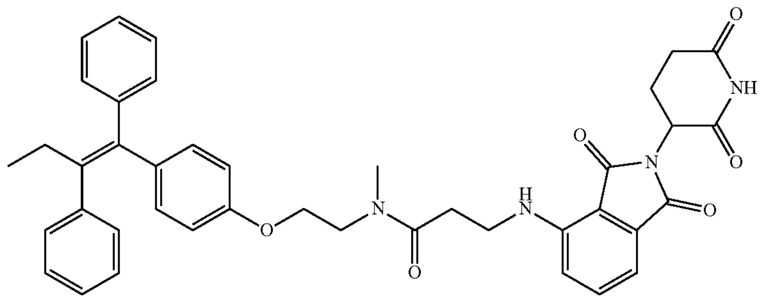 [SMILES: CC/C(=C(\c1ccccc1)c1ccc(OCCN(C)C(=O)CCNc2cccc3c2C(=O)N(C2CCC(=O)NC2=O)C3=O)cc1)c1ccccc1] | (Z)-3-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylpropanamide |
| 90 | 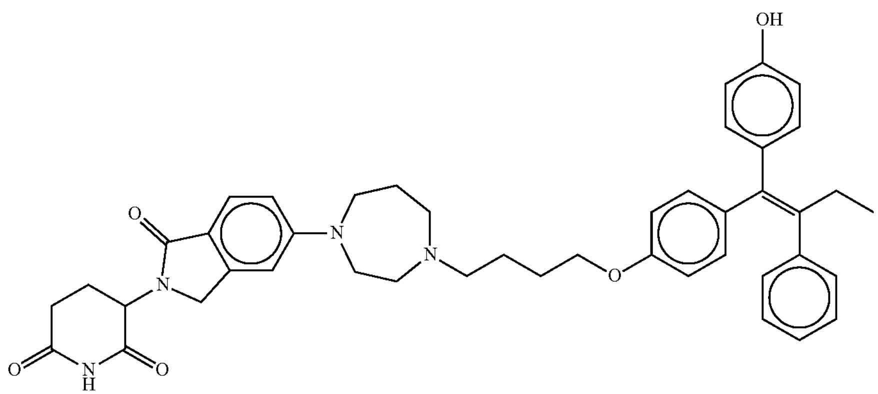 | (Z)-3-(5-(4-(4-(1-(4-hydroxyphenyl)-2-phenylbut-1-en-1-yl)phenoxy)butyl)-1,4-diazepan-1-yl)-1-oxoisoindolin-2-yl)piperidine-2,6-dione |

TABLE 1-continued

Exemplary Compound of the Present Disclosure

| # | Structure | IUPAC Name |
|---|---|---|
| 91 | 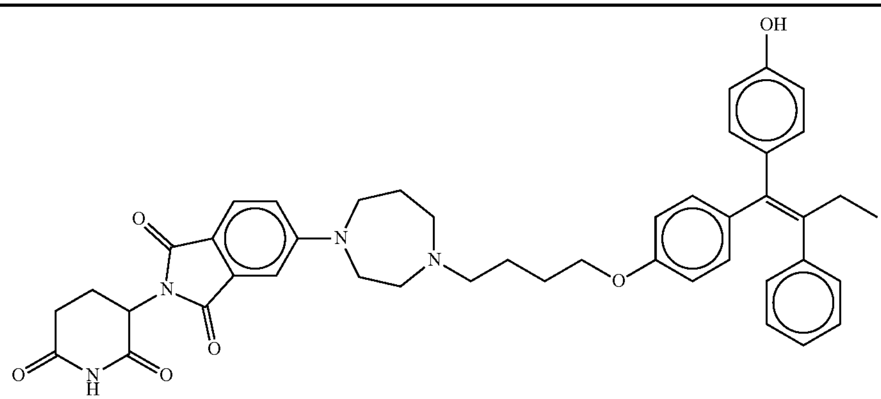 | (Z)-2-(2,6-dioxopiperidin-3-yl)-5-(4-(4-(1-(4-hydroxyphenyl)-2-phenylbut-1-en-1-yl)phenoxy)butyl)-1,4-diazepan-1-yl)isoindoline-1,3-dione |
| 92 | 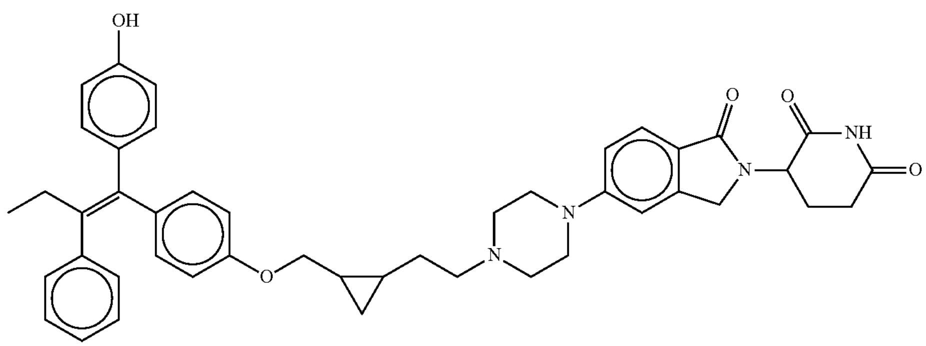 | (Z)-3-(5-(4-(2-(2-((4-(1-(4-hydroxyphenyl)-2-phenylbut-1-en-1-yl)phenoxy)methyl)cyclopropyl)ethyl)piperazin-1-yl)-1-oxoisoindolin-2-yl)piperidine-2,6-dione |

TABLE 1-continued

Exemplary Compound of the Present Disclosure

| # | Structure | IUPAC Name |
|---|---|---|
| 93 | 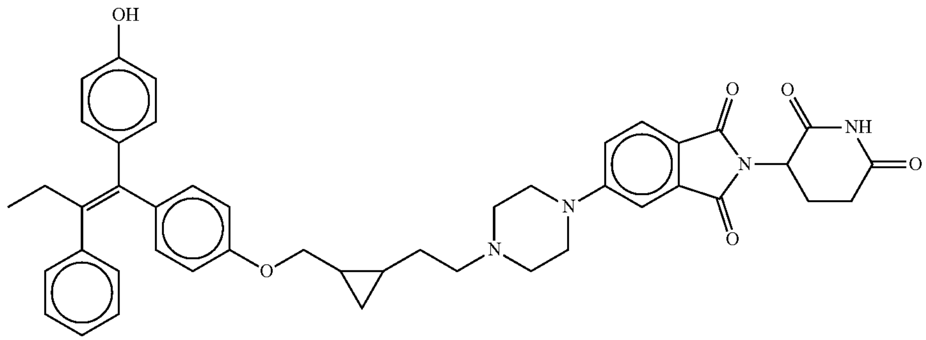 | (Z)-2-(2,6-dioxopiperidin-3-yl)-5-(4-(2-(2-((4-(1-(4-hydroxyphenyl)-2-phenylbut-1-en-1-yl)phenoxy)methyl)cyclopropyl)ethyl)piperazin-1-yl)isoindoline-1,3-dione |
| 94 | 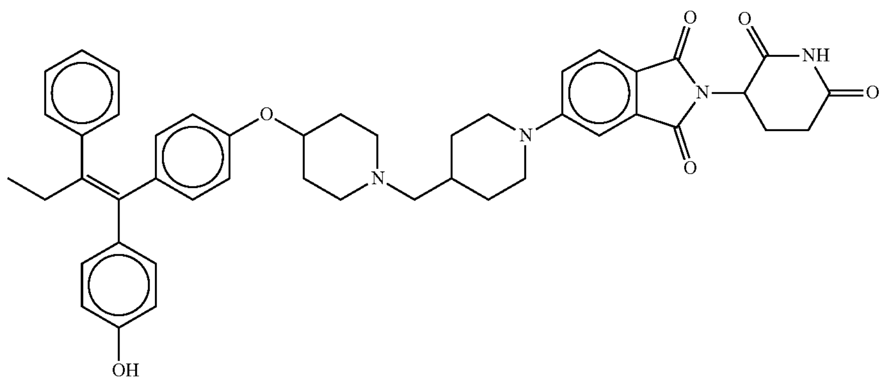 | (Z)-2-(2,6-dioxopiperidin-3-yl)-5-(4-((4-(1-(4-hydroxyphenyl)-2-phenylbut-1-en-1-yl)phenoxy)piperidin-1-yl)methyl)piperidin-1-yl)isoindoline-1,3-dione |

TABLE 1-continued

Exemplary Compound of the Present Disclosure

| # | Structure | IUPAC Name |
|---|---|---|
| 95 | 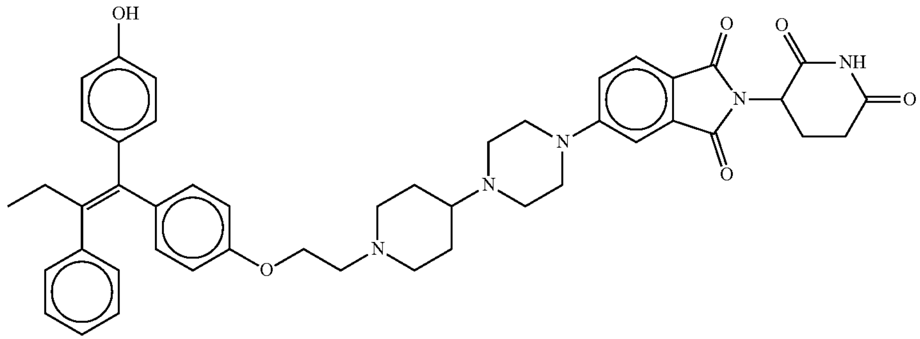 | (Z)-2-(2,6-dioxopiperidin-3-yl)-5-(4-(1-(2-(4-(1-(4-hydroxyphenyl)-2-phenylbut-1-en-1-yl)phenoxy)ethyl)piperidin-4-yl)piperazin-1-yl)isoindoline-1,3-dione |
| 96 | 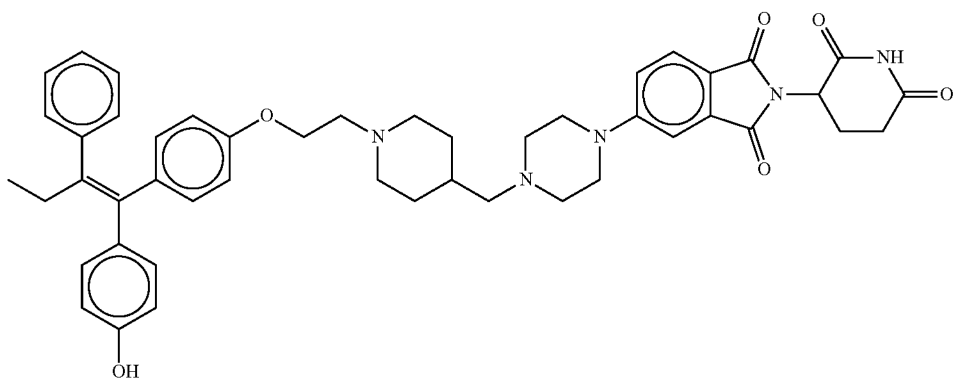 | (Z)-2-(2,6-dioxopiperidin-3-yl)-5-(4-((1-(2-(4-(1-(4-hydroxyphenyl)-2-phenylbut-1-en-1-yl)phenoxy)ethyl)piperidin-4-yl)methyl)piperazin-1-yl)isoindoline-1,3-dione |

TABLE 1-continued

Exemplary Compound of the Present Disclosure

| # | Structure | IUPAC Name |
|---|---|---|
| 97 | 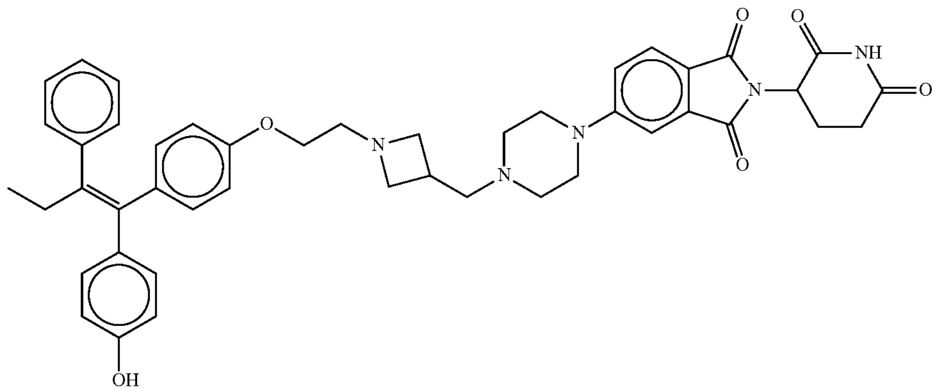 | (Z)-2-(2,6-dioxopiperidin-3-yl)-5-(4-((1-(2-(4-(1-(4-hydroxyphenyl)-2-phenylbut-1-en-1-yl)phenoxy)ethyl)azetidin-3-yl)methyl)piperazin-1-yl)isoindoline-1,3-dione |
| 98 | 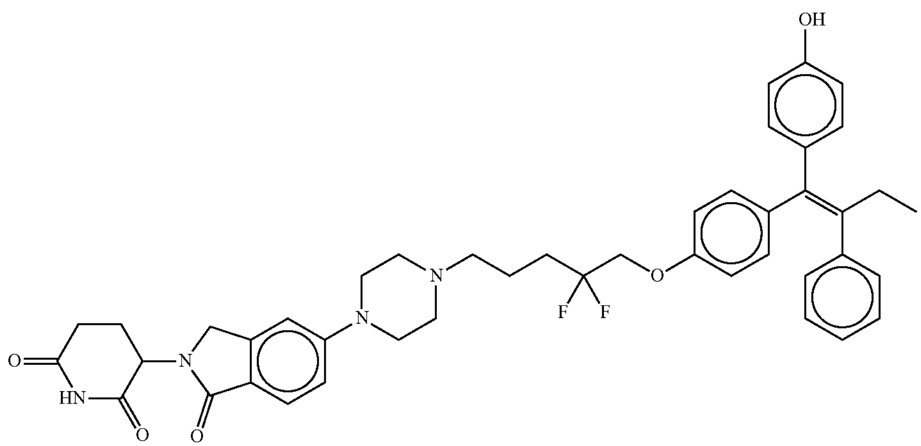 | (Z)-3-(5-(4-(4,4-difluoro-5-(4-(1-(4-hydroxyphenyl)-2-phenylbut-1-en-1-yl)phenoxy)pentyl)piperazin-1-yl)-1-oxoisoindolin-2-yl)piperidine-2,6-dione |

TABLE 1-continued
Exemplary Compound of the Present Disclosure
| # | Structure | IUPAC Name |
|---|---|---|
| 99 | 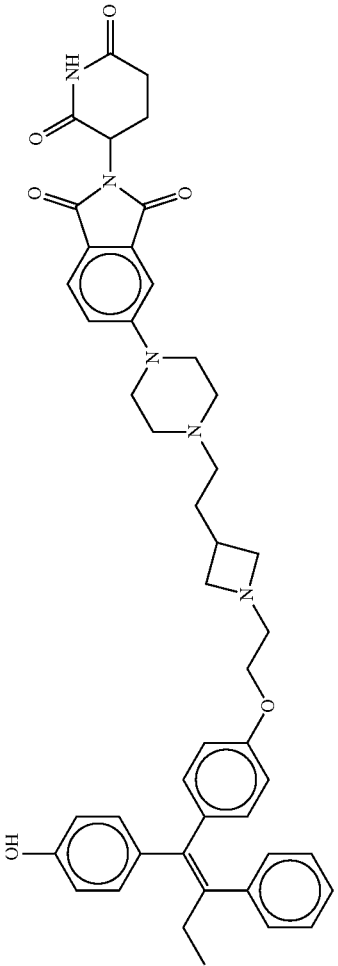 | (Z)-2-(2,6-dioxopiperidin-3-yl)-5-(4-(2-(1-(2-(4-(1-(4-hydroxyphenyl)-2-phenylbut-1-en-1-yl)phenoxy)ethyl)azetidin-3-yl)ethyl)piperazin-1-yl)isoindoline-1,3-dione |
| 100 | 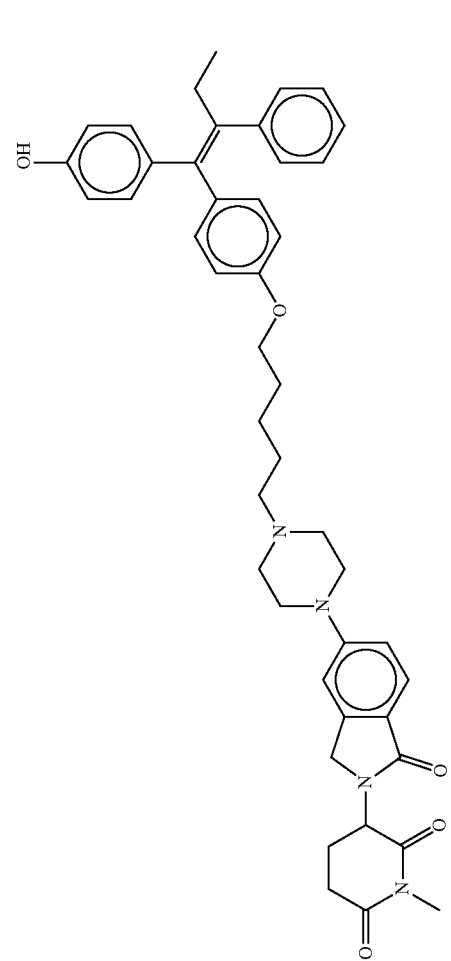 | (Z)-3-(5-(4-(5-(4-(1-(4-hydroxyphenyl)-2-phenylbut-1-en-1-yl)phenoxy)pentyl)piperazin-1-yl)-1-oxoisoindolin-2-yl)-1-methylpiperidine-2,6-dione |

TABLE 1-continued
Exemplary Compound of the Present Disclosure
| # | Structure | IUPAC Name |
|---|---|---|
| 101 | 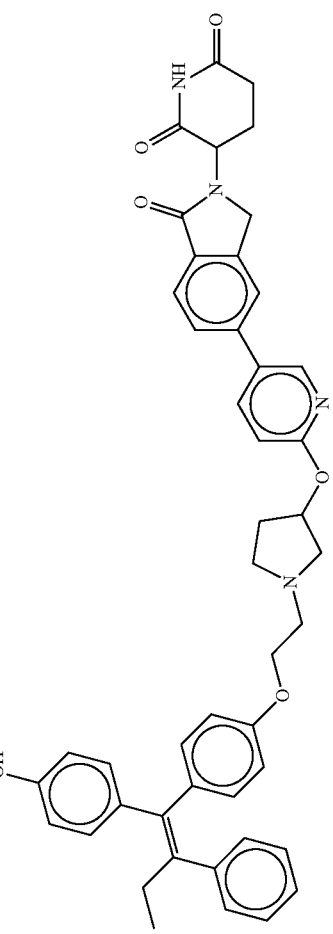 | (Z)-3-(5-(6-((1-(2-(4-(1-(4-hydroxyphenyl)-2-phenylbut-1-en-1-yl)phenoxy)ethyl)pyrrolidin-3-yl)oxy)pyridin-3-yl)-1-oxoisoindolin-2-yl)piperidine-2,6-dione |
| 102 | 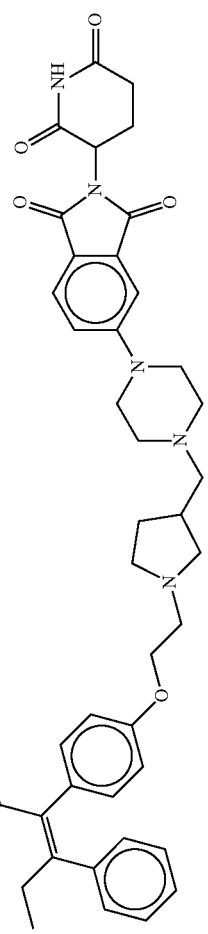 | (Z)-2-(2,6-dioxopiperidin-3-yl)-5-(4-((1-(2-(4-(1-(4-hydroxyphenyl)-2-phenylbut-1-en-1-yl)phenoxy)ethyl)pyrrolidin-3-yl)methyl)piperazin-1-yl)isoindoline-1,3-dione |

TABLE 1-continued

Exemplary Compound of the Present Disclosure

| # | Structure | IUPAC Name |
|---|---|---|
| 103 | 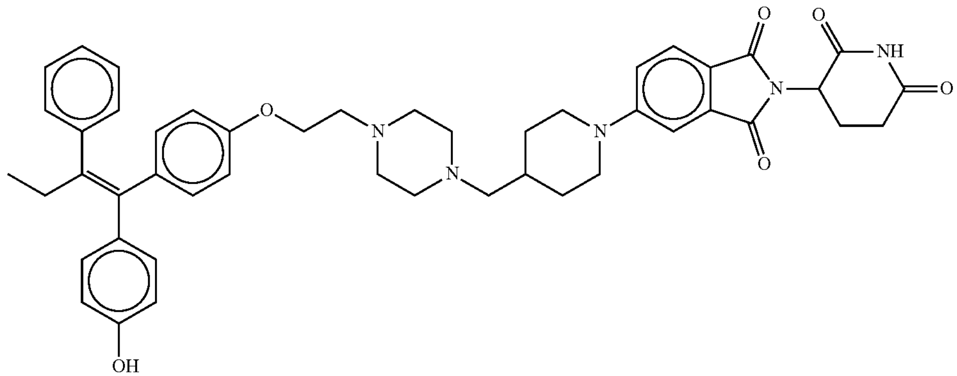 | (Z)-2-(2,6-dioxopiperidin-3-yl)-5-(4-((4-(2-(4-(1-(4-hydroxyphenyl)-2-phenylbut-1-en-1-yl)phenoxy)ethyl)piperazin-1-yl)methyl)piperidin-1-yl)isoindoline-1,3-dione |
| 104 | 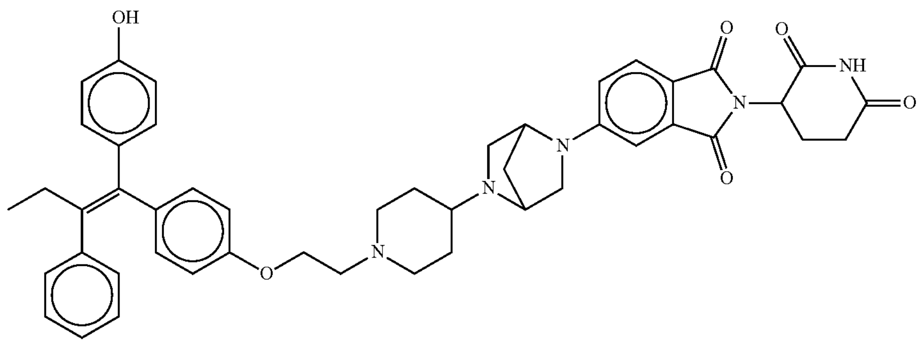 | (Z)-2-(2,6-dioxopiperidin-3-yl)-5-(1-(2-(4-(1-(4-hydroxyphenyl)-2-phenylbut-1-en-1-yl)phenoxy)ethyl)piperidin-4-yl)-2,5-diazabicyclo[2.2.1]heptan-2-yl)isoindoline-1,3-dione |

TABLE 1-continued

Exemplary Compound of the Present Disclosure

| # | Structure | IUPAC Name |
|---|---|---|
| 105 | 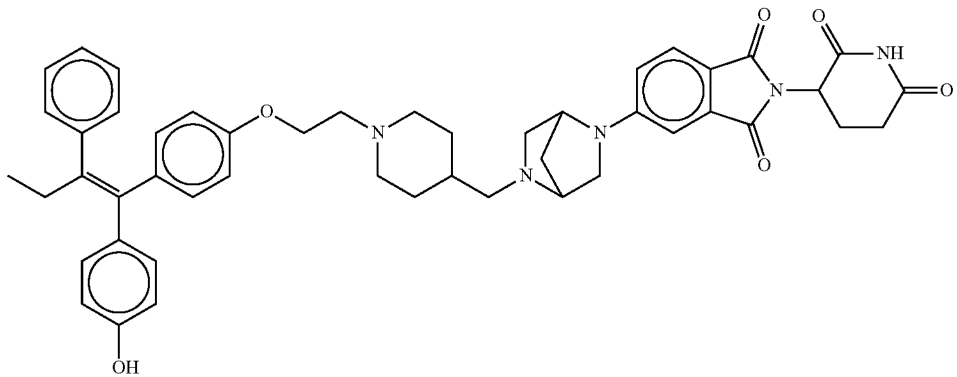 | (Z)-2-(2,6-dioxopiperidin-3-yl)-5-(5-((1-(2-(4-(1-(4-hydroxyphenyl)-2-phenylbut-1-en-1-yl)phenoxy)ethyl)piperidin-4-yl)methyl)-2,5-diazabicyclo[2.2.1]heptan-2-yl)isoindoline-1,3-dione |
| 106 | 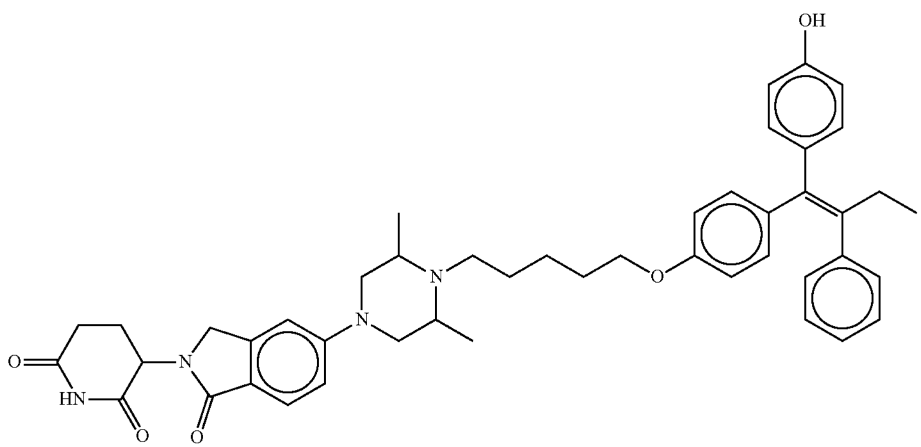 | (Z)-3-(5-(4-(5-(4-(1-(4-hydroxyphenyl)-2-phenylbut-1-en-1-yl)phenoxy)pentyl)-3,5-dimethylpiperazin-1-yl)-1-oxoisoindolin-2-yl)piperidine-2,6-dione |

TABLE 1-continued
Exemplary Compound of the Present Disclosure
| # | Structure | IUPAC Name |
|---|---|---|
| 107 | 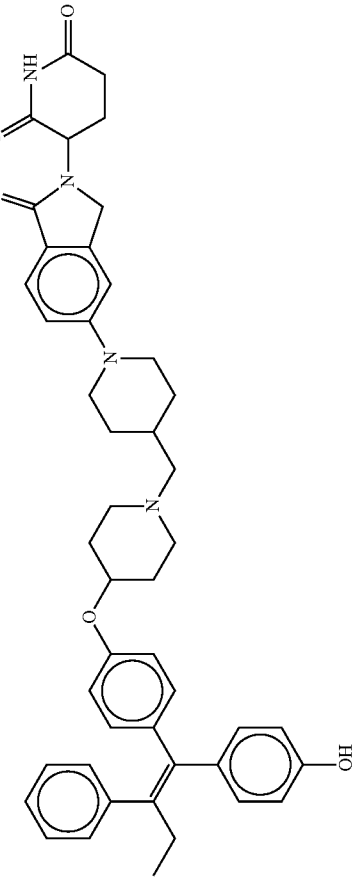 | (Z)-3-(5-(4-((4-(4-(1-(4-hydroxyphenyl)-2-phenylbut-1-en-1-yl)phenoxy)piperidin-1-yl)methyl)piperidin-1-yl)-1-oxoisoindolin-2-yl)piperidine-2,6-dione |
| 108 | 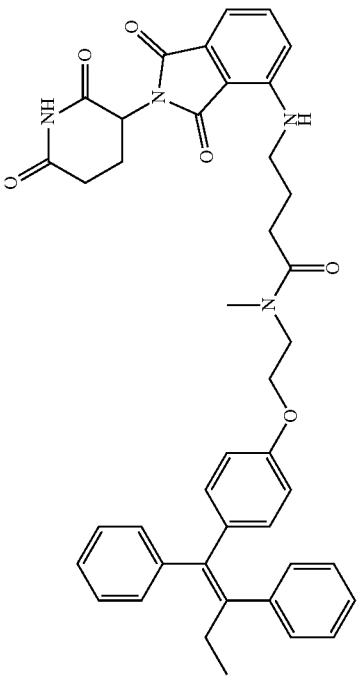 | (Z)-4-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylbutanamide |

TABLE 1-continued
Exemplary Compound of the Present Disclosure
| # | Structure | IUPAC Name |
|---|---|---|
| 109 | 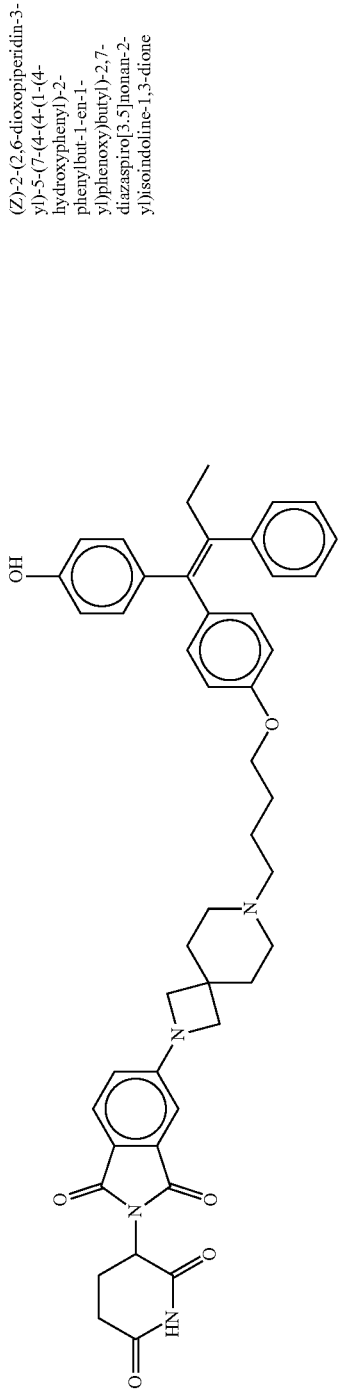 | (Z)-2-(2,6-dioxopiperidin-3-yl)-5-(7-(4-(4-(1-(4-hydroxyphenyl)-2-phenylbut-1-en-1-yl)phenoxy)butyl)-2,7-diazaspiro[3.5]nonan-2-yl)isoindoline-1,3-dione |
| 110 | 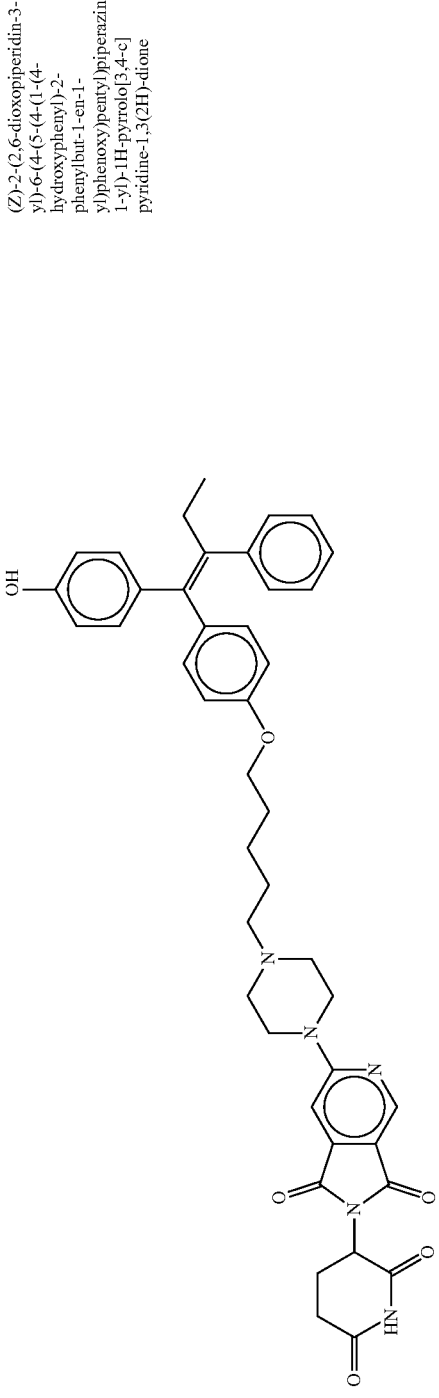 | (Z)-2-(2,6-dioxopiperidin-3-yl)-6-(4-(5-(4-(1-(4-hydroxyphenyl)-2-phenylbut-1-en-1-yl)phenoxy)pentyl)piperazin-1-yl)-1H-pyrrolo[3,4-c]pyridine-1,3(2H)-dione |

TABLE 1-continued

Exemplary Compound of the Present Disclosure

| # | Structure | IUPAC Name |
|---|---|---|
| 111 | 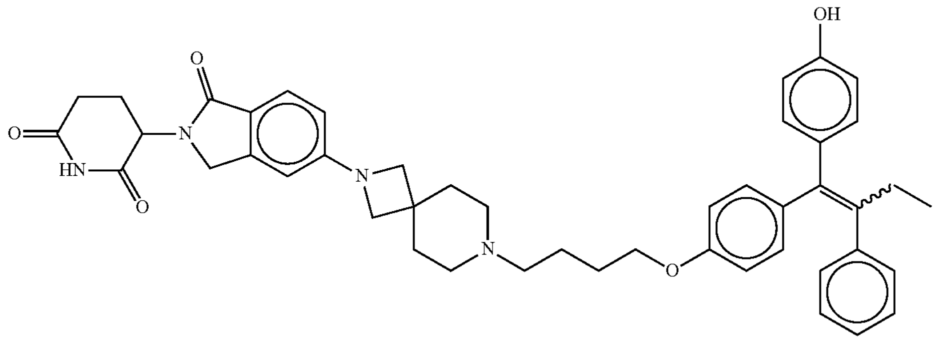 | (Z)/(E)-3-(5-(7-(4-(4-(1-(4-hydroxyphenyl)-2-phenylbut-1-en-1-yl)phenoxy)butyl)-2,7-diazaspiro[3.5]nonan-2-yl)-1-oxoisoindolin-2-yl)piperidine-2,6-dione |
| 112 | 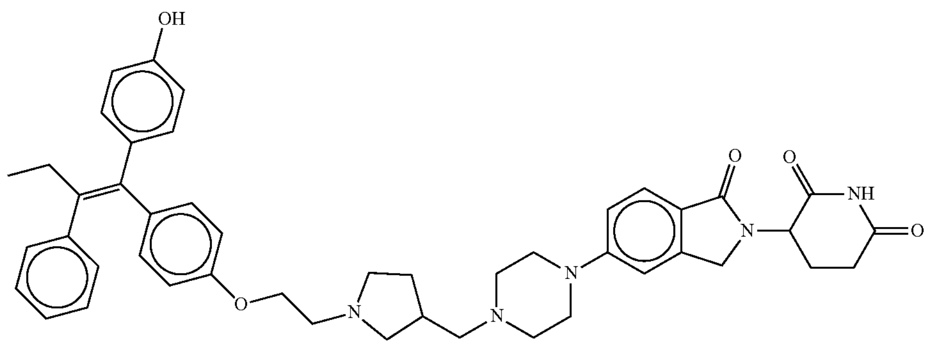 | (Z)-3-(5-(4-((1-(2-(4-(1-(4-hydroxyphenyl)-2-phenylbut-1-en-1-yl)phenoxy)ethyl)pyrrolidin-3-yl)methyl)piperazin-1-yl)-1-oxoisoindolin-2-yl)piperidine-2,6-dione |
| 113 | 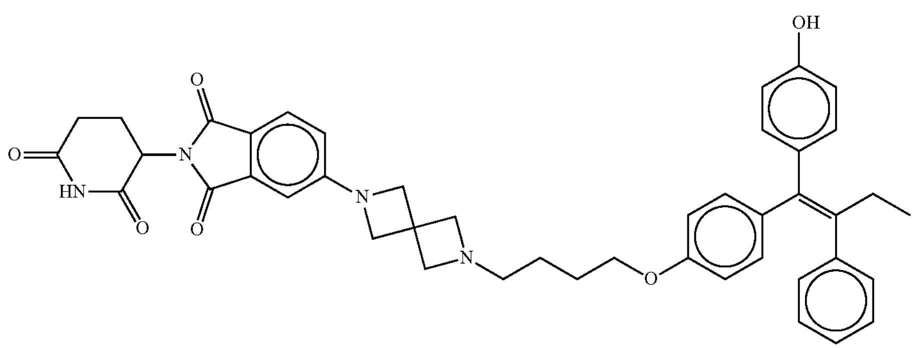 | (Z)-2-(2,6-dioxopiperidin-3-yl)-5-(6-(4-(1-(4-hydroxyphenyl)-2-phenylbut-1-en-1-yl)phenoxy)butyl)-2,6-diazaspiro[3.3]heptan-2-yl)isoindoline-1,3-dione |

TABLE 1-continued
Exemplary Compound of the Present Disclosure
| # | Structure | IUPAC Name |
|---|---|---|
| 114 | 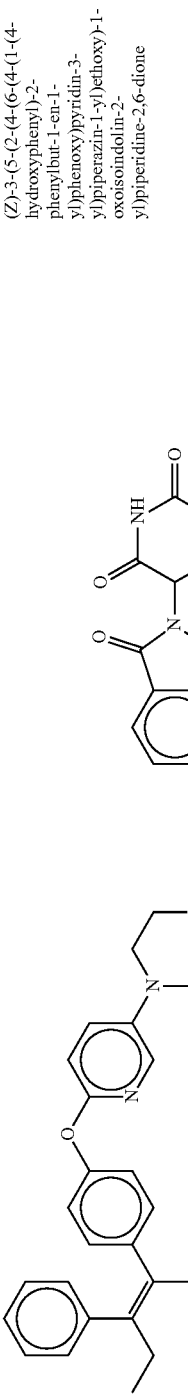 | (Z)-3-(5-(2-(4-(6-(4-(1-(4-hydroxyphenyl)-2-phenylbut-1-en-1-yl)phenoxy)pyridin-3-yl)piperazin-1-yl)ethoxy)-1-oxoisoindolin-2-yl)piperidine-2,6-dione |
| 115 | 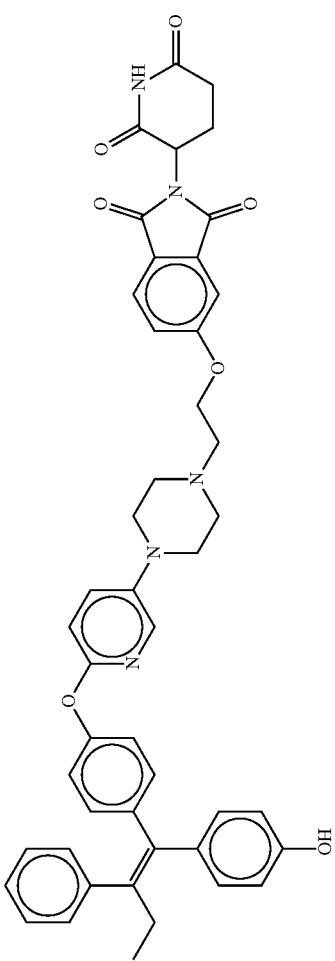 | (Z)-2-(2,6-dioxopiperidin-3-yl)-5-(2-(4-(6-(4-(1-(4-hydroxyphenyl)-2-phenylbut-1-en-1-yl)phenoxy)pyridin-3-yl)piperazin-1-yl)ethoxy)isoindoline-1,3-dione |

TABLE 1-continued

Exemplary Compound of the Present Disclosure

| # | Structure | IUPAC Name |
|---|---|---|
| 116 | 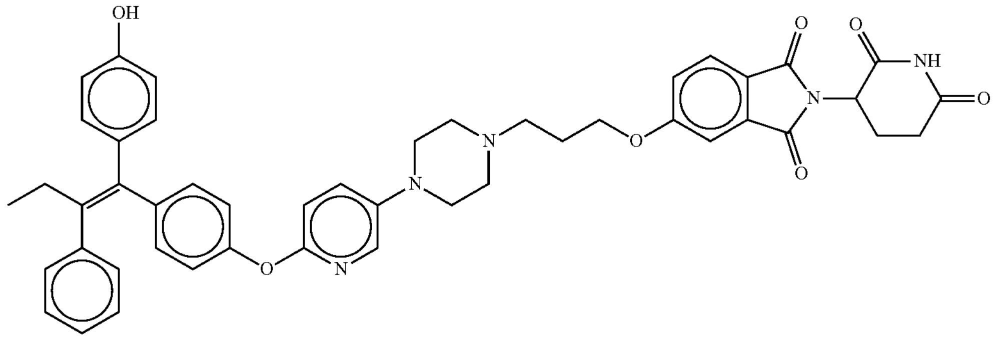 | (Z)-2-(2,6-dioxopiperidin-3-yl)-5-(3-(4-(6-(4-(1-(4-hydroxyphenyl)-2-phenylbut-1-en-1-yl)phenoxy)pyridin-3-yl)piperazin-1-yl)propoxy)isoindoline-1-dione |
| 117 | 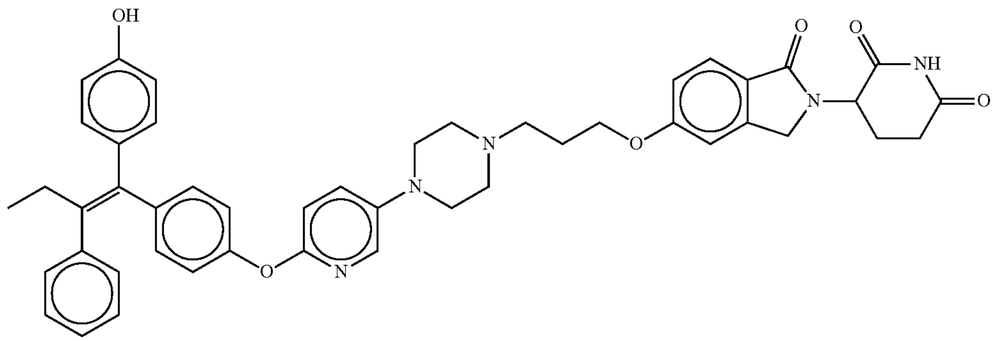 | (Z)-3-(5-(3-(4-(6-(4-(1-(4-hydroxyphenyl)-2-phenylbut-1-en-1-yl)phenoxy)pyridin-3-yl)piperazin-1-yl)propoxy)-1-oxoisoindolin-2-yl)piperidine-2,6-dione |
| 118 | 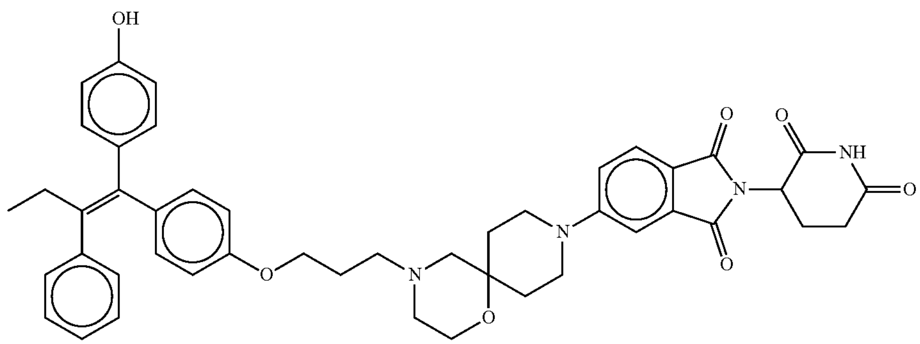 | (Z)-2-(2,6-dioxopiperidin-3-yl)-5-(4-(3-(4-(1-(4-hydroxyphenyl)-2-phenylbut-1-en-1-yl)phenoxy)propyl)-1-oxa-4,9-diazaspiro[5.5]undecan-9-yl)isoindoline-1,3-dione |

TABLE 1-continued
Exemplary Compound of the Present Disclosure
| # | Structure | IUPAC Name |
|---|---|---|
| 119 | 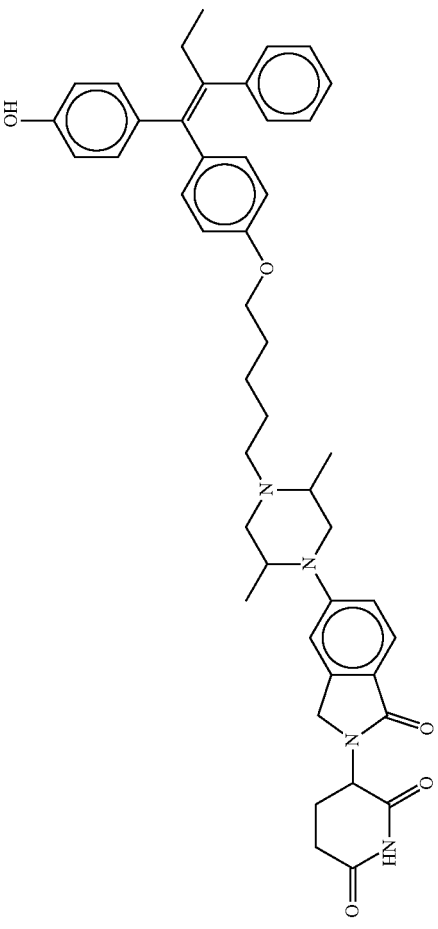 | (Z)-3-(5-(4-(5-(4-(1-(4-hydroxyphenyl)-2-phenylbut-1-en-1-yl)phenoxy)pentyl)-2,5-dimethylpiperazin-1-yl)-1-oxoisoindolin-2-yl)piperidine-2,6-dione |
| 120 | 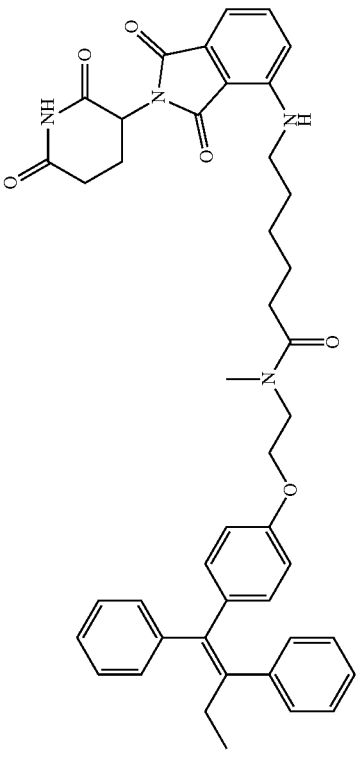 | (Z)-6-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylhexanamide |

TABLE 1-continued

Exemplary Compound of the Present Disclosure

| # | Structure | IUPAC Name |
|---|---|---|
| 121 | 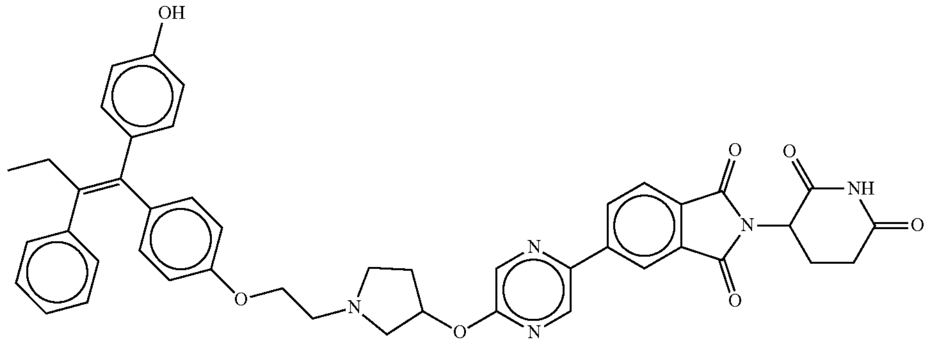 | (Z)-2-(2,6-dioxopiperidin-3-yl)-5-(5-((1-(2-(4-(1-(4-hydroxyphenyl)-2-phenylbut-1-en-1-yl)phenoxy)ethyl)pyrrolidin-3-yl)oxy)pyrazin-2-yl)isoindoline-1,3-dione |
| 122 | 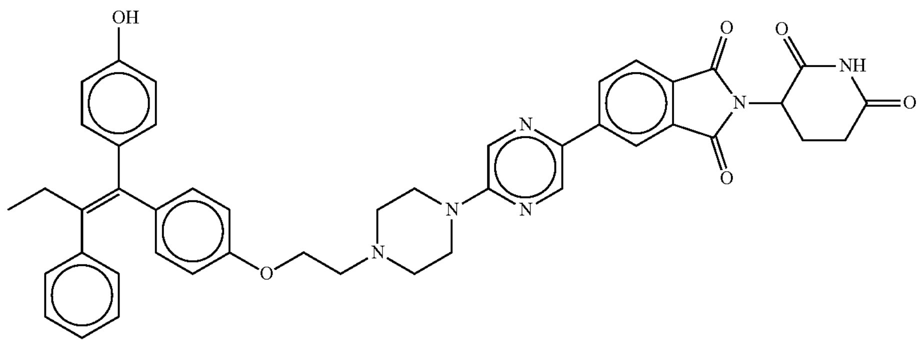 | (Z)-2-(2,6-dioxopiperidin-3-yl)-5-(5-(4-(2-(4-(1-(4-hydroxyphenyl)-2-phenylbut-1-en-1-yl)phenoxy)ethyl)piperazin-1-yl)pyrazin-2-yl)isoindoline-1,3-dione |
| 123 | 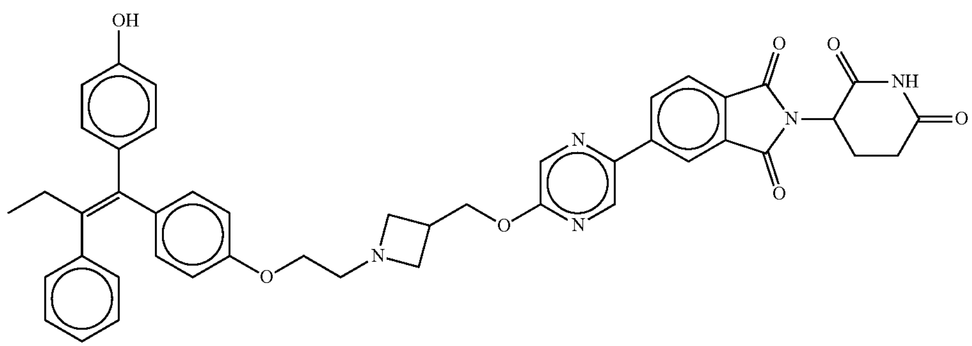 | (Z)-2-(2,6-dioxopiperidin-3-yl)-5-(5-((1-(2-(4-(1-(4-hydroxyphenyl)-2-phenylbut-1-en-1-yl)phenoxy)ethyl)azetidin-3-yl)methoxy)pyrazin-2-yl)isoindoline-1,3-dione |

TABLE 1-continued

Exemplary Compound of the Present Disclosure

| # | Structure | IUPAC Name |
|---|---|---|
| 124 | | (Z)-2-(2,6-dioxopiperidin-3-yl)-5-((2-(4-(2-(4-(1-(4-hydroxyphenyl)-2-phenylbut-1-en-1-yl)phenoxy)ethyl)piperazin-1-yl)pyrimidin-5-yl)oxy)isoindoline-1,3-dione |
| 125 | | (Z)-6-(2,6-dioxopiperidin-3-yl)-2-(4-(5-(4-(1-(4-hydroxyphenyl)-2-phenylbut-1-en-1-yl)phenoxy)pentyl)piperazin-1-yl)-5H-pyrrolo[3,4-b]pyrazine-5,7(6H)-dione |

| # | Structure | IUPAC Name |
|---|---|---|
| 126 | 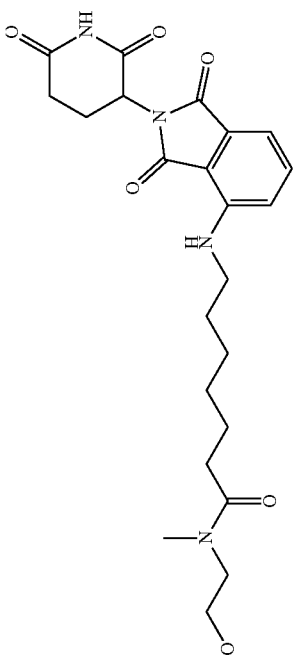 | (Z)-7-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylheptanamide |
| 127 | 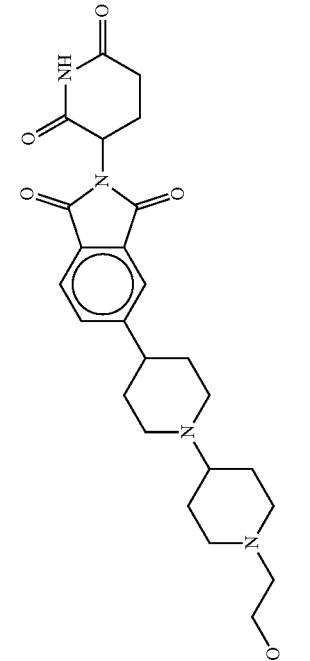 | (Z)-2-(2,6-dioxopiperidin-3-yl)-5-(1'-(2-(4-(1-(4-hydroxyphenyl)-2-phenylbut-1-en-1-yl)phenoxy)ethyl)-[1,4'-bipiperidin]-4-yl)isoindoline-1,3-dione |
| 128 | 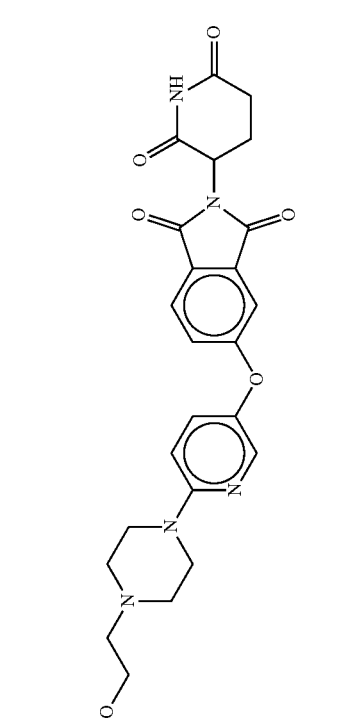 | (Z)-2-(2,6-dioxopiperidin-3-yl)-5-((6-(4-(2-(4-(1-(4-hydroxyphenyl)-2-phenylbut-1-en-1-yl)phenoxy)ethyl)piperazin-1-yl)pyridin-3-yl)oxy)isoindoline-1,3-dione |

TABLE 1-continued
Exemplary Compound of the Present Disclosure
| # | Structure | IUPAC Name |
|---|---|---|
| 129 | 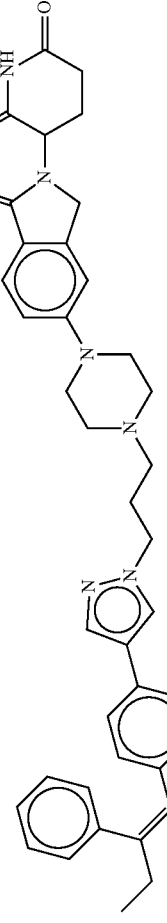 | (E)-3-(5-(4-(3-(4-(4-(1-(4-hydroxyphenyl)-2-phenylbut-1-en-1-yl)phenyl)-1H-pyrazol-1-yl)propyl)piperazin-1-yl)-1-oxoisoindolin-2-yl)piperidine-2,6-dione |
| 130 | 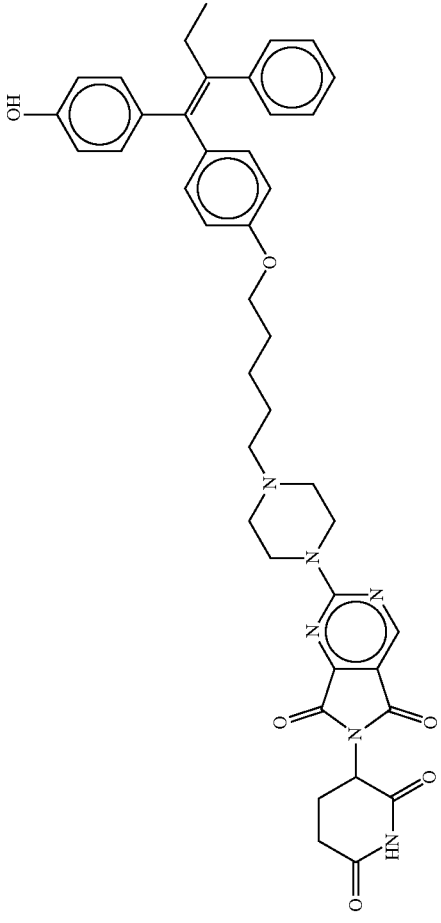 | (Z)-6-(2,6-dioxopiperidin-3-yl)-2-(4-(5-(4-(1-(4-hydroxyphenyl)-2-phenylbut-1-en-1-yl)phenoxy)pentyl)piperazin-1-yl)-5H-pyrrolo[3,4-d]pyrimidine-5,7(6H)-dione |

TABLE 1-continued

Exemplary Compound of the Present Disclosure

| # | Structure | IUPAC Name |
|---|---|---|
| 131 | 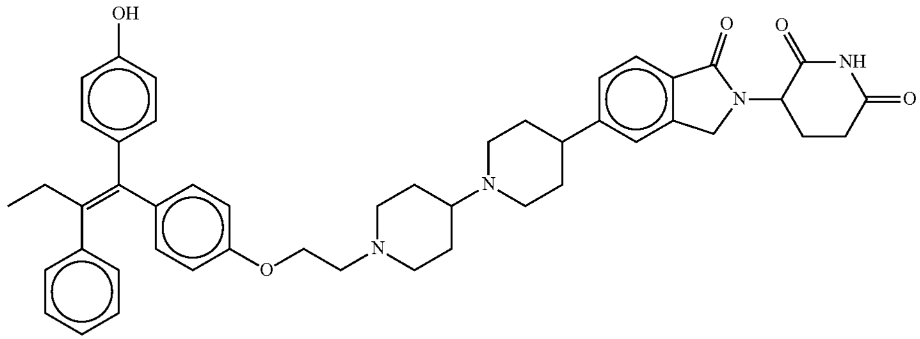 | (Z)-3-(5-(1'-(2-(4-(1-(4-hydroxyphenyl)-2-phenylbut-1-en-1-yl)phenoxy)ethyl)-[1,4'-bipiperidin]-4-yl)-1-oxoisoindolin-2-yl)piperidine-2,6-dione |
| 132 | 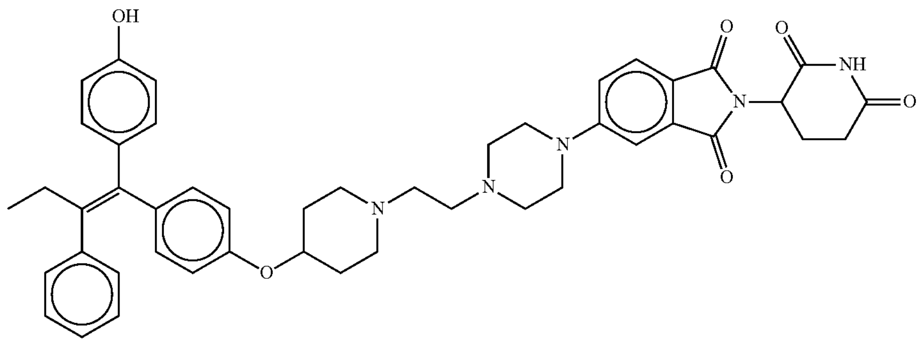 | (Z)-2-(2,6-dioxopiperidin-3-yl)-5-(4-(1-(2-(4-(1-(4-hydroxyphenyl)-2-phenylbut-1-en-1-yl)phenoxy)piperidin-1-yl)ethyl)piperazin-1-yl)isoindoline-1,3-dione |

TABLE 1-continued

Exemplary Compound of the Present Disclosure

| # | Structure | IUPAC Name |
|---|---|---|
| 133 | 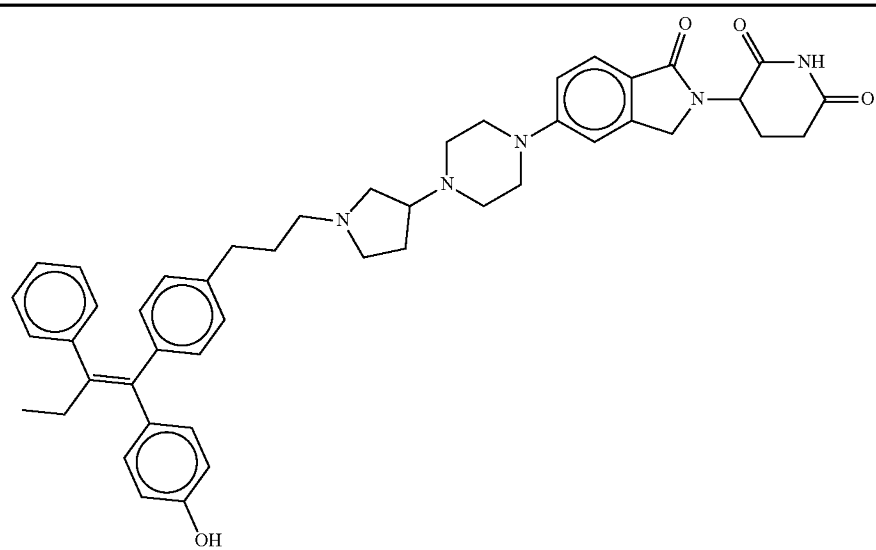 | (E)-3-(5-(4-(1-(3-(4-(1-(4-hydroxyphenyl)-2-phenylbut-1-en-1-yl)phenyl)propyl)pyrrolidin-3-yl)piperazin-1-yl)-1-oxoisoindolin-2-yl)piperidine-2,6-dione |
| 134 | 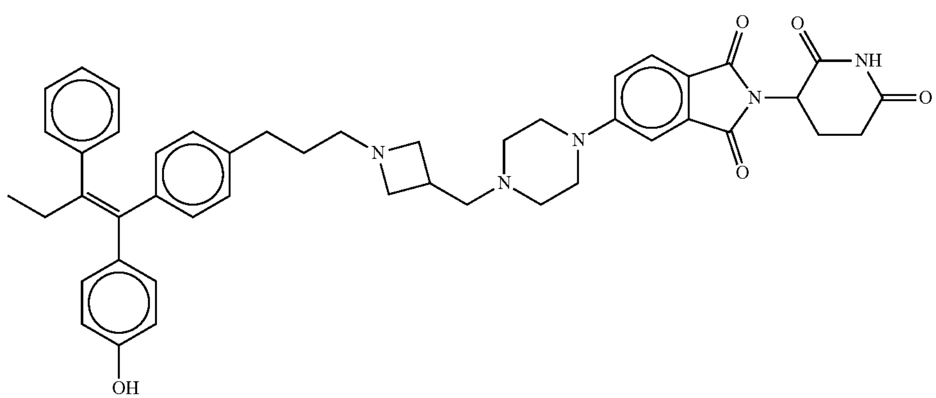 | (E)-2-(2,6-dioxopiperidin-3-yl)-5-(4-((1-(3-(4-(1-(4-hydroxyphenyl)-2-phenylbut-1-en-1-yl)phenyl)propyl)azetidin-3-yl)methyl)piperazin-1-yl)isoindoline-1,3-dione |

TABLE 1-continued

Exemplary Compound of the Present Disclosure

| # | Structure | IUPAC Name |
|---|---|---|
| 135 | 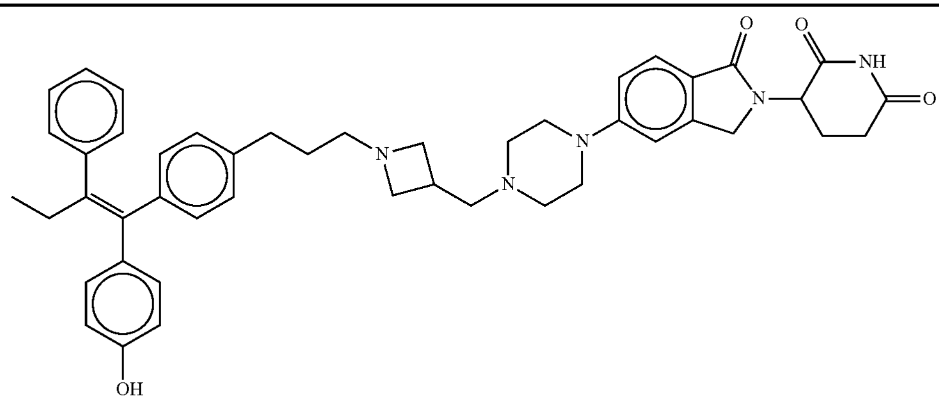 | (E)-3-(5-(4-((1-(3-(4-(1-(4-hydroxyphenyl)-2-phenylbut-1-en-1-yl)phenyl)propyl)azetidin-3-yl)methyl)piperazin-1-yl)-1-oxoisoindolin-2-yl)piperidine-2,6-dione |
| 136 | 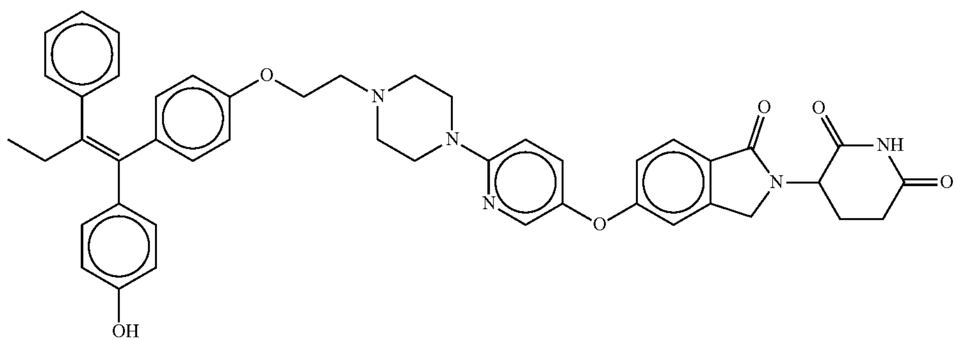 | (Z)-3-(5-((6-(4-(2-(4-(1-(4-hydroxyphenyl)-2-phenylbut-1-en-1-yl)phenoxy)ethyl)piperazin-1-yl)pyridin-3-yl)oxy)-1-oxoisoindolin-2-yl)piperidine-2,6-dione |

TABLE 1-continued
Exemplary Compound of the Present Disclosure
| # | Structure | IUPAC Name |
|---|---|---|
| 137 | 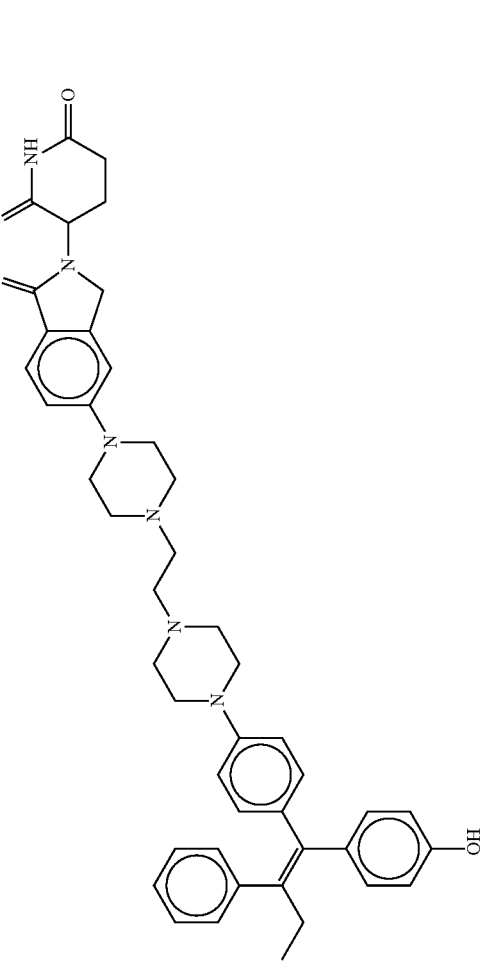 | (E)-3-(5-(4-(2-(4-(4-(1-(4-hydroxyphenyl)-2-phenylbut-1-en-1-yl)phenyl)piperazin-1-yl)ethyl)piperazin-1-yl)-1-oxoisoindolin-2-yl)piperidine-2,6-dione |
| 138 | 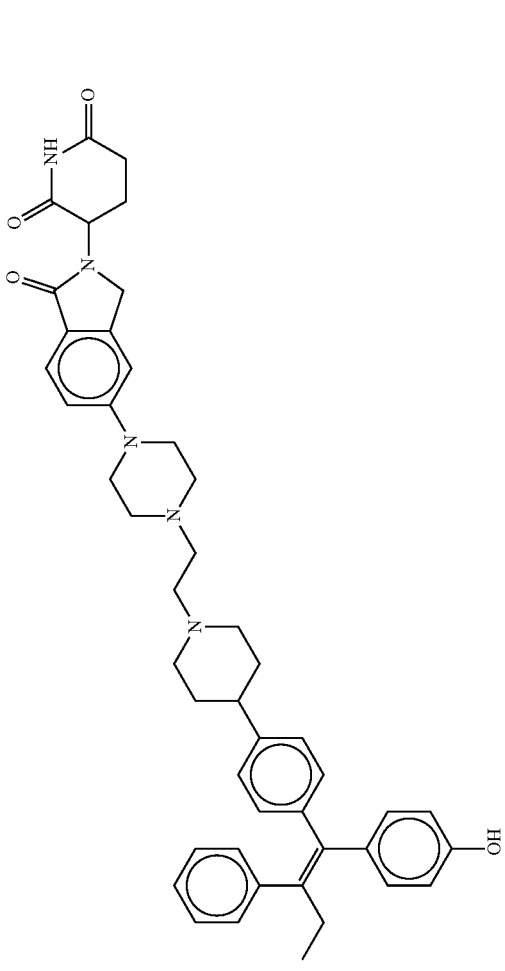 | (E)-3-(5-(4-(2-(4-(4-(1-(4-hydroxyphenyl)-2-phenylbut-1-en-1-yl)phenyl)piperidin-1-yl)ethyl)piperazin-1-yl)-1-oxoisoindolin-2-yl)piperidine-2,6-dione |

TABLE 1-continued
Exemplary Compound of the Present Disclosure
| # | Structure | IUPAC Name |
|---|---|---|
| 139 | 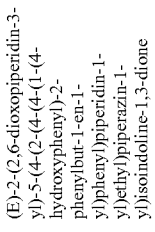 | (E)-2-(2,6-dioxopiperidin-3-yl)-5-(4-(2-(4-(4-(1-(4-hydroxyphenyl)-2-phenylbut-1-en-1-yl)phenyl)piperidin-1-yl)ethyl)piperazin-1-yl)isoindoline-1,3-dione |
| 140 | 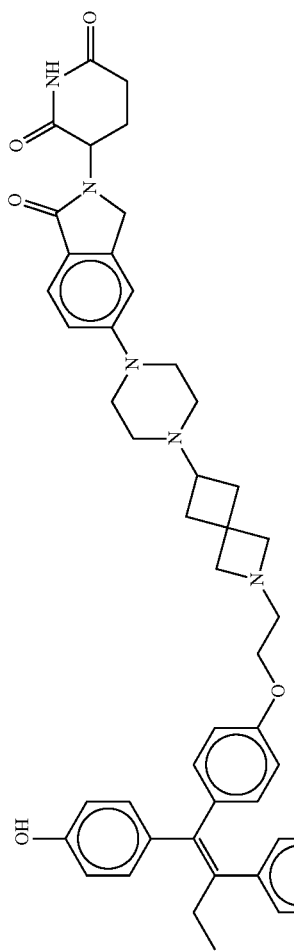 | (Z)-3-(5-(4-(2-(2-(4-(1-(4-hydroxyphenyl)-2-phenylbut-1-en-1-yl)phenoxy)ethyl)-2-azaspiro[3.3]heptan-6-yl)piperazin-1-yl)-1-oxoisoindolin-2-yl)piperidine-2,6-dione |

TABLE 1-continued
Exemplary Compound of the Present Disclosure
| # | Structure | IUPAC Name |
|---|-----------|------------|
| 141 | 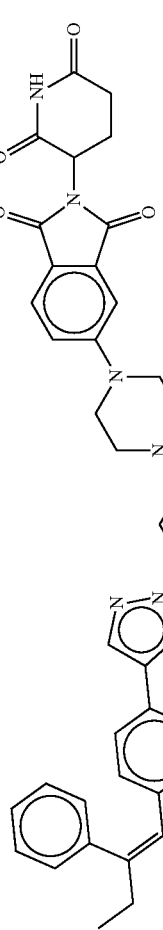 | (E)-2-(2,6-dioxopiperidin-3-yl)-5-(4-(3-(4-(4-(1-(4-hydroxyphenyl)-2-phenylbut-1-en-1-yl)phenyl)-1H-pyrazol-1-yl)propyl)piperazin-1-yl)isoindoline-1,3-dione |
| 142 | 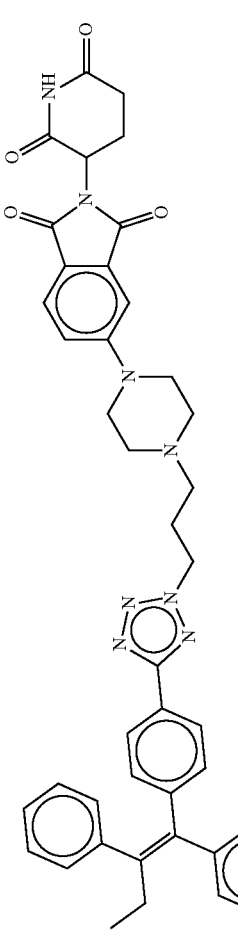 | (E)-2-(2,6-dioxopiperidin-3-yl)-5-(4-(3-(5-(4-(1-(4-hydroxyphenyl)-2-phenylbut-1-en-1-yl)phenyl)-2H-tetrazol-2-yl)propyl)piperazin-1-yl)isoindoline-1,3-dione |

TABLE 1-continued

Exemplary Compound of the Present Disclosure

| # | Structure | IUPAC Name |
|---|---|---|
| 143 | 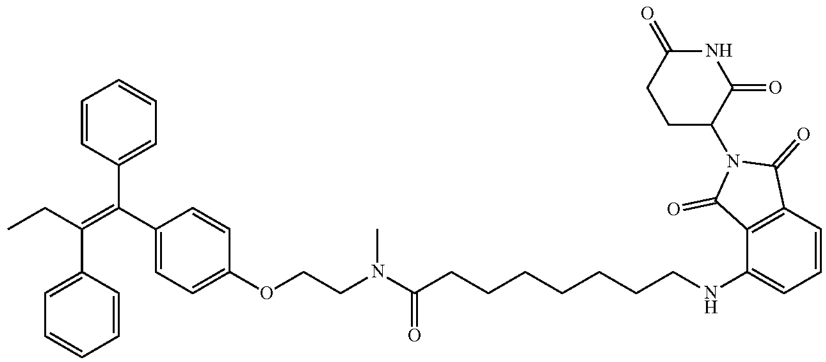 [SMILES: CC/C(=C(\c1ccccc1)c1ccc(OCCN(C)C(=O)CCCCCCCNc2cccc3c2C(=O)N(C2CCC(=O)NC2=O)C3=O)cc1)c1ccccc1] | (Z)-8-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methyloctanamide |
| 144 | 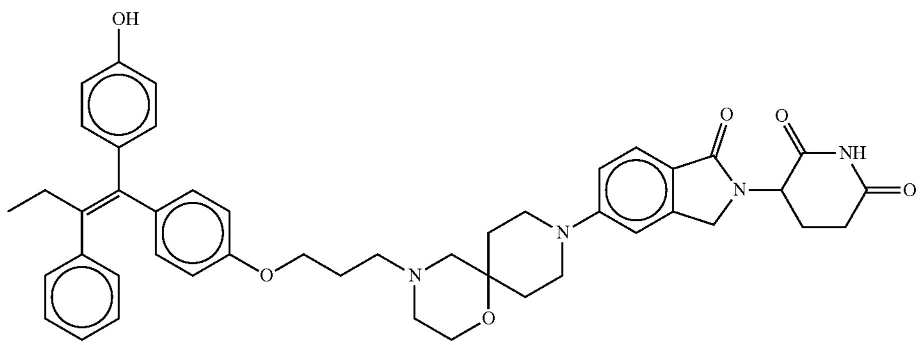 | (Z)-3-(5-(4-(3-(4-(1-(4-hydroxyphenyl)-2-phenylbut-1-en-1-yl)phenoxy)propyl)-1-oxa-4,9-diazaspiro[5.5]undecan-9-yl)-1-oxoisoindolin-2-yl)piperidine-2,6-dione |

TABLE 1-continued
Exemplary Compound of the Present Disclosure
| # | Structure | IUPAC Name |
|---|---|---|
| 145 | 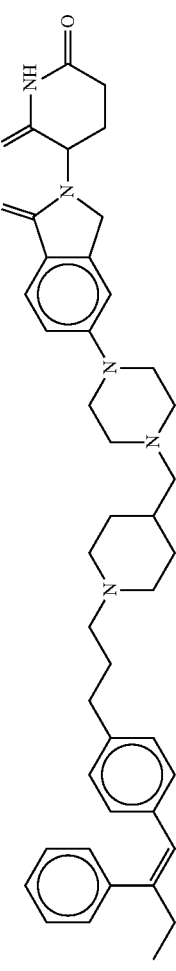 | (E)-3-(5-(4-((1-(3-(4-(1-(4-hydroxyphenyl)-2-phenylbut-1-en-1-yl)phenyl)propyl)piperidin-4-yl)methyl)piperazin-1-yl)-1-oxoisoindolin-2-yl)piperidine-2,6-dione |
| 146 | 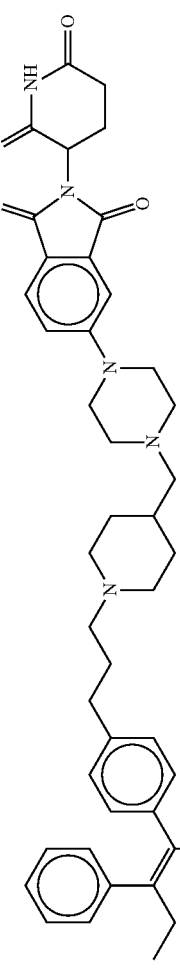 | (E)-2-(2,6-dioxopiperidin-3-yl)-5-(4-((1-(3-(4-(1-(4-hydroxyphenyl)-2-phenylbut-1-en-1-yl)phenyl)propyl)piperidin-4-yl)methyl)piperazin-1-yl)isoindoline-1,3-dione |

TABLE 1-continued

Exemplary Compound of the Present Disclosure

| # | Structure | IUPAC Name |
|---|---|---|
| 147 | 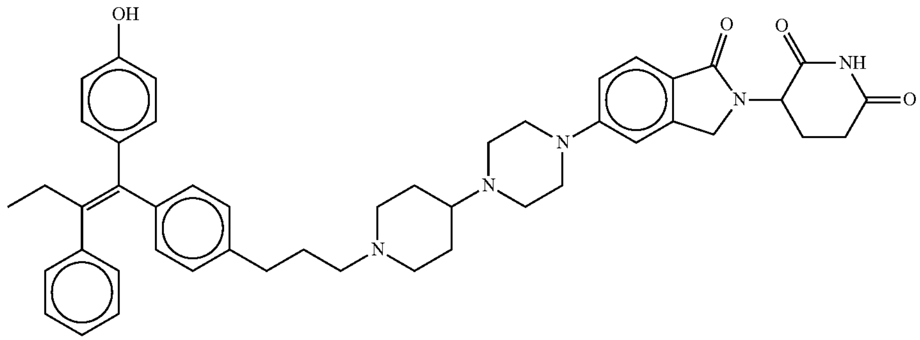 | (E)-3-(5-(4-(1-(3-(4-(1-(4-hydroxyphenyl)-2-phenylbut-1-en-1-yl)phenyl)propyl)piperidin-4-yl)piperazin-1-yl)-1-oxoisoindolin-2-yl)piperidine-2,6-dione |
| 148 | 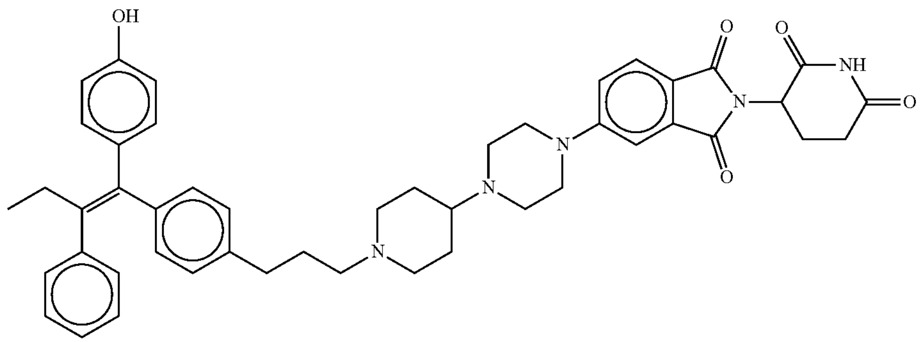 | (E)-2-(2,6-dioxopiperidin-3-yl)-5-(4-(1-(3-(4-(1-(4-hydroxyphenyl)-2-phenylbut-1-en-1-yl)phenyl)propyl)piperidin-4-yl)piperazin-1-yl)isoindoline-1,3-dione |
| 149 | 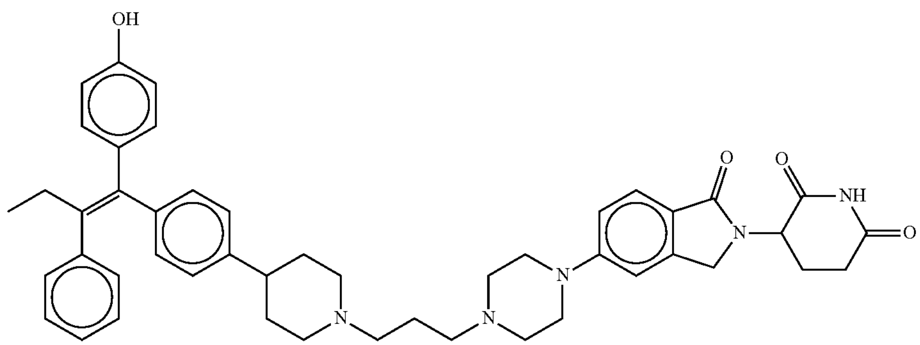 | (E)-3-(5-(4-(3-(4-(1-(4-hydroxyphenyl)-2-phenylbut-1-en-1-yl)phenyl)piperidin-1-yl)propyl)piperazin-1-yl)-1-oxoisoindolin-2-yl)piperidine-2,6-dione |

TABLE 1-continued

Exemplary Compound of the Present Disclosure

| # | Structure | IUPAC Name |
|---|---|---|
| 150 | 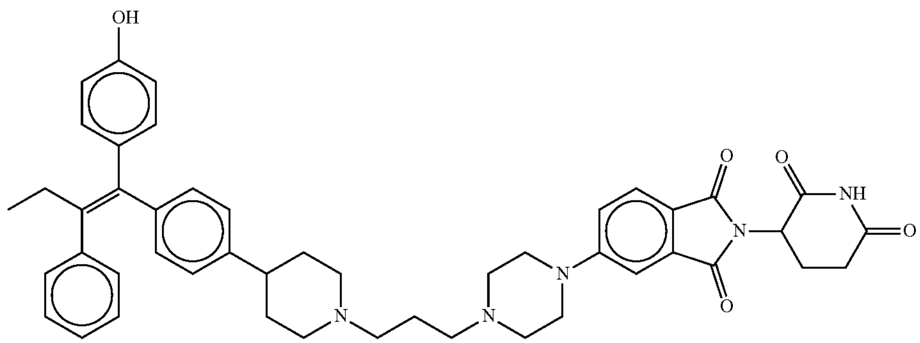 | (E)-2-(2,6-dioxopiperidin-3-yl)-5-(4-(3-(4-(4-(1-(4-hydroxyphenyl)-2-phenylbut-1-en-1-yl)phenyl)piperidin-1-yl)propyl)piperazin-1-yl)isoindoline-1,3-dione |
| 151 | 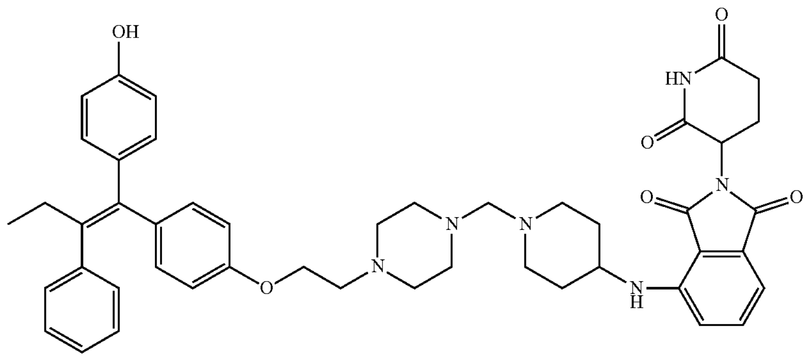 [SMILES: CC/C(=C(\c1ccc(O)cc1)c1ccc(OCCN2CCN(CN3CCC(Nc4cccc5c4C(=O)N(C4CCC(=O)NC4=O)C5=O)CC3)CC2)cc1)c1ccccc1] | (Z)-2-(2,6-dioxopiperidin-3-yl)-4-((1-((4-(2-(4-(1-(4-hydroxyphenyl)-2-phenylbut-1-en-1-yl)phenoxy)ethyl)piperazin-1-yl)methyl)piperidin-4-yl)amino)isoindoline-1,3-dione |

TABLE 1-continued
Exemplary Compound of the Present Disclosure
| # | Structure | IUPAC Name |
|---|---|---|
| 152 | 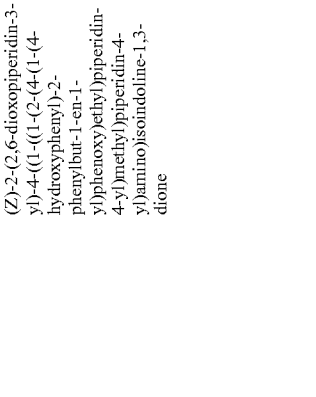 | (Z)-2-(2,6-dioxopiperidin-3-yl)-4-((1-((1-(2-(4-(1-(4-hydroxyphenyl)-2-phenylbut-1-en-1-yl)phenoxy)ethyl)piperidin-4-yl)methyl)piperidin-4-yl)amino)isoindoline-1,3-dione |
| 153 | 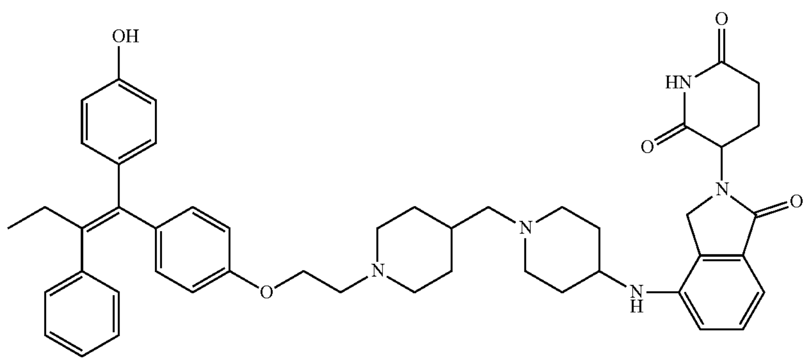 [SMILES: CC/C(=C(\c1ccc(O)cc1)c1ccc(OCCN2CCC(CN3CCC(Nc4cccc5c4CN(C4CCC(=O)NC4=O)C5=O)CC3)CC2)cc1)c1ccccc1] | (Z)-3-(4-((1-((1-(2-(4-(1-(4-hydroxyphenyl)-2-phenylbut-1-en-1-yl)phenoxy)ethyl)piperidin-4-yl)methyl)piperidin-4-yl)amino)-1-oxoisoindolin-2-yl)piperidine-2,6-dione |

TABLE 1-continued

Exemplary Compound of the Present Disclosure

| # | Structure | IUPAC Name |
|---|---|---|
| 154 | 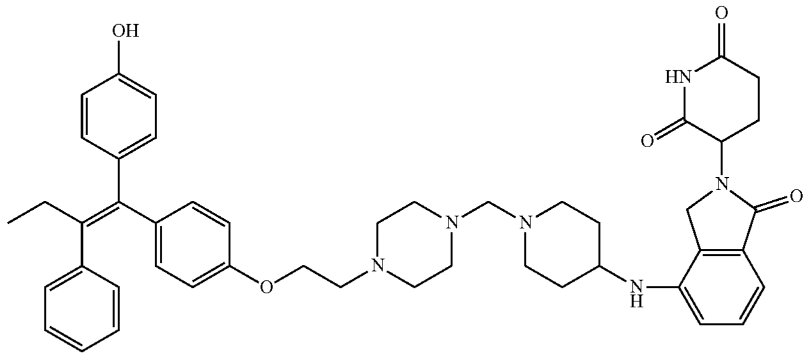 | (Z)-3-(4-((1-((4-(2-(4-(1-(4-hydroxyphenyl)-2-phenylbut-1-en-1-yl)phenoxy)ethyl)piperazin-1-yl)methyl)piperidin-4-yl)amino)-1-oxoisoindolin-2-yl)piperidine-2,6-dione |
| 155 | 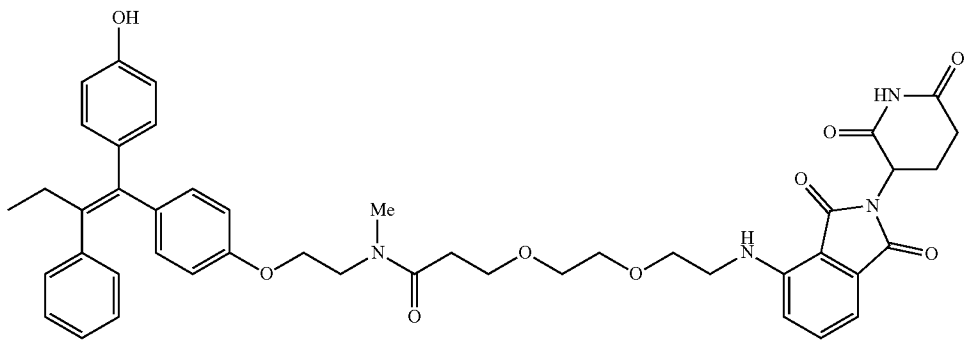 [SMILES: CC/C(=C(\c1ccc(O)cc1)c1ccc(OCCN(C)C(=O)CCOCCOCCNc2cccc3c2C(=O)N(C2CCC(=O)NC2=O)C3=O)cc1)c1ccccc1] | (Z)-3-(2-(2-((2-(2,6-dioxopiperidin-3-yl)-1,3-dioxoisoindolin-4-yl)amino)ethoxy)ethoxy)-N-(2-(4-(1-(4-hydroxyphenyl)-2-phenylbut-1-en-1-yl)phenoxy)ethyl)-N-methylpropanamide |

TABLE 1-continued
Exemplary Compound of the Present Disclosure
| # | Structure | IUPAC Name |
|---|---|---|
| 156 | 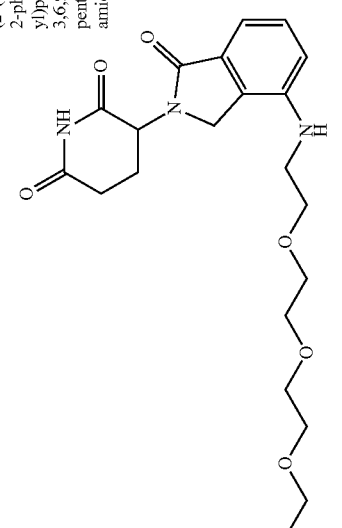 | (Z)-1-((2-(2,6-dioxopiperidin-3-yl)-1-oxoisoindolin-4-yl)amino)-N-(2-(4-(1-(4-hydroxyphenyl)-2-phenylbut-1-en-1-yl)phenoxy)ethyl)-N-methyl-3,6,9,12,15-pentaoxaoctadecan-18-amide |
| 157 | 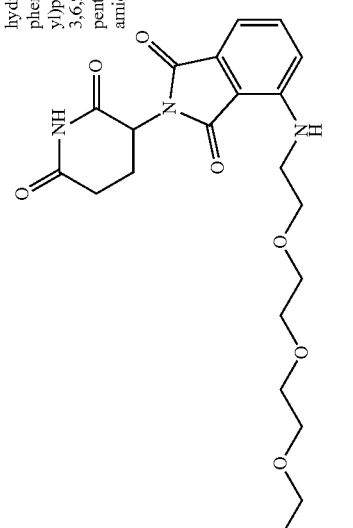 | (Z)-1-((2-(2,6-dioxopiperidin-3-yl)-1,3-dioxoisoindolin-4-yl)amino)-N-(2-(4-(1-(4-hydroxyphenyl)-2-phenylbut-1-en-1-yl)phenoxy)ethyl)-N-methyl-3,6,9,12,15-pentaoxaoctadecan-18-amide |

TABLE 1-continued

Exemplary Compound of the Present Disclosure

| # | Structure | IUPAC Name |
|---|---|---|
| 158 | 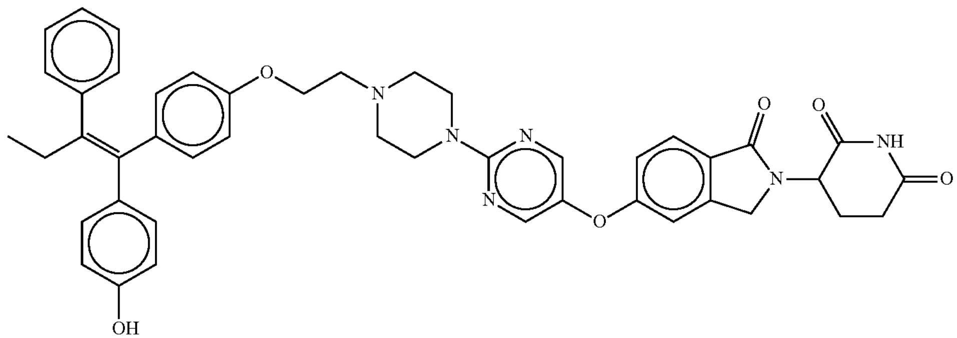 | (Z)-3-(5-((2-(4-(2-(4-(1-(4-hydroxyphenyl)-2-phenylbut-1-en-1-yl)phenoxy)ethyl)piperazin-1-yl)pyrimidin-5-yl)oxy)-1-oxoisoindolin-2-yl)piperidine-2,6-dione |
| 159 | 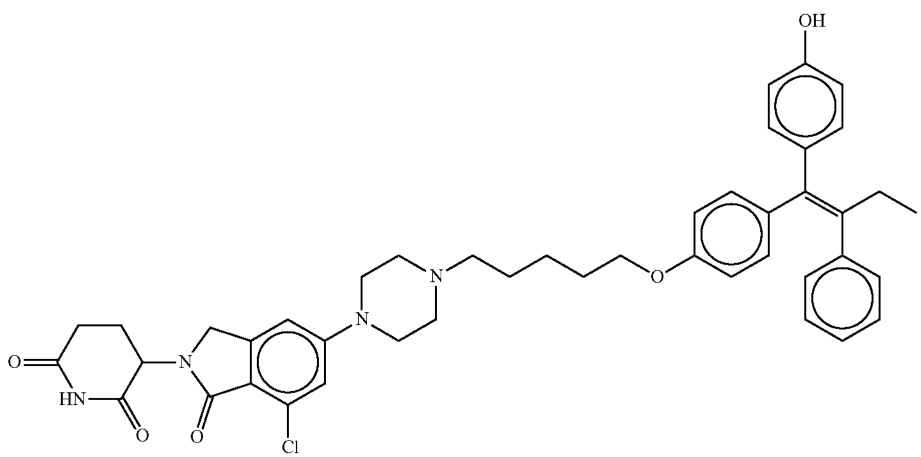 | (Z)-3-(7-chloro-5-(4-(5-(4-(1-(4-hydroxyphenyl)-2-phenylbut-1-en-1-yl)phenoxy)pentyl)piperazin-1-yl)-1-oxoisoindolin-2-yl)piperidine-2,6-dione |

TABLE 1-continued

Exemplary Compound of the Present Disclosure

| # | Structure | IUPAC Name |
|---|---|---|
| 160a | 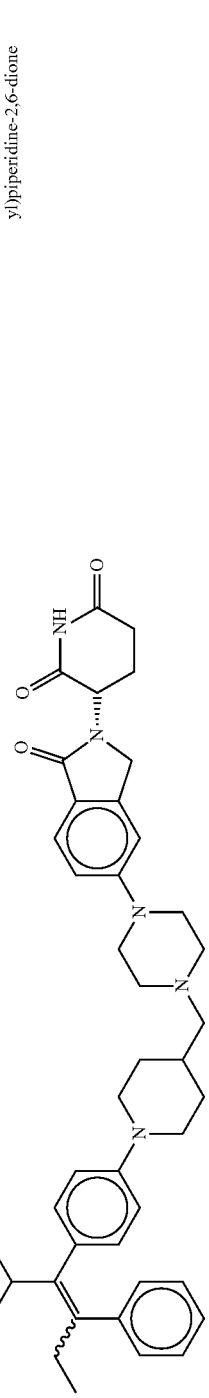 | (E)/(Z)-(S)-3-(5-(4-((1-(4-(1-(4-hydroxyphenyl)-2-phenylbut-1-en-1-yl)phenyl)piperidin-4-yl)methyl)piperazin-1-yl)-1-oxoisoindolin-2-yl)piperidine-2,6-dione |
| 160 | 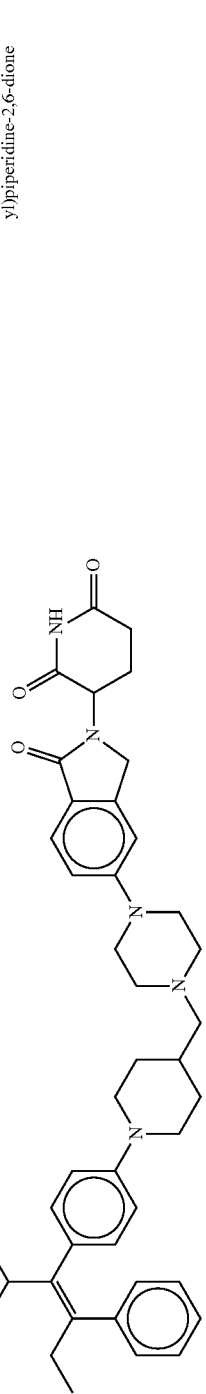 | (E)-3-(5-(4-((1-(4-(1-(4-hydroxyphenyl)-2-phenylbut-1-en-1-yl)phenyl)piperidin-4-yl)methyl)piperazin-1-yl)-1-oxoisoindolin-2-yl)piperidine-2,6-dione |
| 160b | 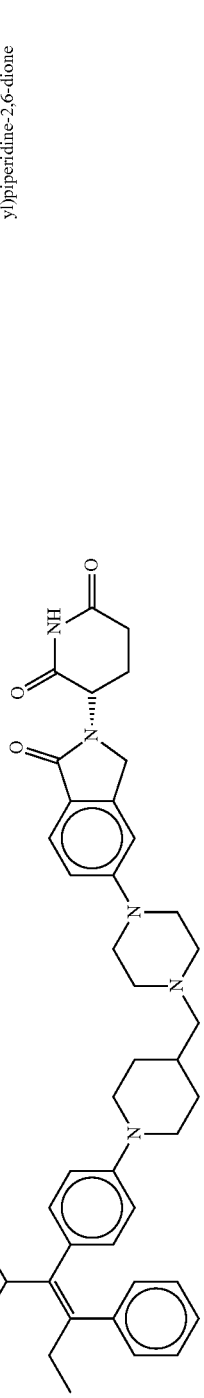 | (E)-(S)-3-(5-(4-((1-(4-(1-(4-hydroxyphenyl)-2-phenylbut-1-en-1-yl)phenyl)piperidin-4-yl)methyl)piperazin-1-yl)-1-oxoisoindolin-2-yl)piperidine-2,6-dione |

TABLE 1-continued
Exemplary Compound of the Present Disclosure
| # | Structure | IUPAC Name |
|---|---|---|
| 161a | 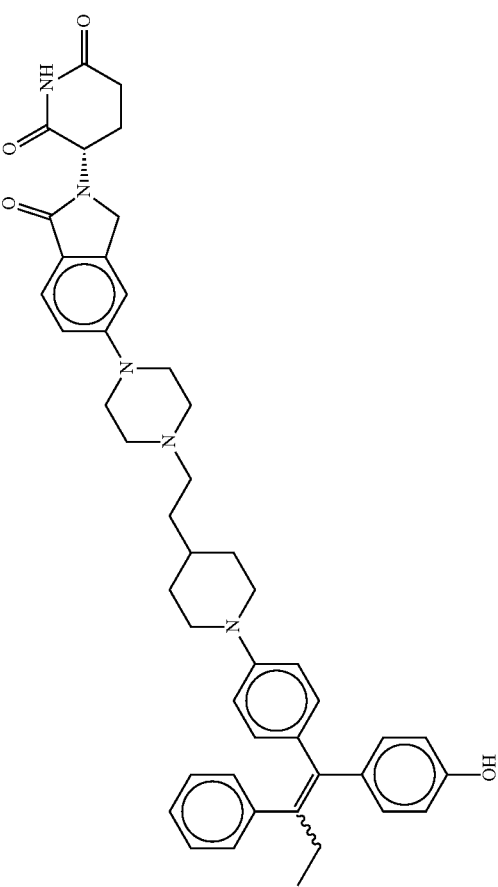 | (E)/(Z)-(S)-3-(5-(4-(2-(1-(4-(1-(4-hydroxyphenyl)-2-phenylbut-1-en-1-yl)phenyl)piperidin-4-yl)ethyl)piperazin-1-yl)-1-oxoisoindolin-2-yl)piperidine-2,6-dione |
| 161 | 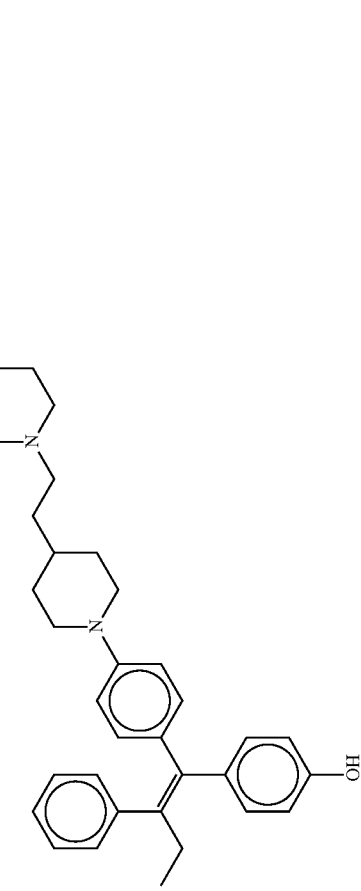 | (E)-3-(5-(4-(2-(1-(4-(1-(4-hydroxyphenyl)-2-phenylbut-1-en-1-yl)phenyl)piperidin-4-yl)ethyl)piperazin-1-yl)-1-oxoisoindolin-2-yl)piperidine-2,6-dione |

TABLE 1-continued
Exemplary Compound of the Present Disclosure
| # | Structure | IUPAC Name |
|---|---|---|
| 162 | 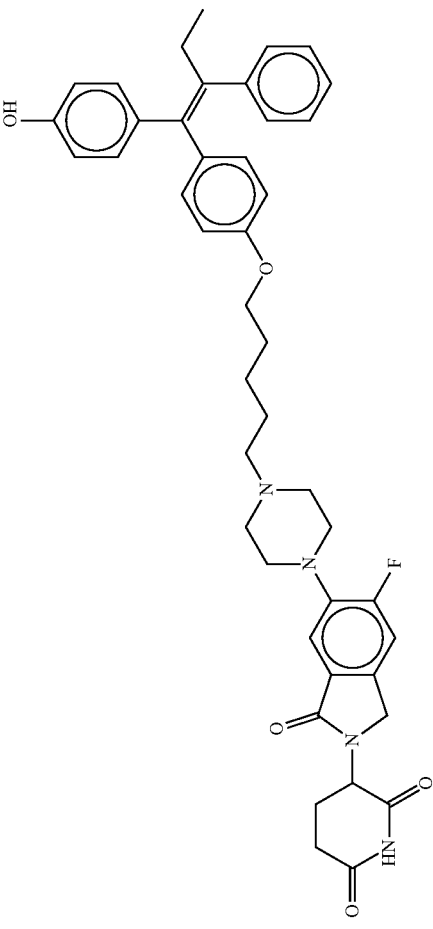 | (Z)-3-(5-fluoro-6-(4-(5-(4-(1-(4-hydroxyphenyl)-2-phenylbut-1-en-1-yl)phenoxy)pentyl)piperazin-1-yl)-1-oxoisoindolin-2-yl)piperidine-2,6-dione |
| 163 | 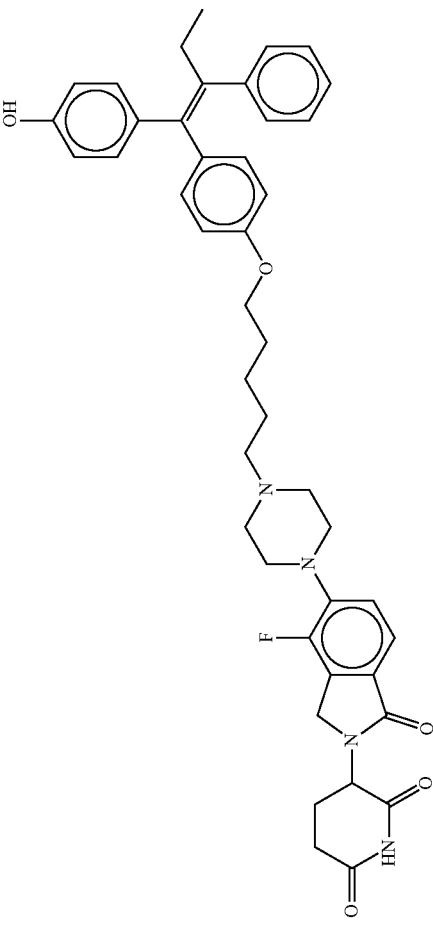 | (Z)-3-(4-fluoro-5-(4-(5-(4-(1-(4-hydroxyphenyl)-2-phenylbut-1-en-1-yl)phenoxy)pentyl)piperazin-1-yl)-1-oxoisoindolin-2-yl)piperidine-2,6-dione |

TABLE 1-continued

Exemplary Compound of the Present Disclosure

| # | Structure | IUPAC Name |
|---|---|---|
| 164 | 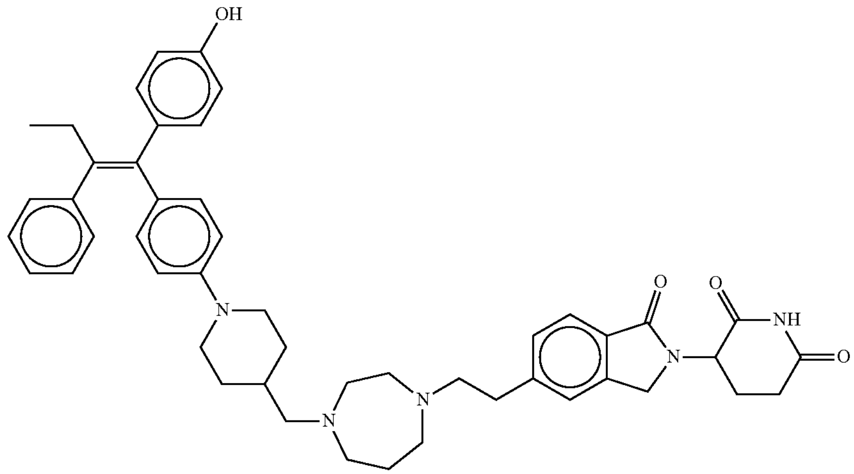 | (E)-3-(5-(2-(4-((1-(4-(1-(4-hydroxyphenyl)-2-phenylbut-1-en-1-yl)phenyl)piperidin-4-yl)methyl)-1,4-diazepan-1-yl)ethyl)-1-oxoisoindolin-2-yl)piperidine-2,6-dione |
| 165 | 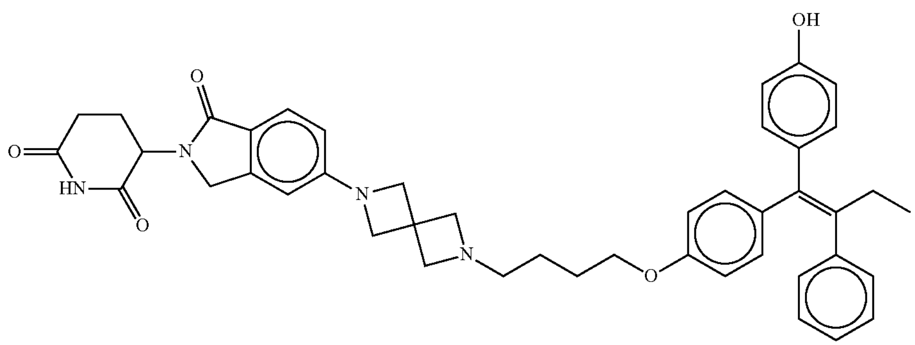 | (Z)-3-(5-(6-(4-(4-(1-(4-hydroxyphenyl)-2-phenylbut-1-en-1-yl)phenoxy)butyl)-2,6-diazaspiro[3.3]heptan-2-yl)-1-oxoisoindolin-2-yl)piperidine-2,6-dione |

TABLE 1-continued
Exemplary Compound of the Present Disclosure
| # | Structure | IUPAC Name |
|---|---|---|
| 166 | 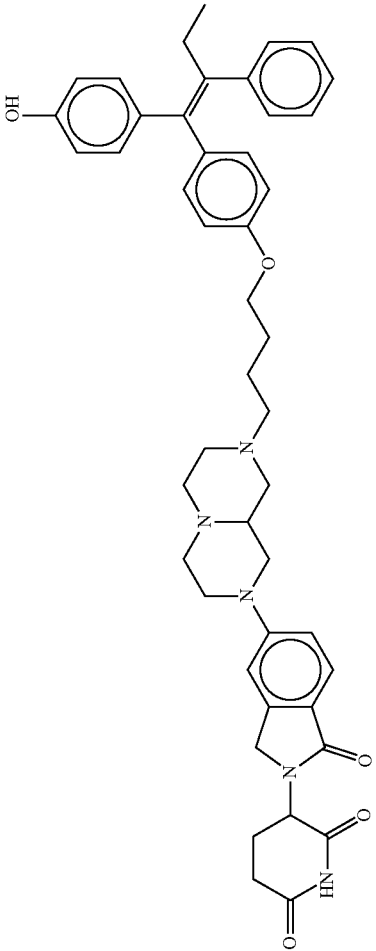 | (Z)-3-(5-(8-(4-(4-(1-(4-hydroxyphenyl)-2-phenylbut-1-en-1-yl)phenoxy)butyl)octahydro-2H-pyrazino[1,2-a]pyrazin-2-yl)-1-oxoisoindolin-2-yl)piperidine-2,6-dione |
| 167 | 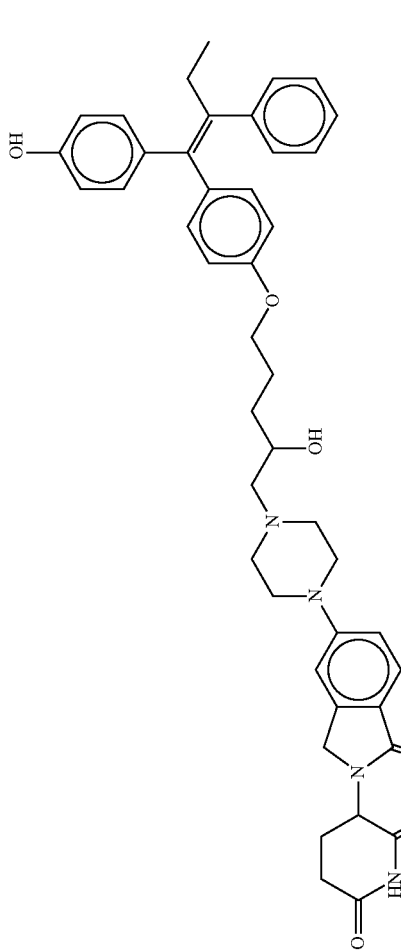 | (Z)-3-(5-(4-(2-hydroxy-5-(4-(1-(4-hydroxyphenyl)-2-phenylbut-1-en-1-yl)phenoxy)pentyl)piperazin-1-yl)-1-oxoisoindolin-2-yl)piperidine-2,6-dione |

TABLE 1-continued
Exemplary Compound of the Present Disclosure
| # | Structure | IUPAC Name |
|---|---|---|
| 168 | 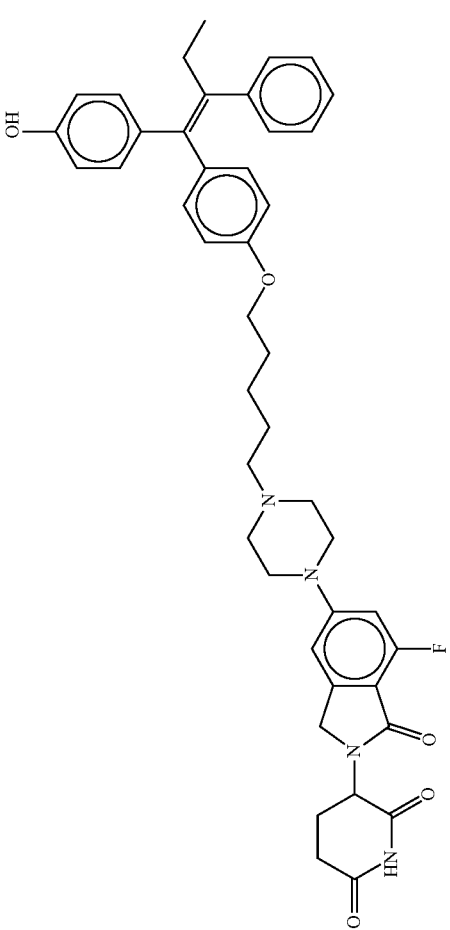 | (Z)-3-(7-fluoro-5-(4-(5-(4-(1-(4-hydroxyphenyl)-2-phenylbut-1-en-1-yl)phenoxy)pentyl)piperazin-1-yl)-1-oxoisoindolin-2-yl)piperidine-2,6-dione |
| 169 | 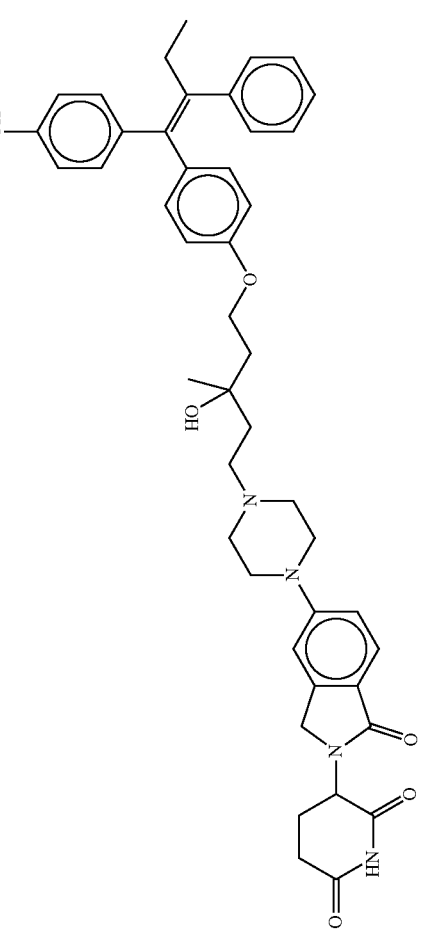 | (Z)-3-(5-(4-(3-hydroxy-5-(4-(1-(4-hydroxyphenyl)-2-phenylbut-1-en-1-yl)phenoxy)-3-methylpentyl)piperazin-1-yl)-1-oxoisoindolin-2-yl)piperidine-2,6-dione |

TABLE 1-continued
Exemplary Compound of the Present Disclosure
| # | Structure | IUPAC Name |
|---|-----------|------------|
| 170 | 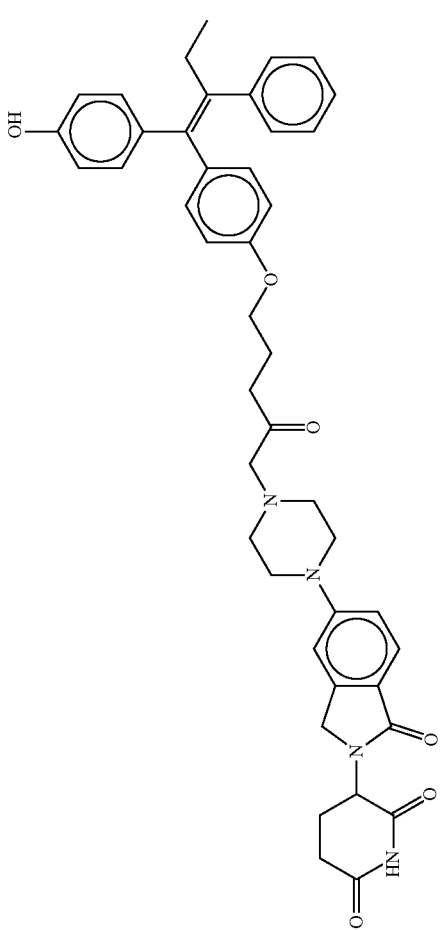 | (Z)-3-(5-(4-(5-(4-(1-(4-hydroxyphenyl)-2-phenylbut-1-en-1-yl)phenoxy)-2-oxopentyl)piperazin-1-yl)-1-oxoisoindolin-2-yl)piperidine-2,6-dione |
| 171 | 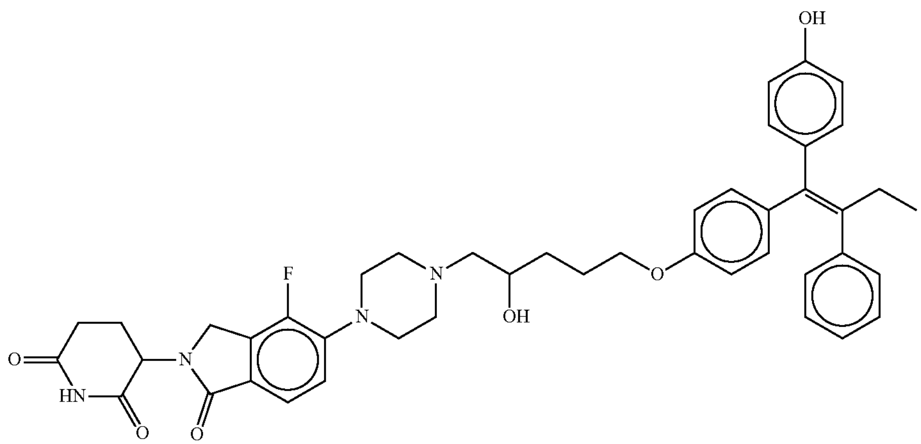 | (Z)-3-(4-fluoro-5-(4-(2-hydroxy-5-(4-(1-(4-hydroxyphenyl)-2-phenylbut-1-en-1-yl)phenoxy)pentyl)piperazin-1-yl)-1-oxoisoindolin-2-yl)piperidine-2,6-dione |

TABLE 1-continued
Exemplary Compound of the Present Disclosure
| # | Structure | IUPAC Name |
|---|---|---|
| 172 | 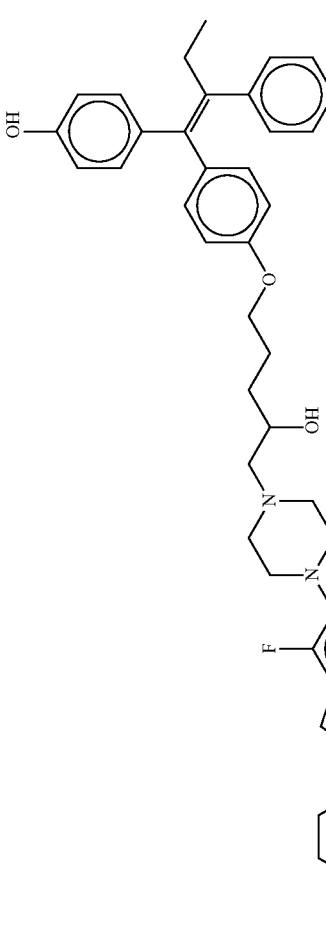 | (Z)-3-(4,6-difluoro-5-(4-(2-hydroxy-5-(4-(1-(4-hydroxyphenyl)-2-phenylbut-1-en-1-yl)phenoxy)pentyl)piperazin-1-yl)-1-oxoisoindolin-2-yl)piperidine-2,6-dione |
| 173 | 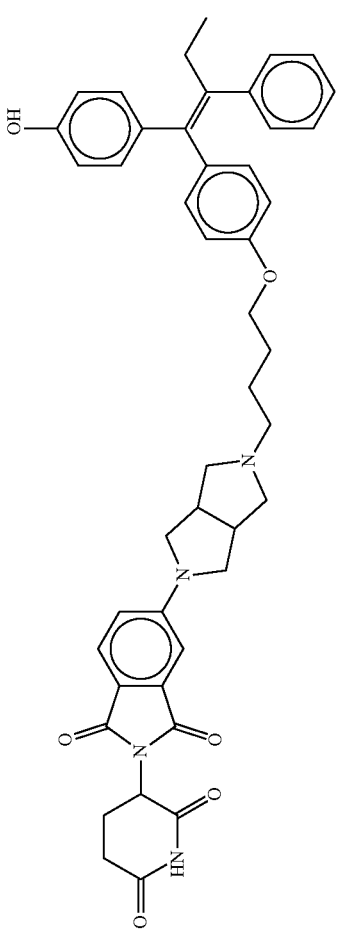 | (Z)-2-(2,6-dioxopiperidin-3-yl)-5-(5-(4-(1-(4-hydroxyphenyl)-2-phenylbut-1-en-1-yl)phenoxy)butyl)hexahydropyrrolo[3,4-c]pyrrol-2(1H)-yl)isoindoline-1,3-dione |

TABLE 1-continued
Exemplary Compound of the Present Disclosure
| # | Structure | IUPAC Name |
|---|---|---|
| 174 | 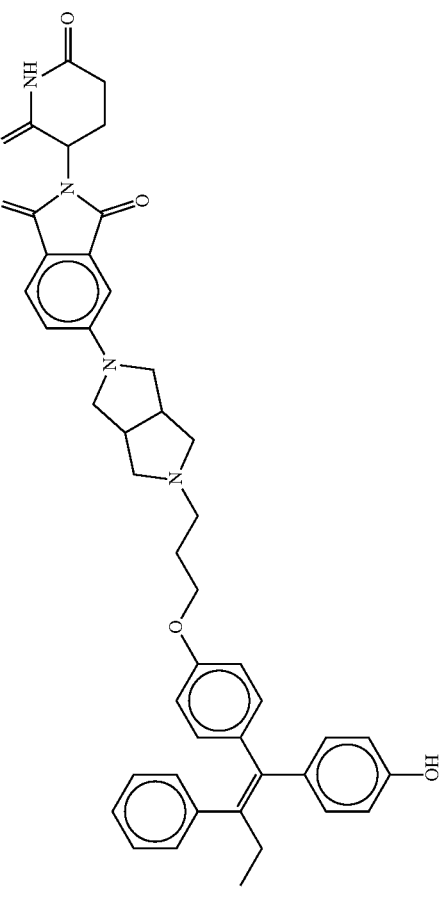 | (Z)-2-(2,6-dioxopiperidin-3-yl)-5-(5-(3-(4-(1-(4-hydroxyphenyl)-2-phenylbut-1-en-1-yl)phenoxy)propyl)hexahydropyrrolo[3,4-c]pyrrol-2(1H)-yl)isoindoline-1,3-dione |
| 175 | 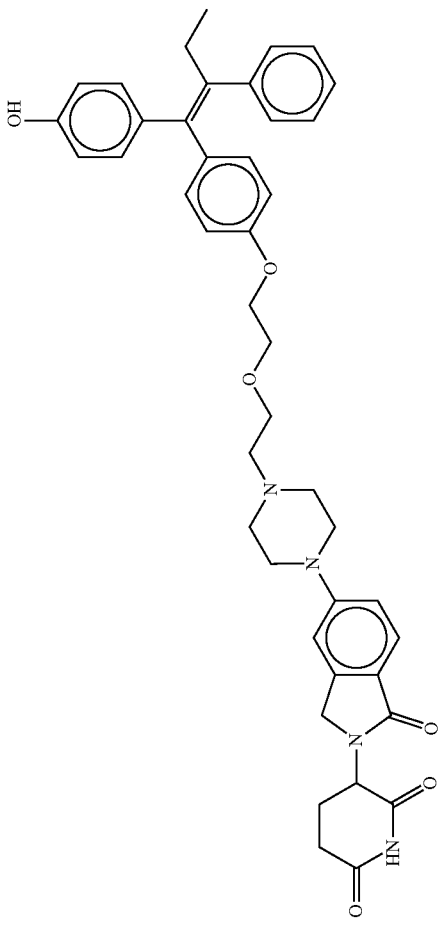 | (Z)-3-(5-(4-(2-(2-(4-(1-(4-hydroxyphenyl)-2-phenylbut-1-en-1-yl)phenoxy)ethoxy)ethyl)piperazin-1-yl)-1-oxoisoindolin-2-yl)piperidine-2,6-dione |

TABLE 1-continued
Exemplary Compound of the Present Disclosure
| # | Structure | IUPAC Name |
|---|---|---|
| 176 | 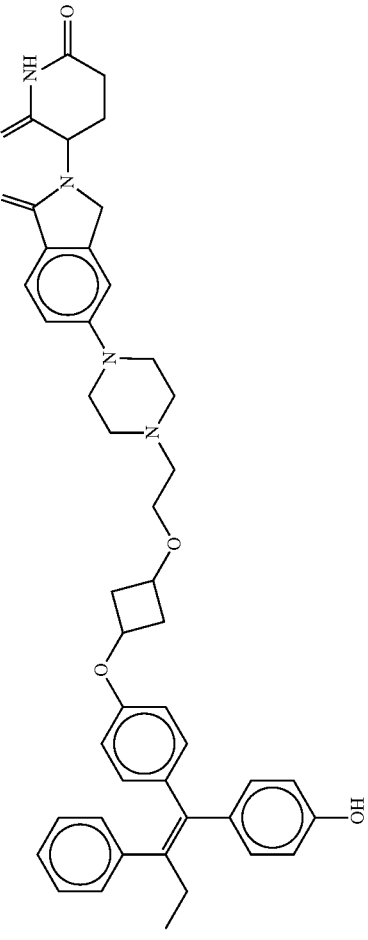 | (Z)-3-(5-(4-(2-(3-(4-(1-(4-hydroxyphenyl)-2-phenylbut-1-en-1-yl)phenoxy)cyclobutoxy)ethyl)piperazin-1-yl)-1-oxoisoindolin-2-yl)piperidine-2,6-dione |
| 177 | 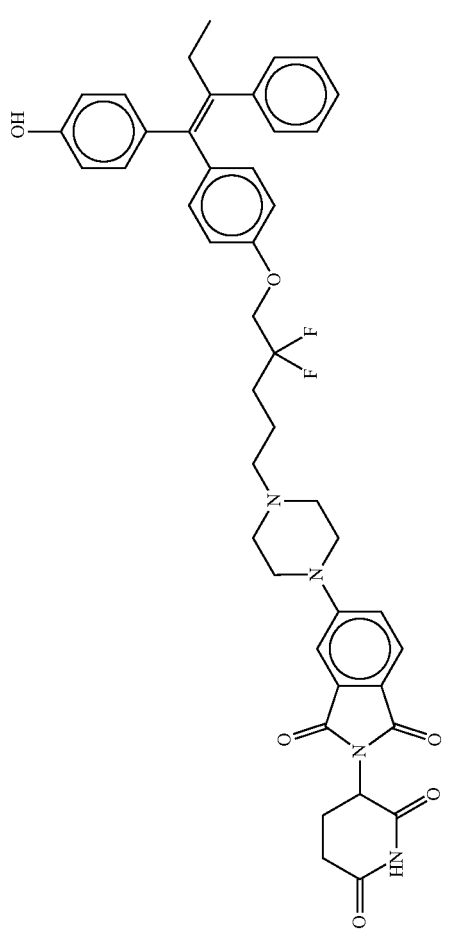 | (Z)-5-(4-(4,4-difluoro-5-(4-(1-(4-hydroxyphenyl)-2-phenylbut-1-en-1-yl)phenoxy)pentyl)piperazin-1-yl)-2-(2,6-dioxopiperidin-3-yl)isoindoline-1,3-dione |

TABLE 1-continued
Exemplary Compound of the Present Disclosure
| # | Structure | IUPAC Name |
|---|---|---|
| 178 | 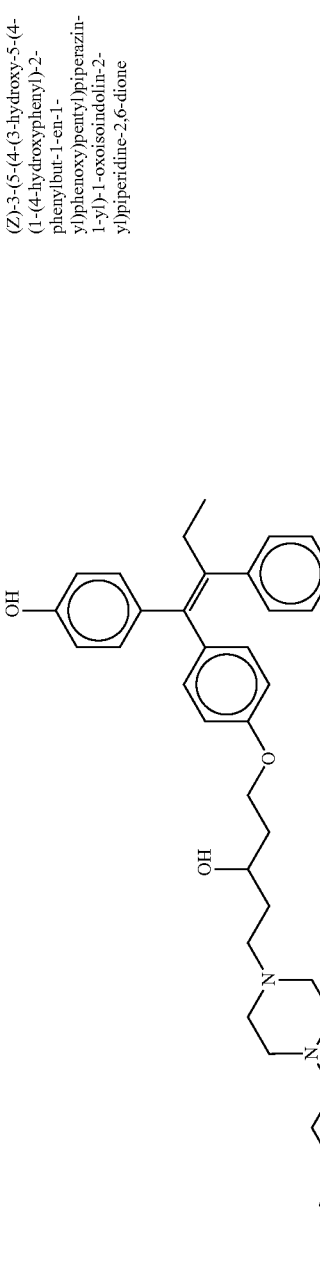 | (Z)-3-(5-(4-(3-hydroxy-5-(4-(1-(4-hydroxyphenyl)-2-phenylbut-1-en-1-yl)phenoxy)pentyl)piperazin-1-yl)-1-oxoisoindolin-2-yl)piperidine-2,6-dione |
| 179 | 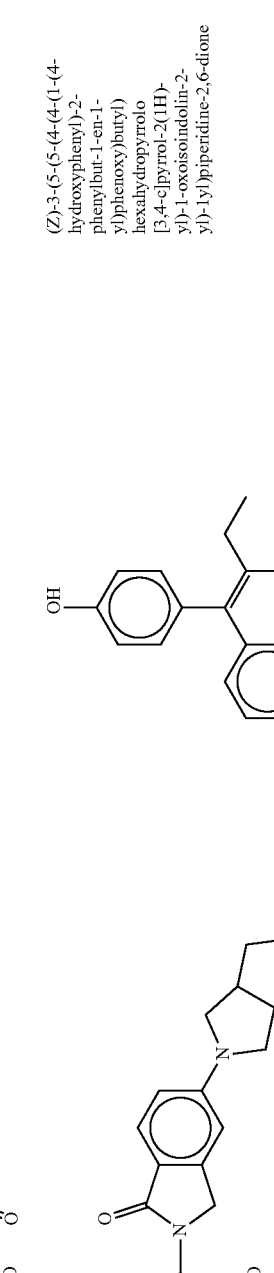 | (Z)-3-(5-(4-(4-(1-(4-hydroxyphenyl)-2-phenylbut-1-en-1-yl)phenoxy)butyl)hexahydropyrrolo[3,4-c]pyrrol-2(1H)-yl)-1-oxoisoindolin-2-yl)piperidine-2,6-dione |

TABLE 1-continued
Exemplary Compound of the Present Disclosure
| # | Structure | IUPAC Name |
|---|---|---|
| 180 | 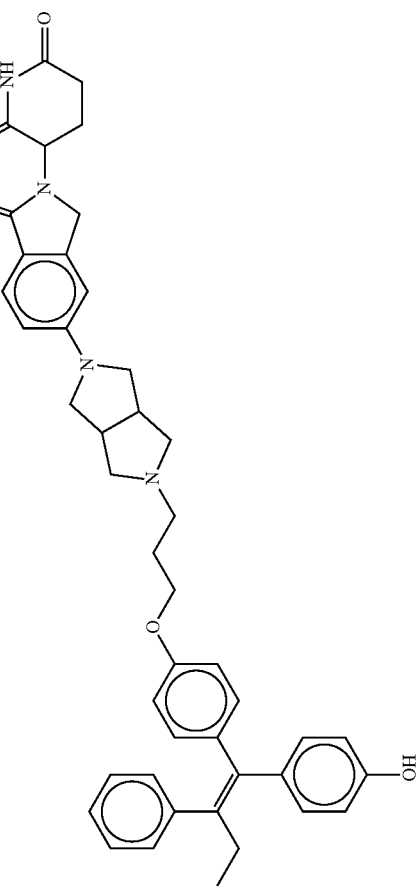 | (Z)-3-(5-(3-(4-(1-(4-hydroxyphenyl)-2-phenylbut-1-en-1-yl)phenoxy)propyl)hexahydropyrrolo[3,4-c]pyrrol-2(1H)-yl)-1-oxoisoindolin-2-yl)piperidine-2,6-dione |
| 181 | 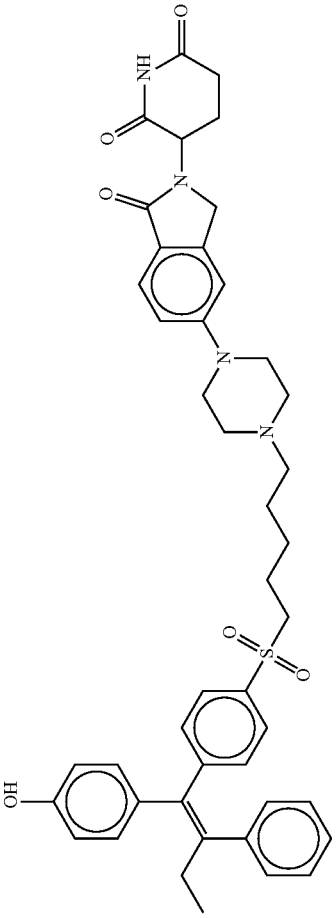 | (Z)-3-(5-(4-(5-((4-(1-(4-hydroxyphenyl)-2-phenylbut-1-en-1-yl)phenyl)sulfonyl)pentyl)piperazin-1-yl)-1-oxoisoindolin-2-yl)piperidine-2,6-dione |

TABLE 1-continued
Exemplary Compound of the Present Disclosure
| # | Structure | IUPAC Name |
|---|-----------|------------|
| 182 | 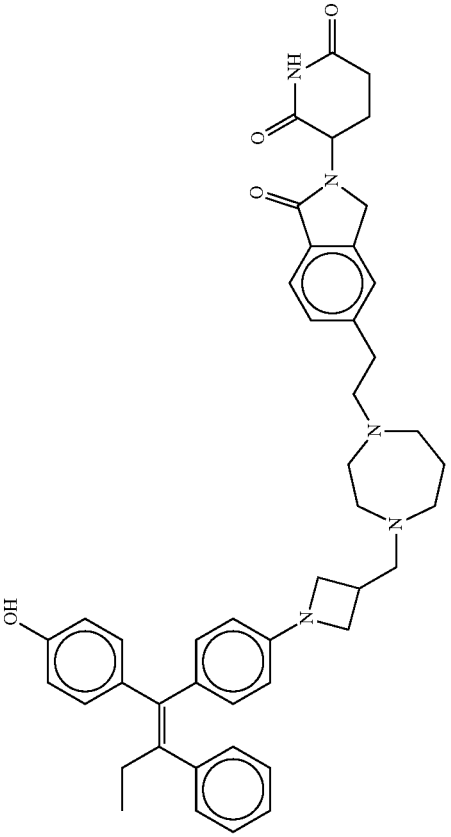 | (E)-3-(5-(2-(4-((1-(4-(1-(4-hydroxyphenyl)-2-phenylbut-1-en-1-yl)phenyl)azetidin-3-yl)methyl)-1,4-diazepan-1-yl)ethyl)-1-oxoisoindolin-2-yl)piperidine-2,6-dione |
| 183 | 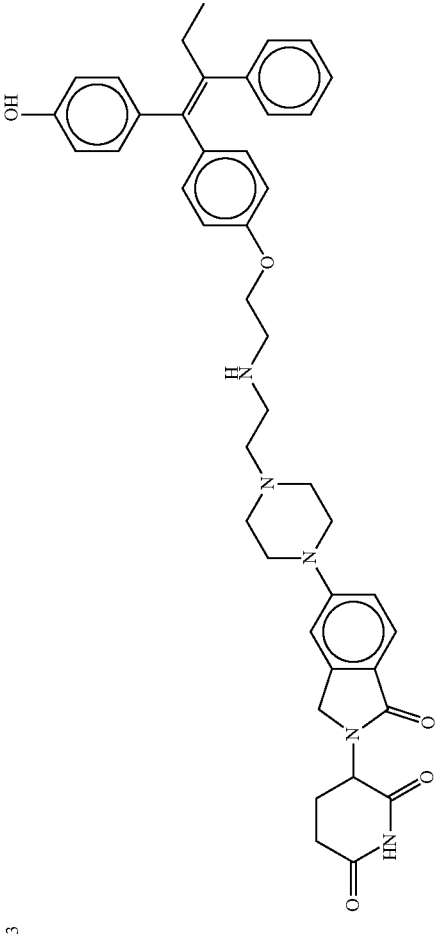 | (Z)-3-(5-(4-(2-((2-(4-(1-(4-hydroxyphenyl)-2-phenylbut-1-en-1-yl)phenoxy)ethyl)amino)ethyl)piperazin-1-yl)-1-oxoisoindolin-2-yl)piperidine-2,6-dione |

TABLE 1-continued
Exemplary Compound of the Present Disclosure
| # | Structure | IUPAC Name |
|---|---|---|
| 184a | 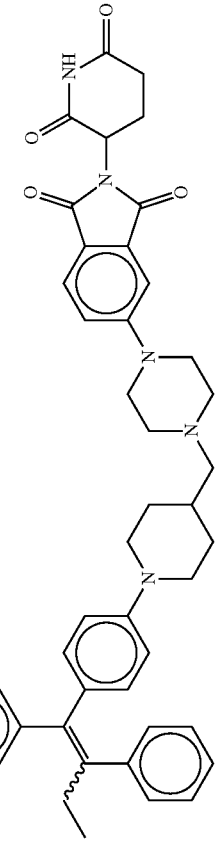 | (E)/(Z)-2-(2,6-dioxopiperidin-3-yl)-5-(4-((1-(4-(1-(4-hydroxyphenyl)-2-phenylbut-1-en-1-yl)phenyl)piperidin-4-yl)methyl)piperazin-1-yl)isoindoline-1,3-dione |
| 184 | 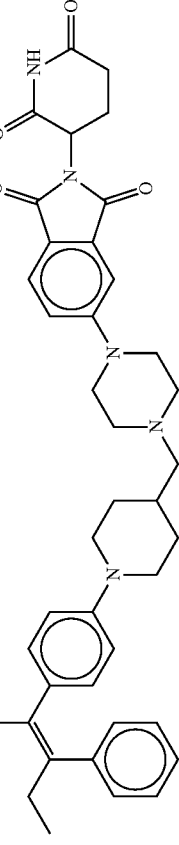 | (E)-2-(2,6-dioxopiperidin-3-yl)-5-(4-((1-(4-(1-(4-hydroxyphenyl)-2-phenylbut-1-en-1-yl)phenyl)piperidin-4-yl)methyl)piperazin-1-yl)isoindoline-1,3-dione |

TABLE 1-continued
Exemplary Compound of the Present Disclosure
| # | Structure | IUPAC Name |
|---|---|---|
| 185a | 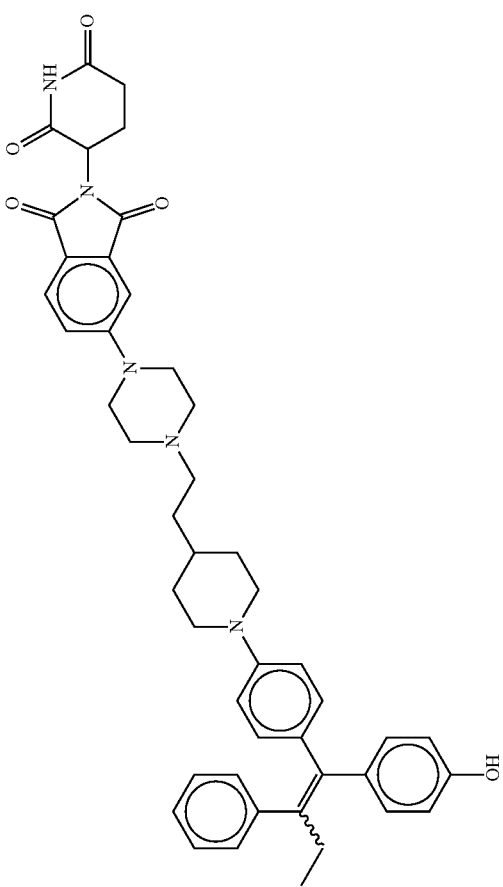 | (E)/(Z)-2-(2,6-dioxopiperidin-3-yl)-5-(4-(2-(1-(4-(1-(4-hydroxyphenyl)-2-phenylbut-1-en-1-yl)phenyl)piperidin-4-yl)pethyl)piperazin-1-yl)isoindoline-1,3-dione |
| 185 | 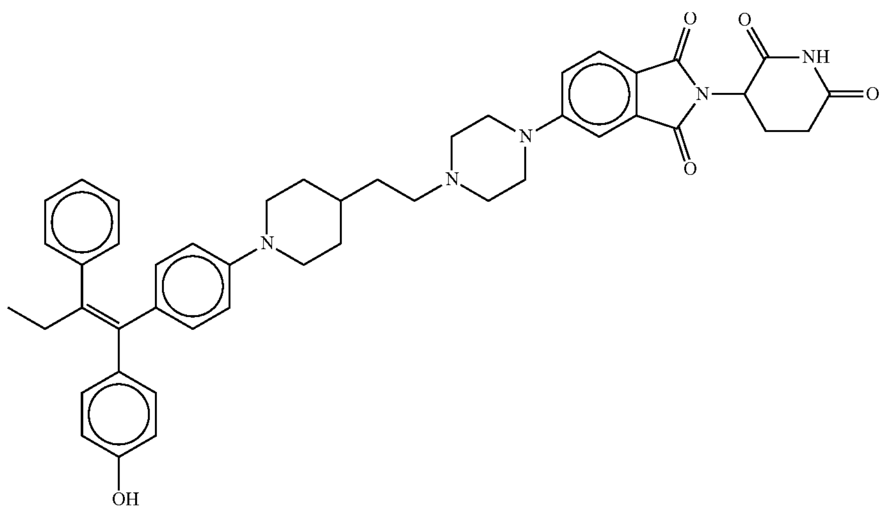 | (E)-2-(2,6-dioxopiperidin-3-yl)-5-(4-(2-(1-(4-(1-(4-hydroxyphenyl)-2-phenylbut-1-en-1-yl)phenyl)piperidin-4-yl)pethyl)piperazin-1-yl)isoindoline-1,3-dione |

TABLE 1-continued
Exemplary Compound of the Present Disclosure
| # | Structure | IUPAC Name |
|---|---|---|
| 186 | 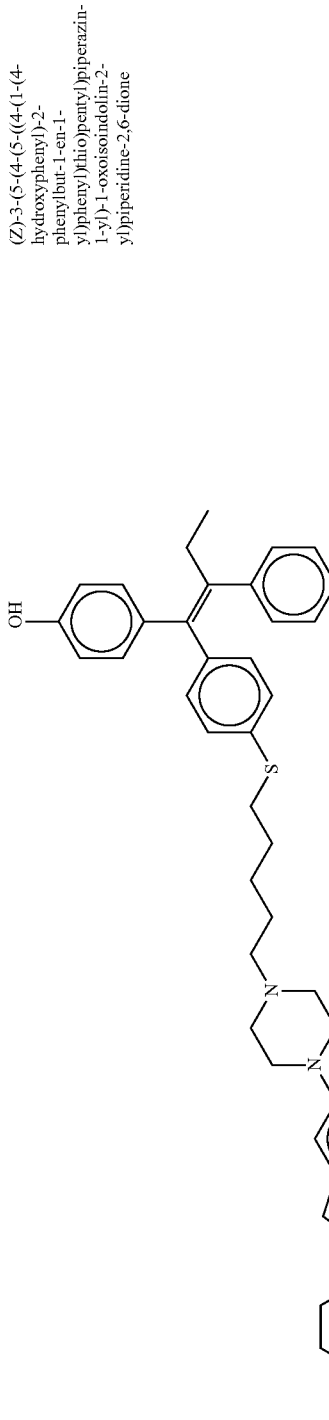 | (Z)-3-(5-(4-(5-((4-(1-(4-hydroxyphenyl)-2-phenylbut-1-en-1-yl)phenyl)thio)pentyl)piperazin-1-yl)-1-oxoisoindolin-2-yl)piperidine-2,6-dione |
| 187 | 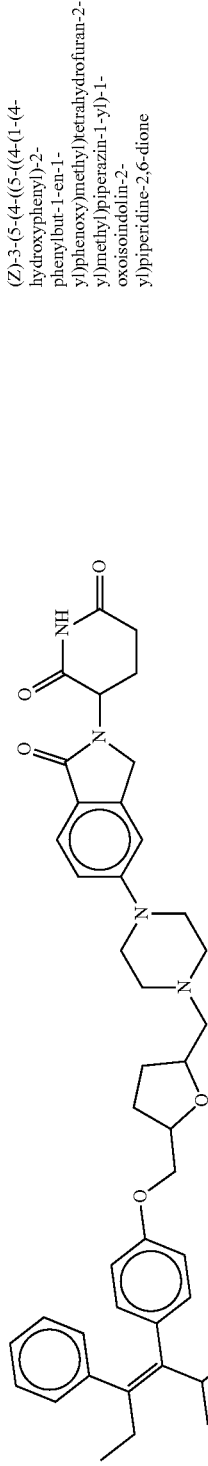 | (Z)-3-(5-(4-((5-((4-(1-(4-hydroxyphenyl)-2-phenylbut-1-en-1-yl)phenoxy)methyl)tetrahydrofuran-2-yl)methyl)piperazin-1-yl)methyl)piperazin-1-yl)-1-oxoisoindolin-2-yl)piperidine-2,6-dione |

TABLE 1-continued
Exemplary Compound of the Present Disclosure
| # | Structure | IUPAC Name |
|---|---|---|
| 188 | 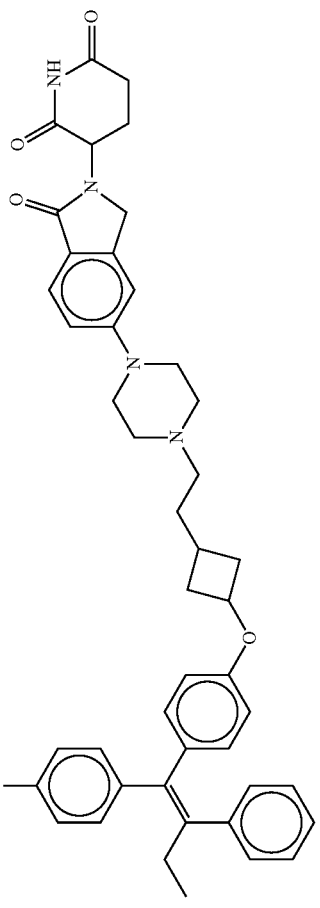 | (Z)-3-(5-(4-(2-(3-(4-(1-(4-hydroxyphenyl)-2-phenylbut-1-en-1-yl)phenoxy)cyclobutyl)ethyl)piperazin-1-yl)-1-oxoisoindolin-2-yl)piperidine-2,6-dione |
| 189 | 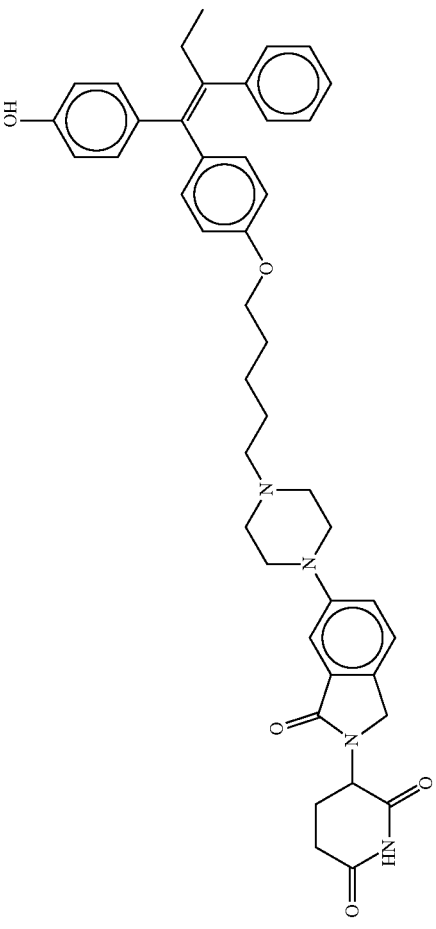 | (Z)-3-(6-(4-(5-(4-(1-(4-hydroxyphenyl)-2-phenylbut-1-en-1-yl)phenoxy)pentyl)piperazin-1-yl)-1-oxoisoindolin-2-yl)piperidine-2,6-dione |

TABLE 1-continued
Exemplary Compound of the Present Disclosure
| # | Structure | IUPAC Name |
|---|---|---|
| 190 | 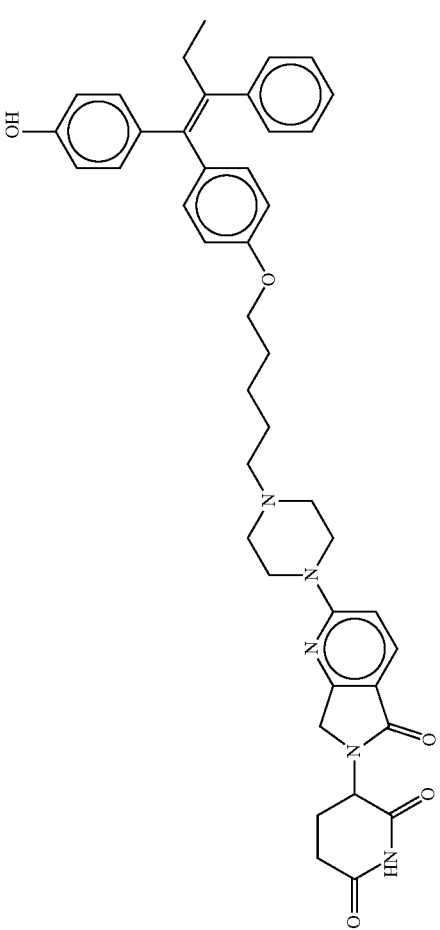 | (Z)-3-(2-(4-(5-(4-(1-(4-hydroxyphenyl)-2-phenylbut-1-en-1-yl)phenoxy)pentyl)piperazin-1-yl)-5-oxo-5,7-dihydro-6H-pyrrolo[3,4-b]pyridin-6-yl)piperidine-2,6-dione |
| 191 | 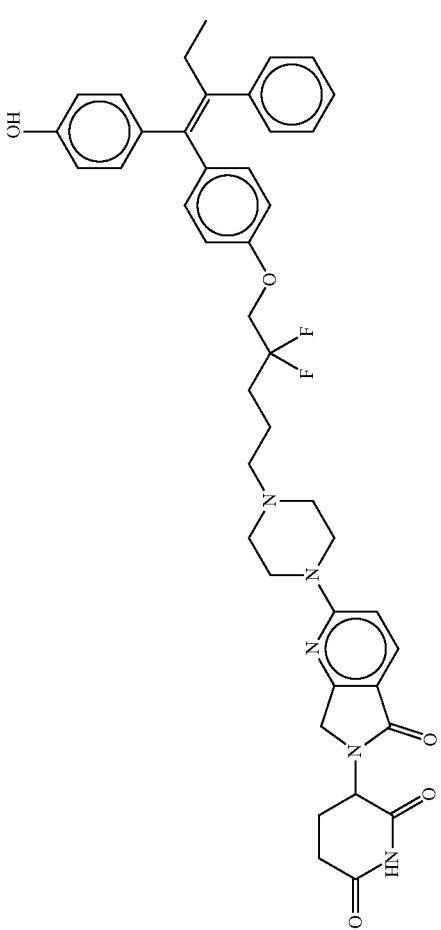 | (Z)-3-(2-(4-(4,4-difluoro-5-(4-(1-(4-hydroxyphenyl)-2-phenylbut-1-en-1-yl)phenoxy)pentyl)piperazin-1-yl)-5-oxo-5,7-dihydro-6H-pyrrolo[3,4-b]pyridin-6-yl)piperidine-2,6-dione |

TABLE 1-continued
Exemplary Compound of the Present Disclosure
| # | Structure | IUPAC Name |
|---|---|---|
| 192 | 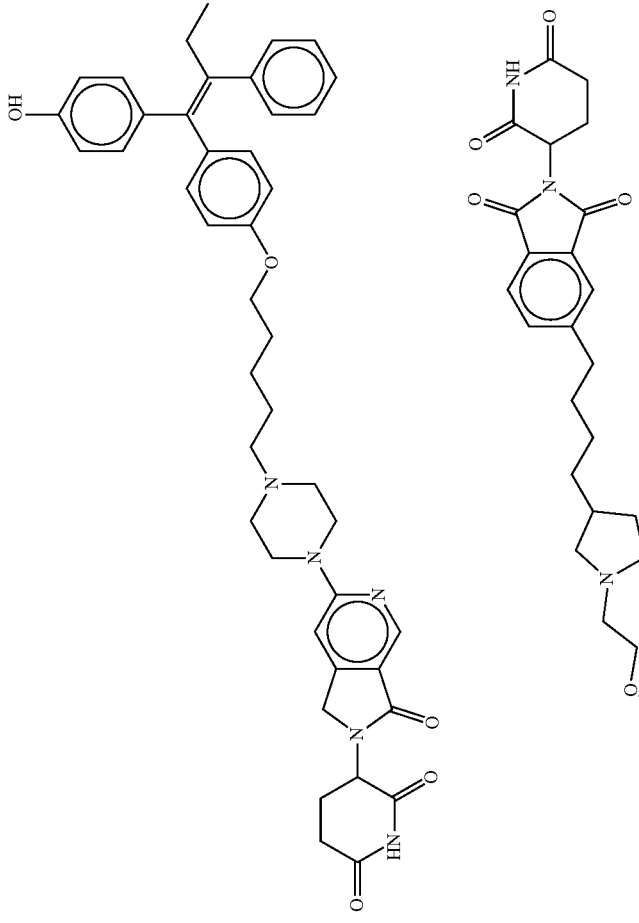 | (Z)-3-(6-(4-(5-(4-(1-(4-hydroxyphenyl)-2-phenylbut-1-en-1-yl)phenoxy)pentyl)piperazin-1-yl)-3-oxo-1,3-dihydro-2H-pyrrolo[3,4-c]pyridin-2-yl)piperidine-2,6-dione |
| 193 | 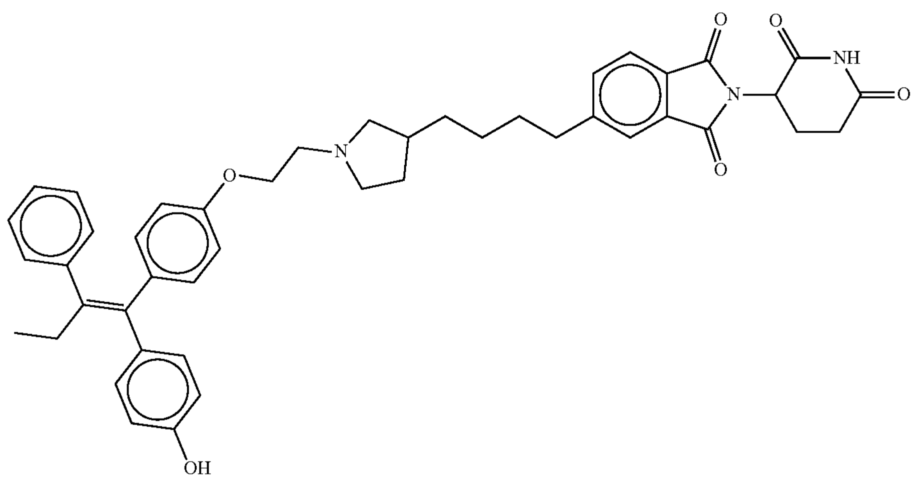 | (Z)-2-(2,6-dioxopiperidin-3-yl)-5-(4-(1-(2-(4-(1-(4-hydroxyphenyl)-2-phenylbut-1-en-1-yl)phenoxy)ethyl)pyrrolidin-3-yl)butyl)isoindoline-1,3-dione |

TABLE 1-continued
Exemplary Compound of the Present Disclosure
| # | Structure | IUPAC Name |
|---|---|---|
| 194 | 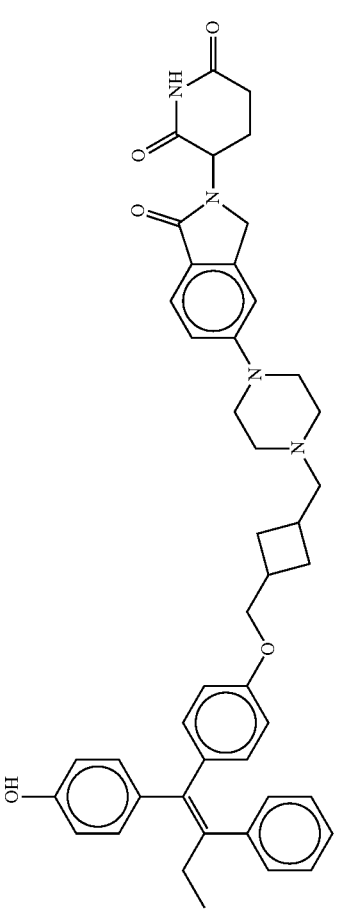 | (Z)-3-(5-(4-((3-((4-(1-(4-hydroxyphenyl)-2-phenylbut-1-en-1-yl)phenoxy)methyl)cyclobutyl)methyl)piperazin-1-yl)-1-oxoisoindolin-2-yl)piperidine-2,6-dione |
| 195 | 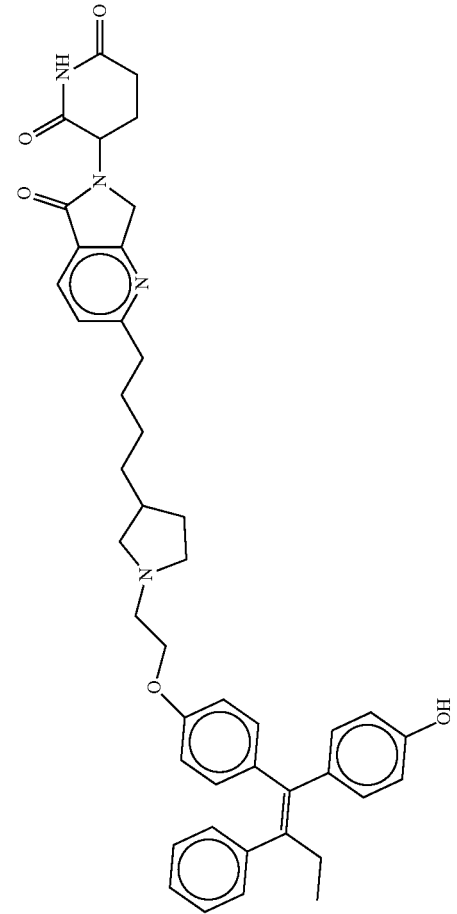 | (Z)-3-(2-(4-(1-(2-(4-(1-(4-hydroxyphenyl)-2-phenylbut-1-en-1-yl)phenoxy)ethyl)pyrrolidin-3-yl)butyl)-5-oxo-5,7-dihydro-6H-pyrrolo[3,4-b]pyridin-6-yl)piperidine-2,6-dione |

TABLE 1-continued
Exemplary Compound of the Present Disclosure
| # | Structure | IUPAC Name |
|---|---|---|
| 196 | 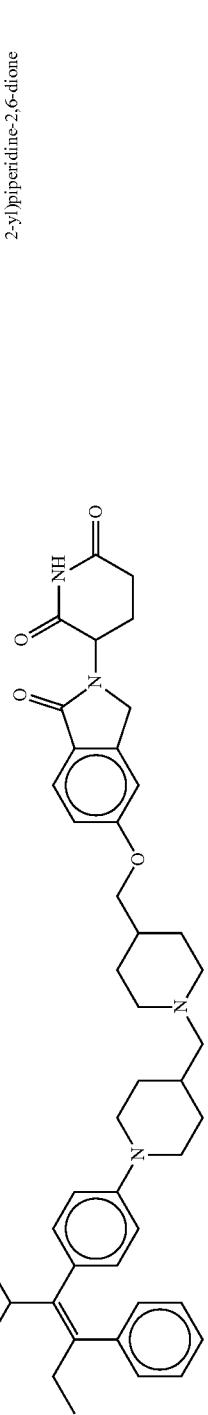 | (E)-3-(5-((1-(1-(4-(1-(4-hydroxyphenyl)-2-phenylbut-1-en-1-yl)phenyl)piperidin-4-yl)methyl)piperidin-4-yl)methoxy)-1-oxoisoindolin-2-yl)piperidine-2,6-dione |
| 197 | 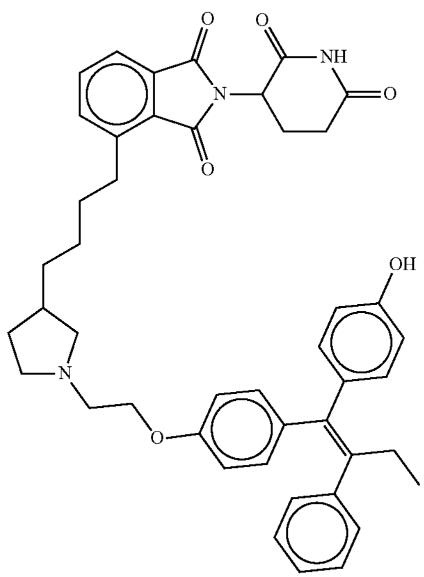 | (Z)-2-(2,6-dioxopiperidin-3-yl)-4-(4-(1-(2-(4-(1-(4-hydroxyphenyl)-2-phenylbut-1-en-1-yl)phenoxy)ethyl)pyrrolidin-3-yl)butyl)isoindoline-1,3-dione |

TABLE 1-continued

Exemplary Compound of the Present Disclosure

| # | Structure | IUPAC Name |
|---|-----------|------------|
| 198 | 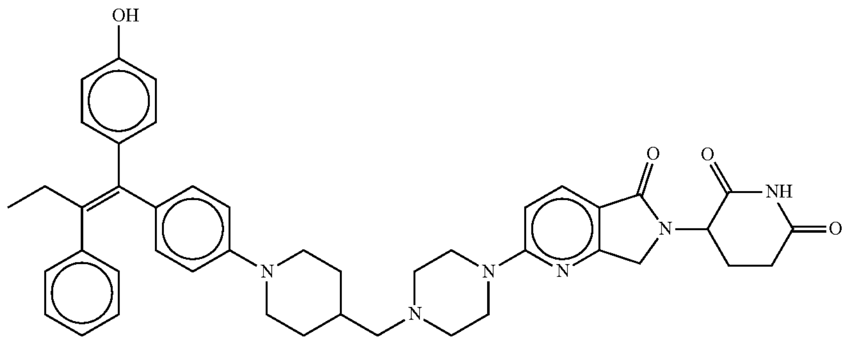 | (E)-3-(2-(4-((1-(4-(4-hydroxyphenyl)-2-phenylbut-1-en-1-yl)phenyl)piperidin-4-yl)methyl)piperazin-1-yl)-5-oxo-5,7-dihydro-6H-pyrrolo[3,4-b]pyridin-6-yl)piperidine-2,6-dione |
| 199 | 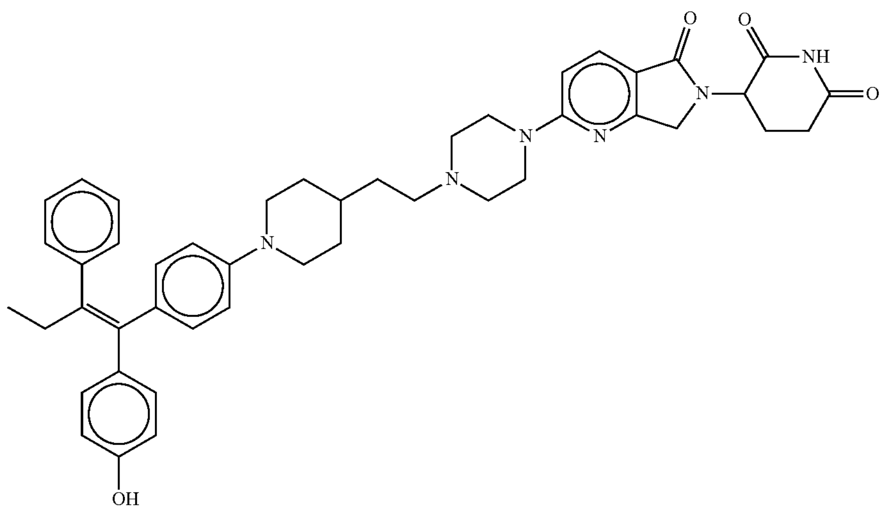 | (E)-3-(2-(4-(2-(1-(4-(4-hydroxyphenyl)-2-phenylbut-1-en-1-yl)phenyl)piperidin-4-yl)ethyl)piperazin-1-yl)-5-oxo-5,7-dihydro-6H-pyrrolo[3,4-b]pyridin-6-yl)piperidine-2,6-dione |

TABLE 1-continued

Exemplary Compound of the Present Disclosure

| # | Structure | IUPAC Name |
|---|---|---|
| 200 | 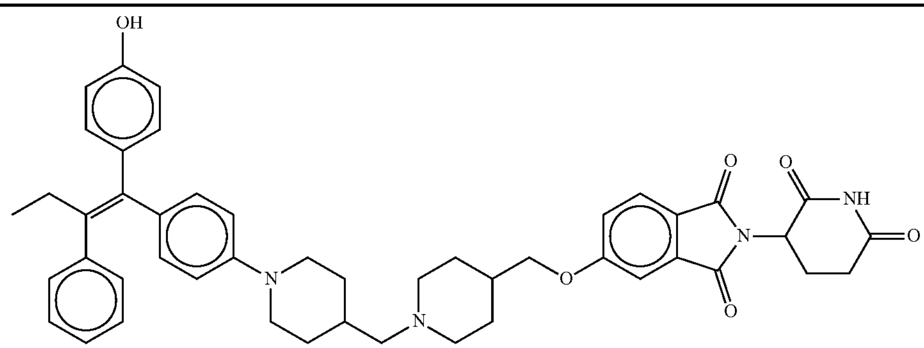 | (E)-2-(2,6-dioxopiperidin-3-yl)-5-((1-(4-(1-(4-hydroxyphenyl)-2-phenylbut-1-en-1-yl)phenyl)piperidin-4-yl)methyl)piperidin-4-yl)methoxy)isoindoline-1,3-dione |
| 201 | 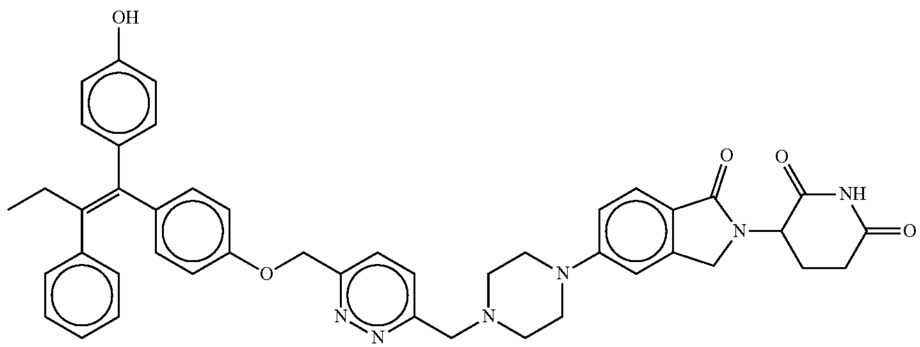 | (Z)-3-(5-(4-((6-((4-(1-(4-hydroxyphenyl)-2-phenylbut-1-en-1-yl)phenoxy)methyl)pyridazin-3-yl)methyl)piperazin-1-yl)-1-oxoisoindolin-2-yl)piperidine-2,6-dione |
| 202 | 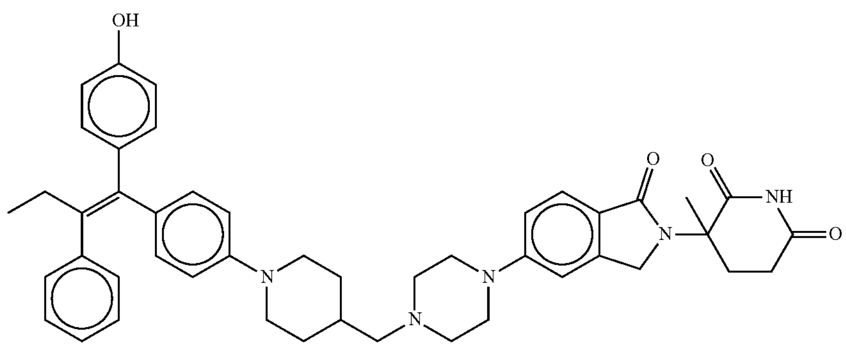 | (E)-3-(5-(4-((1-(4-(1-(4-hydroxyphenyl)-2-phenylbut-1-en-1-yl)phenyl)piperidin-4-yl)methyl)piperazin-1-yl)-1-oxoisoindolin-2-yl)-3-methylpiperidine-2,6-dione |

TABLE 1-continued

Exemplary Compound of the Present Disclosure

| # | Structure | IUPAC Name |
|---|---|---|
| 203 | 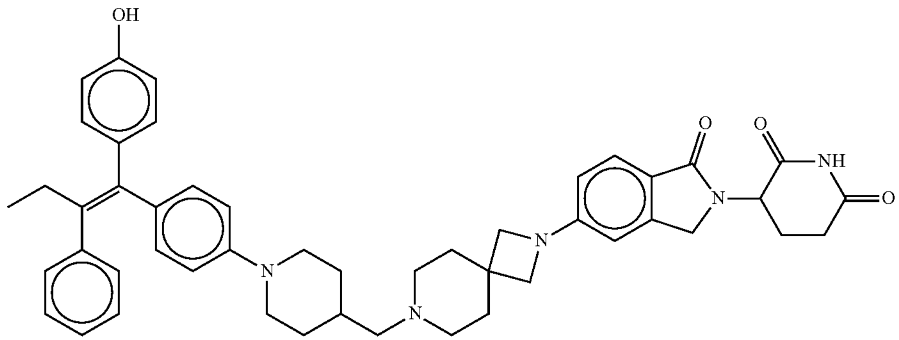 | (E)-3-(5-(7-((1-(4-(1-(4-hydroxyphenyl)-2-phenylbut-1-en-1-yl)phenyl)piperidin-4-yl)methyl)-2,7-diazaspiro[3.5]nonan-2-yl)-1-oxoisoindolin-2-yl)piperidine-2,6-dione |
| 204 | 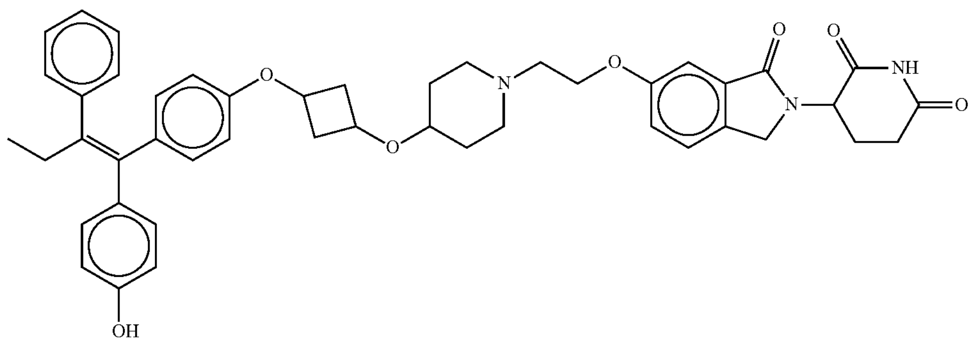 | (Z)-3-(6-(2-(4-(3-(4-(1-(4-hydroxyphenyl)-2-phenylbut-1-en-1-yl)phenoxy)cyclobutoxy)piperidin-1-yl)ethoxy)-1-oxoisoindolin-2-yl)piperidine-2,6-dione |

TABLE 1-continued
Exemplary Compound of the Present Disclosure
| # | Structure | IUPAC Name |
|---|---|---|
| 205 | 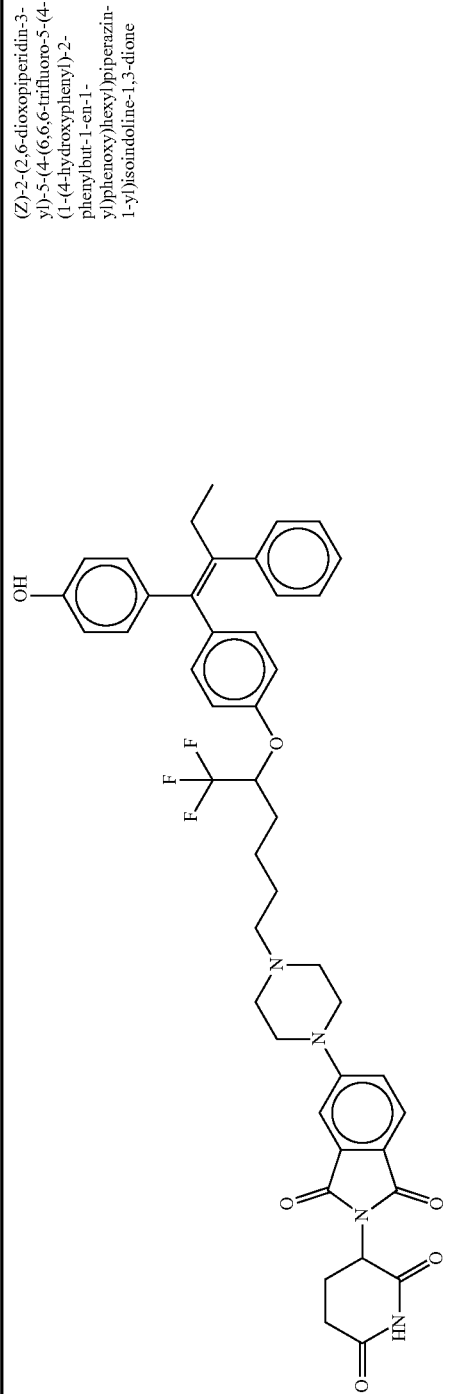 | (Z)-2-(2,6-dioxopiperidin-3-yl)-5-(4-(6,6,6-trifluoro-5-(4-(1-(4-hydroxyphenyl)-2-phenylbut-1-en-1-yl)phenoxy)hexyl)piperazin-1-yl)isoindoline-1,3-dione |
| 206 | 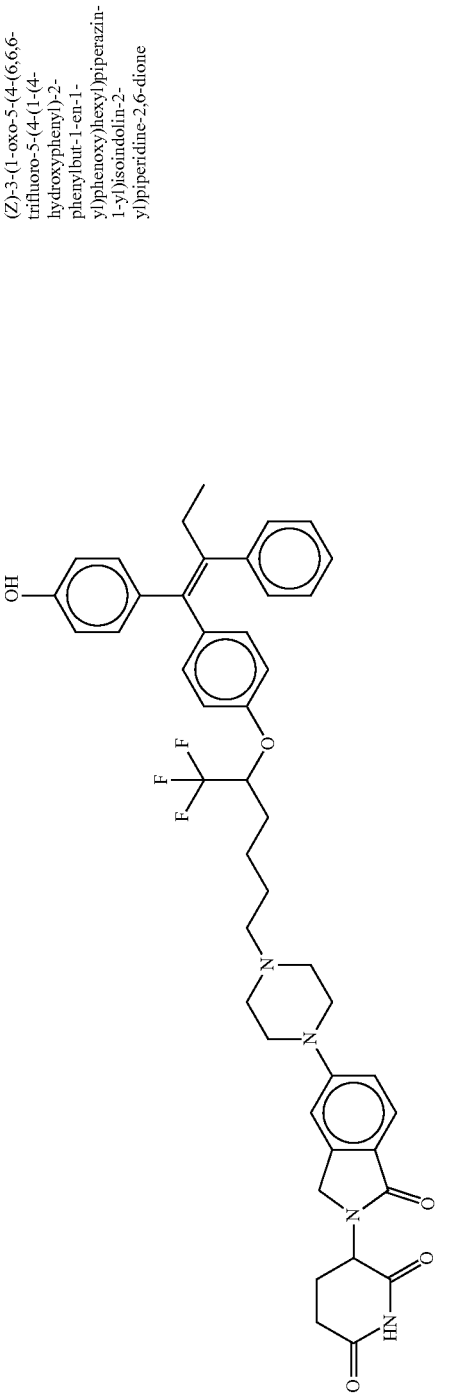 | (Z)-3-(1-oxo-5-(4-(6,6,6-trifluoro-5-(4-(1-(4-hydroxyphenyl)-2-phenylbut-1-en-1-yl)phenoxy)hexyl)piperazin-1-yl)isoindolin-2-yl)piperidine-2,6-dione |

TABLE 1-continued
Exemplary Compound of the Present Disclosure
| # | Structure | IUPAC Name |
|---|---|---|
| 207 | 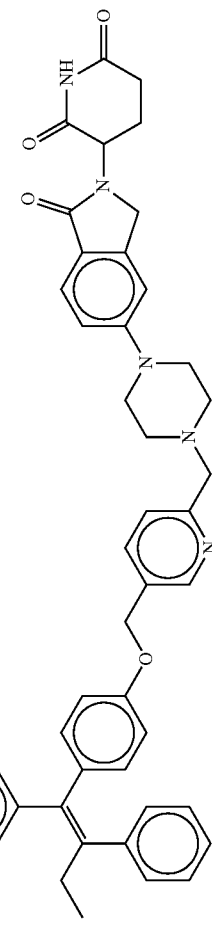 | (Z)-3-(5-(4-((5-((4-(1-(4-hydroxyphenyl)-2-phenylbut-1-en-1-yl)phenoxy)methyl)pyridin-2-yl)methyl)piperazin-1-yl)-1-oxoisoindolin-2-yl)piperidine-2,6-dione |
| 208 | 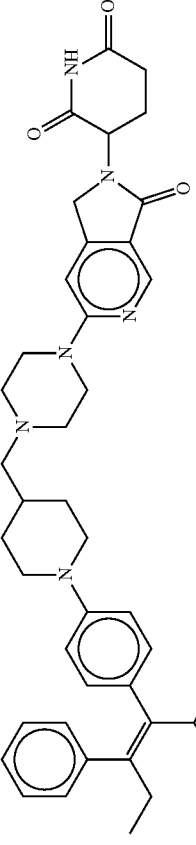 | (E)-3-(6-(4-((1-(4-(1-(4-hydroxyphenyl)-2-phenylbut-1-en-1-yl)phenyl)piperidin-4-yl)methyl)piperazin-1-yl)-3-oxo-1,3-dihydro-2H-pyrrolo[3,4-c]pyridin-2-yl)piperidine-2,6-dione |

TABLE 1-continued

Exemplary Compound of the Present Disclosure

| # | Structure | IUPAC Name |
|---|---|---|
| 209 | 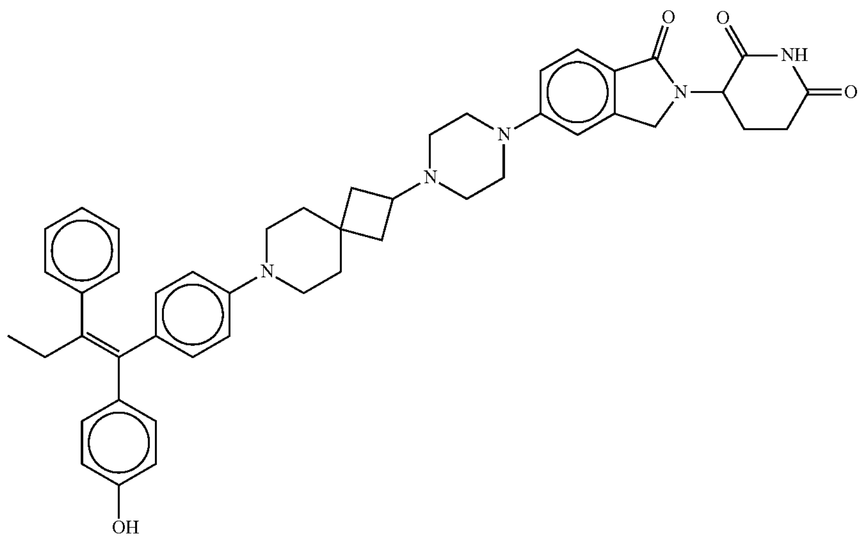 | (E)-3-(5-(4-(7-(4-(1-(4-hydroxyphenyl)-2-phenylbut-1-en-1-yl)phenyl)-7-azaspiro[3.5]nonan-2-yl)piperazin-1-yl)-1-oxoisoindolin-2-yl)piperidine-2,6-dione |

TABLE 1-continued
Exemplary Compound of the Present Disclosure
| # | Structure | IUPAC Name |
|---|---|---|
| 210 | 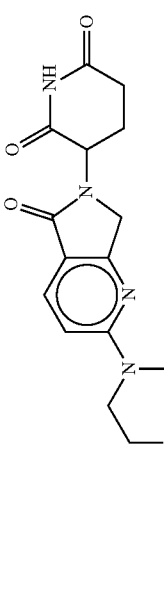 | (E)-3-(2-(4-(7-(4-(1-(4-hydroxyphenyl)-2-phenylbut-1-en-1-yl)phenyl)-7-azaspiro[3.5]nonan-2-yl)piperazin-1-yl)-5-oxo-5,7-dihydro-6H-pyrrolo[3,4-b]pyridin-6-yl)piperidine-2,6-dione |
| 211 | 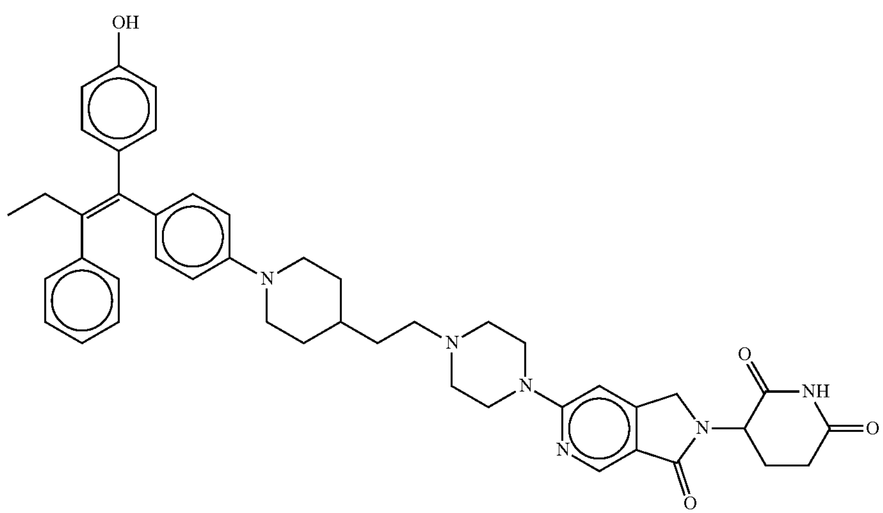 | (E)-3-(6-(4-(2-(1-(4-(1-(4-hydroxyphenyl)-2-phenylbut-1-en-1-yl)phenyl)piperidin-4-yl)ethyl)piperazin-1-yl)-3-oxo-1,3-dihydro-2H-pyrrolo[3,4-c]pyridin-2-yl)piperidine-2,6-dione |

TABLE 1-continued

Exemplary Compound of the Present Disclosure

| # | Structure | IUPAC Name |
|---|---|---|
| 212 | 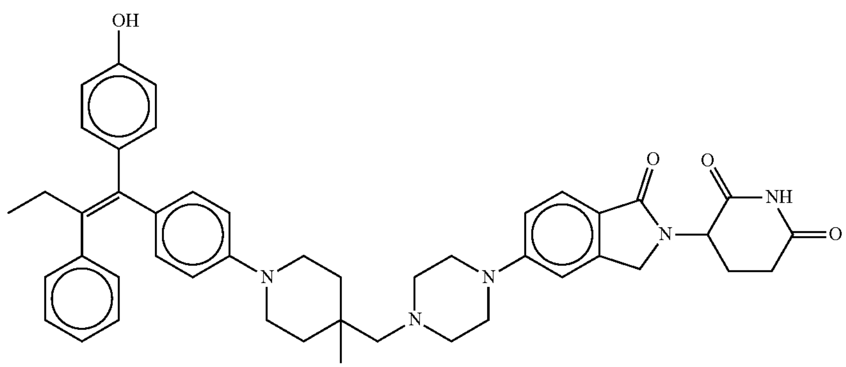 | (E)-3-(5-(4-((1-(4-(4-(1-(4-hydroxyphenyl)-2-phenylbut-1-en-1-yl)phenyl)-4-methylpiperidin-4-yl)methyl)piperazin-1-yl)-1-oxoisoindolin-2-yl)piperidine-2,6-dione |
| 213 | 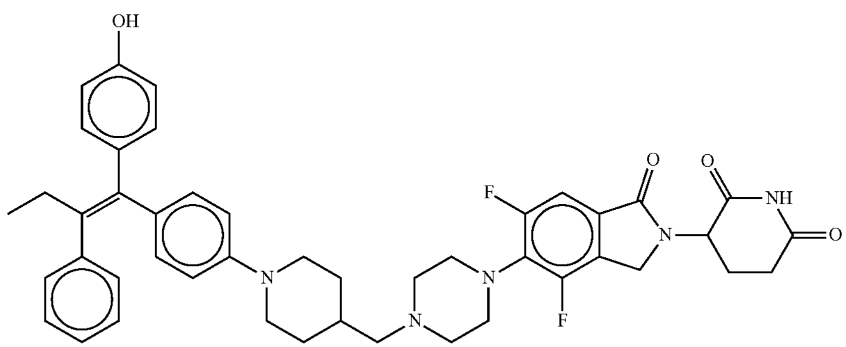 | (E)-3-(4,6-difluoro-5-(4-((1-(4-(1-(4-hydroxyphenyl)-2-phenylbut-1-en-1-yl)phenyl)piperidin-4-yl)methyl)piperazin-1-yl)-1-oxoisoindolin-2-yl)piperidine-2,6-dione |

TABLE 1-continued
Exemplary Compound of the Present Disclosure
| # | Structure | IUPAC Name |
|---|---|---|
| 214 | 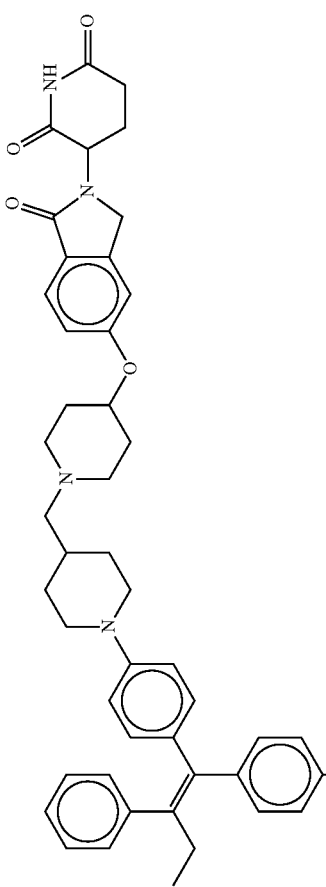 | (E)-3-(5-(((1-(4-((1-(4-(1-(4-hydroxyphenyl)-2-phenylbut-1-en-1-yl)phenyl)piperidin-4-yl)methyl)piperidin-4-yl)oxy)-1-oxoisoindolin-2-yl)piperidine-2,6-dione |
| 215 | 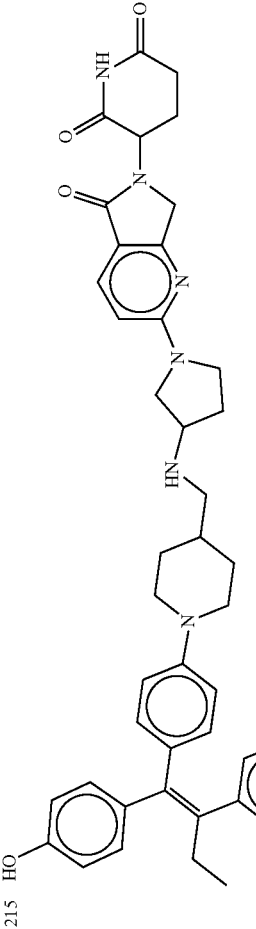 | (E)-3-(2-(3-(((1-(4-(1-(4-hydroxyphenyl)-2-phenylbut-1-en-1-yl)phenyl)piperidin-4-yl)methyl)amino)pyrrolidin-1-yl)-5-oxo-5,7-dihydro-6H-pyrrolo[3,4-b]pyridin-6-yl)piperidine-2,6-dione |

TABLE 1-continued

Exemplary Compound of the Present Disclosure

| # | IUPAC Name |
|---|---|
| 216 | (E)-3-(4-fluoro-5-(4-((1-(4-(1-(4-hydroxyphenyl)-2-phenylbut-1-en-1-yl)phenyl)piperidin-4-yl)methyl)piperazin-1-yl)-1-oxoisoindolin-2-yl)piperidine-2,6-dione |
| 217 | (E)-3-(6-(4-((1-(4-(1-(4-hydroxyphenyl)-2-phenylbut-1-en-1-yl)phenyl)piperidin-4-yl)methyl)piperazin-1-yl)-1-oxoisoindolin-2-yl)piperidine-2,6-dione |
| 218 | (E)-3-(5-(3-(((1-(4-(1-(4-hydroxyphenyl)-2-phenylbut-1-en-1-yl)phenyl)piperidin-4-yl)methyl)amino)pyrrolidin-1-yl)-1-oxoisoindolin-2-yl)piperidine-2,6-dione |

TABLE 1-continued

Exemplary Compound of the Present Disclosure

| # | Structure | IUPAC Name |
|---|-----------|------------|
| 219 | 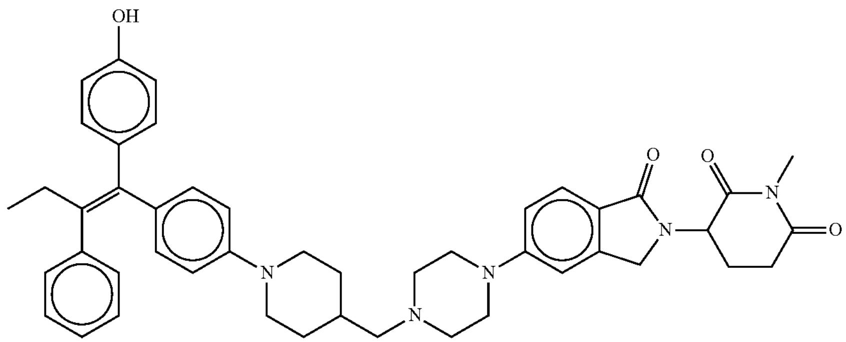 | (E)-3-(5-(4-((1-(4-(1-(4-hydroxyphenyl)-2-phenylbut-1-en-1-yl)phenyl)piperidin-4-yl)methyl)piperazin-1-yl)-1-oxoisoindolin-2-yl)-1-methylpiperidine-2,6-dione |
| 220 | 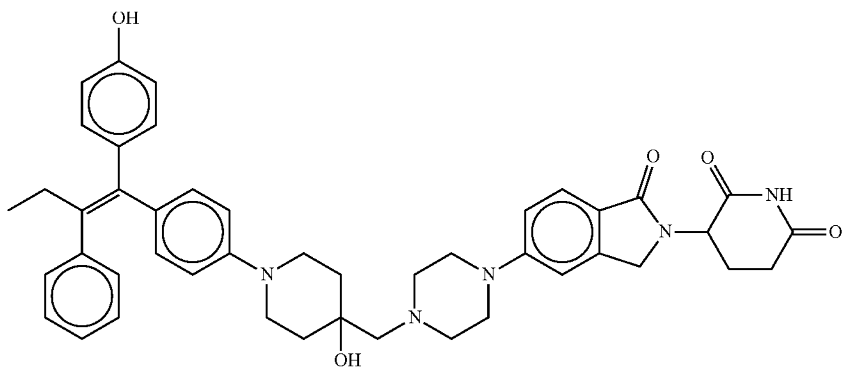 | (E)-3-(5-(4-((4-hydroxy-1-(4-(1-(4-hydroxyphenyl)-2-phenylbut-1-en-1-yl)phenyl)piperidin-4-yl)methyl)piperazin-1-yl)-1-oxoisoindolin-2-yl)piperidine-2,6-dione |

TABLE 1-continued
Exemplary Compound of the Present Disclosure
| # | Structure | IUPAC Name |
|---|-----------|------------|
| 221 | 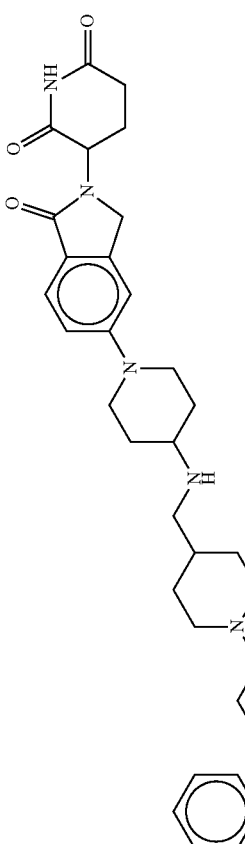 | (E)-3-(5-(4-(((1-(4-(1-(4-hydroxyphenyl)-2-phenylbut-1-en-1-yl)phenyl)piperidin-4-yl)methyl)amino)piperidin-1-yl)-1-oxoisoindolin-2-yl)piperidine-2,6-dione |
| 222 | 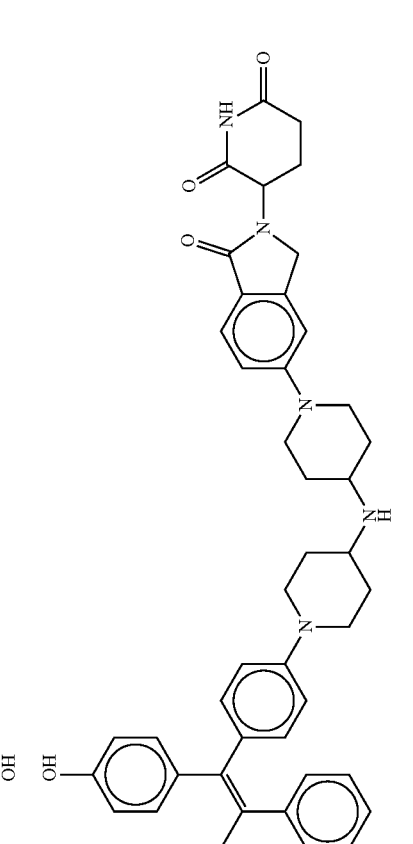 | (E)-3-(5-(4-((1-(4-(1-(4-hydroxyphenyl)-2-phenylbut-1-en-1-yl)phenyl)piperidin-4-yl)amino)piperidin-1-yl)-1-oxoisoindolin-2-yl)piperidine-2,6-dione |

TABLE 1-continued
Exemplary Compound of the Present Disclosure
| # | Structure | IUPAC Name |
|---|---|---|
| 223 | 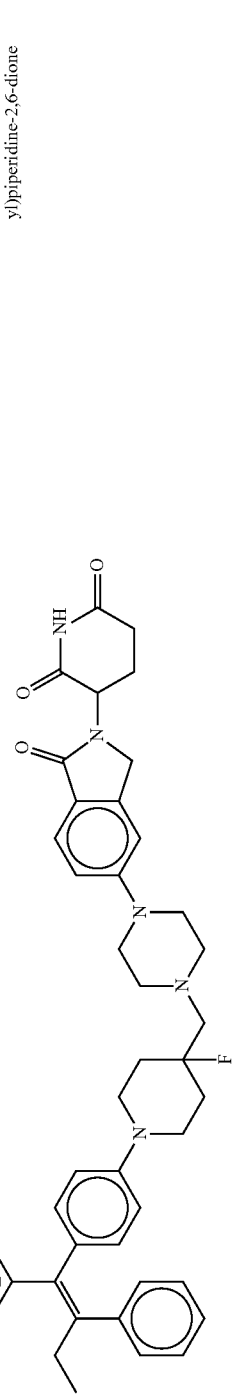 | (E)-3-(5-(4-((4-fluoro-1-(4-(1-(4-hydroxyphenyl)-2-phenylbut-1-en-1-yl)phenyl)piperidin-4-yl)methyl)piperazin-1-yl)-1-oxoisoindolin-2-yl)piperidine-2,6-dione |
| 224 | 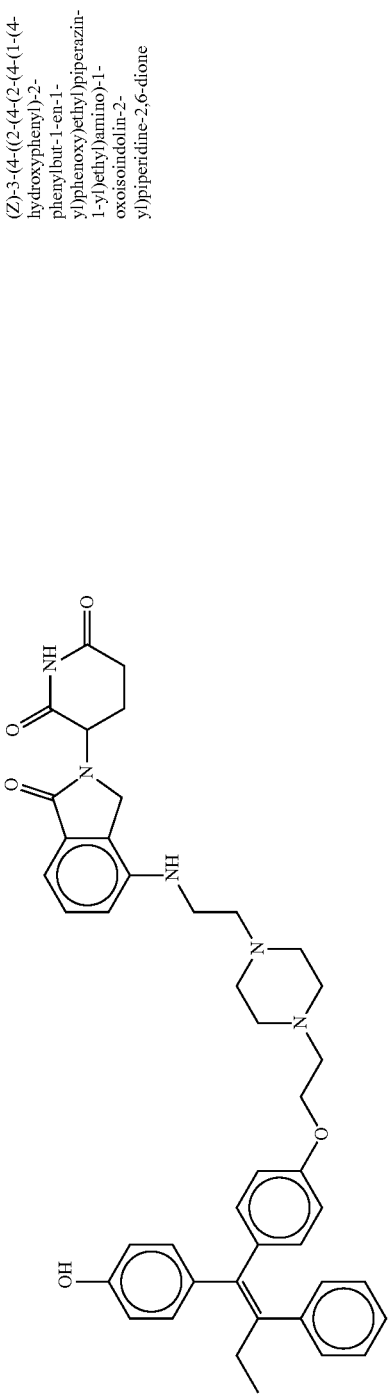 | (Z)-3-(4-((2-(4-(2-(4-(1-(4-hydroxyphenyl)-2-phenylbut-1-en-1-yl)phenoxy)ethyl)piperazin-1-yl)ethyl)amino)-1-oxoisoindolin-2-yl)piperidine-2,6-dione |

TABLE 1-continued

Exemplary Compound of the Present Disclosure

| # | Structure | IUPAC Name |
|---|---|---|
| 225 | 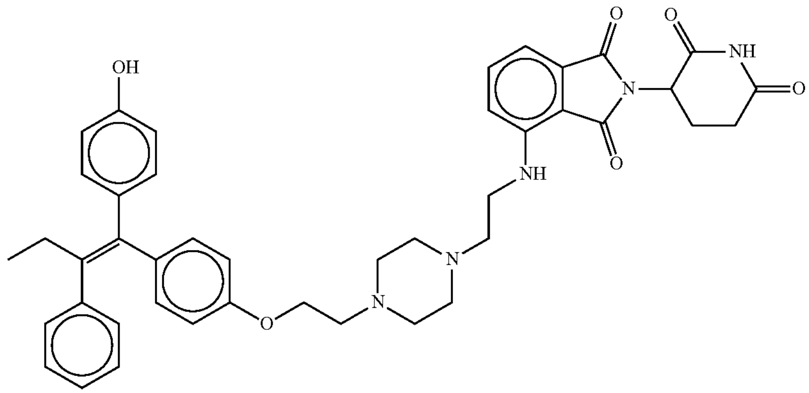 | (Z)-2-(2,6-dioxopiperidin-3-yl)-4-((2-(4-(2-(4-(1-(4-hydroxyphenyl)-2-phenylbut-1-en-1-yl)phenoxy)ethyl)piperazin-1-yl)ethyl)amino)isoindoline-1,3-dione |
| 226 | 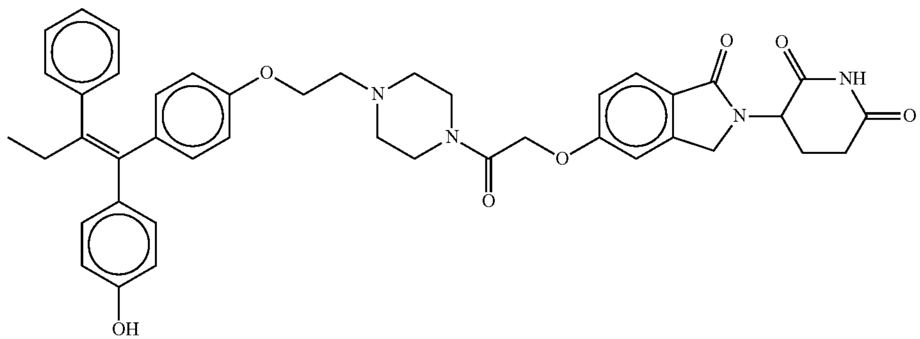 | (Z)-3-(5-(2-(4-(2-(4-(1-(4-hydroxyphenyl)-2-phenylbut-1-en-1-yl)phenoxy)ethyl)piperazin-1-yl)-2-oxoethoxy)-1-oxoisoindolin-2-yl)piperidine-2,6-dione |

TABLE 1-continued
Exemplary Compound of the Present Disclosure
| # | Structure | IUPAC Name |
|---|---|---|
| 227 | 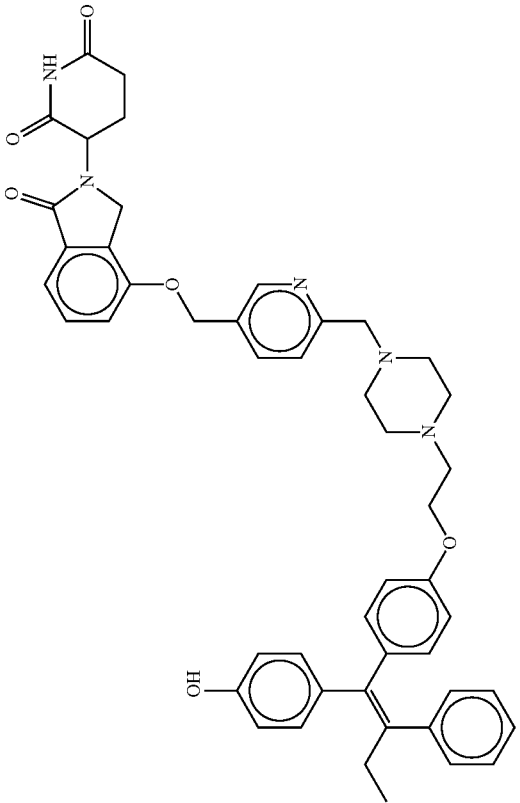 | (Z)-3-(4-((6-((4-(2-(4-(1-(4-hydroxyphenyl)-2-phenylbut-1-en-1-yl)phenoxy)ethyl)piperazin-1-yl)methyl)pyridin-3-yl)methoxy)-1-oxoisoindolin-2-yl)piperidine-2,6-dione |
| 228 | 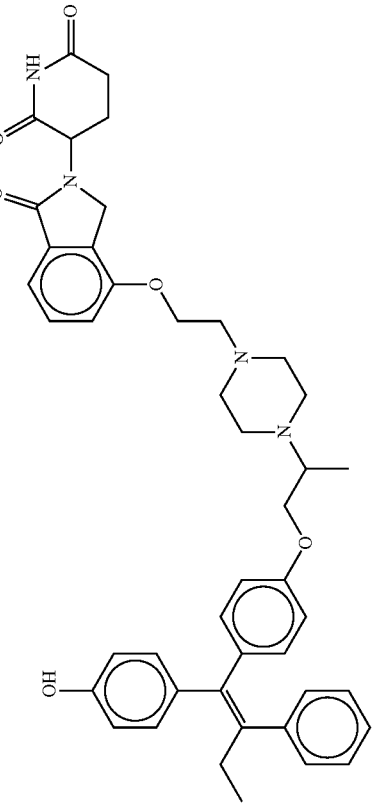 | (Z)-3-(4-(2-(4-(1-(4-(1-(4-hydroxyphenyl)-2-phenylbut-1-en-1-yl)phenoxy)propan-2-yl)piperazin-1-yl)ethoxy)-1-oxoisoindolin-2-yl)piperidine-2,6-dione |

TABLE 1-continued

Exemplary Compound of the Present Disclosure

| # | Structure | IUPAC Name |
|---|---|---|
| 229 | 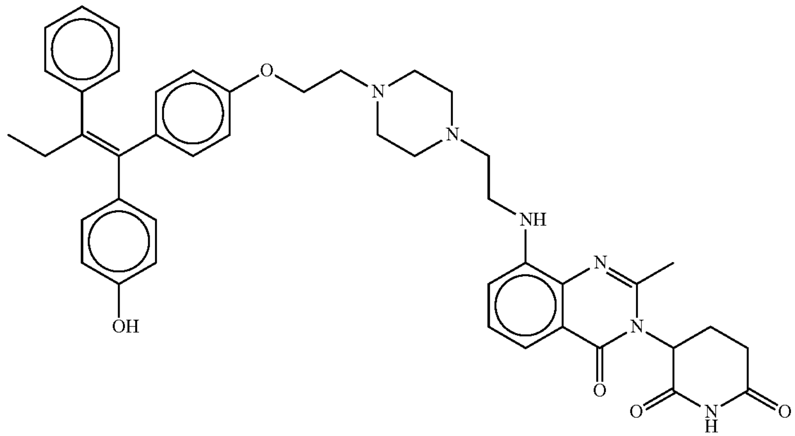 | (Z)-3-(8-((2-(4-(2-(4-(1-(4-hydroxyphenyl)-2-phenylbut-1-en-1-yl)phenoxy)ethyl)piperazin-1-yl)ethyl)amino)-2-methyl-4-oxoquinazolin-3(4H)-yl)piperidine-2,6-dione |
| 230 | 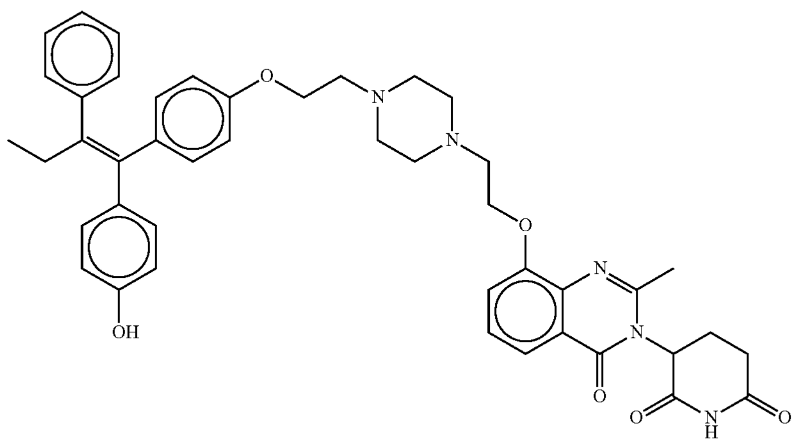 | (Z)-3-(8-(2-(4-(2-(4-(1-(4-hydroxyphenyl)-2-phenylbut-1-en-1-yl)phenoxy)ethyl)piperazin-1-yl)ethoxy)-2-methyl-4-oxoquinazolin-3(4H)-yl)piperidine-2,6-dione |

TABLE 1-continued
Exemplary Compound of the Present Disclosure
| # | Structure | IUPAC Name |
|---|-----------|------------|
| 231 | 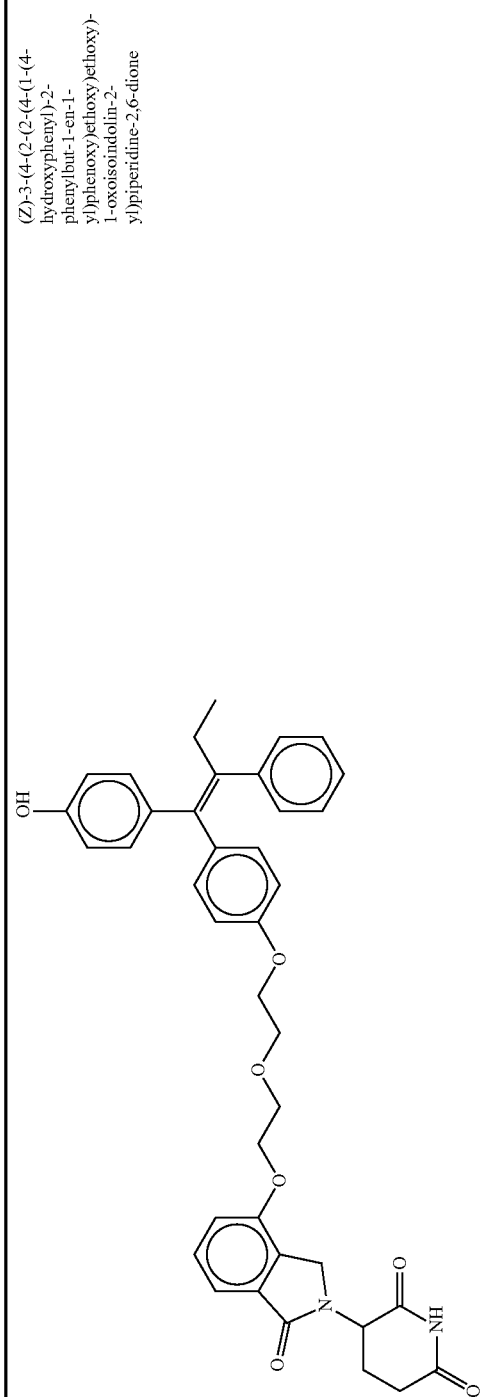 | (Z)-3-(4-(2-(2-(4-(1-(4-hydroxyphenyl)-2-phenylbut-1-en-1-yl)phenoxy)ethoxy)ethoxy)-1-oxoisoindolin-2-yl)piperidine-2,6-dione |
| 232 | 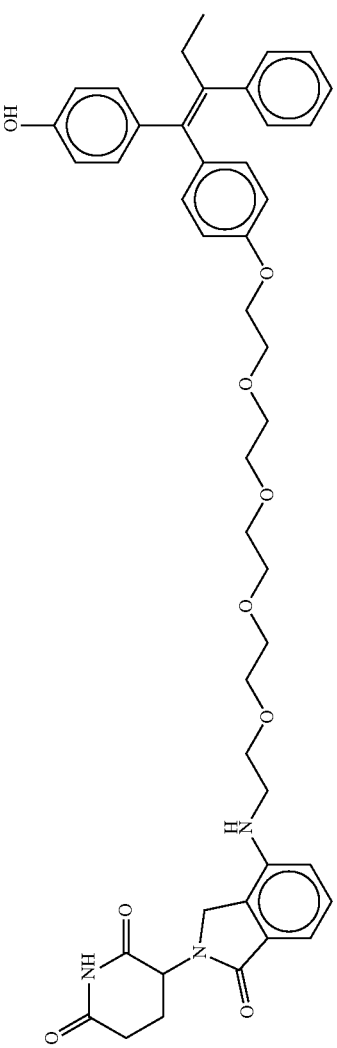 | (Z)-3-(4-((14-(4-(1-(4-hydroxyphenyl)-2-phenylbut-1-en-1-yl)phenoxy)-3,6,9,12-tetraoxatetradecyl)amino)-1-oxoisoindolin-2-yl)piperidine-2,6-dione |

TABLE 1-continued
Exemplary Compound of the Present Disclosure
| # | Structure | IUPAC Name |
|---|---|---|
| 233 | 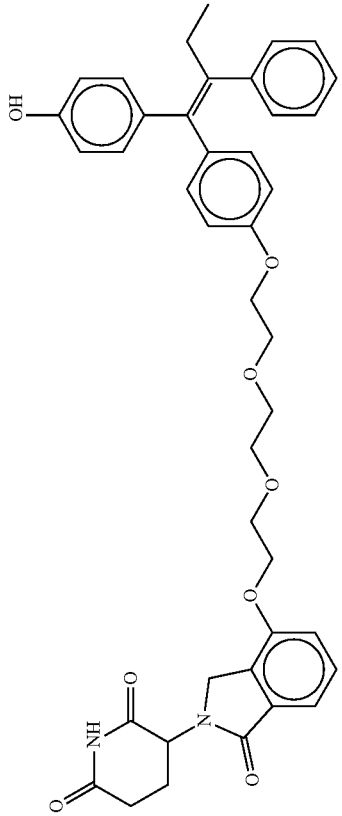 | (Z)-3-(4-(2-(2-(2-(4-(1-(4-hydroxyphenyl)-2-phenylbut-1-en-1-yl)phenoxy)ethoxy)ethoxy)ethoxy)-1-oxoisoindolin-2-yl)piperidine-2,6-dione |
| 234 | 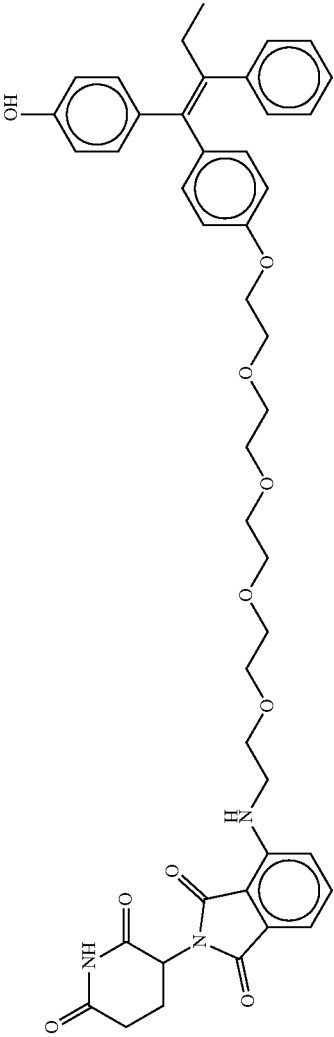 | (Z)-2-(2,6-dioxopiperidin-3-yl)-4-((14-(4-(1-(4-hydroxyphenyl)-2-phenylbut-1-en-1-yl)phenoxy)-3,6,9,12-tetraoxatetradecyl)amino)isoindoline-1,3-dione |

TABLE 1-continued
Exemplary Compound of the Present Disclosure
| # | Structure | IUPAC Name |
|---|-----------|------------|
| 235 | 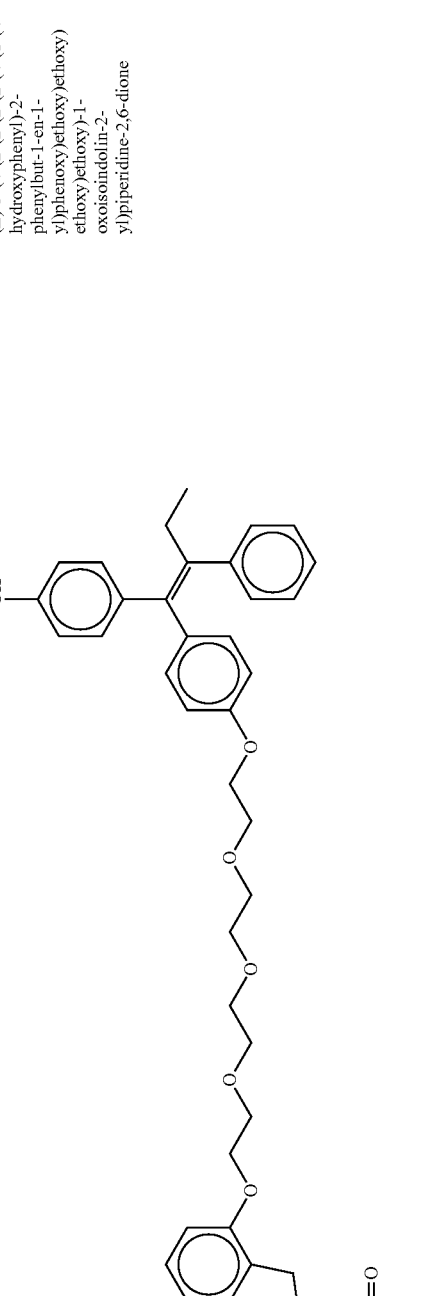 | (Z)-3-(4-(2-(2-(2-(2-(4-(1-(4-hydroxyphenyl)-2-phenylbut-1-en-1-yl)phenoxy)ethoxy)ethoxy)ethoxy)ethoxy)-1-oxoisoindolin-2-yl)piperidine-2,6-dione |
| 236 | 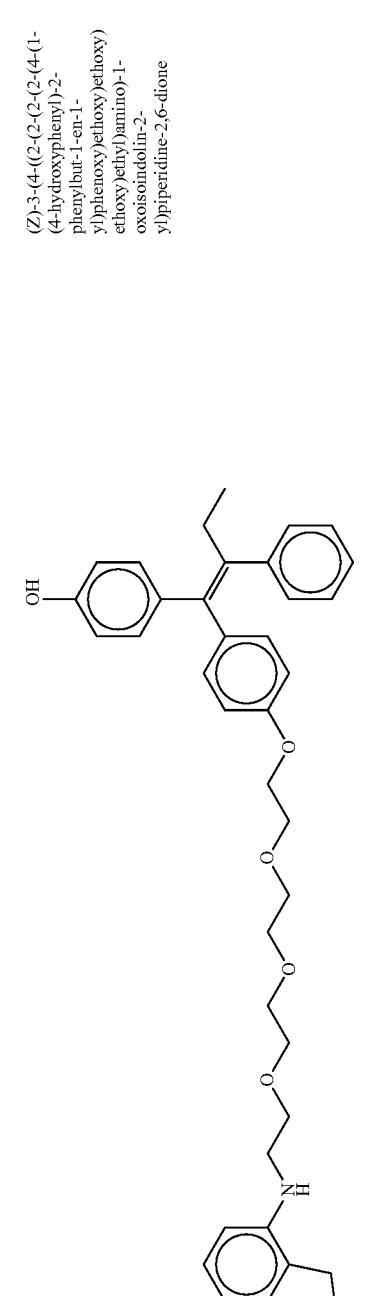 | (Z)-3-(4-((2-(2-(2-(2-(4-(1-(4-hydroxyphenyl)-2-phenylbut-1-en-1-yl)phenoxy)ethoxy)ethoxy)ethoxy)ethyl)amino)-1-oxoisoindolin-2-yl)piperidine-2,6-dione |

TABLE 1-continued
Exemplary Compound of the Present Disclosure
| # | Structure | IUPAC Name |
|---|---|---|
| 237 | 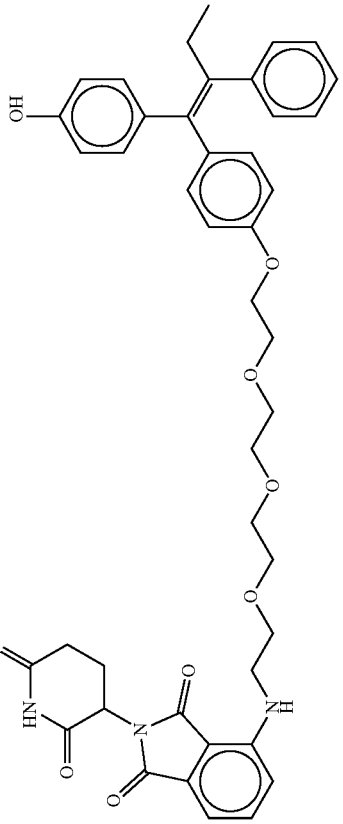 | (Z)-2-(2,6-dioxopiperidin-3-yl)-4-((2-(2-(2-(2-(4-(1-(4-hydroxyphenyl)-2-phenylbut-1-en-1-yl)phenoxy)ethoxy)ethoxy)ethoxy)ethyl)amino)isoindoline-1,3-dione |
| 238 | 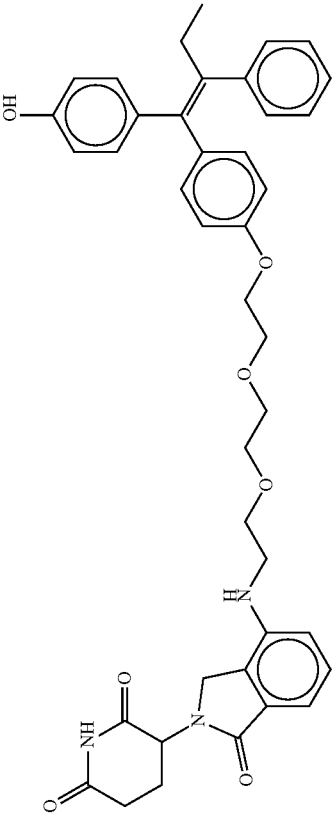 | (Z)-3-(4-((2-(2-(2-(4-(1-(4-hydroxyphenyl)-2-phenylbut-1-en-1-yl)phenoxy)ethoxy)ethoxy)ethyl)amino)-1-oxoisoindolin-2-yl)piperidine-2,6-dione |

TABLE 1-continued
Exemplary Compound of the Present Disclosure
| # | Structure | IUPAC Name |
|---|---|---|
| 239 | 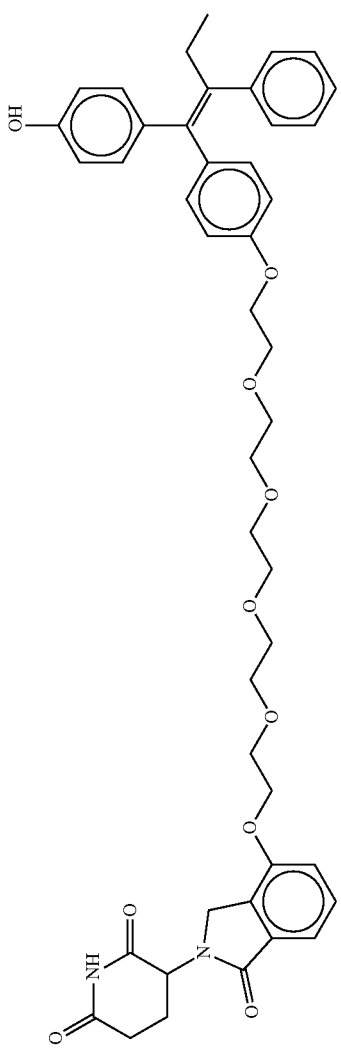 | (Z)-3-(4-((14-(4-(1-(4-hydroxyphenyl)-2-phenylbut-1-en-1-yl)phenoxy)-3,6,9,12-tetraoxatetradecyl)oxy)-1-oxoisoindolin-2-yl)piperidine-2,6-dione |
| 240 | 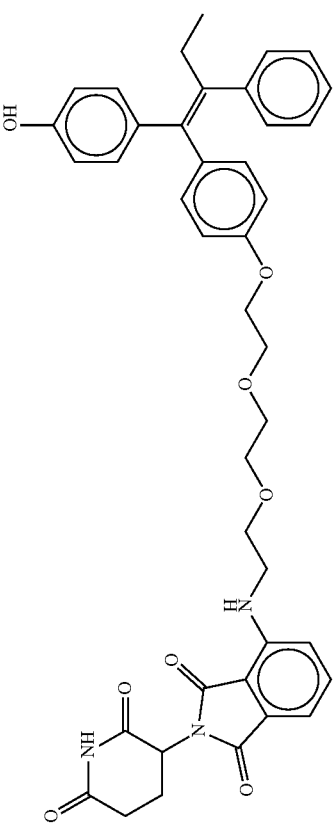 | (Z)-2-(2,6-dioxopiperidin-3-yl)-4-((2-(2-(4-(1-(4-hydroxyphenyl)-2-phenylbut-1-en-1-yl)phenoxy)ethoxy)ethyl)amino)isoindoline-1,3-dione |

TABLE 1-continued
Exemplary Compound of the Present Disclosure
| # | Structure | IUPAC Name |
|---|---|---|
| 241 | 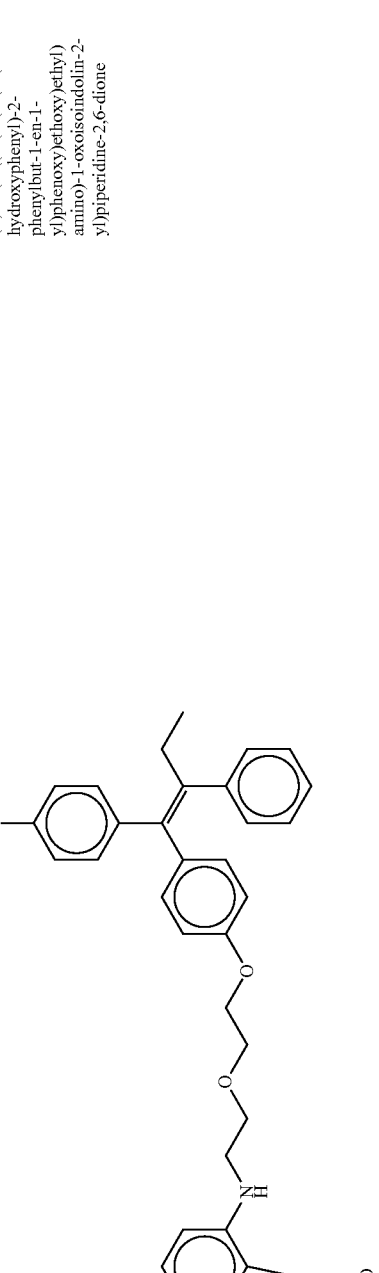 | (Z)-3-(4-((2-(2-(4-(1-(4-hydroxyphenyl)-2-phenylbut-1-en-1-yl)phenoxy)ethoxy)ethyl)amino)-1-oxoisoindolin-2-yl)piperidine-2,6-dione |
| 242 | 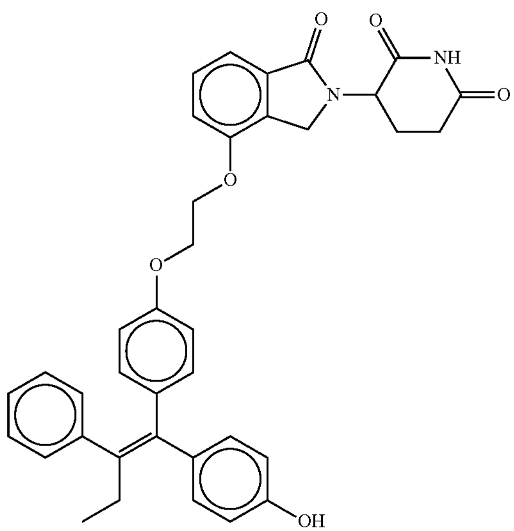 | (Z)-3-(4-(2-(4-(1-(4-hydroxyphenyl)-2-phenylbut-1-en-1-yl)phenoxy)ethoxy)-1-oxoisoindolin-2-yl)piperidine-2,6-dione |

TABLE 1-continued
Exemplary Compound of the Present Disclosure
| # | Structure | IUPAC Name |
|---|---|---|
| 243 | 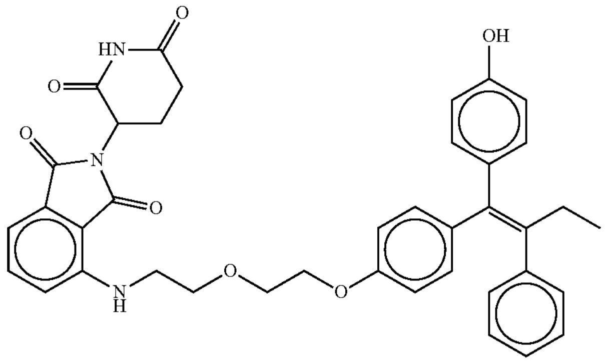 | (Z)-2-(2,6-dioxopiperidin-3-yl)-4-((2-(2-(4-(1-(4-hydroxyphenyl)-2-phenylbut-1-en-1-yl)phenoxy)ethoxy)ethyl)amino)isoindoline-1,3-dione |
| 244 | 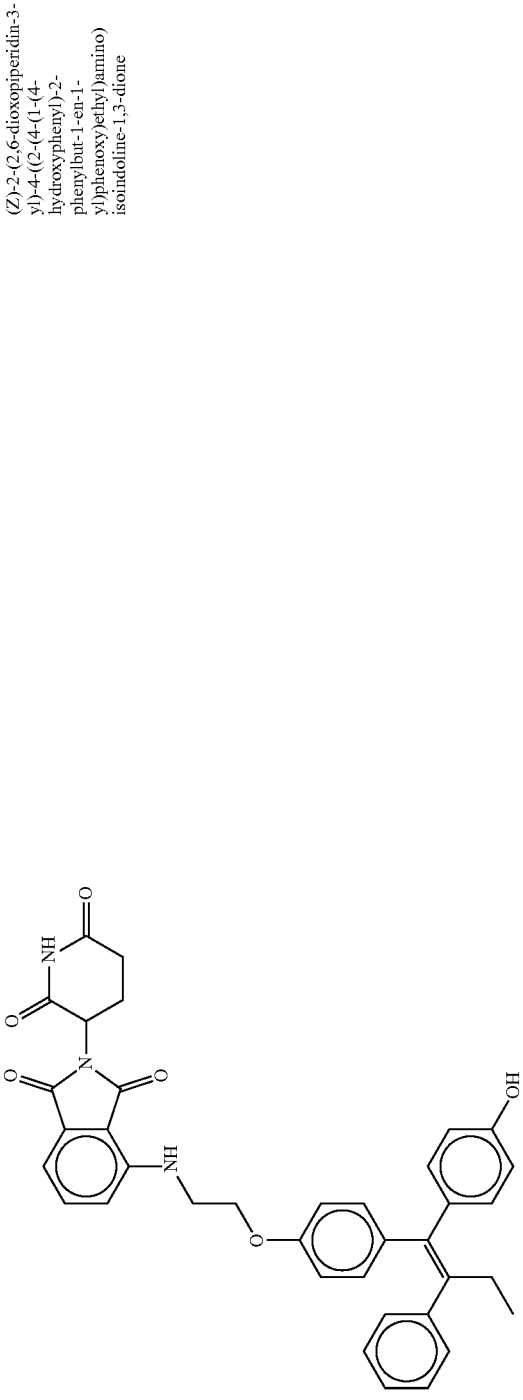 | (Z)-2-(2,6-dioxopiperidin-3-yl)-4-((2-(4-(1-(4-hydroxyphenyl)-2-phenylbut-1-en-1-yl)phenoxy)ethyl)amino)isoindoline-1,3-dione |

TABLE 1-continued
Exemplary Compound of the Present Disclosure
| # | Structure | IUPAC Name |
|---|---|---|
| 245 | 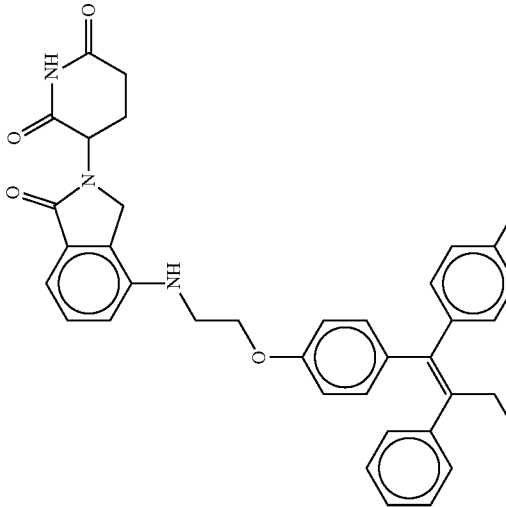 | (Z)-3-(4-((2-(4-(1-(4-hydroxyphenyl)-2-phenylbut-1-en-1-yl)phenoxy)ethyl)amino)-1-oxoisoindolin-2-yl)piperidine-2,6-dione |
| 246 | 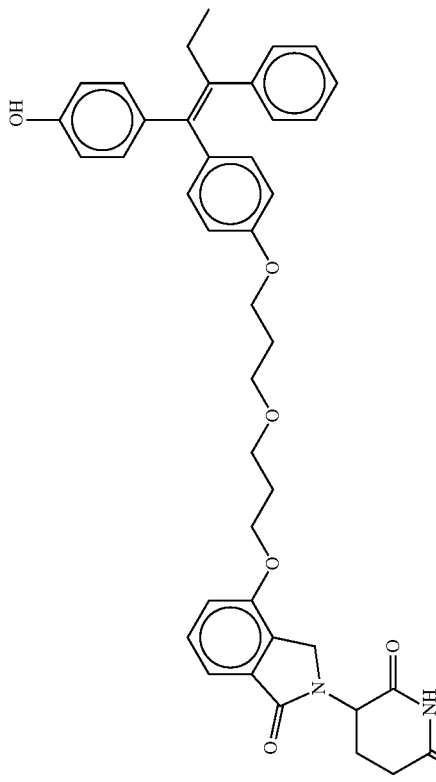 | (Z)-3-(4-(3-(4-(1-(4-hydroxyphenyl)-2-phenylbut-1-en-1-yl)phenoxy)propoxy)propoxy)-1-oxoisoindolin-2-yl)piperidine-2,6-dione |

TABLE 1-continued
Exemplary Compound of the Present Disclosure
| # | Structure | IUPAC Name |
|---|---|---|
| 247 | 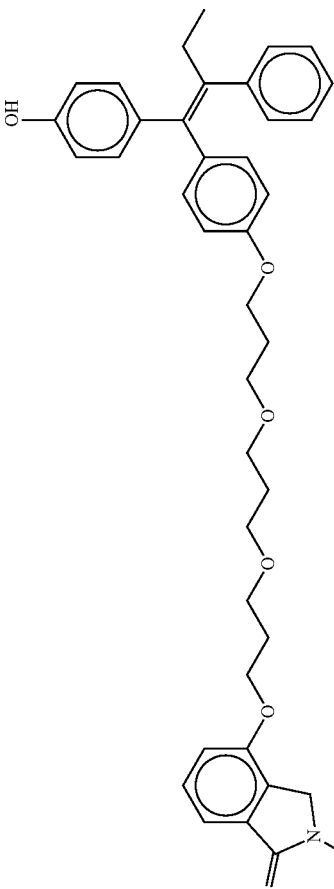 | (Z)-3-(4-(3-(3-(3-(4-(1-(4-hydroxyphenyl)-2-phenylbut-1-en-1-yl)phenoxy)propoxy)propoxy)propoxy)-1-oxoisoindolin-2-yl)piperidine-2,6-dione |
| 248 | 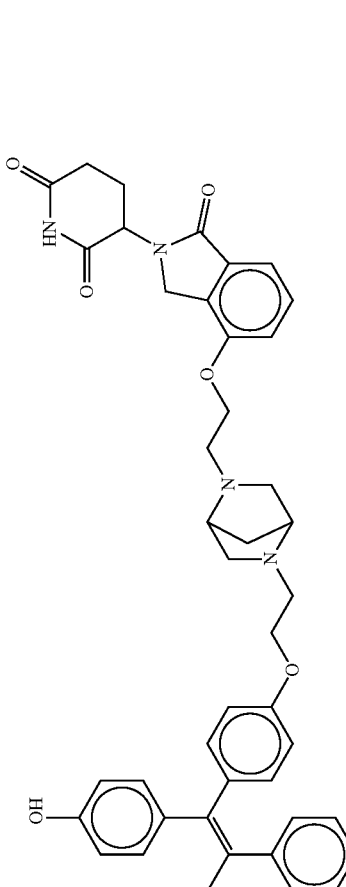 | (Z)-3-(4-(2-(5-(2-(4-(1-(4-hydroxyphenyl)-2-phenylbut-1-en-1-yl)phenoxy)ethyl)-2,5-diazabicyclo[2.2.1]heptan-2-yl)ethoxy)-1-oxoisoindolin-2-yl)piperidine-2,6-dione |

TABLE 1-continued

Exemplary Compound of the Present Disclosure

| # | Structure | IUPAC Name |
|---|---|---|
| 249 | 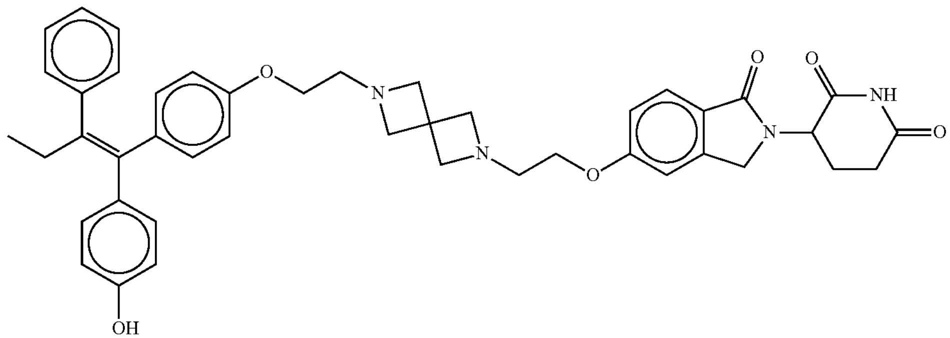 | (Z)-3-(5-(2-(6-(2-(4-(1-(4-hydroxyphenyl)-2-phenylbut-1-en-1-yl)phenoxy)ethyl)-2,6-diazaspiro[3.3]heptan-2-yl)ethoxy)-1-oxoisoindolin-2-yl)piperidine-2,6-dione |
| 250 | 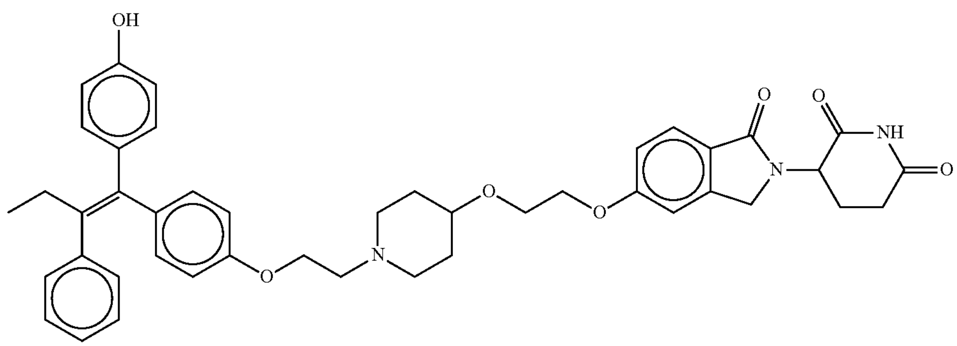 | (Z)-3-(5-(2-((1-(2-(4-(1-(4-hydroxyphenyl)-2-phenylbut-1-en-1-yl)phenoxy)ethyl)piperidin-4-yl)oxy)ethoxy)-1-oxoisoindolin-2-yl)piperidine-2,6-dione |
| 251 | 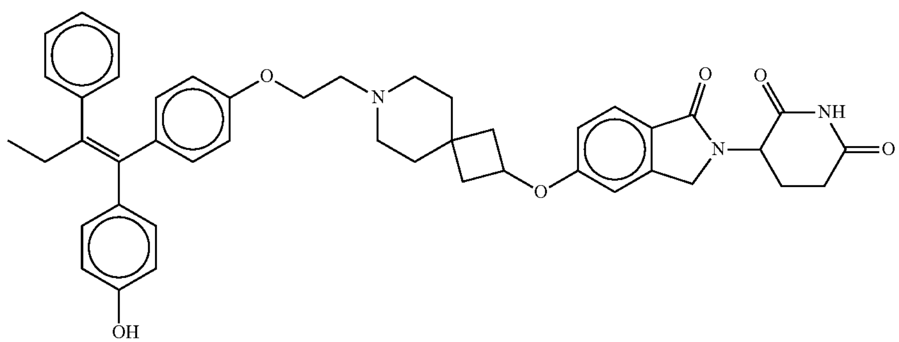 | (Z)-3-(5-((7-(2-(4-(1-(4-hydroxyphenyl)-2-phenylbut-1-en-1-yl)phenoxy)ethyl)-7-azaspiro[3.5]nonan-2-yl)oxy)-1-oxoisoindolin-2-yl)piperidine-2,6-dione |

TABLE 1-continued

Exemplary Compound of the Present Disclosure

| # | Structure | IUPAC Name |
|---|---|---|
| 252 | 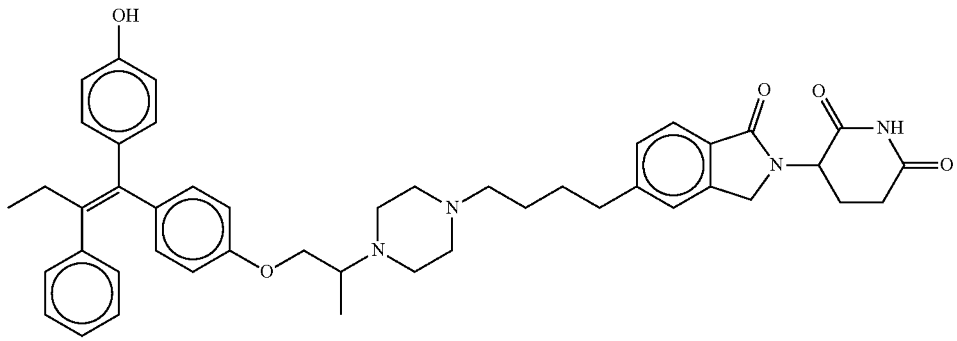 | (Z)-3-(5-(4-(4-(1-(4-(1-(4-hydroxyphenyl)-2-phenylbut-1-en-1-yl)phenoxy)propan-2-yl)piperazin-1-yl)butyl)-1-oxoisoindolin-2-yl)piperidine-2,6-dione |
| 253 | 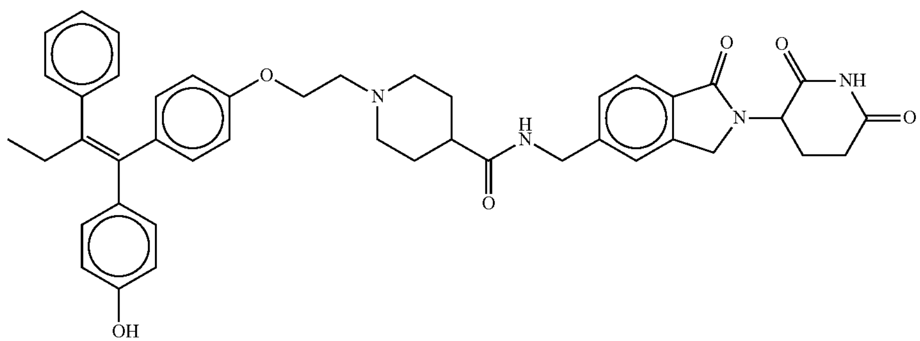 | (Z)-N-((2-(2,6-dioxopiperidin-3-yl)-1-oxoisoindolin-5-yl)methyl)-1-(2-(4-(1-(4-hydroxyphenyl)-2-phenylbut-1-en-1-yl)phenoxy)ethyl)piperidine-4-carboxamide |

TABLE 1-continued
Exemplary Compound of the Present Disclosure
| # | Structure | IUPAC Name |
|---|---|---|
| 254 | 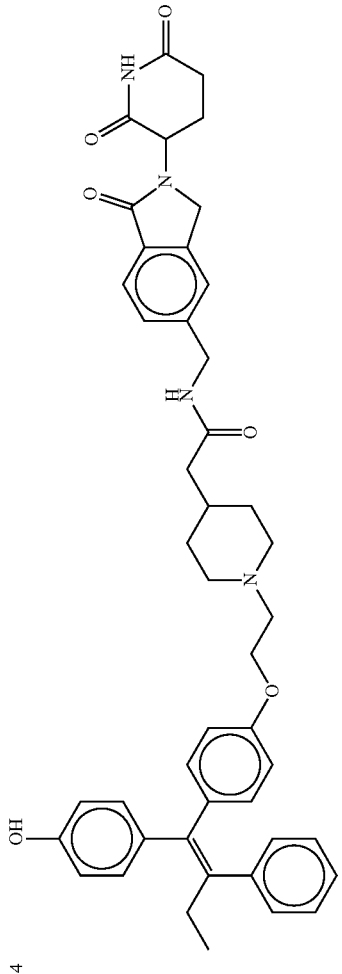 | (Z)-N-((2-(2,6-dioxopiperidin-3-yl)-1-oxoisoindolin-5-yl)methyl)-2-(1-(2-(4-(1-(4-hydroxyphenyl)-2-phenylbut-1-en-1-yl)phenoxy)ethyl)piperidin-4-yl)acetamide |
| 255 | 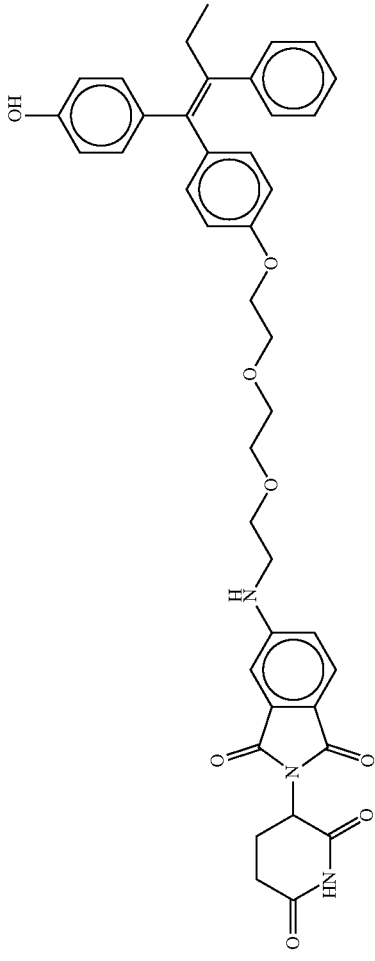 | (Z)-2-(2,6-dioxopiperidin-3-yl)-5-((2-(2-(2-(4-(1-(4-hydroxyphenyl)-2-phenylbut-1-en-1-yl)phenoxy)ethoxy)ethoxy)ethyl)amino)isoindoline-1,3-dione |

TABLE 1-continued
Exemplary Compound of the Present Disclosure
| # | Structure | IUPAC Name |
|---|-----------|------------|
| 256 | 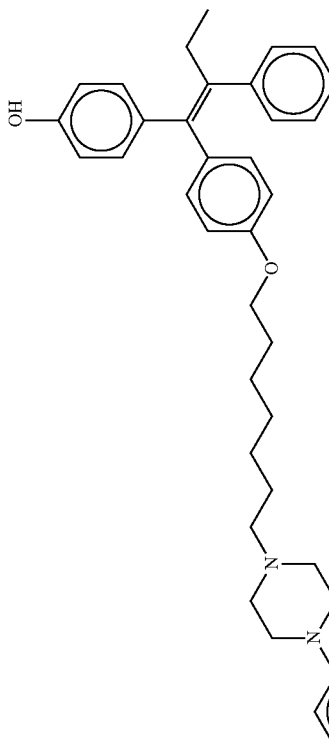 | (Z)-2-(2,6-dioxopiperidin-3-yl)-5-(4-(7-(4-(1-(4-hydroxyphenyl)-2-phenylbut-1-en-1-yl)phenoxy)heptyl)piperazin-1-yl)isoindoline-1,3-dione |
| 257 | 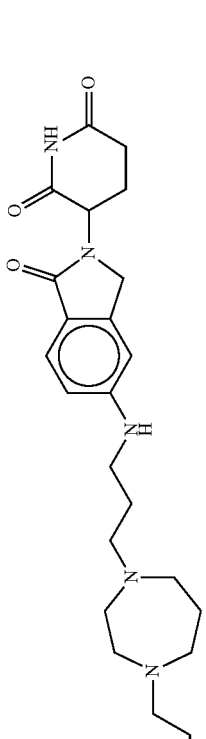 | (Z)-3-(5-((3-(4-(2-(4-(1-(4-hydroxyphenyl)-2-phenylbut-1-en-1-yl)phenoxy)ethyl)-1,4-diazepan-1-yl)propyl)amino)-1-oxoisoindolin-2-yl)piperidine-2,6-dione |

TABLE 1-continued
Exemplary Compound of the Present Disclosure
| # | Structure | IUPAC Name |
|---|---|---|
| 258 | 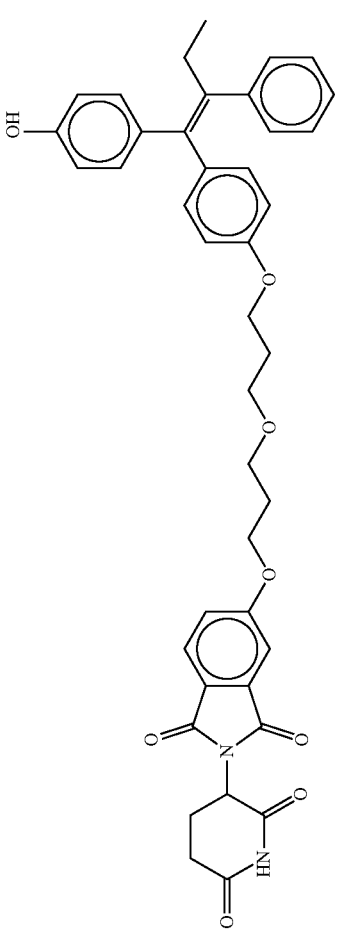 | (Z)-2-(2,6-dioxopiperidin-3-yl)-5-(3-(4-(1-(4-hydroxyphenyl)-2-phenylbut-1-en-1-yl)phenoxy)propoxy)isoindoline-1,3-dione |
| 259 | 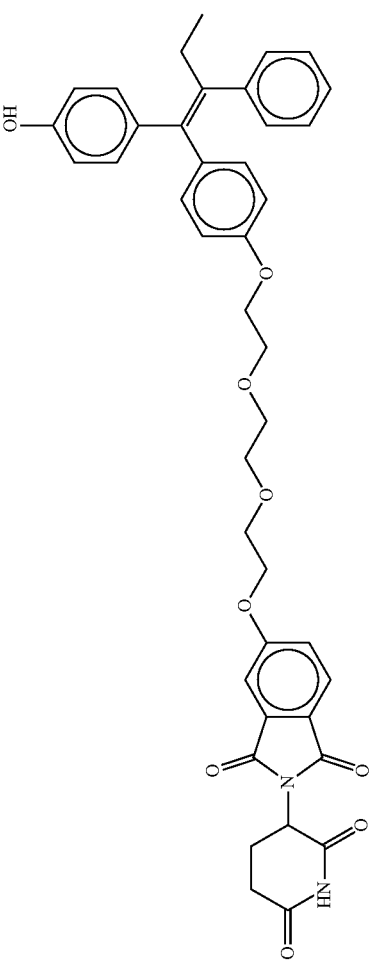 | (Z)-2-(2,6-dioxopiperidin-3-yl)-5-(2-(2-(4-(1-(4-hydroxyphenyl)-2-phenylbut-1-en-1-yl)phenoxy)ethoxy)ethoxy)isoindoline-1,3-dione |

TABLE 1-continued

Exemplary Compound of the Present Disclosure

| # | Structure | IUPAC Name |
|---|---|---|
| 260 | 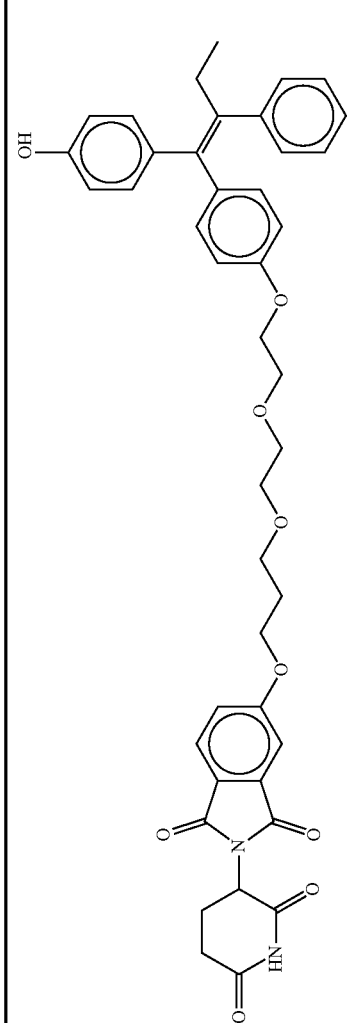 | (Z)-2-(2,6-dioxopiperidin-3-yl)-5-(3-(2-(2-(4-(1-(4-hydroxyphenyl)-2-phenylbut-1-en-1-yl)phenoxy)ethoxy)ethoxy)propoxy)isoindoline-1,3-dione |
| 261 | 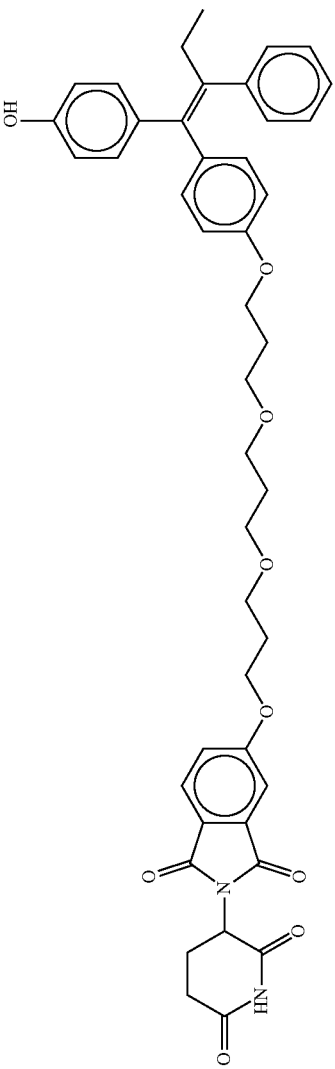 | (Z)-2-(2,6-dioxopiperidin-3-yl)-5-(3-(3-(4-(1-(4-hydroxyphenyl)-2-phenylbut-1-en-1-yl)phenoxy)propoxy)propoxy)isoindoline-1,3-dione |
| 262 | 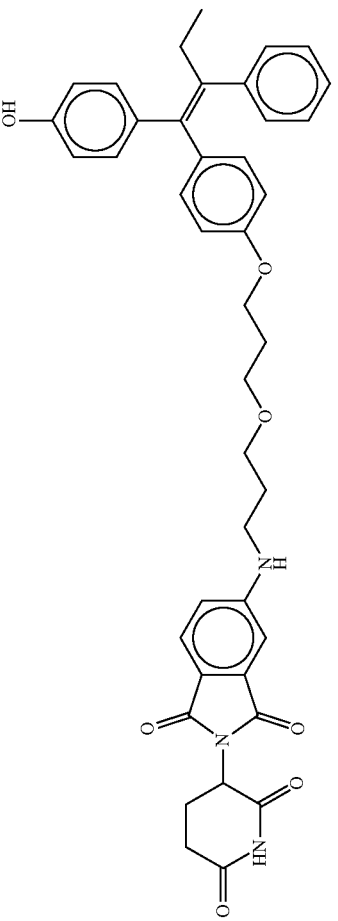 | (Z)-2-(2,6-dioxopiperidin-3-yl)-5-(3-(4-(1-(4-hydroxyphenyl)-2-phenylbut-1-en-1-yl)phenoxy)propoxy)propyl)amino)isoindoline-1,3-dione |

TABLE 1-continued
Exemplary Compound of the Present Disclosure
| # | Structure | IUPAC Name |
|---|---|---|
| 263 | 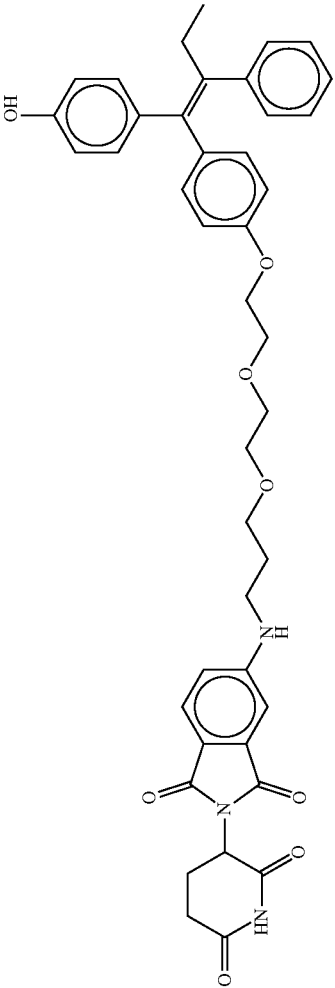 | (Z)-2-(2,6-dioxopiperidin-3-yl)-5-((3-(2-(2-(4-(1-(4-hydroxyphenyl)-2-phenylbut-1-en-1-yl)phenoxy)ethoxy)ethoxy)propyl)amino)isoindoline-1,3-dione |
| 264 | 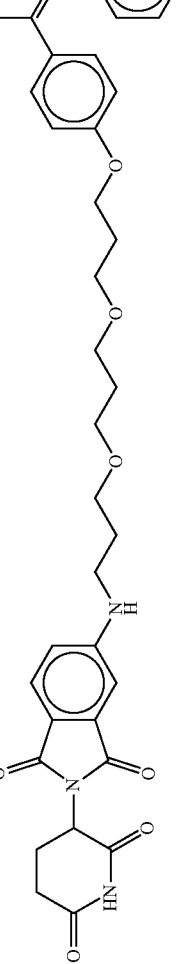 | (Z)-2-(2,6-dioxopiperidin-3-yl)-5-((3-(3-(4-(1-(4-hydroxyphenyl)-2-phenylbut-1-en-1-yl)phenoxy)propoxy)propyl)amino)isoindoline-1,3-dione |

TABLE 1-continued
Exemplary Compound of the Present Disclosure
| # | Structure | IUPAC Name |
|---|---|---|
| 265 | 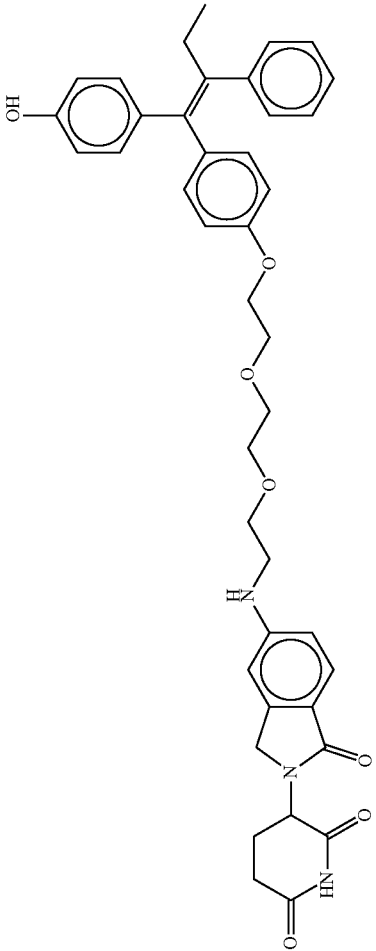 | (Z)-3-(5-((2-(2-(2-(4-(1-(4-hydroxyphenyl)-2-phenylbut-1-en-1-yl)phenoxy)ethoxy)ethoxy)ethyl)amino)-1-oxoisoindolin-2-yl)piperidine-2,6-dione |
| 266 | 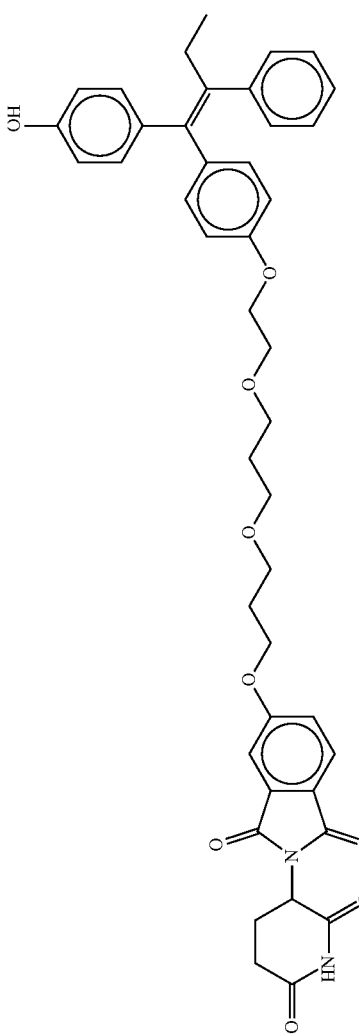 | (Z)-2-(2,6-dioxopiperidin-3-yl)-5-(3-(2-(4-(1-(4-hydroxyphenyl)-2-phenylbut-1-en-1-yl)phenoxy)ethoxy)propoxy)isoindoline-1,3-dione |

TABLE 1-continued
Exemplary Compound of the Present Disclosure
| # | Structure | IUPAC Name |
|---|---|---|
| 267 | 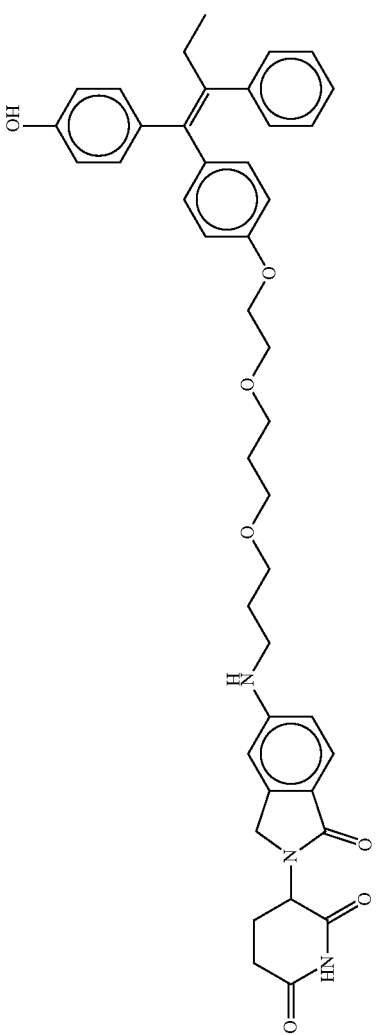 | (Z)-3-(5-((3-(2-(4-(1-(4-hydroxyphenyl)-2-phenylbut-1-en-1-yl)phenoxy)ethoxy)propoxy)propyl)amino)-1-oxoisoindolin-2-yl)piperidine-2,6-dione |
| 268 | 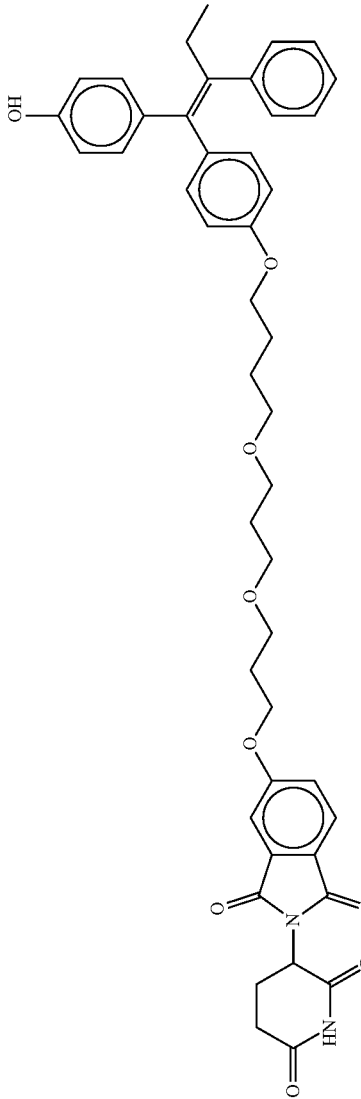 | (Z)-2-(2,6-dioxopiperidin-3-yl)-5-(3-(4-(4-(1-(4-hydroxyphenyl)-2-phenylbut-1-en-1-yl)phenoxy)butoxy)propoxy)isoindoline-1,3-dione |

TABLE 1-continued
Exemplary Compound of the Present Disclosure
| # | Structure | IUPAC Name |
|---|---|---|
| 269 | 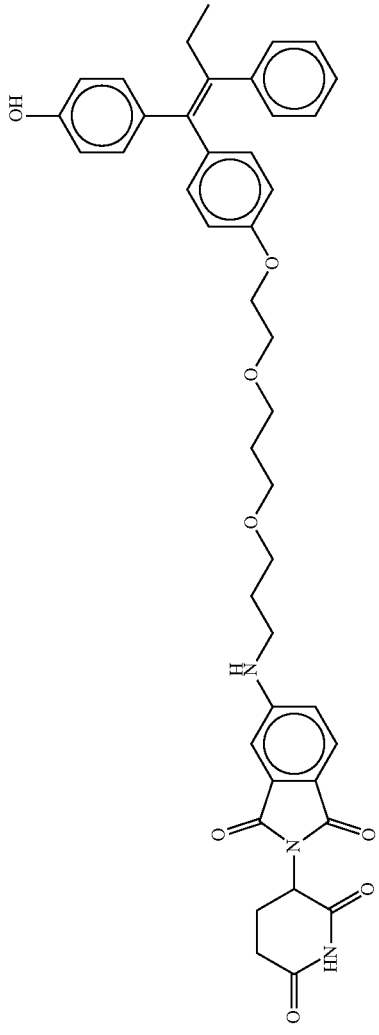 | (Z)-2-(2,6-dioxopiperidin-3-yl)-5-((3-(2-(4-(1-(4-hydroxyphenyl)-2-phenylbut-1-en-1-yl)phenoxy)ethoxy)propoxy)propyl)amino)isoindoline-1,3-dione |
| 270 | 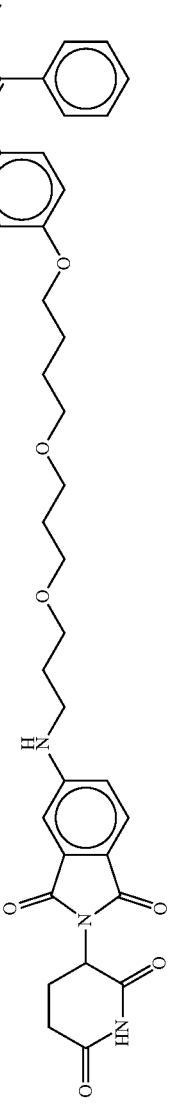 | (Z)-2-(2,6-dioxopiperidin-3-yl)-5-((3-(4-(4-(1-(4-hydroxyphenyl)-2-phenylbut-1-en-1-yl)phenoxy)butoxy)propoxy)propyl)amino)isoindoline-1,3-dione |

TABLE 1-continued
Exemplary Compound of the Present Disclosure
| # | Structure | IUPAC Name |
|---|---|---|
| 271 | 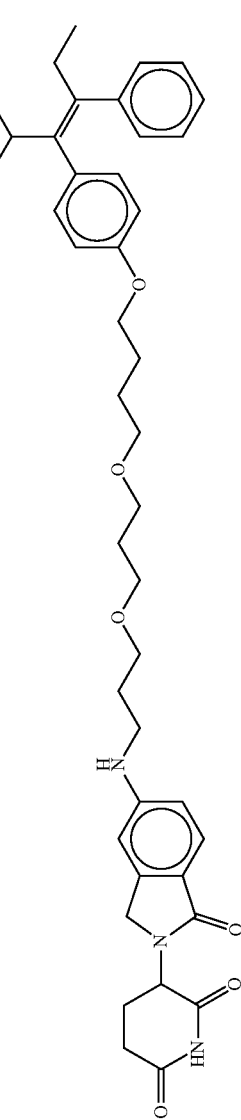 | (Z)-3-(5-((3-(4-(4-(1-(4-hydroxyphenyl)-2-phenylbut-1-en-1-yl)phenoxy)butoxy)propoxy)propyl)amino)-1-oxoisoindolin-2-yl)piperidine-2,6-dione |
| 272 | 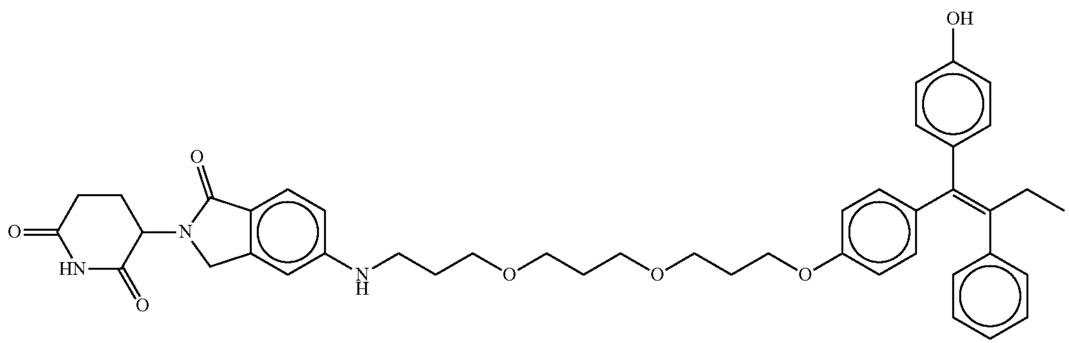 | (Z)-3-(5-((3-(4-(3-(4-(1-(4-hydroxyphenyl)-2-phenylbut-1-en-1-yl)phenoxy)propoxy)propoxy)propyl)amino)-1-oxoisoindolin-2-yl)piperidine-2,6-dione |

TABLE 1-continued
Exemplary Compound of the Present Disclosure
| # | Structure | IUPAC Name |
|---|-----------|------------|
| 273 | 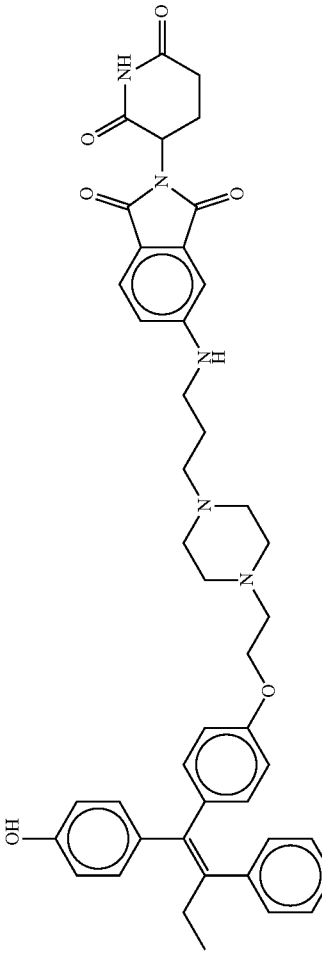 | (Z)-2-(2,6-dioxopiperidin-3-yl)-5-((3-(4-(2-(4-(1-(4-hydroxyphenyl)-2-phenylbut-1-en-1-yl)phenoxy)ethyl)piperazin-1-yl)propyl)amino)isoindoline-1,3-dione |
| 274 | 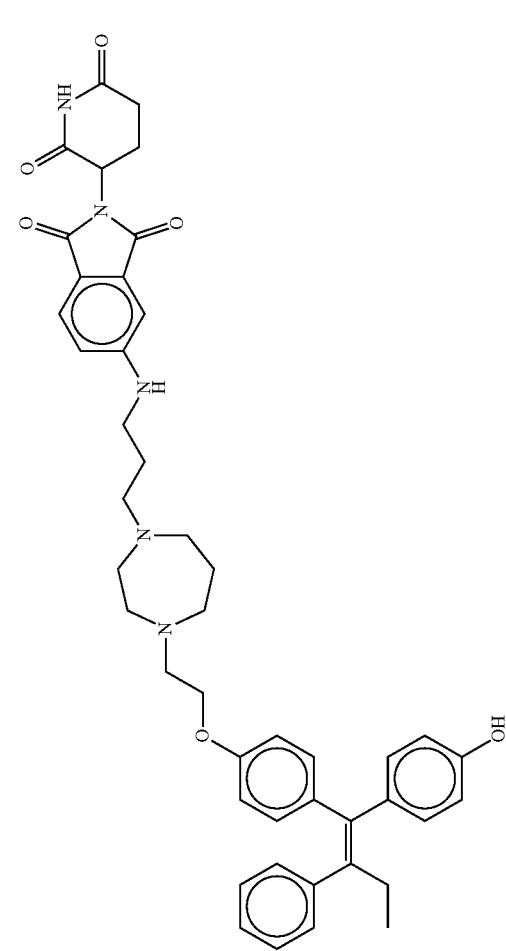 | (Z)-2-(2,6-dioxopiperidin-3-yl)-5-((3-(4-(2-(4-(1-(4-hydroxyphenyl)-2-phenylbut-1-en-1-yl)phenoxy)ethyl)-1,4-diazepan-1-yl)propyl)amino)isoindoline-1,3-dione |

TABLE 1-continued
Exemplary Compound of the Present Disclosure
| # | Structure | IUPAC Name |
|---|-----------|------------|
| 275 | 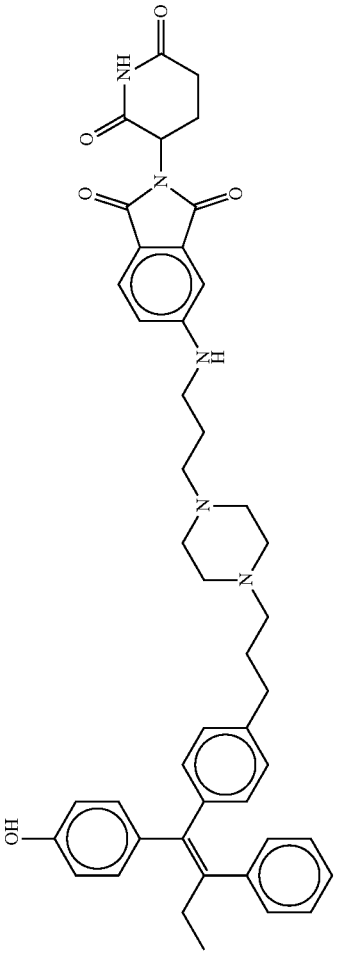 | (E)-2-(2,6-dioxopiperidin-3-yl)-5-((3-(4-(3-(4-(1-(4-hydroxyphenyl)-2-phenylbut-1-en-1-yl)phenyl)propyl)piperazin-1-yl)propyl)amino)isoindoline-1,3-dione |
| 276 | 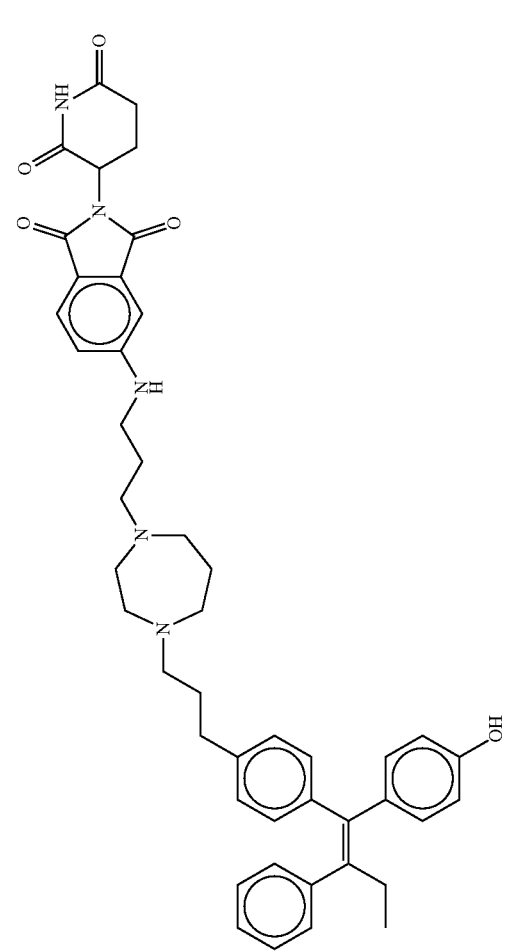 | (E)-2-(2,6-dioxopiperidin-3-yl)-5-((3-(4-(3-(4-(1-(4-hydroxyphenyl)-2-phenylbut-1-en-1-yl)phenyl)propyl)-1,4-diazepan-1-yl)propyl)amino)isoindoline-1,3-dione |

TABLE 1-continued
Exemplary Compound of the Present Disclosure
| # | Structure | IUPAC Name |
|---|---|---|
| 277 | 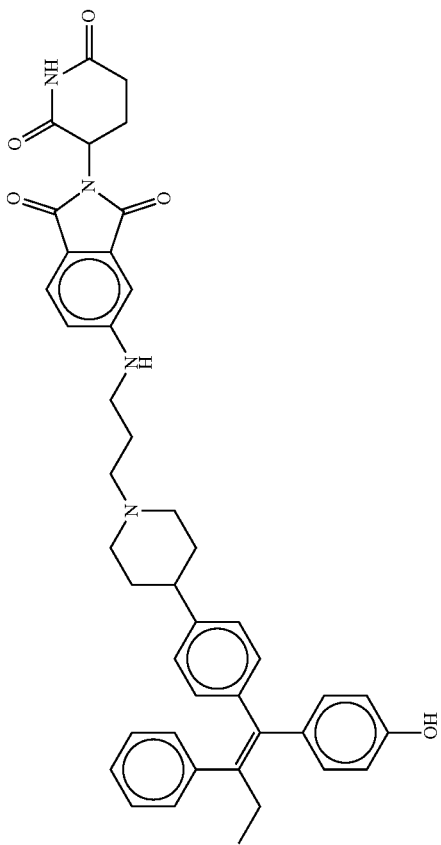 | (E)-2-(2,6-dioxopiperidin-3-yl)-5-((3-(4-(4-(1-(4-hydroxyphenyl)-2-phenylbut-1-en-1-yl)phenyl)piperidin-1-yl)propyl)amino)isoindoline-1,3-dione |
| 278 | 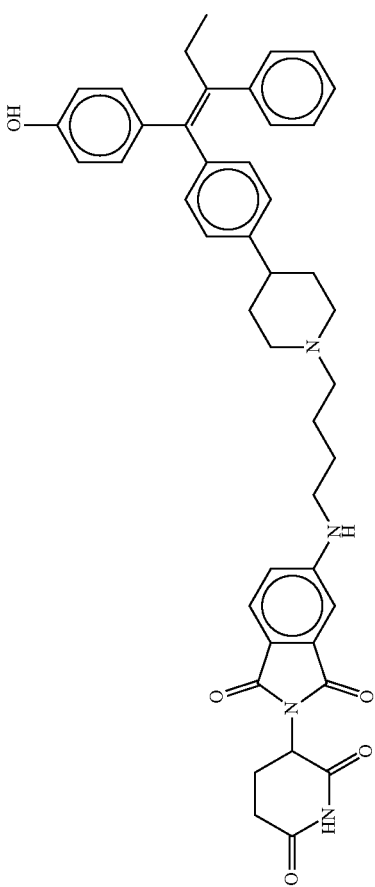 | (E)-2-(2,6-dioxopiperidin-3-yl)-5-((4-(4-(1-(4-hydroxyphenyl)-2-phenylbut-1-en-1-yl)phenyl)piperidin-1-yl)butyl)amino)isoindoline-1,3-dione |

TABLE 1-continued
Exemplary Compound of the Present Disclosure
| # | Structure | IUPAC Name |
|---|---|---|
| 279 | 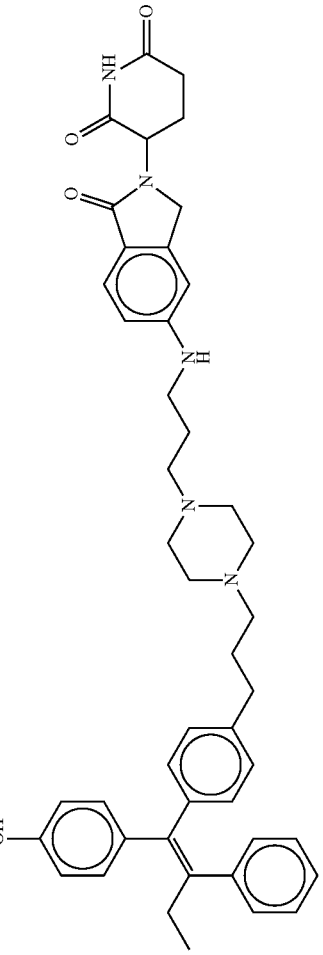 | (E)-3-(5-((3-(4-(3-(4-(1-(4-hydroxyphenyl)-2-phenylbut-1-en-1-yl)phenyl)propyl)piperazin-1-yl)propyl)amino)-1-oxoisoindolin-2-yl)piperidine-2,6-dione |
| 280 | 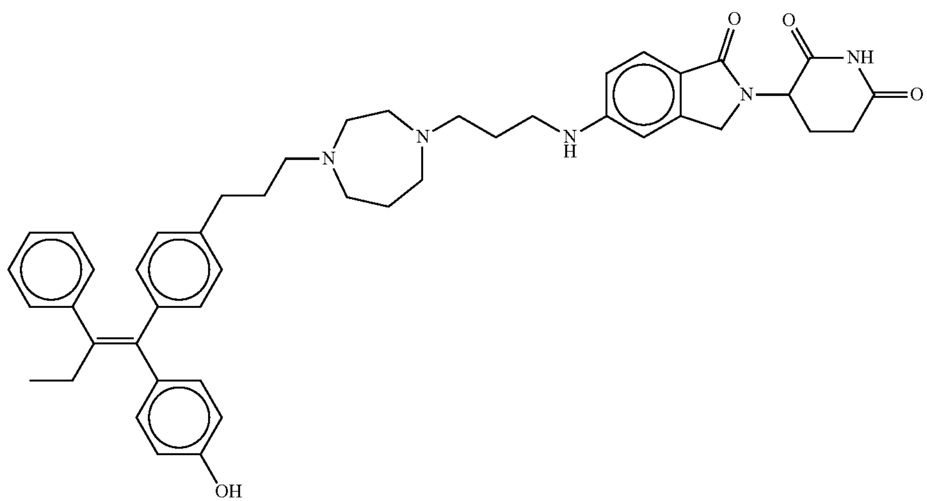 | (E)-3-(5-((3-(4-(4-(1-(4-hydroxyphenyl)-2-phenylbut-1-en-1-yl)phenyl)propyl)-1,4-diazepan-1-yl)propyl)amino)-1-oxoisoindolin-2-yl)piperidine-2,6-dione |

TABLE 1-continued
Exemplary Compound of the Present Disclosure
| # | Structure | IUPAC Name |
|---|---|---|
| 281 | 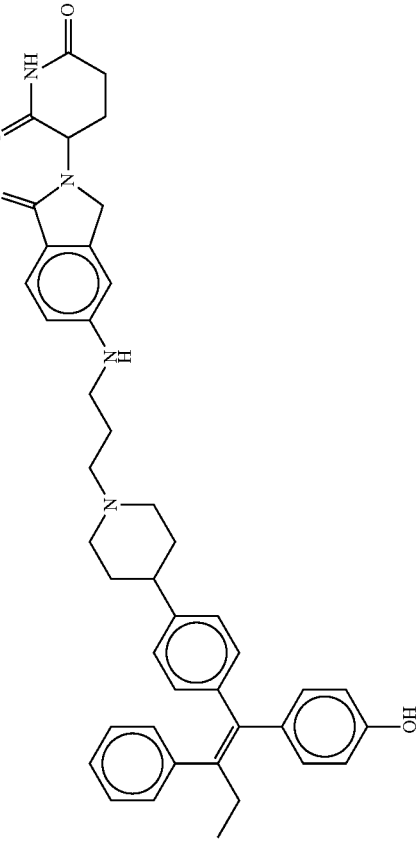 | (E)-3-(5-((3-(4-(4-(1-(4-hydroxyphenyl)-2-phenylbut-1-en-1-yl)phenyl)piperidin-1-yl)propyl)amino)-1-oxoisoindolin-2-yl)piperidine-2,6-dione |
| 282 | 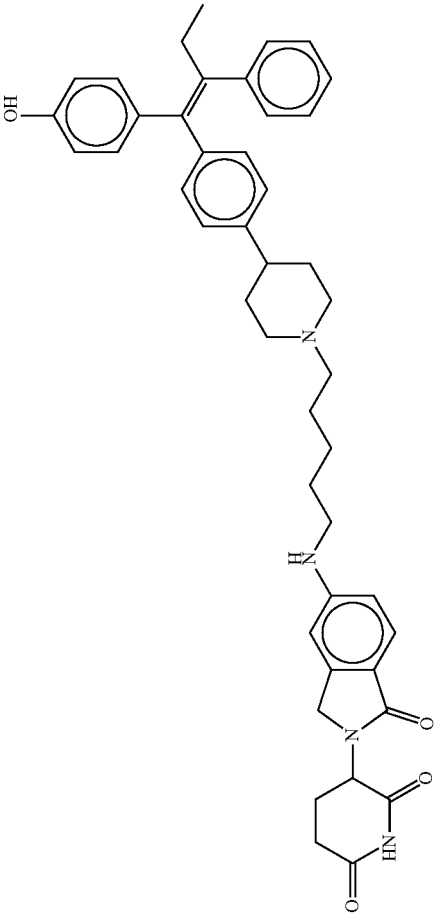 | (E)-3-(5-(4-(4-(1-(4-hydroxyphenyl)-2-phenylbut-1-en-1-yl)phenyl)piperidin-1-yl)pentyl)amino)-1-oxoisoindolin-2-yl)piperidine-2,6-dione |

TABLE 1-continued
Exemplary Compound of the Present Disclosure
| # | Structure | IUPAC Name |
|---|---|---|
| 283 | 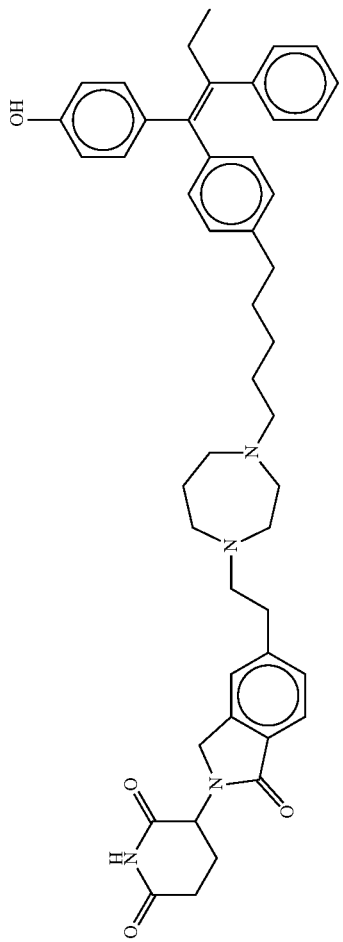 | (E)-3-(5-(2-(4-(5-(4-(1-(4-hydroxyphenyl)-2-phenylbut-1-en-1-yl)phenyl)pentyl)-1,4-diazepan-1-yl)ethyl)-1-oxoisoindolin-2-yl)piperidine-2,6-dione |

Pharmaceutical Compositions

Pharmaceutical compositions of the present disclosure comprise at least one compound of Formulae (I) or (II), or tautomer, stereoisomer, pharmaceutically acceptable salt or hydrate thereof formulated together with one or more pharmaceutically acceptable carriers. These formulations include those suitable for oral, rectal, topical, buccal and parenteral (e.g., subcutaneous, intramuscular, intradermal, or intravenous) administration. The most suitable form of administration in any given case will depend on the degree and severity of the condition being treated and on the nature of the particular compound being used.

Formulations suitable for oral administration may be presented in discrete units, such as capsules, cachets, lozenges, or tablets, each containing a predetermined amount of a compound of the present disclosure as powder or granules; as a solution or a suspension in an aqueous or non-aqueous liquid; or as an oil-in-water or water-in-oil emulsion. As indicated, such formulations may be prepared by any suitable method of pharmacy which includes the step of bringing into association at least one compound of the present disclosure as the active compound and a carrier or excipient (which may constitute one or more accessory ingredients). The carrier must be acceptable in the sense of being compatible with the other ingredients of the formulation and must not be deleterious to the recipient. The carrier may be a solid or a liquid, or both, and may be formulated with at least one compound described herein as the active compound in a unit-dose formulation, for example, a tablet, which may contain from about 0.05% to about 95% by weight of the at least one active compound. Other pharmacologically active substances may also be present including other compounds. The formulations of the present disclosure may be prepared by any of the well-known techniques of pharmacy consisting essentially of admixing the components.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmacologically administrable compositions can, for example, be prepared by, for example, dissolving or dispersing, at least one active compound of the present disclosure as described herein and optional pharmaceutical adjuvants in an excipient, such as, for example, water, saline, aqueous dextrose, glycerol, ethanol, and the like, to thereby form a solution or suspension. In general, suitable formulations may be prepared by uniformly and intimately admixing the at least one active compound of the present disclosure with a liquid or finely divided solid carrier, or both, and then, if necessary, shaping the product. For example, a tablet may be prepared by compressing or molding a powder or granules of at least one compound of the present disclosure, which may be optionally combined with one or more accessory ingredients. Compressed tablets may be prepared by compressing, in a suitable machine, at least one compound of the present disclosure in a free-flowing form, such as a powder or granules, which may be optionally mixed with a binder, lubricant, inert diluent and/or surface active/dispersing agent(s). Molded tablets may be made by molding, in a suitable machine, where the powdered form of at least one compound of the present disclosure is moistened with an inert liquid diluent.

Formulations suitable for buccal (sub-lingual) administration include lozenges comprising at least one compound of the present disclosure in a flavored base, usually sucrose and acacia or tragacanth, and pastilles comprising the at least one compound in an inert base such as gelatin and glycerin or sucrose and acacia.

Formulations of the present disclosure suitable for parenteral administration comprise sterile aqueous preparations of at least one compound of Formula (I) or (II), or tautomers, stereoisomers, pharmaceutically acceptable salts, and hydrates thereof, which are approximately isotonic with the blood of the intended recipient. These preparations are administered intravenously, although administration may also be effected by means of subcutaneous, intramuscular, or intradermal injection. Such preparations may conveniently be prepared by admixing at least one compound described herein with water and rendering the resulting solution sterile and isotonic with the blood. Injectable compositions according to the present disclosure may contain from about 0.1 to about 5% w/w of the active compound.

Formulations suitable for rectal administration are presented as unit-dose suppositories. These may be prepared by admixing at least one compound as described herein with one or more conventional solid carriers, for example, cocoa butter, and then shaping the resulting mixture.

Formulations suitable for topical application to the skin may take the form of an ointment, cream, lotion, paste, gel, spray, aerosol, or oil. Carriers and excipients which may be used include Vaseline, lanoline, polyethylene glycols, alcohols, and combinations of two or more thereof. The active compound (i.e., at least one compound of Formula (I) or (II), or tautomers, stereoisomers, pharmaceutically acceptable salts, and hydrates thereof) is generally present at a concentration of from about 0.1% to about 15% w/w of the composition, for example, from about 0.5 to about 2%.

The amount of active compound administered may be dependent on the subject being treated, the subject's weight, the manner of administration and the judgment of the prescribing physician. For example, a dosing schedule may involve the daily or semi-daily administration of the encapsulated compound at a perceived dosage of about 1 µg to about 1000 mg. In another embodiment, intermittent administration, such as on a monthly or yearly basis, of a dose of the encapsulated compound may be employed. Encapsulation facilitates access to the site of action and allows the administration of the active ingredients simultaneously, in theory producing a synergistic effect. In accordance with standard dosing regimens, physicians will readily determine optimum dosages and will be able to readily modify administration to achieve such dosages.

A therapeutically effective amount of a compound or composition disclosed herein can be measured by the therapeutic effectiveness of the compound. The dosages, however, may be varied depending upon the requirements of the patient, the severity of the condition being treated, and the compound being used. In one embodiment, the therapeutically effective amount of a disclosed compound is sufficient to establish a maximal plasma concentration. Preliminary doses as, for example, determined according to animal tests, and the scaling of dosages for human administration is performed according to art-accepted practices.

Toxicity and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices are preferable.

Data obtained from the cell culture assays or animal studies can be used in formulating a range of dosage for use in humans. Therapeutically effective dosages achieved in one animal model may be converted for use in another animal, including humans, using conversion factors known in the art (see, e.g., Freireich et al., *Cancer Chemother. Reports* 50(4):219-244 (1966) and the following Table for Equivalent Surface Area Dosage Factors).

TABLE 2

Equivalent Surface Area Dosage Factors.

| From: | To: | | | | |
|---|---|---|---|---|---|
| | Mouse (20 g) | Rat (150 g) | Monkey (3.5 kg) | Dog (8 kg) | Human (60 kg) |
| Mouse | 1 | 1/2 | 1/4 | 1/6 | 1/12 |
| Rat | 2 | 1 | 1/2 | 1/4 | 1/7 |
| Monkey | 4 | 2 | 1 | 3/5 | 1/3 |
| Dog | 6 | 4 | 3/5 | 1 | 1/2 |
| Human | 12 | 7 | 3 | 2 | 1 |

The dosage of such compounds lies preferably within a range of circulating concentrations that include the $ED_{50}$ with little or no toxicity. The dosage may vary within this range depending upon the dosage form employed and the route of administration utilized. Generally, a therapeutically effective amount may vary with the subject's age, condition, and gender, as well as the severity of the medical condition in the subject. The dosage may be determined by a physician and adjusted, as necessary, to suit observed effects of the treatment.

Methods of Treatment

In some embodiments, a compound of Formula (I) or (II), or a tautomer, stereoisomer, pharmaceutically acceptable salt or hydrate thereof, is administered to treat cancer in a subject in need thereof. In some embodiments, the cancer is chosen from breast cancer, lung cancer, ovarian cancer, endometrial cancer, prostate cancer, and esophageal cancer. In some embodiments, the cancer is breast cancer. In some embodiments, the cancer is lung cancer. In some embodiments, the cancer is ovarian cancer. In some embodiments, the cancer is endometrial cancer. In some embodiments, the cancer is prostate cancer. In some embodiments, the cancer is esophageal cancer. In some embodiments, the cancer is positive for ERα. In some embodiments, a compound of Formulae (I) or (II), or a tautomer, stereoisomer, pharmaceutically acceptable salt or hydrate thereof, is administered as a pharmaceutical composition. In some embodiments, the subject has been previously treated with tamoxifen.

In some embodiments, provided herein is a use of a compound of Formula (I) or (II), or a tautomer, stereoisomer, pharmaceutically acceptable salt or hydrate thereof, in a therapeutic treatment. In some embodiments, the therapeutic treatment is for the treatment of breast cancer, lung cancer, ovarian cancer, endometrial cancer, prostate cancer, and esophageal cancer. In some embodiments, the therapeutic treatment is for the treatment of breast cancer. In some embodiments, the therapeutic treatment is for lung cancer. In some embodiments, the therapeutic treatment is for the treatment of ovarian cancer. In some embodiments, the therapeutic treatment is for the treatment of endometrial cancer. In some embodiments, the therapeutic treatment is for the treatment of prostate cancer. In some embodiments, the therapeutic treatment is for the treatment of esophageal cancer. In some embodiments, the therapeutic treatment is for the treatment of estrogen-related diseases and conditions. In some embodiments, the therapeutic treatment is for the treatment of infertility. In some embodiments, the therapeutic treatment is for the treatment of ovulatory dysfunction. In some embodiments, the therapeutic treatment is for the treatment of postmenopausal osteoporosis. In some embodiments, the therapeutic treatment is for the treatment of estrogen-related gynecomastia. In some embodiments, the therapeutic treatment is for the treatment of dyspareunia due to menopause. In some embodiments, the therapeutic treatment is for the treatment of retroperitoneal fibrosis. In some embodiments, the therapeutic treatment is for the treatment of idiopathic sclerosing mesenteritis.

In some embodiments, provided herein is a use of a compound of Formula (I) or (II), or a tautomer, stereoisomer, pharmaceutically acceptable salt or hydrate thereof, in the preparation of a medicament. In some embodiments, provided herein is a method of inhibiting cell growth comprising contacting a cell with a compound of Formula (I) or (II), or a tautomer, stereoisomer, pharmaceutically acceptable salt or hydrate thereof. In some embodiments, the cell may express ERα.

In one embodiment, a compound of Formula (I) or (II), or a tautomer, stereoisomer, pharmaceutically acceptable salt or hydrate thereof, is administered in combination with another therapeutic agent. The other therapeutic agent can provide additive or synergistic value relative to the administration of a compound of the present disclosure alone. The therapeutic agent can be selected from, for example, hormones and hormonal analogues; signal transduction pathway inhibitors; topoisomerase I inhibitors; topoisomerase II inhibitors; antimetabolite neoplastic agents; antibiotic neoplastic agents; alkylating agents; anti-microtubule agents; platinum coordination complexes; aromatase inhibitors; and anti-mitotic agents.

In some embodiments, the therapeutic agent may be a hormone or hormonal analogue. In some embodiments, the therapeutic agent may be a signal transduction pathway inhibitor. In some embodiments, the therapeutic agent may be a topoisomerase I inhibitor. In some embodiments, the therapeutic agent may be a topoisomerase II inhibitor. In some embodiments, the therapeutic agent may be an antimetabolite neoplastic agent. In some embodiments, the therapeutic agent may be an antibiotic neoplastic agent. In some embodiments, the therapeutic agent may be an alkylating agent. In some embodiments, the therapeutic agent may be an anti-microtubule agent. In some embodiments, the therapeutic agent may be a platinum coordination complex. In some embodiments, the therapeutic agent may be an aromatase inhibitor. In some embodiments, the therapeutic agent may be an anti-mitotic agent.

In some embodiments, the aromatase inhibitor may be selected from anastrazole, letrozole, vorozole, fadrozole, exemestane, and formestane. In some embodiments, the aromatase inhibitor is anastrazole. In some embodiments, the aromatase inhibitor may be letrozole. In some embodiments, the aromatase inhibitor may be vorozole. In some embodiments, the aromatase inhibitor may be fadrozole. In some embodiments, the aromatase inhibitor may be exemestane. In some embodiments, the aromatase inhibitor may be formestane.

In some embodiments, the anti-mitotic agent may be selected from paclitaxel, docetaxel, and Abraxane. In some embodiments, the anti-mitotic agent may be paclitaxel. In some embodiments, the anti-mitotic agent may be docetaxel. In some embodiments, the anti-mitotic agent may be Abraxane.

In some embodiments, a compound of Formula (I) or (II), or a tautomer, stereoisomer, pharmaceutically acceptable salt or hydrate thereof, may be administered in combination with a hormone or hormonal analog. In some embodiments, a compound of Formula (I) or (II), or a tautomer, stereoisomer, pharmaceutically acceptable salt or hydrate thereof, may be administered in combination with a signal transduction pathway inhibitor. In some embodiments, a compound of Formula (I) or (II), or a tautomer, stereoisomer, pharmaceutically acceptable salt or hydrate thereof, may be administered in combination with an antimetabolite neoplastic agent. In some embodiments, a compound of Formulae (I) or (II), or a tautomer, stereoisomer, pharmaceutically acceptable salt or hydrate thereof, may be administered in combination with a topoisomerase I inhibitor. In some embodiments, a compound of Formula (I) or (II), or a tautomer, stereoisomer, pharmaceutically acceptable salt or hydrate thereof, may be administered in combination with a topoisomerase II inhibitor. In some embodiments, a compound of Formula (I) or (II), or a tautomer, stereoisomer, pharmaceutically acceptable salt or hydrate thereof, may be administered in combination with an aromatase inhibitor. In some embodiments, a compound of Formula (I) or (II), or a tautomer, stereoisomer, pharmaceutically acceptable salt or hydrate thereof, may be administered in combination with one or more anti-cancer agents.

In some embodiments, a compound of Formula (I) or (II), or a tautomer, stereoisomer, pharmaceutically acceptable salt or hydrate thereof, may be administered in combination with an anti-cancer agent, wherein the anti-cancer agent is tamoxifen. In some embodiments, a compound of Formula (I) or (II), or a tautomer, stereoisomer, pharmaceutically acceptable salt or hydrate thereof, may be administered in combination with an anti-cancer agent, wherein the anti-cancer agent is fulvestrant.

EXAMPLES

The examples and preparations provided below further illustrate and exemplify the compounds as disclosed herein and methods of preparing such compounds. It is to be understood that the scope of the present disclosure is not limited in any way by the scope of the following examples and preparations.

The chemical entities described herein can be synthesized according to one or more illustrative schemes herein and/or techniques well known in the art. Unless specified to the contrary, the reactions described herein take place at atmospheric pressure, generally within a temperature range from about −10° C. to about 200° C. Further, except as otherwise specified, reaction times and conditions are intended to be approximate, e.g., taking place at about atmospheric pressure within a temperature range of about −10° C. to about 200° C. over a period that can be, for example, about 1 to about 24 hours; reactions left to run overnight in some embodiments can average a period of about 16 hours.

Isolation and purification of the chemical entities and intermediates described herein can be effected, if desired, by any suitable separation or purification procedure such as, for example, filtration, extraction, crystallization, column chromatography, thin-layer chromatography or thick-layer chromatography, or a combination of these procedures. See, e.g., Carey et al. Advanced Organic Chemistry, $3^{rd}$ Ed., 1990 New York: Plenum Press; Mundy et al., Name Reaction and Reagents in Organic Synthesis, $2^{nd}$ Ed., 2005 Hoboken, N.J.: J. Wiley & Sons. Specific illustrations of suitable separation and isolation procedures are given by reference to the examples hereinbelow. However, other equivalent separation or isolation procedures can also be used.

In all of the methods, it is well understood that protecting groups for sensitive or reactive groups may be employed where necessary, in accordance with general principles of chemistry. Protecting groups are manipulated according to standard methods of organic synthesis (T.W. Greene and P.G.M. Wuts (1999) Protective Groups in Organic Synthesis, $3^{rd}$ Ed., John Wiley & Sons). These groups may be removed at a convenient stage of the compound synthesis using methods that are readily apparent to those skilled in the art.

When desired, the (R)- and (S)-isomers of the nonlimiting exemplary compounds, if present, can be resolved by methods known to those skilled in the art, for example, by formation of diastereoisomeric salts or complexes which can be separated, e.g., by crystallization; via formation of diastereoisomeric derivatives which can be separated, e.g., by crystallization, gas-liquid or liquid chromatography; selective reaction of one enantiomer with an enantiomer-specific reagent, e.g., enzymatic oxidation or reduction, followed by separation of the modified and unmodified enantiomers; or gas-liquid or liquid chromatography in a chiral environment, e.g., on a chiral support, such as silica with a bound chiral ligand or in the presence of a chiral solvent. Alternatively, a specific enantiomer can be synthesized by asymmetric synthesis using optically active reagents, substrates, catalysts or solvents, or by converting one enantiomer to the other by asymmetric transformation.

The compounds described herein can be optionally contacted with a pharmaceutically acceptable acid to form the corresponding acid addition salts. Also, the compounds described herein can be optionally contacted with a pharmaceutically acceptable base to form the corresponding basic addition salts.

In some embodiments, disclosed compounds can generally be synthesized by an appropriate combination of generally well-known synthetic methods. Techniques useful in synthesizing these chemical entities are both readily apparent and accessible to those of skill in the relevant art, based on the instant disclosure. Many of the optionally substituted starting compounds and other reactants are commercially available, e.g., from Millipore Sigma or can be readily prepared by those skilled in the art using commonly employed synthetic methodology.

The discussion below is offered to illustrate certain of the diverse methods available for use in making the disclosed compounds and is not intended to limit the scope of reactions or reaction sequences that can be used in preparing the compounds provided herein. The skilled artisan will understand that standard atom valencies apply to all compounds disclosed herein in genus or named compound for unless otherwise specified.

The following abbreviations have the definitions set forth below:
1. ACN: Acetonitrile
2. BINAP: 2,2'-bis(diphenylphosphino)-1,1'-binaphthyl
3. CbzCl: Benzyloxycarbonyl chloride
4. DEAD: Diethyl azodicarboxylate
5. DCE: 1,2-dichloroethane
6. DCM: dichloromethane
7. DIEA: Diisopropylethylamine
8. DHP: Dihydropyran
9. DMEM: Dulbecco's Modification of Eagle's Medium
10. DMSO: dimethylsulfoxide 11. DMF: N,N-dimethylformamide
12. HATU: 1-[Bis(dimethylamino)methylene]-1H-1,2,3-triazolo[4,5-b]pyridinium 3-oxid hexafluorophosphate
13. EDCl: 1-Ethyl-3-(3-dimethylaminopropyl)carbodiimide
14. ESI-TOF: electrospray ionization time-of-flight mass spectrometry
15. EtOAc: ethyl acetate
16. FBS: fetal bovine serum
17. HOAt: 1-hydroxy-7-azabenzotriazole
18. HPLC: high pressure liquid chromatography
19. HRMS: high resolution mass spectrometry
20. HSQC: Heteronuclear single quantum coherence
21. MeOH: methanol
22. MCF-7: Michigan Cancer Foundation-7 breast cancer cell line
23. NMM: N-methylmorpholine
24. NMP: N-methyl-2-pyrrolidone
25. NMR: nuclear magnetic resonance
26. NOE: Nuclear Overhauser effect
27. O/N: Overnight
28. PE: Petroleum ether
29. PivCl: Pivaloyl chloride
30. RPMI: Roswell Park Memorial Institute medium
31. SDS: sodium dodecyl sulfate
32. SFC: Supercritical fluid chromatography
33. TBST: tris-buffered saline and Tween 20
34. THF: tetrahydrofuran
35. XantPhos: 4,5-Bis(diphenylphosphino)-9,9-dimethylxanthene Chemistry General Procedures.

HPLC spectra for all compounds were acquired using an Agilent 1200 Series system with DAD detector. Chromatography was performed on a 2.1×150 mm Zorbax 300SB-C18 5 μm column with water containing 0.1% formic acid as solvent A and acetonitrile containing 0.1% formic acid as solvent B at a flow rate of 0.4 mL/min. The gradient program was as follows: 1% B (0-1 min), 1-99% B (1-4 min), and 99% B (4-8 min). High-resolution mass spectra (HRMS) data were acquired in positive ion mode using an Agilent G1969A API-TOF with an electrospray ionization (ESI) source. Nuclear Magnetic Resonance (NMR) spectra were acquired on a Bruker DRX-600 spectrometer with 600 MHz for proton ($^1$H NMR) and 150 MHz for carbon ($^{13}$C NMR); chemical shifts are reported in (δ). Preparative HPLC was performed on Agilent Prep 1200 series with UV detector set to 254 nm. Samples were injected onto a Phenomenex Luna 75×30 mm, 5 μm, $C_{18}$ column at room temperature. The flow rate was 40 mL/min. A linear gradient was used with 10% (or 50%) of MeOH (A) in $H_2O$ (with 0.1% TFA) (B) to 100% of MeOH (A). HPLC was used to establish the purity of target compounds. All final compounds were determined to be >95% purity when analyzed according to the HPLC methods described above.

Compounds with structures of Formula (I) claimed in this application can be prepared by connecting two ligands through a linker. In general, the claimed molecules can be approached in a stepwise or modular fashion. The following schemes represent the general methods used in preparing these compounds. However, the synthesis of Formula (I) is not limited to these representative methods, as they can also be prepared by those skilled in the art of synthetic chemistry.

In the case of Formula (I) where X1 is O, and X2 is O, the following scheme provides a general method in synthesizing the claimed compounds.

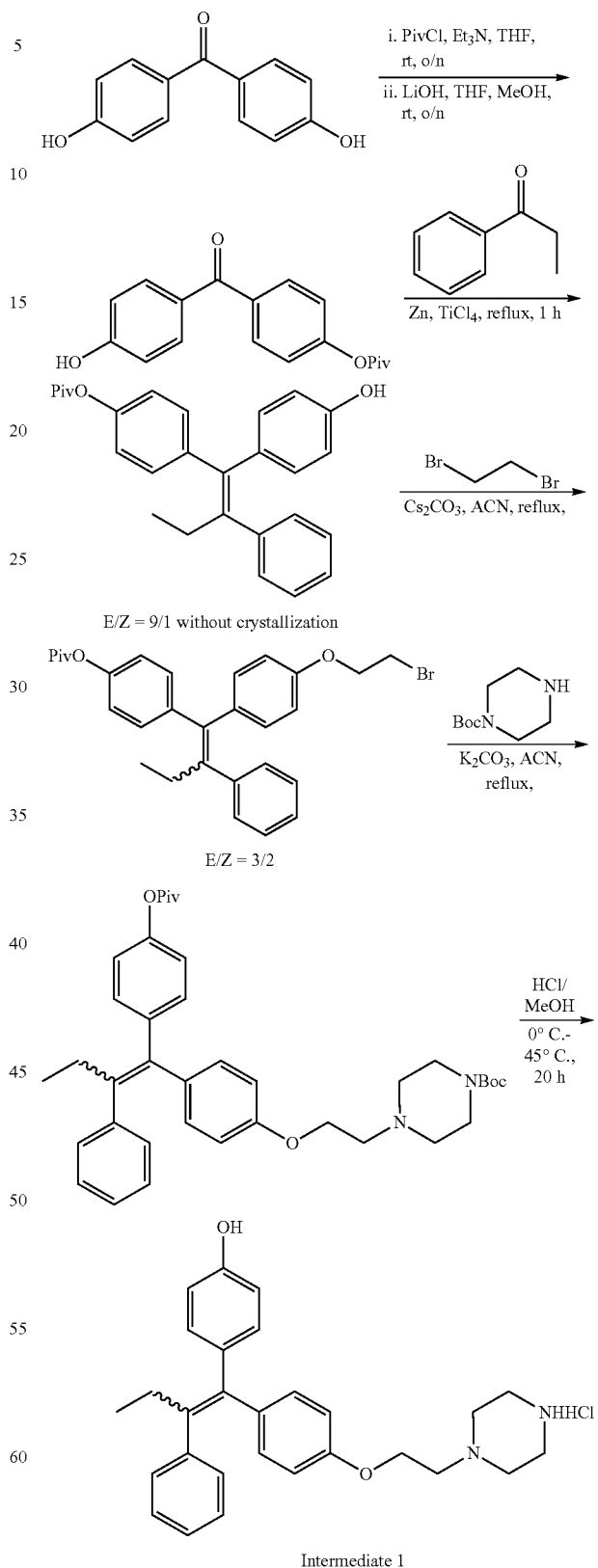

Scheme 1: Synthesis of compound 1.

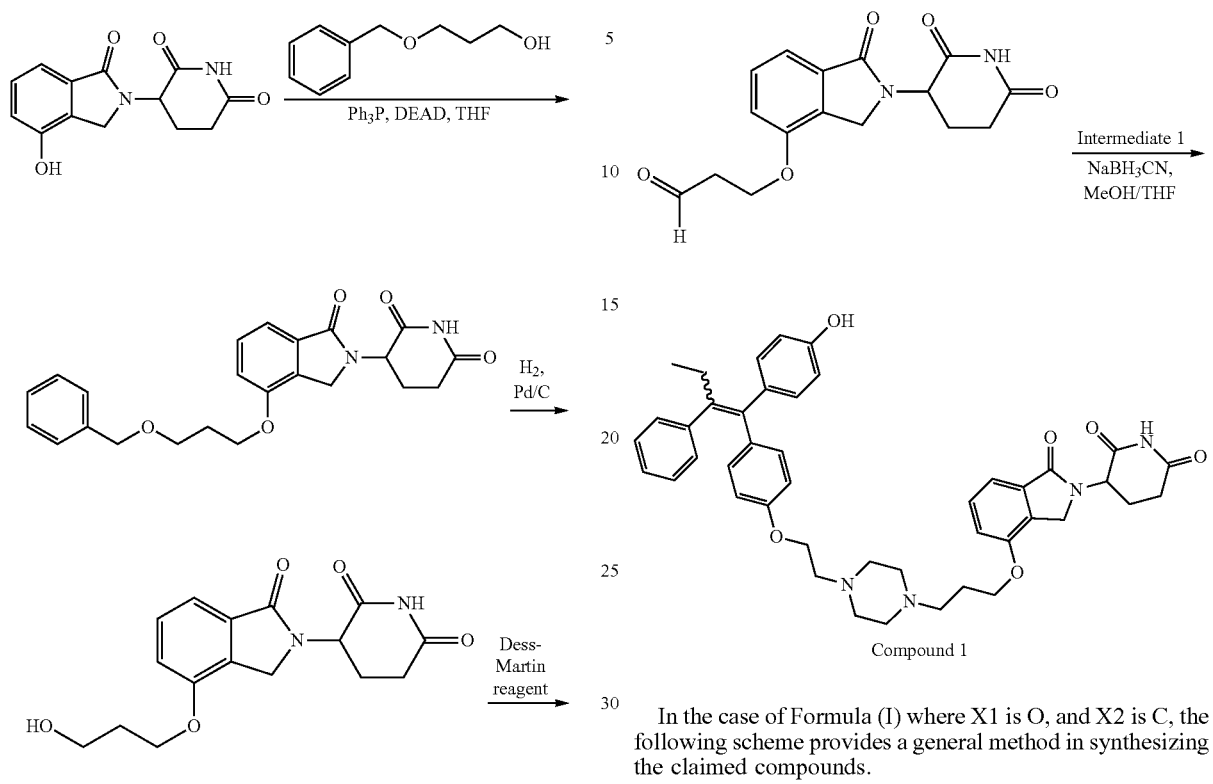
In the case of Formula (I) where X1 is O, and X2 is C, the following scheme provides a general method in synthesizing the claimed compounds.
Scheme 2: Synthesis of compound 10.
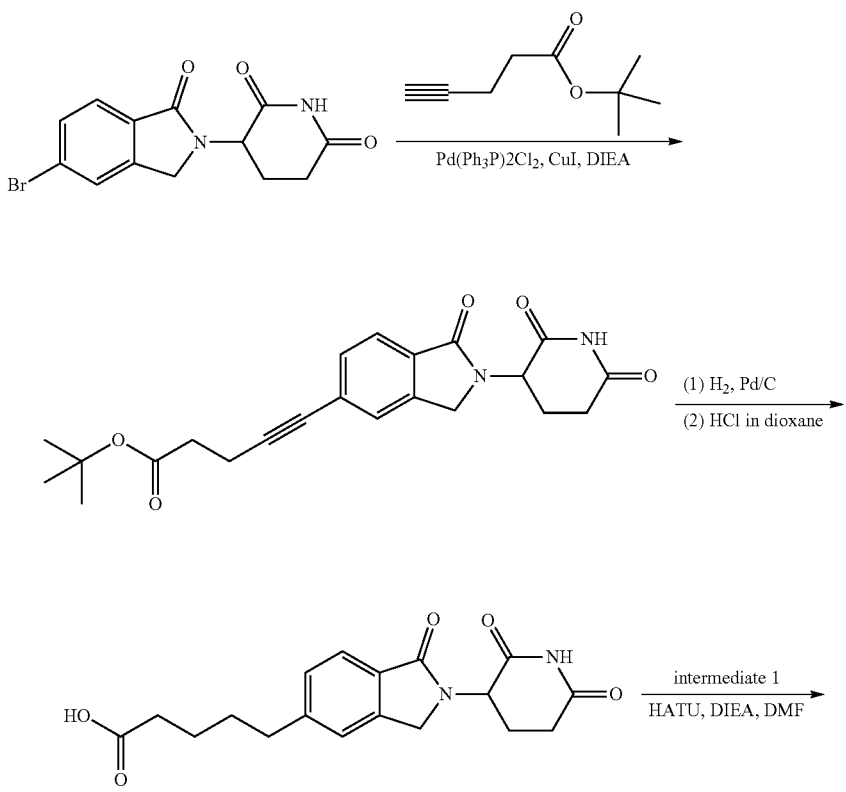

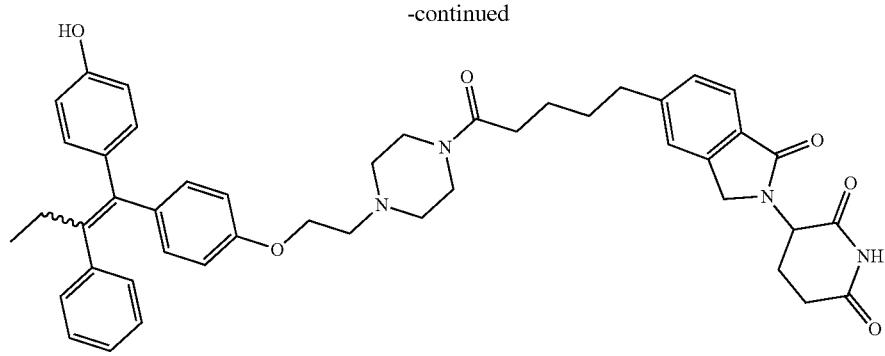
Compound 10
In the case of Formula (I) where X1 is O, and X2 is N, the following schemes provide general methods in synthesizing the claimed compounds.
Scheme 3: Synthesis of compound 8, 15, 54 and 64.
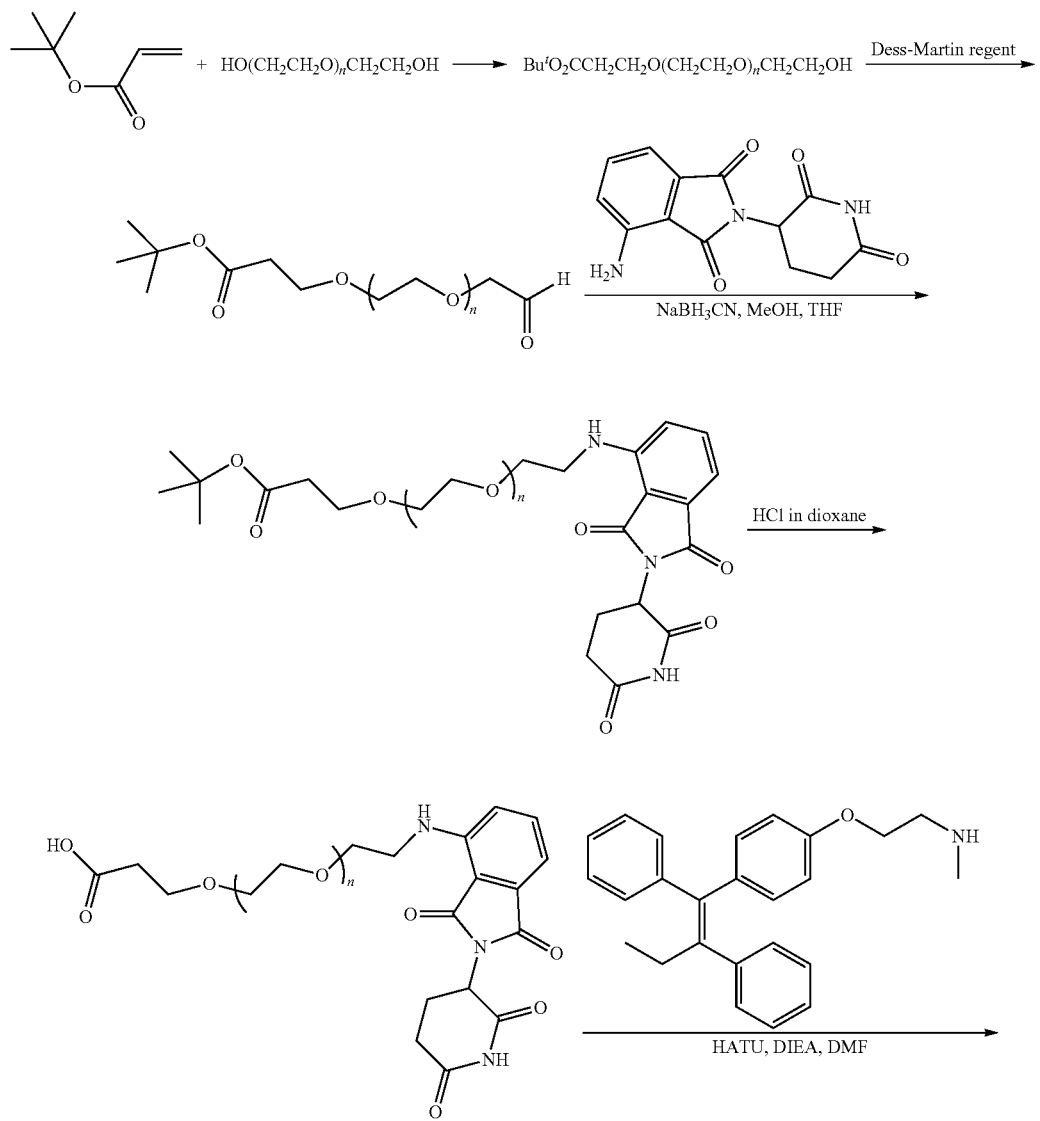

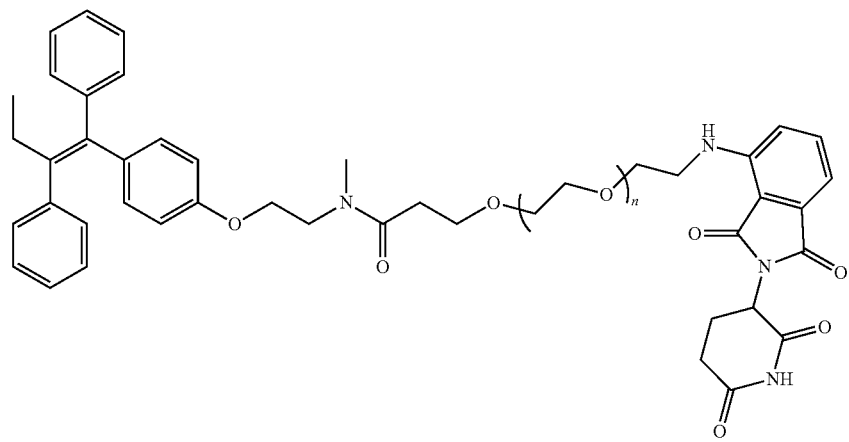
N = 0, Compound 8
N = 1, compound 15
N = 2, compound 34
N = 3, compound 54
N = 4, compound 64
Scheme 4: Synthesis of compound 88, 89, 108, 120, 126 and 143.
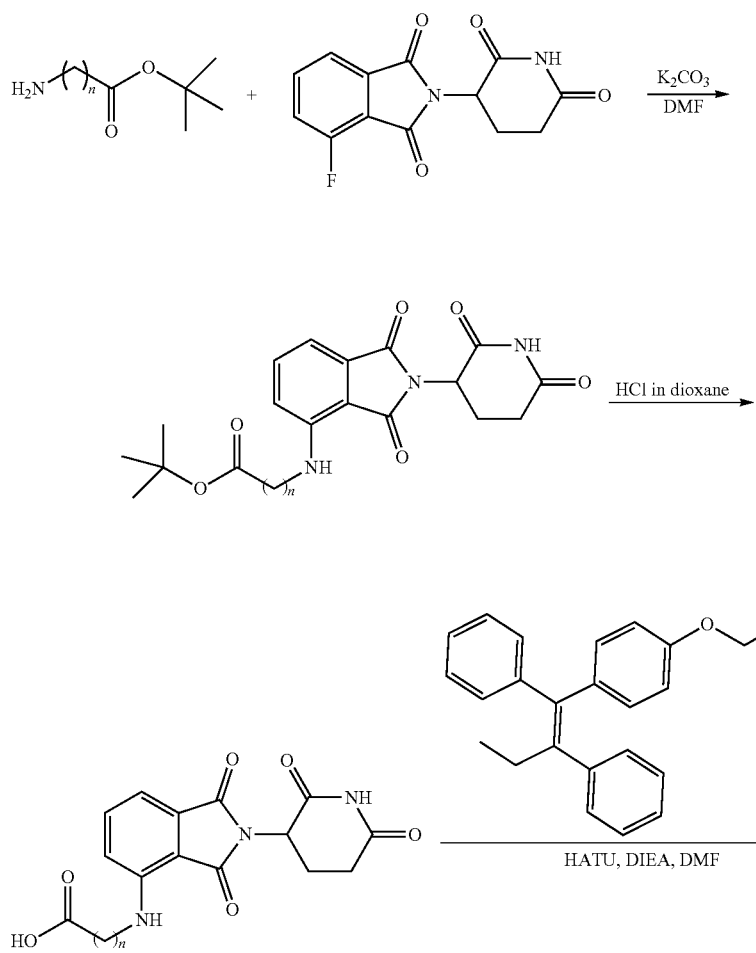

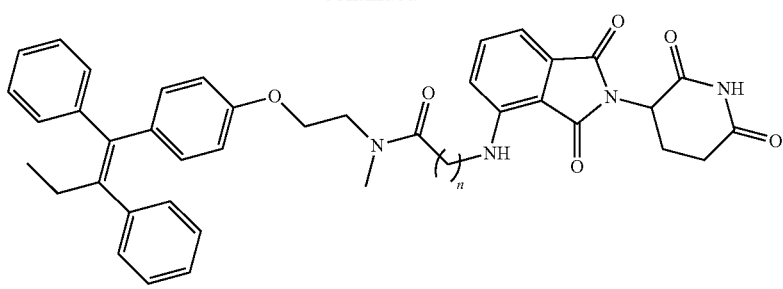
N = 1, Compound 88
N = 2, compound 89
N = 3, compound 108
N = 5, compound 120
N = 6, compound 126
N = 7, compound 143
Scheme 5: Synthesis of compound 16a, 28a and 29a.
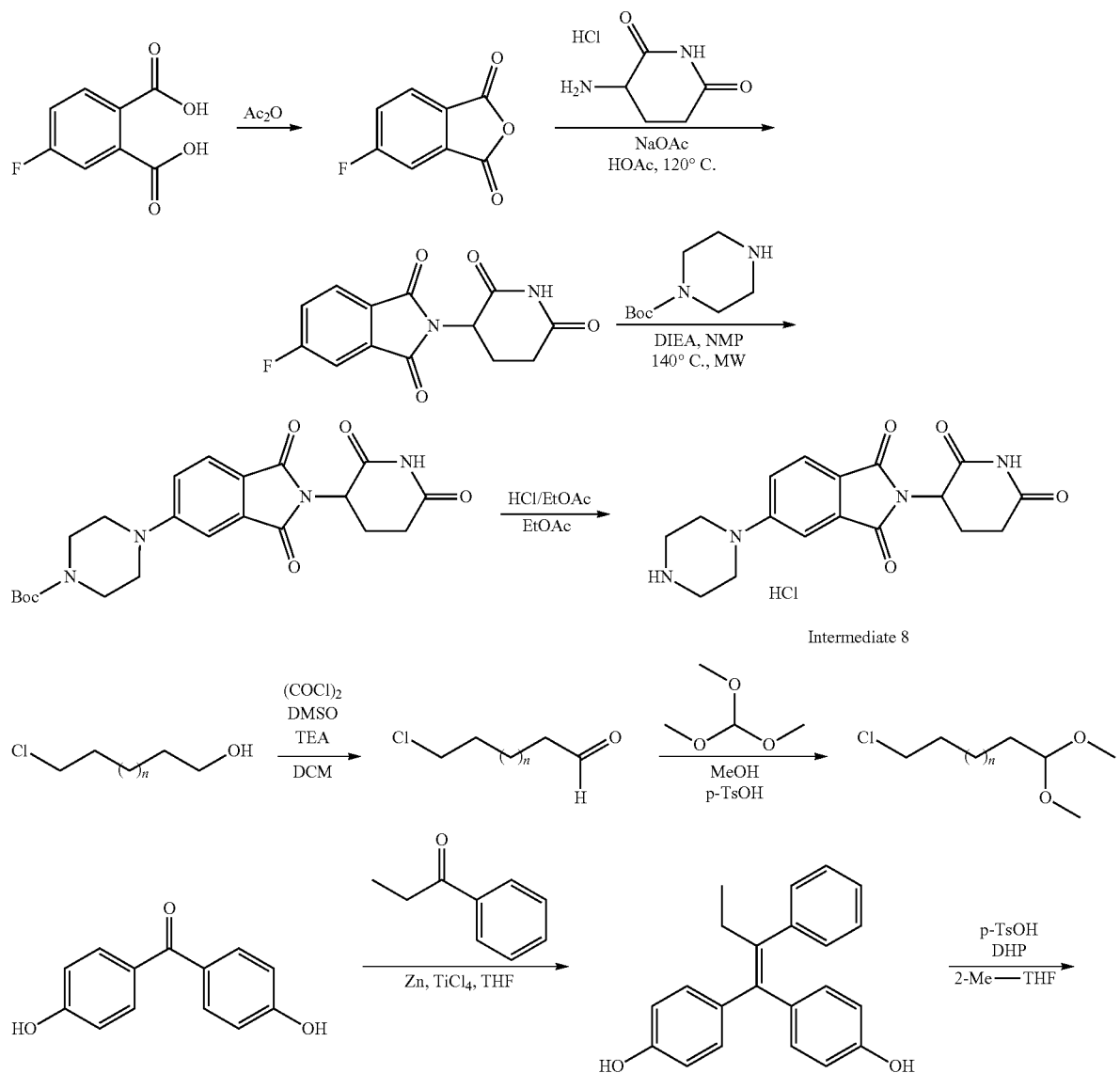

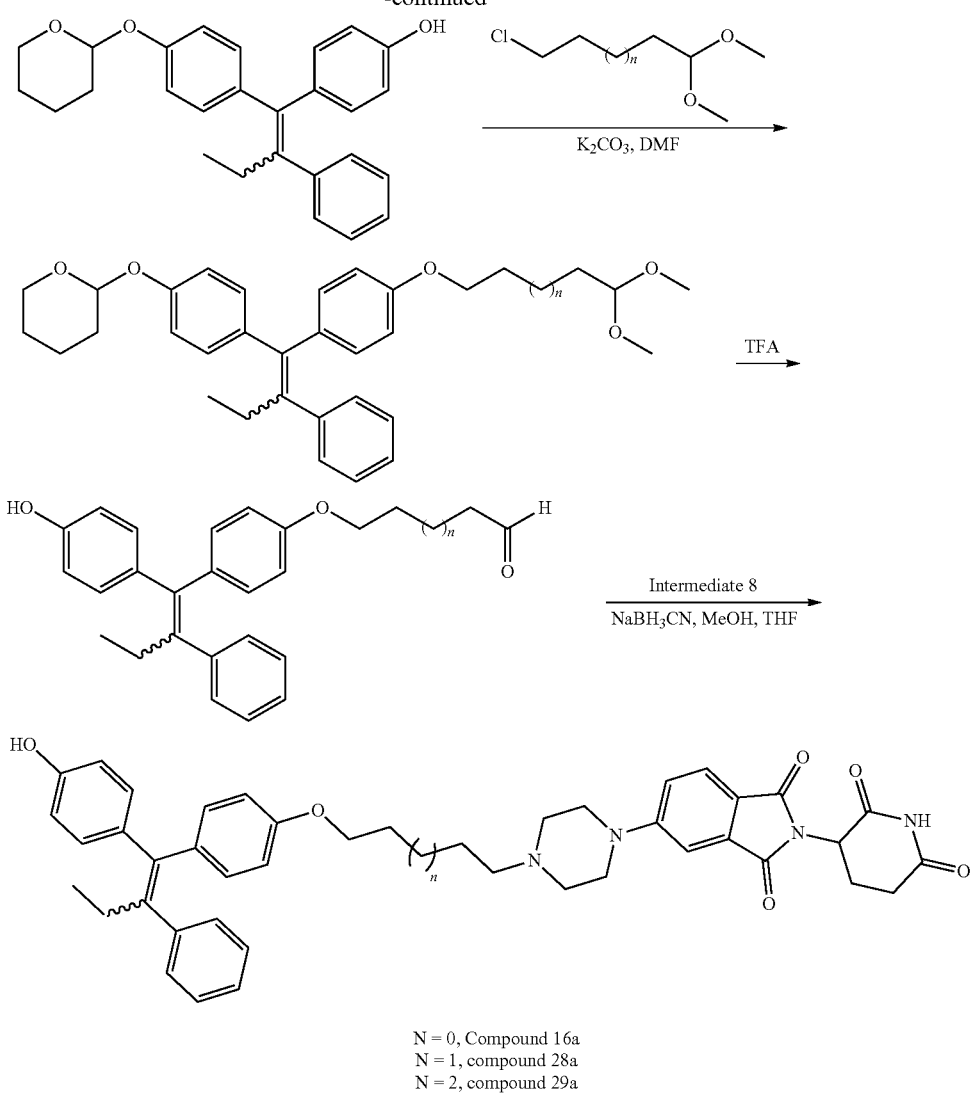
N = 0, Compound 16a
N = 1, compound 28a
N = 2, compound 29a
Scheme 6: Synthesis of compound 17a, 31a and 32a.
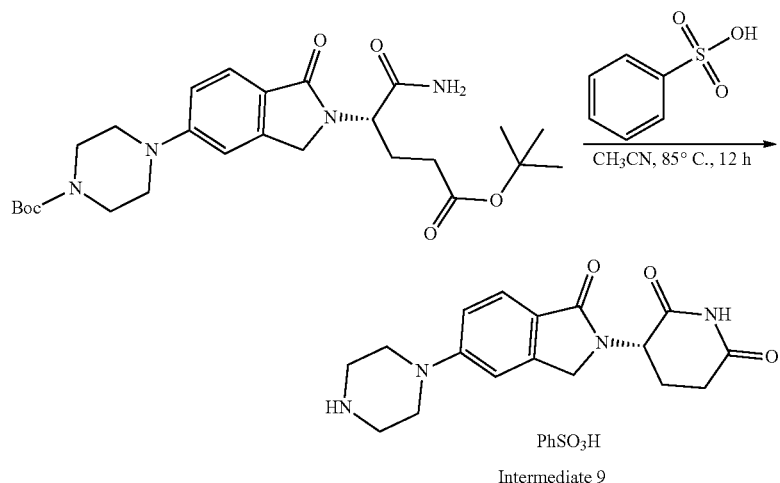
Intermediate 9

-continued
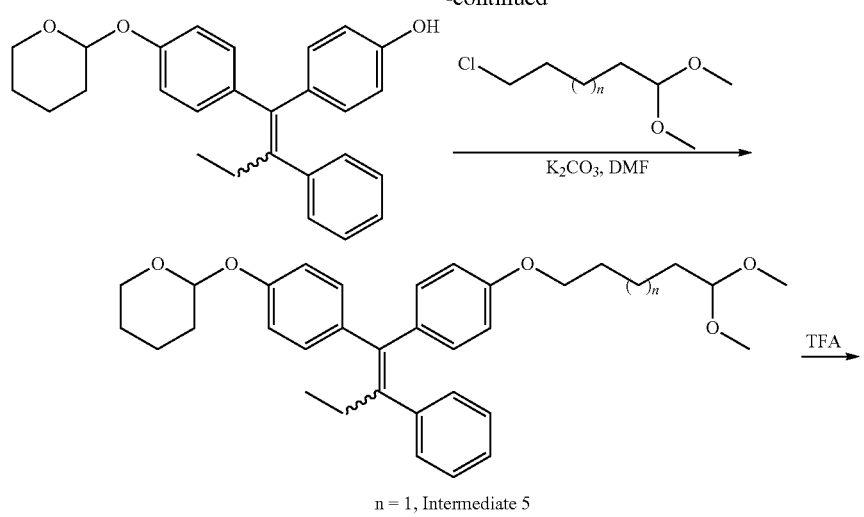
n = 1, Intermediate 5
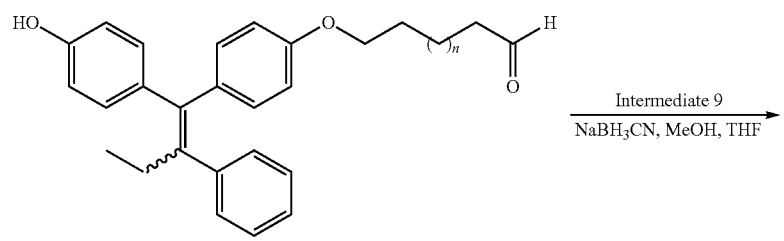
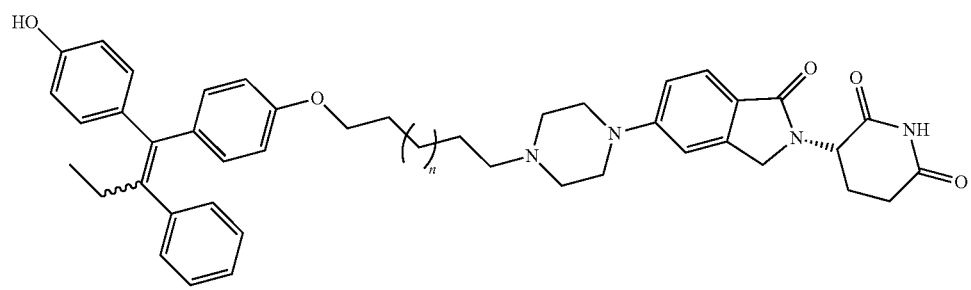
N = 0, Compound 17a
N = 1, compound 31a
N = 2, compound 32a
Scheme 7: Synthesis of compound 111.
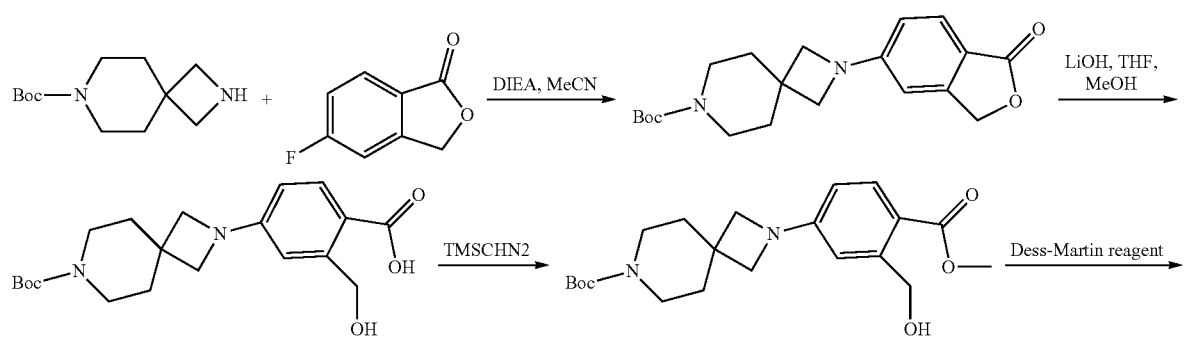

-continued
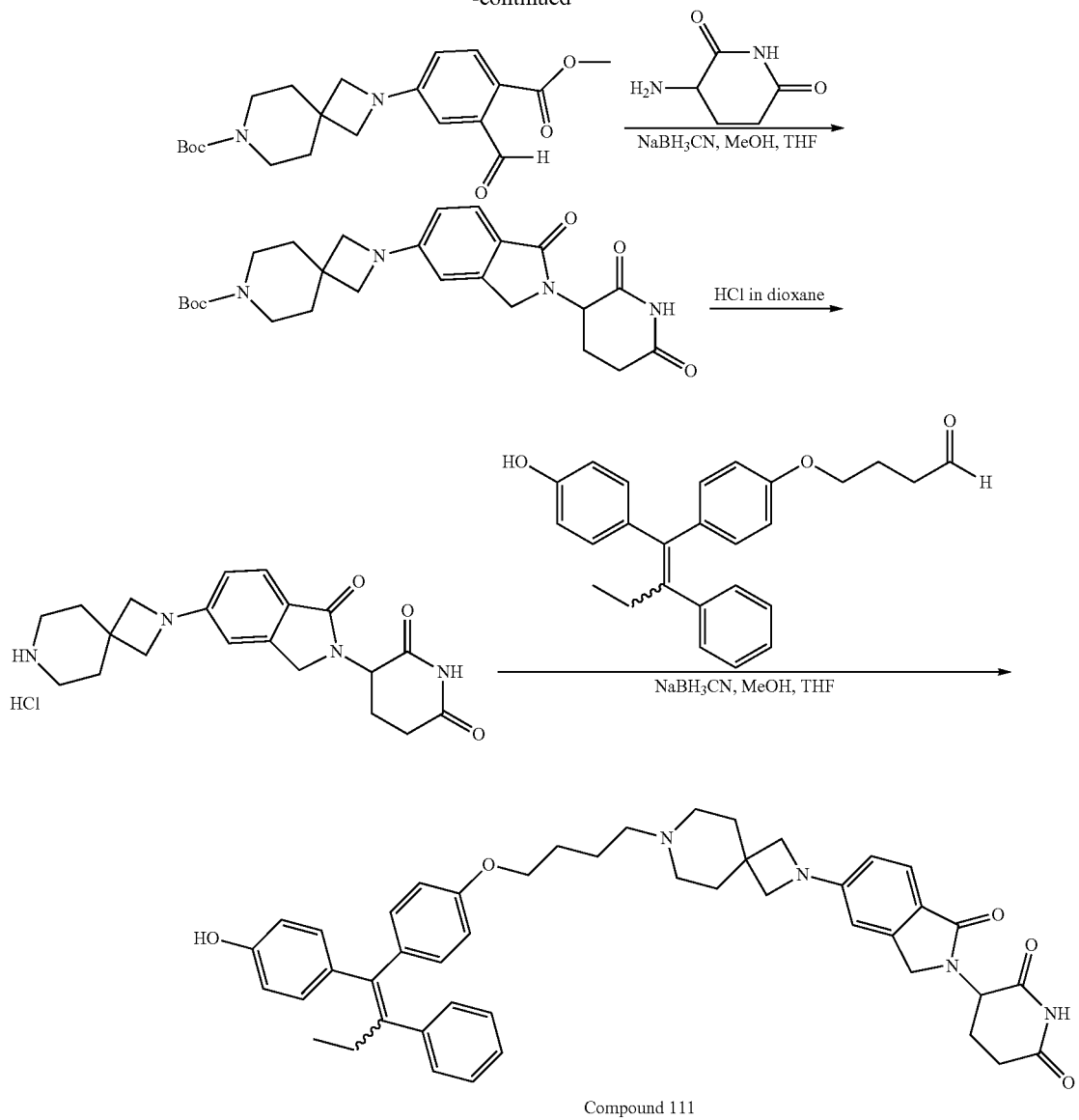
Compound 111
In the case of Formula (I) where X1 is N, and X2 is N, the following schemes provide general methods in synthesizing the claimed compounds.
Scheme 8: Synthesis of compound 160a and 184a.
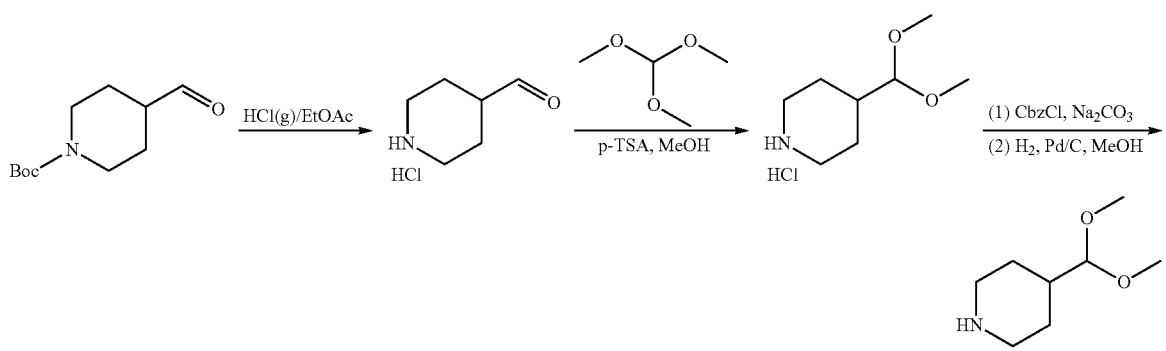

-continued
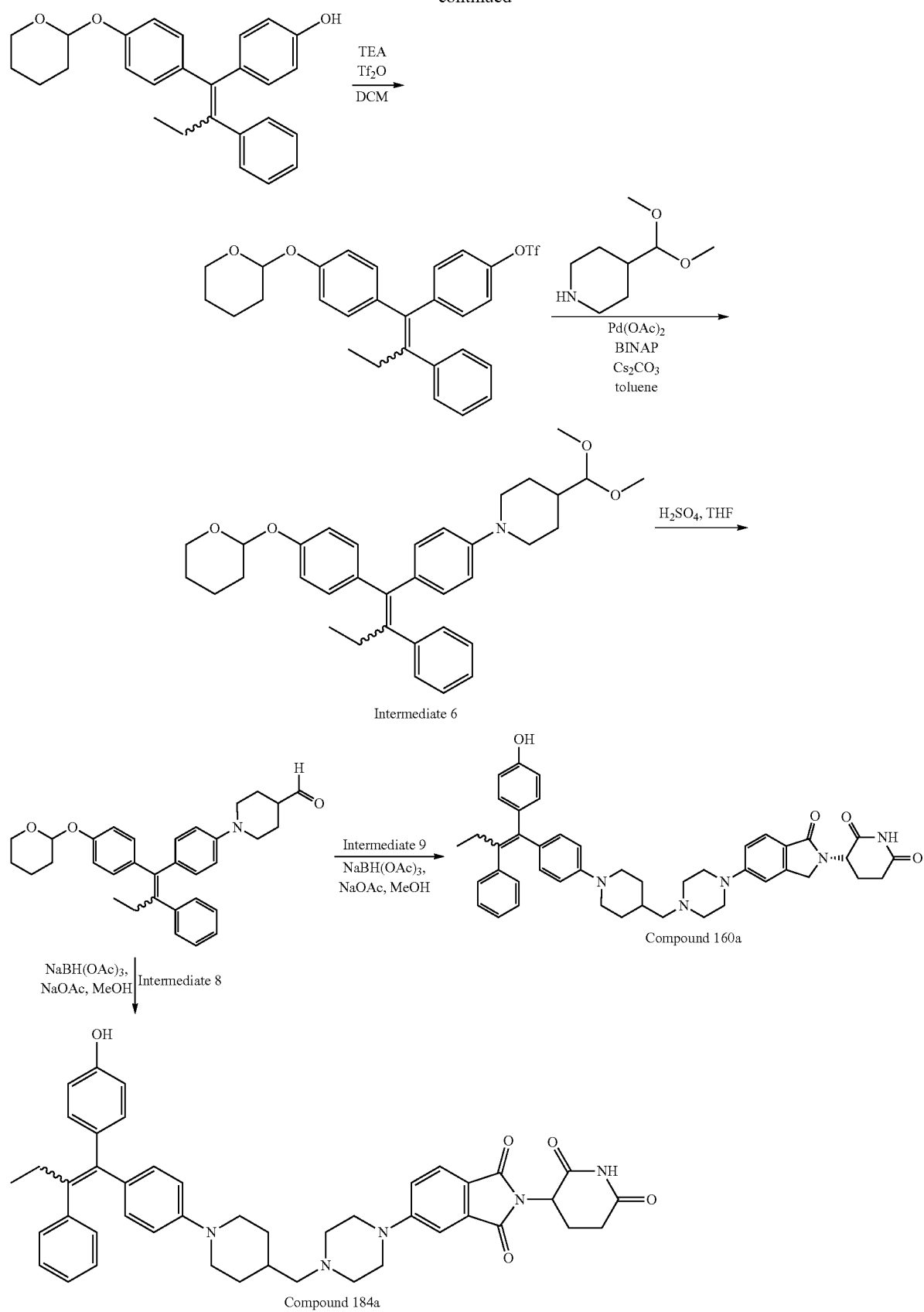
Intermediate 6
Compound 160a
Compound 184a

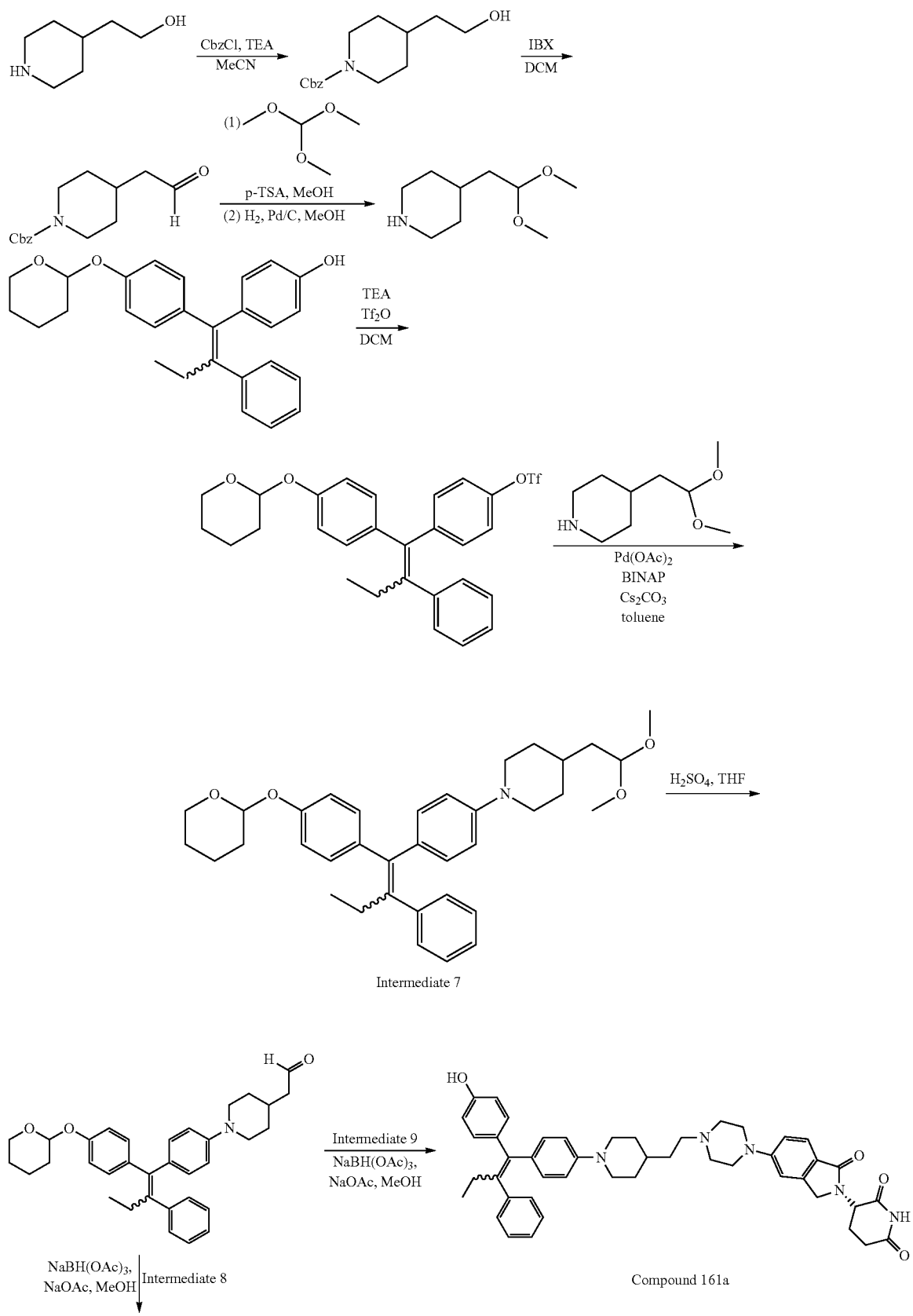

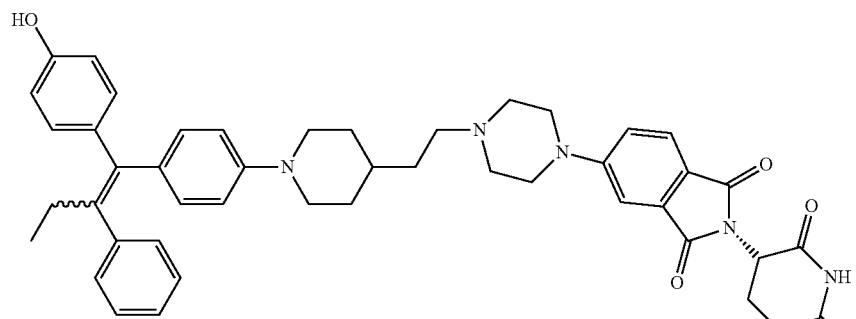
Compound 185a
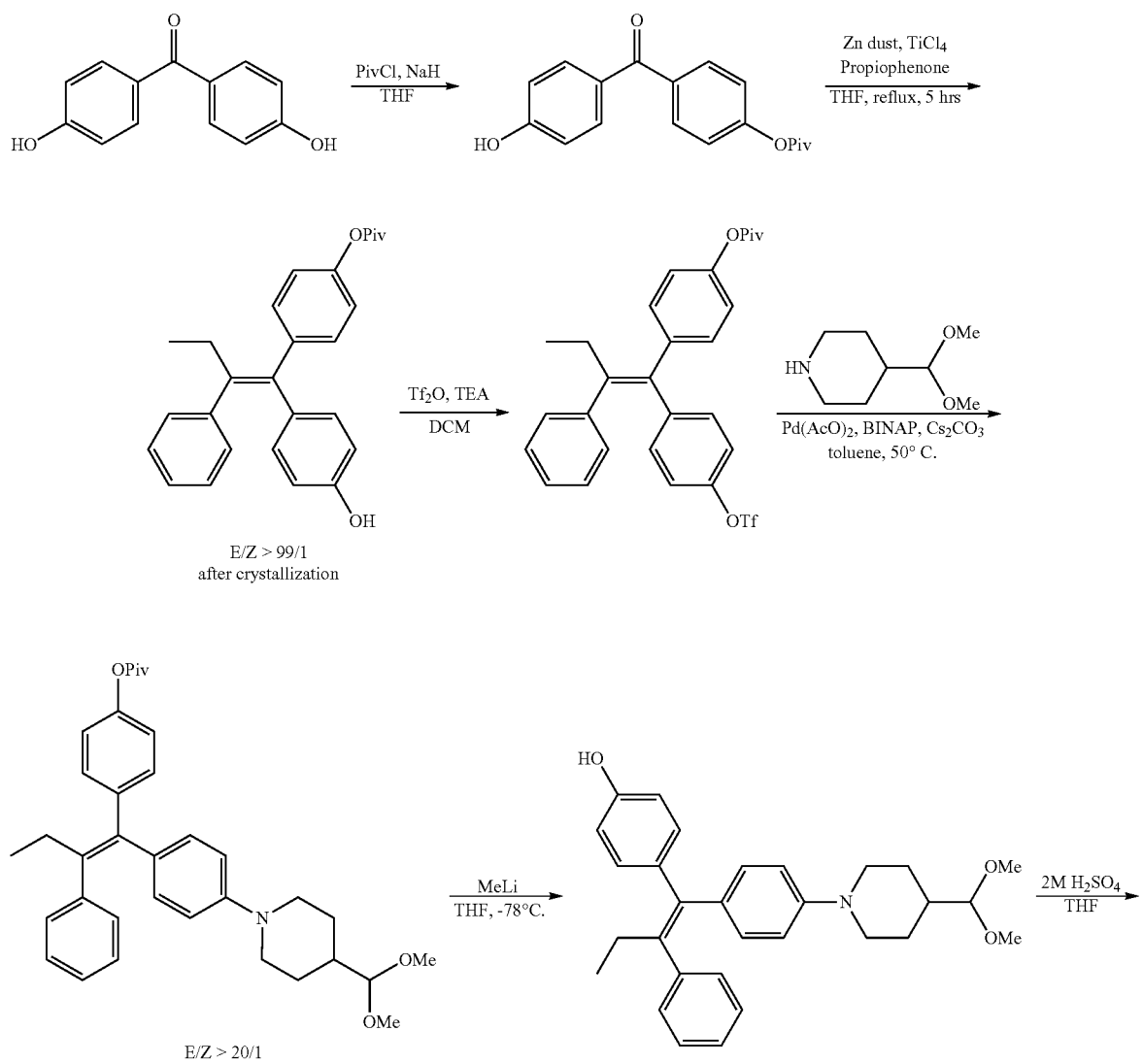
Scheme 10: Synthesis of compound 160b.

-continued
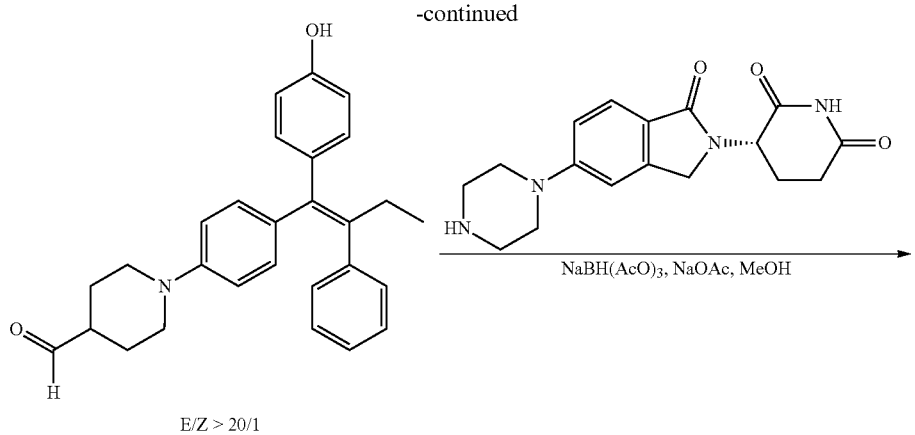
E/Z > 20/1
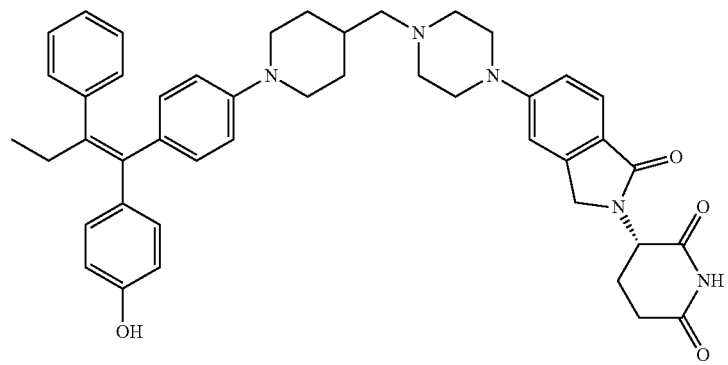
compound 160b
E/Z > 20/1, (E)-olefin confirmed by 2D NMR (HSQC, NOE)
Chiral purity > 95% confirmed by chiral SFC
Preparation of Intermediates
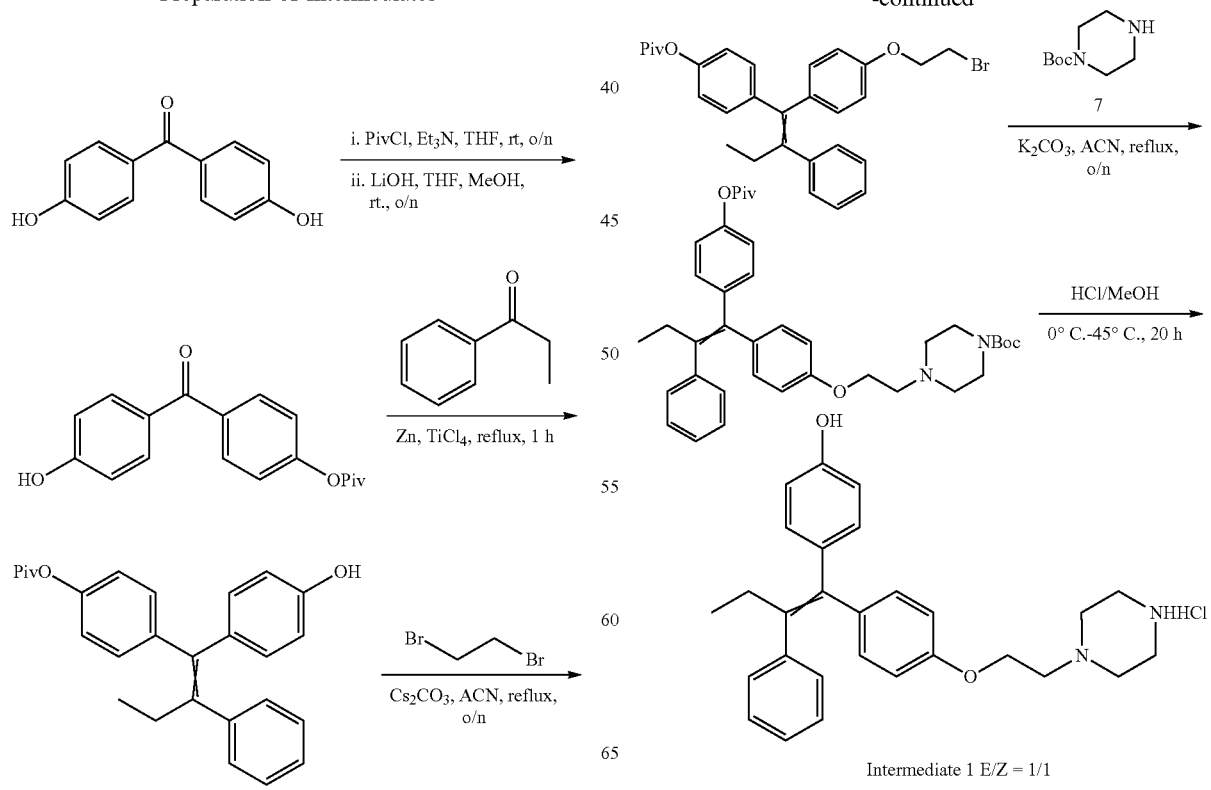
Intermediate 1 E/Z = 1/1

Step 1: Synthesis of 4-(4-hydroxybenzoyl)phenyl Pivalate

To a solution of bis(4-hydroxyphenyl)methanone (200 g, 0.93 mol) in 2 L THF was added Et3N (378.2 g, 3.74 mol), and then PivCl (281.7 g, 2.33 mol) was added dropwise to the mixture at 0° C. The mixture was warmed to rt and stirred overnight. TLC showed the reaction was completed. The reaction mixture was quenched with water and extracted with EtOAC. The organic layer was washed with 1N HCl and brine, dried over $Na_2SO_4$, concentrated under reduced pressure to give crude product (350 g) as a white solid. To the solution of the crude product (350 g) in THF (2 L) was added MeOH (400 mL) and $LiOH·H_2O$ (40.3 g, 0.96 mol) and the mixture was stirred at rt for 1 h. Another LiOH.H2O (9.6 g, 0.23 mol) was added and the mixture was stirred at rt for another 2 h. TLC showed the reaction was completed. The reaction mixture was concentrated under reduce pressure and purified by silica gel chromatography using (DCM:EtOAc=30:1) to give 4-(4-hydroxybenzoyl)phenyl pivalate 2 (130 g, 46%) as a white solid.

Step 2: Synthesis of 4-(1-(4-hydroxyphenyl)-2-phenylbut-1-enyl)phenyl Pivalate To a suspension of Zn (370.4 g, 5.66 mol) in dry THF (1.3 L) under $N_2$ was added $TiCl_4$ (496.0 g, 2.61 mol) at 0° C. The mixture was refluxed for 2 h and cooled to 40° C. A mixture of 4-(4-hydroxybenzoyl)phenyl pivalate (130 g, 0.43 mol) and propiophenone (187.1 g, 1.39 mol) in anhydrous THF (500 ml) was added at once and the mixture was refluxed for 1 h. TLC showed the reaction was completed. Celite was added and the mixture was stirred for 30 minutes before being filtered over Celite. The organic layer was washed with 10% $K_2CO_3$, brine, dried over $Na_2SO_4$ and concentrated under reduced pressure to give the crude product. The residue was dispersed in 200 mL of methanol and filtered to give the pure product. The filtrate was concentrated under reduced pressure and purified by silica gel chromatography using (PE:EtOAc=10:1 to 6:1) to give another batch of pure product. The combined solid was 4-(1-(4-hydroxyphenyl)-2-phenylbut-1-enyl)phenyl pivalate (140 g). LC/MS indicated a ratio of 1 to 9 (with a minor peak 10%).

Step 3: Synthesis of 4-(1-(4-(2-bromoethoxy)phenyl)-2-phenylbut-1-enyl)phenyl pivalate To a solution of 4-(1-(4-hydroxyphenyl)-2-phenylbut-1-enyl)phenyl pivalate (51 g, 0.13 mol) in ACN (500 mL) were added 1,2-dibromoethane (239 g, 1.27 mol) and $Cs_2CO_3$ (166 g, 0.51 mol). The resulting mixture was heated to 85° C. and stirred overnight. TLC showed the reaction was completed. The reaction mixture was filtered, concentrated under reduce pressure and purified by silica gel chromatography using (DCM:EtOAc=30:1) to give 4-(1-(4-(2-bromoethoxy)phenyl)-2-phenylbut-1-enyl)phenyl pivalate (68 g) as a green oil, which was used into next step without further purification.

Step 4: Synthesis of tert-butyl 4-(2-(4-(2-phenyl-1-(4-(pivaloyloxy) phenyl)but-1-enyl)phenoxy)ethyl) piperazine-1-carboxylate To a solution of 4-(1-(4-(2-bromoethoxy)phenyl)-2-phenylbut-1-enyl)phenyl pivalate (84 g, crude) in ACN (500 mL) was added tert-butyl piperazine-1-carboxylate (31 g, 0.16 mol) and $K_2CO_3$ (51 g, 0.36 mol). The resulting mixture was heated to 85° C. and stirred overnight. TLC showed the reaction was completed. The reaction mixture was filtered, concentrated under reduce pressure and purified by silica gel chromatography using (DCM:EtOAc=10:1 to 2:1) to get 4-(2-(4-(2-phenyl-1-(4-(pivaloyloxy)phenyl)but-1-enyl)phenoxy)ethyl)piperazine-1-carboxylate (68 g, 64% for two steps) as a green oil. LCMS indicated a ratio to 2/3, M/Z 613.5 (M+1)+.

Step 5: Synthesis of 4-(2-phenyl-1-(4-(2-(piperazin-1-yl)ethoxy)phenyl)but-1-enyl)phenol Hydrochloride (Intermediate 1)

To a solution of 4-(2-(4-(2-phenyl-1-(4-(pivaloyloxy)phenyl)but-1-enyl)phenoxy)ethyl)piperazine-1-carboxylate (68 g, 0.11 mol) in MeOH (100 mL) was added HCl/MeOH (500 mL, 4 M) at 0° C. The resulting mixture was stirred at 45° C. overnight. LCMS showed the reaction was completed. The reaction mixture was concentrated under reduce pressure and washed with MTBE and PE to give 4-(2-phenyl-1-(4-(2-(piperazin-1-yl)ethoxy)phenyl)but-1-enyl)phenol hydrochloride (51 g, 100%) as a white solid. HPLC purity: 98%, 1H-NMR indicated a mixture of cis- and trans-olefin with a ratio of 1:1, LCMS: 429.3 (M+1)+. 1H NMR (400 MHz, Methanol-d4) δ 7.21-6.97 (m, 8H), 6.84 (d, 1H), 6.75 (d, 1H), 6.68 (d, 1H), 6.66 (d, 1H), 6.43 (d, 1H), 4.49 (t, 1H), 4.30 (t, 1H), 4.04-3.43 (m, 10H), 2.46 (m, 2H), 0.90 (t, 3H).

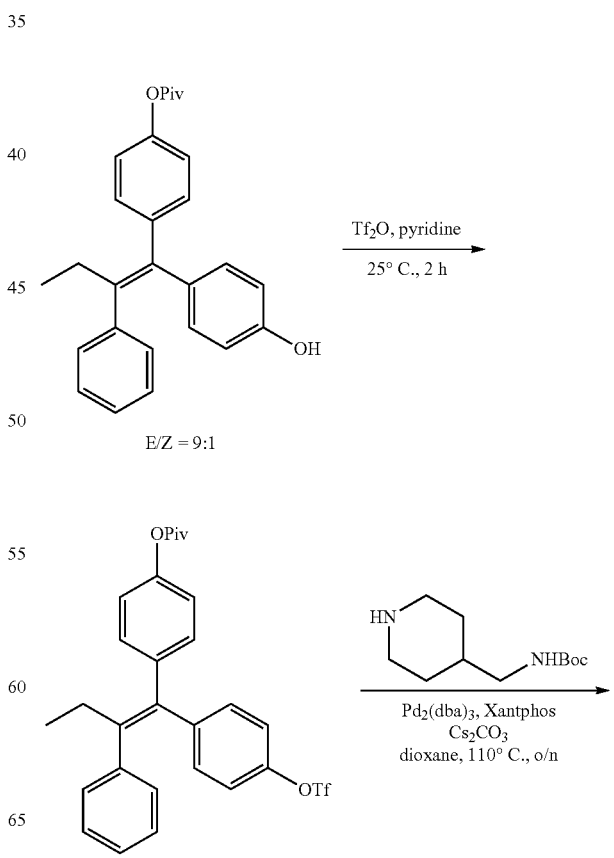

357

-continued

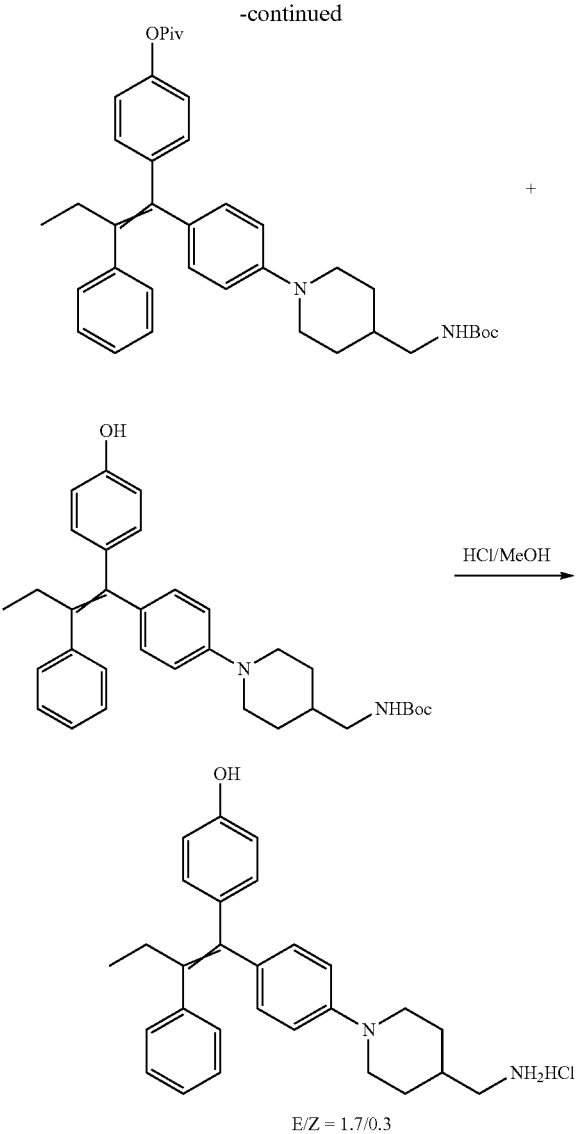

E/Z = 1.7/0.3

Step 1: Synthesis of 4-(2-phenyl-1-(4-(((trifluoromethyl)sulfonyl)oxy)phenyl)but-1-en-1-yl)phenyl Pivalate To the solution of 4-(1-(4-hydroxyphenyl)-2-phenylbut-1-en-1-yl)phenyl pivalate 1 (50.0 g, 124.8 mmol) in dry DCM (200 mL) was added pyridine (21.7 g, 274.6 mmol) and Tf₂O (105.7 g, 374.5 mmol) at 0° C., then the mixture was warmed to 250° C. and stirred for 2 h. The mixture was concentrated under reduce pressure to get the crude material, which was purified by column chromatography on silica gel (PE:EA=20:1) to give 4-(2-phenyl-1-(4-(((trifluoromethyl)sulfonyl)oxy)phenyl)but-1-en-1-yl)phenyl pivalate (51.5 g, 77%) as a white solid.

Step 2: Synthesis of tert-butyl ((1-(4-(1-(4-hydroxyphenyl)-2-phenylbut-1-en-1-yl)phenyl)piperidin-4-yl)methyl)carbamate To the solution of 4-(2-phenyl-1-(4-(((trifluoromethyl)sulfonyl)oxy)phenyl)but-1-en-1-yl)phenyl pivalate (55.0 g, 103.3 mmol) in dioxane (500 mL) was added tert-butyl (piperidin-4-ylmethyl)carbamate (26.6 g, 123.9 mmol), Pd₂(dba)₂ (9.4 g, 10.3 mmol), Cs₂CO₃ (100.9 g, 309.8 g) and Xphos (4.9 g, 10.3 mmol). The mixture was stirred at 110° C. under N₂ atmosphere overnight. The mixture was cooled to rt, added water (500 mL), extracted with EA (200 mL×3). The combined organic layer was washed with brine and concentrated under reduce pressure to get the crude material, which was purified by column chromatography on silica gel (PE:EA=5:1 to 4:1 and to 3:1) to give tert-butyl ((1-(4-(1-(4-hydroxyphenyl)-2-phenylbut-1-en-1-yl)phenyl)piperidin-4-yl)methyl)carbamate (19.0 g, 34%) and 4-(1-(4-(4-(((tert-butoxycarbonyl)amino)methyl) piperidin-1-yl)phenyl)-2-phenylbut-1-en-1-yl)phenyl pivalate (700.0 mg, 1%). LCMS (ESI): m/z 513.4 (M+H)⁺, and 597.5 (M+H)⁺.

Step 3: Synthesis of 4-(1-(4-(4-(aminomethyl)piperidin-1-yl)phenyl)-2-phenylbut-1-en-1-yl)phenol Hydrochloride (Intermediate 2)

To the solution of HCl/MeOH (120 mL) was added tert-butyl ((1-(4-(1-(4-hydroxyphenyl)-2-phenylbut-1-en-1-yl)phenyl)piperidin-4-yl)methyl)carbamate (35.0 g, 68.3 mmol). The mixture was stirred at 25° C. for 2 h and concentrated under reduce pressure to give 4-(1-(4-(4-(aminomethyl)piperidin-1-yl)phenyl)-2-phenylbut-1-en-1-yl)phenol hydrochloride (29.0 g, 95%) as a brown solid.

To another solution of HCl/MeOH (20 mL) was added 4-(1-(4-(4-(((tert-butoxycarbonyl) amino)methyl)piperidin-1-yl)phenyl)-2-phenylbut-1-en-1-yl)phenyl pivalate (2.0 g, 3.4 mmol), the mixture was stirred at 45° C. overnight and concentrated under reduce pressure to give 4-(1-(4-(4-(aminomethyl)piperidin-1-yl)phenyl)-2-phenylbut-1-en-1-yl)phenol hydrochloride (1.4 g, 95%) as a brown solid. Both of the hydrochloride salts showed the same based on analysis. 1H-NMR indicated a mixture of trans- and cis-olefin with a ratio of 1.7/0.3. LCMS (ESI): m/z 413.3 (M+H)⁺, HPLC: 98% purity; 1H NMR (400 MHz, DMSO-d6) δ 8.30 (br, 3H, NH2 salt), 7.94 (d, 0.3H), 7.58 (d, 1.7H), 7.36 (d, 0.3H), 7.21 (m, 2H), 7.17 (m, 3H), 6.98 (m, 3.3H), 6.80 (d, 1.7H), 6.53 (d, 0.3H), 6.46 (d, 0.3H), 3.60 (m, 0.6H), 3.43 (m, 3.4H), 2.75 (m, 2H), 2.48 (q, 1.7H), 2.43 (q, 0.3H), 2.10-1.80 (m, 5H), 0.84 (t, 3H).

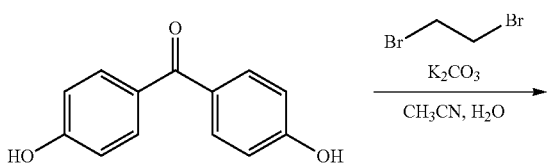

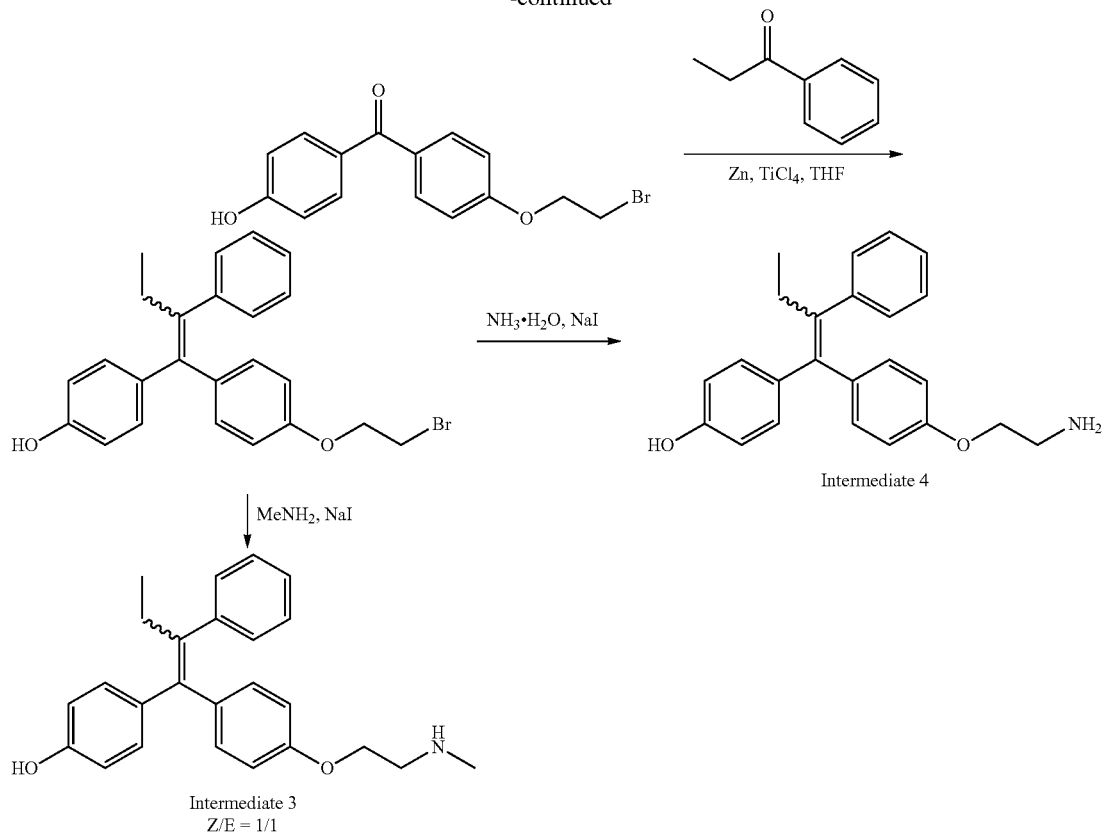

Intermediate 3
Z/E = 1/1

Intermediate 4

Step 1: Synthesis of (4-(2-bromoethoxy)phenyl)(4-hydroxyphenyl)methanone

To a solution of bis(4-hydroxyphenyl)methanone (1.00 kg, 4.67 mol, 1.00 eq) and 1,2-dibromoethane (4.38 kg, 23.3 mol, 1.76 L, 5.00 eq) in CH$_3$CN (5.00 L) and H$_2$O (1.00 L) was added K$_2$CO$_3$ (1.29 kg, 9.34 mol, 2.00 eq) at 20° C. Then the mixture was at 80° C. for 16 hrs. TLC (Petroleum ether/EtOAc=3:1, Rf (starting material)=0.1, Rf (product)=0.3) showed 30% starting material was remained. Total 10 batches were repeated. The reaction was adjusted to pH=3 with con. HCl and filtered. The filter cake was washed with EtOAc (2.00 L). The organic phase was dried over Na$_2$SO$_4$ and concentrated under reduced pressure. The residue was purified by column chromatography (SiO$_2$, Petroleum ether/Ethyl acetate=50/1 to 8:1) to afford 4-(2-bromoethoxy)phenyl)(4-hydroxyphenyl)methanone (3.50 kg, 10.9 mol, 23.3% yield) as a yellow solid. 1H NMR: (CDCl3, 400 MHz) δ: 7.67-7.73 (m, 4H), 6.90 (d, 2H), 6.83 (d, 2H), 4.30 (t, 2H), 3.60 (t, 2H).

Step 2: Synthesis of 4-(1-(4-(2-bromoethoxy)phenyl)-2-phenylbut-1-en-1-yl)phenol To a suspension of Zn (1.02 kg, 15.5 mol, 10.0 eq) in THF (25.0 L) was added TiCl$_4$ (1.48 kg, 7.78 mol, 5.00 eq) dropwise at 0° C. The mixture was stirred at 80° C. for 3 hrs. Then the mixture was cooled to 0° C. and (4-(2-bromoethoxy)phenyl)(4-hydroxyphenyl)methanone (500.0 g, 1.56 mol, 1.00 eq) and propiophenone (626.6 g, 4.67 mol, 620.4 mL, 3.00 eq) was added at 0° C. The mixture was stirred at 80° C. for 16 hrs. TLC (Petroleum ether/EtOAc=3:1, Rf (starting material)=0.1, Rf (product)=0.4) showed that the reaction was complete. The six batches were repeated and combined for workup and purification. The crude product was purified by column chromatography (SiO$_2$, Petroleum ether/Ethyl acetate=20:1 to 3:1) to afford 4-(1-(4-(2-bromoethoxy)phenyl)-2-phenylbut-1-en-1-yl)phenol (400.0 g, 944.8 mmol, 10.1% yield) as a yellow solid. 1H NMR (CDCl3, 400 MHz) δ: 7.07-7.22 (m, 7H), 6.83 (d, 1H), 6.75 (m, 2H), 6.69 (d, 1H), 6.49 d, 1H), 6.41 (d, 1H), 4.69 (s, 0.5H), 4.45 (s, 0.5H), 4.25 (t, 1H), 4.09 (t, 1H), 3.60 (t, 1H), 3.48 (t, 1H), 2.41 (m, 2H), 0.85 (t, 3H).

Step 3: Synthesis of 4-(1-(4-(2-(methylamino)ethoxy)phenyl)-2-phenylbut-1-en-1-yl)phenol (Intermediate 3) and 4-(1-(4-(2-aminoethoxy)phenyl)-2-phenylbut-1-en-1-yl)phenol (Intermediate 4)

To a solution of MeNH$_2$ (1.37 kg, 13.2 mol, 33% purity, 28.0 eq) in THF (2.00 L) was added NaI (297.4 g, 1.98 mol, 4.20 eq) and 4-(1-(4-(2-bromoethoxy)phenyl)-2-phenylbut-1-en-1-yl)phenol (200.0 g, 472.4 mmol, 1.00 eq). Then the mixture was heated to 70° C. in an autoclave for 16 hrs. TLC (Petroleum ether/EtOAc=3:1, Rf (starting material)=0.4, Rf (product)=0) showed that the reaction was complete. Then the mixture was concentrated in vacuum. The residue was purified by column chromatography (SiO$_2$, DCM: MeOH=100/1 to 10/1) to afford 4-(1-(4-(2-(methylamino)ethoxy)phenyl)-2-phenylbut-1-en-1-yl)phenol (Intermediate 3) (100.0 g, 263.4 mmol, 55.7% yield, 98.4% purity) as a purple gum. LCMS [M+H]$^+$ 374.2; 1 H NMR (CD3OD, 400 MHz) δ: 6.96-7.10 (m, 6H), 6.91 (m, 2H), 6.68 (m, 2H), 6.55

(m, 2H), 6.31 (d, 1H), 4.17 (t, 1H), 4.00 (t, 1H), 3.25 (t, 1H), 3.15 (t, 1H), 2.62 (s, 1.5H), 2.56 (s, 1.5H), 2.38 (m, 2H), 0.81 (t, 3H).

To a solution of NH$_3$.H$_2$O (1.82 kg, 12.9 mol, 2.00 mL, 25.0% purity, 27.4 eq) in THF (2.00 L) was added NaI (297.4 g, 1.98 mol, 4.20 eq) and 4-(1-(4-(2-bromoethoxy)phenyl)-2-phenylbut-1-en-1-yl)phenol (200.0 g, 472.4 mmol, 1.00 eq). Then the mixture was heated to 70° C. in an autoclave for 16 hrs. TLC (Petroleum ether/EtOAc=3/1, Rf (starting material)=0.4, Rf (product)=0) showed that the reaction was complete. Then the mixture was concentrated in vacuum to afford crude product. The residue was purified by column chromatography (SiO$_2$, DCM:MeOH=100/1 to 10/1) to afford 4-(1-(4-(2-aminoethoxy)phenyl)-2-phenylbut-1-en-1-yl)phenol (Intermediate 4)

(100.0 g, 277.0 mmol, 58.6% yield, 99.6% purity) as off-white solid. LCMS [M+H]$^+$ 360.2; 1H NMR (CD3OD 400 MHz) δ: 7.14-7.22 (m, 6.6H), 7.16 (d, 0.6H), 6.96 (d, 1.4H), 6.80 (d, 1H), 6.68 (d, 1.4H). 6.60 (d, 0.6H), 6.41 (d, 1.4H), 4.06 (t, 1.4H), 3.90 (t, 0.6H), 3.06 (t, 1.4H), 2.95 (t, 0.6H), 2.49 (m, 2H), 0.92 (t, 3H).

Step 1: Synthesis of 4,4'-(2-phenylbut-1-ene-1,1-diyl)diphenol

To a suspension of Zn (183.1 g, 2.80 mol, 4.00 eq) in dry THF (3.75 L) at 0° C. was added dropwise TiCl4 (265.6 g, 1.40 mol, 2.00 eq) under argon. The mixture was warmed to 20° C. and was heated to reflux for 3 h. A solution of bis(4-hydroxyphenyl)methanone (150.0 g, 700.2 mmol, 1.00 eq) and propiophenone (103.3 g, 770.2 mmol, 102.3 mL, 1.10 eq) in THF was added at 0° C., and the mixture was heated at 80° C. for 16 h. TLC (Petroleum ether:Ethyl acetate=3:1, Rf (starting material)=0.10, Rf (product)=0.20) indicated all of the starting material was consumed completely. This reaction was repeated and the two batches were combined for workup and purification. The mixture was poured into H$_2$O (15.0 L), extracted with EtOAc (5.00 L×3), the combined organic phase was dried over Na$_2$SO$_4$, filtered and concentrated in vacuum. The residue was purified by column chromatography (SiO$_2$, Petroleum ether:Ethyl acetate=5:1 to 1:1). 4,4'-(2-Phenylbut-1-ene-1,1-diyl)diphenol (145.0 g, 458.2 mmol, 32.7% yield) was obtained as a white solid. 1H NMR (CDCl3 400 MHz) δ: 7.09-7.20 (m, 7H), 6.82 (d, J=8.60 Hz, 2H), 6.74 (d, J=8.60 Hz, 2H), 6.48 (d, J=8.80 Hz, 2H), 4.70 (s, 1H), 4.47 (s, 1H), 2.49 (q, J=7.36 Hz, 2H), 0.93 (t, J=7.52 Hz, 3H).

Step 2: Synthesis of 4-(2-phenyl-1-(4-((tetrahydro-2H-pyran-2-yl)oxy)phenyl)but-1-en-1-yl)phenol To a solution of 4,4'-(2-phenylbut-1-ene-1,1-diyl)diphenol (95.0 g, 300.2 mmol, 1.00 eq) and p-TsOH (5.16 g, 30.0 mmol, 0.100 eq) in 2-Me-THF (1.00 L) was added DHP (50.4 g, 600.4 mmol, 54.9 mL, 2.00 eq) at 10° C. Then the mixture was stirred at 20° C. for 16 h. TLC (Petroleum ether:Ethyl acetate=3:1, Rf (starting material)=0.20, Rf (product)=0.56) indicated 70.0% of the starting material was consumed, and two new spots with lower polarity was detected. The mixture was extracted with ethyl acetate (500.0 mL×2), the combined organic layer was washed with brine (100.0 mL), dried over Na$_2$SO$_4$, filtered and the filtrate was concentrated in vacuum. The residue was purified by ISCO flash silica gel chromatography (018.0% ethyl acetate: petroleum ether gradient, @ 200.0 mL/min) to provide 4-(2-phenyl-1-(4-((tetrahydro-2H-pyran-2-yl)oxy)phenyl) but-1-en-1-yl)phenol (53.2 g, 128.1 mmol, 42.7% yield) as a yellow gum.

1H NMR (DMSO-d6, 400 MHz) δ: 9.40 (s, 0.5H), 9.15 (s, 0.5H), 7.14-7.21 (m, 2H), 7.07-7.13 (m, 4H), 6.95-7.03 (m, 2H), 6.69-6.78 (m, 2H), 6.58-6.67 (m, 2H), 6.40 (d, J=8.60 Hz, 1H), 5.46 (br s, 0.5H), 5.28 (br s, 0.5H), 3.75-3.83 (m, 1H), 3.60-3.40 (m, 1H), 2.40 (br quin, J=7.16 Hz, 2H), 1.45-1.78 (m, 6H), 0.84 (t, J=7.38 Hz, 3H).

Step 3: Synthesis of 2-(4-(1-(4-((5,5-dimethoxypentyl)oxy)phenyl)-2-phenylbut-1-en-1-yl)phenoxy) tetrahydro-2H-pyran To a solution of 4-(2-phenyl-1-(4-((tetrahydro-2H-pyran-2-yl)oxy)phenyl)but-1-en-1-yl)phenol (5.00 g, 12.5 mmol, 1.00 eq.) in DMF (40.0 mL) was added NaH (600.0 mg, 15.0 mmol, 60.0% purity, 1.20 eq.) in portions at 0° C. The mixture was stirred at 0° C. for 0.5 h. Then 5-chloro-1,1-dimethoxypentane (2.50 g, 15.0 mmol, 1.20 eq.) was added into the mixture at 0° C. The mixture was stirred at 0° C. for 8 h. TLC (petroleum ether:ethyl acetate=3:1, Rf (starting material)=0.37, Rf (product)=0.45) showed the starting

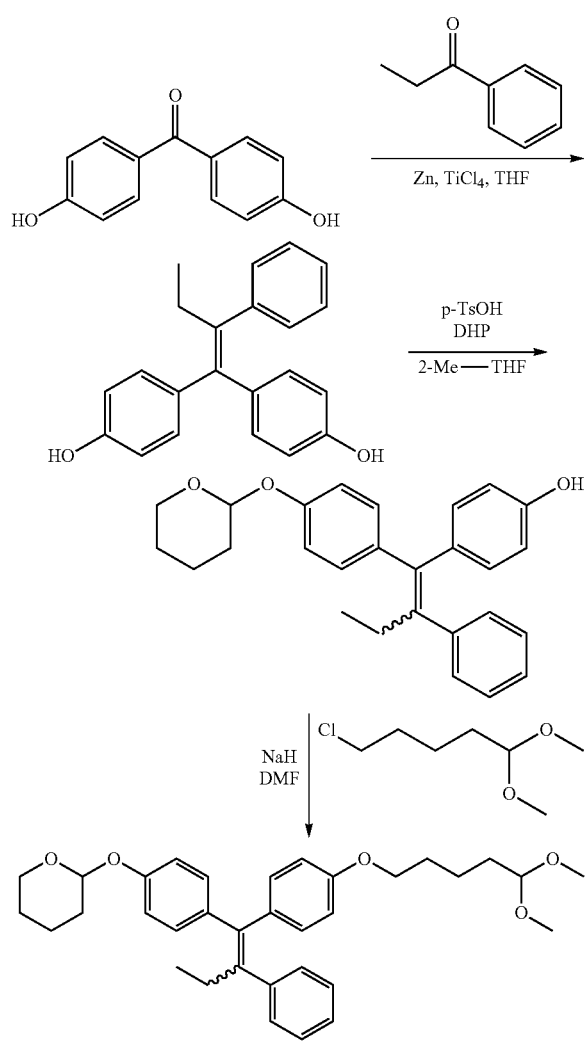

Intermediate 5 material was consumed completely. The reaction was quenched by addition of 10.0 mL of ice water, and a gray-orange solution was obtained. The mixture was partitioned between ethyl acetate (150.0 mL) and water (350.0 mL) for three times. The separated organic layer was washed with brine (50.0 mL), dried over sodium sulfate and filtered. The filtrate was evaporated to dryness. The crude product was purified by column chromatography on silica gel eluted with petroleum ether:ethyl acetate=45:1 to 40:1 to afford 2-(4-(1-(4-((5,5-dimethoxypentyl)oxy)phenyl)-2-phenyl-but-1-en-1-yl)phenoxy)tetrahydro-2H-pyran (2.16 g, 4.07 mmol, 32.5% yield, purity 97.6%) as yellow oil. LCMS [M+Na]$^+$=553.3; 1 H NMR (400 MHz, DMSO-d6) δ: 7.15-7.21 (m, 2H), 7.06-7.13 (m, 5H), 6.98-7.03 (d, 1H), 6.91 (d, J=8.56 Hz, 1H), 6.63-6.74 (m, 3H), 6.57 (d, J=8.68 Hz, 1H), 5.47 (m, 0.5H), 5.27 (m, 0.5H), 4.40-4.25 (m, 1H), 3.96 (t, J=6.36 Hz, 1H), 3.80 (br t, J=6.32 Hz, 1.5H), 3.65 (m, 0.5H), 3.57 (m, 1H), 3.50 (m, 1H), 3.22 (s, 3H), 3.19 (s, 3H), 2.40 (q, J=7.20 Hz, 2H), 1.68-1.95 (m, 2H), 1.31-1.64 (m, 9H), 0.85 (t, J=7.36 Hz, 3H).

Step 1: Synthesis of 4-(2-phenyl-1-(4-((tetrahydro-2H-pyran-2-yl)oxy)phenyl)but-1-en-1-yl)phenyl trifluoromethanesulfonate A mixture of 4-(2-phenyl-1-(4-((tetrahydro-2H-pyran-2-yl)oxy)phenyl)but-1-en-1-yl)phenol (48.2 g, 120.3 mmol, 1.00 eq) in DCM (500.0 mL) was added dropwise TEA (30.4 g, 300.8 mmol, 2.50 eq) and Tf2O (40.7 g, 144.4 mmol, 23.8 mL, 1.20 eq) at 10° C. Then the mixture was stirred at 20° C. for 5 h. TLC (petroleum ether/ethyl acetate=10/1, Rf (starting material)=0.20, Rf (product)=0.70) indicated the starting material was consumed. The mixture was poured into water (500.0 mL) and the mixture was extracted with DCM (100.0 mL×2). The combined organic phase was washed with brine (50.0 mL), dried over Na$_2$SO$_4$, filtered and the filtrate was concentrated in vacuum. The residue was purified by column chromatography (SiO$_2$, petroleum ether/ethyl acetate=1/0 to 10/1) to afford 4-(2-phenyl-1-(4-((tetrahydro-2H-pyran-2-yl)oxy)phenyl)but-1-en-1-yl)phenyl trifluoromethanesulfonate (36.0 g, 67.6 mmol, 56.1% yield) as yellow oil.

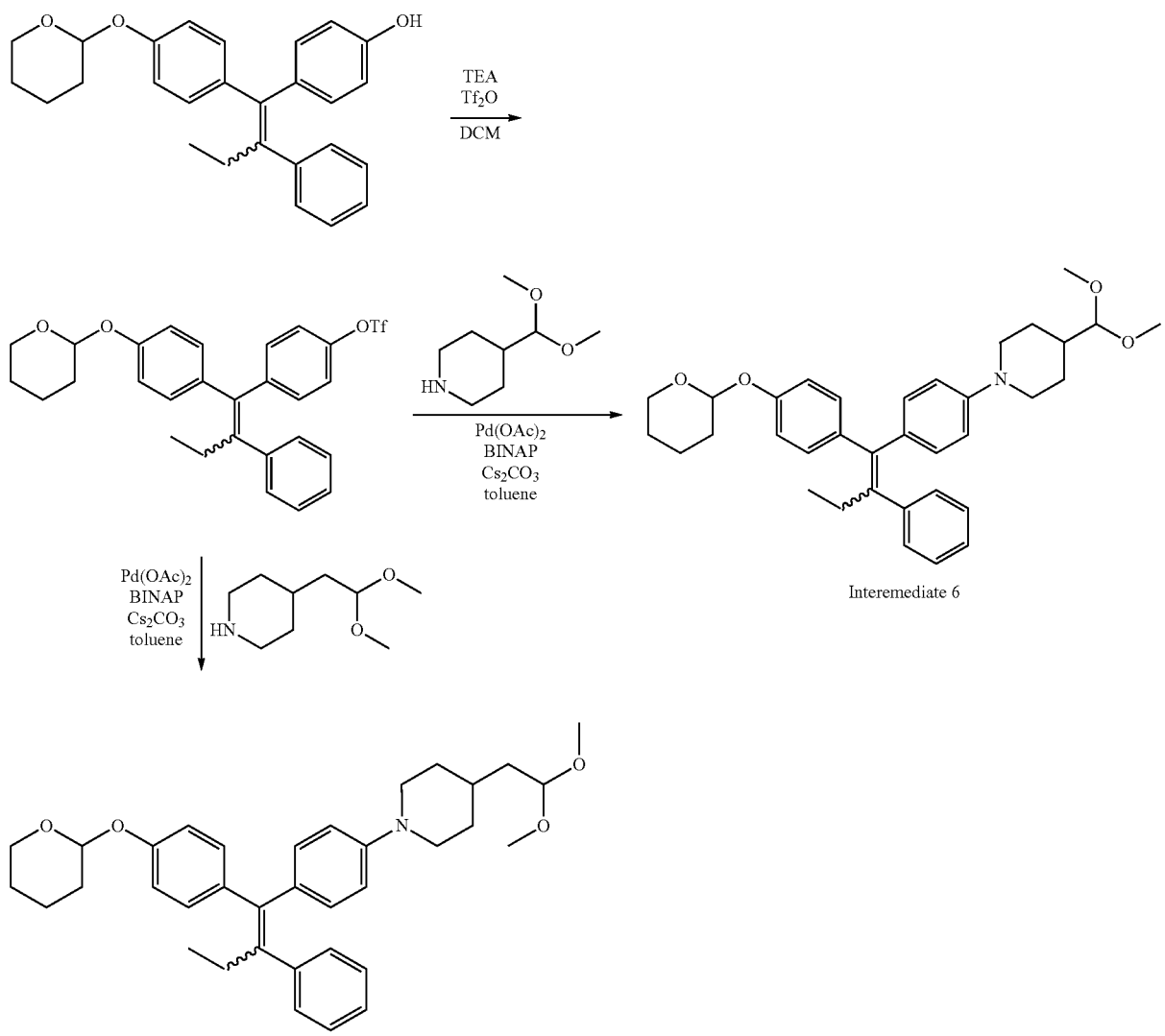

Step 2a: Synthesis of 4-(dimethoxymethyl)-1-(4-(2-phenyl-1-(4-((tetrahydro-2H-pyran-2-yl)oxy)phenyl)but-1-en-1-yl)phenyl)piperidine (Intermediate 6)

To a mixture of 4-(2-phenyl-1-(4-((tetrahydro-2H-pyran-2-yl)oxy)phenyl)but-1-en-1-yl)phenyl trifluoromethanesulfonate (13.0 g, 24.1 mmol, 1.00 eq) in toluene (100.0 mL) was added $Cs_2CO_3$ (15.9 g, 48.8 mmol, 2.00 eq), BINAP (1.52 g, 2.44 mmol, 0.100 eq) and Pd(OAc)$_2$ (274.0 mg, 1.22 mmol, 0.05 eq) and 4-(dimethoxymethyl)piperidine (4.60 g, 28.9 mmol, 1.2 eq) in portions under $N_2$ atmosphere at 20° C. The mixture was stirred at 100° C. for 24 h. TLC (petroleum ether/ethyl acetate=5/1, Rf (starting material)=0.72, Rf (product)=0.38) indicated the starting material was consumed completely. The same reaction was repeated and the two batches were combined for workup and purification. The mixture was filtered. The cake was washed with ethyl acetate (200.0 mL×2) and filtrate was concentrated in vacuum. The residue was purified by ISCO flash silica gel chromatography (0 to 18.0% ethyl acetate in petroleum ether) to afford 4-(dimethoxymethyl)-1-(4-(2-phenyl-1-(4-((tetrahydro-2H-pyran-2-yl)oxy)phenyl)but-1-en-1-yl)phenyl)piperidine (8.50 g, 151.6 mmol, 31.0% yield, 97.9% purity) as yellow gum. LCMS [M+H]$^+$ 542.3; 1H NMR (DMSO-d6, 400 MHz) δ: 7.12-7.20 (m, 2H), 7.04-7.12 (m, 4H), 6.99 (br d, J=8.80 Hz, 2H), 6.89 (br d, J=8.80 Hz, 1H), 6.51-6.72 (m, 4H), 5.45 (br, 0.5H), 5.27 (br, 0.5H), 3.98-4.12 (m, 1H), 3.62-3.83 (m, 2H), 3.43-3.60 (m, 2H), 3.26 (s, 3H), 3.24 (s, 3H), 2.59 (m, 1H), 2.30-2.45 (m, 3H), 1.17-1.86 (m, 11H), 0.83 (q, 3H).

Step 2b: Synthesis of 4-(2,2-dimethoxyethyl)-1-(4-(2-phenyl-1-(4-((tetrahydro-2H-pyran-2-yl)oxy)phenyl)but-1-en-1-yl)phenyl)piperidine (Intermediate 7)

This compound was synthesized using the same method as described in Step 2a except 4-(2,2-dimethoxyethyl)piperidine was used. The desired 4-(2,2-dimethoxyethyl)-1-(4-(2-phenyl-1-(4-((tetrahydro-2H-pyran-2-yl)oxy)phenyl)but-1-en-1-yl)phenyl)piperidine was obtained as a gummy material (20.8% yield, 94.5% purity). LCMS [M+H]$^+$=556; 1H NMR (DMSO-d6, 400 MHz) δ: 7.14-7.21 (m, 2H), 7.06-7.13 (m, 4H), 7.00 (d, J=9.04 Hz, 2H), 6.90 (d, J=8.60 Hz, 1H), 6.69-6.73 (m, 1H), 6.59-6.68 (m, 2H), 6.53-6.58 (m, 1H), 5.46 (br, 0.5H), 5.28 (br, 0.5H), 4.40-4.52 (m, 1H), 3.62-3.85 (m, 2H), 3.44-3.61 (m, 2H), 3.23 (s, 3H), 3.20 (s, 3H), 2.56-2.70 (m, 1H), 2.30-2.48 (m, 3H), 1.40-1.85 (m, 11H), 1.12-1.33 (m, 2H), 0.84 (q, 3H).

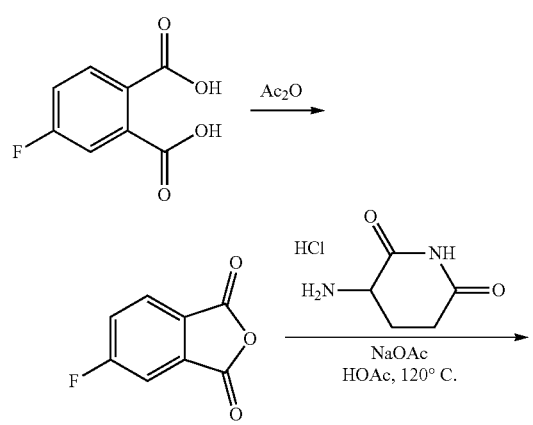

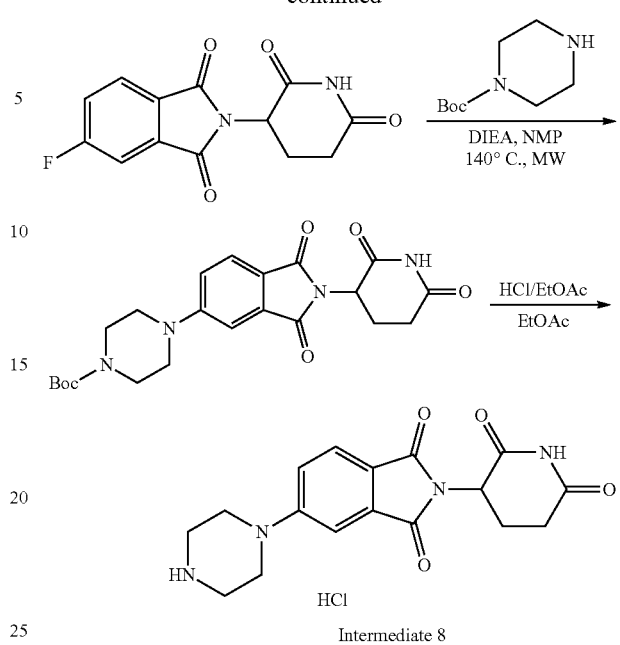

Intermediate 8

Intermediate 8 was prepared according to the above scheme as a hydrochloride salt. LC/MS 343.1 [M+H]+; 1H-NMR (400 MHz, CD3OD) δ ppm 7.76 (d, J=8.36 Hz, 1H), 7.47 (s, 1H), 7.35 (dd, J=8.36, 1.54 Hz, 1H), 5.09 (br dd, J=12.8, 5.40 Hz, 1H), 3.67-3.74 (m, 4H), 3.37-3.42 (m, 4H), 2.63-2.94 (m, 3H), 2.07-2.17 (m, 1H).

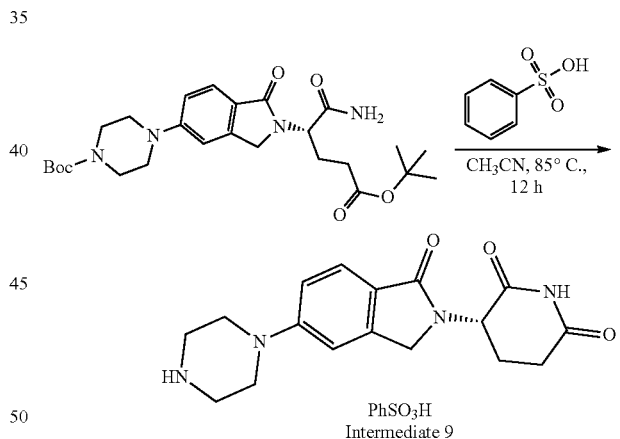

PhSO$_3$H
Intermediate 9

To a solution of (S)-tert-butyl 4-(2-(1-amino-5-tert-butoxy-1,5-dioxopentan-2-yl)-1-oxoisoindolin-5-yl)piperazine-1-carboxylate (5.8 g, 12 mol) in acetonitrile (90 mL) was added benzenesulfonic acid (3.64 g, 23 mol). The mixture was stirred at 85° C. for 12 h. LC/MS showed the reaction was complete. The mixture was concentrated in vacuum. The residue was triturated with ethyl acetate to afford (S)-3-(1-oxo-5-(piperazin-1-yl)isoindolin-2-yl)piperidine-2,6-dione benzenesulfonate (5.2 g, 93%) as off-white solid. LC/MS 329.1 [M+1]+; 1H NMR (400 MHz, DMSO-d6) δ 1.95-1.99 (m, 1H), 2.36-2.41 (m, 1H), 2.58-2.62 (d, 1H), 2.88-2.91 (m, 1H), 3.26 (s, 4H), 3.49-3.52 (m, 4H), 4.21-4.38 (dd, 2H), 5.05-5.10 (dd, 1H), 7.12-7.16 (m, 2H), 7.30-7.358 (m, 3H), 7.58-7.62 (m, 3H), 8.72 (s, 2H).

Preparation of Final Compounds 160a, 160b, 184a, 185a, 161a, 17a, 16a, 28a, 29a, 31a, and 32a

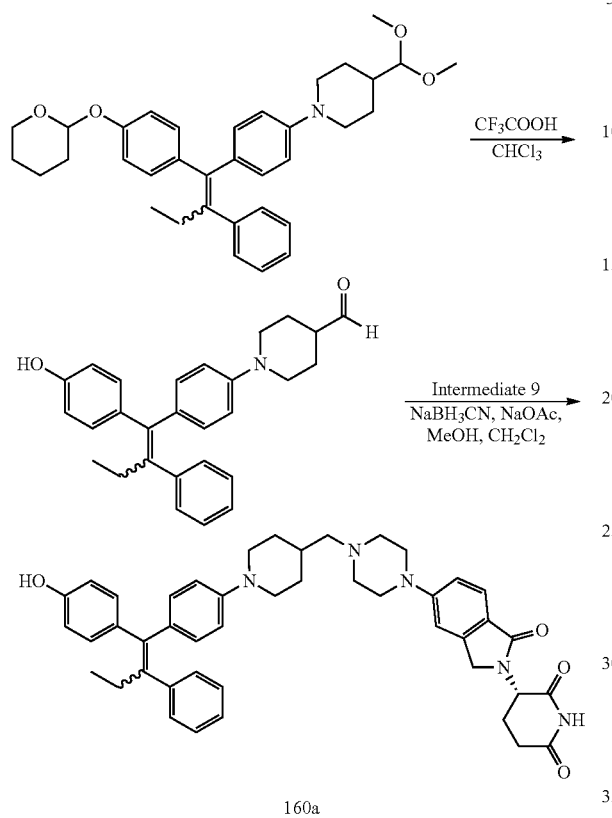

Step 1: Preparation of 1-(4-(1-(4-hydroxyphenyl)-2-phenylbut-1-en-1-yl)phenyl)piperidine-4-carbaldehyde A mixture of 4-(dimethoxymethyl)-1-(4-(2-phenyl-1-(4-((tetrahydro-2H-pyran-2-yl)oxy)phenyl)but-1-en-1-yl)phenyl)piperidine (Intermediate 6) (200 mg, 0.37 mmol), chloroform (16 mL) and TFA (4 mL) was stirred at 25° C. for 2 hours. The reaction mixture was concentrated to afford the desired compound (180 mg, 90%). LC/MS: 412.2 [M+H]+.

Step 2: Preparation of (S)-3-(5-(4-((1-(4-(1-(4-hydroxyphenyl)-2-phenylbut-1-en-1-yl)phenyl)piperidin-4-yl)methyl)piperazin-1-yl)-1-oxoisoindolin-2-yl)piperidine-2,6-dione (160a)

To a solution of the aldehyde prepared above (156.3 mg, 0.32 mmol) in dichloromethane (21 mL) and methanol (6 mL) was added sodium acetate (36 mg, 0.435 mmol). The mixture was stirred at 15° C. for 0.5 hours. Then acetic acid (35 mg, 0.58 mmol) and (S)-3-(1-oxo-5-(piperazin-1-yl)isoindolin-2-yl)piperidine-2,6-dione benzenesulfonate (120 mg, 0.29 mmol) were added to the mixture. The mixture was stirred at 15° C. for 0.5 hours. Then the sodium cyanoborohydride (27.5 mg, 0.435 mmol) was added to the mixture. The mixture was stirred at 15° C. for 2 hours. The residue was diluted with water (10 mL) and extracted with dichloromethane (20 mL×3). The combined organic layers were dried with anhydrous sodium sulfate, filtered and concentrated in vacuum. The residue was purified by reverse phase preparative HPLC to give the desired compound as a white solid of formic acid salt (41.6 mg, 60% yield, purity 98% by HPLC at 214 nm and 254 nm UV detection). LC/MS: 724.2 [M+H]+; 1H NMR (400 MHz, DMSO) δ 10.96 (s, 1H, imide NH), 9.43 (s, 0.5H, phenol), 9.21 (s, 0.5H, phenol), 8.15 (s, 1H, formate aldehyde), 7.54 (m, 1H), 7.14-7.21 (m, 2H), 7.06-7.12 (m, 5H), 6.88-7.00 (m, 3H), 6.74 (d, 1H), 6.59 (m, 3H), 6.40 (d, 1H), 5.07 (m, 1H), 4.33 (dd, 1H), 4.22 (dd, 1H), 3.73 (br d, 1H), 3.55 (br d, 1H), 3.25-3.45 (m, 6H, overlap with DMSO-d6), 2.89 (m, 1H). 2.28-2.76 (m, 7H, overlap with DMSO-d6), 2.27 (m, 2H), 1.63-2.00 (m, 5H), 1.10-1.27 (m, 2H), 0.84 (m, 3H). LC/MS 724.6 [M+1]+

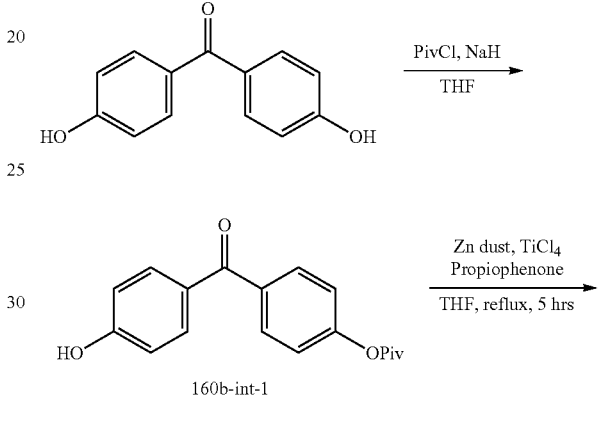

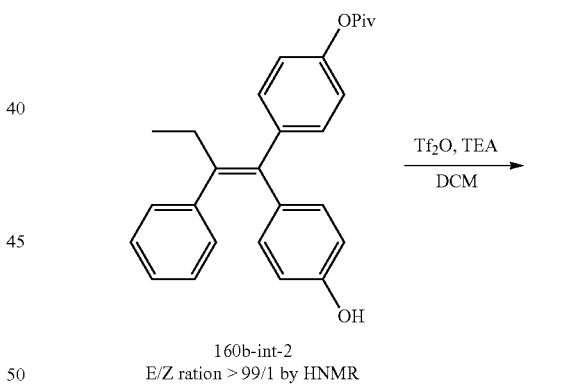

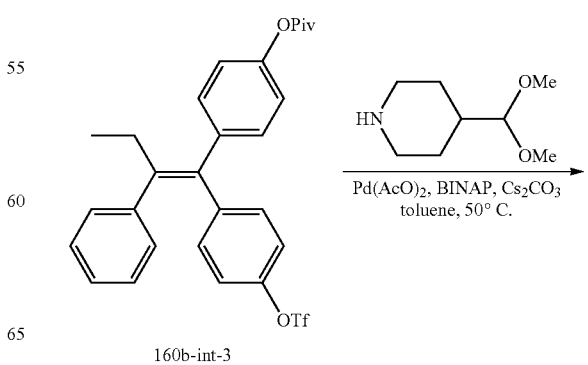

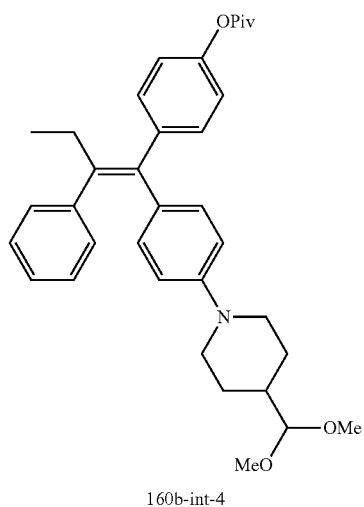

160b-int-4

MeLi, THF, -78° C.

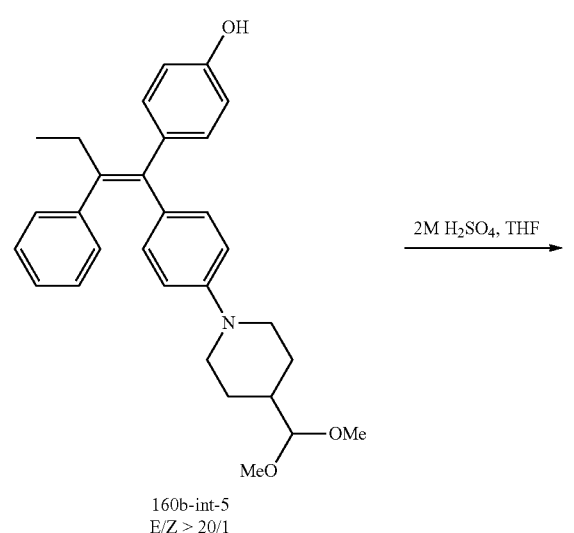

160b-int-5
E/Z > 20/1

2M H₂SO₄, THF

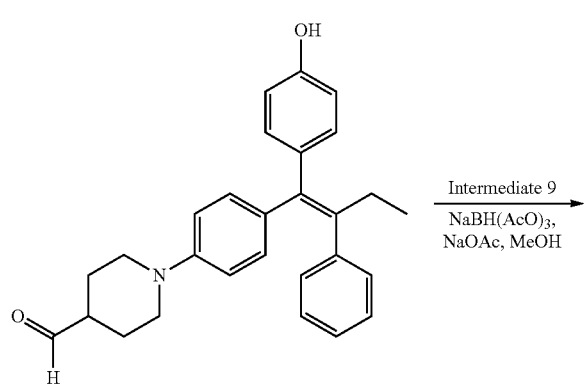

160b-int-6
E/Z > 20/1

Intermediate 9
NaBH(AcO)₃,
NaOAc, MeOH

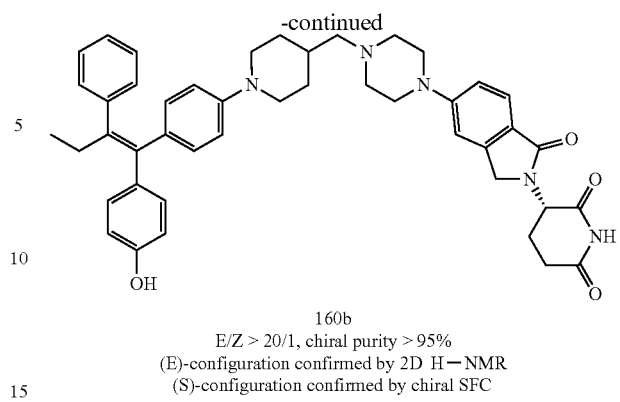

160b
E/Z > 20/1, chiral purity > 95%
(E)-configuration confirmed by 2D H—NMR
(S)-configuration confirmed by chiral SFC Step 1 through Step 6: Synthesis of (E)-1-(4-(1-(4-hydroxyphenyl)-2-phenylbut-1-en-1-yl)phenyl)piperidine-4-carbaldehyde (160b-int-6)

This key aldehyde intermediate was synthesized according to the scheme described above by the deprotection of acetal (160b-int-5), which was synthesized with the similar procedure as described in the synthesis of Intermediate 2 except slight modifications. The second step product 160b-int-2 was obtained as a pure trans-olefin after crystallization (confirmed by H-NMR) and the fourth step Buchwald amination reaction was carried out under 50° C. to prevent olefin isomerization. The deprotection of pivaloyl group followed the procedure as described in the literature (Bioorg. Med. Chem. Lett. 2018, 1352-1356) provided 160b-int-5 with a ratio of E/Z larger than 20/1. The deprotection of acetal under acidic condition gave the desired trans-olefin aldehyde 160b-int-6 without the observation of olefin isomerization as demonstrated by H-NMR. 160b-int-6: 1H-NMR (CDCl3, 400 MHz) δ 9.59 (s, 1H, aldehyde), 7.01-7.11 (m, 7H), 6.72 (d, 2H), 6.65 (d, 2H), 6.49 (d, 2H), 4.92 (br s, 1H, phenol), 3.43 (m, 2H), 2.67 (m, 2H), 2.36 (q, 2H), 2.25 (m, 1H), 1.88 (m, 2H), 1.63 (m, 2H), 0.84 (t, 3H). Purity analysis by SFC indicated one single isomer. To further confirm single olefin configuration, this material was dissolved in toluene and heated to 100° C. and solvents were removed completely. The heated sample was analyzed by SFC and indicated two peaks with 1/1 ratio. The resulting material after heating was also analyzed by H-NMR and confirmed it changed to 1/1 ratio of E/Z mixture as shown: 1H-NMR (CDCl3, 400 MHz) δ 9.73 (s, 0.5H), 9.67 (s, 0.5H), 7.07-7.15 (m, 7H), 6.92 (d, 1H), 6.70-6.85 (m, 3H), 6.60 (d, 1H), 6.43 (d, 1H), 4.75-5.20 (br, not integrated), 3.68 (m, 1H), 3.50 (m, 1H), 2.85-2.95 (m, 1H), 2.70-2.80 (m, 1H), 2.26-2.57 (m, 3H), 1.93-2.00 (m, 1H), 2.00-2.10 (m, 1H), 1.75-1.90 (m, 1H), 1.65-1.75 (m, 1H), 0.94 (m, 3H).

Step 7: Synthesis of (S,E)-3-(5-(4-((1-(4-(1-(4-hydroxyphenyl)-2-phenylbut-1-en-1-yl)phenyl)piperidin-4-yl)methyl)piperazin-1-yl)-1-oxoisoindolin-2-yl)piperidine-2,6-dione (160b)

The reductive amination of (E)-160b-int-6 with intermediate 9 followed the similar procedure as in the preparation of 160a to provide the desired (E,S)-160b as a single isomer. Chiral purity was analyzed by chiral SFC in comparison with the epimer of (R)/(S)-160b prepared from (S)/(R)-Intermediate 9 and indicated chiral purity as 97.2%. The (E)-configuration was further confirmed by 2D-NMR (HSQC, NOE). 1H-NMR (DMSO-d6, 400 MHz) δ 10.95 (s, 1H), 9.41 (s, 1H), 7.53 (d, 1H), 7.17-7.22 (m, 2H), 7.06-7.15 (m, 5H), 6.98 (d, 2H), 6.75 (d, 2H), 6.62 (d, 2H), 6.58 (d, 2H), 5.06 (dd, 1H), 4.33 (d, J=17 Hz, 1H), 4.20 (d, J=17 Hz, 1H), 3.55 (br d, 2H), 3.25-3.41 (m, 6H, overlap with DMSO-d6), 2.88 (m, 1H), 2.27-2.75 (m, 7H, overlap with DMSO-d6), 2.21-2.26 (m, 2H), 1.97 (m, 2H), 1.75 (m, 2H), 1.63 (m, 1H), 1.15 (m, 2H), 0.84 (t, 3H). LC/MS 724.6 [M+1]$^+$ Synthesis of 2- (2,6-dioxopiperidin-3-yl)-5- (4-(4-(1-(4-hydroxyphenyl) -2-phenylbut-1-en-1-yl)phenyl)piperidin-4-yl)methyl)piperazin-1-yl) isoindoline-1,3-dione (184a)

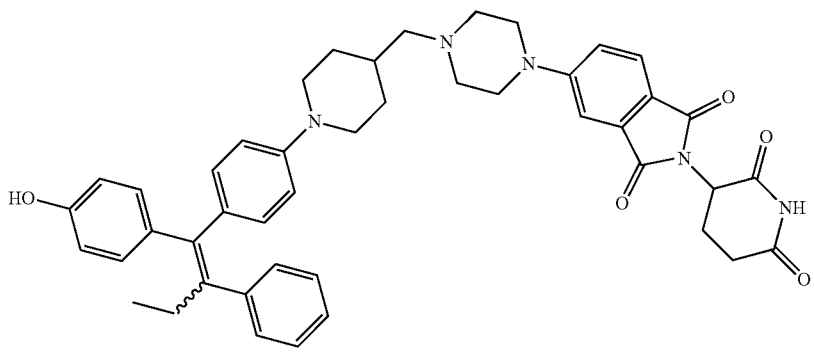 [SMILES: CCC(=C(c1ccc(O)cc1)c1ccc(N2CCC(CN3CCN(c4ccc5c(c4)C(=O)N(C4CCC(=O)NC4=O)C5=O)CC3)CC2)cc1)c1ccccc1]

This compound was prepared using the same procedure as described in the preparation of 160a except Intermediate 8 was used in the reductive amination step. LC/MS 738.2 [M+H]$^+$; 1H NMR (400 MHz, DMSO) δ 11.09 (s, 1H), 8.37 (br s, 1H), 7.70-7.68 (m, 1H), 7.35 (d, 1H), 7.26 (t, 1H), 7.13-7.20 (m, 2H), 7.05-7.12 (m, 3H). 6.98 (m, 2H), 6.90 (d, 1H), 6.75 (d, 1H), 6.65 (m, 3H), 6.40 (d, 1H), 5.08 (m, 1H), 3.71 (br d, 1H), 3.54 (br d, 1H), 3.25-3.50 (m, 6H, overlap with DMSO-d6), 2.88 (m, 1H), 2.36-2.75 (m, 7H), 2.18-2.26 (dd, 2H), 2.04 (m, 2H), 1.85 (m, 1H), 1.73 (m, 1H), 1.61 (m, 1H), 1.13-1.27 (m, 2H), 0.85 (q, 3H).

Synthesis of 2-(2,6-dioxopiperidin-3-yl)-5-(4-(2-(1-(4-(1-(4-hydroxyphenyl) -2-phenylbut-1-en-1-yl)phenyl)piperidin-4-yl)ethyl)piperazin-1-yl) isoindoline-1,3-dione trifluoroacetic acid salt (185a)

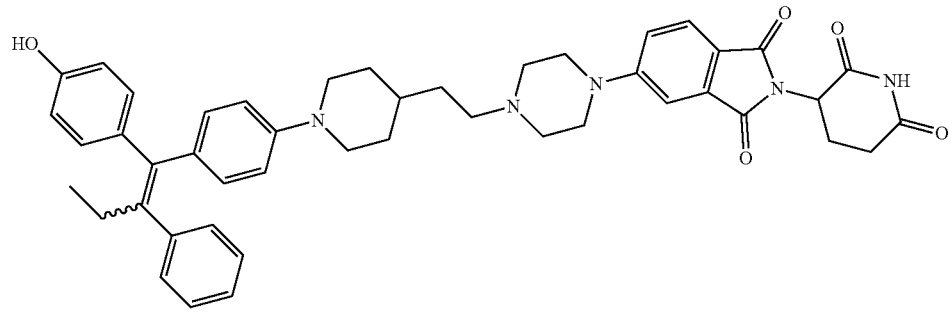

CF$_3$COOH

This compound was prepared using intermediate 7 and intermediate 8 according to the same procedure as described for the preparation of 160a. LC/MS 752.3 [M+H]⁺; 1H NMR (400 MHz, MeOD-d4) δ 7.80 (dd, 1H), 7.47-7.55 (m, 2H), 7.37-7.42 (m, 2H), 7.10-7.22 (m, 6H), 7.05 (d, 2H), 6.80 (d, 1H), 6.67 (d, 1H), 6.44 (d, 1H), 5.12 (m, 1H), 3.79 (br d, 2H), 3.62 (br d, 2H), 3.52-3.37 (m, 7H, overlap with MeOH-d4), 2.90-2.70 (m, 5H), 2.59-2.45 (m, 2H), 2.21-2.01 (m, 3H), 1.94-1.60 (m, 6H), 0.94 (t, 3H).

Synthesis (S)-3-(5-(4-(2-(1-(4-(1-(4-hydroxyphenyl)-2-phenylbut-1-en-1-yl)phenyl)piperidin-4-yl)ethyl)piperazin-1-yl)-1-oxoisoindolin-2-yl)piperidine-2,6-dione (161a)

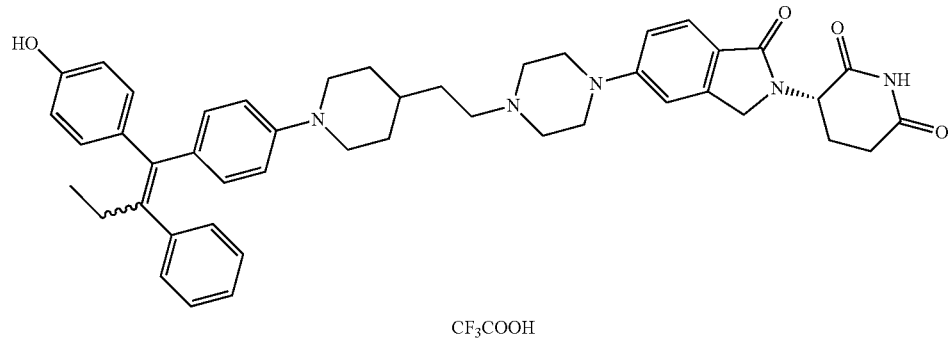 [SMILES: CCC(=C(c1ccc(O)cc1)c1ccc(N2CCC(CCN3CCN(c4ccc5c(c4)CN([C@H]4CCC(=O)NC4=O)C5=O)CC3)CC2)cc1)c1ccccc1 ; "CF3COOH"]

CF₃COOH

This compound was prepared using intermediate 7 and intermediate 9 according to the same procedure as described for the preparation of 160a. LC/MS 738.3 [M+H]⁺; 1 H NMR (400 MHz, MeOD) δ 7.73 (dd, 1H), 7.43 (d, 1H), 7.35 (d, 1H), 7.25-7.06 (m, 8H), 7.04 (t, 2H), 6.80 (d, 1H), 6.67 (d, 1H), 6.43 (d, 1H), 5.14 (m, 1H), 4.58-4.30 (m, 2H), 3.84-3.50 (m, 6H), 2.93 (m, 1H), 2.84-2.71 (m, 1H), 2.51 (m, 4H), 2.20-1.98 (m, 5H), 1.94-1.55 (m, 8H), 0.94 (t, J=7.4 Hz, 3H).

Synthesis of (S)-3-(5-(4-(4-(4-(1-(4-hydroxyphenyl)-2-phenylbut-1-en-1-yl) phenoxy)butyl)piperazin-1-yl)-1-oxoisoindolin-2-yl)piperidine-2,6-dione trifluoroacetic acid salt (17a)

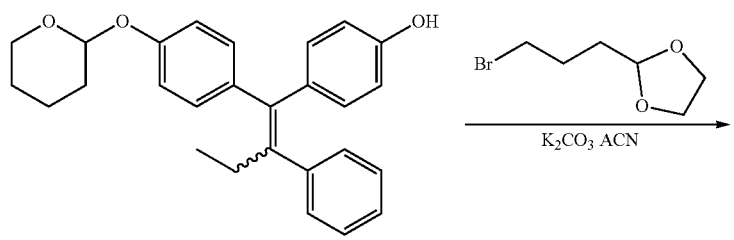

K₂CO₃ ACN

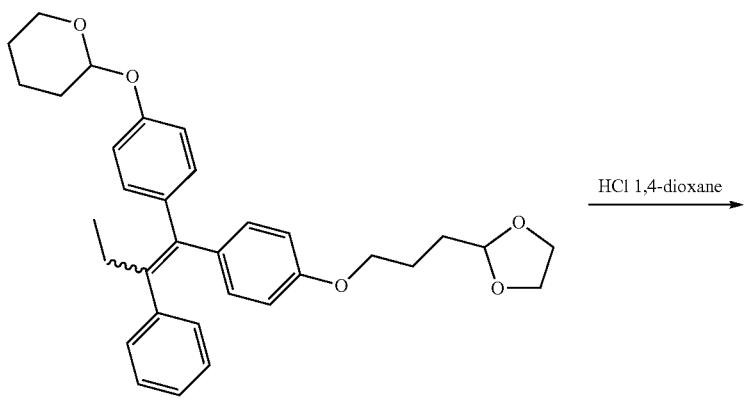

HCl 1,4-dioxane

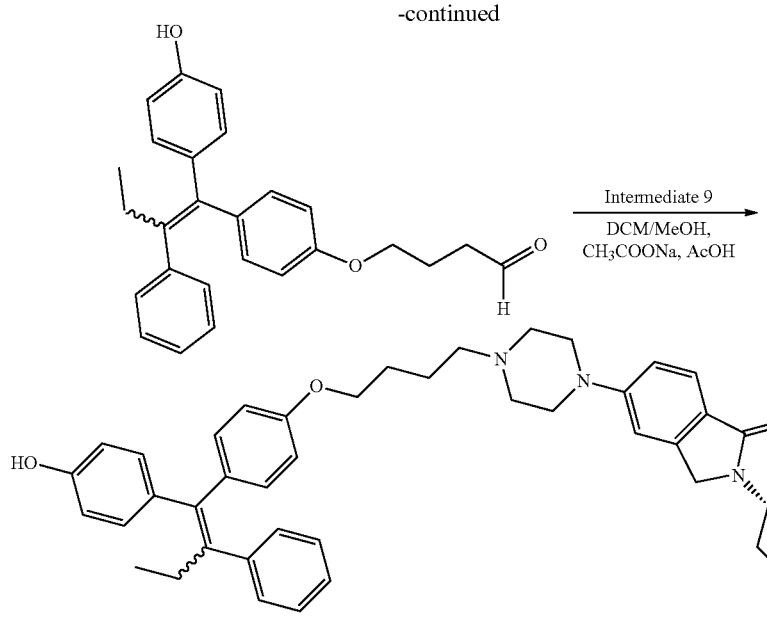

Step 1: Synthesis of 2-(4-(1-(4-(3-(1,3-dioxolan-2-yl)propoxy)phenyl)-2-phenylbut-1-en-1-yl)phenoxy)tetrahydro-2H-pyran A solution of 2-(3-bromopropyl)-1,3-dioxolane (200 mg 0.5 mmol, 1 eq), 4-(2-phenyl-1-(4-((tetrahydro-2H-pyran-2-yl)oxy)phenyl)but-1-en-1-yl)phenol (195.05 mg 1 mmol, 2 eq), K$_2$CO$_3$ (138.21 mg, 1 mmol, 2 eq) in acetonitrile (2 mL) was stirred at 75° C. for 20 hours, LCMS showed the reaction completed. The mixture was partitioned between DCM and H$_2$O. The organic phase was washed with brine, dried over magnesium sulfate and evaporated to dryness. The crude product was purified by silica gel chromatography using with 10-30% EtOAc in DCM as eluent to afford the desired compound as a white solid (190 mg, 74% yield). LCMS 537.3 [M+Na]$^+$.

Step 2: Synthesis of 4-(4-(1-(4-hydroxyphenyl)-2-phenylbut-1-en-1-yl)phenoxy)butanal A solution of 2-(4-(1-(4-(3-(1,3-dioxolan-2-yl)propoxy)phenyl)-2-phenylbut-1-en-1-yl)phenoxy)tetrahydro-2H-pyran (100 mg 0.41 mmol, 1 eq) in 1,4-dioxane (10 mL) and 1 N HCl (10 mL) was stirred at 90° C. for 24 hours, LCMS showed the reaction was completed. The reaction mixture was extracted with dichloromethane (50 mL×3). The combined organic layers were dried with anhydrous sodium sulfate, filtered and concentrated in vacuum. The residue was evaporated to dryness to give the desired compound as a white solid (60 mg, 39% yield). LCMS 387.2 [M+1]$^+$

Step 3: Synthesis of (S)-3-(5-(4-(4-(4-(1-(4-hydroxyphenyl)-2-phenylbut-1-en-1-yl)phenoxy)butyl)piperazin-1-yl)-1-oxoisoindolin-2-yl)piperidine-2,6-dione (17a)

The reductive amination of the aldehyde from step 2 with intermediate 9 using the same procedure as in the preparation of 160a afforded 17a as a white solid after HPLC purification (triflate salt). LC/MS 699.3 [M+H]$^+$; 1H NMR (400 MHz, DMSO) b 10.97 (s, 1H), 9.64, 9.44 and 9.19 (3 broad s, 2H), 7.60 (m, 1H), 7.25-7.07 (m, 8H), 6.96 (m, 2H), 6.75 (m, 2H), 6.60 (d, 2H), 6.41 (d, 1H), 5.07 (m, 1H), 4.37 (d, J=17.2 Hz, 1H), 4.24 (d, J=17.2 Hz, 1H), 4.04 (m, 3H), 3.88 (m, 1H), 3.60 (m, 2H), 3.28-3.03 (m, 6H), 2.87 (m, 1H), 2.77-2.50 (m, 2H), 2.40 (m, 3H), 2.01-1.60 (m, 4H), 0.85 (t, 3H).

Synthesis of 2-(2,6-dioxopiperidin-3-yl)-5-(4-(4-(4-(1-(4-hydroxyphenyl)-2-phenylbut-1-en-1-yl)phenoxy)butyl)piperazin-1-yl)isoindoline-1,3-dione trifluoroacetic acid salt (16a)

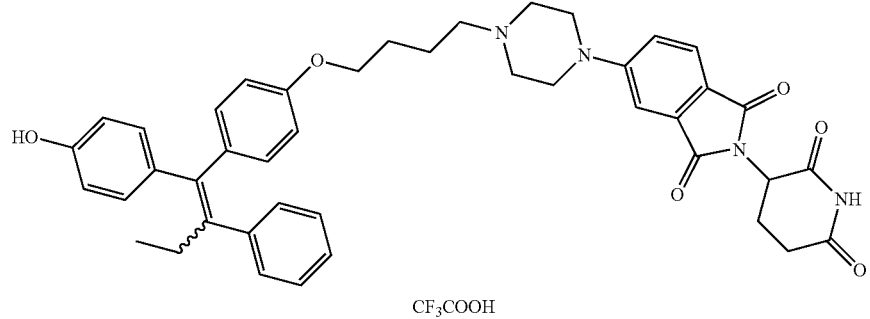 [SMILES: CCC(=C(c1ccc(O)cc1)c1ccc(OCCCCN2CCN(c3ccc4c(c3)C(=O)N(C3CCC(=O)NC3=O)C4=O)CC2)cc1)c1ccccc1 ; "CF3COOH"]

CF$_3$COOH

This compound was prepared using the same method as described for the preparation of 17a except intermediate 8 was used. LC/MS 713.3 [M+H]+; 1H NMR (400 MHz, DMSO) δ 11.11 (s, 1H), 9.67, 9.43 and 9.19 (3 br s, 2H), 7.78 (dd, 1H), 7.51 (d, 1H), 7.35 (t, 1H), 7.17-7.04 (m, 6H), 6.97 (m, 2H), 6.77 (m, 2H), 6.59 (d, 2H), 6.40 (d, 1H), 5.11 (dd, 1H), 4.24 (m, 2H), 4.03 (m, 1H), 3.88 (m, 1H), 3.64 (m, 2H), 3.20 (m, 5H), 2.88 (m, 1H), 2.70-2.50 (m, 2H), 2.40 (m, 3H), 2.05 (m, 1H), 1.90-1.65 (m, 4H), 0.85 (t, 3H).

Synthesis of 2-(2,6-dioxopiperidin-3-yl)-5-(4-(5-(4-(1-(4-hydroxyphenyl) -2-phenylbut-1-en-1-yl)phenoxy)pentyl)piperazin-1-yl)isoindoline-1,3-dione formic acid salt (28a)

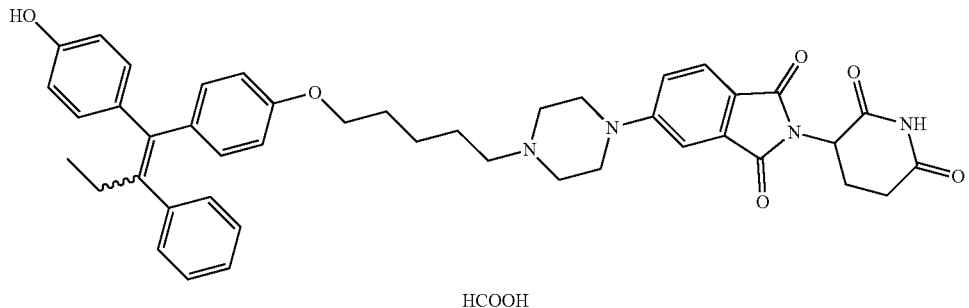 [SMILES: CCC(=C(c1ccc(O)cc1)c1ccc(OCCCCCN2CCN(c3ccc4c(c3)C(=O)N(C3CCC(=O)NC3=O)C4=O)CC2)cc1)c1ccccc1 ; "HCOOH"]

HCOOH

This compound was prepared by reacting Intermediate 5 with Intermediate 8 using the same procedure as described in 160a. LC/MS 727.1 [M+H]+; 1H NMR (400 MHz, DMSO): δ 11.10 (s, 1H), 9.42 (s, 0.5H), 9.16 (s, 0.5H), 8.15 (s, 1H, formic acid), 7.70-7.68 (m, 1H), 7.50-7.06 (m, 8H), 7.04-6.91 (m, 2H), 6.81-6.52 (m, 4H), 6.41 (m, 1H), 5.09-5.07 (m, 1H), 3.99 (m, 1H), 3.83 (m, 1H), 3.52-3.22 (m, 6H), 2.89 (m, 1H), 2.63-2.51 (m, 4H), 2.51-2.30 (m, 4H), 2.02 (m, 1H), 1.76-1.15 (m, 6H), 0.85 (m, 3H).

Synthesis of 2-(2,6-dioxopiperidin-3-yl)-5-(4-(6-(4-(1-(4-hydroxyphenyl) -2-phenylbut-1-en-1-yl)phenoxy)hexyl)piperazin-1-yl)isoindoline-1,3-dione (29a)

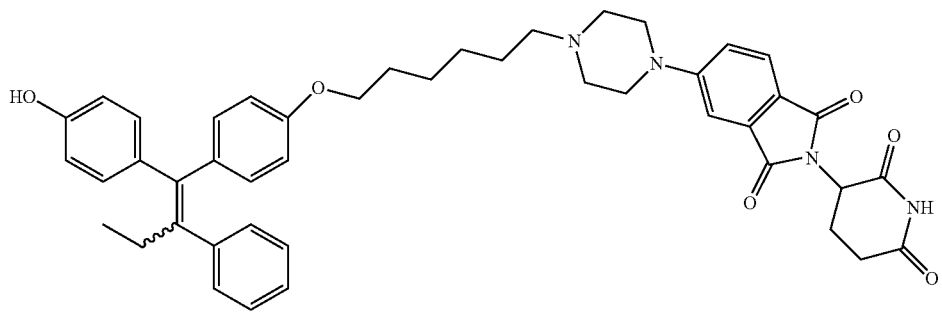 [SMILES: CCC(=C(c1ccc(O)cc1)c1ccc(OCCCCCCN2CCN(c3ccc4c(c3)C(=O)N(C3CCC(=O)NC3=O)C4=O)CC2)cc1)c1ccccc1]

This compound was prepared with a similar method as in the preparation of 17a. LC/MS 741.3 [M+H]+; 1 H NMR (400 MHz, DMSO) δ=11.10 (s, 1H), 9.43 (s, 0.5H), 9.18 (s, 0.5H), 7.72 (m, 1H), 7.40 (m, 1H), 7.30 (m, 1H), 7.18 (m, 2H), 7.10 (m, 4H), 6.98 (d, 1H), 6.92 (d, 1H), 6.76 (d, 1H), 6.71 (d, 1H), 6.59 (t, 2H), 6.40 (d, 1H), 5.09 (dd, 1H), 3.98 (t, 1H), 3.82 (t, 1H), 3.45-3.30 (m, 5H), 2.96-2.83 (m, 2H), 2.64-2.54 (m, 2H), 2.45-2.35 (m, 4H), 2.06-1.98 (m, 1H), 1.78-1.70 (m, 2H), 1.69-1.59 (m, 2H), 1.52-1.43 (m, 2H), 1.43-1.28 (m, 4H), 0.85 (t, 3H).

Synthesis of (S)-3-(5-(4-(5-(4-(1-(4-hydroxyphenyl)-2-phenylbut-1-en-1-yl) phenoxy)pentyl)piperazin-1-yl)-1-oxoisoindolin-2-yl)piperidine-2,6-dione formic acid salt (31 a)

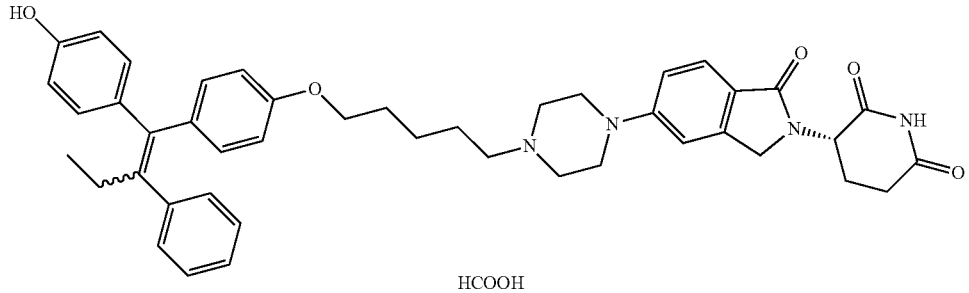 [SMILES: CCC(=C(c1ccc(O)cc1)c1ccc(OCCCCCN2CCN(c3ccc4c(c3)CN([C@H]3CCC(=O)NC3=O)C4=O)CC2)cc1)c1ccccc1 ; "HCOOH"]

HCOOH

This compound was prepared using the same method as described for the preparation of 17a. LC/MS 713.2 [M+H]$^+$; 1H NMR (400 MHz, DMSO): δ 10.95 (s, 1H), 9.45 and 9.18 (2 br s, 1H), 8.35 (s, 1H, formic acid), 7.52 (d, 1H), 7.20-7.16 (m, 3H), 7.15-7.06 (m, 5H), 6.96 (d, 1H), 6.92 (d, 1H), 6.76 (d, 1H), 6.71 (d, 1H), 6.59 (t, 2H), 6.41 (d, 1H), 5.06 (dd, 1H), 4.35-4.19 (dd, J=17 Hz, 2H), 3.99 (t, 1H), 3.82 (t, 1H), 3.34-3.28 (m, 3H), 2.91-2.88 (m, 2H), 2.70-2.51 (m, 2H), 2.45-2.29 (m, 7H), 1.98-1.95 (m, 1H), 1.76-1.64 (m, 2H), 1.58-1.40 (m, 5H), 0.85 (t, 3H).

Synthesis of (S)-3-(5-(4-(6-(4-(1-(4-hydroxyphenyl)-2-phenylbut-1-en-1-yl) phenoxy)hexyl)piperazin-1-yl)-1-oxoisoindolin-2-yl)piperidine-2,6-dione (32a)

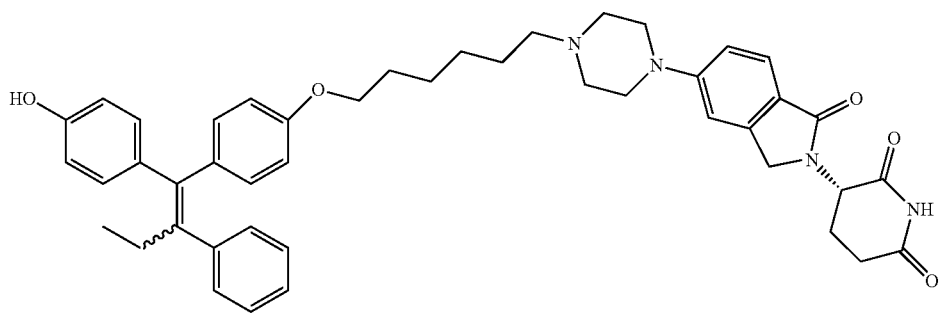 [SMILES: CCC(=C(c1ccc(O)cc1)c1ccc(OCCCCCCN2CCN(c3ccc4c(c3)CN([C@H]3CCC(=O)NC3=O)C4=O)CC2)cc1)c1ccccc1]

This compound was prepared using the same method as described for the preparation of 17a. The crude product was purified by preparative TLC (DCM/MeOH=10/1) to afford the desired compound (35.8 mg, 25.9%) as a white solid. LC/MS 727.3 [M+H]$^+$; 1H NMR (400 MHz, DMSO) δ=10.96 (s, 1H), 9.44 (s, 0.5H), 9.18 (s, 0.5H), 7.56 (m, 1H), 7.21-7.15 (m, 3H), 7.10 (m, 5H), 6.98 (d, 1H), 6.92 (d, 1H), 6.76 (d, 1H), 6.71 (d, 1H), 6.59 (t, 2H), 6.41 (d, 1H), 5.06 (dd, J=13.6, 5.2 Hz, 1H), 4.35 (d, J=17 Hz, 1H), 4.23 (d, J=17 Hz, 1H), 3.99 (t, 1H), 3.82 (t, 1H), 3.25 (m, 3H), 2.97-2.82 (m, 2H), 2.59 (m, 2H), 2.46-2.31 (m, 4H), 2.03-1.92 (m, 1H), 1.79-1.70 (m, 1H), 1.69-1.61 (m, 2H), 1.54-1.47 (m, 2H), 1.43-1.27 (m, 4H), 0.85 (t, 3H). (2 protons overlapped with DMSO-d6, not assigned).

General Procedure for Synthesis of Tamoxifen-Linked Degrader:

N-Desmethyltamoxifen (0.1 mmol) was dissolved in DMSO/DCM (1 mL/5 mL) followed by addition of NMM (0.2 mmol), Linker (0.1 mmol), HOAt (0.15 mmol) and EDCl (0.15 mmol). The mixture was allowed to stir at room temperature overnight. The progress of the reaction was monitored by LCMS. The crude product was then purified by prep-HPLC to yield the desired product.

Other Final Compounds of Formula (I)

(Z)-3-(2-((2-(2,6-dioxopiperidin-3-yl)-1,3-dioxoisoindolin-4-yl)amino)ethoxy)-N-(2-(4-(1,2-diphenylbut-1-en-1-yl)phenoxy)ethyl)-N-methylpropanamide (compound 8) (22 mg, 78%) as yellow solid. $^1$H NMR (600 MHz, Methanol-d$_4$) δ 7.50-7.47 (m, 1H), 7.33 (td, J=7.6, 2.0 Hz, 2H), 7.27-7.23 (m, 1H), 7.18 (t, J=7.2 Hz, 2H), 7.16-7.12 (m, 2H), 7.11-7.05 (m, 3H), 7.02 (d, J=7.1 Hz, 1H), 6.99 (dd, J=8.6, 3.2 Hz, 1H), 6.74-6.70 (m, 1H), 6.68-6.66 (m, 1H), 6.54-6.46 (m, 2H), 5.04-4.97 (m, 1H), 3.98 (q, J=5.3 Hz, 2H), 3.75 (dd, J=12.9, 6.1 Hz, 2H), 3.73-3.70 (m, 1H), 3.65-3.61 (m, 3H), 3.40-3.36 (m, 2H), 3.08 (s, 1.5H), 2.93 (s, 1.5H), 2.80-2.74 (m, 1H), 2.70-2.68 (m, 1H), 2.67-2.64 (m, 1H), 2.63-2.61 (m, 1H), 2.60-2.58 (m, 1H), 2.42 (qd, J=7.4, 2.9 Hz, 2H), 2.04-1.93 (m, 1H), 0.88 (td, J=7.5, 1.6 Hz, 3H). HRMS (ESI-TOF) m/z: [M+H]$^+$ calculated for C$_{43}$H$_{45}$N$_4$O$_7$, 729.3283; found: 729.3279.

(Z)-3-(2-(2-((2-(2,6-Dioxopiperidin-3-yl)-1,3-dioxoisoindolin-4-yl)amino)ethoxy)ethoxy)-N-(2-(4-(1,2-diphenylbut-1-en-1-yl)phenoxy)ethyl)-N-methylpropanamide (compound 15) (17 mg, 72%) as yellow solid. $^1$H NMR (600 MHz, Methanol-d$_4$) δ 7.53-7.45 (m, 1H), 7.35-7.31 (m, 2H), 7.27-7.24 (m, 1H), 7.21-7.19 (m, 1H), 7.17-7.13 (m, 2H), 7.12-7.08 (m, 3H), 7.04-6.99 (m, 2H), 6.78-6.75 (m, 2H), 6.56-6.55 (m, 2H), 5.05-4.97 (m, 1H), 3.98-3.95 (m, 2H), 3.72 (dt, J=7.9, 6.3 Hz, 2H), 3.68 (t, J=5.3 Hz, 1H), 3.64-3.59 (m, 4H), 3.57-3.54 (m, 3H), 3.40 (dt, J=8.4, 5.3 Hz, 2H), 3.06 (s, 1.5H), 2.92 (s, 1.5H), 2.80-2.73 (m, 1H), 2.71-2.63 (m, 3H), 2.56 (t, J=6.3 Hz, 1H), 2.46-2.41 (m, 2H), 2.07-1.96 (m, 1H), 0.90-0.88 (m, 3H). HRMS (ESI-TOF) m/z: [M+H]$^+$ calcd for $C_{45}H_{49}N_4O_8$, 773.3545; found: 773.3553.

(Z)-3-(2-(2-(2-((2-(2,6-dioxopiperidin-3-yl)-1,3-dioxoisoindolin-4-yl)amino)ethoxy)ethoxy)ethoxy)-N-(2-(4-(1,2-diphenylbut-1-en-1-yl)phenoxy)ethyl)-N-methylpropanamide (compound 34) (12 mg, 63%) as yellow solid. $^1$H NMR (600 MHz, Methanol-$d_4$) δ 7.56-7.48 (m, 1H), 7.34 (t, J=7.5 Hz, 2H), 7.25 (t, J=7.3 Hz, 1H), 7.20 (d, J=7.5 Hz, 2H), 7.16 (t, J=7.5 Hz, 2H), 7.12-7.08 (m, 3H), 7.07-7.03 (m, 2H), 6.75 (dd, J=8.5, 1.7 Hz, 2H), 6.54 (dd, J=8.6, 3.2 Hz, 2H), 5.06-5.00 (m, 1H), 3.98 (dt, J=14.5, 5.2 Hz, 2H), 3.70 (t, J=5.8 Hz, 2H), 3.68-3.63 (m, 3H), 3.62-3.53 (m, 9H), 3.47-3.43 (m, 2H), 3.08 (s, 1.5H), 2.92 (s, 1.5H), 2.83-2.77 (m, 1H), 2.72-2.63 (m, 3H), 2.57 (t, J=6.3 Hz, 1H), 2.43 (q, J=7.4 Hz, 2H), 2.06-2.01 (m, 1H), 0.89 (t, J=7.4 Hz, 3H).

(Z)-1-((2-(2,6-dioxopiperidin-3-yl)-1,3-dioxoisoindolin-4-yl)amino)-N-(2-(4-(1,2-diphenyl but-1-en-1-yl)phenoxy)ethyl)-N-methyl-3,6,9,12-tetraoxapentadecan-15-amide (compound 54) (8 mg, 50%) as yellow solid. $^1$H NMR (600 MHz, Methanol-$d_4$) δ 7.53-7.49 (m, 1H), 7.33 (t, J=7.6 Hz, 2H), 7.26-7.23 (m, 1H), 7.21-7.18 (m, 2H), 7.17-7.13 (m, 2H), 7.12-7.02 (m, 5H), 6.77-6.73 (m, 2H), 6.56-6.52 (m, 2H), 5.05-4.99 (m, 1H), 4.00 (t, J=5.2 Hz, 1H), 3.96 (t, J=5.4 Hz, 1H), 3.72-3.51 (m, 18H), 3.48-3.43 (m, 2H), 3.08 (s, 1.5H), 2.92 (s, 1.5H), 2.84-2.76 (m, 1H), 2.73-2.65 (m, 3H), 2.57 (t, J=6.3 Hz, 1H), 2.43 (q, J=7.4 Hz, 2H), 2.08-2.02 (m, 1H), 0.89 (t, J=7.4 Hz, 3H). HRMS (ESI-TOF) m/z: [M+H]$^+$ calculated for $C_{49}H_{57}N_4O_{10}$, 861.4069; found: 861.4076.

(Z)-1-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methyl-3,6,9,12,15-pentaoxaoctadecan-18-amide (compound 64) (15 mg, 52%). $^1$H NMR (600 MHz, Methanol-$d_4$) δ 7.54-7.49 (m, 1H), 7.34 (td, J=2.8, 7.6 Hz, 2H), 7.27-7.23 (m, 1H), 7.22-7.18 (m, 2H), 7.18-7.13 (m, 2H), 7.12-7.02 (m, 5H), 6.78-6.73 (m, 2H), 6.57-6.52 (m, 2H), 5.05-5.00 (m, 1H), 4.00 (t, J=5.4 Hz, 1H), 3.98-3.95 (m, 1H), 3.73-3.51 (m, 22H), 3.46 (q, J=5.6 Hz, 2H), 3.08 (s, 1.5H), 2.92 (s, 1.5H), 2.85-2.77 (m, 1H), 2.73-2.71 (m, 1H), 2.70-2.66 (m, 2H), 2.58 (t, J=6.3 Hz, 1H), 2.43 (q, J=7.4 Hz, 2H), 2.08-2.02 (m, 1H), 0.89 (t, J=7.4 Hz, 3H). HRMS (ESI-TOF) m/z: [M+H]$^+$ calculated for $C_{51}H_{61}N_4O_{11}$, 905.4331; found: 905.4331.

(Z)-2-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylacetamide (compound 88) (20 mg, 66%) as yellow solid. $^1$H NMR (600 MHz, Methanol-$d_4$) δ 7.49-7.39 (m, 1H), 7.33 (t, J=7.6 Hz, 2H), 7.27-7.24 (m, 1H), 7.20 (d, J=7.6 Hz, 2H), 7.17-7.13 (m, 2H), 7.12-7.06 (m, 3H), 7.05 (dd, J=7.1, 1.4 Hz, 1H), 6.92-6.85 (m, 1H), 6.78-6.75 (m, 2H), 6.59-6.55 (m, 2H), 5.10-5.02 (m, 1H), 4.27 (s, 1H), 4.11 (s, 1H), 4.09 (t, J=5.0 Hz, 1H), 4.02 (t, J=5.3 Hz, 1H), 3.73 (dt, J=12.7, 5.2 Hz, 2H), 3.12 (s, 1.5H), 2.99 (s, 1.5H), 2.88-2.82 (m, 1H), 2.77-2.69 (m, 2H), 2.44 (q, J=7.4 Hz, 2H), 2.14-2.06 (m, 1H), 0.90 (t, J=7.4 Hz, 3H). HRMS (ESI-TOF) m/z: [M+H]$^+$ calculated for $C_{40}H_{39}N_4O_6$, 671.2864; found: 671.2869.

(Z)-3-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylpropanamide (compound 89) (18 mg, 60%) as yellow solid. $^1$H NMR (600 MHz, Methanol-$d_4$) δ 7.53-7.44 (m, 1H), 7.34 (td, J=7.5, 3.3 Hz, 2H), 7.28-7.23 (m, 1H), 7.19 (d, J=7.0 Hz, 2H), 7.17-7.13 (m, 2H), 7.10-7.07 (m, 3H), 7.05 (d, J=8.6 Hz, 1H), 7.01 (dd, J=9.4, 7.1 Hz, 1H), 6.74-6.66 (m, 2H), 6.52-6.50 (m, 1H), 6.40 (d, J=8.8 Hz, 1H), 5.03-4.97 (m, 1H), 3.99-3.94 (m, 2H), 3.68-3.64 (m, 2H), 3.61 (dt, J=11.0, 6.3 Hz, 2H), 3.00 (s, 1.5H), 2.92 (s, 1.5H), 2.84-2.76 (m, 2H), 2.72-2.59 (m, 3H), 2.43 (q, J=7.4 Hz, 2H), 2.02-1.94 (m, 1H), 0.89 (t, J=7.4 Hz, 3H). HRMS (ESI-TOF) m/z: [M+H]$^+$ calculated for $C_{41}H_{41}N_4O_6$, 685.3021; found: 685.3022.

(Z)-4-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylbutanamide (compound 108) (14 mg, 48%) as yellow solid. $^1$H NMR (600 MHz, Methanol-$d_4$) δ 7.56-7.48 (m, 1H), 7.35-7.32 (m, 2H), 7.25 (t, J=7.3 Hz, 1H), 7.20 (d, J=7.5 Hz, 2H), 7.16-7.13 (m, 2H), 7.10-7.06 (m, 3H), 7.04-7.02 (m, 1H), 7.00-6.97 (m, 1H), 6.75 (dd, J=8.5, 1.7 Hz, 2H), 6.54-6.52 (m, 1H), 6.47-6.45 (m, 1H), 5.06-5.00 (m, 1H), 3.98 (dt, J=14.5, 5.2 Hz, 2H), 3.68-3.64 (m, 2H), 3.33-3.30 (m, 2H), 3.08 (s, 1.5H), 2.92 (s, 1.5H), 2.83-2.77 (m, 1H), 2.72-2.63 (m, 2H), 2.57 (t, J=6.3 Hz, 1H), 2.45-2.40 (m, 3H), 2.06-2.01 (m, 1H), 1.97-1.89 (m, 2H), 0.89 (t, J=7.4 Hz, 3H). HRMS (ESI-TOF) m/z: [M+H]$^+$ calculated for $C_{42}H_{43}N_4O_6$, 699.3177; found: 699.3175.

(Z)-6-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylhexanamide (compound 120) (17 mg, 60%) as yellow solid. $^1$H NMR (600 MHz, Methanol-$d_4$) δ 7.54-7.47 (m, 1H), 7.36-7.30 (m, 2H), 7.27-7.22 (m, 1H), 7.20-7.17 (m, 2H), 7.16-7.12 (m, 2H), 7.11-7.06 (m, 3H), 7.04-6.98 (m, 2H), 6.75-6.73 (m, 2H), 6.56-6.51 (m, 2H), 5.06-5.00 (m, 1H), 4.03-3.96 (m, 2H), 3.68 (t, J=5.1 Hz, 1H), 3.65 (t, J=5.4 Hz, 1H), 3.27 (dd, J=14.5, 7.2 Hz, 2H), 3.07-3.04 (s, 1.5H), 2.92 (s, 1.5H), 2.85-2.79 (m, 1H), 2.75-2.62 (m, 2H), 2.45-2.41 (m, 3H), 2.34 (t, J=7.3 Hz, 1H), 2.07-2.03 (m, 1H), 1.69-1.57 (m, 4H), 1.45-1.37 (m, 2H), 0.92-0.86 (m, 3H). HRMS (ESI-TOF) m/z: [M+H]$^+$ calculated for $C_{44}H_{47}N_4O_6$, 727.3490; found: 727.3495.

(Z)-7-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylheptanamide (compound 126) (19 mg, 69%) as yellow solid. $^1$H NMR (600 MHz, Methanol-$d_4$) δ 7.53-7.50 (m, 1H), 7.33 (td, J=7.6, 1.8 Hz, 2H), 7.26-7.23 (m, 1H), 7.21-7.18 (m, 2H), 7.17-7.12 (m, 2H), 7.12-7.06 (m, 3H), 7.01 (dd, J=11.3, 7.9 Hz, 2H), 6.77-6.72 (m, 2H), 6.55-6.53 (m, 2H), 5.09-4.99 (m, 1H), 4.02-3.98 (m, 2H), 3.68 (t, J=5.1 Hz, 1H), 3.65 (t, J=5.4 Hz, 1H), 3.27 (t, J=7.0 Hz, 2H), 3.06 (s, 1.5H), 2.91 (s, 1.5H), 2.86-2.78 (m, 1H), 2.75-2.63 (m, 2H), 2.45-2.39 (m, 3H), 2.33 (t, J=7.4 Hz, 1H), 2.10-2.03 (m, 1H), 1.67-1.55 (m, 4H), 1.45-1.32 (m, 4H), 0.90-0.88 (m, 3H). HRMS (ESI-TOF) m/z: [M+H]$^+$ calculated for $C_{45}H_{49}N_4O_6$, 741.3647; found: 741.3650.

(Z)-8-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methyloctanamide (compound 143) (22 mg, 81%) as yellow solid. HRMS (ESI-TOF) m/z: [M+H]$^+$ calculated for $C_{46}H_{51}N_4O_6$, 755.3803; found: 755.3809.

Example 2. ERα Degradative Activity of Compounds of the Present Disclosure in T47D Cells T47D cells were plated in 24-well plates at 1.5×10$^5$ cells/well in the RPMI growth medium containing 10% FBS and 1× Penicillin Streptomycin, and then incubated at 37° C. overnight. The following day, the test compound was administered to the cells by using 1000× compound stock solution prepared in DMSO at various concentrations. After administration of the compound, the cells were then incubated at 37 C for various period of treatment time, e.g., as indicated in the figures.

Upon completion, the cells were washed with PBS and protein was collected in Laemmli sample buffer (1×; VWR International). Protein was isolated from cell lysate (approximately 25 μg) by SDS-PAGE and transferred to nitrocellulose membranes. Non-specific binding was blocked by incubtation with blocking buffer (5% milk in Tris-buffered saline with 0.1% Tween 20 ("TBS-T")) at rt for 60 minutes.

The membrane was then incubated with primary antibodies (mouse anti-ERα (1:500, Santa Cruz), mouse anti-GAPDH (1:5,000, Santa Cruz), or mouse anti-actin (1:4,000, Santa Cruz)) overnight at 4° C., followed by washing (3 times) with TBS-T, and then incubation with horseradish peroxidase-conjugated rabbit anti-mouse IgG (1:5,000) for 60 minutes. After the TBS-T washes, blots were developed with an enhanced chemiluminescence kit (ThermoFisher Scientific) and the bands were imaged and quantified by densitometry (Bio-Rad).

FIGS. 2A, 2B, 2C, and 2D show the ERα degradation ability of compounds 8, 15, 54, 64, 88, 89, 108, 120, 126, and 143 in T47D cells at various concentrations and time points. Similarly, FIG. 2E shows the ERα degradation ability of compound 64 in T47D cells at a concentration of 100 nM at various time points.

The $DC_{50}$ values (i.e., the concentration of test compound at which 50% of the target protein is degraded) was calculated for various compounds of the present disclosure and are shown in the Table 3, below. A corresponds to a $DC_{50}$ value less than or equal to 1.5 μM; B corresponds to a $DC_{50}$ value greater than 1.5 μM and less than 3 μM; and C corresponds to a $DC_{50}$ value greater than 3 μM.

TABLE 3

DC50 Values in T47D Cell Line.

| Compound | $DC_{50}$ Value |
|---|---|
| 8 | C |
| 15 | C |
| 54 | A |
| 64 | A |
| 88 | C |
| 89 | A |
| 108 | A |
| 120 | A |
| 126 | B |
| 143 | B |

Example 3. ERα Degradative Activity of Compounds of the Present Disclosure in MCF7 Cells MCF7 cells were plated in 24-well plates at $1.5 \times 10^5$ cells/well in the DMEM growth medium containing 10% FBS and 1× Penicillin Streptomycin, and then incubated at 37° C. overnight. The following day, the test compound was administered to the cells by using 1000× compound stock solution prepared in DMSO at various concentrations. After administration of the compound, the cells were then incubated at 37° C. for various period of treatment time, e.g., as indicated in the figures.

Upon completion, the cells were washed with PBS and protein was collected in Laemmli sample buffer (1×; VWR International). Protein was isolated from cell lysate (approximately 25 μg) by SDS-PAGE and transferred to nitrocellulose membranes. Non-specific binding was blocked by incubtation with blocking buffer (5% milk in Tris-buffered saline with 0.1% Tween 20 ("TBS-T")) at rt for 60 minutes.

Figure 3B:
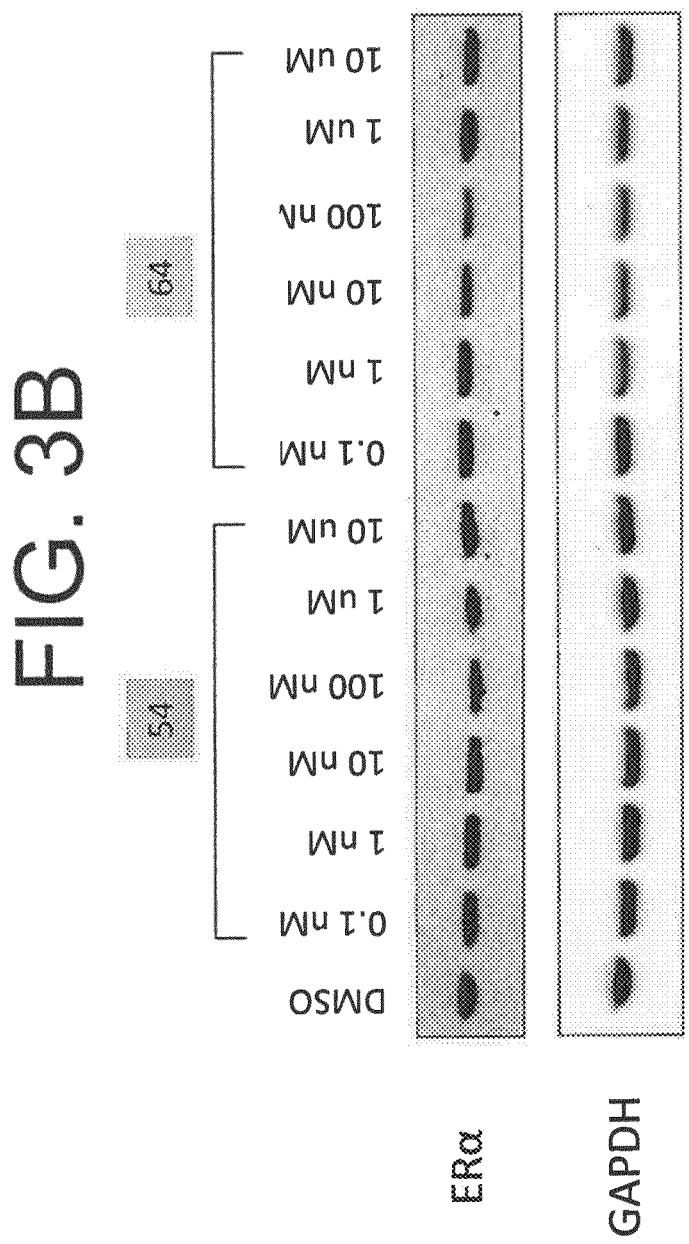
FIG. 3B illustrates the ERα degradative activity of exemplary compounds 54 and 64 of the present disclosure in an MCF7 cell line 6 hours after administration.

The membrane was then incubated with primary antibodies (mouse anti-ERα (1:500, Santa Cruz), mouse anti-GAPDH (1:5,000, Santa Cruz), or mouse anti-actin (1:4,000, Santa Cruz)) overnight at 4° C., followed by washing (3 times) with TBS-T, and then incubation with horseradish peroxidase-conjugated rabbit anti-mouse IgG (1:5,000) for 60 minutes. After the TBS-T washes, blots were developed with an enhanced chemiluminescence kit (ThermoFisher Scientific) and the bands were imaged and quantified by densitometry (Bio-Rad). FIGS. 3A and 3B show the ERα degradation ability of compounds 15, 54, and 64 in MCF7 cells at various concentrations at 4 and 6 hours, respectively.

FIG. 3C shows the ERα degradation ability of exemplary compounds 160a, 184a, 17a, 16a, 31a, 28a, 32a, 29a, 161a, and 185a of the present disclosure in an MCF7 cell line 6 hours after administration.

Figure 3D:
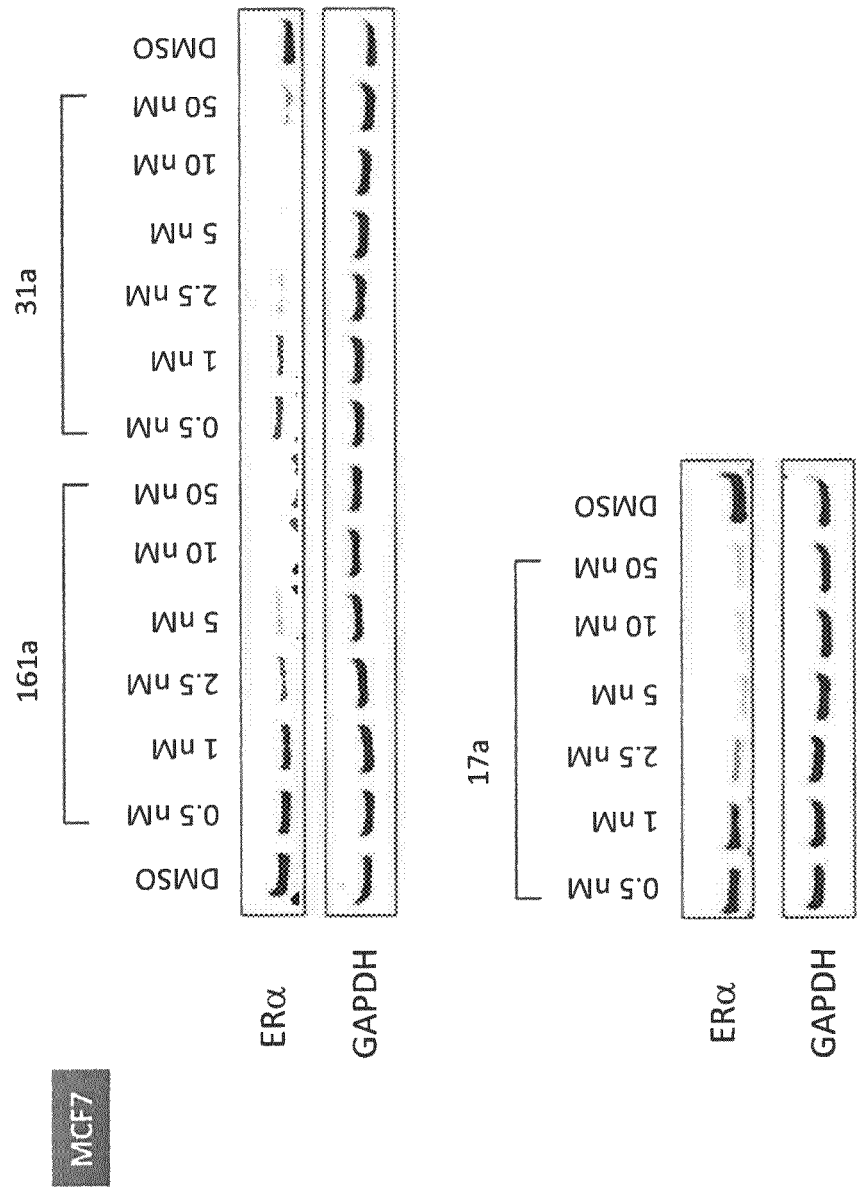
FIG. 3D illustrates the ERα degradative activity of exemplary compounds 161a, 31a, and 17a of the present disclosure in an MCF7 cell line 6 hours after administration.

FIG. 3D shows the ERα degradation ability of exemplary compounds 161a, 31a, and 17a of the present disclosure in an MCF7 cell line 6 hours after administration.

Example 4. ERα Degradative Activity of Compounds of the Present Disclosure in CAMA1 Cells CAMA1 cells were plated in 24-well plates at $2 \times 10^5$ cells/well in the RPMI growth medium containing 20% FBS and 1× Penicillin Streptomycin, and then incubated at 37° C. overnight. The following day, the test compound was administered to the cells by using 1000× compound stock solution prepared in DMSO at various concentrations. After administration of the compound, the cells were then incubated at 37° C. for various period of treatment time, e.g., as indicated in the figures.

Upon completion, the cells were washed with PBS and protein was collected in Laemmli sample buffer (1×; VWR International). Protein was isolated from cell lysate (approximately 25 μg) by SDS-PAGE and transferred to nitrocellulose membranes. Non-specific binding was blocked by incubtation with blocking buffer (5% milk in Tris-buffered saline with 0.1% Tween 20 ("TBS-T")) at rt for 60 minutes.

The membrane was then incubated with primary antibodies (mouse anti-ERα (1:500, Santa Cruz), mouse anti-GAPDH (1:5,000, Santa Cruz), or mouse anti-actin (1:4,000, Santa Cruz)) overnight at 4° C., followed by washing (3 times) with TBS-T, and then incubation with horseradish peroxidase-conjugated rabbit anti-mouse IgG (1:5,000) for 60 minutes. After the TBS-T washes, blots were developed with an enhanced chemiluminescence kit (ThermoFisher Scientific) and the bands were imaged and quantified by densitometry (Bio-Rad).

Figure 4B:
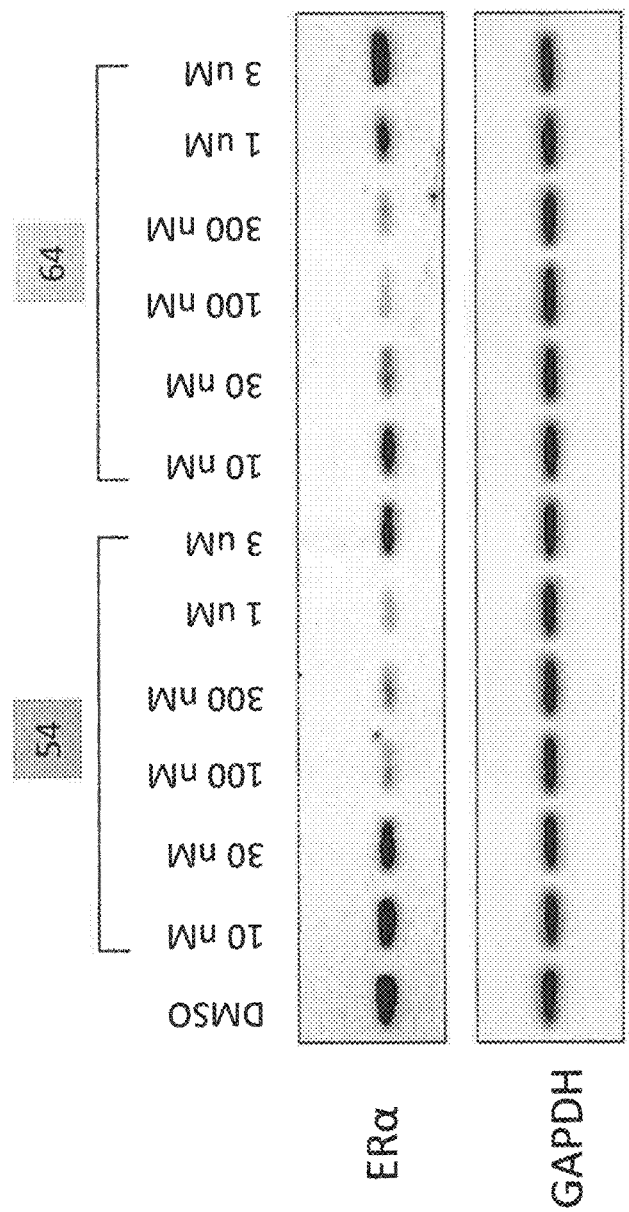
FIG. 4B illustrates the ERα degradative activity of exemplary compounds 54 and 64 of the present disclosure at various concentrations in a CAMA1 cell line 6 hours after administration.

FIGS. 4A and 4B show the ERα degradation ability of compounds 54 and 64 in CAMA1 cells at various concentrations at 6 hours after administration. FIG. 4C shows the ERα degradation ability of compound 64 at a concentration of 100 nM at various time points in CAMA1 cells.

Example 5. ERα Degradative Activity of Compounds of the Present Disclosure in ZR-75-1 Cells ZR-75-1 cells were plated in 24-well plates at $1.8 \times 10^5$ cells/well in the RPMI growth medium containing 20% FBS and 1× Penicillin Streptomycin, and then incubated at 37° C. overnight. The following day, the test compound was administered to the cells by using 1000× compound stock solution prepared in DMSO at various concentrations. After administration of the compound, the cells were then incubated at 37° C. for various period of treatment time, e.g., as indicated in the figures.

Upon completion, the cells were washed with PBS and protein was collected in Laemmli sample buffer (1×; VWR International). Protein was isolated from cell lysate (approximately 25 μg) by SDS-PAGE and transferred to nitrocellulose membranes. Non-specific binding was blocked by incubtation with blocking buffer (5% milk in Tris-buffered saline with 0.1% Tween 20 ("TBS-T")) at rt for 60 minutes. The membrane was then incubated with primary antibodies (mouse anti-ERα (1:500, Santa Cruz), mouse anti-GAPDH (1:5,000, Santa Cruz), or mouse anti-actin (1:4,000, Santa Cruz)) overnight at 4° C., followed by washing (3 times) with TBS-T, and then incubation with horseradish peroxidase-conjugated rabbit anti-mouse IgG (1:5,000) for 60 minutes. After the TBS-T washes, blots were developed with an enhanced chemiluminescence kit (ThermoFisher Scientific) and the bands were imaged and quantified by densitometry (Bio-Rad).

Figure 5B:
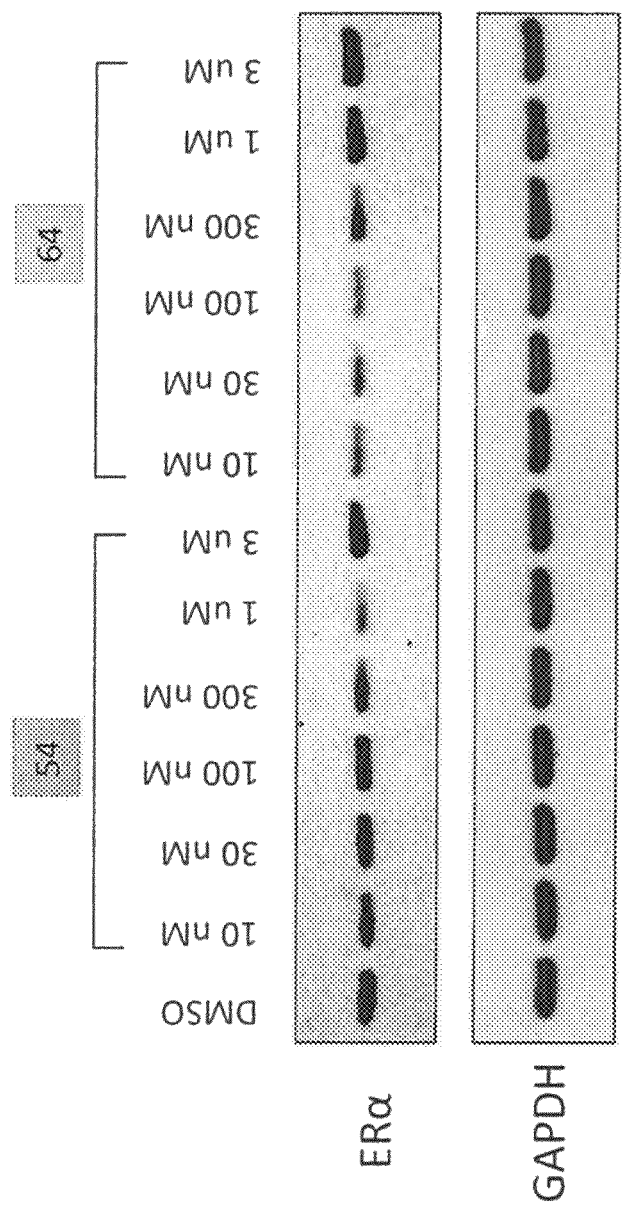
FIG. 5B illustrates the ERα degradative activity of exemplary compounds 54 and 64 of the present disclosure at various concentrations in a ZR-75-1 cell line 6 hours after administration.
Figure 5C:
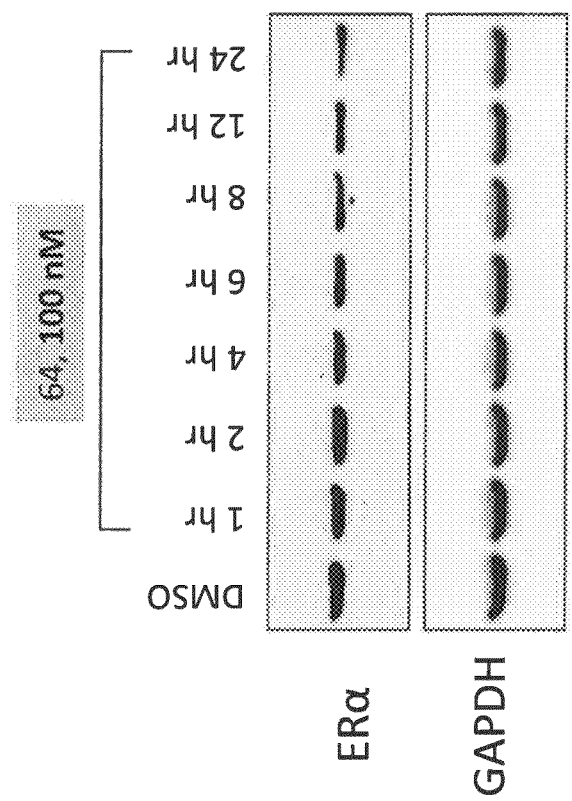
FIG. 5C illustrates the ERα degradative activity of an exemplary compound 64 of the present disclosure at a concentration of 100 nM, as a function of time, in a ZR-75-1 cell line.

FIGS. 5A and 5B show the ERα degradation ability of compounds 54 and 64 in ZR-75-1 cells at various concentrations at 6 hours after administration. FIG. 5C shows the ERα degradation ability of compound 64 at a concentration of 100 nM at various time points in ZR-75-1 cells.

Example 6. ERα Degradative Activity of Compounds of the Present Disclosure in a Number of Cell Lines Proteins in cell lysate were separated by SDS-PAGE and transferred to Odyssey nitrocellulose membranes (Licor) with Iblot® dry blotting transfer system (ThermoFisher). Nonspecific binding was blocked by incubating membranes with Intercept Blocking Buffer (Licor) for 1 hour at room temperature with gentle shaking. The membranes were then incubated overnight at 4° C. with Primary antibodies rabbit anti-ER (Cell Signaling, 8644), rabbit anti-PR (Cell Signaling, 8757), rabbit anti-IKZF1 (Cell Signaling, 14859), rabbit anti-IKZF3 (Abcam, ab139408), rabbit anti-GSPT1 (Abcam, ab126090) and mouse anti-GAPDH (1:5,000, Santa Cruz Biotechnology, sc-47724) diluted in Intercept Blocking Buffer containing 0.1% Tween 20. After washing 3 times with TBS-T, the membranes were incubated with IRDye® 800CW goat anti-mouse IgG (1:20,000, Licor) or IRDye® 800CW goat anti-rabbit IgG (1:20,000, Licor) for 1 hour. After TBS-T washes, membranes were rinsed in TBS and scanned on Odyssey® CLx Imaging System (Licor). The bands were quantified using Image Studio™ Software (Licor).

Figure 6:
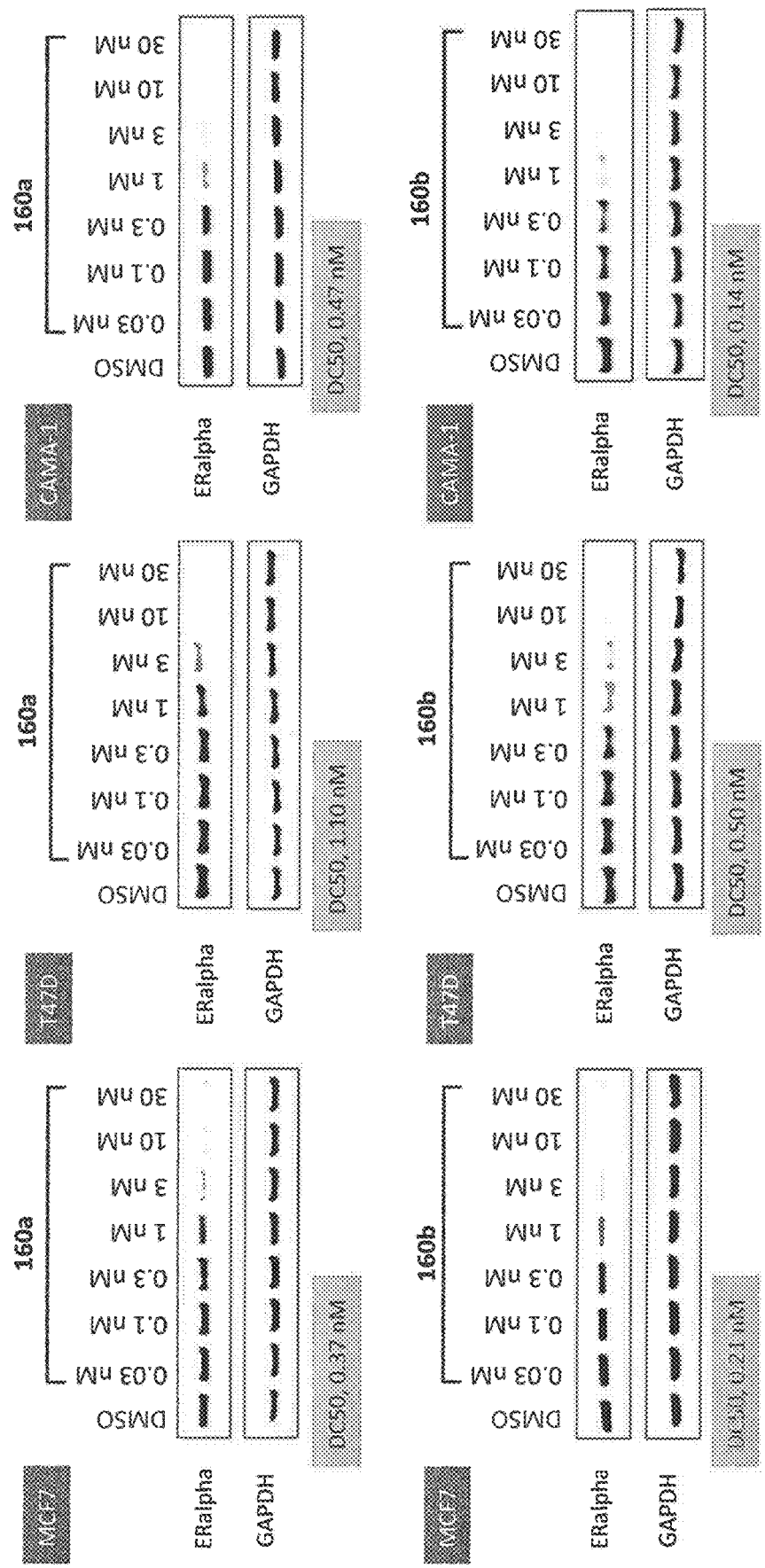
FIG. 6 illustrates the ERα degradative activity of exemplary compounds 160a and 160b of the present disclosure in MCF7, T47D, and CAMA-1 cell lines 6 hours after administration.
Figure 7:
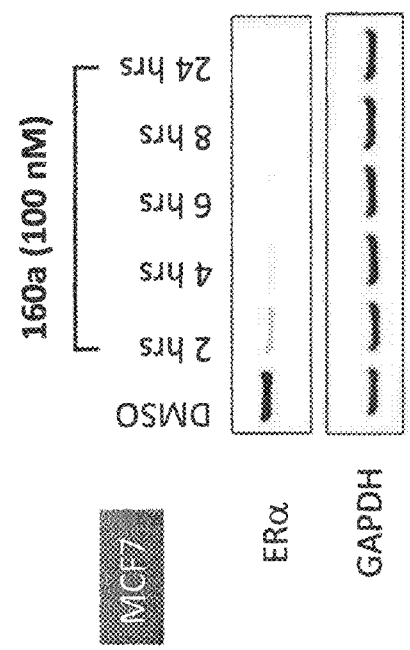
FIG. 7 illustrates the ERα degradative activity of exemplary compound 160a of the present disclosure at a concentration of 100 nM, as a function of time, in an MCF7 cell line.

FIG. 6 shows the ERα degradation ability of compounds 160a and 160b in MCF7, T47D, and CAMA-1 cell lines at various concentrations 6 hours after administration. FIG. 7 shows the ERα degradation ability of exemplary compound 160a of the present disclosure at a concentration of 100 nM, as a function of time, in a MCF7 cell line.

Figure 8:
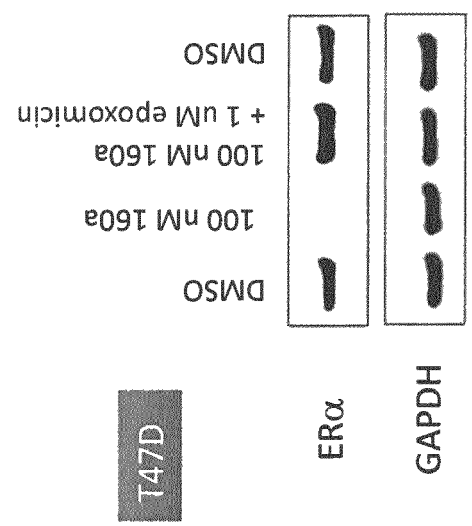
FIG. 8 illustrates the ERα degradative activity of an exemplary compound 160a of the present disclosure at a concentration of 100 nM, in the absence and presence of 1 uM proteasome inhibitor epoxomicin, in a T47D cell line, 6 hours after administration.

FIG. 8 shows the ERα degradation ability of exemplary compound 160a of the present disclosure at a concentration of 100 nM, in the absence and presence of 1 uM proteasome inhibitor epoxomicin, in a T47D cell line, 6 hours after administration.

Figure 9:
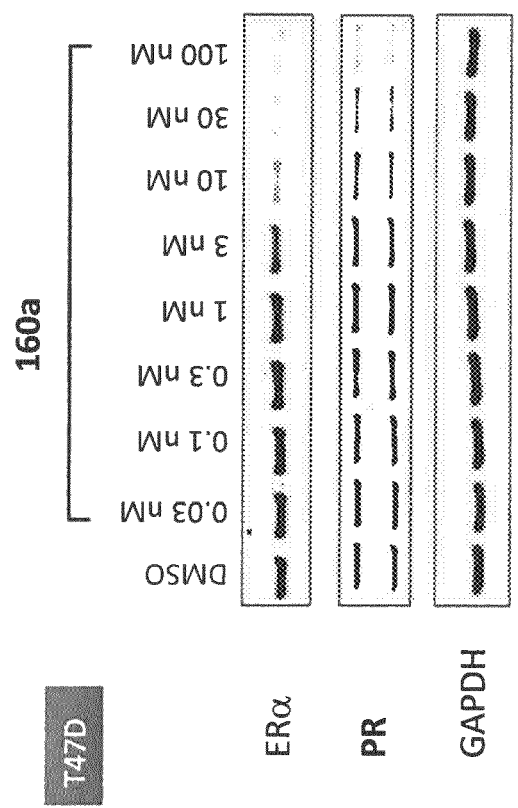
FIG. 9 illustrates the downregulation of PR resulted from ERα degradation by exemplary compound 160a of the present disclosure in a T47D cell line 24 hours after administration.

FIG. 9 shows the downregulation of PR resulted from ERα degradation by exemplary compound 160a of the present disclosure in a T47D cell line 24 hours after administration.

Figure 10:
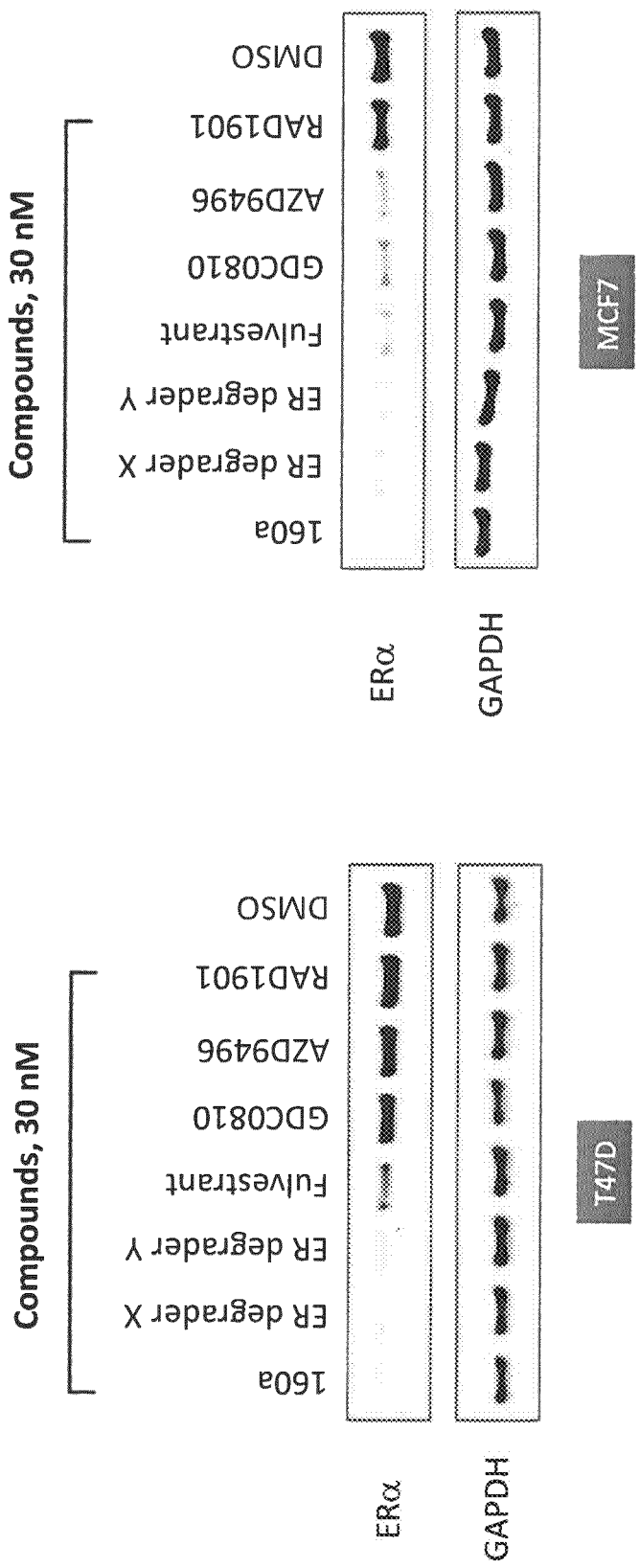
FIG. 10 illustrates the ERα degradative activity of exemplary compound 160a of the present disclosure and several published SERDs at a concentration of 30 nM, in T47D and MCF7 cell lines 6 hours after administration.

FIG. 10 shows the ERα degradation ability of exemplary compound 160a of the present disclosure and several published SERDs at a concentration of 30 nM, in T47D and MCF7 cell lines 6 hours after administration.

Figure 11:
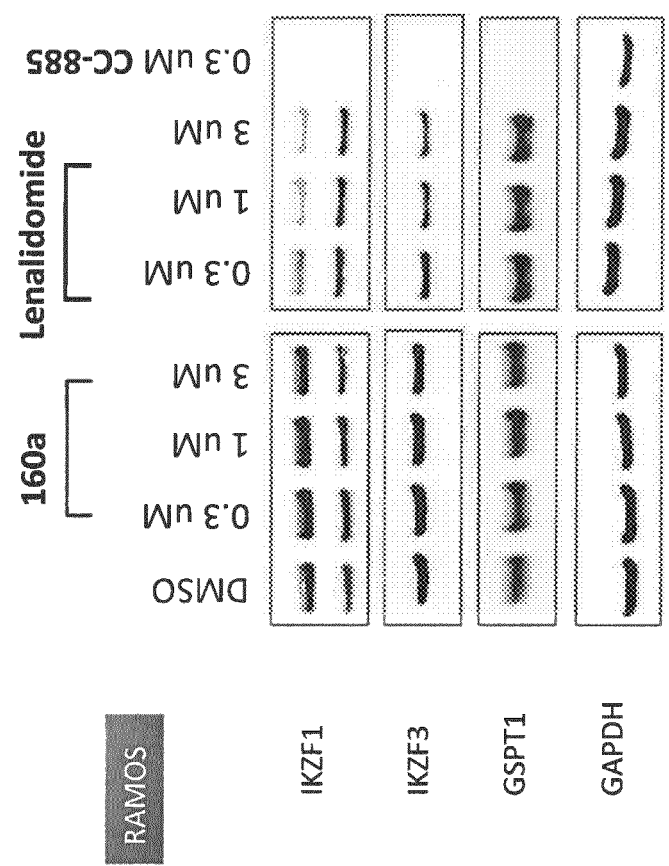
FIG. 11 illustrates lack of IKZF1, IKZF3 and GSPT1 degradative activity of exemplary compound 160a of the present disclosure, in a RAMOS cell line 24 hours after administration.

FIG. 11 shows the lack of IKZF1, IKZF3 and GSPT1 degradation ability of exemplary compound 160a of the present disclosure, in a RAMOS cell line 24 hours after administration. Lenalidomide and CC-885 were used as controls.

Example 7. Growth Inhibitory Activity of Exemplary Compound 160a of the Present Disclosure in MCF7, T47D, CAMA-1, and RAMOS MCF7 (ATCC), T47D(ATCC) and CAMA-1 (ATCC) were plated in 96-well plates at 3,000 cell/well in 90 ul of RPMI growth medium containing 10% FBS and 1% Penicillin Streptomycin. RAMOS (ATCC) cells were plated in 96-well plates at 5,000 cell/well in 90 ul of RPMI growth medium containing 10% heat inactive serum and 1% Penicillin Streptomycin. Cells were incubated at 37° C. overnight. The following day, the test compound was administered to the cells by using 10× compound stock solution prepared in growth medium at various concentrations. After administration of the compound, the MCF7, T47D, CAMA-1 cells were then incubated at 37° C. for 6 days. RAMOS cells were incubated for 3 days. Before CellTiter-Glo assay, the plates were equilibrated at room temperature for approximately 10 minutes. 100 ul of CellTiter-Glo® Reagent (Promega) was added to each well. The plates were then incubated at room temperature for 10 minutes and luminescence was recorded by EnSpire plate reader (PerkinElmer).

Table 4 shows the growth inhibitory activity (see EC50 value) of exemplary compound 160a of the present disclosure in 4 cell lines (i.e. MCF7, T47D, CAMA-1, and RAMOS) 6 days after administration.

TABLE 4

| Growth inhibitory activity of compound 160a. | |
|---|---|
| Cell line | EC50 (nM) |
| MCF7 | 8.3 |
| T47D | 14 |
| CAMA-1 | 3.8 |
| RAMOS | >3,000 |

Example 8. Inhibition of the ERα Luciferase Reporter by Compound 160a in a T47D ERE-Luc Reporter Cell Line 24 Hours after Administration T47D-KBluc (ATCC) cells were plated in 96-well plates at 20,000 cells/well in 90 ul of RPMI growth medium containing 10% FBS, 5 μg/ml bovine insulin and 1% Penicillin Streptomycin, and then incubated at 37° C. overnight. The following day, the test compound was administered to the cells by using 10× compound stock solution prepared in growth medium at various concentrations. After administration of the compound, the cells were then incubated at 37° C. for 24 hours. Before One-Glo assay, the plate was equilibrated at room temperature for approximately 10 minutes. 100 ul of One-Glo® Reagent (Promega) was added to each well. The plates were then incubated at room temperature for 10 minutes and luminescence was recorded by EnSpire plate reader (PerkinElmer).

Figure 12:
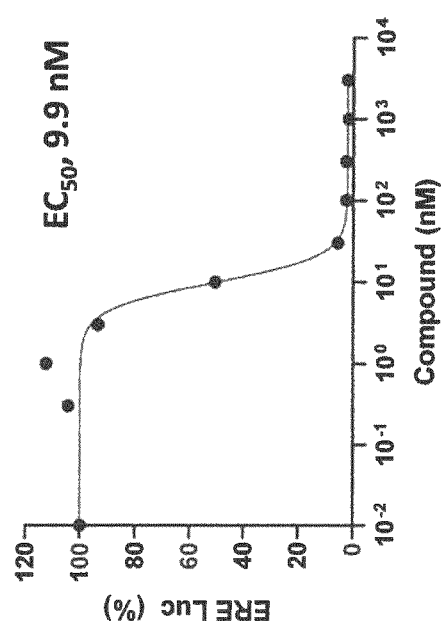
FIG. 12 illustrates inhibition of the ERα luciferase reporter by an exemplary compound 160a of the present disclosure in a T47D ERE-Luc reporter cell line 24 hours after administration.

FIG. 12 shows inhibition of the ERα luciferase reporter by an exemplary compound 160a of the present disclosure in a T47D ERE-Luc reporter cell line 24 hours after administration.

Example 9. ERα Degradative Activity of Compound 160a in MCF7 Xenograft Tumors

MCF-7 tumor bearing BALB/c nude mice were randomized when the average tumor volume reaches approximately 300-500 mm3, with 5 mice per treatment group. Dosing regimen for each group was indicated in FIG. 13. 8 hours after the last dose, tumors were collected and snap frozen in liquid nitrogen. Tumor lysates were prepared by grinding tumors in RIPA Buffer (contains 1% Protease Inhibitor Cocktail and 1% Phosphatase Inhibitor Cocktail 2) with Tissuelyser LT at 50 Hz for 5 min. Proteins in tumor lysates were separated by SDS-PAGE and transferred to Odyssey nitrocellulose membranes with Iblot® dry blotting transfer system (ThermoFisher). Nonspecific binding was blocked by incubation with blocking buffer (5% milk in TBS-T) at room temperature for 60 min. The membrane was then incubated with primary antibodies, anti-ERα and anti-GAPDH, overnight at 4 C. The following day, the membranes were washed 5 times with TBS-T, and then incubated with horseradish peroxidase-conjugated secondary antibody for 60 min. After TBS-T washes, blots were developed with West Femto Maximum Sensitivity kit (thermo fisher scientific). The bands were imaged and quantified by Amersham Imager 680.

Figure 13:
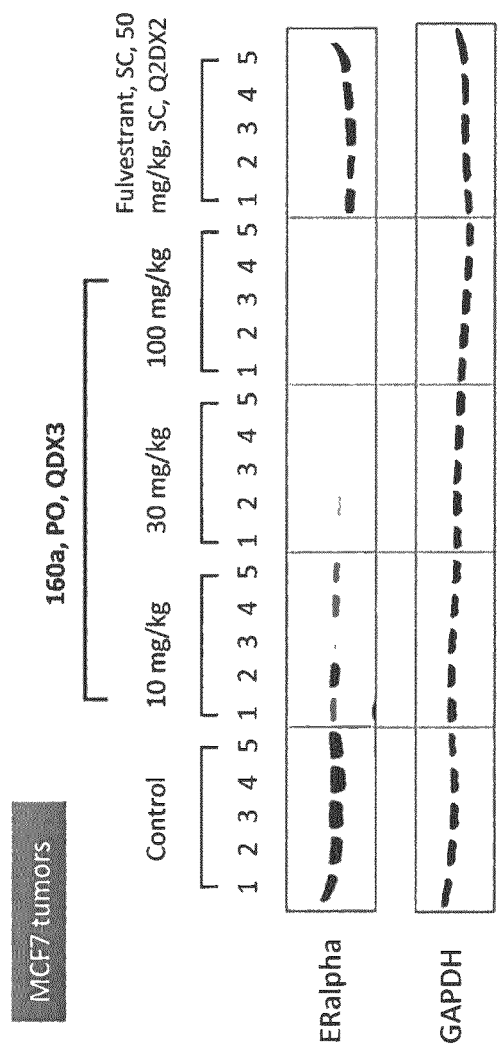
FIG. 13 illustrates the dose-dependent ERα degradative activity of exemplary compound 160a of the present disclosure in MCF7 xenograft tumors after three daily doses.

FIG. 13 shows the dose-dependent ERα degradation ability of exemplary compound 160a of the present disclosure in MCF7 xenograft tumors after three daily doses. Tumors were collected 8 hours after last dose. Fulvestrant at indicated dose was used as comparison.

Figure 14:
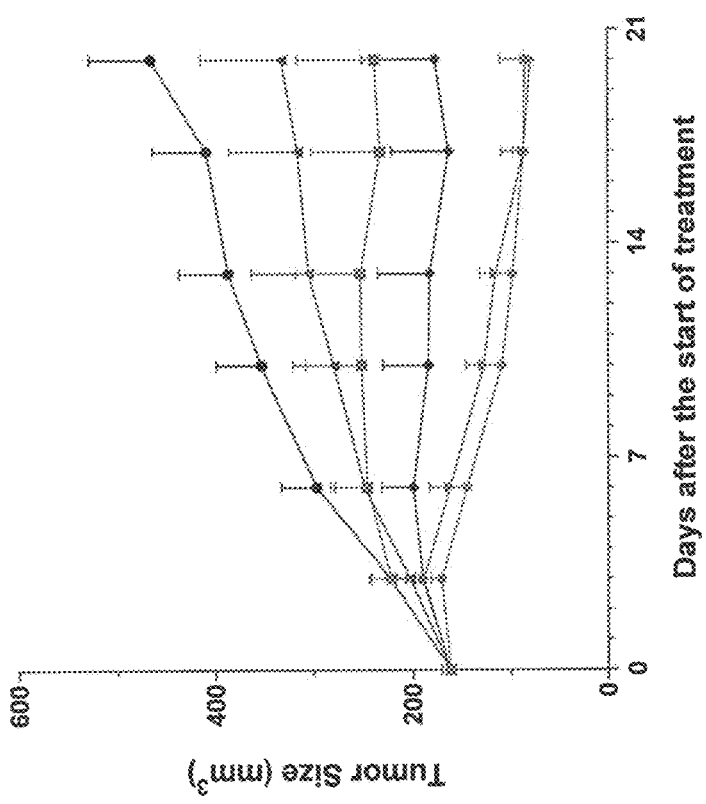
FIG. 14 illustrates the dose-dependent growth inhibitory activity of exemplary compound 160a of the present disclosure in MCF7 xenograft tumors after 21 daily doses.

Example 10. Inhibitory Activity of Exemplary Compound 160a of the Present Disclosure in MCF7 Xenograft Tumors MCF-7 tumor bearing mice BALB/c nude mice were randomized when the average tumor volume reaches approximately 150-200 mm$^3$, with 10 mice per treatment group. Dosing regimen for each group is indicated in FIG. 14. Tumor weight was measured twice every week.

FIG. 14 shows the dose-dependent growth inhibitory activity of exemplary compound 160a of the present disclosure in MCF7 xenograft tumors after 21 daily doses. Fulvestrant at indicated dose was used as comparison.

The many features and advantages of the present disclosure are apparent from the detailed specification, and thus it is intended by the appended claims to cover all such features and advantages of the present disclosure that fall within the true spirit and scope of the present disclosure. Further, since numerous modifications and variations will readily occur to those skilled in the art, it is not desired to limit the present disclosure to the exact construction and operation illustrated and described and accordingly, all suitable modifications and equivalents may be resorted to, falling within the scope of the present disclosure.

Moreover, those skilled in the art will appreciate that the conception upon which this disclosure is based may readily be used as a basis for designing other structures, methods, and systems for carrying out the several purposes of the present disclosure. Accordingly, the claims are not to be considered as limited by the foregoing description or examples.

What is claimed is:

1. A compound of Formula (I) or a tautomer, stereoisomer or a mixture of stereoisomers, or a pharmaceutically acceptable salt, or hydrate thereof:

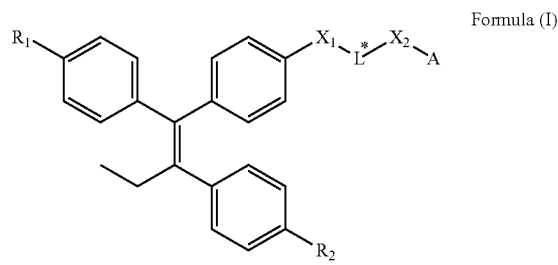

Formula (I)

wherein:

$X^1$ and $X^2$ are each independently selected from $C(R^3)_2$, $NR^4$, O, S, cycloalkyl, aryl, heterocycle, and heteroaryl, each of which is independently substituted with 0, 1, 2, or 3 $R^5$;

A is selected from:

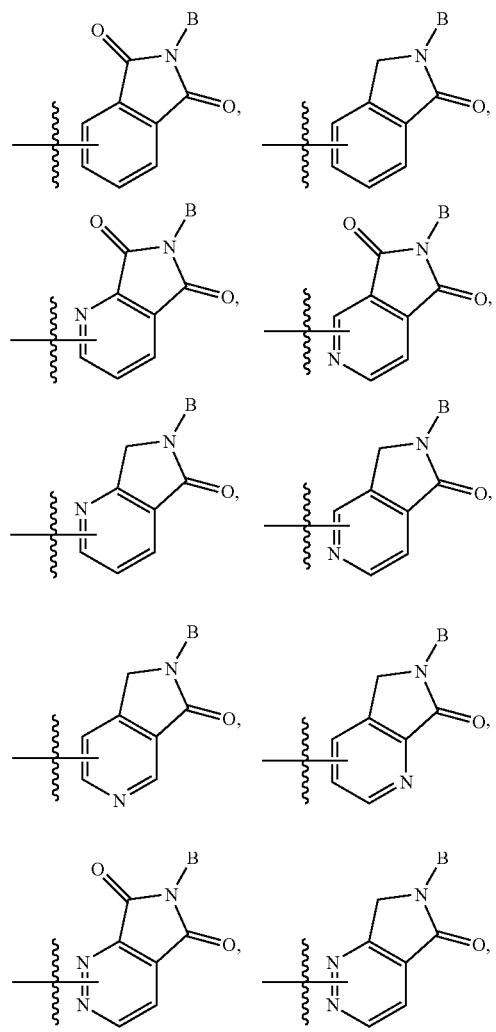

-continued

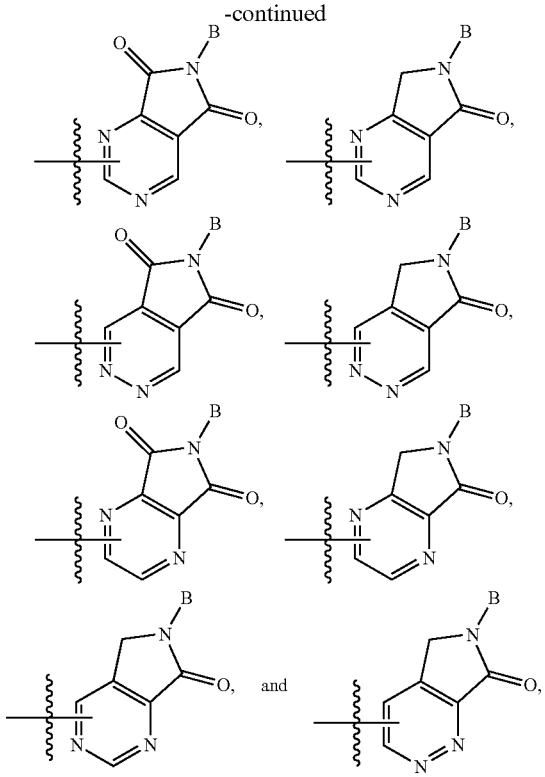

each of which is substituted with 0, 1, 2, or 3 $R^5$;

B is selected from 5- to 6-member cycloalkyl, 5- to 6-member aryl, 5- to 6-member heterocycle, and 5- to 6-member heteroaryl, each of which is substituted with 0, 1, 2, or 3 $R^5$;

L* is a linker of 1 to 22 carbon atoms in length, wherein one or more carbon atoms are each optionally and independently replaced by a group selected from C(O), O, $NR^4$, S, $C_2$-alkenyl, $C_2$-alkynyl, cycloalkyl, aryl, heterocycle, and heteroaryl, each of which is substituted with 0, 1, 2, or 3 $R^5$;

$R^1$ and $R^2$ are each independently selected from H, $C_1$-$C_6$ alkyl, halo, alkoxy, acyloxy, hydroxy, and sulfhydryl, each of which is substituted with 0, 1, 2, or 3 $R^5$;

each $R^3$ is independently selected from H, $C_1$-$C_6$ alkyl, halo, and hydroxy;

each $R^4$ is independently selected from H, $C_1$-$C_6$ alkyl, and acyl, each of which is substituted with 0, 1, 2, or 3 $R^5$; and each $R^5$ is independently selected from $C_1$-$C_6$ alkyl, halo, cyano, and hydroxy, wherein

represents the point of attachment of A to $X^2$.

2. The compound according to claim 1, or a pharmaceutically acceptable salt thereof, wherein A is chosen from

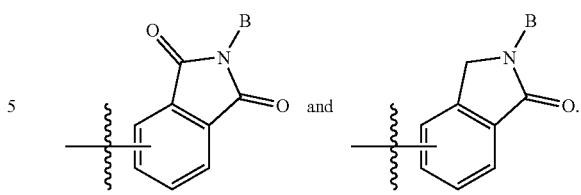

3. The compound according to claim 1, or a pharmaceutically acceptable salt thereof, wherein B is a 5-member heterocycle substituted with 0, 1, 2, or 3 $R^5$.

4. The compound according to claim 1, or a pharmaceutically acceptable salt thereof,
wherein B is selected from:

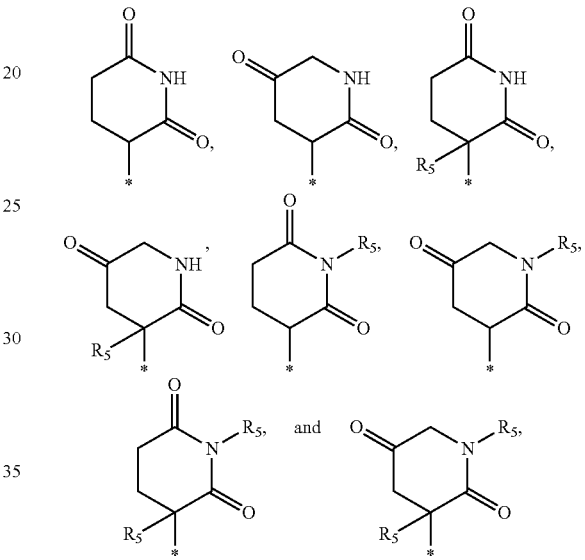

wherein

represents the point of attachment of B to A.

5. The compound according to claim 1, or a pharmaceutically acceptable salt thereof, wherein B is a 6-member heterocycle substituted with 0, 1, 2, or 3 $R^5$.

6. The compound according to claim 1, or a pharmaceutically acceptable salt thereof, wherein $R^1$ and $R^2$ are each independently selected from H, $C_1$-$C_3$ alkyl, halo, alkoxy, acyloxy, hydroxy, and sulfhydryl, each of which may be substituted with 0, 1, 2, or 3 $R^5$.

7. The compound according to claim 6, or a pharmaceutically acceptable salt thereof, wherein $R^1$ and $R^2$ are each independently H or OH.

8. The compound according to claim 1, or a pharmaceutically acceptable salt thereof, wherein $X^1$ and $X^2$ are each independently selected from $C(R^3)_2$, $NR^4$, O, S, 5 or 6-member cycloalkyl, 5- or 6-member aryl, 5- or 6-member heterocycle, and 5- or 6-member heteroaryl, each of which is independently substituted with 0, 1, 2, or 3 $R^5$.

9. The compound according to claim 8, or a pharmaceutically acceptable salt thereof, wherein $R^4$ is selected from H, $C_1$-$C_3$ alkyl, and acyl, each of which is substituted with 0, 1, 2, or 3 $R^5$.

10. The compound according to claim 8, or a pharmaceutically acceptable salt thereof, wherein $X^1$ is selected from 5 or 6-member cycloalkyl, 5- or 6-member aryl, 5- or 6-member heterocycle, and 5- or 6-member heteroaryl.

11. The compound according to claim 1, or a pharmaceutically acceptable salt thereof, wherein $X^1$ is selected from aziridinyl, azetidinyl, pyrrolidinyl, piperidinyl, piperazinyl, pyrrolyl, pyridinyl, pyrimidinyl, oxiranyl, oxetanyl, tetrahydrofuranyl, furanyl, pyranyl, tetrahydropyranyl, dioxanyl, imidazolyl, pyrazolyl, oxazole, isoxazole, thiazole, isothiazole, triazole, tetrazole, indole, benzimidazole, benzofuran, benzoxazole, benzothiazole, quinoline, isoquinoline, and quinazoline, each of which is independently substituted with 0, 1, 2, or 3 $R^5$.

12. The compound according to claim 1, or a pharmaceutically acceptable salt thereof, wherein $X^1$ is selected from

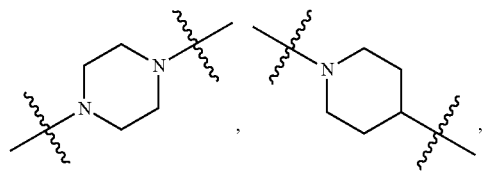

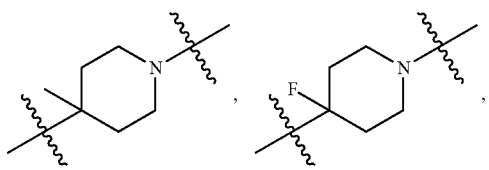

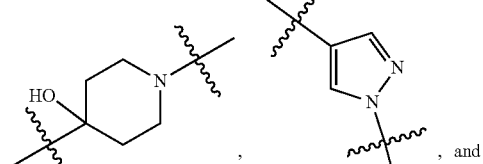

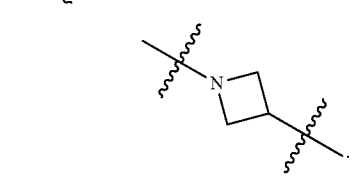, and

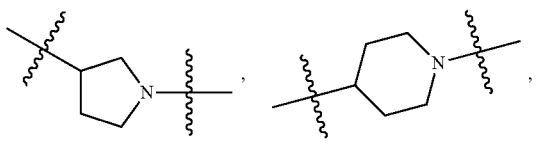

13. The compound according to claim 1, or a pharmaceutically acceptable salt thereof, wherein $X^2$ is selected from

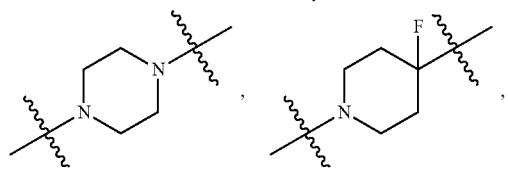

-continued

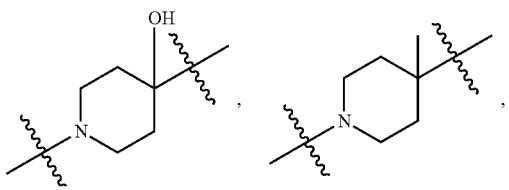

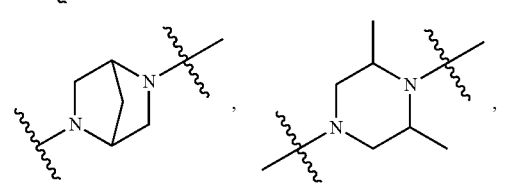

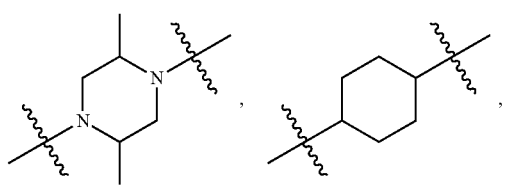

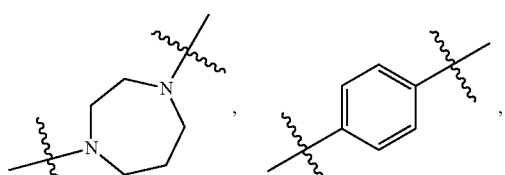

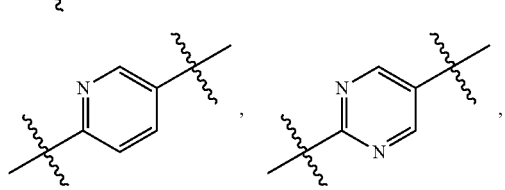

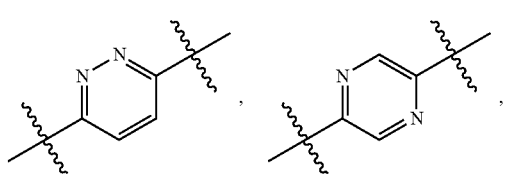

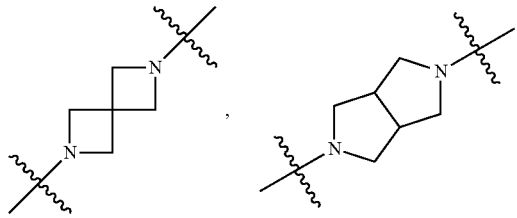

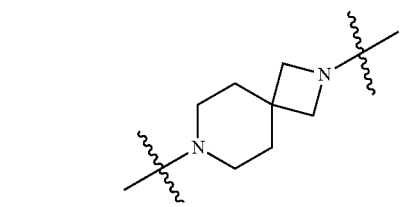

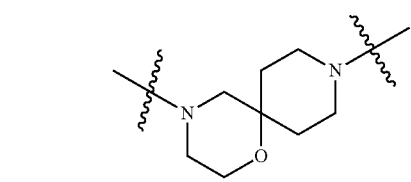

-continued

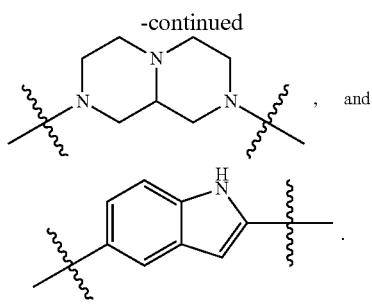

14. The compound according to claim 1, or pharmaceutically acceptable salt thereof, wherein L* is a linker of 1 to 16 carbon atoms in length, wherein one or more carbon atoms are each optionally and independently replaced by a group selected from C(O), O, $NR^4$, S, $C_2$-alkenyl, $C_2$-alkynyl, cycloalkyl, aryl, heterocycle, and heteroaryl, each of which is independently substituted with 0, 1, 2, or 3 $R^5$.

15. The compound according to claim 1, or a pharmaceutically acceptable salt thereof, wherein L* is a linker wherein one carbon atom is replaced by a heterocycle and one carbon atom is replaced by a cycloalkyl, each of which is independently substituted with 0, 1, 2, or 3 $R^5$.

16. The compound according to claim 1, or a pharmaceutically acceptable salt thereof, wherein L* is selected from

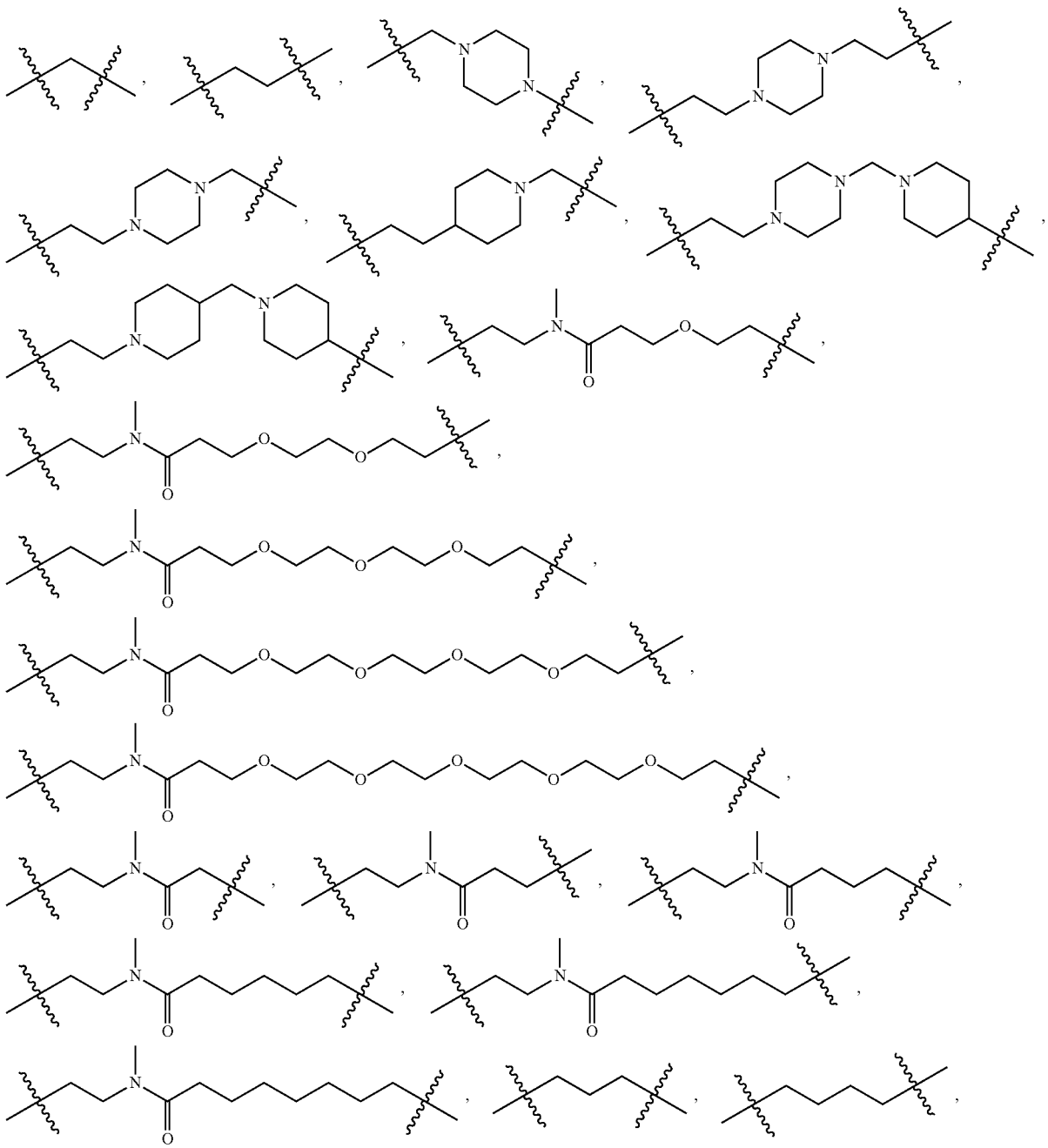

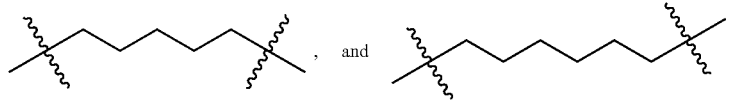

17. The compound according to claim 1, or a pharmaceutically acceptable salt thereof, selected from:
(Z)-3-(4-(3-(4-(2-(4-(1-(4-hydroxyphenyl)-2-phenylbut-1-en-1-yl)phenoxy)ethyl)piperazin-1-yl)propoxy)-1-oxoisoindolin-2-yl)piperidine-2,6-dione;
(Z)-3-(4-(2-(4-(2-(4-(1-(4-hydroxyphenyl)-2-phenylbut-1-en-1-yl)phenoxy)ethyl)piperazin-1-yl)ethoxy)-1-oxoisoindolin-2-yl)piperidine-2,6-dione;
(Z)-3-(5-(2-(4-(2-(4-(1-(4-hydroxyphenyl)-2-phenylbut-1-en-1-yl)phenoxy)ethyl)piperazin-1-yl)ethoxy)-1-oxoisoindolin-2-yl)piperidine-2,6-dione;
(Z)-3-(5-(2-(5-(2-(4-(1-(4-hydroxyphenyl)-2-phenylbut-1-en-1-yl)phenoxy)ethyl)-2,5-diazabicyclo[2.2.1]heptan-2-yl)ethoxy)-1-oxoisoindolin-2-yl)piperidine-2,6-dione;
(Z)-3-(5-((2-(4-(2-(4-(1-(4-hydroxyphenyl)-2-phenylbut-1-en-1-yl)phenoxy)ethyl)piperazin-1-yl)ethyl)amino)-1-oxoisoindolin-2-yl)piperidine-2,6-dione;
(Z)-3-(5-((3-(4-(2-(4-(1-(4-hydroxyphenyl)-2-phenylbut-1-en-1-yl)phenoxy)ethyl)piperazin-1-yl)propyl)amino)-1-oxoisoindolin-2-yl)piperidine-2,6-dione;
(Z)-3-(5-((3-(2-(2-(4-(1-(4-hydroxyphenyl)-2-phenylbut-1-en-1-yl)phenoxy)ethoxy)ethoxy)propyl)amino)-1-oxoisoindolin-2-yl)piperidine-2,6-dione;
(Z)-3-(2-((2-(2-(2,6-dioxopiperidin-3-yl)-1,3-dioxoisoindolin-4-yl)amino)ethoxy)-N-(2-(4-(1,2-diphenylbut-1-en-1-yl)phenoxy)ethyl)-N-methylpropanamide;
(Z)-3-(4-(2-(6-(2-(4-(1-(4-hydroxyphenyl)-2-phenylbut-1-en-1-yl)phenoxy)ethyl)-2,6-diazaspiro[3.3]heptan-2-yl)ethoxy)-1-oxoisoindolin-2-yl)piperidine-2,6-dione;
(Z)-3-(5-(5-(4-(2-(4-(1-(4-hydroxyphenyl)-2-phenylbut-1-en-1-yl)phenoxy)ethyl)piperazin-1-yl)-5-oxopentyl)-1-oxoisoindolin-2-yl)piperidine-2,6-dione;
(Z)-2-(2,6-dioxopiperidin-3-yl)-5-(4-(2-(4-(1-(4-hydroxyphenyl)-2-phenylbut-1-en-1-yl)phenoxy)ethyl)piperazin-1-yl)isoindoline-1,3-dione;
(Z)-3-(5-((4-(4-(2-(4-(1-(4-hydroxyphenyl)-2-phenylbut-1-en-1-yl)phenoxy)ethyl)piperazin-1-yl)butyl)amino)-1-oxoisoindolin-2-yl)piperidine-2,6-dione;
(Z)-3-(5-(3-(4-(2-(4-(1-(4-hydroxyphenyl)-2-phenylbut-1-en-1-yl)phenoxy)ethyl)piperazin-1-yl)-3-oxopropyl)-1-oxoisoindolin-2-yl)piperidine-2,6-dione;
(Z)-3-(5-((3-(3-(4-(1-(4-hydroxyphenyl)-2-phenylbut-1-en-1-yl)phenoxy)propoxy)propyl)amino)-1-oxoisoindolin-2-yl)piperidine-2,6-dione;
(Z)-3-(2-(2-((2-(2,6-dioxopiperidin-3-yl)-1,3-dioxoisoindolin-4-yl)amino)ethoxy)ethoxy)-N-(2-(4-(1,2-diphenylbut-1-en-1-yl)phenoxy)ethyl)-N-methylpropanamide;
(E)/(Z)-2-(2,6-dioxopiperidin-3-yl)-5-(4-(4-(4-(1-(4-hydroxyphenyl)-2-phenylbut-1-en-1-yl)phenoxy)butyl)piperazin-1-yl)isoindoline-1,3-dione;
(Z)-2-(2,6-dioxopiperidin-3-yl)-5-(4-(4-(4-(1-(4-hydroxyphenyl)-2-phenylbut-1-en-1-yl)phenoxy)butyl)piperazin-1-yl)isoindoline-1,3-dione;
(E)/(Z)—(S)-3-(5-(4-(4-(4-(4-hydroxyphenyl)-2-phenyl but-1-en-1-yl)phenoxy)butyl)piperazin-1-yl)-1-oxoisoindolin-2-yl)piperidine-2,6-dione;
(Z)-3-(5-(4-(4-(4-(1-(4-hydroxyphenyl)-2-phenylbut-1-en-1-yl)phenoxy)butyl)piperazin-1-yl)-1-oxoisoindolin-2-yl)piperidine-2,6-dione;
(Z)-3-(5-(4-(2-(4-(1-(4-hydroxyphenyl)-2-phenylbut-1-en-1-yl)phenoxy)ethyl)piperazin-1-yl)-1-oxoisoindolin-2-yl)piperidine-2,6-dione;
(Z)-2-(2,6-dioxopiperidin-3-yl)-5-((2-(1-(2-(4-(1-(4-hydroxyphenyl)-2-phenylbut-1-en-1-yl)phenoxy)ethyl)piperidin-4-yl)ethyl)amino)isoindoline-1,3-dione;
(Z)-3-(5-((2-(1-(2-(4-(1-(4-hydroxyphenyl)-2-phenylbut-1-en-1-yl)phenoxy)ethyl)piperidin-4-yl)ethyl)amino)-1-oxoisoindolin-2-yl)piperidine-2,6-dione;
(Z)-2-(2,6-dioxopiperidin-3-yl)-5-((3-(1-(2-(4-(1-(4-hydroxyphenyl)-2-phenylbut-1-en-1-yl)phenoxy)ethyl)piperidin-4-yl)propyl)amino)isoindoline-1,3-dione;
(Z)-3-(5-((3-(1-(2-(4-(1-(4-hydroxyphenyl)-2-phenylbut-1-en-1-yl)phenoxy)ethyl)piperidin-4-yl)propyl)amino)-1-oxoisoindolin-2-yl)piperidine-2,6-dione;
(Z)-2-(2,6-dioxopiperidin-3-yl)-5-(((1-(2-(4-(1-(4-hydroxyphenyl)-2-phenylbut-1-en-1-yl)phenoxy)ethyl)piperidin-4-yl)methyl)amino)isoindoline-1,3-dione;
(Z)-3-(5-((1-(2-(4-(1-(4-hydroxyphenyl)-2-phenylbut-1-en-1-yl)phenoxy)ethyl)piperidin-4-yl)amino)-1-oxoisoindolin-2-yl)piperidine-2,6-dione;
(Z)-2-(2,6-dioxopiperidin-3-yl)-5-((1-(2-(4-(1-(4-hydroxyphenyl)-2-phenylbut-1-en-1-yl)phenoxy)ethyl)piperidin-4-yl)amino)isoindoline-1,3-dione;
(Z)-3-(5-(3-((1-(2-(4-(1-(4-hydroxyphenyl)-2-phenylbut-1-en-1-yl)phenoxy)ethyl)piperidin-4-yl)oxy)propyl)-1-oxoisoindolin-2-yl)piperidine-2,6-dione;
(Z)-2-(2,6-dioxopiperidin-3-yl)-5-(3-((1-(2-(4-(1-(4-hydroxyphenyl)-2-phenylbut-1-en-1-yl)phenoxy)ethyl)piperidin-4-yl)oxy)propyl)isoindoline-1,3-dione;
(E)/(Z)-2-(2,6-dioxopiperidin-3-yl)-5-(4-(5-(4-(1-(4-hydroxyphenyl)-2-phenylbut-1-en-1-yl)phenoxy)pentyl)piperazin-1-yl)isoindoline-1,3-dione;
(Z)-2-(2,6-dioxopiperidin-3-yl)-5-(4-(5-(4-(1-(4-hydroxyphenyl)-2-phenylbut-1-en-1-yl)phenoxy)pentyl)piperazin-1-yl)isoindoline-1,3-dione;
(E)/(Z)-2-(2,6-dioxopiperidin-3-yl)-5-(4-(6-(4-(1-(4-hydroxyphenyl)-2-phenylbut-1-en-1-yl)phenoxy)hexyl)piperazin-1-yl)isoindoline-1,3-dione;
(Z)-2-(2,6-dioxopiperidin-3-yl)-5-(4-(6-(4-(1-(4-hydroxyphenyl)-2-phenylbut-1-en-1-yl)phenoxy)hexyl)piperazin-1-yl)isoindoline-1,3-dione;
(Z)-3-(5-(3-(3-(4-(1-(4-hydroxyphenyl)-2-phenylbut-1-en-1-yl)phenoxy)propoxy)propoxy)-1-oxoisoindolin-2-yl)piperidine-2,6-dione;
(E)/(Z)—(S)-3-(5-(4-(5-(4-(1-(4-hydroxyphenyl)-2-phenylbut-1-en-1-yl)phenoxy)pentyl)piperazin-1-yl)-1-oxoisoindolin-2-yl)piperidine-2,6-dione;
(Z)-3-(5-(4-(5-(4-(1-(4-hydroxyphenyl)-2-phenylbut-1-en-1-yl)phenoxy)pentyl)piperazin-1-yl)-1-oxoisoindolin-2-yl)piperidine-2,6-dione;
(E)/(Z)—(S)-3-(5-(4-(6-(4-(1-(4-hydroxyphenyl)-2-phenylbut-1-en-1-yl)phenoxy)hexyl)piperazin-1-yl)-1-oxoisoindolin-2-yl)piperidine-2,6-dione;

(Z)-3-(5-(4-(6-(4-(1-(4-hydroxyphenyl)-2-phenylbut-1-en-1-yl)phenoxy)hexyl)piperazin-1-yl)-1-oxoisoindolin-2-yl)piperidine-2,6-dione;

(Z)-3-(5-(4-(3-(4-(1-(4-hydroxyphenyl)-2-phenylbut-1-en-1-yl)phenoxy)propoxy)butoxy)-1-oxoisoindolin-2-yl)piperidine-2,6-dione;

(Z)-3-(2-(2-(2-((2-(2,6-dioxopiperidin-3-yl)-1,3-dioxoisoindolin-4-yl)amino)ethoxy)ethoxy)ethoxy)-N-(2-(4-(1,2-diphenylbut-1-en-1-yl)phenoxy)ethyl)-N-methylpropanamide;

(Z)-3-(5-((6-(4-(1-(4-hydroxyphenyl)-2-phenylbut-1-en-1-yl)phenoxy)hexa-2,4-diyn-1-yl)oxy)-1-oxoisoindolin-2-yl)piperidine-2,6-dione;

(Z)-3-(5-(4-(3-(4-(1-(4-hydroxyphenyl)-2-phenylbut-1-en-1-yl)phenoxy)propyl)piperazin-1-yl)-1-oxoisoindolin-2-yl)piperidine-2,6-dione;

(Z)-2-(2,6-dioxopiperidin-3-yl)-5-(4-(3-(4-(1-(4-hydroxyphenyl)-2-phenylbut-1-en-1-yl)phenoxy)propyl)piperazin-1-yl)isoindoline-1,3-dione;

(Z)-3-(5-(2-(4-(2-(4-(1-(4-hydroxyphenyl)-2-phenylbut-1-en-1-yl)phenoxy)ethyl)-1,4-diazepan-1-yl)ethoxy)-1-oxoisoindolin-2-yl)piperidine-2,6-dione;

(E)-2-(2,6-dioxopiperidin-3-yl)-5-((5-(4-(4-(1-(4-hydroxyphenyl)-2-phenylbut-1-en-1-yl)phenyl)piperazin-1-yl)pentyl)oxy)isoindoline-1,3-dione;

(E)-3-(5-((5-(4-(4-(1-(4-hydroxyphenyl)-2-phenylbut-1-en-1-yl)phenyl)piperazin-1-yl)pentyl)oxy)-1-oxoisoindolin-2-yl)piperidine-2,6-dione;

(E)-2-(2,6-dioxopiperidin-3-yl)-5-(4-(4-(4-(1-(4-hydroxyphenyl)-2-phenylbut-1-en-1-yl)phenyl)piperazin-1-yl)butoxy)isoindoline-1,3-dione;

(E)-3-(5-(4-(4-(4-(1-(4-hydroxyphenyl)-2-phenylbut-1-en-1-yl)phenyl)piperazin-1-yl)butoxy)-1-oxoisoindolin-2-yl)piperidine-2,6-dione;

(E)-2-(2,6-dioxopiperidin-3-yl)-5-((5-(4-(4-(1-(4-hydroxyphenyl)-2-phenylbut-1-en-1-yl)phenyl)piperazin-1-yl)pentyl)amino)isoindoline-1,3-dione;

(E)-2-(2,6-dioxopiperidin-3-yl)-5-((4-(4-(4-(1-(4-hydroxyphenyl)-2-phenylbut-1-en-1-yl)phenyl)piperazin-1-yl)butyl)amino)isoindoline-1,3-dione;

(Z)—N-((2-(2,6-dioxopiperidin-3-yl)-1-oxoisoindolin-5-yl)methyl)-2-(4-(2-(4-(1-(4-hydroxyphenyl)-2-phenylbut-1-en-1-yl)phenoxy)ethyl)piperazin-1-yl)acetamide;

(Z)-3-(5-(3-(3-(3-(4-(1-(4-hydroxyphenyl)-2-phenylbut-1-en-1-yl)phenoxy)propoxy)propoxy)propoxy)-1-oxoisoindolin-2-yl)piperidine-2,6-dione;

(Z)-3-(5-(2-(2-(2-(4-(1-(4-hydroxyphenyl)-2-phenylbut-1-en-1-yl)phenoxy)ethoxy)ethoxy)ethoxy)-1-oxoisoindolin-2-yl)piperidine-2,6-dione;

(Z)-3-(5-(3-(2-(2-(4-(1-(4-hydroxyphenyl)-2-phenylbut-1-en-1-yl)phenoxy)ethoxy)ethoxy)propoxy)-1-oxoisoindolin-2-yl)piperidine-2,6-dione;

(Z)-3-(5-(2-(1-(2-(4-(1-(4-hydroxyphenyl)-2-phenylbut-1-en-1-yl)phenoxy)ethyl)piperidin-3-yl)ethoxy)-1-oxoisoindolin-2-yl)piperidine-2,6-dione;

(Z)-3-(5-(4-((4-(4-(1-(4-hydroxyphenyl)-2-phenylbut-1-en-1-yl)phenoxy)butyl)amino)phenyl)-1-oxoisoindolin-2-yl)piperidine-2,6-dione;

(Z)-3-(5-(2-(2-(4-(1-(4-hydroxyphenyl)-2-phenylbut-1-en-1-yl)phenoxy)ethoxy)ethoxy)-1-oxoisoindolin-2-yl)piperidine-2,6-dione;

(Z)-2-(2,6-dioxopiperidin-3-yl)-5-(2-(2-(4-(1-(4-hydroxyphenyl)-2-phenylbut-1-en-1-yl)phenoxy)ethoxy)ethoxy)isoindoline-1,3-dione;

(Z)-3-(5-(4-(5-(4-(1-(4-hydroxyphenyl)-2-phenylbut-1-en-1-yl)phenoxy)pentyl)-2,5-dimethylpiperazin-1-yl)-1-oxoisoindolin-2-yl)piperidine-2,5-dione;

(Z)-1-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methyl-3,6,9,12-tetraoxapentadecan-15-amide;

(Z)-3-(5-(4-(5-(4-(1-(4-hydroxyphenyl)-2-phenylbut-1-en-1-yl)phenoxy)pentyl)piperazin-1-yl)-1-oxoisoindolin-2-yl)piperidine-2,5-dione;

(Z)-2-(2,5-dioxopiperidin-3-yl)-5-(4-(5-(4-(1-(4-hydroxyphenyl)-2-phenylbut-1-en-1-yl)phenoxy)pentyl)piperazin-1-yl)isoindoline-1,3-dione;

(Z)-2-(2,6-dioxopiperidin-3-yl)-5-(4-((4-(4-(1-(4-hydroxyphenyl)-2-phenylbut-1-en-1-yl)phenoxy)cyclohexyl)methyl)piperazin-1-yl)isoindoline-1,3-dione;

(Z)-3-(5-(4-((4-(4-(1-(4-hydroxyphenyl)-2-phenylbut-1-en-1-yl)phenoxy)cyclohexyl)methyl)piperazin-1-yl)-1-oxoisoindolin-2-yl)piperidine-2,6-dione;

(Z)-2-(2,6-dioxopiperidin-3-yl)-5-(4-(2-((4-(4-(1-(4-hydroxyphenyl)-2-phenylbut-1-en-1-yl)phenoxy)cyclohexyl)oxy)ethyl)piperazin-1-yl)isoindoline-1,3-dione;

(Z)-3-(5-(4-(2-((4-(4-(1-(4-hydroxyphenyl)-2-phenylbut-1-en-1-yl)phenoxy)cyclohexyl)oxy)ethyl)piperazin-1-yl)-1-oxoisoindolin-2-yl)piperidine-2,6-dione;

(Z)-3-(5-(2-((2-(2-(4-(1-(4-hydroxyphenyl)-2-phenylbut-1-en-1-yl)phenoxy)ethyl)-2-azaspiro[3.3]heptan-6-yl)oxy)ethoxy)-1-oxoisoindolin-2-yl)piperidine-2,6-dione;

(E)-3-(6-((4-(4-(4-(1-(4-hydroxyphenyl)-2-phenylbut-1-en-1-yl)phenyl)piperazin-1-yl)butyl)amino)-1-oxoisoindolin-2-yl)piperidine-2,6-dione;

(Z)-3-(5-((2-(2-(4-(1-(4-hydroxyphenyl)-2-phenylbut-1-en-1-yl)phenoxy)ethoxy)ethyl)amino)-1-oxoisoindolin-2-yl)piperidine-2,6-dione;

(Z)-1-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methyl-3,6,9,12,15-pentaoxaoctadecan-18-amide;

(Z)-2-(2,6-dioxopiperidin-3-yl)-5-((2-(2-(4-(1-(4-hydroxyphenyl)-2-phenylbut-1-en-1-yl)phenoxy)ethoxy)ethyl)amino)isoindoline-1,3-dione;

(Z)—N-((2-(2,6-dioxopiperidin-3-yl)-1-oxoisoindolin-5-yl)methyl)-2-(4-(1-(4-(1-(4-hydroxyphenyl)-2-phenylbut-1-en-1-yl)phenoxy)propan-2-yl)piperazin-1-yl)acetamide;

(Z)-3-(5-(3-(4-(3-(4-(1-(4-hydroxyphenyl)-2-phenylbut-1-en-1-yl)phenoxy)propyl)-1,4-diazepan-1-yl)propyl)-1-oxoisoindolin-2-yl)piperidine-2,6-dione;

(E)-3-(5-((5-(4-(4-(1-(4-hydroxyphenyl)-2-phenylbut-1-en-1-yl)phenyl)piperazin-1-yl)pentyl)amino)-1-oxoisoindolin-2-yl)piperidine-2,6-dione;

(Z)-3-(5-(3-(2-(4-(1-(4-hydroxyphenyl)-2-phenylbut-1-en-1-yl)phenoxy)ethoxy)propoxy)-1-oxoisoindolin-2-yl)piperidine-2,6-dione;

(Z)-2-(2,6-dioxopiperidin-3-yl)-5-(3-(2-(4-(1-(4-hydroxyphenyl)-2-phenylbut-1-en-1-yl)phenoxy)ethoxy)propoxy)isoindoline-1,3-dione;

(Z)-3-(5-(3-(3-(2-(4-(1-(4-hydroxyphenyl)-2-phenylbut-1-en-1-yl)phenoxy)ethoxy)propoxy)propoxy)-1-oxoisoindolin-2-yl)piperidine-2,6-dione;

(Z)-3-(5-(2-(4-(4-(4-(1-(4-hydroxyphenyl)-2-phenylbut-1-en-1-yl)phenoxy)butyl)-1,4-diazepan-1-yl)ethyl)-1-oxoisoindolin-2-yl)piperidine-2,6-dione;

(Z)-3-(5-(4-amino-3-((5-(4-(1-(4-hydroxyphenyl)-2-phenylbut-1-en-1-yl)phenoxy)pentyl)oxy)phenyl)-1-oxoisoindolin-2-yl)piperidine-2,6-dione;

(Z)-3-(5-(4-amino-3-(4-(4-(1-(4-hydroxyphenyl)-2-phenylbut-1-en-1-yl)phenoxy)butoxy)phenyl)-1-oxoisoindolin-2-yl)piperidine-2,6-dione;

(Z)-3-(5-((3-(2-(4-(1-(4-hydroxyphenyl)-2-phenylbut-1-en-1-yl)phenoxy)ethoxy)propyl)amino)-1-oxoisoindolin-2-yl)piperidine-2,6-dione;

(Z)-2-(2,6-dioxopiperidin-3-yl)-5-((3-(2-(4-(1-(4-hydroxyphenyl)-2-phenylbut-1-en-1-yl)phenoxy)ethoxy) propyl)amino)isoindoline-1,3-dione;

(Z)-3-(5-(3-(3-(4-(4-(1-(4-hydroxyphenyl)-2-phenylbut-1-en-1-yl)phenoxy)butoxy)propoxy)propoxy)-1-oxoisoindolin-2-yl)piperidine-2,6-dione;

(Z)-3-(5-(3-(1-(2-(4-(1-(4-hydroxyphenyl)-2-phenylbut-1-en-1-yl)phenoxy)ethyl)piperidin-3-yl)propyl)-1-oxoisoindolin-2-yl)piperidine-2,6-dione;

(Z)-3-(5-(2-(4-(2-(4-(1-(4-hydroxyphenyl)-2-phenylbut-1-en-1-yl)phenoxy)ethyl)-1,4-diazepan-1-yl)ethyl)-1-oxoisoindolin-2-yl)piperidine-2,6-dione;

(Z)-3-(5-(2-(3-(4-(1-(4-hydroxyphenyl)-2-phenylbut-1-en-1-yl)phenoxy)propyl)-1H-indol-5-yl)-1-oxoisoindolin-2-yl)piperidine-2,6-dione;

(Z)-3-(5-(2-(4-(4-(1-(4-hydroxyphenyl)-2-phenylbut-1-en-1-yl)phenoxy)butyl)-1H-indol-5-yl)-1-oxoisoindolin-2-yl)piperidine-2,6-dione;

(Z)-3-(5-(2-(5-(4-(1-(4-hydroxyphenyl)-2-phenylbut-1-en-1-yl)phenoxy)pentyl)-1H-indol-5-yl)-1-oxoisoindolin-2-yl)piperidine-2,6-dione;

(Z)-3-(5-(2-((1-(3-(4-(1-(4-hydroxyphenyl)-2-phenylbut-1-en-1-yl)phenoxy)propyl)piperidin-3-yl)oxy)ethyl)-1-oxoisoindolin-2-yl)piperidine-2,6-dione;

(Z)-3-(5-(2-((1-(2-(4-(1-(4-hydroxyphenyl)-2-phenylbut-1-en-1-yl)phenoxy)ethyl)piperidin-3-yl)oxy)ethyl)-1-oxoisoindolin-2-yl)piperidine-2,6-dione;

(E)-3-(5-(4-((2-((4-(1-(4-hydroxyphenyl)-2-phenylbut-1-en-1-yl)benzyl)oxy)ethyl)(methyl)amino)cyclohexyl)-1-oxoisoindolin-2-yl)piperidine-2,6-dione;

(Z)-3-(5-(4-(5-(4-(1-(4-hydroxyphenyl)-2-phenylbut-1-en-1-yl)phenoxy)pentyl)-1,4-diazepan-1-yl)-1-oxoisoindolin-2-yl)piperidine-2,6-dione;

(Z)-2-(2,6-dioxopiperidin-3-yl)-5-(4-(5-(4-(1-(4-hydroxyphenyl)-2-phenylbut-1-en-1-yl)phenoxy)pentyl)-1,4-diazepan-1-yl)isoindoline-1,3-dione;

(Z)-2-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylacetamide;

(Z)-3-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylpropanamide;

(Z)-3-(5-(4-(4-(4-(1-(4-hydroxyphenyl)-2-phenylbut-1-en-1-yl)phenoxy)butyl)-1,4-diazepan-1-yl)-1-oxoisoindolin-2-yl)piperidine-2,6-dione;

(Z)-2-(2,6-dioxopiperidin-3-yl)-5-(4-(4-(4-(1-(4-hydroxyphenyl)-2-phenylbut-1-en-1-yl)phenoxy)butyl)-1,4-diazepan-1-yl)isoindoline-1,3-dione;

(Z)-3-(5-(4-(2-(2-((4-(1-(4-hydroxyphenyl)-2-phenylbut-1-en-1-yl)phenoxy)methyl)cyclopropyl)ethyl)piperazin-1-yl)-1-oxoisoindolin-2-yl)piperidine-2,6-dione;

(Z)-2-(2,6-dioxopiperidin-3-yl)-5-(4-(2-(2-((4-(1-(4-hydroxyphenyl)-2-phenylbut-1-en-1-yl)phenoxy)methyl)cyclopropyl)ethyl)piperazin-1-yl)isoindoline-1,3-dione;

(Z)-2-(2,6-dioxopiperidin-3-yl)-5-(4-((4-(4-(1-(4-hydroxyphenyl)-2-phenylbut-1-en-1-yl)phenoxy)piperidin-1-yl)methyl)piperidin-1-yl)isoindoline-1,3-dione;

(Z)-2-(2,6-dioxopiperidin-3-yl)-5-(4-(1-(2-(4-(1-(4-hydroxyphenyl)-2-phenylbut-1-en-1-yl)phenoxy)ethyl)piperidin-4-yl)piperazin-1-yl)isoindoline-1,3-dione;

(Z)-2-(2,6-dioxopiperidin-3-yl)-5-(4-((1-(2-(4-(1-(4-hydroxyphenyl)-2-phenylbut-1-en-1-yl)phenoxy)ethyl)piperidin-4-yl)methyl)piperazin-1-yl)isoindoline-1,3-dione;

(Z)-2-(2,6-dioxopiperidin-3-yl)-5-(4-((1-(2-(4-(1-(4-hydroxyphenyl)-2-phenylbut-1-en-1-yl)phenoxy)ethyl)azetidin-3-yl)methyl)piperazin-1-yl)isoindoline-1,3-dione;

(Z)-3-(5-(4-(4,4-difluoro-5-(4-(1-(4-hydroxyphenyl)-2-phenylbut-1-en-1-yl)phenoxy)pentyl)piperazin-1-yl)-1-oxoisoindolin-2-yl)piperidine-2,6-dione;

(Z)-2-(2,6-dioxopiperidin-3-yl)-5-(4-(2-(1-(2-(4-(1-(4-hydroxyphenyl)-2-phenylbut-1-en-1-yl)phenoxy)ethyl)azetidin-3-yl)ethyl)piperazin-1-yl)isoindoline-1,3-dione;

(Z)-3-(5-(4-(5-(4-(1-(4-hydroxyphenyl)-2-phenylbut-1-en-1-yl)phenoxy)pentyl)piperazin-1-yl)-1-oxoisoindolin-2-yl)-1-methylpiperidine-2,6-dione;

(Z)-3-(5-(6-((1-(2-(4-(1-(4-hydroxyphenyl)-2-phenylbut-1-en-1-yl)phenoxy)ethyl)pyrrolidin-3-yl)oxy)pyridin-3-yl)-1-oxoisoindolin-2-yl)piperidine-2,6-dione;

(Z)-2-(2,6-dioxopiperidin-3-yl)-5-(4-((1-(2-(4-(1-(4-hydroxyphenyl)-2-phenylbut-1-en-1-yl)phenoxy)ethyl)pyrrolidin-3-yl)methyl)piperazin-1-yl)isoindoline-1,3-dione;

(Z)-2-(2,6-dioxopiperidin-3-yl)-5-(4-((4-(2-(4-(1-(4-hydroxyphenyl)-2-phenylbut-1-en-1-yl)phenoxy)ethyl)piperazin-1-yl)methyl)piperidin-1-yl)isoindoline-1,3-dione;

(Z)-2-(2,6-dioxopiperidin-3-yl)-5-(5-(1-(2-(4-(1-(4-hydroxyphenyl)-2-phenylbut-1-en-1-yl)phenoxy)ethyl)piperidin-4-yl)-2,5-diazabicyclo[2.2.1]heptan-2-yl)isoindoline-1,3-dione;

(Z)-2-(2,6-dioxopiperidin-3-yl)-5-(5-((1-(2-(4-(1-(4-hydroxyphenyl)-2-phenylbut-1-en-1-yl)phenoxy)ethyl)piperidin-4-yl)methyl)-2,5-diazabicyclo[2.2.1]heptan-2-yl)isoindoline-1,3-dione;

(Z)-3-(5-(4-(5-(4-(1-(4-hydroxyphenyl)-2-phenylbut-1-en-1-yl)phenoxy)pentyl)-3,5-dimethylpiperazin-1-yl)-1-oxoisoindolin-2-yl)piperidine-2,6-dione;

(Z)-3-(5-(4-((4-(4-(1-(4-hydroxyphenyl)-2-phenylbut-1-en-1-yl)phenoxy)piperidin-1-yl)methyl)piperidin-1-yl)-1-oxoisoindolin-2-yl)piperidine-2,6-dione;

(Z)-4-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylbutanamide;

(Z)-2-(2,6-dioxopiperidin-3-yl)-5-(7-(4-(4-(1-(4-hydroxyphenyl)-2-phenylbut-1-en-1-yl)phenoxy)butyl)-2,7-diazaspiro[3.5]nonan-2-yl)isoindoline-1,3-dione;

(Z)-2-(2,6-dioxopiperidin-3-yl)-6-(4-(5-(4-(1-(4-hydroxyphenyl)-2-phenylbut-1-en-1-yl)phenoxy)pentyl)piperazin-1-yl)-1H-pyrrolo[3,4-c]pyridine-1,3(2H)-dione;

(Z)-3-(5-(7-(4-(4-(1-(4-hydroxyphenyl)-2-phenylbut-1-en-1-yl)phenoxy)butyl)-2,7-diazaspiro[3.5]nonan-2-yl)-1-oxoisoindolin-2-yl)piperidine-2,6-dione;

(Z)-3-(5-(4-((1-(2-(4-(1-(4-hydroxyphenyl)-2-phenylbut-1-en-1-yl)phenoxy)ethyl)pyrrolidin-3-yl)methyl)piperazin-1-yl)-1-oxoisoindolin-2-yl)piperidine-2,6-dione;

(Z)-2-(2,6-dioxopiperidin-3-yl)-5-(6-(4-(4-(1-(4-hydroxyphenyl)-2-phenylbut-1-en-1-yl)phenoxy)butyl)-2,6-diazaspiro[3.3]heptan-2-yl)isoindoline-1,3-dione;

(Z)-3-(5-(2-(4-(6-(4-(1-(4-hydroxyphenyl)-2-phenylbut-1-en-1-yl)phenoxy)pyridin-3-yl)piperazin-1-yl)ethoxy)-1-oxoisoindolin-2-yl)piperidine-2,6-dione;

(Z)-2-(2,6-dioxopiperidin-3-yl)-5-(2-(4-(6-(4-(1-(4-hydroxyphenyl)-2-phenylbut-1-en-1-yl)phenoxy)pyridin-3-yl)piperazin-1-yl)ethoxy)isoindoline-1,3-dione;

(Z)-2-(2,6-dioxopiperidin-3-yl)-5-(3-(4-(6-(4-(1-(4-hydroxyphenyl)-2-phenylbut-1-en-1-yl)phenoxy)pyridin-3-yl)piperazin-1-yl)propoxy)isoindoline-1,3-dione;

(Z)-3-(5-(3-(4-(6-(4-(1-(4-hydroxyphenyl)-2-phenylbut-1-en-1-yl)phenoxy)pyridin-3-yl)piperazin-1-yl)propoxy)-1-oxoisoindolin-2-yl)piperidine-2,6-dione;

(Z)-2-(2,6-dioxopiperidin-3-yl)-5-(4-(3-(4-(1-(4-hydroxyphenyl)-2-phenylbut-1-en-1-yl)phenoxy)propyl)-1-oxa-4,9-diazaspiro[5.5]undecan-9-yl)isoindoline-1,3-dione;

(Z)-3-(5-(4-(5-(4-(1-(4-hydroxyphenyl)-2-phenylbut-1-en-1-yl)phenoxy)pentyl)-2,5-dimethylpiperazin-1-yl)-1-oxoisoindolin-2-yl)piperidine-2,6-dione;

(Z)-6-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylhexanamide;

(Z)-2-(2,6-dioxopiperidin-3-yl)-5-(5-((1-(2-(4-(1-(4-hydroxyphenyl)-2-phenylbut-1-en-1-yl)phenoxy)ethyl)pyrrolidin-3-yl)oxy)pyrazin-2-yl)isoindoline-1,3-dione;

(Z)-2-(2,6-dioxopiperidin-3-yl)-5-(5-(4-(2-(4-(1-(4-hydroxyphenyl)-2-phenylbut-1-en-1-yl)phenoxy)ethyl)piperazin-1-yl)pyrazin-2-yl)isoindoline-1,3-dione;

(Z)-2-(2,6-dioxopiperidin-3-yl)-5-(5-((1-(2-(4-(1-(4-hydroxyphenyl)-2-phenylbut-1-en-1-yl)phenoxy)ethyl)azetidin-3-yl)methoxy)pyrazin-2-yl)isoindoline-1,3-dione;

(Z)-2-(2,6-dioxopiperidin-3-yl)-5-((2-(4-(2-(4-(1-(4-hydroxyphenyl)-2-phenylbut-1-en-1-yl)phenoxy)ethyl)piperazin-1-yl)pyrimidin-5-yl)oxy)isoindoline-1,3-dione;

(Z)-6-(2,6-dioxopiperidin-3-yl)-2-(4-(5-(4-(1-(4-hydroxyphenyl)-2-phenylbut-1-en-1-yl)phenoxy)pentyl)piperazin-1-yl)-5H-pyrrolo[3,4-b]pyrazine-5,7(6H)-dione;

(Z)-7-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylheptanamide;

(Z)-2-(2,6-dioxopiperidin-3-yl)-5-(1'-(2-(4-(1-(4-hydroxyphenyl)-2-phenylbut-1-en-1-yl)phenoxy)ethyl)-[1,4'-bipiperidin]-4-yl)isoindoline-1,3-dione;

(Z)-2-(2,6-dioxopiperidin-3-yl)-5-((6-(4-(2-(4-(1-(4-hydroxyphenyl)-2-phenylbut-1-en-1-yl)phenoxy)ethyl)piperazin-1-yl)pyridin-3-yl)oxy)isoindoline-1,3-dione;

(E)-3-(5-(4-(3-(4-(4-(1-(4-hydroxyphenyl)-2-phenylbut-1-en-1-yl)phenyl)-1H-pyrazol-1-yl)propyl)piperazin-1-yl)-1-oxoisoindolin-2-yl)piperidine-2,6-dione;

(Z)-6-(2,6-dioxopiperidin-3-yl)-2-(4-(5-(4-(1-(4-hydroxyphenyl)-2-phenylbut-1-en-1-yl)phenoxy)pentyl)piperazin-1-yl)-5H-pyrrolo[3,4-d]pyrimidine-5,7(6H)-dione;

(Z)-3-(5-(1'-(2-(4-(1-(4-hydroxyphenyl)-2-phenylbut-1-en-1-yl)phenoxy)ethyl)-[1,4'-bipiperidin]-4-yl)-1-oxoisoindolin-2-yl)piperidine-2,6-dione;

(Z)-2-(2,6-dioxopiperidin-3-yl)-5-(4-(2-(4-(4-(1-(4-hydroxyphenyl)-2-phenylbut-1-en-1-yl)phenoxy)piperidin-1-yl)ethyl)piperazin-1-yl)isoindoline-1,3-dione;

(E)-3-(5-(4-(1-(3-(4-(1-(4-hydroxyphenyl)-2-phenylbut-1-en-1-yl)phenyl)propyl)pyrrolidin-3-yl)piperazin-1-yl)-1-oxoisoindolin-2-yl)piperidine-2,6-dione;

(E)-2-(2,6-dioxopiperidin-3-yl)-5-(4-((1-(3-(4-(1-(4-hydroxyphenyl)-2-phenylbut-1-en-1-yl)phenyl)propyl)azetidin-3-yl)methyl)piperazin-1-yl)isoindoline-1,3-dione;

(E)-3-(5-(4-((1-(3-(4-(1-(4-hydroxyphenyl)-2-phenylbut-1-en-1-yl)phenyl)propyl)azetidin-3-yl)methyl)piperazin-1-yl)-1-oxoisoindolin-2-yl)piperidine-2,6-dione;

(Z)-3-(5-((6-(4-(2-(4-(1-(4-hydroxyphenyl)-2-phenylbut-1-en-1-yl)phenoxy)ethyl)piperazin-1-yl)pyridin-3-yl)oxy)-1-oxoisoindolin-2-yl)piperidine-2,6-dione;

(E)-3-(5-(4-(2-(4-(4-(1-(4-hydroxyphenyl)-2-phenylbut-1-en-1-yl)phenyl)piperazin-1-yl)ethyl)piperazin-1-yl)-1-oxoisoindolin-2-yl)piperidine-2,6-dione;

(E)-3-(5-(4-(2-(4-(4-(1-(4-hydroxyphenyl)-2-phenylbut-1-en-1-yl)phenyl)piperidin-1-yl)ethyl)piperazin-1-yl)-1-oxoisoindolin-2-yl)piperidine-2,6-dione;

(E)-2-(2,6-dioxopiperidin-3-yl)-5-(4-(2-(4-(4-(1-(4-hydroxyphenyl)-2-phenylbut-1-en-1-yl)phenyl)piperidin-1-yl)ethyl)piperazin-1-yl)isoindoline-1,3-dione;

(Z)-3-(5-(4-(2-(2-(4-(1-(4-hydroxyphenyl)-2-phenylbut-1-en-1-yl)phenoxy)ethyl)-2-azaspiro[3.3]heptan-6-yl)piperazin-1-yl)-1-oxoisoindolin-2-yl)piperidine-2,6-dione;

(E)-2-(2,6-dioxopiperidin-3-yl)-5-(4-(3-(4-(4-(1-(4-hydroxyphenyl)-2-phenylbut-1-en-1-yl)phenyl)-1H-pyrazol-1-yl)propyl)piperazin-1-yl)isoindoline-1,3-dione;

(E)-2-(2,6-dioxopiperidin-3-yl)-5-(4-(3-(5-(4-(1-(4-hydroxyphenyl)-2-phenylbut-1-en-1-yl)phenyl)-2H-tetrazol-2-yl)propyl)piperazin-1-yl)isoindoline-1,3-dione;

(Z)-8-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methyloctanamide;

(Z)-3-(5-(4-(3-(4-(1-(4-hydroxyphenyl)-2-phenylbut-1-en-1-yl)phenoxy)propyl)-1-oxa-4,9-diazaspiro[5.5]undecan-9-yl)-1-oxoisoindolin-2-yl)piperidine-2,6-dione;

(E)-3-(5-(4-((1-(3-(4-(1-(4-hydroxyphenyl)-2-phenylbut-1-en-1-yl)phenyl)propyl)piperidin-4-yl)methyl)piperazin-1-yl)-1-oxoisoindolin-2-yl)piperidine-2,6-dione;

(E)-2-(2,6-dioxopiperidin-3-yl)-5-(4-((1-(3-(4-(1-(4-hydroxyphenyl)-2-phenylbut-1-en-1-yl)phenyl)propyl)piperidin-4-yl)methyl)piperazin-1-yl)isoindoline-1,3-dione;

(E)-3-(5-(4-(1-(3-(4-(1-(4-hydroxyphenyl)-2-phenylbut-1-en-1-yl)phenyl)propyl)piperidin-4-yl)piperazin-1-yl)-1-oxoisoindolin-2-yl)piperidine-2,6-dione;

(E)-2-(2,6-dioxopiperidin-3-yl)-5-(4-(1-(3-(4-(1-(4-hydroxyphenyl)-2-phenylbut-1-en-1-yl)phenyl)propyl)piperidin-4-yl)piperazin-1-yl)isoindoline-1,3-dione;

(E)-3-(5-(4-(3-(4-(4-(1-(4-hydroxyphenyl)-2-phenylbut-1-en-1-yl)phenyl)piperidin-1-yl)propyl)piperazin-1-yl)-1-oxoisoindolin-2-yl)piperidine-2,6-dione;

(E)-2-(2,6-dioxopiperidin-3-yl)-5-(4-(3-(4-(4-(1-(4-hydroxyphenyl)-2-phenylbut-1-en-1-yl)phenyl)piperidin-1-yl)propyl)piperazin-1-yl)isoindoline-1,3-dione;

(Z)-2-(2,6-dioxopiperidin-3-yl)-4-((1-(4-(2-(4-(1-(4-hydroxyphenyl)-2-phenylbut-1-en-1-yl)phenoxy)ethyl)piperazin-1-yl)methyl)piperidin-4-yl)amino)isoindoline-1,3-dione;

(Z)-2-(2,6-dioxopiperidin-3-yl)-4-((1-((1-(2-(4-(1-(4-hydroxyphenyl)-2-phenylbut-1-en-1-yl)phenoxy)ethyl)piperidin-4-yl)methyl)piperidin-4-yl)amino)isoindoline-1,3-dione;

(Z)-3-(4-((1-((1-(2-(4-(1-(4-hydroxyphenyl)-2-phenylbut-1-en-1-yl)phenoxy)ethyl)piperidin-4-yl)methyl)piperidin-4-yl)amino)-1-oxoisoindolin-2-yl)piperidine-2,6-dione;

(Z)-3-(4-((1-((4-(2-(4-(1-(4-hydroxyphenyl)-2-phenylbut-1-en-1-yl)phenoxy)ethyl)piperazin-1-yl)methyl)piperidin-4-yl)amino)-1-oxoisoindolin-2-yl)piperidine-2,6-dione;

(Z)-3-(2-(2-((2-(2,6-dioxopiperidin-3-yl)-1,3-dioxoisoin-
dolin-4-yl)amino)ethoxy)ethoxy)-N-(2-(4-(1-(4-hy-
droxyphenyl)-2-phenylbut-1-en-1-yl)phenoxy)ethyl)-
N-methylpropanamide;

(Z)-1-((2-(2,6-dioxopiperidin-3-yl)-1-oxoisoindolin-4-yl)
amino)-N-(2-(4-(1-(4-hydroxyphenyl)-2-phenylbut-1-
en-1-yl)phenoxy)ethyl)-N-methyl-3,6,9,12,15-pen-
taoxaoctadecan-18-amide;

(Z)-1-((2-(2,6-dioxopiperidin-3-yl)-1,3-dioxoisoindolin-
4-yl)amino)-N-(2-(4-(1-(4-hydroxyphenyl)-2-phenyl-
but-1-en-1-yl)phenoxy)ethyl)-N-methyl-3,6,9,12,15-
pentaoxaoctadecan-18-amide;

(Z)-3-(5-((2-(4-(2-(4-(1-(4-hydroxyphenyl)-2-phenylbut-
1-en-1-yl)phenoxy)ethyl)piperazin-1-yl)pyrimidin-5-
yl)oxy)-1-oxoisoindolin-2-yl)piperidine-2,6-dione;

(Z)-3-(7-chloro-5-(4-(5-(4-(1-(4-hydroxyphenyl)-2-phe-
nylbut-1-en-1-yl)phenoxy)pentyl)piperazin-1-yl)-1-
oxoisoindolin-2-yl)piperidine-2,6-dione;

(E)/(Z)—(S)-3-(5-(4-((1-(4-(1-(4-hydroxyphenyl)-2-phe-
nylbut-1-en-1-yl)phenyl)piperidin-4-yl)methyl)piper-
azin-1-yl)-1-oxoisoindolin-2-yl)piperidine-2,6-dione;

(E)-3-(5-(4-((1-(4-(1-(4-hydroxyphenyl)-2-phenylbut-1-
en-1-yl)phenyl)piperidin-4-yl)methyl)piperazin-1-yl)-
1-oxoisoindolin-2-yl)piperidine-2,6-dione;

(E)-(S)-3-(5-(4-((1-(4-(1-(4-hydroxyphenyl)-2-phenyl-
but-1-en-1-yl)phenyl)piperidin-4-yl)methyl)piperazin-
1-yl)-1-oxoisoindolin-2-yl)piperidine-2,6-dione;

(E)/(Z)—(S)-3-(5-(4-(2-(1-(4-(1-(4-hydroxyphenyl)-2-
phenylbut-1-en-1-yl)phenyl)piperidin-4-yl)ethyl)pip-
erazin-1-yl)-1-oxoisoindolin-2-yl)piperidine-2,6-di-
one;

(E)-3-(5-(4-(2-(1-(4-(1-(4-hydroxyphenyl)-2-phenylbut-
1-en-1-yl)phenyl)piperidin-4-yl)ethyl)piperazin-1-yl)-
1-oxoisoindolin-2-yl)piperidine-2,6-dione;

(Z)-3-(5-fluoro-6-(4-(5-(4-(1-(4-hydroxyphenyl)-2-phe-
nylbut-1-en-1-yl)phenoxy)pentyl)piperazin-1-yl)-1-
oxoisoindolin-2-yl)piperidine-2,6-dione;

(Z)-3-(4-fluoro-5-(4-(5-(4-(1-(4-hydroxyphenyl)-2-phe-
nylbut-1-en-1-yl)phenoxy)pentyl)piperazin-1-yl)-1-
oxoisoindolin-2-yl)piperidine-2,6-dione;

(E)-3-(5-(2-(4-((1-(4-(1-(4-hydroxyphenyl)-2-phenylbut-
1-en-1-yl)phenyl)piperidin-4-yl)methyl)-1,4-diazepan-
1-yl)ethyl)-1-oxoisoindolin-2-yl)piperidine-2,6-dione;

(Z)-3-(5-(6-(4-(4-(1-(4-hydroxyphenyl)-2-phenylbut-1-
en-1-yl)phenoxy)butyl)-2,6-diazaspiro[3.3]heptan-2-
yl)-1-oxoisoindolin-2-yl)piperidine-2,6-dione;

(Z)-3-(5-(8-(4-(4-(1-(4-hydroxyphenyl)-2-phenylbut-1-
en-1-yl)phenoxy)butyl)octahydro-2H-pyrazino[1,2-a]
pyrazin-2-yl)-1-oxoisoindolin-2-yl)piperidine-2,6-di-
one;

(Z)-3-(5-(4-(2-hydroxy-5-(4-(1-(4-hydroxyphenyl)-2-
phenylbut-1-en-1-yl)phenoxy)pentyl)piperazin-1-yl)-
1-oxoisoindolin-2-yl)piperidine-2,6-dione;

(Z)-3-(7-fluoro-5-(4-(5-(4-(1-(4-hydroxyphenyl)-2-phe-
nylbut-1-en-1-yl)phenoxy)pentyl)piperazin-1-yl)-1-
oxoisoindolin-2-yl)piperidine-2,6-dione;

(Z)-3-(5-(4-(3-hydroxy-5-(4-(1-(4-hydroxyphenyl)-2-
phenylbut-1-en-1-yl)phenoxy)-3-methylpentyl)piper-
azin-1-yl)-1-oxoisoindolin-2-yl)piperidine-2,6-dione;

(Z)-3-(5-(4-(5-(4-(1-(4-hydroxyphenyl)-2-phenylbut-1-
en-1-yl)phenoxy)-2-oxopentyl)piperazin-1-yl)-1-ox-
oisoindolin-2-yl)piperidine-2,6-dione;

(Z)-3-(4-fluoro-5-(4-(2-hydroxy-5-(4-(1-(4-hydroxyphe-
nyl)-2-phenylbut-1-en-1-yl)phenoxy)pentyl)piperazin-
1-yl)-1-oxoisoindolin-2-yl)piperidine-2,6-dione;

(Z)-3-(4,6-difluoro-5-(4-(2-hydroxy-5-(4-(1-(4-hydroxy-
phenyl)-2-phenylbut-1-en-1-yl)phenoxy)pentyl)piper-
azin-1-yl)-1-oxoisoindolin-2-yl)piperidine-2,6-dione;

(Z)-2-(2,6-dioxopiperidin-3-yl)-5-(5-(4-(4-(1-(4-hy-
droxyphenyl)-2-phenylbut-1-en-1-yl)phenoxy)butyl)
hexahydropyrrolo[3,4-c]pyrrol-2(1H)-yl)isoindoline-1,
3-dione;

(Z)-2-(2,6-dioxopiperidin-3-yl)-5-(5-(3-(4-(1-(4-hy-
droxyphenyl)-2-phenylbut-1-en-1-yl)phenoxy)propyl)
hexahydropyrrolo[3,4-c]pyrrol-2(1H)-yl)isoindoline-1,
3-dione;

(Z)-3-(5-(4-(2-(2-(4-(1-(4-hydroxyphenyl)-2-phenylbut-
1-en-1-yl)phenoxy)ethoxy)ethyl)piperazin-1-yl)-1-ox-
oisoindolin-2-yl)piperidine-2,6-dione;

(Z)-3-(5-(4-(2-(3-(4-(1-(4-hydroxyphenyl)-2-phenylbut-
1-en-1-yl)phenoxy)cyclobutoxy)ethyl)piperazin-1-yl)-
1-oxoisoindolin-2-yl)piperidine-2,6-dione;

(Z)-5-(4-(4,4-difluoro-5-(4-(1-(4-hydroxyphenyl)-2-phe-
nylbut-1-en-1-yl)phenoxy)pentyl)piperazin-1-yl)-2-(2,
6-dioxopiperidin-3-yl)isoindoline-1,3-dione;

(Z)-3-(5-(4-(3-hydroxy-5-(4-(1-(4-hydroxyphenyl)-2-
phenylbut-1-en-1-yl)phenoxy)pentyl)piperazin-1-yl)-
1-oxoisoindolin-2-yl)piperidine-2,6-dione;

(Z)-3-(5-(4-(4-(4-(1-(4-hydroxyphenyl)-2-phenylbut-1-
en-1-yl)phenoxy)butyl)hexahydropyrrolo[3,4-c]pyr-
rol-2(1H)-yl)-1-oxoisoindolin-2-yl)piperidine-2,6-di-
one;

(Z)-3-(5-(5-(3-(4-(1-(4-hydroxyphenyl)-2-phenylbut-1-
en-1-yl)phenoxy)propyl)hexahydropyrrolo[3,4-c]pyr-
rol-2(1H)-yl)-1-oxoisoindolin-2-yl)piperidine-2,6-di-
one;

(Z)-3-(5-(4-(5-((4-(1-(4-hydroxyphenyl)-2-phenylbut-1-
en-1-yl)phenyl)sulfonyl)pentyl)piperazin-1-yl)-1-ox-
oisoindolin-2-yl)piperidine-2,6-dione;

(E)-3-(5-(2-(4-((1-(4-(1-(4-hydroxyphenyl)-2-phenylbut-
1-en-1-yl)phenyl)azetidin-3-yl)methyl)-1,4-diazepan-
1-yl)ethyl)-1-oxoisoindolin-2-yl)piperidine-2,6-dione;

(Z)-3-(5-(4-(2-((2-(4-(1-(4-hydroxyphenyl)-2-phenylbut-
1-en-1-yl)phenoxy)ethyl)amino)ethyl)piperazin-1-yl)-
1-oxoisoindolin-2-yl)piperidine-2,6-dione;

(E)/(Z)-2-(2,6-dioxopiperidin-3-yl)-5-(4-((1-(4-(1-(4-hy-
droxyphenyl)-2-phenylbut-1-en-1-yl)phenyl)piperidin-
4-yl)methyl)piperazin-1-yl)isoindoline-1,3-dione;

(E)-2-(2,6-dioxopiperidin-3-yl)-5-(4-((1-(4-(1-(4-hy-
droxyphenyl)-2-phenylbut-1-en-1-yl)phenyl)piperidin-
4-yl)methyl)piperazin-1-yl)isoindoline-1,3-dione;

(E)/(Z)-2-(2,6-dioxopiperidin-3-yl)-5-(4-(2-(1-(4-(1-(4-
hydroxyphenyl)-2-phenylbut-1-en-1-yl)phenyl)piperi-
din-4-yl)ethyl)piperazin-1-yl)isoindoline-1,3-dione;

(E)-2-(2,6-dioxopiperidin-3-yl)-5-(4-(2-(1-(4-(1-(4-hy-
droxyphenyl)-2-phenylbut-1-en-1-yl)phenyl)piperidin-
4-yl)ethyl)piperazin-1-yl)isoindoline-1,3-dione;

(Z)-3-(5-(4-(5-((4-(1-(4-hydroxyphenyl)-2-phenylbut-1-
en-1-yl)phenyl)thio)pentyl)piperazin-1-yl)-1-oxoisoin-
dolin-2-yl)piperidine-2,6-dione;

(Z)-3-(5-(4-((5-((4-(1-(4-hydroxyphenyl)-2-phenylbut-1-
en-1-yl)phenoxy)methyl)tetrahydrofuran-2-yl)methyl)
piperazin-1-yl)-1-oxoisoindolin-2-yl)piperidine-2,6-
dione;

(Z)-3-(5-(4-(2-(3-(4-(1-(4-hydroxyphenyl)-2-phenylbut-
1-en-1-yl)phenoxy)cyclobutyl)ethyl)piperazin-1-yl)-1-
oxoisoindolin-2-yl)piperidine-2,6-dione;

(Z)-3-(6-(4-(5-(4-(1-(4-hydroxyphenyl)-2-phenylbut-1-
en-1-yl)phenoxy)pentyl)piperazin-1-yl)-1-oxoisoindo-
lin-2-yl)piperidine-2,6-dione;

(Z)-3-(2-(4-(5-(4-(1-(4-hydroxyphenyl)-2-phenylbut-1-en-1-yl)phenoxy)pentyl)piperazin-1-yl)-5-oxo-5,7-dihydro-6H-pyrrolo[3,4-b]pyridin-6-yl)piperidine-2,6-dione;

(Z)-3-(2-(4-(4,4-difluoro-5-(4-(1-(4-hydroxyphenyl)-2-phenylbut-1-en-1-yl)phenoxy)pentyl)piperazin-1-yl)-5-oxo-5,7-dihydro-6H-pyrrolo[3,4-b]pyridin-6-yl)piperidine-2,6-dione;

(Z)-3-(6-(4-(5-(4-(1-(4-hydroxyphenyl)-2-phenylbut-1-en-1-yl)phenoxy)pentyl)piperazin-1-yl)-3-oxo-1,3-dihydro-2H-pyrrolo[3,4-c]pyridin-2-yl)piperidine-2,6-dione;

(Z)-2-(2,6-dioxopiperidin-3-yl)-5-(4-(1-(2-(4-(1-(4-hydroxyphenyl)-2-phenylbut-1-en-1-yl)phenoxy)ethyl)pyrrolidin-3-yl)butyl)isoindoline-1,3-dione;

(Z)-3-(5-(4-((3-((4-(1-(4-hydroxyphenyl)-2-phenylbut-1-en-1-yl)phenoxy)methyl)cyclobutyl)methyl)piperazin-1-yl)-1-oxoisoindolin-2-yl)piperidine-2,6-dione;

(Z)-3-(2-(4-(1-(2-(4-(1-(4-hydroxyphenyl)-2-phenylbut-1-en-1-yl)phenoxy)ethyl)pyrrolidin-3-yl)butyl)-5-oxo-5,7-dihydro-6H-pyrrolo[3,4-b]pyridin-6-yl)piperidine-2,6-dione;

(E)-3-(5-((1-((1-(4-(1-(4-hydroxyphenyl)-2-phenylbut-1-en-1-yl)phenyl)piperidin-4-yl)methyl)piperidin-4-yl)methoxy)-1-oxoisoindolin-2-yl)piperidine-2,6-dione;

(Z)-2-(2,6-dioxopiperidin-3-yl)-4-(4-(1-(2-(4-(1-(4-hydroxyphenyl)-2-phenylbut-1-en-1-yl)phenoxy)ethyl)pyrrolidin-3-yl)butyl)isoindoline-1,3-dione;

(E)-3-(2-(4-((1-(4-(1-(4-hydroxyphenyl)-2-phenylbut-1-en-1-yl)phenyl)piperidin-4-yl)methyl)piperazin-1-yl)-5-oxo-5,7-dihydro-6H-pyrrolo[3,4-b]pyridin-6-yl)piperidine-2,6-dione;

(E)-3-(2-(4-(2-(1-(4-(1-(4-hydroxyphenyl)-2-phenylbut-1-en-1-yl)phenyl)piperidin-4-yl)ethyl)piperazin-1-yl)-5-oxo-5,7-dihydro-6H-pyrrolo[3,4-b]pyridin-6-yl)piperidine-2,6-dione;

(E)-2-(2,6-dioxopiperidin-3-yl)-5-((1-((1-(4-(1-(4-hydroxyphenyl)-2-phenylbut-1-en-1-yl)phenyl)piperidin-4-yl)methyl)piperidin-4-yl)methoxy)isoindoline-1,3-dione;

(Z)-3-(5-(4-((6-((4-(1-(4-hydroxyphenyl)-2-phenylbut-1-en-1-yl)phenoxy)methyl)pyridazin-3-yl)methyl)piperazin-1-yl)-1-oxoisoindolin-2-yl)piperidine-2,6-dione;

(E)-3-(5-(4-((1-(4-(1-(4-hydroxyphenyl)-2-phenylbut-1-en-1-yl)phenyl)piperidin-4-yl)methyl)piperazin-1-yl)-1-oxoisoindolin-2-yl)-3-methylpiperidine-2,6-dione;

(E)-3-(5-(7-((1-(4-(1-(4-hydroxyphenyl)-2-phenylbut-1-en-1-yl)phenyl)piperidin-4-yl)methyl)-2,7-diazaspiro[3.5]nonan-2-yl)-1-oxoisoindolin-2-yl)piperidine-2,6-dione;

(Z)-3-(6-(2-(4-(3-(4-(1-(4-hydroxyphenyl)-2-phenylbut-1-en-1-yl)phenoxy)cyclobutoxy)piperidin-1-yl)ethoxy)-1-oxoisoindolin-2-yl)piperidine-2,6-dione;

(Z)-2-(2,6-dioxopiperidin-3-yl)-5-(4-(6,6,6-trifluoro-5-(4-(1-(4-hydroxyphenyl)-2-phenylbut-1-en-1-yl)phenoxy)hexyl)piperazin-1-yl)isoindoline-1,3-dione;

(Z)-3-(1-oxo-5-(4-(6,6,6-trifluoro-5-(4-(1-(4-hydroxyphenyl)-2-phenylbut-1-en-1-yl)phenoxy)hexyl)piperazin-1-yl)isoindolin-2-yl)piperidine-2,6-dione;

(Z)-3-(5-(4-((5-((4-(1-(4-hydroxyphenyl)-2-phenylbut-1-en-1-yl)phenoxy)methyl)pyridin-2-yl)methyl)piperazin-1-yl)-1-oxoisoindolin-2-yl)piperidine-2,6-dione;

(E)-3-(6-(4-((1-(4-(1-(4-hydroxyphenyl)-2-phenylbut-1-en-1-yl)phenyl)piperidin-4-yl)methyl)piperazin-1-yl)-3-oxo-1,3-dihydro-2H-pyrrolo[3,4-c]pyridin-2-yl)piperidine-2,6-dione;

(E)-3-(5-(4-(7-(4-(1-(4-hydroxyphenyl)-2-phenylbut-1-en-1-yl)phenyl)-7-azaspiro[3.5]nonan-2-yl)piperazin-1-yl)-1-oxoisoindolin-2-yl)piperidine-2,6-dione;

(E)-3-(2-(4-(7-(4-(1-(4-hydroxyphenyl)-2-phenylbut-1-en-1-yl)phenyl)-7-azaspiro[3.5]nonan-2-yl)piperazin-1-yl)-5-oxo-5,7-dihydro-6H-pyrrolo[3,4-b]pyridin-6-yl)piperidine-2,6-dione;

(E)-3-(6-(4-(2-(1-(4-(1-(4-hydroxyphenyl)-2-phenylbut-1-en-1-yl)phenyl)piperidin-4-yl)ethyl)piperazin-1-yl)-3-oxo-1,3-dihydro-2H-pyrrolo[3,4-c]pyridin-2-yl)piperidine-2,6-dione;

(E)-3-(5-(4-((1-(4-(1-(4-hydroxyphenyl)-2-phenylbut-1-en-1-yl)phenyl)-4-methylpiperidin-4-yl)methyl)piperazin-1-yl)-1-oxoisoindolin-2-yl)piperidine-2,6-dione;

(E)-3-(4,6-difluoro-5-(4-((1-(4-(1-(4-hydroxyphenyl)-2-phenylbut-1-en-1-yl)phenyl)piperidin-4-yl)methyl)piperazin-1-yl)-1-oxoisoindolin-2-yl)piperidine-2,6-dione;

(E)-3-(5-((1-((1-(4-(1-(4-hydroxyphenyl)-2-phenylbut-1-en-1-yl)phenyl)piperidin-4-yl)methyl)piperidin-4-yl)oxy)-1-oxoisoindolin-2-yl)piperidine-2,6-dione;

(E)-3-(2-(3-(((1-(4-(1-(4-hydroxyphenyl)-2-phenylbut-1-en-1-yl)phenyl)piperidin-4-yl)methyl)amino)pyrrolidin-1-yl)-5-oxo-5,7-dihydro-6H-pyrrolo[3,4-b]pyridin-6-yl)piperidine-2,6-dione;

(E)-3-(4-fluoro-5-(4-((1-(4-(1-(4-hydroxyphenyl)-2-phenylbut-1-en-1-yl)phenyl)piperidin-4-yl)methyl)piperazin-1-yl)-1-oxoisoindolin-2-yl)piperidine-2,6-dione;

(E)-3-(6-(4-((1-(4-(1-(4-hydroxyphenyl)-2-phenylbut-1-en-1-yl)phenyl)piperidin-4-yl)methyl)piperazin-1-yl)-1-oxoisoindolin-2-yl)piperidine-2,6-dione;

(E)-3-(5-(3-(((1-(4-(1-(4-hydroxyphenyl)-2-phenylbut-1-en-1-yl)phenyl)piperidin-4-yl)methyl)amino)pyrrolidin-1-yl)-1-oxoisoindolin-2-yl)piperidine-2,6-dione;

(E)-3-(5-(4-((1-(4-(1-(4-hydroxyphenyl)-2-phenylbut-1-en-1-yl)phenyl)piperidin-4-yl)methyl)piperazin-1-yl)-1-oxoisoindolin-2-yl)-1-methylpiperidine-2,6-dione;

(E)-3-(5-(4-((4-hydroxy-1-(4-(1-(4-hydroxyphenyl)-2-phenylbut-1-en-1-yl)phenyl)piperidin-4-yl)methyl)piperazin-1-yl)-1-oxoisoindolin-2-yl)piperidine-2,6-dione;

(E)-3-(5-(4-(((1-(4-(1-(4-hydroxyphenyl)-2-phenylbut-1-en-1-yl)phenyl)piperidin-4-yl)methyl)amino)piperidin-1-yl)-1-oxoisoindolin-2-yl)piperidine-2,6-dione;

(E)-3-(5-(4-((1-(4-(1-(4-hydroxyphenyl)-2-phenylbut-1-en-1-yl)phenyl)piperidin-4-yl)amino)piperidin-1-yl)-1-oxoisoindolin-2-yl)piperidine-2,6-dione;

(E)-3-(5-(4-((4-fluoro-1-(4-(1-(4-hydroxyphenyl)-2-phenylbut-1-en-1-yl)phenyl)piperidin-4-yl)methyl)piperazin-1-yl)-1-oxoisoindolin-2-yl)piperidine-2,6-dione;

(Z)-3-(4-((2-(4-(2-(4-(1-(4-hydroxyphenyl)-2-phenylbut-1-en-1-yl)phenoxy)ethyl)piperazin-1-yl)ethyl)amino)-1-oxoisoindolin-2-yl)piperidine-2,6-dione;

(Z)-2-(2,6-dioxopiperidin-3-yl)-4-((2-(4-(2-(4-(1-(4-hydroxyphenyl)-2-phenylbut-1-en-1-yl)phenoxy)ethyl)piperazin-1-yl)ethyl)amino)isoindoline-1,3-dione;

(Z)-3-(5-(2-(4-(2-(4-(1-(4-hydroxyphenyl)-2-phenylbut-1-en-1-yl)phenoxy)ethyl)piperazin-1-yl)-2-oxoethoxy)-1-oxoisoindolin-2-yl)piperidine-2,6-dione;

(Z)-3-(4-((6-((4-(2-(4-(1-(4-hydroxyphenyl)-2-phenylbut-1-en-1-yl)phenoxy)ethyl)piperazin-1-yl)methyl)pyridin-3-yl)methoxy)-1-oxoisoindolin-2-yl)piperidine-2,6-dione;

(Z)-3-(4-(2-(4-(1-(4-(1-(4-hydroxyphenyl)-2-phenylbut-1-en-1-yl)phenoxy)propan-2-yl)piperazin-1-yl)ethoxy)-1-oxoisoindolin-2-yl)piperidine-2,6-dione;

(Z)-3-(4-(2-(2-(4-(1-(4-hydroxyphenyl)-2-phenylbut-1-en-1-yl)phenoxy)ethoxy)ethoxy)-1-oxoisoindolin-2-yl)piperidine-2,6-dione;

(Z)-3-(4-((14-(4-(1-(4-hydroxyphenyl)-2-phenylbut-1-en-1-yl)phenoxy)-3,6,9,12-tetraoxatetradecyl)amino)-1-oxoisoindolin-2-yl)piperidine-2,6-dione;

(Z)-3-(4-(2-(2-(2-(4-(1-(4-hydroxyphenyl)-2-phenylbut-1-en-1-yl)phenoxy)ethoxy)ethoxy)ethoxy)-1-oxoisoindolin-2-yl)piperidine-2,6-dione;

(Z)-2-(2,6-dioxopiperidin-3-yl)-4-((14-(4-(1-(4-hydroxyphenyl)-2-phenylbut-1-en-1-yl)phenoxy)-3,6,9,12-tetraoxatetradecyl)amino)isoindoline-1,3-dione;

(Z)-3-(4-(2-(2-(2-(2-(4-(1-(4-hydroxyphenyl)-2-phenylbut-1-en-1-yl)phenoxy)ethoxy)ethoxy)ethoxy)ethoxy)-1-oxoisoindolin-2-yl)piperidine-2,6-dione;

(Z)-3-(4-((2-(2-(2-(2-(4-(1-(4-hydroxyphenyl)-2-phenylbut-1-en-1-yl)phenoxy)ethoxy)ethoxy)ethoxy)ethyl)amino)-1-oxoisoindolin-2-yl)piperidine-2,6-dione;

(Z)-2-(2,6-dioxopiperidin-3-yl)-4-((2-(2-(2-(2-(4-(1-(4-hydroxyphenyl)-2-phenylbut-1-en-1-yl)phenoxy)ethoxy)ethoxy)ethoxy)ethyl)amino)isoindoline-1,3-dione;

(Z)-3-(4-((2-(2-(2-(4-(1-(4-hydroxyphenyl)-2-phenylbut-1-en-1-yl)phenoxy)ethoxy)ethoxy)ethyl)amino)-1-oxoisoindolin-2-yl)piperidine-2,6-dione;

(Z)-3-(4-((14-(4-(1-(4-hydroxyphenyl)-2-phenylbut-1-en-1-yl)phenoxy)-3,6,9,12-tetraoxatetradecyl)oxy)-1-oxoisoindolin-2-yl)piperidine-2,6-dione;

(Z)-2-(2,6-dioxopiperidin-3-yl)-4-((2-(2-(2-(4-(1-(4-hydroxyphenyl)-2-phenylbut-1-en-1-yl)phenoxy)ethoxy)ethoxy)ethyl)amino)isoindoline-1,3-dione;

(Z)-3-(4-((2-(2-(4-(1-(4-hydroxyphenyl)-2-phenylbut-1-en-1-yl)phenoxy)ethoxy)ethyl)amino)-1-oxoisoindolin-2-yl)piperidine-2,6-dione;

(Z)-3-(4-(2-(4-(1-(4-hydroxyphenyl)-2-phenylbut-1-en-1-yl)phenoxy)ethoxy)-1-oxoisoindolin-2-yl)piperidine-2,6-dione;

(Z)-2-(2,6-dioxopiperidin-3-yl)-4-((2-(2-(4-(1-(4-hydroxyphenyl)-2-phenylbut-1-en-1-yl)phenoxy)ethoxy)ethyl)amino)isoindoline-1,3-dione;

(Z)-2-(2,6-dioxopiperidin-3-yl)-4-((2-(4-(1-(4-hydroxyphenyl)-2-phenylbut-1-en-1-yl)phenoxy)ethyl)amino)isoindoline-1,3-dione;

(Z)-3-(4-((2-(4-(1-(4-hydroxyphenyl)-2-phenylbut-1-en-1-yl)phenoxy)ethyl)amino)-1-oxoisoindolin-2-yl)piperidine-2,6-dione;

(Z)-3-(4-(3-(3-(4-(1-(4-hydroxyphenyl)-2-phenylbut-1-en-1-yl)phenoxy)propoxy)propoxy)-1-oxoisoindolin-2-yl)piperidine-2,6-dione;

(Z)-3-(4-(3-(3-(3-(4-(1-(4-hydroxyphenyl)-2-phenylbut-1-en-1-yl)phenoxy)propoxy)propoxy)propoxy)-1-oxoisoindolin-2-yl)piperidine-2,6-dione;

(Z)-3-(4-(2-(5-(2-(4-(1-(4-hydroxyphenyl)-2-phenylbut-1-en-1-yl)phenoxy)ethyl)-2,5-diazabicyclo[2.2.1]heptan-2-yl)ethoxy)-1-oxoisoindolin-2-yl)piperidine-2,6-dione;

(Z)-3-(5-(2-(6-(2-(4-(1-(4-hydroxyphenyl)-2-phenylbut-1-en-1-yl)phenoxy)ethyl)-2,6-diazaspiro[3.3]heptan-2-yl)ethoxy)-1-oxoisoindolin-2-yl)piperidine-2,6-dione;

(Z)-3-(5-(2-((1-(2-(4-(1-(4-hydroxyphenyl)-2-phenylbut-1-en-1-yl)phenoxy)ethyl)piperidin-4-yl)oxy)ethoxy)-1-oxoisoindolin-2-yl)piperidine-2,6-dione;

(Z)-3-(5-((7-(2-(4-(1-(4-hydroxyphenyl)-2-phenylbut-1-en-1-yl)phenoxy)ethyl)-7-azaspiro[3.5]nonan-2-yl)oxy)-1-oxoisoindolin-2-yl)piperidine-2,6-dione;

(Z)-3-(5-(4-(4-(1-(4-(1-(4-hydroxyphenyl)-2-phenylbut-1-en-1-yl)phenoxy)propan-2-yl)piperazin-1-yl)butyl)-1-oxoisoindolin-2-yl)piperidine-2,6-dione;

(Z)—N-((2-(2,6-dioxopiperidin-3-yl)-1-oxoisoindolin-5-yl)methyl)-1-(2-(4-(1-(4-hydroxyphenyl)-2-phenylbut-1-en-1-yl)phenoxy)ethyl)piperidine-4-carboxamide;

(Z)—N-((2-(2,6-dioxopiperidin-3-yl)-1-oxoisoindolin-5-yl)methyl)-2-(1-(2-(4-(1-(4-hydroxyphenyl)-2-phenylbut-1-en-1-yl)phenoxy)ethyl)piperidin-4-yl)acetamide;

(Z)-2-(2,6-dioxopiperidin-3-yl)-5-((2-(2-(2-(4-(1-(4-hydroxyphenyl)-2-phenylbut-1-en-1-yl)phenoxy)ethoxy)ethoxy)ethyl)amino)isoindoline-1,3-dione;

(Z)-2-(2,6-dioxopiperidin-3-yl)-5-(4-(7-(4-(1-(4-hydroxyphenyl)-2-phenylbut-1-en-1-yl)phenoxy)heptyl)piperazin-1-yl)isoindoline-1,3-dione;

(Z)-3-(5-((3-(4-(2-(4-(1-(4-hydroxyphenyl)-2-phenylbut-1-en-1-yl)phenoxy)ethyl)-1,4-diazepan-1-yl)propyl)amino)-1-oxoisoindolin-2-yl)piperidine-2,6-dione;

(Z)-2-(2,6-dioxopiperidin-3-yl)-5-(3-(3-(4-(1-(4-hydroxyphenyl)-2-phenylbut-1-en-1-yl)phenoxy)propoxy)propoxy)isoindoline-1,3-dione;

(Z)-2-(2,6-dioxopiperidin-3-yl)-5-(2-(2-(2-(4-(1-(4-hydroxyphenyl)-2-phenylbut-1-en-1-yl)phenoxy)ethoxy)ethoxy)isoindoline-1,3-dione;

(Z)-2-(2,6-dioxopiperidin-3-yl)-5-(3-(2-(2-(4-(1-(4-hydroxyphenyl)-2-phenylbut-1-en-1-yl)phenoxy)ethoxy)ethoxy)propoxy)isoindoline-1,3-dione;

(Z)-2-(2,6-dioxopiperidin-3-yl)-5-(3-(3-(3-(4-(1-(4-hydroxyphenyl)-2-phenylbut-1-en-1-yl)phenoxy)propoxy)propoxy)propoxy)isoindoline-1,3-dione;

(Z)-2-(2,6-dioxopiperidin-3-yl)-5-((3-(3-(4-(1-(4-hydroxyphenyl)-2-phenylbut-1-en-1-yl)phenoxy)propoxy)propyl)amino)isoindoline-1,3-dione;

(Z)-2-(2,6-dioxopiperidin-3-yl)-5-((3-(2-(2-(4-(1-(4-hydroxyphenyl)-2-phenylbut-1-en-1-yl)phenoxy)ethoxy)ethoxy)propyl)amino)isoindoline-1,3-dione;

(Z)-2-(2,6-dioxopiperidin-3-yl)-5-((3-(3-(3-(4-(1-(4-hydroxyphenyl)-2-phenylbut-1-en-1-yl)phenoxy)propoxy)propoxy)propyl)amino)isoindoline-1,3-dione;

(Z)-3-(5-((2-(2-(2-(4-(1-(4-hydroxyphenyl)-2-phenylbut-1-en-1-yl)phenoxy)ethoxy)ethoxy)ethyl)amino)-1-oxoisoindolin-2-yl)piperidine-2,6-dione;

(Z)-2-(2,6-dioxopiperidin-3-yl)-5-(3-(3-(2-(4-(1-(4-hydroxyphenyl)-2-phenylbut-1-en-1-yl)phenoxy)ethoxy)propoxy)propoxy)isoindoline-1,3-dione;

(Z)-3-(5-((3-(3-(2-(4-(1-(4-hydroxyphenyl)-2-phenylbut-1-en-1-yl)phenoxy)ethoxy)propoxy)propyl)amino)-1-oxoisoindolin-2-yl)piperidine-2,6-dione;

(Z)-2-(2,6-dioxopiperidin-3-yl)-5-(3-(3-(4-(4-(1-(4-hydroxyphenyl)-2-phenylbut-1-en-1-yl)phenoxy)butoxy)propoxy)propoxy)isoindoline-1,3-dione;

(Z)-2-(2,6-dioxopiperidin-3-yl)-5-((3-(3-(2-(4-(1-(4-hydroxyphenyl)-2-phenylbut-1-en-1-yl)phenoxy)ethoxy)propoxy)propyl)amino)isoindoline-1,3-dione;

(Z)-2-(2,6-dioxopiperidin-3-yl)-5-((3-(3-(4-(4-(1-(4-hydroxyphenyl)-2-phenylbut-1-en-1-yl)phenoxy)butoxy)propoxy)propyl)amino)isoindoline-1,3-dione;

(Z)-3-(5-((3-(3-(4-(4-(1-(4-hydroxyphenyl)-2-phenylbut-1-en-1-yl)phenoxy)butoxy)propoxy)propyl)amino)-1-oxoisoindolin-2-yl)piperidine-2,6-dione;

(Z)-3-(5-((3-(3-(3-(4-(1-(4-hydroxyphenyl)-2-phenylbut-1-en-1-yl)phenoxy)propoxy)propoxy)propyl)amino)-1-oxoisoindolin-2-yl)piperidine-2,6-dione;

(Z)-2-(2,6-dioxopiperidin-3-yl)-5-((3-(4-(2-(4-(1-(4-hydroxyphenyl)-2-phenylbut-1-en-1-yl)phenoxy)ethyl)piperazin-1-yl)propyl)amino)isoindoline-1,3-dione;

(Z)-2-(2,6-dioxopiperidin-3-yl)-5-((3-(4-(2-(4-(1-(4-hydroxyphenyl)-2-phenylbut-1-en-1-yl)phenoxy)ethyl)-1,4-diazepan-1-yl)propyl)amino)isoindoline-1,3-dione;

(E)-2-(2,6-dioxopiperidin-3-yl)-5-((3-(4-(3-(4-(1-(4-hydroxyphenyl)-2-phenylbut-1-en-1-yl)phenyl)propyl)piperazin-1-yl)propyl)amino)isoindoline-1,3-dione;

(E)-2-(2,6-dioxopiperidin-3-yl)-5-((3-(4-(3-(4-(1-(4-hydroxyphenyl)-2-phenylbut-1-en-1-yl)phenyl)propyl)-1,4-diazepan-1-yl)propyl)amino)isoindoline-1,3-dione;

(E)-2-(2,6-dioxopiperidin-3-yl)-5-((3-(4-(4-(1-(4-hydroxyphenyl)-2-phenylbut-1-en-1-yl)phenyl)piperidin-1-yl)propyl)amino)isoindoline-1,3-dione;

(E)-2-(2,6-dioxopiperidin-3-yl)-5-((4-(4-(1-(4-hydroxyphenyl)-2-phenylbut-1-en-1-yl)phenyl)piperidin-1-yl)butyl)amino)isoindoline-1,3-dione;

(E)-3-(5-((3-(4-(3-(4-(1-(4-hydroxyphenyl)-2-phenylbut-1-en-1-yl)phenyl)propyl)piperazin-1-yl)propyl)amino)-1-oxoisoindolin-2-yl)piperidine-2,6-dione;

(E)-3-(5-((3-(4-(3-(4-(1-(4-hydroxyphenyl)-2-phenylbut-1-en-1-yl)phenyl)propyl)-1,4-diazepan-1-yl)propyl)amino)-1-oxoisoindolin-2-yl)piperidine-2,6-dione;

(E)-3-(5-((3-(4-(4-(1-(4-hydroxyphenyl)-2-phenylbut-1-en-1-yl)phenyl)piperidin-1-yl)propyl)amino)-1-oxoisoindolin-2-yl)piperidine-2,6-dione;

(E)-3-(5-((5-(4-(4-(1-(4-hydroxyphenyl)-2-phenylbut-1-en-1-yl)phenyl)piperidin-1-yl)pentyl)amino)-1-oxoisoindolin-2-yl)piperidine-2,6-dione; and (E)-3-(5-(2-(4-(5-(4-(1-(4-hydroxyphenyl)-2-phenylbut-1-en-1-yl)phenyl)pentyl)-1,4-diazepan-1-yl)ethyl)-1-oxoisoindolin-2-yl)piperidine-2,6-dione.

18. A compound of Formula (II), or a tautomer, stereoisomer, or a pharmaceutically acceptable salt, or hydrate thereof:

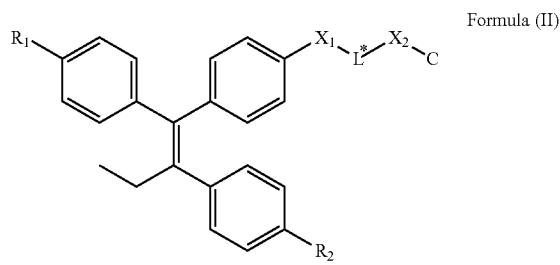

Formula (II)

wherein:

$X^1$ and $X^2$ are each independently selected from $C(R^3)_2$, $NR^4$, O, S, cycloalkyl, aryl, heterocycle, and heteroaryl, each of which is independently substituted with 0, 1, 2, or 3 $R^5$;

B is selected from 5- to 6-member cycloalkyl, 5- to 6-member aryl, 5- to 6-member heterocycle, and 5- to 6-member heteroaryl, each of which is substituted with 0, 1, 2, or 3 $R^5$;

C is selected from:

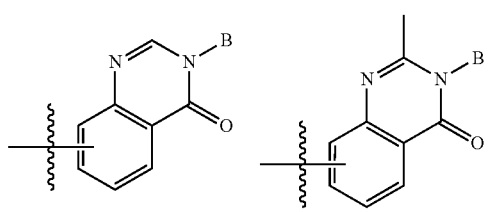

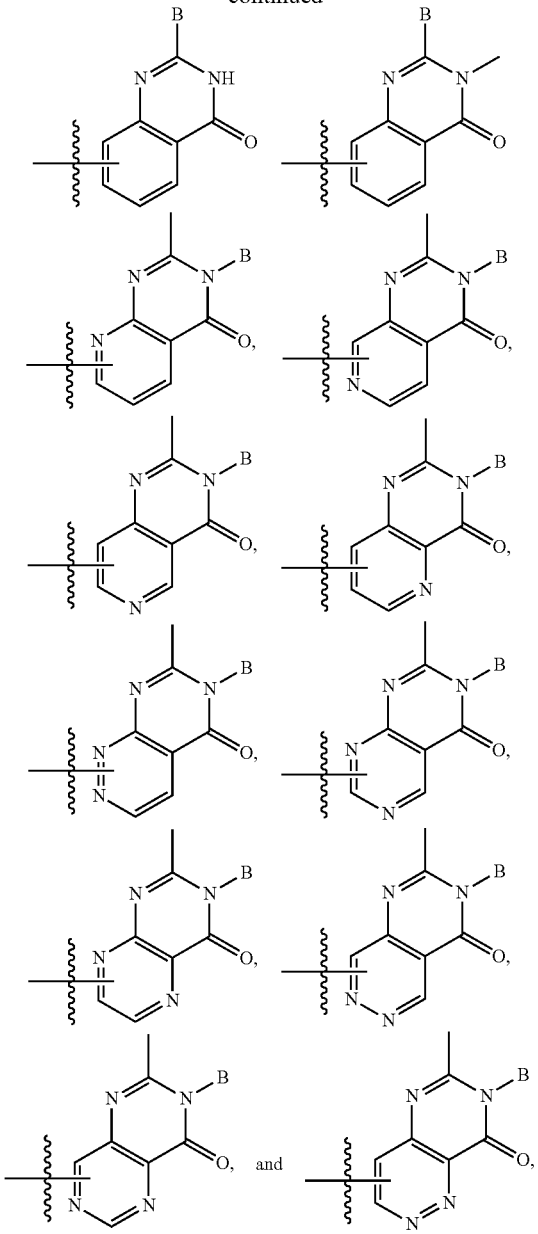

each of which is substituted with 0, 1, 2, or 3 $R^5$;

L* is a linker of 1 to 22 carbon atoms in length, wherein one or more carbon atoms are each optionally and independently replaced by a group selected from C(O), O, $NR^4$, S, $C_2$-alkenyl, $C_2$-alkynyl, cycloalkyl, aryl, heterocycle, and heteroaryl, each of which is substituted with 0, 1, 2, or 3 $R^5$;

$R^1$ and $R^2$ are each independently selected from H, $C_1$-$C_6$ alkyl, halo, alkoxy, acyloxy, hydroxy, and sulfhydryl, each of which is substituted with 0, 1, 2, or 3 $R^5$;

each $R^3$ is independently selected from H, $C_1$-$C_6$ alkyl, halo, and hydroxy;

each $R^4$ is independently selected from H, $C_1$-$C_6$ alkyl, and acyl, each of which is substituted with 0, 1, 2, or 3 $R^5$; and each $R^5$ is independently selected from $C_1$-$C_6$ alkyl, halo, cyano, and hydroxy, wherein

represents the point of attachment of C to $X^2$.

19. The compound according to claim 18, or a pharmaceutically acceptable salt thereof, wherein C is

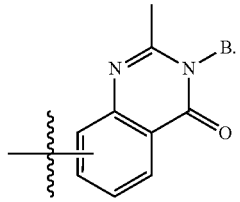

20. The compound according to claim 18, or a pharmaceutically acceptable salt thereof, wherein B is a 5-member heterocycle substituted with 0, 1, 2, or 3 $R^5$.

21. The compound according to claim 18, or a pharmaceutically acceptable salt thereof,
wherein B is selected from:

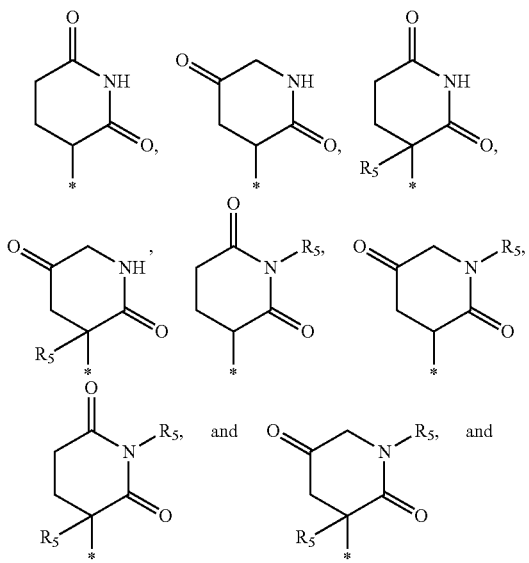

wherein

represents the point of attachment of B to C.

22. The compound according to claim 18, or a pharmaceutically acceptable salt thereof, wherein B is a 6-member heterocycle substituted with 0, 1, 2, or 3 $R^5$.

23. The compound according to claim 18, or a pharmaceutically acceptable salt thereof, wherein $R^1$ and $R^2$ are each independently selected from H, $C_1$-$C_3$ alkyl, halo, hydroxy, and sulfhydryl, each of which may be substituted with 0, 1, 2, or 3 $R^5$.

24. The compound according to claim 18, or a pharmaceutically acceptable salt thereof, wherein $X^1$ and $X^2$ are each independently selected from $C(R^3)_2$, $NR^4$, O, S, 5 or 6-member cycloalkyl, 5- or 6-member aryl, 5- or 6-member heterocycle, and 5- or 6-member heteroaryl, each of which is independently substituted with 0, 1, 2, or 3 $R^5$.

25. The compound according to claim 18, or a pharmaceutically acceptable salt thereof, wherein $X^1$ is selected from

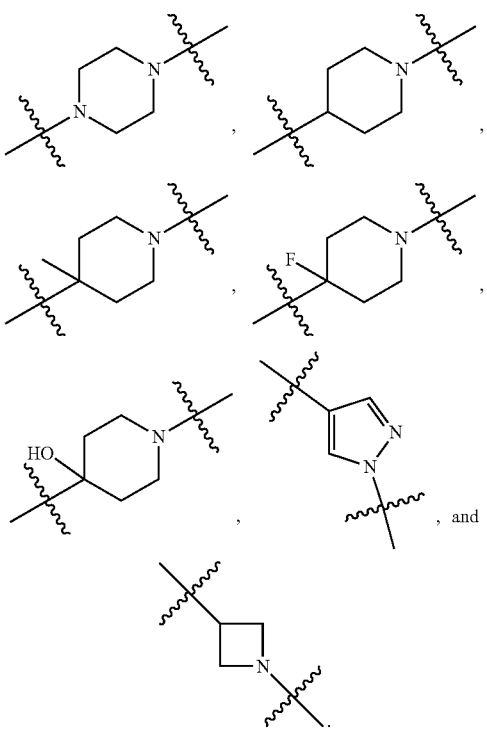

26. The compound according to claim 18, or a pharmaceutically acceptable salt thereof, wherein $X^2$ is selected from

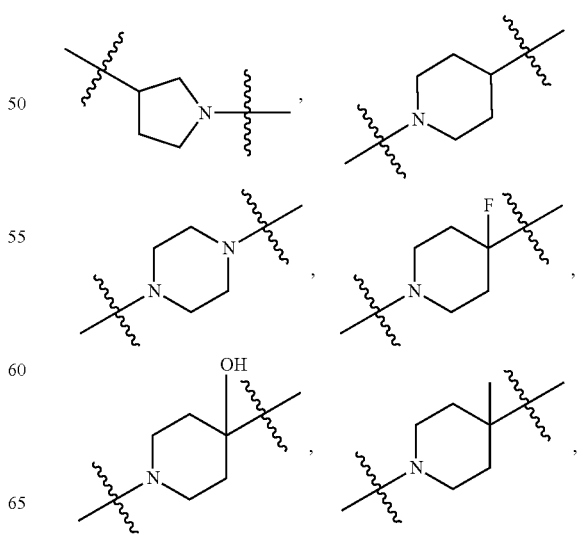

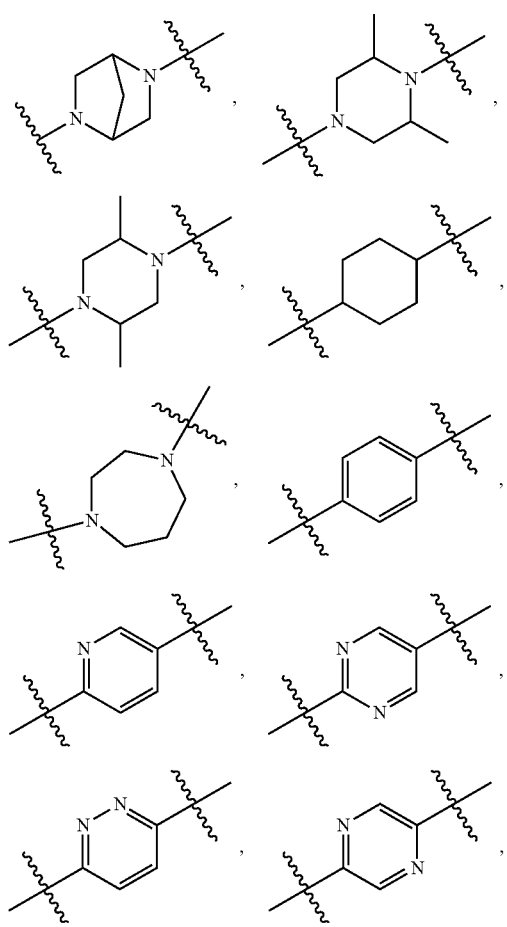
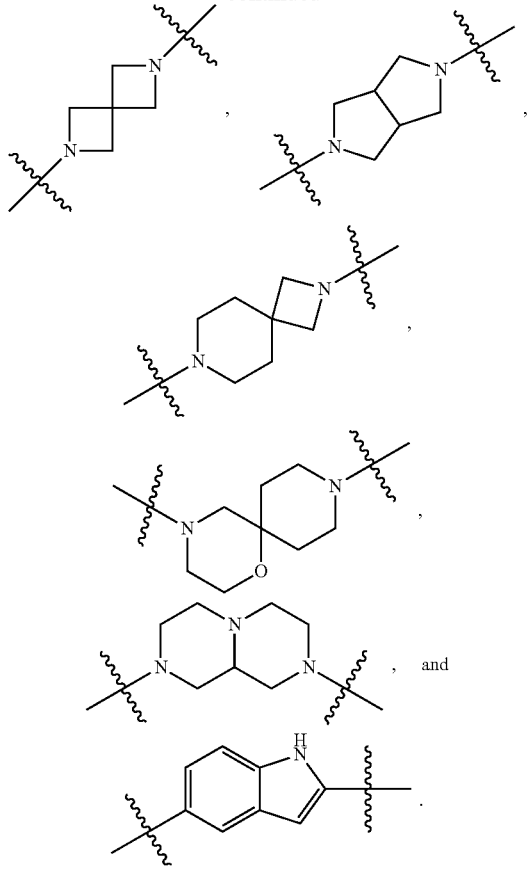
27. The compound according to claim 18, or a pharmaceutically acceptable salt thereof, wherein L* is selected from
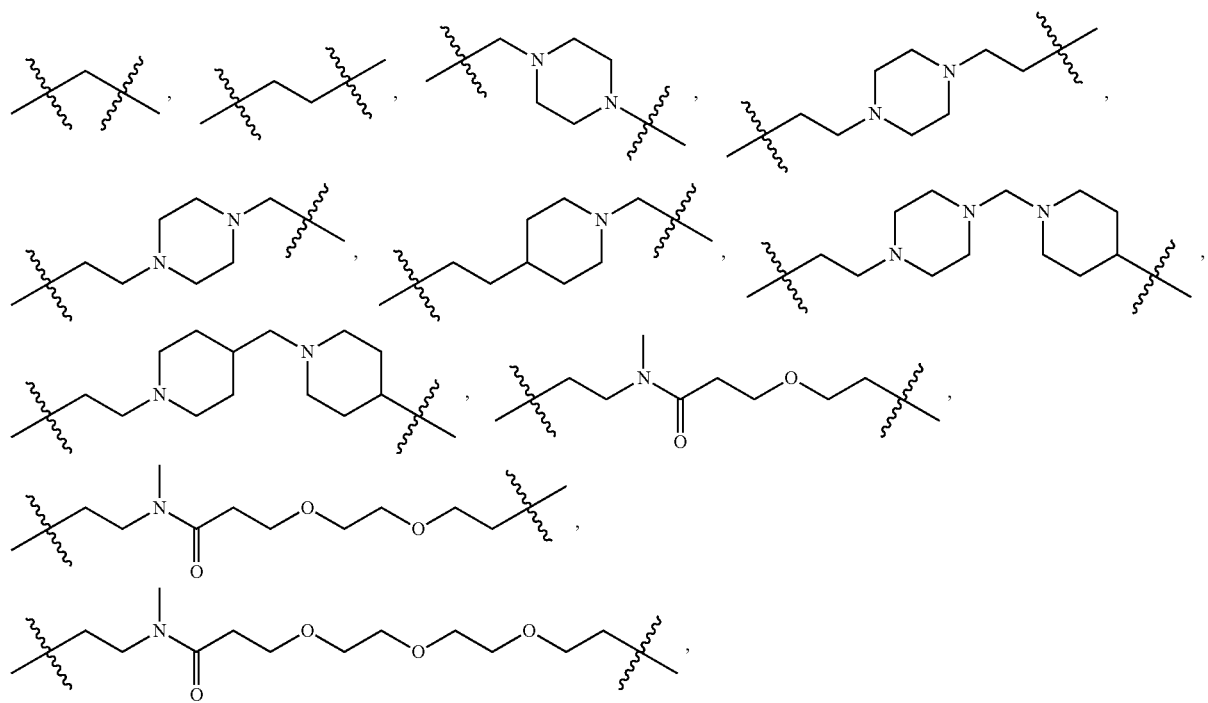

-continued

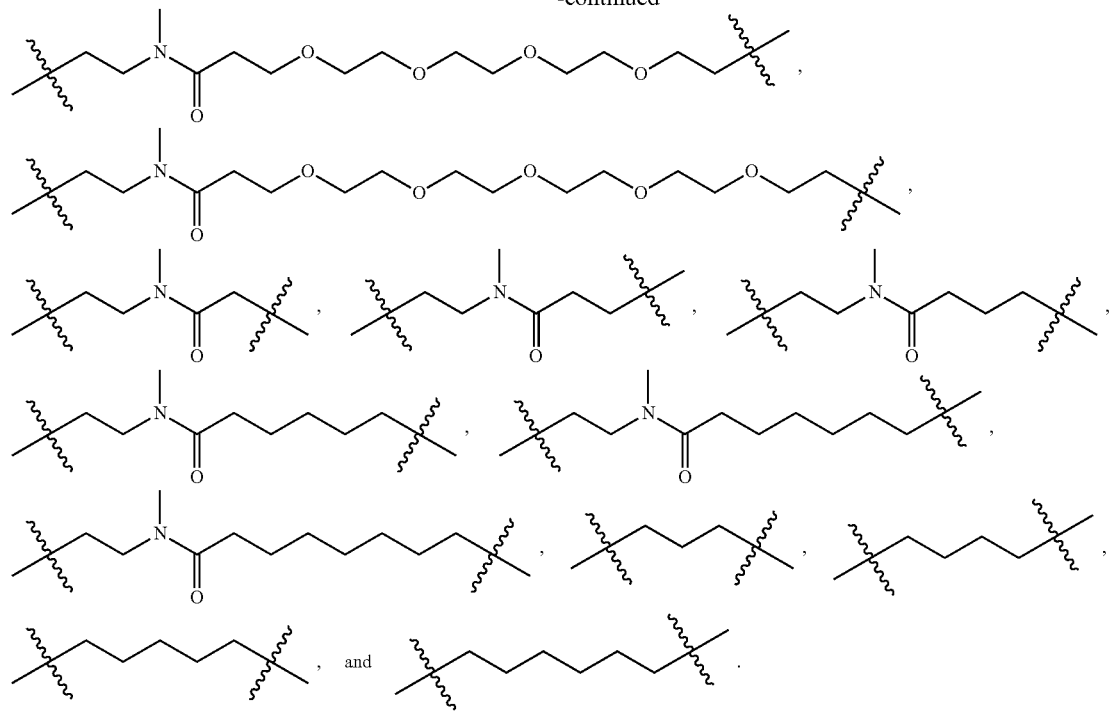

28. A method of treating cancer in a subject in need thereof, comprising administering to said subject an effective amount of the compound according to claim 1, wherein the cancer is selected from breast cancer, lung cancer, ovarian cancer, endometrial cancer, prostate cancer, and esophageal cancer.

29. A method of treating cancer in a subject in need thereof, comprising administering to said subject an effective amount of the compound according to claim 18, wherein the cancer is selected from breast cancer, lung cancer, ovarian cancer, endometrial cancer, prostate cancer, and esophageal cancer.

30. A method of treating a disease or condition in a subject in need thereof, comprising administering to said subject an effective amount of the compound according to claim 1, wherein the disease or condition is selected from breast cancer, lung cancer, ovarian cancer, endometrial cancer, prostate cancer, esophageal cancer, infertility, ovulatory dysfunction, postmenopausal osteoporosis, estrogen-related gynecomastia, dyspareunia due to menopause, retroperitoneal fibrosis, and idiopathic sclerosing mesenteritis.

* * * * *